US011866408B2

(12) United States Patent
Duncton et al.

(10) Patent No.: US 11,866,408 B2
(45) Date of Patent: Jan. 9, 2024

(54) N,N-DIMETHYLTRYPTAMINE AND RELATED PSYCHEDELICS AND USES THEREOF

(71) Applicant: Terran Biosciences Inc., New York, NY (US)

(72) Inventors: Matthew Alexander James Duncton, San Bruno, CA (US); Sam Clark, New York, NY (US)

(73) Assignee: TERRAN BIOSCIENCES INC., New York, NY (US)

( * ) Notice: Subject to any disclaimer, the term of this patent is extended or adjusted under 35 U.S.C. 154(b) by 0 days.

(21) Appl. No.: 18/173,717

(22) Filed: Feb. 23, 2023

(65) Prior Publication Data

US 2023/0212119 A1    Jul. 6, 2023

Related U.S. Application Data

(63) Continuation of application No. PCT/US2022/036396, filed on Jul. 7, 2022.

(60) Provisional application No. 63/276,516, filed on Nov. 5, 2021, provisional application No. 63/219,312, filed on Jul. 7, 2021.

(51) Int. Cl.
  *C07D 209/32* (2006.01)
  *C07D 209/12* (2006.01)
  *C07D 209/14* (2006.01)

(52) U.S. Cl.
  CPC ......... *C07D 209/32* (2013.01); *C07D 209/12* (2013.01); *C07D 209/14* (2013.01)

(58) Field of Classification Search
  CPC ... C07D 209/14; C07D 209/12; C07D 209/32
  See application file for complete search history.

(56) References Cited

U.S. PATENT DOCUMENTS

| | | | |
|---|---|---|---|
| 3,075,992 | A | 1/1963 | Hofmann et al. |
| 3,182,071 | A | 5/1965 | Shavel, Jr. et al. |
| 6,187,805 | B1 | 2/2001 | Pineiro et al. |
| 2012/0289515 | A1 | 11/2012 | Migaly |
| 2014/0350064 | A1 | 11/2014 | Chen |
| 2015/0231126 | A1 | 8/2015 | Peters et al. |
| 2017/0281652 | A1 | 10/2017 | Altschul et al. |
| 2019/0105313 | A1 | 4/2019 | Stamets |
| 2019/0119310 | A1 | 4/2019 | Londesbrough et al. |
| 2019/0142851 | A1 | 5/2019 | Chadeayne |
| 2019/0350949 | A1 | 11/2019 | Kucuksen et al. |
| 2020/0179349 | A1 | 6/2020 | Yun et al. |
| 2020/0397752 | A1 | 12/2020 | Perez Castillo et al. |
| 2021/0403425 | A1 | 12/2021 | Bryson |
| 2022/0273680 | A1 | 9/2022 | Scott |
| 2023/0000885 | A1 | 1/2023 | Thompson |

FOREIGN PATENT DOCUMENTS

| | | |
|---|---|---|
| GB | 2341549 A | 3/2000 |
| WO | WO-9320066 A1 | 10/1993 |
| WO | WO-03035061 A1 | 5/2003 |
| WO | WO-2016023082 A1 | 2/2016 |
| WO | WO-2017041139 A1 | 3/2017 |
| WO | WO-2018135943 A1 | 7/2018 |
| WO | WO-2019081764 A1 | 5/2019 |
| WO | WO-2020212948 A1 | 10/2020 |
| WO | WO-2020212951 A1 | 10/2020 |
| WO | WO-2020212952 A1 | 10/2020 |
| WO | WO-2021030571 A1 | 2/2021 |
| WO | WO-2022212854 A1 | 10/2022 |
| WO | WO-2022235587 A1 | 11/2022 |
| WO | WO-2023283364 A2 | 1/2023 |
| WO | WO-2023023347 A1 | 2/2023 |

OTHER PUBLICATIONS

Castro, et al. GB 2341549 A (abstract), Mar. 22, 2000, Accession No. 200:738911, retrieved from STN.*
Couch, et al. Analytical Biochemistry (abstract), 1972, 50(2), 612-22, Accession No. 1973:3422, retrieved from STN.*
Wu, et al. Organic Letters (abstract) 2002, 4 (23), 4033-4036, Accession No. 2002:808586, retrieved from STN.*
Hiemke, et al. Journal of Chromatography (abstract) 1978, 153 (2), 451-60, Accession No. 1978:499491, retrieved from STN.*
Arnt et al. Facilitation of 8-OHDPAT-induced forepaw treading of rats by the 5-HT2 agonist DOI. Eur. J. Pharmacol., 161:45 (1989).
Barrett et al. Emotions and brain function are altered up to one month after a single high dose of psilocybin. Sci. Rep. 10:2214 (2020).
Bartolucci et al., Observations concerning the synthesis of tryptamine homologues and branched tryptamine derivatives via the borrowing hydrogen process: synthesis of psilocin, bufotenin, and serotonin. Tetrahedron 72:2233-2238 (2016).
Beaton et al., A comparison of the behavioral effects of proteo-and deutero-N, N-dimethyltryptamine. Pharmacol Biochem Behav. 16(5):811-4 (1982).
Belmaker et al. Major depressive disorder. N Engl J Med 358:55-68 (2008).
Billings et al. Social-environmental factors in unipolar depression; comparisons of depressed patients and nondepressed controls. J Abnormal Psychol 92:119-133 (1983).
Boldrini et al., Antidepressants increase neural progenitor cells in the human hippocampus. Neuropsychopharmacology. 34(11):2376-89 (2009).
Boulenguez et al. Modulation of dopamine release in the nucleus accumbens by 5-HT1E1 agonists: involvement of the hippocampo-accumbens pathway. Neuropharmacology 35:1521-1529 (1996).
Brandt et al., Characterization of the synthesis of N, N-dimethyltryptamine by reductive amination using gas chromatography ion trap mass spectrometry. Drug Test Anal 2(7):330-338 (2010).

(Continued)

*Primary Examiner* — Shawquia Jackson
(74) *Attorney, Agent, or Firm* — WILSON SONSINI GOODRICH & ROSATI

(57) ABSTRACT

Described herein are compounds that are derivatives of DMT or 5-MeO-DMT and can be metabolically converted to N,N-dimethyltryptamine or analogs thereof upon administration to a subject. In certain embodiments, the compounds described herein are useful for the treatment of conditions associated with a neurological disease.

28 Claims, 35 Drawing Sheets

(56) References Cited

OTHER PUBLICATIONS

Brun et al. Place cells and place recognition maintained by direct entorhinal-hippocampal circuitry. Science 296:2243-2246 (2002).
Bryson et al., Performed Mannich salts: a facile preparation of dimethyl(methylene)ammonium iodide. J Org Chem 45:524-525 (1980).
Bundgaard et al. Pro-drugs as drug delivery systems XIX. Bioreversiblf derivatization of aromatic amines by formation of N-Mannich bases with succinimide. Int'l J Pharm 8(3):183-192 (1981).
Burgdorf et al. Extinction of contextual cocaine memories requires Ca(v)1. 2 within D1R-expressing cells and recruits hippocampal Ca(v)1,2-dependent signaling mechanisms. J Neurosci 37:11894-11911 (2017).
Burmeister et al. Differential roles of 5-HT receptor subtypes in cue and cocaine reinstatement of cocaine-seeking behavior in rats. Neuropsychopharmacology 29:660-668 (2004).
Cai et al. Local potentiation of excitatory synapses by serotonin and its alteration in rodent models of depression. Nat Neurosci 16:464-472 (2013).
Canal et al. Head-twitch response in rodents induced by the hallucinogen 2,5-dimethoxy-4-iodoamphetamine: a comprehensive history, a re-evaluation of mechanisms, and its utility as a model. Drug Test Anal., 4:556-576 (2012).
Canel et al. Support for 5-HT2C receptor functional selectivity in vivo utilizing structurally diverse, selective 5-HT2C receptor ligands and the 2,5-dimethoxy-4-iodoamphetamine elicited head-twitch response model. Neuropharmacol 70:112-121 (2013).
Carhart-Harris et al. Psilocybin for treatment-resistant depression: fMRI-measured brain mechanisms. Sci. Rep. 7:13187 (2017).
Carhart-Harris et al.: Psilocybin with psychological support for treatment-resistant depression: an open-label feasibility study. Lancet Psychiatry 3: 619-627. Published Online May 17, 2016 (2016).
Carhart-Harris et al.: Psilocybin with psychological support for treatment-resistant depression: six-month follow-up. Psychopharmacology (Berl). 235(2):399-408 doi:10.1007/s00213-017-4771-x (2018).
Carr et al. The role of serotonin receptor subtypes in treating depression: a review of animal studies, Psychopharmacology (Berl.) 213:265-287 (2011).
Catlow et al. Effects of psilocybin on hippocampal neurogenesis and extinction of trace fear conditioning. Exper Brain Res 228(4):481-491 (2013).
Chan et al. Strained in Planning Your Mouse Background? Using the HPA Stress Axis as a Biological Readout for Backcrossing Strategies. Neuropsychopharmacology 42:1749-1751 (2017).
Chen et al., Antidepressant administration modulates neural stem cell survival and serotoninergic differentiation through bcl-2. Curr. Neurovasc. Res. 4(1):19-29 (2007).
Compass Pathways. Compass Pathways Receives FDA Breakthrough Therapy Designation for Psilocybin Therapy for Treatment-resistant Depression. Available at https://www.prnewswire.com/news-releases/compass-pathways-receives-fda-breakthrough-therapy-designation-for-psilocybin-therapy-for-treatment-resistant-depression-834088100.html (Oct. 23, 2018).
Co-pending U.S. Appl. No. 17/945,865, inventor Clark; Sam, filed Sep. 15, 2022.
Cozzi et al. Receptor binding profiles and quantitative structure-affinity relationships of some 5-substituted-N, N-diallyltryptamines. Bioorg Med Chem Lett. 26(3):959-964 (2016).
Darmani et al., Do functional relationships exist between 5-HT1A and 5-HT2 receptors?. Pharmacol. Biochem. Behav., 36:901-606 (1990).
Deverre et al., In-vitro evaluation of filaricidal activity of GABA and 1,3-dipalmitoyl-2-(4-aminobutyryl)glycerol HCI: a diglyceride prodrug. J. Pharm. Pharmacol. 41(3):191-193 (1989).
Di Vona et al., Ring-opening reactions. Part 4. The role of strain and stereochemical effects on the elimination and substitution reactions of small rings; the reactivity of 1, 1-dimethylaziridinium systems. Journal of The Chemical Society, Perkin Transactions II 12:1943-1946 (1980).
Dinis-Oliveira. Metabolism of psilocybin and psilocin: clinical and forensic toxicological relevance. Drug Metab. Rev., 49(1):84-91 (2017).
Dolen et al. Social reward requires coordinated activity of nucleus accumbens oxytocin and serotonin. Nature 501:179-184 (2013).
Drysdale et al. Resting-state connectivity biomarkers define neurophysiological subtypes of depression. Nature Med 23:28-38 (2017).
Duman et al. Altered connectivity in depression: GABA and glutamate neurotransmitter deficits and reversal by novel treatments. Neuron 102:75-90 (2019).
Engel et al. Identity of inhibitory presynaptic 5-hydroxytryptamine (5-1-IT) autoreceptors in the rat brain cortex with 5-HT1B binding sites Naunyn Schmiedebergs Arch Pharmacol 332:1-7 (1986).
Evans et al. Default mode connectivity in major depressive disorder measured up to 10 days after ketamine administration. Biol Psychiatry 84:582-590 (2018).
Fava et al. Major depressive disorder. Neuron 28:335-341 (2000).
Fontanilla et al., The hallucinogen N,N-dimethyltryptamine (DMT) is an endogenous sigma-1 receptor regulator. Science 323(5916):934-7 (2009).
Frecksa et al., The Therapeutic Potentials of Ayahuasca: Possible Effects against Various Diseases of Civilization. Front. Pharmacol. 7:35 (2016).
Fricke et al., Production Options for Psilocybin: Making of the Magic. Chemistry 25:897-903 (2019).
Furay et al. 5-HT1B mRNA expression after chronic social stress. Behav Brain Res 224:350-357 (2011).
Gage. Mammalian neural stem cells. Science 287(5457):1433-8 (2000).
Garzon-Aburbeh et al., 1,3-dipalmitoylglycerol ester of chlorambucil as a lymphotropic, orally administrable antineoplastic agent . J. Med. Chem. 26(8):1200-1203 (1983).
Garzon-Aburbeh et al., A lymphotropic prodrug of L-dopa: synthesis, pharmacological properties, and pharmacokinetic behavior of 1,3-dihexadecanoyl-2-[(S)-2-amino-3-(3,4-dihydroxyphenyl)prop anoyl]propane-1,2,3-triol. J. Med. Chem. 29(5):687-69 (1986).
Gaynes et al. What did STAR*D teach US? Results from a large-scale, practical, clinical trial for patients with depression. Psychiart Serv. 60:1439-1445 (2009).
Gerfen et al. D1 and D2 dopamine receptor-regulated gene expression of striatonigral and striatopallidal neurons. Science 250(4986):1429-1432 (1990).
Gothert et al. Classification of serotonin receptors. J Cardiovasc Pharmacol 10 Suppl 3:S3-S7 (1987).
Halberstadt et al., Behavioral effects of a,a, B, B-tetradeutero-5-MeO-DMT in rats: comparison with 5-MeO-DMT administered in combination with a monoamine oxidase inhibitor. Psychopharmacology (Berl) 221(4):709-18 (2012).
Halberstadt et al. Multiple receptors contribute to the behavioral effects of indoleamine hallucinogens. Neuropharmacol 61:364-381 (2011).
Hall et al., Hydrogen-Borrowing Alkylation of 1,2-Amino Alcohols in the Synthesis of Enantioenriched γ-Aminobutyric Acids. Angew. Chem. Int. Ed., 60:6981-6985 (2021).
Hamet et al. Genetics and genomics of depression. Metabolism 54:10-15 (2005).
Han et al., Targeted delivery of a model immunomodulator to the lymphatic system: comparison of alkyl ester versus triglyceride mimetic lipid prodrug strategies. J. Control. Release 177:1-10 (2014).
Hasler et al.: Determination of psilocin and 4-hydroxyindole-3-acetic acid in plasma by HPLC-ECD and pharmacokinetic profiles of oral and intravenous psilocybin in man. Pharm Acta Helv. 72(3):175-184 (1997).
Hayashi et al. Sigma-1 receptor chaperones at the ER-mitochondrion interface regulate Ca(2+) signaling and cell survival. Cell 131(3):596-610 (2007).
Heneka et al., Neuroinflammation in Alzheimer's Disease. Lancet Neural., 14(4):388-405 (2015).

(56) References Cited

OTHER PUBLICATIONS

Herrera-Arozamena et al., Recent Advances in Neurogenic Small Molecules as Innovative Treatments for Neurodegenerative Diseases. Molecules 21(9):1165 (2016).
Hibicke et al. Psychedelics, but Not Ketamine, Produce Persistent Antidepressant-like Effects in a Rodent Experimental System for the Study of Depression. ACS Chem Neurosci. 11(6):864-871 (2020).
Hofmann et al., Psilocybin und Psilocin, zwei psychotrope Wirkstoffe aus mexikanischen Rauschpilzen. Helvetica Chimica Acta 42(5):1557-72 (1959).
Holy. A Convenient Tertiary Amine Synthesis. Use of Methylenedimethylammonium Trifluoroacetate. Synthetic Communications 6:539-542 (1976).
Hoyer et al. International Union of Pharmacology classification of receptors for 5-hydroxytryptamine (Serotonin). Pharmacol Rev 46:157-203 (1994).
Jefsen et al. Psilocybin lacks antidepressant-like effect in the Flinders Sensitive Line rat. Acta Neuropsychiatr. 31:213-219 (2019).
Johnson et al. The abuse potential of medical psilocybin according to the 8 factors of the Controlled Substances Act. Neuropharmacology 142:143-166 (2018).
Julia et al., Bulletin de la Societe Chimique de France. pp. 1424-1426 (1973).
Kallarackal et al. Chronic stress induces a selective decrease in AMPA receptor-mediated synaptic excitation at hippocampal temporoammonic-CA1 synapses. Neurosci 33:15669-15674 (2013).
Kargbo et al., Direct Phosphorylation of Psilocin Enables Optimized cGMP Kilogram-Scale Manufacture of Psilocybin. ACS Omega, 5:16959-16966 (2020).
Keller et al. Permanent alteration of behavior in mice by chemical and psychological means. Science 124:723 (1956).
Kennett et al., In vivo properties of Sb 200646A, a 5-HT2C/2B receptor antagonist. J. Pharmacol., 111:797-802 (1994).
Kessler et al. Lifetime prevalence and age-of-onset distributions of DSM-IV disorders in the National Comorbidity Survey Replication. Arch Gen Psychiatry 62:593-602 (2005).
Kessler, et al. The epidemiology of major depressive disorder: results from the National Comorbidity Survey Replication (NCS-R). JAMA. Jun. 18, 2003;289(23):3095-105.
Kometer et al. Psilocybin Biases Facial Recognition, Goal-Directed Behavior, and Mood State Toward Positive Relative to Negative Emotions Through Different Serotonergic Subreceptors. Biol Psych 72(11):898-906 (2012).
Lee et al. Specific roles of AMPA receptor subunit GluR1 (GluA1) phosphorylation sites in regulating synaptic plasticity in the CA1 region of hippocampus. J Neurephysiol 103:479-489 (2010).
Legates et al. Reward behaviour is regulated by the strength of hippocampus-nucleus accumbens synapses. Nature 564:258-262 (2018).
Legates et al. Sex differences in antidepressant efficacy. Neuropsychopharmacol 44:140-154 (2019).
Li et al. Synaptic potentiation onto habenula neurons in the learned helplessness model of depression. Nature 470:535-539 (2011).
Lienard et al., Structural basis for the broad-spectrum inhibition of metallo-beta-lactamases by thiols. Org. Biomol. Chem. 6(13):2282-2292 (2008).
Lim et al. Anhedonia requires MC4R-mediated synaptic adaptations in nucleus act umbens. Nature 87:183-189 (2012).
Ly et al., Psychedelics promote structural and functional neural plasticity. Cell Rep. 23(11):3170-3182 (2018).
Madsen et al.: Psychedelic effects of psilocybin correlate with serotonin 2A receptor occupancy and plasma psilocin levels. Neuropsychopharmacology 44(7):1328-1334 (2019).
Mathur et al. Serotonin induces long-term depression at corticostriatal synapses. J Neurosci 31:7402-7411 (2011).
Maura et al. Serotonin autoreceptor in rat hippocampus: pharmacological characterization as a subtype of the 5-HT1 receptor. Naunyn Schmiedebergs Arch Pharmacol 334:323-326 (1986).
McEwen. Stress and hippocampal plasticity. Ann Rev Neurosci 22:105-122 (1999).
McKenna et al., Differential interactions of indolealkylamines with 5-hydroxytryptamine receptor subtypes. Neuropharmacology 29(3):193-198 (1990).
Mergen et al., Antiepileptic activity of 1,3-dihexadecanoylamino-2-valproyl-propan-2-ol, a prodrug of valproic acid endowed with a tropism for the central nervous system. J. Pharm. Pharmacol. 43(11):815-816 (1991).
Moda-Sava et al. Sustained rescue of prefrontal circuit dysfunction by antidepressant-induced spine formation. Science 364(6436):eaaat8078 (2019).
Morales-Garcia et al., Phosphodiesterase7 Inhibition Activates Adult Neurogenesis in Hippocampus and Subventricular Zone In Vitro and In Vivo. Stem Cells 35:458-472 (2017).
Mori et al., Sigma-1 receptor chaperone at the ER-mitochondrion interface mediates the mitochondrion-ER-nucleus signaling for cellular survival . PLoS One 8(10):e76941 (2013).
Nautiyal et al. Distinct circuits underlie the effects of 5-HT1B receptors on aggression and impulsivity. Neuron 86:813-826 (2015).
Nestler, et al. Neurobiology of depression. Neuron. Mar. 28, 2002;34(1):13-25.
Nestler et al. The mesolimbic dopamine reward circuit in depression. Biol Psychiatry 59:1151—1159 (2006).
Neumaier et al. Chronic fluoxetine reduces serotonin transporter mRNA and 5-HT1B mRNA in a sequential manner in the rat dorsal raphe nucleus. Neuropsychopharmacology 15:515-522 (1996).
Nichols., Hallucinogens. Pharmacol. Ther. 101(2):131-81 (2004).
Nichols. Psychedelics. Pharmacol Rev. 68:264-35 (2016).
Nutt et al. Independent Scientific Committee on Drugs. Drug harms in the UK: a multicriteria decision analysis. Lancet 376:1558-1565 (2010).
Nutt et al. Psychedelic Psychiatry's Brave New World. Cell 181:24-28 (2020).
Ociepa et al., Mild and Chemoselective Phosphorylation of Alcohols Using a ψ-Reagent. Org. Lett., 23:9337-9342 (2021).
Omi et al., Fluvoxamine alleviates ER stress via induction of Sigma-1 receptor . Cell Death Dis. 5:e1332 (2014).
Osorio et al., Antidepressant effects of a single dose of ayahuasca in patients with recurrent depression: a preliminary report. Revista Brasileira de Psiquiatria. 37(1):13-20 (2015).
Pal et al., The sigma-1 receptor protects against cellular oxidative stress and activates antioxidant response elements. Eur. J. Pharmacol. 682(1-3):12-20 (2012).
Paris et al., Glycerides as prodrugs. 1. Synthesis and antiinflammatory activity of 1,3-bis(alkanoyl)-2-(O-acetylsalicyloyl)glycerides (aspirin triglycerides). J. Med. Chem. 22(6):683-687 (1979).
PCT/US2022/027336 International Invitation to Pay Additional Fees dated Jul. 14, 2022.
PCT/US2022/027336 International Search Report and Written Opinion dated Sep. 14, 2022.
PCT/US2022/036396 International Invitation to Pay Additional Fees dated Sep. 9, 2022.
PCT/US2022/036396 International Search Report and Written Opinion dated Nov. 17, 2022.
PCT/US2022/040922 International Search Report and Written Opinion dated Dec. 19, 2022.
Pfeil et al., Synthesis of Oxalactams (2-Morpholinones) from Aziridinium Tetrafluoroborates and Hydroxy Esters. Angewante Chemie International Edition in English 6:178 (1967).
Preller et al., The Fabric of Meaning and Subjective Effects in LSD-Induced States Depend on Serotonin 2A Receptor Activation. Curr. Biol. 27(3):451-457 (2017).
Pubchem CID 644073 Buprenorphine [https://pubchem.ncbi.nlm.nih.gov/compound/644073] (2005).
PubChem SID 248075807 https://pubchem.ncbi.nlm.nih.gov/substance/248075807 (2015).
PubChem SID 348957218 https://pubchem.ncbi.nlm.nih.gov/substance/348957218 (2017).
Ray., Psychedelics and the human receptorome. PLoS One 5(2):e9019 (2010).

(56) References Cited

OTHER PUBLICATIONS

Remondes et al. Role for a cortical input to hippocampal area CA1 in the consolidation of a long-term memory. Nature 431:699-703 (2004).
Repke et al., Psilocin analogs II. Synthesis of 3-[2-(dialkylamino)ethyl]-, 3-[2-(N-methyl-N-alkylamino)ethyl]-, and 3-[2-(cycloalkylamino)ethyl]indol-4-ols. Journal of Heterocyclic Chemistry, 18:175-178 (1981).
Repke et al., Psilocin analogs. III. Synthesis of 5-methoxy- and 5-hydroxy-1,2,3,4-tetrahydro-9H-pyrido[3,4-b]indoles. Journal of Heterocyclic Chemistry, 845-848 (1982).
Riba et al., Human pharmacology of ayahuasca: subjective and cardiovascular effects, monoamine metabolite excretion, and pharmacokinetics. J. Pharmacol. Exp. Ther 306(1):73-83 (2003).
Rickli et al., Receptor interaction profiles of novel psychoactive tryptamines compared with classic hallucinogens. Eur Neuropharmacol. 26(8):1327-1337 (2016).
Rinehart et al., Eudistomins A-Q, .beta.-carbolines from the antiviral Caribbean tunicate Eudistoma olivaceum. J. Am. Chem. Soc., 109:3378-3387 (1987).
Roseman et al. Quality of Acute Psychedelic Experience Predicts Therapeutic Efficacy of Psilocybin for Treatment-Resistant Depression Front. Pharmacol. 8:974 (2018).
Roth et al. Serotonin 5-HT2A receptors: molecular biology and mechanisms of regulation. Crit Rev. Neurobiol 12:319-338 (1998).
Ruscher et al. The involvement of the sigma-1 receptor in neurodegeneration and neurorestoration. J. Pharmacol. Sci. 127(1):30-5 (2015).
Sachs et al. Chronic fluoxetine increases extra-hippocampal neurogenesis in adult mice. Int. J. Neuropsychopharmacol. 18(4):pyu029 (2015).
Sakakura et al., Selective synthesis of phosphate monoesters by dehydrative condensation of phosphoric acid and alcohols promoted by nucleophilic bases. Org. Lett. 7:1999-2002 (2005).
Scriba et al., Bioavailability of phenytoin following oral administration of phenytoin-lipid conjugates to rats. J. Pharm. Pharmacol. 47(11):945-948 (1995).
Scriba. Synthesis and in vitro degradation of testosterone-lipid conjugates. Arch. Pharm. (Weinheim) 328(3):271-276 (1995).
Sherwood et al., Synthesis and characterization of 5-MeO-DMT succinate for clinical use. ACS Omega 5(49):32067-32075 (2020).
Somei et al., The chemistry of indoles. CIII. Simple syntheses of serotonin, N-methylserotonin, bufotenine, 5-methoxy-N-methyltryptamine, bufobutanoic acid, N-(indol-3-yl)methyl-5-methoxy-N-methyltryptamine, and lespedamine based on 1-hydroxyindole chemistry. Chem Pharm Bull (Tokyo) 49(1):87-96 (2001).
Somei et al., The Chemistry of Indoles. CVII.1) A Novel Synthesis of 3,4,5,6-Tetrahydra-7-hydroxy-1H-azepina[5,4,3-cd]indoles and a New Finding on Pictet-Spengler Reaction. Chem Pharm Bull (Tokyo) 49(9):1159-1165 (2001).
Strassmann et al., Dose-response study of N, N-dimethyltryptamine in humans. II. Subjective effects and preliminary results of a new rating scale. Arch. Gen Psychiatry 51(2):98-108 (1994).
Sugihara et al., Studies on intestinal lymphatic absorption of drugs. I. Lymphatic absorption of alkyl ester derivatives and alpha-monoglyceride derivatives of drugs. J. Pharmacobiodyn. 11(5):369-376 (1988).
Sugihara et al., Studies on intestinal lymphatic absorption of drugs. II. Glyceride prodrugs for improving lymphatic absorption of naproxen and nicotinic acid. J Pharmacobiodyn. 11(8):555-562 (1988).
Svenningsson et al. Alterations in 5-HT(1B) receptor function by p11 in depression-like states. Science 311:77-80 (2006).
Szabo et al. Dimethyltryptamine (DMT): a biochemical Swiss Army knife in neuroinflammation and neuroprotection? Neural Regen. Res. 11(3):396-7 (2016).
Szabo et al., Psychedelic N, N-dimethyltryptamine and 5-methoxy-N,N-dimethyltryptamine modulate innate and adaptive inflammatory responses through the sigma-1 receptor of human monocyte-derived dendritic cells. PLoS One 9(8):e106533 (2014).
Szabo et al., The Endogenous Hallucinogen and Trace Amine N,N-Dimethyltryptamine (DMT) Displays Potent Protective Effects against Hypoxia via Sigma-1 Receptor Activation in Human Primary iPSC-Derived Cortical Neurons and Microglia-Like Immune Cells. Front. Neurosci. 10:423 (2016).
Temple., Stem cell plasticity—building the brain of our dreams. Nat. Rev. Neurosci. 2(7):513-20 (2001).
Thompson et al. An excitatory synapse hypothesis of depression. Trends Neurosci 38:279-294 (2015).
Tittarelli et al., Recreational use, analysis and toxicity of tryptamines. Cut Neuropharmacol. 13:26-46 (2015).
Tye et al. Dopamine neurons modulate neural encoding and expression of depression-related behaviour. Nature 493:537-541 (2013).
Tyls et al. Sex differences and serotonergic mechanisms in the behavioural effects of psilocin. Behav Phamacol 27(4):309-320 (2016).
Valle et al. Inhibition of alpha oscillations through serotonin-2A receptor activation underlies the visual effects of ayahuasca in humans. Eur Neuropsychopharmacol 26(7):1161-75 (2016).
Van Dyke et al. Chronic fluoxetine treatment in vivo enhances excitatory synaptic transmission in the hippocampus. Neumpharmacology 150:38-45 (2019).
Vollenweider et al., Psilocybin induces schizophrenia-like psychosis in humans via a serotonin-2 agonist action. Neuroreport 9(17):3897-3902 (1998).
Weisstaub et al. Cortical 5-HT2A receptor signaling modulates anxiety-like behaviors in mice. Science 313:536-540 (2006).
Wiens et al., Concerning the preparation of 6-bromotryptamine. Tetrahedron 81:132055 (2021).
Willner. The chronic mild stress (CMS) model of depression: History, evaluation and usage. Neurobiol Stress 6:78-93 (2016).
Winter et al. Psilocybin-induced stimulus control in the rat. Pharmacol Biochem Behav. 87:472-480 (2007).
Wolfard et al., Synthesis of Chiral Tryptamines via a Regioselective Indole Alkylation. Org. Lett., 20:5431 (2018).
Xu et al., Synthesis of deuterium labeled standards of 5-methoxy-N,N-dimethyltryptamine (5-Meo-DMT). J. Label Compd Radiopharm. 49(10):897-902 (2006).
Yamada et al., Synthetic studies of psilocin analogs having either a formyl group or bromine atom at the 5- or 7-position. Chem. Pharm. Bull. 50(1):92-99 (2002).
Yi et al., Arylation of N-vinylsuccinimide and preparation of 2-arylethylamines. Chemical Research in Chinese Universities 12:136-141 (1996).
Yuen et al. Repeated stress causes cognitive impairment by suppressing glutamate receptor expression and function in prefrontal cortex. Neuron 73:962-977 (2012).
Zhang et al. Direct Reductive Amination of Aldehydes with Nitroarenes using Bio-renewable Formic Acid as a Hydrogen Source. Green Chemistry 18(8):2507-2513 (2016).

\* cited by examiner

N,N-DIMETHYLTRYPTAMINE AND RELATED PSYCHEDELICS AND USES THEREOF

CROSS REFERENCE TO RELATED APPLICATIONS

This application is a continuation of international patent application no. PCT/US2022/036396 filed on Jul. 7, 2022, which claims the benefit of U.S. Provisional Patent Application No. 63/219,312, filed Jul. 7, 2021, and U.S. Provisional Patent Application No. 63/276,516, filed on Nov. 5, 2021, the contents of each is incorporated by reference herein in their entireties.

BACKGROUND OF THE INVENTION

Nearly 1 in 5 adults in the United States suffer from mental illness, and over 50% of Americans will be diagnosed with a psychiatric disorder at some point in their lifetime. 1 in 25 Americans is afflicted with severe mental illness, such as major depression, schizophrenia, or bipolar disorder.

SUMMARY OF THE INVENTION

In one aspect, the present disclosure provides a compound of Formula (I), or a pharmaceutically acceptable salt thereof:

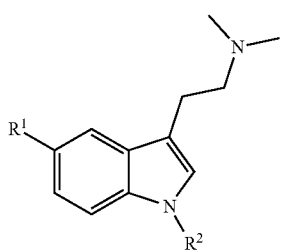

(I)

wherein:
$R^1$ is methoxy or hydrogen;
$R^2$ is —C(O)OR$^3$, —C(O)R$^4$, —CH(R$^5$)OR$^6$, —C(O)OCH(R$^5$)OC(O)R$^6$, —C(O)OCH(R$^5$)OC(O)OR$^6$, —CH(R$^5$)C(O)R$^6$, —CH(R$^5$)OC(O)R$^6$, —CH(R$^5$)OC(O)OR$^6$, —S(O)$_2$OR$^7$, —P(O)OR$^8$[N(R$^9$)R$^{10}$], —P(O)[N(R$^9$)R$^{10}$][N(R$^{11}$)R$^{12}$], —C(O)N(R$^9$)R$^{10}$, —P(O)OR$^{11}$ (OR$^{12}$), —CH(R$^5$)OP(O)OR$^8$[N(R$^9$)R$^{10}$], or —CH(R$^5$)OP(O)OR$^{11}$ (OR$^{12}$);
each of $R^3$, $R^4$, $R^5$, $R^6$, $R^7$, and $R^8$ is independently hydrogen, alkyl, heteroalkyl, cycloalkyl, heterocyclylalkyl, aryl, or heteroaryl, wherein each alkyl, heteroalkyl, cycloalkyl, heterocyclylalkyl, aryl, and heteroaryl is independently unsubstituted or substituted with one or more $R^A$;
each of $R^9$ and $R^{10}$ is independently alkyl, heteroalkyl, cycloalkyl, heterocyclylalkyl, aryl, heteroaryl, or hydrogen, wherein each alkyl, heteroalkyl, cycloalkyl, heterocyclylalkyl, aryl, and heteroaryl is independently unsubstituted or substituted with one or more $R^A$, or $R^9$ and $R^{10}$ together with the atom to which they are attached form a heterocyclylalkyl ring that is unsubstituted or substituted with one or more $R^A$;
each of $R^{11}$ and $R^{12}$ is independently alkyl, heteroalkyl, cycloalkyl, heterocyclylalkyl, aryl, heteroaryl, or hydrogen, wherein each alkyl, heteroalkyl, cycloalkyl, heterocyclylalkyl, aryl, and heteroaryl is independently unsubstituted or substituted with one or more $R^A$, or $R^{11}$ and $R^{12}$ together with the atoms to which they are attached form a heterocyclylalkyl ring that is unsubstituted or substituted with one or more $R^A$;
each $R^A$ is independently alkyl, heteroalkyl, cycloalkyl, heterocyclylalkyl, aryl, heteroaryl, an amino acid side chain, —OR$^{13}$, —N(R$^{18}$)R$^{19}$, —C(O)OR$^{13}$, —N(R$^{13}$)C(O)OR$^{14}$, —N(R$^{13}$)C(O)R$^{14}$, —C(O)R$^{14}$, —OC(O)R$^{15}$, —OC(O)OR$^{16}$, —OP(O)OR$^{17}$[N(R$^{18}$)R$^{19}$], —C(O)N(R$^{18}$)R$^{19}$, —OC(O)N(R$^{18}$)R$^{19}$, or —OP(O)OR$^{20}$ (OR$^{21}$), wherein each alkyl, heteroalkyl, cycloalkyl, heterocyclylalkyl, amino acid side chain, aryl, and heteroaryl is independently unsubstituted or substituted with one or more alkyl, aryl, halogen, —OR$^{13}$, —NR(R$^{18}$)R$^{19}$, —C(O)R$^{14}$, —OC(O)R$^{15}$, —OC(O)OR$^{16}$, or —OC(O)N(R$^{18}$)R$^{19}$;
each of $R^{13}$, $R^{14}$, $R^{15}$, $R^{16}$, or $R^{17}$ is independently alkyl, heteroalkyl, cycloalkyl, heterocyclylalkyl, aryl, heteroaryl, or hydrogen, wherein each alkyl, heteroalkyl, cycloalkyl, heterocyclylalkyl, aryl, and heteroaryl is independently unsubstituted or substituted with one or more $R^B$;
each of $R^{18}$ and $R^{19}$ is independently alkyl, heteroalkyl, cycloalkyl, heterocyclylalkyl, aryl, heteroaryl, or hydrogen, wherein each alkyl, heteroalkyl, cycloalkyl, heterocyclylalkyl, aryl, and heteroaryl is independently unsubstituted or substituted with one or more $R^B$; or $R^{18}$ and $R^{19}$ together with the atom to which they are attached form a heterocyclylalkyl ring that is unsubstituted or substituted with one or more $R^B$;
each of $R^{20}$ and $R^{21}$ is independently alkyl, alkyl, heteroalkyl, cycloalkyl, heterocyclylalkyl, aryl, heteroaryl, or hydrogen, wherein each alkyl, heteroalkyl, cycloalkyl, heterocyclylalkyl, aryl, and heteroaryl is independently unsubstituted or substituted with one or more $R^B$, or $R^{20}$ and $R^{21}$ together with the atoms to which they are attached form a heterocyclylalkyl ring that is unsubstituted or substituted with one or more $R^B$; and
each $R^B$ is independently halogen, amino, cyano, hydroxyl, alkyl, heteroalkyl, cycloalkyl, heterocyclylalkyl, aryl, heteroaryl, arylalkyl, —C(O)CH$_3$, —C(O)Ph, or heteroarylalkyl, wherein each cycloalkyl, heterocyclylalkyl, aryl, and heteroaryl is independently unsubstituted or substituted with one or more halogen, amino, cyano, hydroxyl, alkyl, acetyl, or benzoyl,
provided that when $R^1$ is hydrogen, then $R^3$ is not tert-butyl.

In some embodiments, the compound of Formula (I) having the structure of Formula (Ia), or a pharmaceutically acceptable salt thereof:

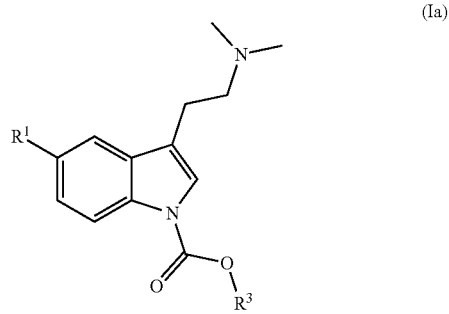

(Ia)

wherein R¹ is methoxy or hydrogen, and R³ is alkyl, cycloalkyl, aryl, heteroaryl, heteroalkyl, or heterocyclylalkyl, each of which is independently unsubstituted or substituted with one or more $R^A$.

In some embodiments, the compound of Formula (I) has the structure of Formula (Ib), or a pharmaceutically acceptable salt thereof:

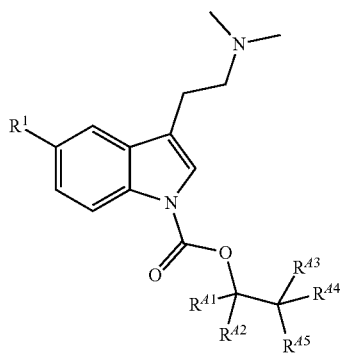

(Ib)

wherein:
R¹ is methoxy or hydrogen;
each of $R^{A1}$, $R^{A2}$, $R^{A3}$, and $R^{A4}$ is independently hydrogen or alkyl that is independently unsubstituted or substituted with one or more alkyl, aryl, halogen, $-OR^{13}$, $-NR(R^{18})R^{19}$, $-C(O)R^{14}$, $-OC(O)R^{15}$, $-OC(O)OR^{16}$, or $-OC(O)N(R^{18})R^{19}$, and
$R^{A5}$ is heteroalkyl, heterocyclylalkyl, heteroaryl, or $-C(O)OR^{13}$, $-N(R^{13})C(O)OR^{14}$, $-N(R^{13})C(O)R^{14}$, $-C(O)R^{14}$, $-OC(O)R^{15}$, or $-OC(O)OR^{16}$, wherein each heteroalkyl, heterocyclylalkyl, and heteroaryl is independently unsubstituted or substituted with one or more alkyl, aryl, halogen, $-OR^{13}$, $-NR(R^{18})R^{19}$, $-C(O)R^{14}$, $-OC(O)R^{15}$, $-OC(O)OR^{16}$, or $-OC(O)N(R^{18})R^{19}$.

In some embodiments is a compound of Formula (I) having the structure of Formula (Ib-1), or a pharmaceutically acceptable salt thereof:

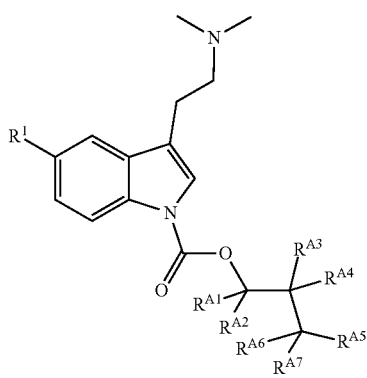

(Ib-1)

wherein:
R¹ is methoxy or hydrogen;
each of $R^{A1}$, $R^{A2}$, $R^{A3}$, $R^{A4}$, $R^{A6}$, and $R^{A7}$ is independently hydrogen or alkyl that is independently unsubstituted or substituted with one or more alkyl, aryl, halogen, $-OR^3$, $-NR(R^{18})R^{19}$, $-C(O)R^{14}$, $-OC(O)R^{15}$, $-OC(O)OR^{16}$, or $-OC(O)N(R^{18})R^{19}$, and $R^{A5}$ is heteroalkyl, heterocyclylalkyl, heteroaryl, or $-C(O)OR^{13}$, $-N(R^{13})C(O)OR^{14}$, $-N(R^{13})C(O)R^{14}$, $-C(O)R^{14}$, $-OC(O)R^{15}$, or $-OC(O)OR^{16}$, wherein each heteroalkyl, heterocyclylalkyl, and heteroaryl is independently unsubstituted or substituted with one or more alkyl, aryl, halogen, $-OR^{13}$, $-NR(R^{18})R^{19}$, $-C(O)R^{14}$, $-OC(O)R^{15}$, $-OC(O)OR^{16}$, or $-OC(O)N(R^{18})R^{19}$.

In some embodiments, the compound of Formula (I) or (Ib) has the structure of Formula (Ib1), or a pharmaceutically acceptable salt thereof:

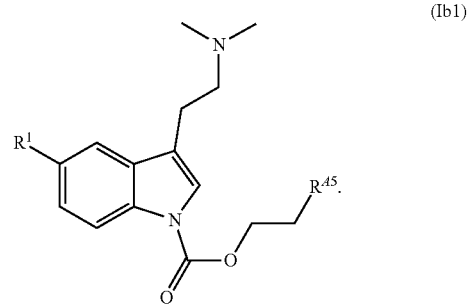

(Ib1)

In some embodiments, the compound of Formula (I) having the structure of Formula (Ic), or a pharmaceutically acceptable salt thereof:

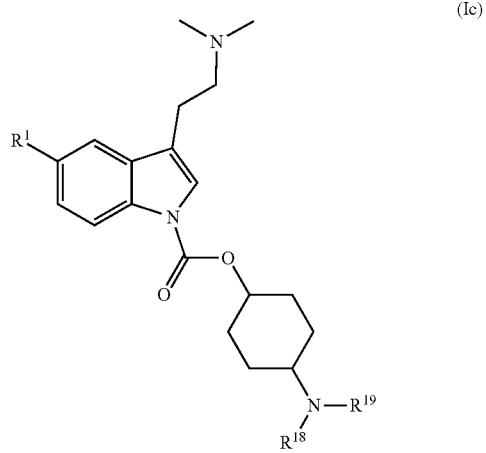

(Ic)

wherein R¹ is hydrogen or methoxy, and each of $R^{18}$ and $R^{19}$ is independently hydrogen, alkyl, cycloalkyl, or heteroalkyl, wherein each alkyl, cycloalkyl, and heteroalkyl is independently unsubstituted or substituted with one or more $R^B$; or $R^{18}$ and $R^{19}$ together with the atom to which they are attached form a heterocyclylalkyl ring that is unsubstituted or substituted with one or more $R^B$.

In some embodiments, the compound of Formula (I) having the structure of Formula (Id), or a pharmaceutically acceptable salt thereof:

(Id)

wherein $R^1$ is hydrogen or methoxy; R is alkyl or cycloalkyl, each of which is independently unsubstituted or substituted with one or more $R^A$, or hydrogen; and $R^{46}$ is hydrogen or alkyl that is unsubstituted or substituted with one or more alkyl, aryl, halogen, —$OR^{13}$, —$NR(R^{18})R^{19}$, —$C(O)R^4$, —$OC(O)R^{15}$, —$OC(O)OR^{16}$, or —$OC(O)N(R^{18})R^{19}$.

In some embodiments, the compound of Formula (I) having the structure of Formula (Ie), or a pharmaceutically acceptable salt thereof:

(Ie)

wherein $R^1$ is hydrogen or methoxy, and $R^5$ is hydrogen, alkyl or cycloalkyl, wherein each alkyl and cycloalkyl is independently unsubstituted or substituted with one or more $R^A$.

In some embodiments, the compound of Formula (I) having the structure of Formula (If), or a pharmaceutically acceptable salt thereof:

(If)

wherein $R^1$ is methoxy or hydrogen, and each of $R^9$ and $R^{10}$ is independently hydrogen, alkyl, cycloalkyl, aryl, heteroaryl, heteroalkyl, or heterocyclylalkyl, wherein each alkyl, cycloalkyl, aryl, heteroaryl, heteroalkyl, and heterocyclylalkyl is independently unsubstituted or substituted with one or more $R^A$, or $R^9$ and $R^{10}$ together with the atom to which they are attached form a heterocyclylalkyl ring that is unsubstituted or substituted with one or more $R^A$.

In some embodiments, the compound of Formula (I) or (If) having the structure of Formula (If1), or a pharmaceutically acceptable salt thereof:

(If1)

wherein:
$R^1$ is methoxy or hydrogen;
$R^{10}$ is hydrogen, alkyl, heteroalkyl, cycloalkyl, or heterocyclylalkyl, wherein each of alkyl, heteroalkyl, cycloalkyl, and heterocyclylalkyl is unsubstituted or substituted with one or more $R^A$; and
each of $X^1$ and $X^2$ are independently selected from —$CH_2$—, —O—, —NH—, —S—, —S(O)—, —$S(O)_2$—, or —$N(Y^1)$—, wherein each $Y^1$ is independently hydrogen, cycloalkyl, heteroalkyl, or alkyl.

In some embodiments, the compound of Formula (I) having the structure of Formula (Ig), or a pharmaceutically acceptable salt thereof:

(Ig)

wherein:
$R^1$ is methoxy or hydrogen;
each of $R^{41}$, $R^{42}$, $R^{43}$, and $R^{44}$ is independently hydrogen or alkyl that is unsubstituted or substituted with one or more alkyl, aryl, halogen, —$OR^{13}$, —$NR(R^{18})R^{19}$, —$C(O)R^{14}$, —$OC(O)R^5$, —$OC(O)OR^{16}$, or —$OC(O)N(R^{18})R^{19}$;
$R^{10}$ is hydrogen, alkyl, heteroalkyl, or cycloalkyl, wherein each of alkyl, heteroalkyl, and cycloalkyl is unsubstituted or substituted with one or more $R^A$; and
$R^{45}$ is heteroalkyl, heterocyclylalkyl, heteroaryl, or —$C(O)OR^{13}$, —$N(R^{13})C(O)OR^{14}$, —$N(R^{13})C(O)R^{14}$, —$C(O)R^{14}$, —$OC(O)R^{16}$, or —$OC(O)OR^{16}$, wherein each of heteroalkyl, heterocyclylalkyl, heteroaryl is unsubstituted or substituted with one or more alkyl, aryl, halogen, —OR$^3$, —NR(R$^{18}$)R$^{19}$, —C(O)R$^{14}$, —OC(O)R$^{15}$, —OC(O)OR$^{16}$, or —OC(O)N(R$^{18}$)R$^{19}$.

In some embodiments, the compound of Formula (I) having the structure of Formula (Ih), or a pharmaceutically acceptable salt thereof:

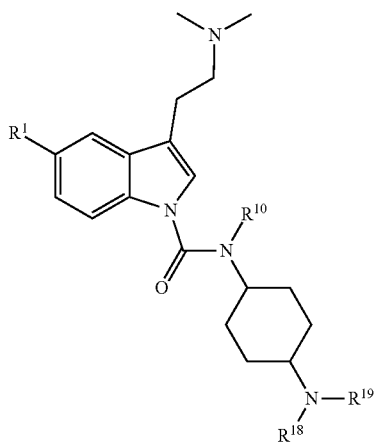

(Ih)

wherein:
R$^1$ is hydrogen or methoxy;
R$^{10}$ is hydrogen, alkyl, heteroalkyl, or cycloalkyl, wherein each of alkyl, heteroalkyl, and cycloalkyl is unsubstituted or substituted with one or more R$^A$; and
each of R$^{18}$ and R$^{19}$ is independently hydrogen, alkyl, cycloalkyl, or heteroalkyl, wherein each alkyl, cycloalkyl, or heterocyclylalkyl is independently unsubstituted or substituted with one or more R$^B$; or R$^{18}$ and R$^{19}$ together with the atom to which they are attached form a heterocyclylalkyl ring that is unsubstituted or substituted with one or more R$^B$.

In some embodiments, the compound of Formula (I) having the structure of Formula (Ii), or a pharmaceutically acceptable salt thereof:

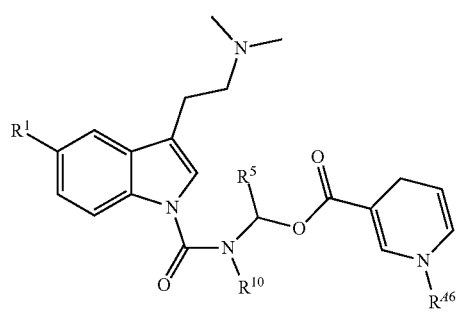

(Ii)

wherein:
R$^1$ is hydrogen or methoxy; and
each of R$^5$ and R$^{10}$ is independently hydrogen, alkyl, heteroalkyl, or cycloalkyl, wherein each alkyl, heteroalkyl, and cycloalkyl is independently unsubstituted or substituted with one or more R$^A$; and R$^{46}$ is independently hydrogen, alkyl, heteroalkyl, or cycloalkyl, wherein each of alkyl, heteroalkyl, or cycloalkyl is unsubstituted or substituted with one or more alkyl, aryl, halogen, —OR$^{13}$, —NR(R$^{18}$)R$^{19}$, —C(O)R$^{14}$, —OC(O)R$^{15}$, —OC(O)OR$^{16}$, or —OC(O)N(R$^{18}$)R$^{19}$.

In some embodiments, the compound of Formula (I) having the structure of Formula (Ij), or a pharmaceutically acceptable salt thereof:

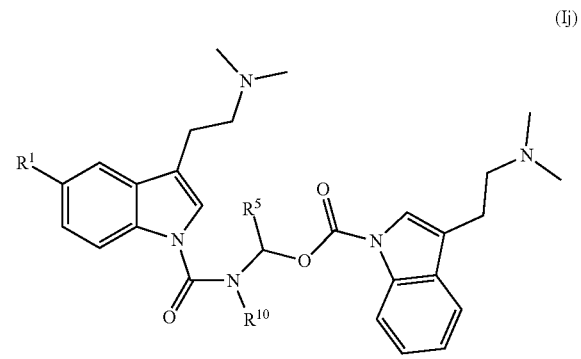

(Ij)

wherein R$^1$ is hydrogen or methoxy, and each of R$^5$ and R$^{10}$ is hydrogen, alkyl, or heteroalkyl, wherein each of alkyl and heteroalkyl is independently unsubstituted or substituted with one or more R$^A$.

In some embodiments, the compound of Formula (I) having the structure of Formula (Ik), or a pharmaceutically acceptable salt thereof:

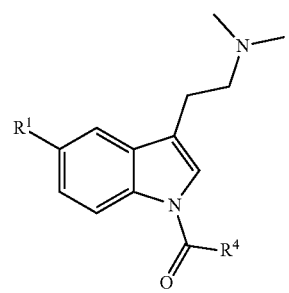

(Ik)

wherein R$^1$ is hydrogen or methoxy, and R$^4$ is alkyl, heterocyclylalkyl, aryl, heteroaryl, or heteroalkyl, each of which is unsubstituted or substituted with one or more R$^A$.

In some embodiments, the compound of Formula (I) or (Ik) having the structure of Formula (Ik1), or a pharmaceutically acceptable salt thereof:

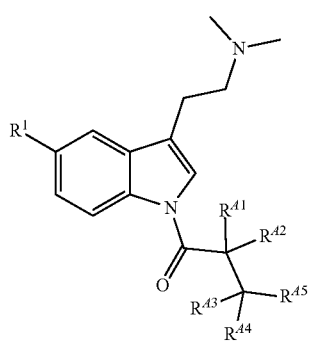

(Ik1)

wherein:
R$^1$ is methoxy or hydrogen;
each of R$^{A1}$, R$^{A2}$, R$^{A3}$, and R$^{A4}$ is independently hydrogen, alkyl, or an amino acid side chain, wherein each alkyl or amino acid side chain is independently unsubstituted or substituted with one or more alkyl, aryl, halogen, —OR$^{13}$, —NR(R$^{18}$)R$^{19}$, —C(O)R$^{14}$, —OC(O)R$^{15}$, —OC(O)OR$^{16}$, or —OC(O)N(R$^{18}$)R$^{19}$;
R$^{10}$ is hydrogen, alkyl, heteroalkyl, or cycloalkyl, wherein each of alkyl, heteroalkyl, and cycloalkyl is unsubstituted or substituted with one or more R$^A$; and
R$^{A5}$ is heteroalkyl, heterocyclylalkyl, heteroaryl, —C(O)OR$^{13}$, —N(R$^{13}$)C(O)OR$^{14}$, —N(R$^{13}$)C(O)R$^{14}$, —C(O)R$^{14}$, —OC(O)R$^{15}$, or —OC(O)OR$^{16}$, wherein each of heteroalkyl, heterocyclylalkyl, heteroaryl is unsubstituted or substituted with one or more alkyl, aryl, halogen, —OR$^{13}$, —NR(R$^{18}$)R$^{19}$, —C(O)R$^{14}$, —OC(O)R$^{15}$, —OC(O)OR$^{16}$, or —OC(O)N(R$^{18}$)R$^{19}$.

In some embodiments, the compound of Formula (I) or (Ik) having the structure of Formula (Ik2), or a pharmaceutically acceptable salt thereof:

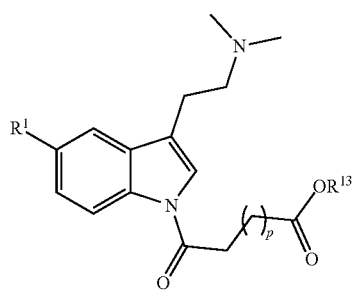

(Ik2)

wherein:
R$^1$ is methoxy or hydrogen;
R$^3$ is hydrogen, alkyl, cycloalkyl, aryl, heteroaryl, heteroalkyl, or heterocyclylalkyl, wherein each of alkyl, cycloalkyl, aryl, heteroaryl, heteroalkyl, and heterocyclylalkyl is unsubstituted or substituted with one or more R$^B$; and
p is 0, 1, 2, 3, 4, 5, 6, 7, 8, 9, or 10.

In some embodiments, the compound of Formula (I) or (Ik) having the structure of Formula (Ik3), or a pharmaceutically acceptable salt thereof:

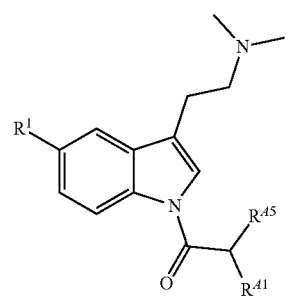

(Ik3)

wherein:
R$^1$ is methoxy or hydrogen;
R$^{A1}$ is alkyl or an amino acid side chain, each of which is unsubstituted or substituted with one or more alkyl, aryl, halogen, —OR$^{13}$, —NR(R$^{15}$)R$^{19}$, —C(O)R$^{14}$, —OC(O)R$^{15}$, —OC(O)OR$^{16}$, or —OC(O)N(R$^{18}$)R$^{19}$; and
R$^{A5}$ is —N(R$^{18}$)R$^{19}$ or —N(R$^{13}$)C(O)R$^{14}$.

In some embodiments, the compound of Formula (I) having the structure of Formula (I1), or a pharmaceutically acceptable salt thereof:

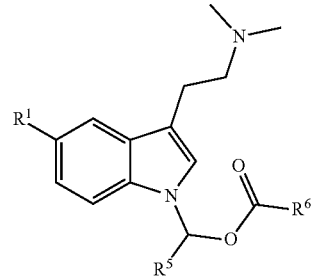

(I1)

wherein:
R$^1$ is methoxy or hydrogen;
R$^5$ is hydrogen, alkyl, or cycloalkyl, wherein each of alkyl or cycloalkyl is unsubstituted or substituted with one or more R$^A$; and
R$^6$ is alkyl, cycloalkyl, heterocyclylalkyl, or heteroalkyl, wherein each of alkyl, cycloalkyl, heterocyclylalkyl, or heteroalkyl is unsubstituted or substituted with one or more R$^A$.

In some embodiments, the compound of Formula (I) having the structure of Formula (Im), or a pharmaceutically acceptable salt thereof:

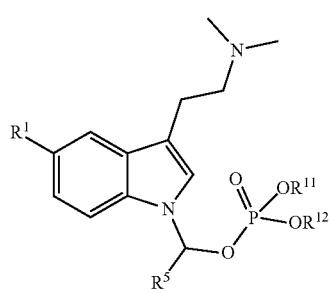

(Im)

wherein:
R¹ is methoxy or hydrogen;
R⁵ hydrogen, alkyl, cycloalkyl, or heteroalkyl, wherein each of alkyl, cycloalkyl, and heteroalkyl is unsubstituted or substituted with one or more R^A; and
each of R¹ and R² is independently hydrogen, cycloalkyl, aryl, heteroaryl, or alkyl, wherein each of alkyl, cycloalkyl, and heteroalkyl is independently unsubstituted or substituted with one or more R^A.

In some embodiments, the compound of Formula (I) or (Im) having the structure of Formula (Im1), or a pharmaceutically acceptable salt thereof:

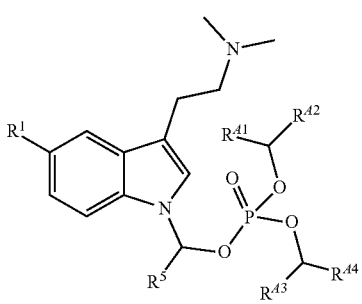

(Im1)

wherein:
R¹ is methoxy or hydrogen;
each of $R^{A1}$, $R^{A3}$, and $R^5$ is independently hydrogen, alkyl, or cycloalkyl; and
each of $R^{A2}$ and $R^{A4}$ is independently alkyl, heteroalkyl, cycloalkyl, heterocyclylalkyl, aryl, or heteroaryl, —OC(O)R¹⁵, or —OC(O)OR¹⁶,
wherein each alkyl, heteroalkyl, cycloalkyl, heterocyclylalkyl, aryl, and heteroaryl is independently unsubstituted or substituted with one or more alkyl, aryl, halogen, —OR¹³, —NR(R¹⁸)R¹⁹, —C(O)R¹⁴, —OC(O)R¹⁵, —OC(O)OR¹⁶, or —OC(O)N(R¹⁸)R¹⁹.

In some embodiments, the compound of Formula (I), (Im), or (Im1) having the structure of Formula (Im1a), or a pharmaceutically acceptable salt thereof:

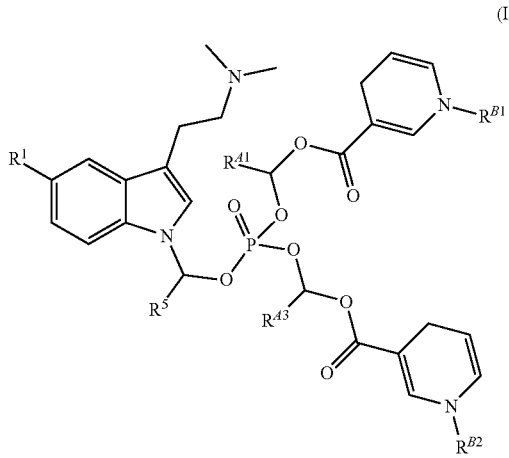

(Im1a)

wherein:
R¹ is methoxy or hydrogen;
each of $R^{A1}$, $R^{A3}$, and $R^5$ is independently hydrogen, alkyl, or cycloalkyl, wherein each of alkyl and cycloalkyl is independently unsubstituted or substituted with one or more alkyl, aryl, halogen, —OR¹³, —NR(R¹⁸)R¹⁹, —C(O)R¹⁴, —OC(O)R¹⁵, —OC(O)OR¹⁶, or —OC(O)N(R¹⁸)R¹⁹; and
each of $R^{B1}$ and $R^{B2}$ is independently hydrogen or alkyl that is unsubstituted or substituted with one or more halogen, amino, cyano, hydroxyl, alkyl, acetyl, or benzoyl.

In some embodiments, the compound of Formula (I) having the structure of Formula (In), or a pharmaceutically acceptable salt thereof:

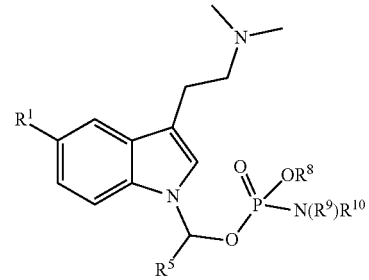

(In)

wherein:
R¹ is methoxy or hydrogen;
R⁵ is hydrogen, alkyl, or cycloalkyl;
R⁸ is hydrogen, alkyl, cycloalkyl, aryl, heterocyclylalkyl, or heteroaryl; and
each of R⁹ and R¹⁰ is independently hydrogen or alkyl, wherein each cycloalkyl, aryl, heterocyclylalkyl, and heteroaryl is independently unsubstituted or substituted with one or more R^A.

In some embodiments, the compound of Formula (I) or (In) having the structure of Formula (In1), or a pharmaceutically acceptable salt thereof:

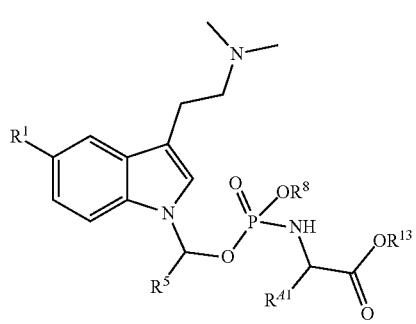

(In1)

wherein:
R¹ is methoxy or hydrogen;
$R^{A1}$ is hydrogen, alkyl, or cycloalkyl, wherein each of alkyl and cycloalkyl is unsubstituted or substituted with alkyl, aryl, halogen, —OR¹³, —NR(R¹³)R¹⁹, —C(O)R¹⁴, —OC(O)R¹⁵, —OC(O)OR¹⁶, or —OC(O)N(R¹⁸)R¹⁹;
each of R⁵ and R⁸ is hydrogen, alkyl, cycloalkyl, aryl, heterocyclylalkyl, or heteroaryl, wherein alkyl, cycloalkyl, aryl, heterocyclylalkyl, and heteroaryl is independently unsubstituted or substituted with one or more R^A; and R[13] is hydrogen or alkyl that is unsubstituted or substituted with one or more R[B].

In some embodiments, the compound of Formula (I) having the structure of Formula (Io), or a pharmaceutically acceptable salt thereof:

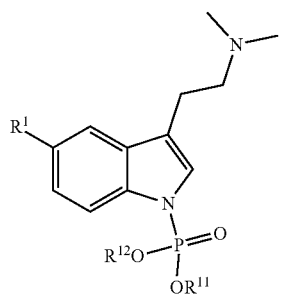

(Io)

wherein:
R[1] is methoxy or hydrogen; and
each of R[11] and R[12] is independently selected from hydrogen, cycloalkyl, aryl, heteroaryl, or alkyl, wherein each cycloalkyl, aryl, heteroaryl, and alkyl is independently unsubstituted or substituted with one or more R[A], or R[11] and R[12] together with the atoms to which they are attached form a heterocyclylalkyl ring that is unsubstituted or substituted with one or more R[A].

In some embodiments, the compound of Formula (I) or (Io) having the structure of Formula (Io1), or a pharmaceutically acceptable salt thereof:

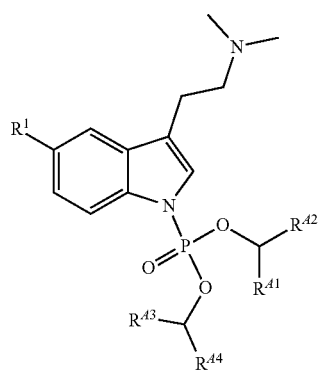

(Io1)

wherein:
R[1] is methoxy or hydrogen;
each of R[A1] and R[A3] is independently hydrogen, alkyl, or cycloalkyl; and
each of R[A2] and R[A4] is independently alkyl, heteroalkyl, cycloalkyl, heterocyclylalkyl, aryl, heteroaryl, —OC(O)R[15], or —OC(O)OR[16],
wherein each alkyl, heteroalkyl, cycloalkyl, heterocyclylalkyl, aryl, and heteroaryl is independently unsubstituted or substituted with one or more alkyl, aryl, halogen, —OR[13], —NR(R[18])R[19], —C(O)R[14], —OC(O)R[15], —OC(O)OR[16], or —OC(O)N(R[18])R[19].

In some embodiments, the compound of Formula (I) or (Io) having the structure of Formula (Io2), or a pharmaceutically acceptable salt thereof:

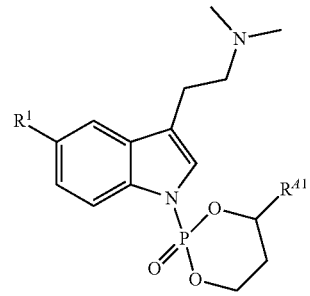

(Io2)

wherein R[1] is methoxy or hydrogen; and R[A1] is aryl or heteroaryl, each of which is unsubstituted or substituted with one or more alkyl, aryl, halogen, —OR[13], —NR(R[18])R[19], —C(O)R[14], —OC(O)R[5], —OC(O)OR[16], or —OC(O)N(R[18])R[19].

In some embodiments, the compound of Formula (I), (Io), or (Io1), having the structure of Formula (Io1a), or a pharmaceutically acceptable salt thereof:

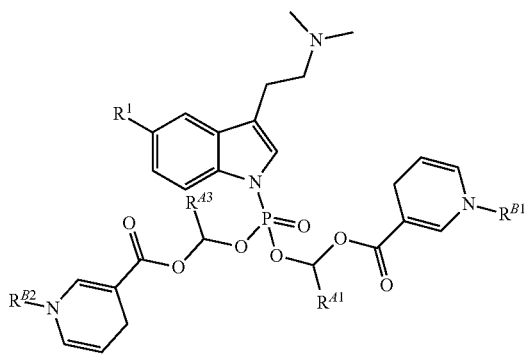

(Io1a)

wherein:
R[1] is methoxy or hydrogen;
each of R[A1] and R[A3] is independently hydrogen, alkyl, or cycloalkyl, wherein each alkyl and cycloalkyl is independently unsubstituted or substituted with one or more alkyl, aryl, halogen, —OR[13], —NR(R[18])R[19], —C(O)R[14], —OC(O)R[15], —OC(O)OR[16], or —OC(O)N(R[18])R[19]; and
each of R[B1] and R[B2] is independently hydrogen or alkyl that is unsubstituted or substituted with one or more halogen, amino, cyano, hydroxyl, alkyl, acetyl, or benzoyl.

In some embodiments, the compound of Formula (I) having the structure of Formula (Ip), or a pharmaceutically acceptable salt thereof:

(Ip)

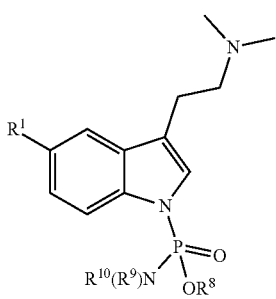

wherein:
R$^1$ is methoxy or hydrogen;
R$^8$ is alkyl, cycloalkyl, aryl, heterocyclylalkyl, or heteroaryl; and
each of R$^9$ and R$^{10}$ is independently hydrogen or alkyl, wherein each alkyl, cycloalkyl, aryl, heterocyclylalkyl, and heteroaryl is independently unsubstituted or substituted with one or more R$^A$.

In some embodiments, the compound of Formula (I) or (Ip) having the structure of Formula (Ip1), or a pharmaceutically acceptable salt thereof:

(Ip1)

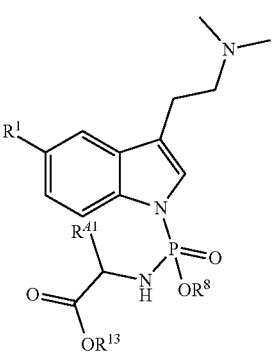

wherein:
R$^1$ is methoxy or hydrogen;
R$^{41}$ is hydrogen, alkyl, or cycloalkyl, wherein each of alkyl and cycloalkyl is unsubstituted or substituted with one or more alkyl, aryl, halogen, —OR$^{13}$, —NR(R$^{18}$)R$^{19}$, —C(O)R$^{14}$, —OC(O)R$^{15}$, —OC(O)OR$^{16}$, or —OC(O)N(R$^{18}$)R$^{19}$;
R$^8$ is hydrogen, alkyl, cycloalkyl, aryl, heterocyclylalkyl, or heteroaryl, wherein each alkyl, cycloalkyl, aryl, heterocyclylalkyl, and heteroaryl is unsubstituted or substituted with one or more R$^A$; and
R$^{13}$ is hydrogen or alkyl that is unsubstituted or substituted with one or more R$^B$.

In some embodiments, the compound of Formula (I) having the structure of Formula (Iq), or a pharmaceutically acceptable salt thereof:

(Iq)

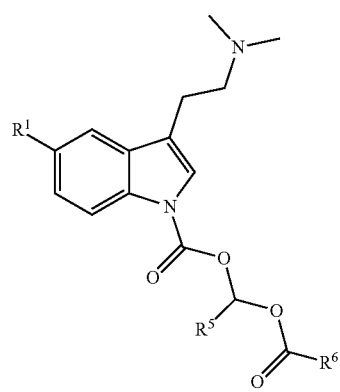

wherein:
R$^1$ is methoxy or hydrogen;
R$^5$ is hydrogen, alkyl, or cycloalkyl; and
R$^6$ is alkyl, cycloalkyl, heteroalkyl, heterocyclylalkyl, aryl, or heteroaryl,
wherein each alkyl, cycloalkyl, heteroalkyl, heterocyclylalkyl, aryl, and heteroaryl is independently unsubstituted or substituted with one or more R$^A$.

In some embodiments, the compound of Formula (I) or (Iq) having the structure of Formula (Iq1), or a pharmaceutically acceptable salt thereof:

(Iq1)

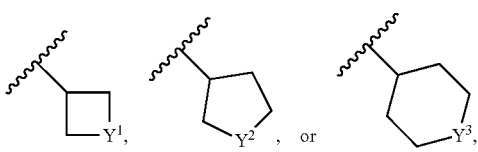

wherein:
R$^1$ is methoxy or hydrogen;
R$^5$ is hydrogen, alkyl, or cycloalkyl, wherein each of alkyl and cycloalkyl is unsubstituted or substituted with one or more R$^A$; and
Q$^1$ is

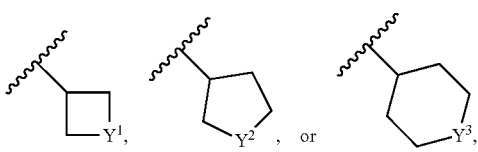

wherein
each of Y$^1$, Y$^2$, or Y$^3$ is independently —O—, —S—, —S(O)—, —S(O)$_2$—, —N(R$^{Y1}$)—, or —NC(O)R$^{Y2}$, wherein each of R$^{Y1}$ and R$^{Y2}$ is independently hydrogen, alkyl, heteroalkyl, or heteroaryl.

In some embodiments, the compound of Formula (I) having the structure of Formula (Ir), or a pharmaceutically acceptable salt thereof:

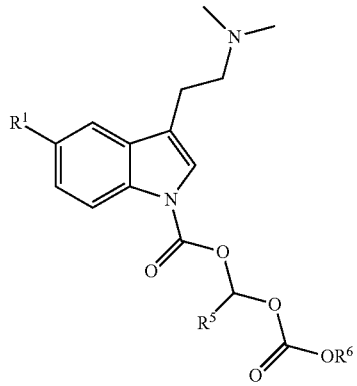

(Ir)

wherein:
R¹ is methoxy or hydrogen;
R⁵ is hydrogen, alkyl, or cycloalkyl; and
R⁶ is alkyl, cycloalkyl, heteroalkyl, heterocyclylalkyl, aryl, or heteroaryl,
wherein each alkyl, cycloalkyl, heteroalkyl, heterocyclylalkyl, aryl, and heteroaryl is independently unsubstituted or substituted with one or more $R^A$.

In some embodiments, the compound of Formula (I) or (Ir) having the structure of Formula (Ir1), or a pharmaceutically acceptable salt thereof:

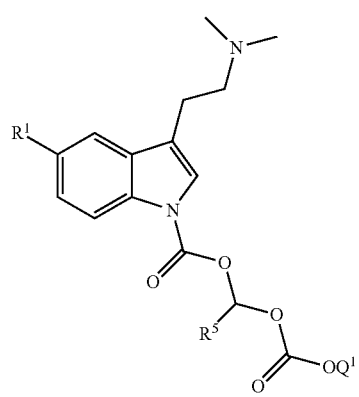

(Ir1)

wherein:
R¹ is methoxy or hydrogen;
R⁵ is hydrogen, alkyl, or cycloalkyl, wherein each of alkyl and cycloalkyl is unsubstituted or substituted with one or more $R^A$; and
Q¹ is

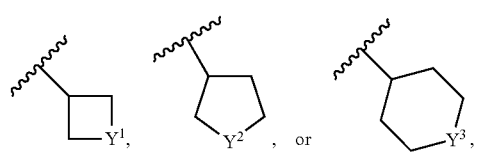

wherein each of Y¹, Y², or Y³ is independently —O—, —S—, —S(O)—, —S(O)₂—, —N(R$^{Y1}$)—, or —NC(O)R$^{Y2}$, wherein each of R$^{Y1}$ and R$^{Y2}$ is independently hydrogen, alkyl, heteroalkyl, or heteroaryl.

In some embodiments, the compound of Formula (I) having the structure of Formula (Is), or a pharmaceutically acceptable salt thereof:

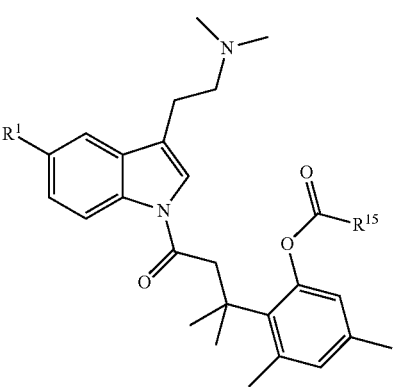

(Is)

wherein R¹ is hydrogen or methoxy, and R¹⁵ is alkyl, heteroalkyl, cycloalkyl, aryl, or heteroaryl, each of which is unsubstituted or substituted with one or more $R^B$.

In some embodiments, the compound of Formula (I) having the structure of Formula (It), or a pharmaceutically acceptable salt thereof:

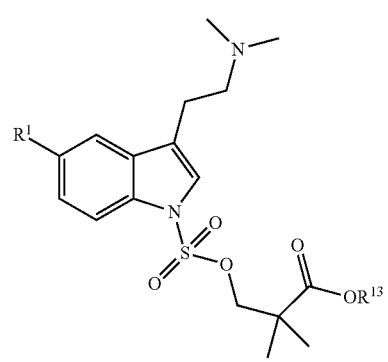

(It)

wherein R¹ is hydrogen or methoxy, and R¹³ is alkyl, cycloalkyl, heterocyclylalkyl, aryl, or heteroaryl, each of which is unsubstituted or substituted with one or more $R^B$.

In some embodiments, the compound of Formula (I) having the structure of Formula (Iu), or a pharmaceutically acceptable salt thereof:

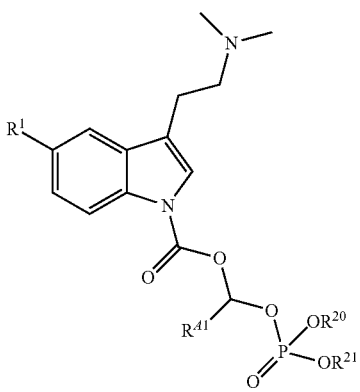

(Iu)

wherein:
R¹ is hydrogen or methoxy;
R^{A1} is hydrogen, alkyl, or cycloalkyl, wherein each of alkyl and cycloalkyl is unsubstituted or substituted with one or more alkyl, aryl, halogen, —OR¹³, —NR(R¹⁸)R¹⁹, —C(O)R¹⁴, —OC(O)R¹⁵, —OC(O)OR¹⁶, or —OC(O)N(R¹⁸)R¹⁹; and
each of R²⁰ and R²¹ is independently hydrogen, alkyl, cycloalkyl, aryl, heterocyclylalkyl, or heteroaryl, wherein each alkyl, cycloalkyl, aryl, heterocyclylalkyl, and heteroaryl is independently unsubstituted or substituted with one or more R^B, or R²⁰ and R²¹ together with the atoms to which they are attached form a heterocyclylalkyl ring that is unsubstituted or substituted with one or more R^B.

In some embodiments is a compound of Formula (I) having the structure of Formula (Iv), or a pharmaceutically acceptable salt thereof:

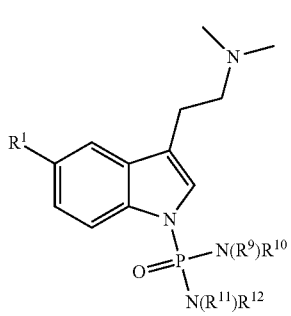

(Iv)

wherein:
R¹ is hydrogen or methoxy;
each of R⁹ and R¹⁰ is independently alkyl, heteroalkyl, cycloalkyl, heterocyclylalkyl, aryl, heteroaryl, or hydrogen, wherein each alkyl, heteroalkyl, cycloalkyl, heterocyclylalkyl, aryl, and heteroaryl is independently unsubstituted or substituted with one or more R^A, or R⁹ and R¹⁰ together with the atom to which they are attached form a heterocyclylalkyl ring that is unsubstituted or substituted with one or more R^A; and
each of R¹¹ and R¹² is independently alkyl, heteroalkyl, cycloalkyl, heterocyclylalkyl, aryl, heteroaryl, or hydrogen, wherein each alkyl, heteroalkyl, cycloalkyl, heterocyclylalkyl, aryl, and heteroaryl is independently unsubstituted or substituted with one or more R^A, or R¹¹ and R¹² together with the atoms to which they are attached form a heterocyclylalkyl ring that is unsubstituted or substituted with one or more R^A. In some embodiments, the compound of Formula (I) having the structure of Formula (Iw), or a pharmaceutically acceptable salt thereof:

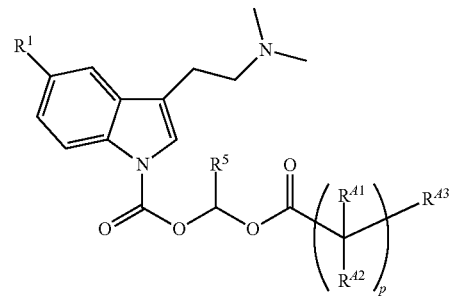

(Iw)

wherein:
R¹ is hydrogen or methoxy;
each R^{A1} and R^{A2} is independently hydrogen, alkyl, or cycloalkyl, wherein each alkyl and cycloalkyl is independently unsubstituted or substituted with one or more alkyl, aryl, halogen, —OR¹³, —NR(R¹⁸)R¹⁹, —C(O)R¹⁴, —OC(O)R¹⁵, —OC(O)OR¹⁶, or —OC(O)N(R¹⁸)R⁹;
R^{A3} is —OR¹³, —N(R¹⁸)R¹⁹, —C(O)OR¹³, —N(R¹³)C(O)OR¹⁴, —N(R¹³)C(O)R¹⁴, —C(O)R¹⁴, —OC(O)R¹⁵, —OC(O)OR¹⁶, —OP(O)OR¹⁷[N(R¹⁸)R¹⁹], —C(O)N(R¹⁸)R¹⁹, —OC(O)N(R¹⁸)R¹⁹, or —OP(O)OR²⁰ (OR²¹), and
p is 1, 2, 3, 4, 5, 6, 7, 8, 9, or 10.

In another aspect, the present disclosure provides a pharmaceutically acceptable composition comprising a compound according to any of Formula (I), (Ia), (Ib), (Ib-1) (Ib1), (Ic), (Id), (Ie), (If), (If1), (Ig), (Ih), (Ii), (Ij), (Ik), (Ik1), (Ik2), (Ik3), (Il), (Im), (Im1), (Im1a), (In), (In1), (Io), (Io1), (Io2), (Io1a), (Ip) (Ip1), (Iq), (Iq1), (Ir), (Ir1), (Is), (It), (Iu), (Iv), or (Iw), or a pharmaceutically acceptable salt thereof, and a pharmaceutically acceptable excipient, carrier, adjuvant, or vehicle.

In another aspect, the present disclosure provides a method of treating a condition in a subject in need thereof, the method comprising administering to the subject a therapeutically-effective amount of a compound of Formula (I), (Ia), (Ib), (Ib-1) (Ib1), (Ic), (Id), (Ie), (If), (If1), (Ig), (Ih), (Ii), (Ij), (Ik), (Ik1), (Ik2), (Ik3), (Il), (Im), (Im1), (Im1a), (In), (In1), (Io), (Io1), (Io2), (Io1a), (Ip) (Ip1), (Iq), (Iq1), (Ir), (Ir1), (Is), (It), (Iu), (Iv), or (Iw), or a pharmaceutically acceptable salt thereof.

BRIEF DESCRIPTION OF THE FIGURES

FIG. 7 shows the mean concentration-time profiles of 5-methoxy-N,N-dimethyltryptamine (5-MeO-DMT) following IV or oral dosing of Compound 19 to Male SD rats (1 mg/kg for IV dosing, 10 mg/kg for oral dosing) are shown in.

DETAILED DESCRIPTION

Figure 1:
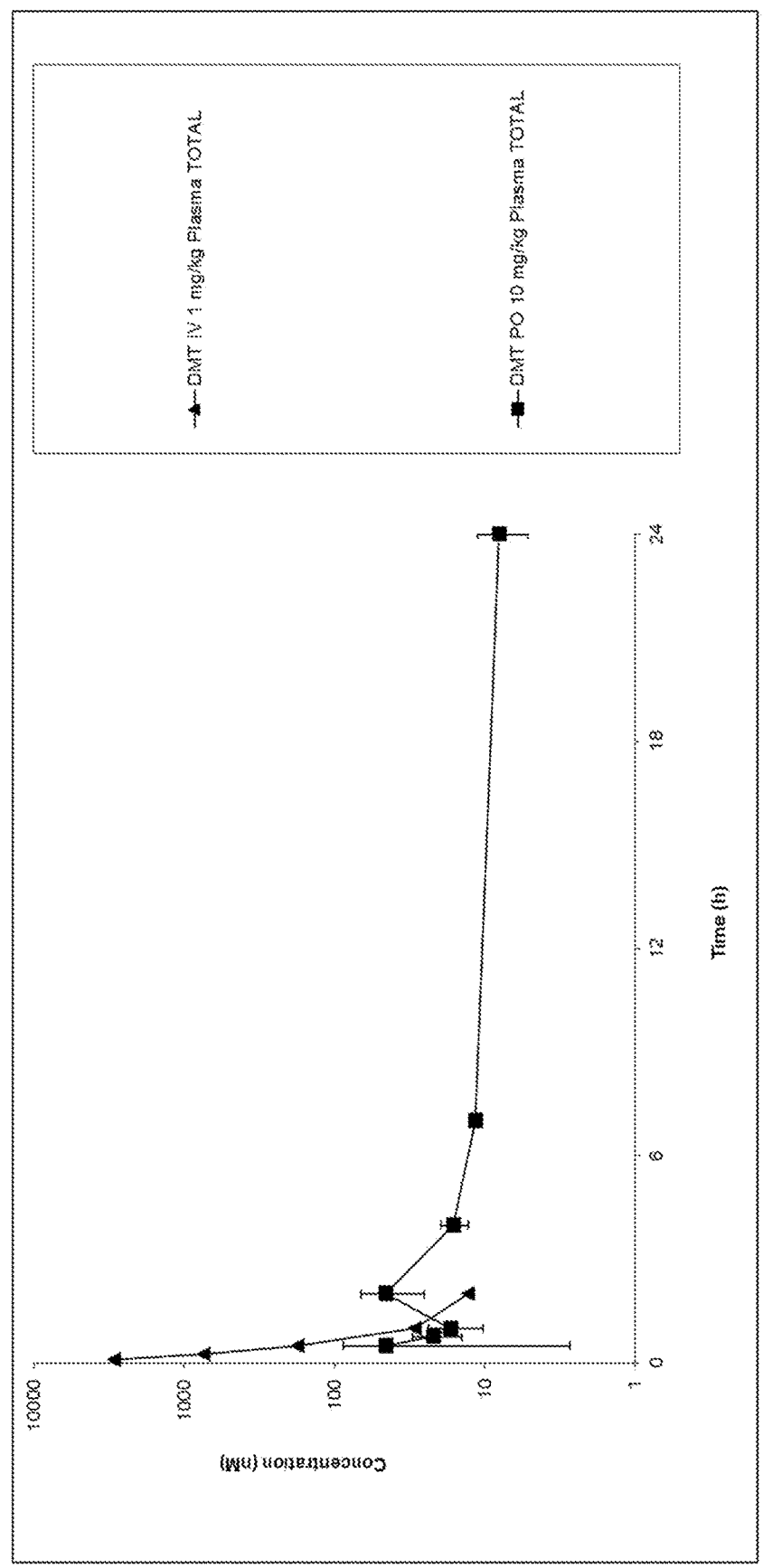
FIG. 1 shows the mean concentration-time profiles of DMT following oral dosing of DMT to Male SD rats (1 mg/kg for IV dosing, and 10 mg/kg for oral dosing).

Described herein are compounds that can be metabolically converted to N,N-dimethyltryptamine or analogs thereof upon administration to a subject. A compound disclosed herein can be useful for the treatment of a neurological disease, such as a psychiatric disorder, a substance abuse disorder, or a condition where increasing neuronal plasticity would be beneficial.

Definitions

Compounds herein can include all stereoisomers, enantiomers, diastereomers, mixtures, racemates, atropisomers, and tautomers thereof.

Unless otherwise specified, any compound disclosed herein can be substituted. Non-limiting examples of optional substituents include hydroxyl groups, sulfhydryl groups, halogens, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclylalkyl groups, heteroaryl groups, cycloalkyl groups, acyl groups, acyloxy groups, carbamate groups, amide groups, ureido groups, epoxy groups, and ester groups.

Non-limiting examples of alkyl groups include straight, branched, and cyclic alkyl and alkylene groups. An alkyl group can be, for example, a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Alkyl groups can include branched and unbranched alkyl groups. Non-limiting examples of straight alkyl groups include methyl, ethyl, propyl, butyl, pentyl, hexyl, heptyl, octyl, nonyl, and decyl.

Branched alkyl groups include any straight alkyl group substituted with any number of alkyl groups. Non-limiting examples of branched alkyl groups include isopropyl, isobutyl, sec-butyl, and t-butyl.

Non-limiting examples of substituted alkyl groups includes hydroxymethyl, chloromethyl, trifluoromethyl, aminomethyl, 1-chloroethyl, 2-hydroxyethyl, 1,2-difluoroethyl, and 3-carboxypropyl.

Non-limiting examples of cycloalkyl groups include cyclopropyl, cyclobutyl, cyclopentyl, cyclohexyl, cycloheptyl, and cyclooctyl groups. Cycloalkyl groups also include fused-, bridged-, and spiro-bicycles and higher fused-, bridged-, and spiro-systems. A cycloalkyl group can be substituted with any number of straight, branched, or cyclic alkyl groups. Non-limiting examples of cyclic alkyl groups include cyclopropyl, 2-methyl-cycloprop-1-yl, cycloprop-2-en-1-yl, cyclobutyl, 2,3-dihydroxycyclobut-1-yl, cyclobut-2-en-1-yl, cyclopentyl, cyclopent-2-en-1-yl, cyclopenta-2,4-dien-1-yl, cyclohexyl, cyclohex-2-en-1-yl, cycloheptyl, cyclooctanyl, 2,5-dimethylcyclopent-1-yl, 3,5-dichlorocyclohex-1-yl, 4-hydroxycyclohex-1-yl, 3,3,5-trimethylcyclohex-1-yl, octahydropentalenyl, octahydro-1H-indenyl, 3a,4,5,6,7,7a-hexahydro-3H-inden-4-yl, decahydroazulenyl, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

Non-limiting examples of alkenyl groups include straight, branched, and cyclic alkenyl groups. The olefin or olefins of an alkenyl group can be, for example, E, Z, cis, trans, terminal, or exo-methylene. An alkenyl group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted. Non-limiting examples of alkenyl and alkenylene groups include ethenyl, prop-1-en-1-yl, isopropenyl, but-1-en-4-yl; 2-chloroethenyl, 4-hydroxybuten-1-yl, 7-hydroxy-7-methyloct-4-en-2-yl, and 7-hydroxy-7-methyloct-3,5-dien-2-yl.

Non-limiting examples of alkynyl groups include straight, branched, and cyclic alkynyl groups. The triple bond of an alkylnyl group can be internal or terminal. An alkylnyl or alkynylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted. Non-limiting examples of alkynyl groups include ethynyl, prop-2-yn-1-yl, prop-1-yn-1-yl, and 2-methyl-hex-4-yn-1-yl; 5-hydroxy-5-methylhex-3-yn-1-yl, 6-hydroxy-6-methylhept-3-yn-2-yl, and 5-hydroxy-5-ethylhept-3-yn-1-yl.

A halo-alkyl group can be any alkyl group substituted with any number of halogen atoms, for example, fluorine, chlorine, bromine, and iodine atoms. A halo-alkenyl group can be any alkenyl group substituted with any number of halogen atoms. A halo-alkynyl group can be any alkynyl group substituted with any number of halogen atoms.

An alkoxy group can be, for example, an oxygen atom substituted with any alkyl, alkenyl, or alkynyl group. An ether or an ether group comprises an alkoxy group. Non-limiting examples of alkoxy groups include methoxy, ethoxy, propoxy, isopropoxy, and isobutoxy.

A heterocycle can be any ring containing a ring atom that is not carbon, for example, N, O, S, P, Si, B, or any other heteroatom. A heterocycle can be substituted with any number of substituents, for example, alkyl groups and halogen atoms. A heterocycle can be aromatic (heteroaryl) or non-aromatic. Non-limiting examples of heterocycles include pyrrole, pyrrolidine, pyridine, piperidine, succinamide, maleimide, morpholine, imidazole, thiophene, furan, tetrahydrofuran, pyran, and tetrahydropyran.

Non-limiting examples of heterocycles include: heterocyclic units having a single ring containing one or more heteroatoms, non-limiting examples of which include, diazirinyl, aziridinyl, azetidinyl, pyrazolidinyl, imidazolidinyl, oxazolidinyl, isoxazolinyl, thiazolidinyl, isothiazolinyl, oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl, 2,3,4,5-tetrahydro-1H-azepinyl, 2,3-dihydro-1H-indole, and 1,2,3,4-tetrahydroquinoline; and ii) heterocyclic units having 2 or more rings one of which is a heterocyclic ring, non-limiting examples of which include hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, and decahydro-1H-cycloocta[b]pyrrolyl.

Non-limiting examples of heteroaryl include: i) heteroaryl rings containing a single ring, non-limiting examples of which include, 1,2,3,4-tetrazolyl, [1,2,3]triazolyl, [1,2,4]triazolyl, triazinyl, thiazolyl, 1H-imidazolyl, oxazolyl, isoxazolyl, isothiazolyl, furanyl, thiophenyl, pyrimidinyl, 2-phenylpyrimidinyl, pyridinyl, 3-methylpyridinyl, and 4-dimethylaminopyridinyl; and ii) heteroaryl rings containing 2 or more fused rings one of which is a heteroaryl ring, non-limiting examples of which include: 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 4,5,6,7-tetrahydro-1-H-indolyl, quinoxalinyl, quinazolinyl, quinolinyl, 8-hydroxy-quinolinyl, and isoquinolinyl.

"Alkyl" refers to an optionally substituted straight-chain, or optionally substituted branched-chain saturated hydrocarbon having from one to about ten carbon atoms, or from one to six carbon atoms, wherein an $sp^3$-hybridized carbon of the alkyl residue is attached to the rest of the molecule by a single bond. Examples include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl, and hexyl, and longer alkyl groups, such as heptyl, octyl, and the like. Whenever it appears herein, a numerical range such as "$C_1$-$C_6$ alkyl" means that the alkyl group consists of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_1$-$C_{10}$ alkyl, a $C_1$-$C_9$ alkyl, a $C_1$-$C_8$ alkyl, a $C_1$-$C_7$ alkyl, a $C_1$-$C_6$ alkyl, a $C_1$-$C_3$ alkyl, a $C_1$-$C_4$ alkyl, a $C_1$-$C_3$ alkyl, a $C_1$-$C_2$ alkyl, or a $C_1$ alkyl. Unless stated otherwise specifically in the specification, an alkyl group is optionally substituted, for example, with oxo, halogen, amino, nitrile, nitro, hydroxyl, haloalkyl, alkoxy, aryl, cycloalkyl, heterocyclylalkyl, heteroaryl, and the like. In some embodiments, the alkyl is optionally substituted with oxo, halogen, —CN, —CF$_3$, —OH, —OMe, —NH$_2$, or —NO$_2$. In some embodiments, the alkyl is optionally substituted with oxo, halogen, —CN, —CF$_3$, —OH, or —OMe. In some embodiments, the alkyl is optionally substituted with halogen.

"Alkenyl" refers to an optionally substituted straight-chain, or optionally substituted branched-chain hydrocarbon having one or more carbon-carbon double-bonds and having from two to about ten carbon atoms, more preferably two to about six carbon atoms, wherein an $sp^2$-hybridized carbon of the alkenyl residue is attached to the rest of the molecule by a single bond. The group may be in either the cis or trans conformation about the double bond(s), and should be understood to include both isomers. Examples include, but are not limited to, ethenyl (—CH=CH$_2$), 1-propenyl (—CH$_2$CH=CH$_2$), isopropenyl[—C(CH$_3$)=CH$_2$], butenyl, 1,3-butadienyl, and the like. Whenever it appears herein, a numerical range such as "$C_2$-$C_6$ alkenyl" means that the alkenyl group may consist of 2 carbon atoms, 3 carbon atoms, 4 carbon atoms, 5 carbon atoms, or 6 carbon atoms, although the present definition also covers the occurrence of the term "alkenyl" where no numerical range is designated. In some embodiments, the alkenyl is a $C_2$-$C_{10}$ alkenyl, a $C_2$-$C_9$ alkenyl, a $C_2$-$C_8$ alkenyl, a $C_2$-$C_7$ alkenyl, a $C_2$-$C_6$ alkenyl, a $C_2$-$C_5$ alkenyl, a $C_2$-$C_4$ alkenyl, a $C_2$-$C_3$ alkenyl, or a $C_2$ alkenyl. Unless stated otherwise specifically in the specification, an alkenyl group is optionally substituted, for example, with oxo, halogen, amino, nitrile, nitro, hydroxyl, haloalkyl, alkoxy, aryl, cycloalkyl, heterocyclylalkyl, heteroaryl, and the like. In some embodiments, an alkenyl is optionally substituted with oxo, halogen, —CN, —CF$_3$, —OH, —OMe, —NH$_2$, or —NO$_2$. In some embodiments, an alkenyl is optionally substituted with oxo, halogen, —CN, —CF$_3$, —OH, or —OMe. In some embodiments, the alkenyl is optionally substituted with halogen.

"Alkynyl" refers to an optionally substituted straight-chain or optionally substituted branched-chain hydrocarbon having one or more carbon-carbon triple-bonds and having from two to about ten carbon atoms, more preferably from two to about six carbon atoms. Examples include, but are not limited to, ethynyl, 2-propynyl, 2-butynyl, 1,3-butadiynyl, and the like. Whenever it appears herein, a numerical range such as "$C_2$-$C_6$ alkynyl" means that the alkynyl group may consist of 2 carbon atoms, 3 carbon atoms, 4 carbon atoms, 5 carbon atoms, or 6 carbon atoms, although the present definition also covers the occurrence of the term "alkynyl" where no numerical range is designated. In some embodiments, the alkynyl is a $C_2$-$C_{10}$ alkynyl, a $C_2$-$C_9$ alkynyl, a $C_2$-$C_8$ alkynyl, a $C_2$-$C_7$ alkynyl, a $C_2$-$C_6$ alkynyl, a $C_2$-$C_5$ alkynyl, a $C_2$-$C_4$ alkynyl, a $C_2$-$C_3$ alkynyl, or a $C_2$ alkynyl. Unless stated otherwise specifically in the specification, an alkynyl group is optionally substituted, for example, with oxo, halogen, amino, nitrile, nitro, hydroxyl, haloalkyl, alkoxy, aryl, cycloalkyl, heterocyclylalkyl, heteroaryl, and the like. In some embodiments, an alkynyl is optionally substituted with oxo, halogen, —CN, —CF$_3$, —OH, —OMe, —NH$_2$, or —NO$_2$. In some embodiments, an alkynyl is optionally substituted with oxo, halogen, —CN, —CF$_3$, —OH, or —OMe. In some embodiments, the alkynyl is optionally substituted with halogen.

"Alkoxy" refers to a radical of the formula —OR$_a$ where R$_a$ is an alkyl radical as defined. Unless stated otherwise specifically in the specification, an alkoxy group may be optionally substituted, for example, with oxo, halogen, amino, nitrile, nitro, hydroxyl, haloalkyl, alkoxy, aryl, cycloalkyl, heterocyclylalkyl, heteroaryl, and the like. In some embodiments, an alkoxy is optionally substituted with oxo, halogen, —CN, —CF$_3$, —OH, —OMe, —NH$_2$, or —NO$_2$. In some embodiments, an alkoxy is optionally substituted with oxo, halogen, —CN, —CF$_3$, —OH, or —OMe. In some embodiments, the alkoxy is optionally substituted with halogen.

"Aminoalkyl" refers to an alkyl radical, as defined above, that is substituted by one or more amines. In some embodiments, the alkyl is substituted with one amine. In some embodiments, the alkyl is substituted with one, two, or three amines. Hydroxyalkyl include, for example, aminomethyl, aminoethyl, aminopropyl, aminobutyl, or aminopentyl. In some embodiments, the hydroxyalkyl is aminomethyl.

"Aryl" refers to a radical derived from a hydrocarbon ring system comprising hydrogen, 6 to 30 carbon atoms, and at least one aromatic ring. The aryl radical may be a monocyclic, bicyclic, tricyclic, or tetracyclic ring system, which may include fused (when fused with a cycloalkyl or heterocyclylalkyl ring, the aryl is bonded through an aromatic ring atom) or bridged ring systems. In some embodiments, the aryl is a 6- to 10-membered aryl. In some embodiments, the aryl is a 6-membered aryl. Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In some embodiments, the aryl is phenyl. Unless stated otherwise specifically in the specification, an aryl may be optionally substituted, for example, with halogen, amino, nitrile, nitro, hydroxyl, alkyl, alkenyl, alkynyl, haloalkyl, alkoxy, aryl, cycloalkyl, heterocyclylalkyl, heteroaryl, and the like. In some embodiments, an aryl is optionally substituted with halogen, methyl, ethyl, —CN, —CF$_3$, —OH, —OMe, —NH$_2$, or —NO$_2$. In some embodiments, an aryl is optionally substituted with halogen, methyl, ethyl, —CN, —CF$_3$, —OH, or —OMe. In some embodiments, the aryl is optionally substituted with halogen.

"Cycloalkyl" refers to a stable, partially or fully saturated, monocyclic or polycyclic carbocyclic ring, which may include fused (when fused with an aryl or a heteroaryl ring, the cycloalkyl is bonded through a non-aromatic ring atom), bridged, or spiro ring systems. Representative cycloalkyls include, but are not limited to, cycloalkyls having from three to fifteen carbon atoms ($C_3$-$C_{15}$ cycloalkyl), from three to ten carbon atoms ($C_3$-$C_{10}$ cycloalkyl), from three to eight carbon atoms ($C_3$-$C_8$ cycloalkyl), from three to six carbon atoms ($C_3$-$C_6$ cycloalkyl), from three to five carbon atoms ($C_3$-$C_5$ cycloalkyl), or three to four carbon atoms ($C_3$-$C_4$ cycloalkyl). In some embodiments, the cycloalkyl is a 3- to 6-membered cycloalkyl. In some embodiments, the cycloalkyl is a 5- to 6-membered cycloalkyl. Monocyclic cycloalkyls include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example, cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocyclylalkyl, heteroaryl, and the like. In some embodiments, a cycloalkyl is optionally substituted with oxo, halogen, methyl, ethyl, —CN, —CF$_3$, —OH, —OMe, —NH$_2$, or —NO$_2$. In some embodiments, a cycloalkyl is optionally substituted with oxo, halogen, methyl, ethyl, —CN, —CF$_3$, —OH, or —OMe. In some embodiments, the cycloalkyl is optionally substituted with halogen.

"Deuteroalkyl" refers to an alkyl radical, as defined above, that is substituted by one or more deuteriums. In some embodiments, the alkyl is substituted with one deuterium. In some embodiments, the alkyl is substituted with one, two, or three deuteriums. In some embodiments, the alkyl is substituted with one, two, three, four, five, or six deuteriums. Deuteroalkyl include, for example, CD3, CH$_2$D, CHD$_2$, CH$_2$CD3, CD$_2$CD$_3$, CHDCD$_3$, CH$_2$CH$_2$D, or CH$_2$CHD$_2$. In some embodiments, the deuteroalkyl is CD3.

"Haloalkyl" refers to an alkyl radical, as defined above, that is substituted by one or more halogens. In some embodiments, the alkyl is substituted with one, two, or three halogens. In some embodiments, the alkyl is substituted with one, two, three, four, five, or six halogens. Haloalkyl include, for example, trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. In some embodiments, the haloalkyl is trifluoromethyl.

"Halo" or "halogen" refers to bromo, chloro, fluoro, or iodo. In some embodiments, halogen is fluoro or chloro. In some embodiments, halogen is fluoro.

"Heteroalkyl" refers to an alkyl group in which one or more skeletal atoms of the alkyl are selected from an atom other than carbon, e.g., oxygen, nitrogen (e.g., —NH—, —N(alkyl)-), sulfur, or combinations thereof. A heteroalkyl is attached to the rest of the molecule at a carbon atom of the heteroalkyl. In one aspect, a heteroalkyl is a $C_1$-$C_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, or combinations thereof wherein the heteroalkyl is attached to the rest of the molecule at a carbon atom of the heteroalkyl. Examples of such heteroalkyl are, for example, —CH$_2$OCH$_3$, —CH$_2$CH$_2$OCH$_3$, —CH$_2$CH$_2$OCH$_2$CH$_2$OCH$_3$, or —CH(CH$_3$)OCH$_3$. Unless stated otherwise specifically in the specification, a heteroalkyl is optionally substituted for example, with oxo, halogen, amino, nitrile, nitro, hydroxyl, alkyl, alkenyl, alkynyl, haloalkyl, alkoxy, aryl, cycloalkyl, heterocyclylalkyl, heteroaryl, and the like. In some embodiments, a heteroalkyl is optionally substituted with oxo, halogen, methyl, ethyl, —CN, —CF$_3$, —OH, —OMe, —NH$_2$, or —NO$_2$. In some embodiments, a heteroalkyl is optionally substituted with oxo, halogen, methyl, ethyl, —CN, —CF$_3$, —OH, or —OMe. In some embodiments, the heteroalkyl is optionally substituted with halogen.

"Hydroxyalkyl" refers to an alkyl radical, as defined above, that is substituted by one or more hydroxyls. In some embodiments, the alkyl is substituted with one hydroxyl. In some embodiments, the alkyl is substituted with one, two, or three hydroxyls. Hydroxyalkyl include, for example, hydroxymethyl, hydroxyethyl, hydroxypropyl, hydroxybutyl, or hydroxypentyl. In some embodiments, the hydroxyalkyl is hydroxymethyl.

"Heterocyclylalkyl" refers to a stable 3- to 24-membered partially or fully saturated ring radical comprising 2 to 23 carbon atoms and from one to 8 heteroatoms selected from the group consisting of nitrogen, oxygen, phosphorous, and sulfur. Unless stated otherwise specifically in the specification, the heterocyclylalkyl radical may be a monocyclic, bicyclic, tricyclic, or tetracyclic ring system, which may include fused (when fused with an aryl or a heteroaryl ring, the heterocyclylalkyl is bonded through a non-aromatic ring atom) or bridged ring systems; and the nitrogen, carbon, or sulfur atoms in the heterocyclylalkyl radical may be optionally oxidized; the nitrogen atom may be optionally quaternized.

Representative heterocyclylalkyls include, but are not limited to, heterocyclylalkyls having from two to fifteen carbon atoms ($C_2$-$C_{15}$ heterocyclylalkyl), from two to ten carbon atoms ($C_2$-$C_{10}$ heterocyclylalkyl), from two to eight carbon atoms ($C_2$-$C_5$ heterocyclylalkyl), from two to six carbon atoms ($C_2$-$C_6$ heterocyclylalkyl), from two to five carbon atoms ($C_2$-$C_5$ heterocyclylalkyl), or two to four carbon atoms ($C_2$-$C_4$ heterocyclylalkyl). In some embodiments, the heterocyclylalkyl is a 3- to 6-membered heterocyclylalkyl. In some embodiments, the cycloalkyl is a 5- to 6-membered heterocyclylalkyl. Examples of such heterocyclylalkyl radicals include, but are not limited to, aziridinyl, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocyclylalkyl also includes all ring forms of the carbohydrates, including but not limited to, the monosaccharides, the disaccharides, and the oligosaccharides. It is understood that when referring to the number of carbon atoms in a heterocyclylalkyl, the number of carbon atoms in the heterocyclylalkyl is not the same as the total number of atoms (including the heteroatoms) that make up the heterocyclylalkyl (i.e. skeletal atoms of the heterocyclylalkyl ring). Unless stated otherwise specifically in the specification, a heterocyclylalkyl is optionally substituted, for example, with oxo, halogen, amino, nitrile, nitro, hydroxyl, alkyl, alkenyl, alkynyl, haloalkyl, alkoxy, aryl, cycloalkyl, heterocyclylalkyl, heteroaryl, and the like. In some embodiments, a heterocyclylalkyl is optionally substituted with oxo, halogen, methyl, ethyl, —CN, —CF$_3$, —OH, —OMe, —NH$_2$, or —NO$_2$. In some embodiments, a heterocyclylalkyl is optionally substituted with oxo, halogen, methyl, ethyl, —CN, —CF$_3$, —OH, or —OMe. In some embodiments, the heterocyclylalkyl is optionally substituted with halogen.

"Heteroaryl" refers to a 5- to 14-membered ring system radical comprising hydrogen atoms, one to thirteen carbon atoms, one to six heteroatoms selected from the group consisting of nitrogen, oxygen, phosphorous, and sulfur, and at least one aromatic ring. The heteroaryl radical may be a monocyclic, bicyclic, tricyclic, or tetracyclic ring system, which may include fused (when fused with a cycloalkyl or heterocyclylalkyl ring, the heteroaryl is bonded through an aromatic ring atom) or bridged ring systems; and the nitrogen, carbon, or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl is optionally substituted, for example, with halogen, amino, nitrile, nitro, hydroxyl, alkyl, alkenyl, alkynyl, haloalkyl, alkoxy, aryl, cycloalkyl, heterocyclylalkyl, heteroaryl, and the like. In some embodiments, a heteroaryl is optionally substituted with halogen, methyl, ethyl, —CN, —CF$_3$, —OH, —OMe, —NH$_2$, or —NO$_2$. In some embodiments, a heteroaryl is optionally substituted with halogen, methyl, ethyl, —CN, —CF$_3$, —OH, or —OMe. In some embodiments, the heteroaryl is optionally substituted with halogen.

Any compound herein can be purified. A compound herein can be least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

Pharmaceutically Acceptable Salts.

The present disclosure provides the use of pharmaceutically-acceptable salts of any compound described herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt.

Metal salts can arise from the addition of an inorganic base to a compound of the present disclosure. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the present disclosure.

In some embodiments, the organic amine is trimethyl amine, triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrazole, pyrazolidine, pyrazoline, pyridazine, pyrimidine, imidazole, or pyrazine.

In some embodiments, an ammonium salt is a triethyl amine salt, trimethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrazole salt, a pyridazine salt, a pyrimidine salt, an imidazole salt, or a pyrazine salt.

Acid addition salts can arise from the addition of an acid to a compound of the present disclosure. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisic acid, gluconic acid, glucuronic acid, saccharic acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisate salt, a gluconate salt, a glucuronate salt, a saccharate salt, a formate salt, a benzoate salt, a glutamate salt, a pantothenate salt, an acetate salt, a propionate salt, a butyrate salt, a fumarate salt, a succinate salt, a methanesulfonate salt, an ethanesulfonate salt, a benzenesulfonate salt, a p-toluenesulfonate salt, a citrate salt, an oxalate salt, or a maleate salt.

Pharmaceutical Compositions.

According to another embodiment, the present disclosure provides a composition comprising a compound of the present disclosure and a pharmaceutically acceptable carrier, adjuvant, or vehicle. The amount of compound in the composition is an amount effective to treat the relevant disease, disorder, or condition in a patient in need thereof (an "effective amount"). In some embodiments, a composition of the present disclosure is formulated for oral administration to a patient.

The term "pharmaceutically acceptable carrier, adjuvant, or vehicle" refers to a non-toxic carrier, adjuvant, or vehicle that does not destroy the pharmacological activity of the agent with which it is formulated. Pharmaceutically acceptable carriers, adjuvants or vehicles that may be used in the disclosed compositions include, but are not limited to, ion exchangers, alumina, stearates such as aluminum stearate, lecithin, serum proteins such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present disclosure may be administered orally, parenterally, enterally, intracistemally, intraperitoneally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the composition is administered orally, intraperitoneally, or intravenously. In some embodiments, the composition is a transmucosal formulation. Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

To aid in delivery of the composition, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, may also be added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, pharmaceutically acceptable compositions may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

In some embodiments, the pharmaceutically acceptable composition is formulated for oral administration. Such formulations may be administered with or without food. In some embodiments, the pharmaceutically acceptable composition is administered without food. In other embodiments, the pharmaceutically acceptable composition is administered with food.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present disclosure, it can be desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing a compound of this disclosure with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinyl pyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

Therapeutic agents can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this disclosure include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this disclosure.

Additionally, the present disclosure contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Compounds of the Disclosure.

Described herein are compounds that can be metabolically converted to N,N-dimethyltryptamine or analogs thereof upon administration to a subject. In certain embodiments, the compounds described herein are useful in the treatment of conditions associated with any brain disease.

In some embodiments, the compounds described herein are prodrugs of dimethyltryptamine (DMT) or prodrugs of 5-MeO-DMT. In some embodiments, the compounds described herein are psychedelics with improved pharmacokinetic properties as compared to DMT or 5-MeO-DMT (e.g., longer half life, longer tmax, and/or longer tlast, etc.).

In one aspect, the present disclosure provides a compound of Formula (I), or a pharmaceutically acceptable salt thereof:

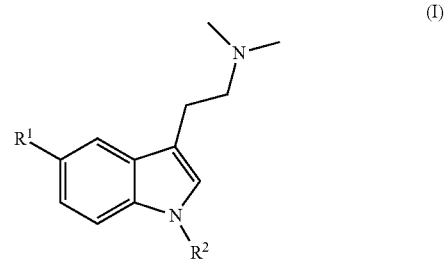

wherein:
$R^1$ is methoxy or hydrogen;
$R^2$ is —C(O)OR$^3$, —C(O)R$^4$, —CH(R$^5$)OR$^6$, —C(O)OCH(R$^5$)OC(O)R$^6$, —C(O)OCH(R$^5$)OC(O)OR$^6$, —CH(R$^5$)C(O)R$^6$, —CH(R$^5$)OC(O)R$^6$, —CH(R$^5$)OC(O)OR$^6$, —S(O)$_2$OR$^7$, —P(O)ORR[N(R$^9$)R$^{10}$], —P(O)[N(R$^9$)R$^{10}$][N(R$^{11}$)R$^{12}$], —C(O)N(R$^9$)R$^{10}$, —P(O)OR$^{11}$(OR$^{12}$), —CH(R$^5$)OP(O)OR$^8$[N(R$^9$)R$^{10}$], or —CH(R$^5$)OP(O)OR$^{11}$ (OR$^{12}$);
each of $R^3$, $R^4$, $R^5$, $R^6$, $R^7$, and $R^8$ is independently hydrogen, alkyl, heteroalkyl, cycloalkyl, heterocyclylalkyl, aryl, or heteroaryl, wherein each alkyl, heteroalkyl, cycloalkyl, heterocyclylalkyl, aryl, and heteroaryl is independently unsubstituted or substituted with one or more $R^A$; each of $R^9$ and $R^{10}$ is independently alkyl, heteroalkyl, cycloalkyl, heterocyclylalkyl, aryl, heteroaryl, or hydrogen, wherein each alkyl, heteroalkyl, cycloalkyl, heterocyclylalkyl, aryl, and heteroaryl is independently unsubstituted or substituted with one or more $R^A$, or $R^9$ and $R^{10}$ together with the atom to which they are attached form a heterocyclylalkyl ring that is unsubstituted or substituted with one or more $R^A$;
each of $R^{11}$ and $R^{12}$ is independently alkyl, heteroalkyl, cycloalkyl, heterocyclylalkyl, aryl, heteroaryl, or hydrogen, wherein each alkyl, heteroalkyl, cycloalkyl, heterocyclylalkyl, aryl, and heteroaryl is independently unsubstituted or substituted with one or more $R^A$, or $R^{11}$ and $R^{12}$ together with the atoms to which they are attached form a heterocyclylalkyl ring that is unsubstituted or substituted with one or more $R^A$;

each $R^A$ is independently alkyl, heteroalkyl, cycloalkyl, heterocyclylalkyl, aryl, heteroaryl, an amino acid side chain, —$OR^{13}$, —$N(R^{18})R^{19}$, —$C(O)OR^{13}$, —$N(R^{13})C(O)OR^{14}$, —$N(R^{13})C(O)R^{14}$, —$C(O)R^{14}$, —$OC(O)R^{15}$, —$OC(O)OR^{16}$, —$OP(O)OR^{17}[N(R^{18})R^{19}]$, —$C(O)N(R^{18})R^{19}$, —$OC(O)N(R^{18})R^{19}$, or —$OP(O)OR^{20}$ ($OR^{21}$), wherein each alkyl, heteroalkyl, cycloalkyl, heterocyclylalkyl, amino acid side chain, aryl, and heteroaryl is independently unsubstituted or substituted with one or more alkyl, aryl, halogen, —$OR^{13}$, —$NR(R^{18})R^{19}$, —$C(O)R^4$, —$OC(O)R^{15}$, —$OC(O)OR^{16}$, or —$OC(O)N(R^{18})R^{19}$;

each of $R^{13}$, $R^{14}$, $R^{15}$, $R^{16}$, or $R^{17}$ is independently alkyl, heteroalkyl, cycloalkyl, heterocyclylalkyl, aryl, heteroaryl, or hydrogen, wherein each alkyl, heteroalkyl, cycloalkyl, heterocyclylalkyl, aryl, and heteroaryl is independently unsubstituted or substituted with one or more $R^B$;

each of $R^{18}$ and $R^{19}$ is independently alkyl, heteroalkyl, cycloalkyl, heterocyclylalkyl, aryl, heteroaryl, or hydrogen, wherein each alkyl, heteroalkyl, cycloalkyl, heterocyclylalkyl, aryl, and heteroaryl is independently unsubstituted or substituted with one or more $R^B$; or $R^{18}$ and $R^{19}$ together with the atom to which they are attached form a heterocyclylalkyl ring that is unsubstituted or substituted with one or more $R^B$;

each of $R^{20}$ and $R^{21}$ is independently alkyl, alkyl, heteroalkyl, cycloalkyl, heterocyclylalkyl, aryl, heteroaryl, or hydrogen, wherein each alkyl, heteroalkyl, cycloalkyl, heterocyclylalkyl, aryl, and heteroaryl is independently unsubstituted or substituted with one or more $R^B$, or $R^{20}$ and $R^{21}$ together with the atoms to which they are attached form a heterocyclylalkyl ring that is unsubstituted or substituted with one or more $R^B$; and each $R^B$ is independently halogen, amino, cyano, hydroxyl, alkyl, heteroalkyl, cycloalkyl, heterocyclylalkyl, aryl, heteroaryl, arylalkyl, —$C(O)CH_3$, —$C(O)Ph$, or heteroarylalkyl, wherein each cycloalkyl, heterocyclylalkyl, aryl, and heteroaryl is independently unsubstituted or substituted with one or more halogen, amino, cyano, hydroxyl, alkyl, acetyl, or benzoyl.

In some embodiments is a compound of Formula (I) or a pharmaceutically acceptable salt thereof, wherein $R^2$ is $R^2$ is —$C(O)OR^3$, —$C(O)R^4$, —$CH(R^5)OR^6$, —$C(O)OCH(R^5)OC(O)R^6$, —$C(O)OCH(R^5)OC(O)OR^6$, —$CH(R^5)C(O)R^6$, —$S(O)_2OR^7$, —$P(O)OR^8[N(R^9)R^{10}]$, —$C(O)N(R^9)R^{10}$, —$P(O)OR^{11}$ ($OR^{12}$), —$CH(R^5)OP(O)OR^8[N(R^9)R^{10}]$, or —$CH(R^5)OP(O)OR^{11}$ ($OR^{12}$).

In some embodiments is a compound of Formula (I) or a pharmaceutically acceptable salt thereof, wherein:
each of $R^3$, $R^4$, $R^6$, $R^7$, and $R^8$ is independently alkyl, heteroalkyl, cycloalkyl, heterocyclylalkyl, aryl, or heteroaryl; and
each $R^5$ is independently hydrogen, alkyl, heteroalkyl, cycloalkyl, heterocyclylalkyl, aryl, or heteroaryl,
wherein each alkyl, heteroalkyl, cycloalkyl, heterocyclylalkyl, aryl, and heteroaryl is independently unsubstituted or substituted with one or more $R^A$.

In some embodiments is a compound of Formula (I) or a pharmaceutically acceptable salt thereof, each of $R^3$, $R^4$, $R^5$, $R^6$, $R^7$, and $R^8$ is independently alkyl, heteroalkyl, cycloalkyl, heterocyclylalkyl, aryl, or heteroaryl, wherein each alkyl, heteroalkyl, cycloalkyl, heterocyclylalkyl, aryl, and heteroaryl is independently unsubstituted or substituted with one or more $R^A$.

In some embodiments is a compound of Formula (I) or a pharmaceutically acceptable salt thereof, wherein $R^2$ is —$C(O)OR^3$. In some embodiments is a compound of Formula (I) or a pharmaceutically acceptable salt thereof, wherein $R^2$ is —$C(O)OR^3$, wherein $R^3$ is alkyl. In some embodiments is a compound of Formula (I) or a pharmaceutically acceptable salt thereof, wherein $R^2$ is —$C(O)OR^3$, wherein $R^3$ is alkyl that is unsubstituted. In some embodiments is a compound of Formula (I) or a pharmaceutically acceptable salt thereof, wherein $R^2$ is —$C(O)OR^3$, wherein $R^3$ is heteroalkyl. In some embodiments is a compound of Formula (I) or a pharmaceutically acceptable salt thereof, wherein $R^2$ is —$C(O)OR^3$, wherein $R^3$ is heteroalkyl that is unsubstituted. In some embodiments is a compound of Formula (I) or a pharmaceutically acceptable salt thereof, wherein $R^2$ is —$C(O)OR^3$, wherein $R^3$ is ethyl.

In some embodiments is a compound of Formula (I) or a pharmaceutically acceptable salt thereof, wherein $R^2$ is —$C(O)OR^3$, wherein $R^3$ is alkyl. In some embodiments is a compound of Formula (I) or a pharmaceutically acceptable salt thereof, wherein $R^2$ is —$C(O)OR^3$, wherein $R^3$ is alkyl substituted with heterocyclylalkyl. In some embodiments is a compound of Formula (I) or a pharmaceutically acceptable salt thereof, wherein $R^2$ is —$C(O)OR^3$, wherein $R^3$ is alkyl substituted with —$N(R^{13})C(O)OR^{14}$. In some embodiments is a compound of Formula (I) or a pharmaceutically acceptable salt thereof, wherein $R^{13}$ is hydrogen or alkyl. In some embodiments is a compound of Formula (I) or a pharmaceutically acceptable salt thereof, wherein $R^{14}$ is alkyl, aryl, or heteroaryl.

In some embodiments is a compound of Formula (I) or a pharmaceutically acceptable salt thereof, wherein $R^2$ is —$C(O)OR^3$, wherein $R^3$ is heteroalkyl. In some embodiments is a compound of Formula (I) or a pharmaceutically acceptable salt thereof, wherein $R^2$ is —$C(O)OR^3$, wherein $R^3$ is heteroalkyl that is substituted with cycloalkyl. In some embodiments is a compound of Formula (I) or a pharmaceutically acceptable salt thereof, wherein $R^2$ is —$C(O)OR^3$, wherein $R^3$ is heteroalkyl that is substituted with alkyl.

In some embodiments is a compound of Formula (I) or a pharmaceutically acceptable salt thereof, wherein $R^2$ is —$C(O)OR^3$, wherein $R^3$ is cycloalkyl. In some embodiments is a compound of Formula (I) or a pharmaceutically acceptable salt thereof, wherein $R^2$ is —$C(O)OR^3$, wherein $R^3$ is cycloalkyl that is substituted with $N(R^{18})R^{19}$. In some embodiments is a compound of Formula (I) or a pharmaceutically acceptable salt thereof, wherein each of $R^{18}$ and $R^{19}$ is hydrogen, alkyl, or heteroalkyl. In some embodiments is a compound of Formula (I) or a pharmaceutically acceptable salt thereof, wherein $R^{18}$ and $R^{19}$ together with the atom to which they are attached form a heterocyclylalkyl ring. In some embodiments is a compound of Formula (I) or a pharmaceutically acceptable salt thereof, wherein $R^{18}$ and $R^{19}$ together with the atom to which they are attached form a heterocyclylalkyl ring. In some embodiments is a compound of Formula (I) or a pharmaceutically acceptable salt thereof, wherein $R^{18}$ and $R^{19}$ together with the atom to which they are attached form a heterocyclylalkyl ring that is unsubstituted.

In some embodiments is a compound of Formula (I) or a pharmaceutically acceptable salt thereof, wherein $R^2$ is —$C(O)OR^3$, wherein $R^3$ is alkyl. In some embodiments is a compound of Formula (I) or a pharmaceutically acceptable salt thereof, wherein $R^2$ is —$C(O)OR^3$, wherein $R^3$ is alkyl substituted with $C(O)R^{14}$, wherein $R^{14}$ is heteroaryl substituted with one or more $R^B$.

In some embodiments is a compound of Formula (I) or a pharmaceutically acceptable salt thereof, wherein $R^2$ is —C(O)OR³, wherein $R^3$ is alkyl substituted with C(O)R¹⁴, wherein $R^{14}$ is heteroaryl. In some embodiments is a compound of Formula (I) or a pharmaceutically acceptable salt thereof, wherein $R^2$ is —C(O)OR³, wherein $R^3$ is alkyl substituted with C(O)R¹⁴, wherein $R^{14}$ is heterocyclylalkyl. In some embodiments is a compound of Formula (I) or a pharmaceutically acceptable salt thereof, wherein $R^2$ is —C(O)OR³, wherein $R^3$ is alkyl substituted with C(O)R¹⁴, wherein $R^{14}$ is heteroaryl that is unsubstituted. In some embodiments is a compound of Formula (I) or a pharmaceutically acceptable salt thereof, wherein $R^2$ is —C(O)OR³, wherein $R^3$ is alkyl substituted with C(O)R¹⁴, wherein $R^{14}$ is heterocyclylalkyl that is unsubstituted.

In some embodiments is a compound of Formula (I) or a pharmaceutically acceptable salt thereof, wherein $R^2$ is —C(O)R⁴, wherein $R^4$ is heterocyclylalkyl.

In some embodiments is a compound of Formula (I) or a pharmaceutically acceptable salt thereof, wherein $R^2$ is —C(O)N(R⁹)R¹⁰. In some embodiments is a compound of Formula (I) or a pharmaceutically acceptable salt thereof, $R^4$ and $R^5$ together with the atom to which they are attached form a heterocyclylalkyl ring that is unsubstituted or substituted with one or more $R^4$.

In some embodiments is a compound of Formula (I) or a pharmaceutically acceptable salt thereof, $R^4$ and $R^5$ together with the atom to which they are attached form a heterocyclylalkyl ring that is substituted with one or more $R^4$.

In some embodiments is a compound of Formula (I) having the structure of Formula (Ia), or a pharmaceutically acceptable salt thereof:

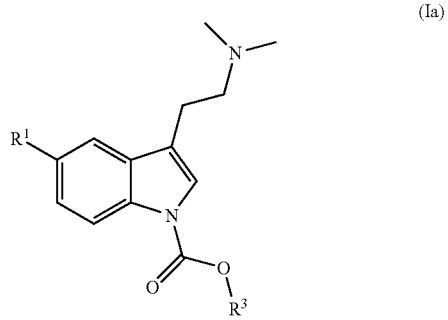

(Ia)

wherein $R^1$ is methoxy or hydrogen, and $R^3$ is alkyl, cycloalkyl, aryl, heteroaryl, heteroalkyl, or heterocyclylalkyl, each of which is independently unsubstituted or substituted with one or more $R^4$. In some embodiments is a compound of Formula (I) or (Ia), or a pharmaceutically acceptable salt thereof, wherein $R^3$ is alkyl or heteroalkyl. In some embodiments is a compound of Formula (I) or (Ia), or a pharmaceutically acceptable salt thereof, wherein $R^3$ is unsubstituted alkyl or unsubstituted heteroalkyl. In some embodiments is a compound of Formula (I) or (La), or a pharmaceutically acceptable salt thereof, wherein $R^3$ is alkyl. In some embodiments is a compound of Formula (I) or (Ia), or a pharmaceutically acceptable salt thereof, wherein $R^3$ is unsubstituted alkyl. In some embodiments is a compound of Formula (I) or (Ia), or a pharmaceutically acceptable salt thereof, wherein $R^1$ is methoxy, and $R^3$ is alkyl. In some embodiments is a compound of Formula (I) or (Ia), or a pharmaceutically acceptable salt thereof, wherein $R^1$ is methoxy, and $R^3$ is unsubstituted alkyl. In some embodiments is a compound of Formula (I) or (Ia), or a pharmaceutically acceptable salt thereof, wherein $R^1$ is hydrogen, and $R^3$ is alkyl. In some embodiments is a compound of Formula (I) or (Ia), or a pharmaceutically acceptable salt thereof, wherein $R^1$ is hydrogen, and $R^3$ is unsubstituted alkyl.

In some embodiments is a compound of Formula (I) or (Ia), or a pharmaceutically acceptable salt thereof, wherein $R^3$ is heteroalkyl. In some embodiments is a compound of Formula (I) or (Ia), or a pharmaceutically acceptable salt thereof, wherein $R^3$ is unsubstituted heteroalkyl. In some embodiments is a compound of Formula (I) or (Ia), or a pharmaceutically acceptable salt thereof, wherein $R^3$ is methyl, ethyl, n-propyl, isopropyl, n-butyl, tert-butyl, isobutyl, n-pentyl, or 3-methyl-1-butyl. In some embodiments is a compound of Formula (I) or (Ia), or a pharmaceutically acceptable salt thereof, wherein $R^3$ is methyl, ethyl, n-propyl, isopropyl, n-butyl, isobutyl, n-pentyl, or 3-methyl-1-butyl. In some embodiments is a compound of Formula (I) or (Ia), or a pharmaceutically acceptable salt thereof, wherein $R^3$ is aryl. In some embodiments is a compound of Formula (I) or (Ia), or a pharmaceutically acceptable salt thereof, wherein $R^3$ is phenyl. In some embodiments is a compound of Formula (I) or (Ta), or a pharmaceutically acceptable salt thereof, wherein $R^3$ is heterocyclylalkyl. In some embodiments is a compound of Formula (I) or (Ia), or a pharmaceutically acceptable salt thereof, wherein $R^3$ is 2-pyridyl, 3-pyridyl, 4-pyridyl, 2-pyrimidyl, 4-pyrimidyl, 5-pyrimidyl, or 6-pyrimidyl. In some embodiments is a compound of Formula (I) or (Ta), or a pharmaceutically acceptable salt thereof, wherein $R^3$ is ethyl. In some embodiments is a compound of Formula (I) or (Ia), or a pharmaceutically acceptable salt thereof, wherein $R^1$ is hydrogen, and $R^3$ is ethyl. In some embodiments is a compound of Formula (I) or (Ia), or a pharmaceutically acceptable salt thereof, wherein $R^1$ is methoxy, and $R^3$ is ethyl. In some embodiments is a compound of Formula (I) or (Ia), or a pharmaceutically acceptable salt thereof, wherein $R^3$ alkyl substituted with heteroaryl. In some embodiments is a compound of Formula (I) or (Ia), or a pharmaceutically acceptable salt thereof, wherein $R^3$ is

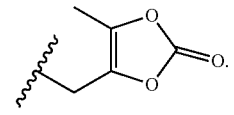 [SMILES: *Cc1oc(=O)oc1C]

In some embodiments is a compound of Formula (I) or (Ia), or a pharmaceutically acceptable salt thereof, wherein $R^1$ is methoxy and $R^3$ is

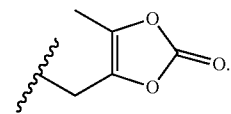 [SMILES: *Cc1oc(=O)oc1C]

In some embodiments is a compound of Formula (I) or (Ia), or a pharmaceutically acceptable salt thereof, wherein $R^1$ is hydrogen and $R^3$ is

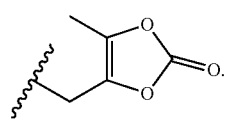

In some embodiments is a compound of Formula (I) or (Ia), or a pharmaceutically acceptable salt thereof, wherein the compound is:

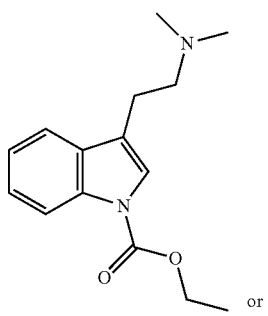

or

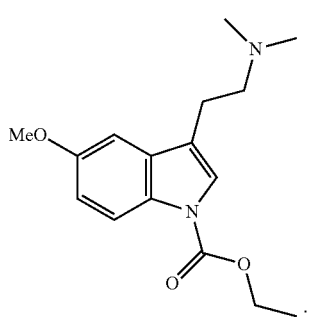

.

In some embodiments is a compound of Formula (I) or (Ia), or a pharmaceutically acceptable salt thereof, wherein the compound is:

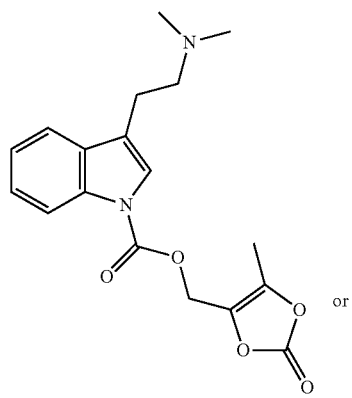

or

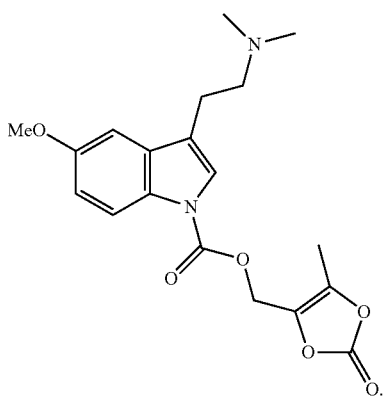

.

In some embodiments is a compound of Formula (I) or (Ia), or a pharmaceutically acceptable salt thereof, wherein the compound is:

,

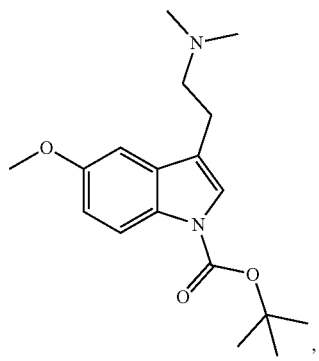

,

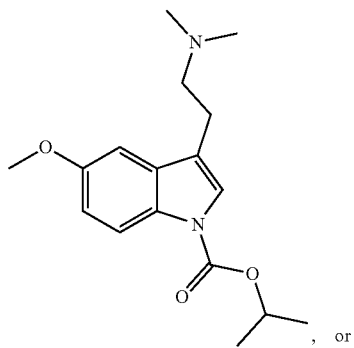

, or

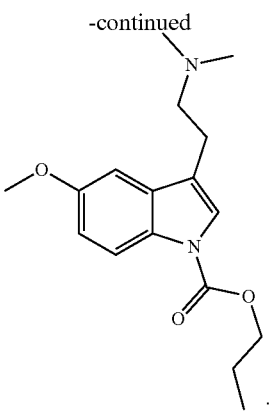

In some embodiments is a compound of Formula (I) or (Ia), or a pharmaceutically acceptable salt thereof, wherein the compound is:

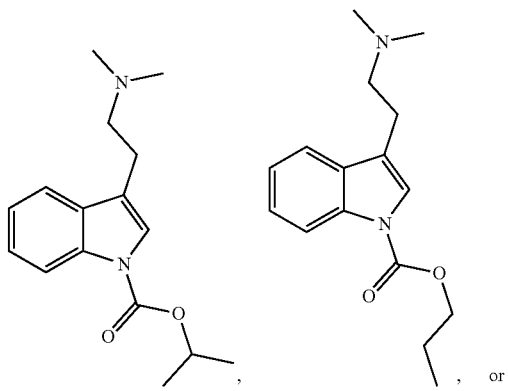

In some embodiments is a compound of Formula (I) or (Ia), or a pharmaceutically acceptable salt thereof, provided that when $R^1$ is hydrogen, then $R^3$ is not tert-butyl. In some embodiments is a compound of Formula (I) or (Ia), or a pharmaceutically acceptable salt thereof, wherein if $R^1$ is hydrogen and $R^3$ is alkyl, then $R^3$ is bound to the atom to which it is attached via a primary or secondary carbon.

In some embodiments is a compound of Formula (I) having the structure of Formula (Ib), or a pharmaceutically acceptable salt thereof:

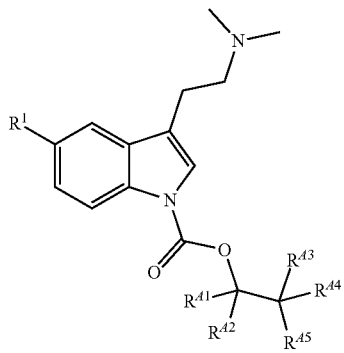

wherein:
$R^1$ is methoxy or hydrogen;
each of $R^{A1}$, $R^{A2}$, $R^{A3}$, and $R^{A4}$ is independently hydrogen or alkyl that is independently unsubstituted or substituted with one or more alkyl, aryl, halogen, —$OR^{13}$, —$NR(R^{18})R^{19}$, —$C(O)R^{14}$, —$OC(O)R^5$, —$OC(O)OR^{16}$, or —$OC(O)N(R^{18})R^{19}$, and
$R^{A5}$ is heteroalkyl, heterocyclylalkyl, heteroaryl, or —$C(O)OR^{13}$, —$N(R^{13})C(O)OR^{14}$, —$N(R^{13})C(O)R^{14}$, —$C(O)R^{14}$, —$OC(O)R^{15}$, or —$OC(O)OR^{16}$, wherein each heteroalkyl, heterocyclylalkyl, and heteroaryl is independently unsubstituted or substituted with one or more alkyl, aryl, halogen, —$OR^{13}$, —$NR(R^{18})R^{19}$, —$C(O)R^{14}$, —$OC(O)R^{15}$, —$OC(O)OR^{16}$, or —$OC(O)N(R^{18})R^{19}$. In some embodiments is a compound of Formula (Ib) or a pharmaceutically acceptable salt thereof, wherein one of $R^{A1}$, $R^{A2}$, $R^{A3}$, and $R^{A4}$ is alkyl, and each of $R^{A1}$, $R^{A2}$, $R^{A3}$, and $R^{A4}$ that is not alkyl is hydrogen. In some embodiments is a compound of Formula (Ib) or a pharmaceutically acceptable salt thereof, wherein two of $R^{A1}$, $R^{A2}$, $R^{A3}$, and $R^{A4}$ is alkyl, and each of $R^{A1}$, $R^{A2}$, $R^{A3}$, and $R^{A4}$ that is not alkyl is hydrogen. In some embodiments is a compound of Formula (Ib) or a pharmaceutically acceptable salt thereof, wherein each of $R^{A1}$, $R^{A2}$, $R^{A3}$, and $R^{A4}$ is hydrogen. In some embodiments is a compound of Formula (Ib) or a pharmaceutically acceptable salt thereof, wherein one of $R^{A1}$, $R^{A2}$, $R^{A3}$, and $R^{A4}$ is alkyl, and each of $R^{A1}$, $R^{A2}$, $R^{A3}$, and $R^{A4}$ that is not alkyl is hydrogen, wherein the alkyl is methyl, ethyl, isopropyl, or tert-butyl. In some embodiments is a compound of Formula (Ib) or a pharmaceutically acceptable salt thereof, wherein two of $R^{A1}$, $R^{A2}$, $R^{A3}$, and $R^{A4}$ is alkyl, and each of $R^{A1}$, $R^{A2}$, $R^{A3}$, and $R^{A4}$ that is not alkyl is hydrogen, wherein each alkyl is independently methyl, ethyl, isopropyl, or tert-butyl. In some embodiments is a compound of Formula (Ib) or a pharmaceutically acceptable salt thereof, wherein $R^{A5}$ is heterocyclylalkyl. In some embodiments is a compound of Formula (Ib) or a pharmaceutically acceptable salt thereof, wherein $R^{A5}$ is —$OC(O)R^{15}$. In some embodiments is a compound of Formula (Ib) or a pharmaceutically acceptable salt thereof, wherein $R^{A5}$ is —$OC(O)R^{15}$, wherein $R^5$ is alkyl. In some embodiments is a compound of Formula (Ib) or a pharmaceutically acceptable salt thereof, wherein $R^{A5}$ is —$OC(O)R^{15}$, wherein $R^{15}$ is methyl, ethyl, isopropyl, n-propyl, tert-butyl, isobutyl, or n-butyl. In some embodiments is a compound of Formula (Ib) or a pharmaceutically acceptable salt thereof, wherein $R^{A5}$ is —$OC(O)R^{15}$, wherein $R^{15}$ is isobutyl.

In some embodiments is a compound of Formula (I) having the structure of Formula (Ib-1), or a pharmaceutically acceptable salt thereof:

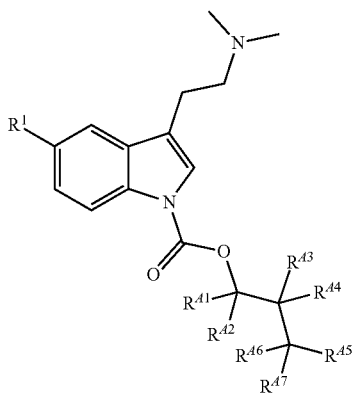

(Ib-1)

wherein:
R¹ is methoxy or hydrogen;
each of $R^{A1}$, $R^{A2}$, $R^{A3}$, $R^{A4}$, $R^{A6}$, and $R^{A7}$ is independently hydrogen or alkyl that is independently unsubstituted or substituted with one or more alkyl, aryl, halogen, —OR¹³, —NR(R¹⁸)R¹⁹, —C(O)R⁴, —OC(O)R⁵, —OC(O)OR¹⁶, or —OC(O)N(R¹⁸)R¹⁹, and $R^{A5}$ is heteroalkyl, heterocyclylalkyl, heteroaryl, or —C(O)OR³, —N(R¹³)C(O)OR¹⁴, —N(R¹³)C(O)R¹⁴, —C(O)R¹⁴, —OC(O)R¹⁵, or —OC(O)OR¹⁶, wherein each heteroalkyl, heterocyclylalkyl, and heteroaryl is independently unsubstituted or substituted with one or more alkyl, aryl, halogen, —OR¹³, —NR(R¹⁸)R¹⁹, —C(O)R⁴, —OC(O)R⁵, —OC(O)OR¹⁶, or —OC(O)N(R¹⁸)R¹⁹.

In some embodiments is a compound of Formula (Ib-1) or a pharmaceutically acceptable salt thereof, wherein one of $R^{A1}$, $R^{A2}$, $R^{A3}$, $R^{A4}$, $R^{A6}$, and $R^{A7}$ is alkyl, and each of $R^{A1}$, $R^{A2}$, $R^{A3}$, $R^{A4}$, $R^{A6}$, and $R^{A7}$ that is not alkyl is hydrogen. In some embodiments is a compound of Formula (Ib-1) or a pharmaceutically acceptable salt thereof, wherein two of $R^{A1}$, $R^{A2}$, $R^{A3}$, $R^{A4}$, $R^{A6}$, and $R^{A7}$ is alkyl, and each of RAI, $R^{A2}$, $R^{A3}$, $R^{A4}$, $R^{A6}$, and $R^{A7}$ that is not alkyl is hydrogen. In some embodiments is a compound of Formula (Ib-1) or a pharmaceutically acceptable salt thereof, wherein each of $R^{A1}$, $R^{A2}$, $R^{A3}$, $R^{A4}$, $R^{A6}$, and $R^{A7}$ is hydrogen. In some embodiments is a compound of Formula (Ib-1) or a pharmaceutically acceptable salt thereof, wherein one of $R^{A1}$, $R^{A2}$, $R^{A3}$, $R^{A4}$, $R^{A6}$, and $R^{A7}$ is alkyl, and each of $R^{A1}$, $R^{A2}$, $R^{A3}$, $R^{A4}$, $R^{A6}$, and $R^{A7}$ that is not alkyl is hydrogen, wherein the alkyl is methyl, ethyl, isopropyl, or tert-butyl. In some embodiments is a compound of Formula (Ib-1) or a pharmaceutically acceptable salt thereof, wherein $R^{A3}$ and $R^{A4}$ are each independently alkyl, and each of $R^{A1}$, $R^{A2}$, $R^{A6}$, and $R^{A7}$ is hydrogen In some embodiments is a compound of Formula (Ib-1) or a pharmaceutically acceptable salt thereof, wherein two of $R^{A1}$, $R^{A2}$, $R^{A3}$, $R^{A4}$, $R^{A6}$, and $R^{A7}$ is alkyl, and each of $R^{A1}$, $R^{A2}$, $R^{A3}$, $R^{A4}$, $R^{A6}$, and $R^{A7}$ that is not alkyl is hydrogen, wherein each alkyl is independently methyl, ethyl, isopropyl, or tert-butyl. In some embodiments is a compound of Formula (Ib-1) or a pharmaceutically acceptable salt thereof, wherein $R^{A5}$ is heterocyclylalkyl. In some embodiments is a compound of Formula (Ib-1) or a pharmaceutically acceptable salt thereof, wherein $R^{A5}$ is —OC(O)R¹⁵. In some embodiments is a compound of Formula (Ib-1) or a pharmaceutically acceptable salt thereof, wherein $R^{A5}$ is —OC(O)R⁵, wherein R¹⁵ is alkyl. In some embodiments is a compound of Formula (Ib-1) or a pharmaceutically acceptable salt thereof, wherein $R^{A5}$ is —OC(O)R¹⁵, wherein R⁵ is methyl, ethyl, isopropyl, n-propyl, tert-butyl, isobutyl, or n-butyl. In some embodiments is a compound of Formula (Ib-1) or a pharmaceutically acceptable salt thereof, wherein $R^{A5}$ is —OC(O)R¹⁵, wherein R¹⁵ is isobutyl.

In some embodiments is a compound of Formula (I) or (Ib-1), or a pharmaceutically acceptable salt thereof, wherein the compound is:

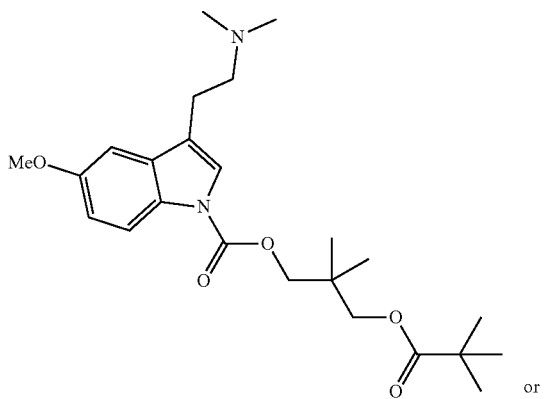

or

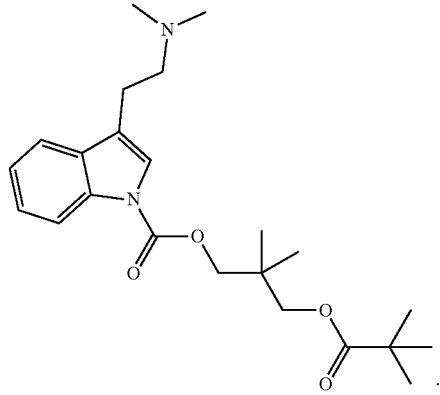

In some embodiments is a compound of Formula (I) or (Ib) having the structure of Formula (Ib1), or a pharmaceutically acceptable salt thereof:

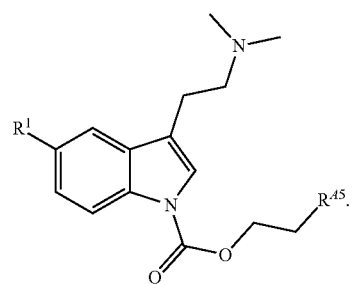

(Ib1)

In some embodiments is a compound of Formula (Ib) or (Ib1), or a pharmaceutically acceptable salt thereof, wherein $R^{A5}$ is heteroalkyl or heterocyclylalkyl. In some embodiments is a compound of Formula (Ib) or (Ib1), or a pharmaceutically acceptable salt thereof, wherein $R^{A}S$ is heteroalkyl. In some embodiments is a compound of Formula (Ib) or (Ib1), or a pharmaceutically acceptable salt thereof, wherein $R^{A5}$ is heteroalkyl that is unsubstituted. In some embodiments is a compound of Formula (Ib) or (Ib1), or a pharmaceutically acceptable salt thereof, wherein $R^{45}$ is heterocyclylalkyl. In some embodiments is a compound of Formula (Ib) or (Ib1), or a pharmaceutically acceptable salt thereof, wherein $R^{45}$ is heterocyclylalkyl that is unsubstituted. In some embodiments is a compound of Formula (Ib) or (Ib1), or a pharmaceutically acceptable salt thereof, wherein $R^{45}$ is methoxy, ethoxy, cyclopropyloxy, methylamino, or dimethylamino. In some embodiments is a compound of Formula (Ib) or (Ib1), or a pharmaceutically acceptable salt thereof, wherein $R^{45}$ is

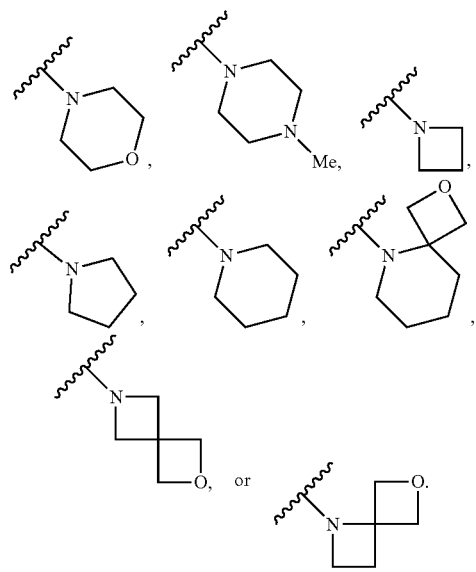

In some embodiments is a compound of Formula (Ib) or (Ib1), or a pharmaceutically acceptable salt thereof, wherein $R^{45}$ is —OC(O)$R^{15}$.

In some embodiments is a compound of Formula (Ib) or (Ib1), or a pharmaceutically acceptable salt thereof, wherein $R^{45}$ is —OC(O)$R^5$, wherein $R^{15}$ is alkyl, cycloalkyl, aryl, or heteroaryl. In some embodiments is a compound of Formula (Ib) or (Ib1), or a pharmaceutically acceptable salt thereof, wherein $R^{45}$ is —OC(O)$R^{15}$, wherein $R^{15}$ is methyl, ethyl, n-propyl, isopropyl, n-butyl, tert-butyl, n-pentyl, or 3-methyl-1-butyl. In some embodiments is a compound of Formula (Ib) or (Ib1), or a pharmaceutically acceptable salt thereof, wherein $R^{45}$ is —OC(O)$R^{15}$, wherein $R^5$ is phenyl. In some embodiments is a compound of Formula (Ib) or (Ib1), or a pharmaceutically acceptable salt thereof, wherein $R^{45}$ is —OC(O)$R^{15}$, wherein $R^{15}$ is 2-pyridyl, 3-pyridyl, 4-pyridyl, 2-pyrimidyl, 4-pyrimidyl, 5-pyrimidyl, or 6-pyrimidyl.

In some embodiments is a compound of Formula (Ib) or (Ib1), or a pharmaceutically acceptable salt thereof, wherein $R^{45}$ is —N($R^{13}$)C(O)O$R^{14}$. In some embodiments is a compound of Formula (Ib) or (Ib1), or a pharmaceutically acceptable salt thereof, wherein $R^{45}$ is —N($R^{13}$)C(O)O$R^{14}$, wherein $R^{13}$ is hydrogen or alkyl. In some embodiments is a compound of Formula (Ib) or (Ib1), or a pharmaceutically acceptable salt thereof, wherein $R^{45}$ is —N($R^{13}$)C(O)O$R^{14}$, wherein $R^{13}$ is hydrogen. In some embodiments is a compound of Formula (Ib) or (Ib1), or a pharmaceutically acceptable salt thereof, wherein $R^{45}$ is —N($R^{13}$)C(O)O$R^{14}$, wherein $R^{13}$ is alkyl. In some embodiments is a compound of Formula (Ib) or (Ib1), or a pharmaceutically acceptable salt thereof, wherein $R^{45}$ is —N($R^{13}$)C(O)O$R^{14}$, wherein $R^{13}$ is unsubstituted alkyl. In some embodiments is a compound of Formula (Ib) or (Ib1), or a pharmaceutically acceptable salt thereof, wherein $R^{45}$ is —N($R^{13}$)C(O)O$R^{14}$, wherein $R^{14}$ is methyl, ethyl, n-propyl, isopropyl, n-butyl, tert-butyl, n-pentyl, or 3-methyl-1-butyl.

In some embodiments is a compound of Formula (Ib) or (Ib1), or a pharmaceutically acceptable salt thereof, wherein $R^{45}$ is —N($R^{13}$)C(O)$R^{14}$. In some embodiments is a compound of Formula (Ib) or (Ib1), or a pharmaceutically acceptable salt thereof, wherein $R^{45}$ is —N($R^{13}$)C(O)$R^{14}$, wherein $R^{13}$ is hydrogen or alkyl. In some embodiments is a compound of Formula (Ib) or (Ib1), or a pharmaceutically acceptable salt thereof, wherein $R^{45}$ is —N($R^{13}$)C(O)$R^{14}$, wherein $R^{13}$ is hydrogen. In some embodiments is a compound of Formula (Ib) or (Ib1), or a pharmaceutically acceptable salt thereof, wherein $R^{45}$ is —N($R^{13}$)C(O)$R^{14}$, wherein $R^{13}$ is alkyl. In some embodiments is a compound of Formula (Ib) or (Ib1), or a pharmaceutically acceptable salt thereof, wherein $R^{45}$ is —N($R^{13}$)C(O)$R^{14}$, wherein $R^{13}$ is unsubstituted alkyl. In some embodiments is a compound of Formula (Ib) or (Ib1), or a pharmaceutically acceptable salt thereof, wherein $R^{45}$ is —N($R^{13}$)C(O)$R^{14}$, wherein $R^{14}$ is methyl, ethyl, n-propyl, isopropyl, n-butyl, tert-butyl, n-pentyl, or 3-methyl-1-butyl. In some embodiments is a compound of Formula (Tb) or (Ib1), or a pharmaceutically acceptable salt thereof, wherein $R^{45}$ is —N($R^{13}$)C(O)$R^{14}$, wherein $R^{14}$ is phenyl. In some embodiments is a compound of Formula (Ib) or (Ib1), or a pharmaceutically acceptable salt thereof, wherein $R^{45}$ is —N($R^{13}$)C(O)$R^{14}$, wherein $R^4$ is 2-pyridyl, 3-pyridyl, 4-pyridyl, 2-pyrimidyl, 4-pyrimidyl, 5-pyrimidyl, or 6-pyrimidyl.

In some embodiments is a compound of Formula (I), (Ib), or (Ib1), or a pharmaceutically acceptable salt thereof, wherein the compound is:

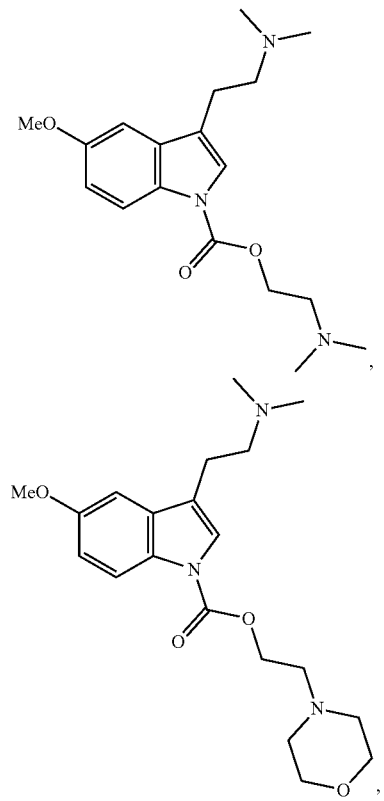

49
-continued
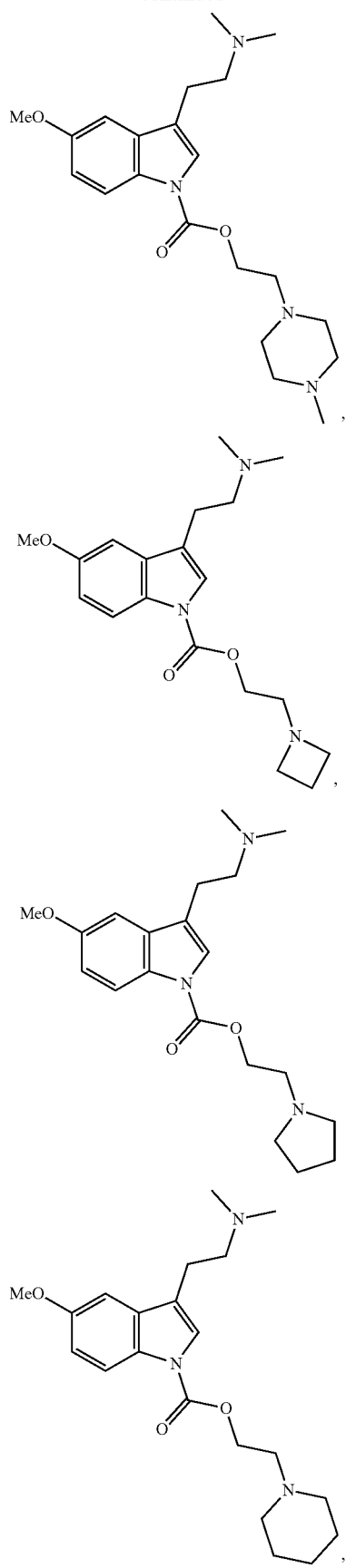
50
-continued
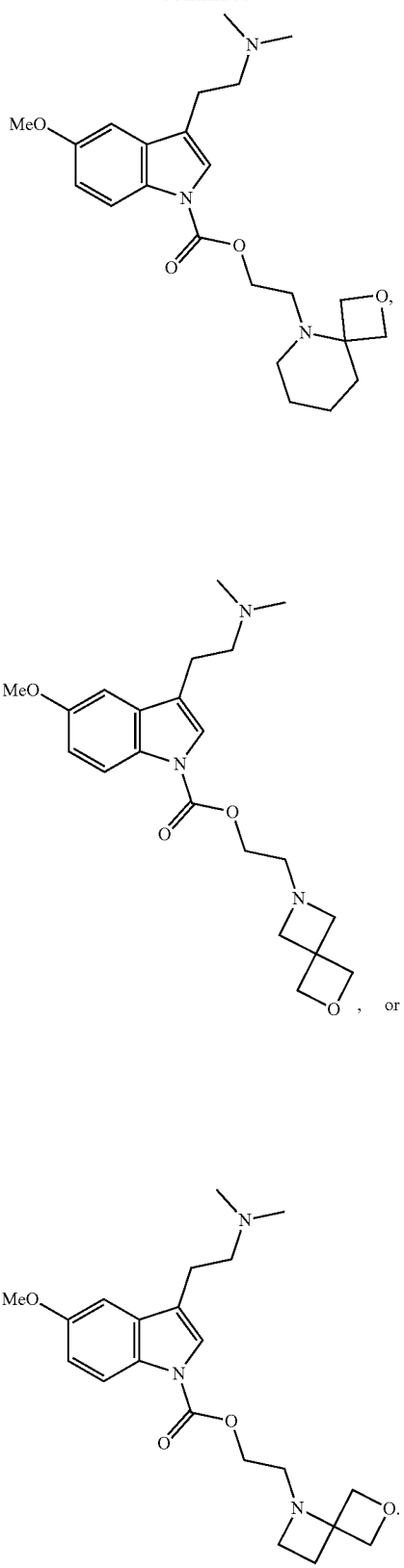
In some embodiments is a compound of Formula (I), (Ib), or (Ib1), or a pharmaceutically acceptable salt thereof, wherein the compound is:

51
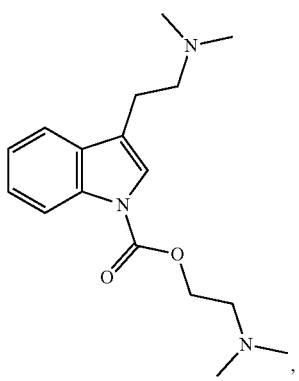
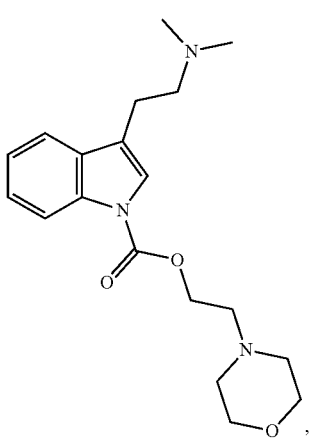
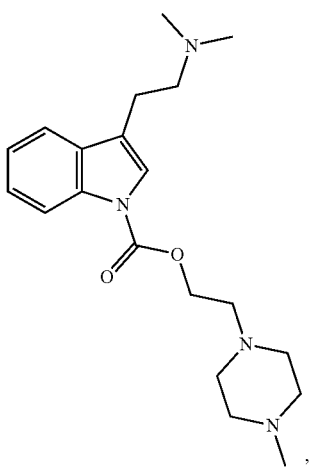
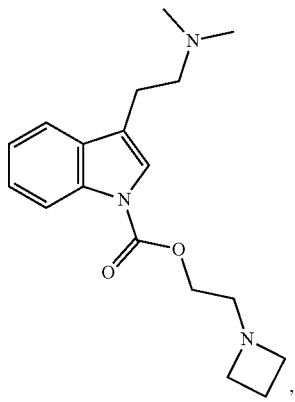
52
-continued
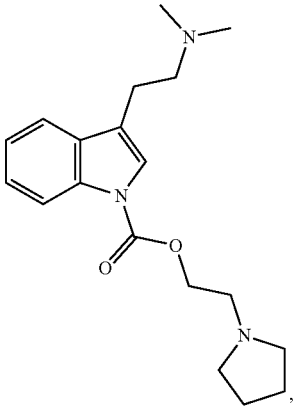
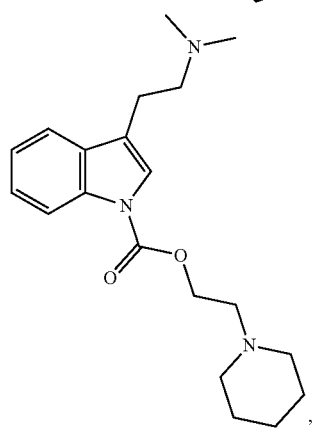
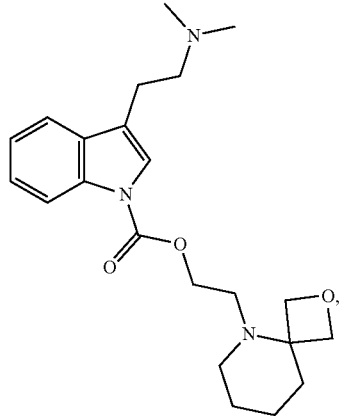
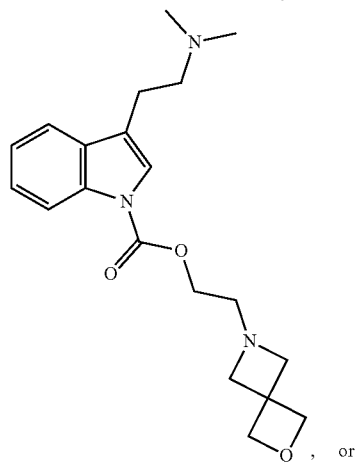, or In some embodiments is a compound of Formula (I), (Ib), or (Ib1), or a pharmaceutically acceptable salt thereof, wherein the compound is

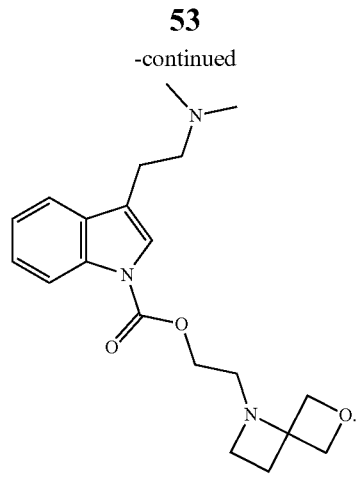

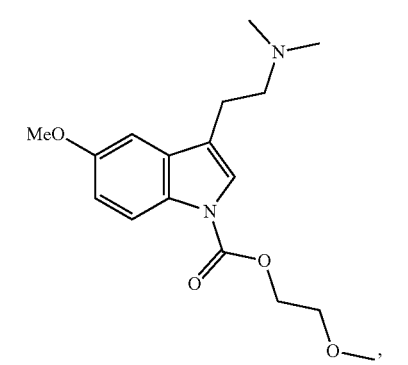

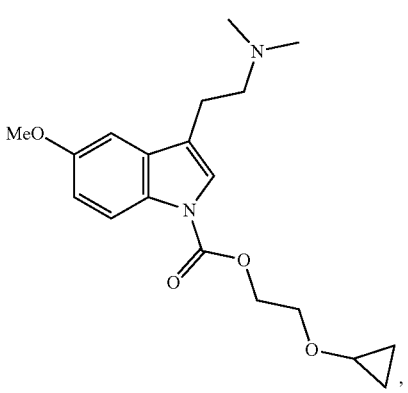

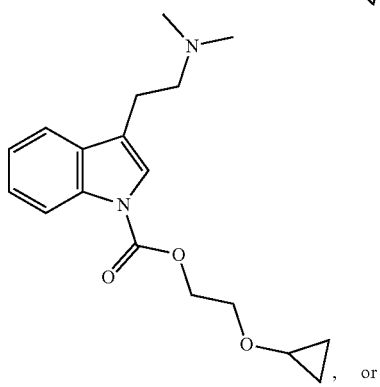, or

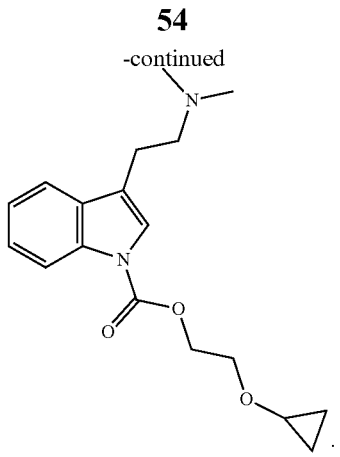

In some embodiments is a compound of Formula (I) having the structure of Formula (Ic), or a pharmaceutically acceptable salt thereof:

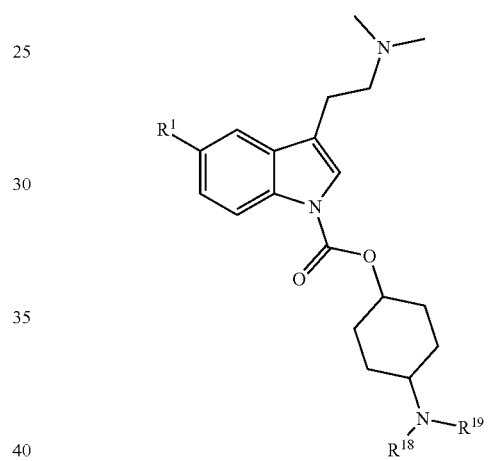

(Ic)

wherein $R^1$ is hydrogen or methoxy, and each of $R^{18}$ and $R^{19}$ is independently hydrogen, alkyl, cycloalkyl, or heteroalkyl, wherein each alkyl, cycloalkyl, and heteroalkyl is independently unsubstituted or substituted with one or more $R^B$; or $R^{18}$ and $R^{19}$ together with the atom to which they are attached form a heterocyclylalkyl ring that is unsubstituted or substituted with one or more $R^B$.

In some embodiments is a compound of Formula (I) or (Ic), or a pharmaceutically acceptable salt or solvate thereof, wherein each of $R^{18}$ and $R^{19}$ is independently methyl, ethyl, n-propyl, isopropyl, cyclopropyl, tert-butyl, —CH$_2$CH$_2$OMe, or —CH$_2$CH$_2$SO$_2$Me. In some embodiments is a compound of Formula (I) or (Ic), or a pharmaceutically acceptable salt or solvate thereof, wherein $R^{18}$ is hydrogen, and $R^{19}$ is methyl, ethyl, n-propyl, isopropyl, cyclopropyl, tert-butyl, —CH$_2$CH$_2$OMe, or —CH$_2$CH$_2$SO$_2$Me. In some embodiments is a compound of Formula (I) or (Ic), or a pharmaceutically acceptable salt or solvate thereof, wherein each of $R^{18}$ and $R^{19}$ is methyl, ethyl, n-propyl, isopropyl, cyclopropyl, tert-butyl, —CH$_2$CH$_2$OMe, or —CH$_2$CH$_2$SO$_2$Me.

In some embodiments is a compound of Formula (I) or (Ic), or a pharmaceutically acceptable salt or solvate thereof, wherein $R^{18}$ and $R^{19}$ together with the atom to which they are attached form a heterocyclylalkyl ring that is substituted or unsubstituted. In some embodiments is a compound of Formula (I) or (Ic), or a pharmaceutically acceptable salt or solvate thereof, wherein $R^{18}$ and $R^{19}$ together with the atom to which they are attached form a azetidine ring, a pyrrolidine ring, or a piperidine ring, each of which is substituted or unsubstituted.

In some embodiments is a compound of Formula (I) or (Ic), or a pharmaceutically acceptable salt or solvate thereof, wherein the compound is:

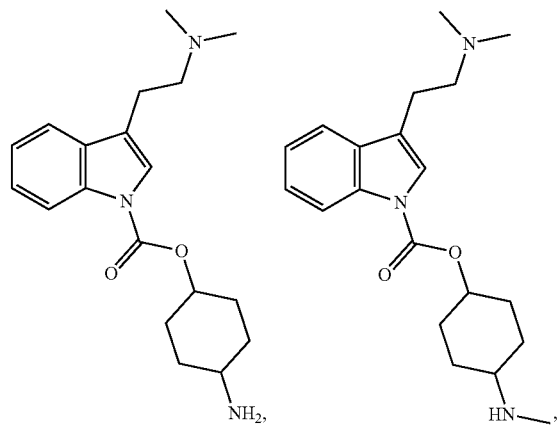

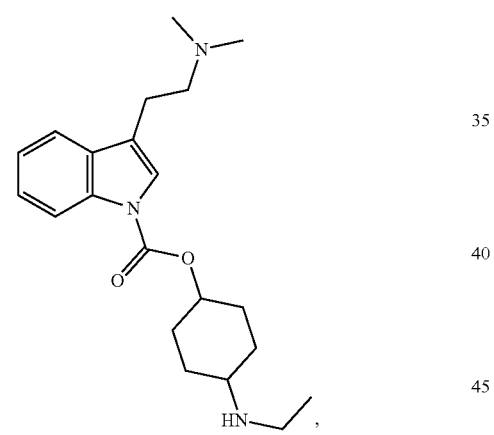

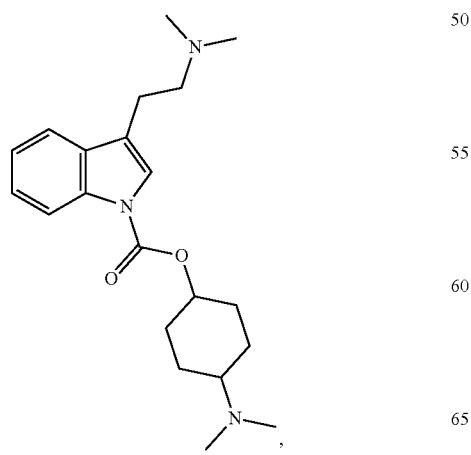

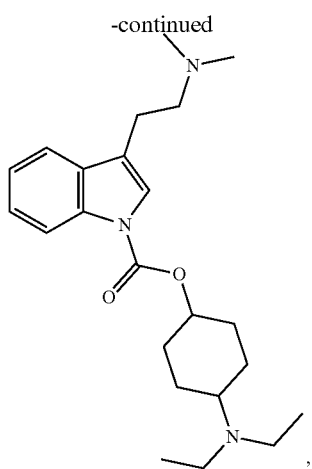

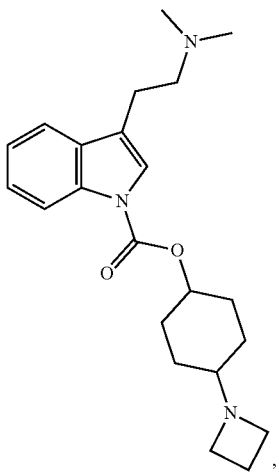

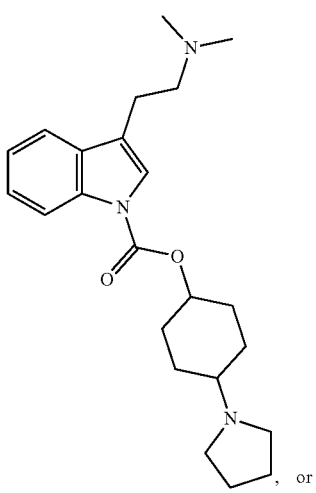, or

57
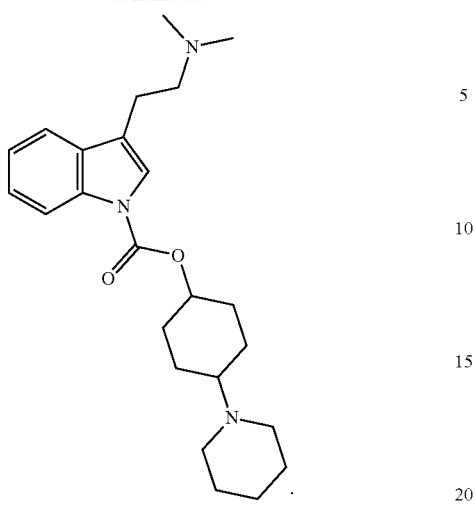
In some embodiments is a compound of Formula (I) or (Ic), or a pharmaceutically acceptable salt or solvate thereof, wherein the compound is:
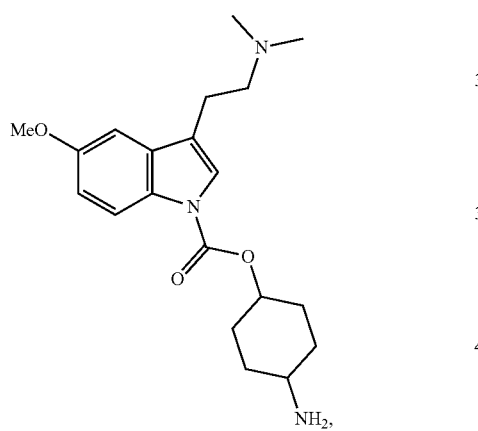
58
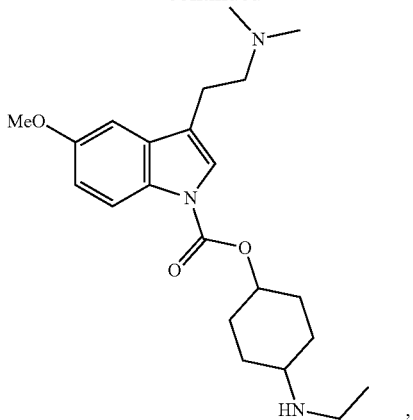
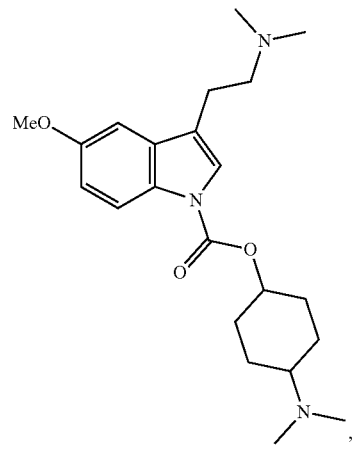
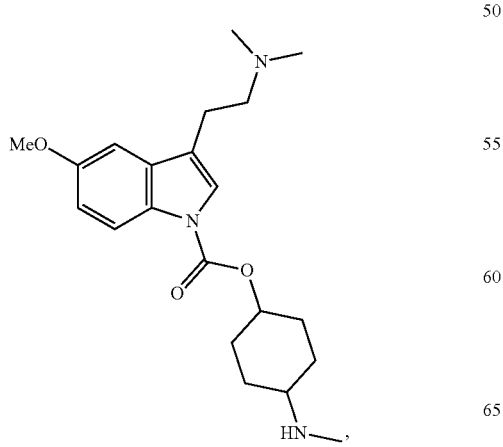
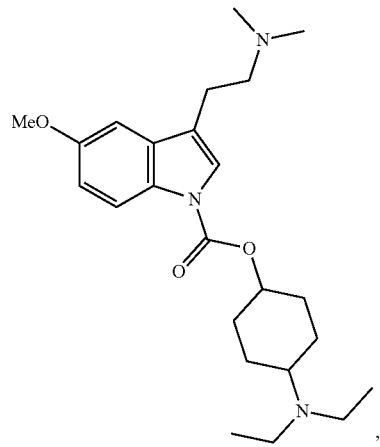

-continued

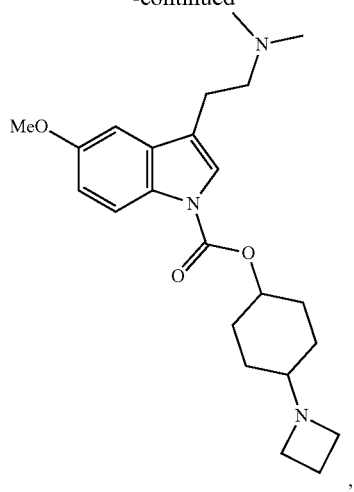

,

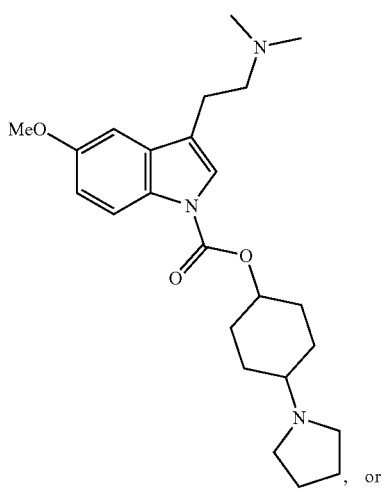

, or

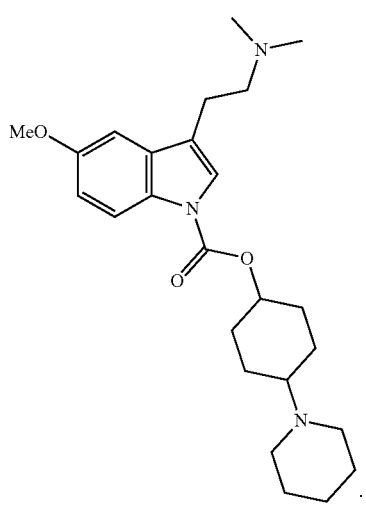 [SMILES: COc1ccc2c(c1)c(CCN(C)C)cn2C(=O)OC1CCC(N2CCCCC2)CC1]

.

In some embodiments is a compound of Formula (I) having the structure of Formula (Id), or a pharmaceutically acceptable salt thereof:

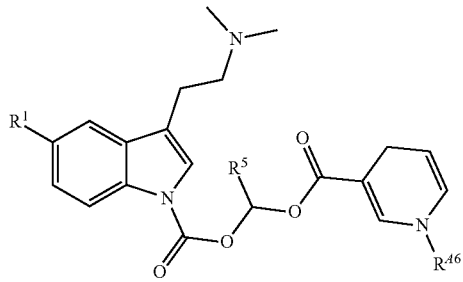

wherein:

R$^1$ is hydrogen or methoxy;

R$^5$ is hydrogen, alkyl, or cycloalkyl, wherein each of alkyl and cycloalykl is independently unsubstituted or substituted with one or more R$^4$; and R$^{46}$ is hydrogen or alkyl that is unsubstituted or substituted with one or more alkyl, aryl, halogen, —OR$^{13}$, —NR(R$^{18}$)R$^{19}$, —C(O)R$^{14}$, —OC(O)R$^{15}$, —OC(O)OR$^{16}$, or —OC(O)N(R$^{18}$)R$^{19}$.

In some embodiments is a compound of Formula (Id), or a pharmaceutically acceptable salt or solvate thereof, wherein R$^5$ is alkyl or cycloalkyl. In some embodiments is a compound of Formula (Id), or a pharmaceutically acceptable salt or solvate thereof, wherein R$^5$ is unsubstituted alkyl. In some embodiments is a compound of Formula (Id), or a pharmaceutically acceptable salt or solvate thereof, wherein R$^5$ is hydrogen, methyl, ethyl, or isopropyl. In some embodiments is a compound of Formula (Id), or a pharmaceutically acceptable salt or solvate thereof, wherein R$^{46}$ is alkyl. In some embodiments is a compound of Formula (Id), or a pharmaceutically acceptable salt or solvate thereof, wherein R$^{46}$ is hydrogen, methyl, ethyl, n-propyl, isopropyl, n-butyl, or benzyl. In some embodiments is a compound of Formula (Id), or a pharmaceutically acceptable salt or solvate thereof, wherein R$^5$ is unsubstituted alkyl, and R$^{46}$ is hydrogen, methyl, ethyl, n-propyl, isopropyl, n-butyl, or benzyl. In some embodiments is a compound of Formula (Id), or a pharmaceutically acceptable salt or solvate thereof, wherein R$^5$ is hydrogen, and R$^{46}$ is hydrogen, methyl, ethyl, n-propyl, isopropyl, n-butyl, or benzyl.

In some embodiments is a compound of Formula (Id), or a pharmaceutically acceptable salt or solvate thereof, wherein the compound is:

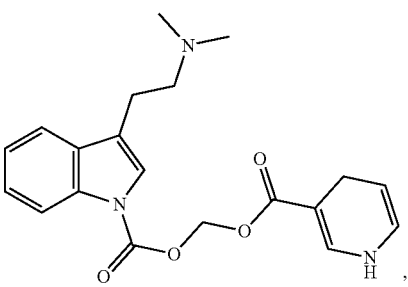

,

-continued

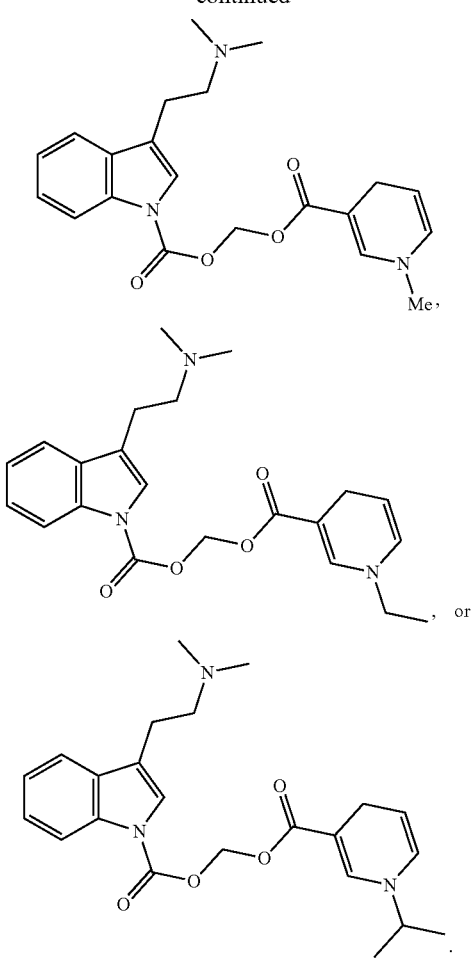

, or

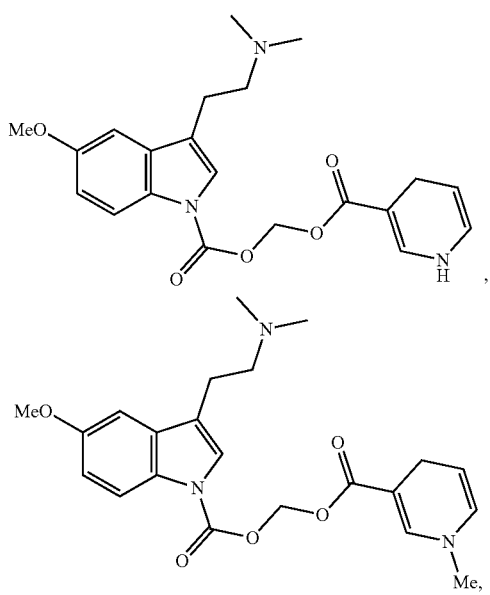

In some embodiments is a compound of Formula (Id), or a pharmaceutically acceptable salt or solvate thereof, wherein the compound is:

-continued

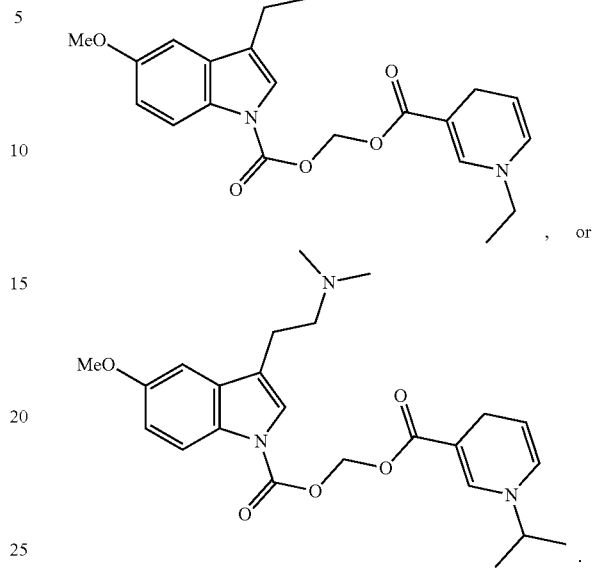

, or

In some embodiments is a compound of Formula (I) having the structure of Formula (Ie), or a pharmaceutically acceptable salt thereof:

(Ie)

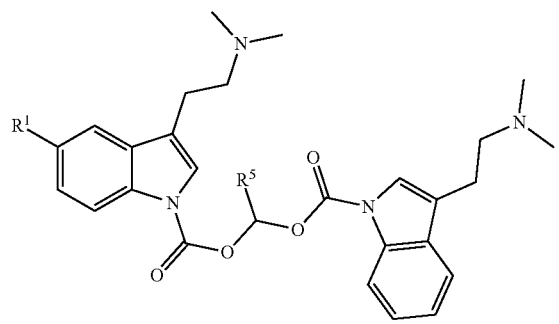

wherein $R^1$ is hydrogen or methoxy, and $R^5$ is hydrogen, alkyl or cycloalkyl, wherein each alkyl and cycloalkyl is independently unsubstituted or substituted with one or more $R^4$.

In some embodiments is a compound of Formula (I) or (Ie), or a pharmaceutically acceptable salt or solvate thereof, wherein $R^5$ is hydrogen. In some embodiments is a compound of Formula (I) or (Id), or a pharmaceutically acceptable salt or solvate thereof, wherein $R^5$ is alkyl. In some embodiments is a compound of Formula (I) or (Ie), or a pharmaceutically acceptable salt or solvate thereof, wherein $R^5$ is unsubstituted alkyl. In some embodiments is a compound of Formula (I) or (Ie), or a pharmaceutically acceptable salt or solvate thereof, wherein $R^5$ is methyl, ethyl, or isopropyl.

In some embodiments is a compound of Formula (I) or (Ie), or a pharmaceutically acceptable salt or solvate thereof, wherein the compound is:

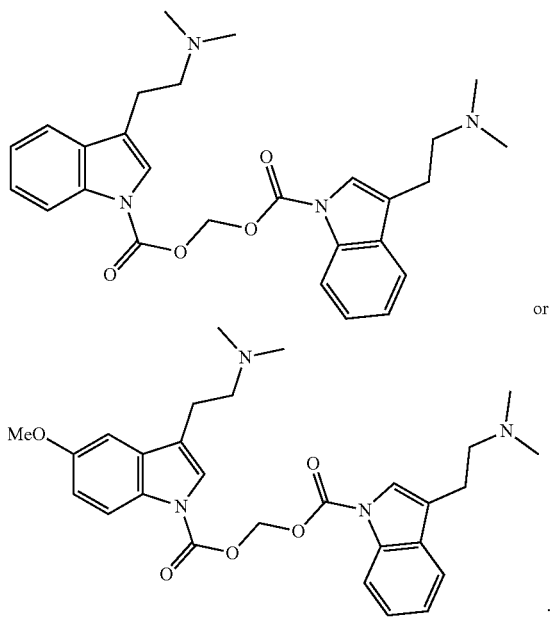

In some embodiments is a compound of Formula (I) having the structure of Formula (If), or a pharmaceutically acceptable salt thereof:

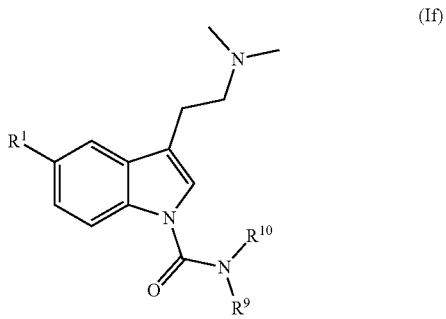

wherein:
R$^1$ is methoxy or hydrogen, and
each of R$^9$ and R$^{10}$ is independently hydrogen, alkyl, cycloalkyl, aryl, heteroaryl, heteroalkyl, or heterocyclylalkyl, wherein each alkyl, cycloalkyl, aryl, heteroaryl, heteroalkyl, and heterocyclylalkyl is independently unsubstituted or substituted with one or more R$^A$, or R$^9$ and R$^{10}$ together with the atom to which they are attached form a heterocyclylalkyl ring that is unsubstituted or substituted with one or more R$^A$.

In some embodiments is a compound of Formula (I) or (If), or a pharmaceutically acceptable salt or solvate thereof, wherein each of R$^9$ and R$^{10}$ is independently alkyl. In some embodiments is a compound of Formula (I) or (If), or a pharmaceutically acceptable salt or solvate thereof, wherein R$^{10}$ is alkyl, cycloalkyl, aryl, heteroaryl, heteroalkyl, or heterocyclylalkyl. In some embodiments is a compound of Formula (I) or (If), or a pharmaceutically acceptable salt or solvate thereof, wherein each of R$^9$ and R$^{10}$ is independently unsubstituted alkyl. In some embodiments is a compound of Formula (I) or (If), or a pharmaceutically acceptable salt or solvate thereof, wherein R$^1$ is methoxy, and each of R$^9$ and R$^{10}$ is independently unsubstituted alkyl. In some embodiments is a compound of Formula (I) or (If), or a pharmaceutically acceptable salt or solvate thereof, wherein R$^1$ is hydrogen, and each of R$^9$ and R$^{10}$ is independently unsubstituted alkyl. In some embodiments is a compound of Formula (I) or (If), or a pharmaceutically acceptable salt or solvate thereof, wherein each of R$^9$ and R$^{10}$ is independently heteroalkyl. In some embodiments is a compound of Formula (I) or (If), or a pharmaceutically acceptable salt or solvate thereof, wherein each of R$^9$ and R$^{10}$ is independently unsubstituted heteroalkyl. In some embodiments is a compound of Formula (I) or (If), or a pharmaceutically acceptable salt or solvate thereof, wherein each of R$^9$ and R$^{10}$ is independently methyl, ethyl, n-propyl, isopropyl, n-butyl, cyclobutyl, cyclopentyl, cyclohexyl, cycloheptyl, cyclooctyl, tert-butyl, n-pentyl, n-heptyl, n-octyl, n-nonyl, or 3-methyl-1-butyl. In some embodiments is a compound of Formula (I) or (If), or a pharmaceutically acceptable salt or solvate thereof, wherein each of R$^9$ and R$^{10}$ is independently CH$_2$CHF$_2$, CH$_2$CF$_3$, or CH$_{2c}$Pr. In some embodiments is a compound of Formula (I) or (If), or a pharmaceutically acceptable salt or solvate thereof, wherein each of R$^9$ and R$^{10}$ is phenyl. In some embodiments is a compound of Formula (I) or (If), or a pharmaceutically acceptable salt or solvate thereof, wherein each of R$^9$ and R$^{10}$ is independently 2-pyridyl, 3-pyridyl, 4-pyridyl, 2-pyrimidyl, 4-pyrimidyl, 5-pyrimidyl, or 6-pyrimidyl. In some embodiments is a compound of Formula (I) or (If), or a pharmaceutically acceptable salt or solvate thereof, wherein each of R$^9$ and R$^{10}$ is ethyl. In some embodiments is a compound of Formula (I) or (If), or a pharmaceutically acceptable salt or solvate thereof, wherein R$^1$ is hydrogen, and each of R$^9$ and R$^{10}$ is ethyl. In some embodiments is a compound of Formula (I) or (If), or a pharmaceutically acceptable salt or solvate thereof, wherein R$^1$ is methoxy, and each of R$^9$ and R$^{10}$ is ethyl. In some embodiments is a compound of Formula (I) or (If), or a pharmaceutically acceptable salt or solvate thereof, wherein each of R$^9$ and R$^{10}$ is methyl. In some embodiments is a compound of Formula (I) or (If), or a pharmaceutically acceptable salt or solvate thereof, wherein R$^1$ is hydrogen, and each of R$^9$ and R$^{10}$ is methyl. In some embodiments is a compound of Formula (I) or (If), or a pharmaceutically acceptable salt or solvate thereof, wherein R$^1$ is methoxy, and each of R$^9$ and R$^{10}$ is methyl.

In some embodiments is a compound of Formula (I) or (If), or a pharmaceutically acceptable salt or solvate thereof, wherein R$^1$ is methoxy or hydrogen, R$^9$ is hydrogen, and R$^{10}$ is alkyl, cycloalkyl, aryl, heteroaryl, heteroalkyl, or heterocyclylalkyl. In some embodiments is a compound of Formula (I) or (If), or a pharmaceutically acceptable salt or solvate thereof, wherein R$^9$ is hydrogen, and R$^{10}$ is alkyl. In some embodiments is a compound of Formula (I) or (If), or a pharmaceutically acceptable salt or solvate thereof, wherein R$^1$ is methoxy, R$^9$ is hydrogen, and R$^{10}$ is alkyl. In some embodiments is a compound of Formula (I) or (If), or a pharmaceutically acceptable salt or solvate thereof, wherein R$^1$ is hydrogen, R$^9$ is hydrogen, and R$^{10}$ is alkyl. In some embodiments is a compound of Formula (I) or (If), or a pharmaceutically acceptable salt or solvate thereof, wherein R$^9$ is hydrogen, and R$^{10}$ is heteroalkyl. In some embodiments is a compound of Formula (I) or (If), or a pharmaceutically acceptable salt or solvate thereof, wherein R$^9$ is hydrogen, and R$^{10}$ is unsubstituted alkyl. In some embodiments is a compound of Formula (I) or (If), or a pharmaceutically acceptable salt or solvate thereof, wherein R$^1$ is methoxy, R$^9$ is hydrogen, and R$^{10}$ is unsubstituted alkyl. In some embodiments is a compound of Formula (I) or (If), or a pharmaceutically acceptable salt or solvate thereof, wherein R¹ is hydrogen, R⁹ is hydrogen, and R¹⁰ is unsubstituted alkyl. In some embodiments is a compound of Formula (I) or (If), or a pharmaceutically acceptable salt or solvate thereof, wherein R⁹ is hydrogen, and R¹⁰ is unsubstituted heteroalkyl. In some embodiments is a compound of Formula (I) or (If), or a pharmaceutically acceptable salt or solvate thereof, wherein R⁹ is hydrogen, and R¹⁰ is methyl, ethyl, n-propyl, isopropyl, n-butyl, cyclobutyl, cyclopentyl, cyclohexyl, cycloheptyl, cyclooctyl, tert-butyl, n-pentyl, n-heptyl, n-octyl, n-nonyl, or 3-methyl-1-butyl. In some embodiments is a compound of Formula (I) or (If), or a pharmaceutically acceptable salt or solvate thereof, wherein R⁹ is hydrogen and R¹⁰ is —CH₂CHF₂, —CH₂CF₃, or —CH₂ₑPr. In some embodiments is a compound of Formula (I) or (If), or a pharmaceutically acceptable salt or solvate thereof, wherein R⁹ is hydrogen, and R¹⁰ is phenyl. In some embodiments is a compound of Formula (I) or (If), or a pharmaceutically acceptable salt or solvate thereof, wherein R⁹ is hydrogen, and R¹⁰ is 2-pyridyl, 3-pyridyl, 4-pyridyl, 2-pyrimidyl, 4-pyrimidyl, 5-pyrimidyl, or 6-pyrimidyl. In some embodiments is a compound of Formula (I) or (If), or a pharmaceutically acceptable salt or solvate thereof, wherein R⁹ is hydrogen, and R¹⁰ is ethyl. In some embodiments is a compound of Formula (I) or (If), or a pharmaceutically acceptable salt or solvate thereof, wherein R¹ is hydrogen, R⁹ is hydrogen, and R¹⁰ is ethyl. In some embodiments is a compound of Formula (I) or (If), or a pharmaceutically acceptable salt or solvate thereof, wherein R¹ is methoxy, R⁹ is hydrogen, and R¹⁰ is ethyl. In some embodiments is a compound of Formula (I) or (If), or a pharmaceutically acceptable salt or solvate thereof, wherein R¹⁰ is

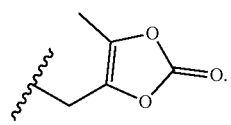 [SMILES: *Cc1oc(=O)oc1C]

In some embodiments is a compound of Formula (I) or (If), or a pharmaceutically acceptable salt or solvate thereof, wherein R¹ is methoxy, R⁹ is hydrogen, and R¹⁰ is

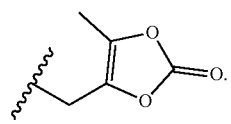 [SMILES: *Cc1oc(=O)oc1C]

In some embodiments is a compound of Formula (I) or (If), or a pharmaceutically acceptable salt or solvate thereof, wherein R¹ is hydrogen, R⁹ is hydrogen, and R¹⁰ is

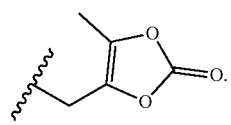 [SMILES: *Cc1oc(=O)oc1C]

In some embodiments is a compound of Formula (I) or (If), or a pharmaceutically acceptable salt thereof, wherein the compound is:

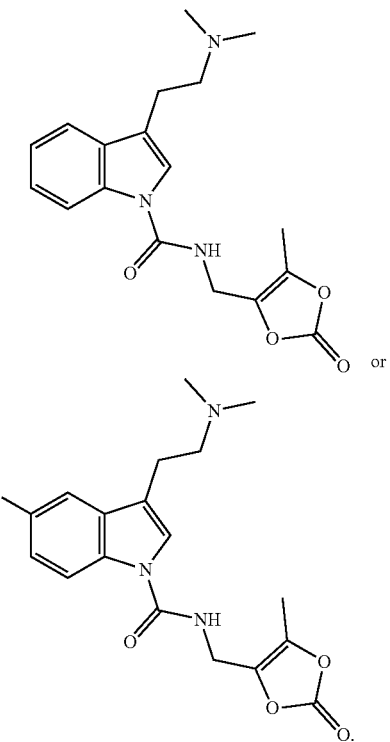

In some embodiments is a compound of Formula (I) or (If) having the structure of Formula (If1), or a pharmaceutically acceptable salt thereof:

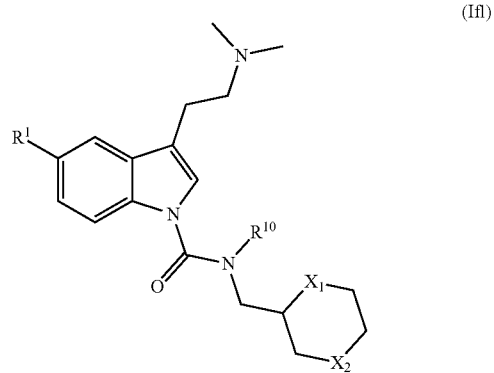

(If1)

wherein:
R¹ is methoxy or hydrogen;
R¹⁰ is hydrogen, alkyl, heteroalkyl, cycloalkyl, or heterocyclylalkyl, wherein each of alkyl, heteroalkyl, cycloalkyl, and heterocyclylalkyl is unsubstituted or substituted with one or more R$^A$; and
each of X¹ and X² are independently selected from —CH₂—, —O—, —NH—, —S—, —S(O)—, —S(O)₂—, or —N(Y¹)—, wherein each Y¹ is independently hydrogen, cycloalkyl, heteroalkyl, or alkyl.

In some embodiments is a compound of Formula (If1), or a pharmaceutically acceptable salt or solvate thereof, wherein each Y¹ is independently hydrogen, methyl, ethyl, n-propyl, isopropyl, cyclopropyl, or CH₂CH₂OMe. In some embodiments is a compound of Formula (If1), or a pharmaceutically acceptable salt or solvate thereof, wherein X¹ is —CH₂— and X² is —N(Y¹)—. In some embodiments is a compound of Formula (If1), or a pharmaceutically acceptable salt or solvate thereof, wherein X² is —CH₂— and X¹ is —N(Y¹)—. In some embodiments is a compound of Formula (If1), or a pharmaceutically acceptable salt or solvate thereof, wherein X¹ is —CH₂— and X² is —N(Y¹)—, wherein Y¹ is hydrogen, methyl, ethyl, n-propyl, isopropyl, cyclopropyl, or —CH₂CH₂OMe. In some embodiments is a compound of Formula (If1), or a pharmaceutically acceptable salt or solvate thereof, wherein X² is —CH₂— and X¹ is —N(Y¹)—, wherein Y¹ is hydrogen, methyl, ethyl, n-propyl, isopropyl, cyclopropyl, or —CH₂CH₂OMe. In some embodiments is a compound of Formula (If1), or a pharmaceutically acceptable salt or solvate thereof, wherein each of X¹ and X² are —O— or —NH—. In some embodiments is a compound of Formula (If1), or a pharmaceutically acceptable salt or solvate thereof, wherein R¹⁰ is hydrogen.

In some embodiments is a compound of Formula (I) having the structure of Formula (Ig), or a pharmaceutically acceptable salt thereof:

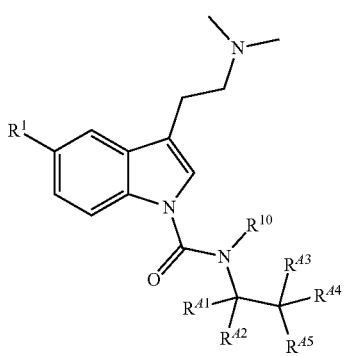

(Ig)

wherein:
R¹ is methoxy or hydrogen;
each of $R^{A1}$, $R^{A2}$, $R^{A3}$, and $R^{A4}$ is independently hydrogen or alkyl that is unsubstituted or substituted with one or more alkyl, aryl, halogen, —OR¹³, —NR(R¹⁸)R¹⁹, —C(O)R¹⁴, —OC(O)R¹⁵, —OC(O)OR¹⁶, or —OC(O)N(R¹⁸)R¹⁹;
R¹⁰ is hydrogen, alkyl, heteroalkyl, or cycloalkyl, wherein each of alkyl, heteroalkyl, and cycloalkyl is unsubstituted or substituted with one or more $R^A$; and
$R^{A5}$ is heteroalkyl, heterocyclylalkyl, heteroaryl, or —C(O)OR¹³, —N(R¹³)C(O)OR¹⁴, —N(R¹³)C(O)R¹⁴, —C(O)R¹⁴, —OC(O)R⁵, or —OC(O)OR¹⁶, wherein each of heteroalkyl, heterocyclylalkyl, heteroaryl is unsubstituted or substituted with one or more alkyl, aryl, halogen, —OR³, —NR(R¹⁸)R¹⁹, —C(O)R¹⁴, —OC(O)R¹⁵, —OC(O)OR¹⁶, or —OC(O)N(R¹⁸)R¹⁹.

In some embodiments is a compound of Formula (Ig), or a pharmaceutically acceptable salt or solvate thereof, wherein one $R^{A1}$, $R^{A2}$, $R^{A3}$, and $R^{A4}$ is alkyl, and each of $R^{A1}$, $R^{A2}$, $R^{A3}$, and $R^{A4}$ that is not alkyl is hydrogen. In some embodiments is a compound of Formula (Ig), or a pharmaceutically acceptable salt or solvate thereof, wherein two of $R^{A1}$, $R^{A2}$, $R^{A3}$, and $R^{A4}$ is alkyl, and each of $R^{A1}$, $R^{A2}$, $R^{A3}$, and $R^{A4}$ that is not alkyl is hydrogen. In some embodiments is a compound of Formula (Ig), or a pharmaceutically acceptable salt or solvate thereof, wherein each of $R^{A1}$, $R^{A2}$, $R^{A3}$, and $R^{A4}$ is hydrogen. In some embodiments is a compound of Formula (Ig) or a pharmaceutically acceptable salt thereof, wherein one $R^{A1}$, $R^{A2}$, $R^{A3}$, and $R^{A4}$ is alkyl, and each of $R^{A1}$, $R^{A2}$, $R^{A3}$, and $R^{A4}$ that is not alkyl is hydrogen, wherein each alkyl is independently methyl, ethyl, tert-butyl, or isopropyl. In some embodiments is a compound of Formula (Ig), or a pharmaceutically acceptable salt or solvate thereof, wherein two of $R^{A1}$, $R^{A2}$, $R^{A3}$, and $R^{A4}$ is alkyl, and each of $R^{A1}$, $R^{A2}$, $R^{A3}$, and $R^{A4}$ that is not alkyl is hydrogen, wherein each alkyl is independently methyl, ethyl, tert-butyl, or isopropyl.

In some embodiments is a compound of Formula (Ig), or a pharmaceutically acceptable salt or solvate thereof, wherein $R^{A5}$ is heteroalkyl. In some embodiments is a compound of Formula (Ig), or a pharmaceutically acceptable salt or solvate thereof, wherein $R^{A5}$ is heteroalkyl that is unsubstituted. In some embodiments is a compound of Formula (Ig), or a pharmaceutically acceptable salt or solvate thereof, wherein $R^{A5}$ is heterocyclylalkyl. In some embodiments is a compound of Formula (Ig), or a pharmaceutically acceptable salt or solvate thereof, wherein $R^{A5}$ is heterocyclylalkyl that is unsubstituted. In some embodiments is a compound of Formula (Ig), or a pharmaceutically acceptable salt or solvate thereof, wherein $R^{A5}$ is methoxy, ethoxy, cyclopropyloxy, methylamino, or dimethylamino. In some embodiments is a compound of Formula (Ig), or a pharmaceutically acceptable salt or solvate thereof, wherein $R^{A5}$ is

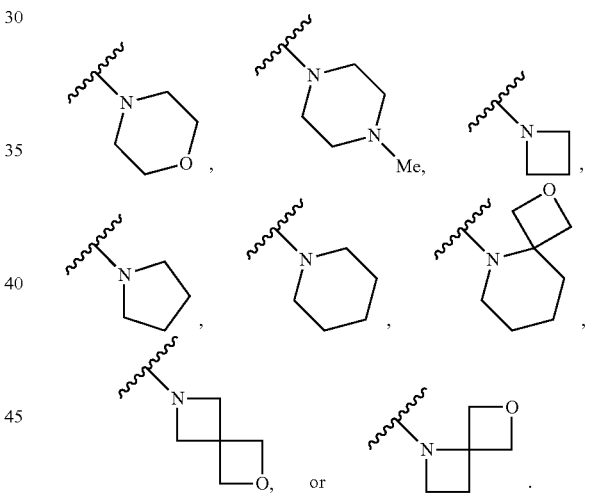

In some embodiments is a compound of Formula (Ig), or a pharmaceutically acceptable salt or solvate thereof, wherein R¹⁰ is hydrogen. In some embodiments is a compound of Formula (Ig), or a pharmaceutically acceptable salt or solvate thereof, wherein R¹⁰ is hydrogen, methyl, ethyl, n-propyl, or isopropyl. In some embodiments is a compound of Formula (Ig), or a pharmaceutically acceptable salt or solvate thereof, wherein R¹⁰ is —CH₂CH₂OMe or —CH₂CH₂SO₂Me.

In some embodiments is a compound of Formula (Ig), or a pharmaceutically acceptable salt or solvate thereof, wherein $R^{A5}$ is —OC(O)R¹⁵. In some embodiments is a compound of Formula (Ig), or a pharmaceutically acceptable salt or solvate thereof, wherein $R^{A5}$ is —OC(O)R¹⁵, wherein R¹⁵ is alkyl, cycloalkyl, aryl, or heteroaryl. In some embodiments is a compound of Formula (Ig), or a pharmaceutically acceptable salt or solvate thereof, wherein $R^AS$ is —OC(O)R¹⁵, wherein R¹⁵ is methyl, ethyl, n-propyl, isopropyl, n-butyl, tert-butyl, n-pentyl, or 3-methyl-1-butyl. In some embodiments is a compound of Formula (Ig), or a pharmaceutically acceptable salt or solvate thereof, wherein R$^{45}$ is —OC(O)R$^{15}$, wherein R$^5$ is phenyl. In some embodiments is a compound of Formula (Ig), or a pharmaceutically acceptable salt or solvate thereof, wherein R$^{45}$ is —OC(O)R$^{15}$, wherein R$^5$ is 2-pyridyl, 3-pyridyl, 4-pyridyl, 2-pyrimidyl, 4-pyrimidyl, 5-pyrimidyl, or 6-pyrimidyl.

In some embodiments is a compound of Formula (Ig), or a pharmaceutically acceptable salt or solvate thereof, wherein R$^{45}$ is N(R$^{13}$)C(O)OR$^{14}$. In some embodiments is a compound of Formula (Ig), or a pharmaceutically acceptable salt or solvate thereof, wherein R$^{45}$ is N(R$^{13}$)C(O)OR$^{14}$, wherein R$^{13}$ is hydrogen or alkyl. In some embodiments is a compound of Formula (Ig), or a pharmaceutically acceptable salt or solvate thereof, wherein R$^{45}$ is N(R$^{13}$)C(O)OR$^{14}$, wherein R$^{13}$ is hydrogen. In some embodiments is a compound of Formula (Ig), or a pharmaceutically acceptable salt or solvate thereof, wherein R$^{45}$ is N(R$^{13}$)C(O)OR$^{14}$, wherein R$^3$ is alkyl. In some embodiments is a compound of Formula (Ig), or a pharmaceutically acceptable salt or solvate thereof, wherein R$^{45}$ is —N(R$^{13}$)C(O)OR$^{14}$, wherein R$^{13}$ is unsubstituted alkyl. In some embodiments is a compound of Formula (Ig), or a pharmaceutically acceptable salt or solvate thereof, wherein R$^{45}$ is —N(R$^3$)C(O)OR$^{14}$, wherein R$^{14}$ is methyl, ethyl, n-propyl, isopropyl, n-butyl, tert-butyl, n-pentyl, or 3-methyl-1-butyl.

In some embodiments is a compound of Formula (Ig), or a pharmaceutically acceptable salt or solvate thereof, wherein R$^{45}$ is —N(R$^{13}$)C(O)R$^{14}$. In some embodiments is a compound of Formula (Ig), or a pharmaceutically acceptable salt or solvate thereof, wherein R$^{45}$ is —N(R$^{13}$)C(O)R$^{14}$, wherein R$^{13}$ is hydrogen or alkyl. In some embodiments is a compound of Formula (Ig), or a pharmaceutically acceptable salt or solvate thereof, wherein R$^{45}$ is —N(R$^{13}$)C(O)R$^{14}$, wherein R$^{13}$ is hydrogen. In some embodiments is a compound of Formula (Ig), or a pharmaceutically acceptable salt or solvate thereof, wherein R$^{45}$ is —N(R$^{13}$)C(O)R$^{14}$, wherein R$^{13}$ is alkyl. In some embodiments is a compound of Formula (Ig), or a pharmaceutically acceptable salt or solvate thereof, wherein R$^{45}$ is —N(R$^{13}$)C(O)R$^{14}$, wherein R$^{13}$ is unsubstituted alkyl. In some embodiments is a compound of Formula (Ig), or a pharmaceutically acceptable salt or solvate thereof, wherein R$^{45}$ is —N(R$^{13}$)C(O)R$^{14}$, wherein R$^{14}$ is alkyl. In some embodiments is a compound of Formula (Ig), or a pharmaceutically acceptable salt or solvate thereof, wherein R$^{45}$ is —N(R$^{13}$)C(O)R$^{14}$, wherein R$^{14}$ is unsubstituted alkyl. In some embodiments is a compound of Formula (Ig), or a pharmaceutically acceptable salt or solvate thereof, wherein R$^{45}$ is —N(R$^{13}$)C(O)R$^{14}$, wherein R$^{14}$ is methyl, ethyl, n-propyl, isopropyl, n-butyl, tert-butyl, n-pentyl, or 3-methyl-1-butyl. In some embodiments is a compound of Formula (Ig), or a pharmaceutically acceptable salt or solvate thereof, wherein R$^{45}$ is —N(R$^{13}$)C(O)R$^{14}$, wherein R$^{14}$ is phenyl. In some embodiments is a compound of Formula (Ig), or a pharmaceutically acceptable salt or solvate thereof, wherein R$^{45}$ is —N(R$^{13}$)C(O)R$^{14}$, wherein R$^{14}$ is 2-pyridyl, 3-pyridyl, 4-pyridyl, 2-pyrimidyl, 4-pyrimidyl, 5-pyrimidyl, or 6-pyrimidyl.

In some embodiments is a compound of Formula (I) or (Ig), or a pharmaceutically acceptable salt thereof, wherein the compound is:

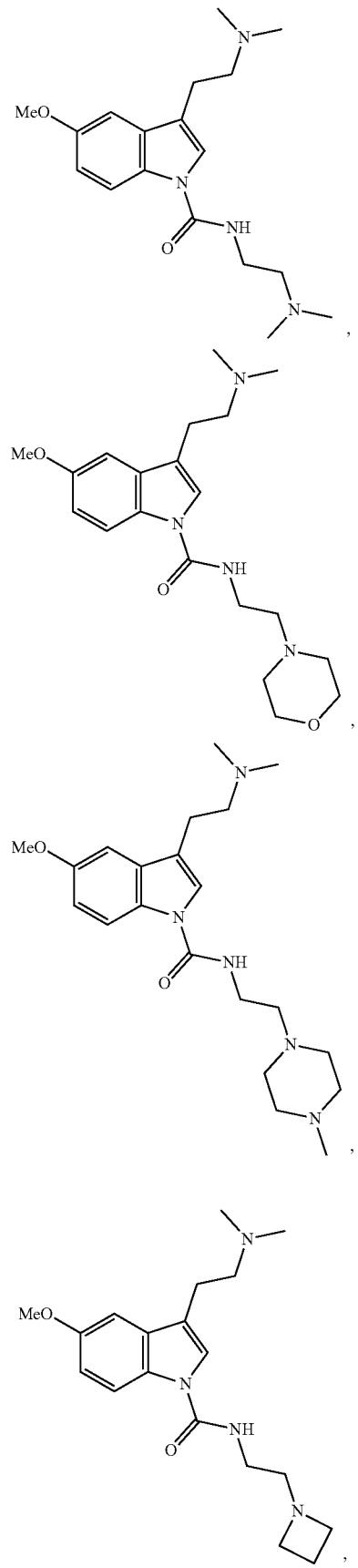

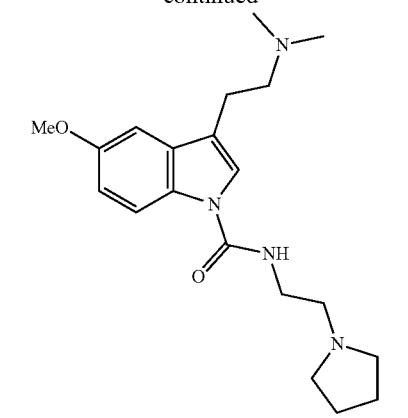
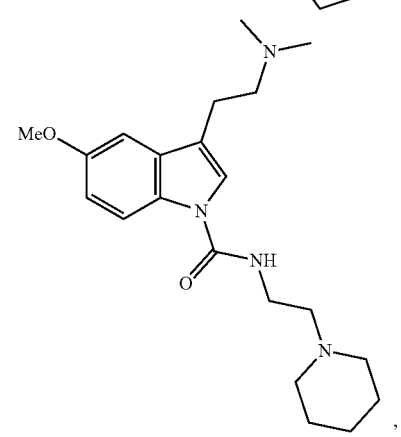
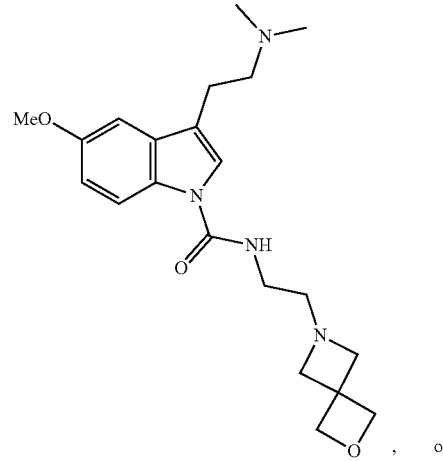, or
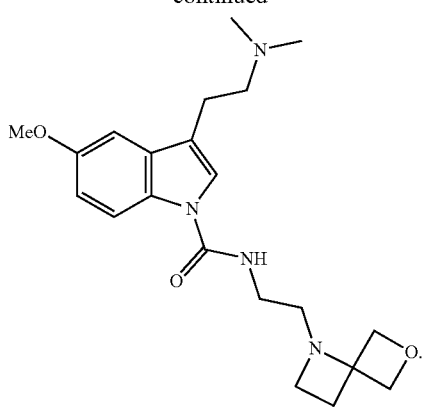
In some embodiments is a compound of Formula (I) or (Ig), or a pharmaceutically acceptable salt thereof, wherein the compound is:
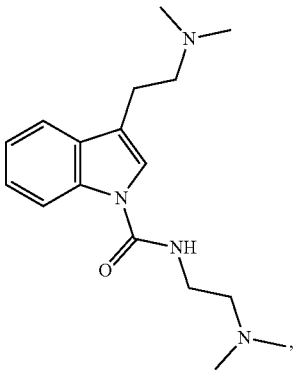
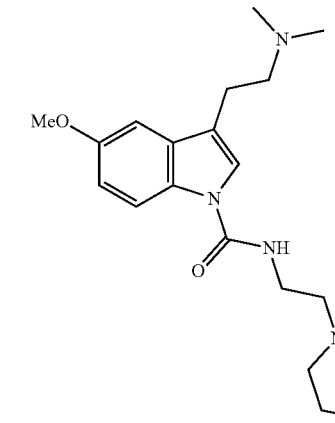

73
-continued
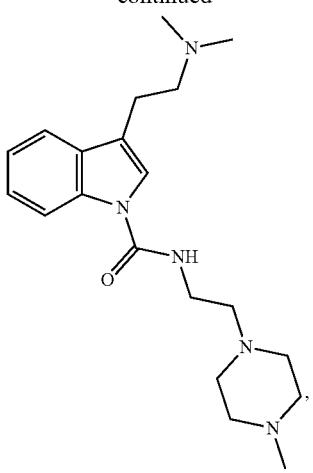
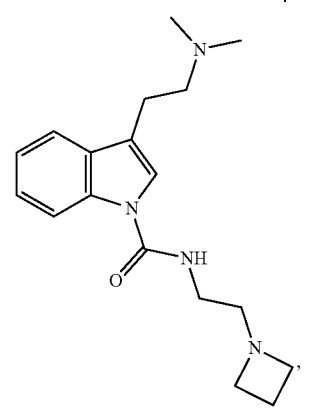
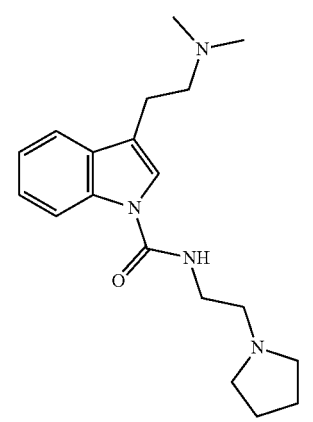
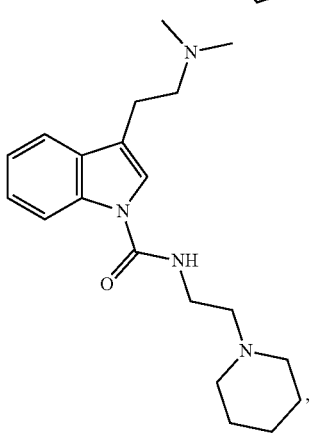
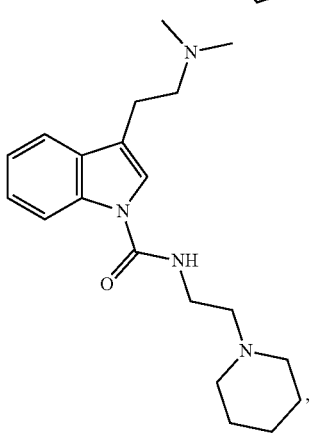
74
-continued
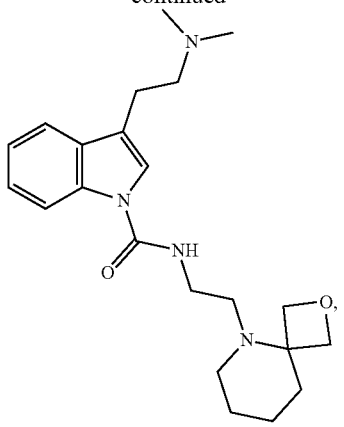
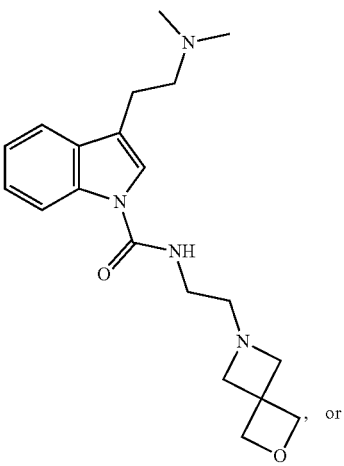
, or
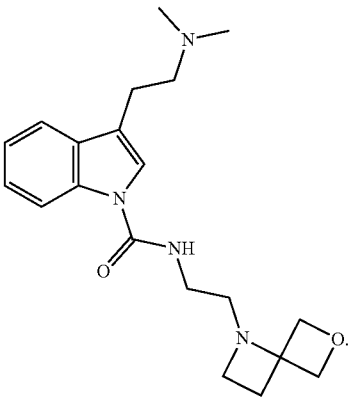 [SMILES: CN(C)CCc1cn(C(=O)NCCN2CCC23COC3)c2ccccc12]
In some embodiments is a compound of Formula (I) or (Ig), or a pharmaceutically acceptable salt thereof, wherein the compound is:

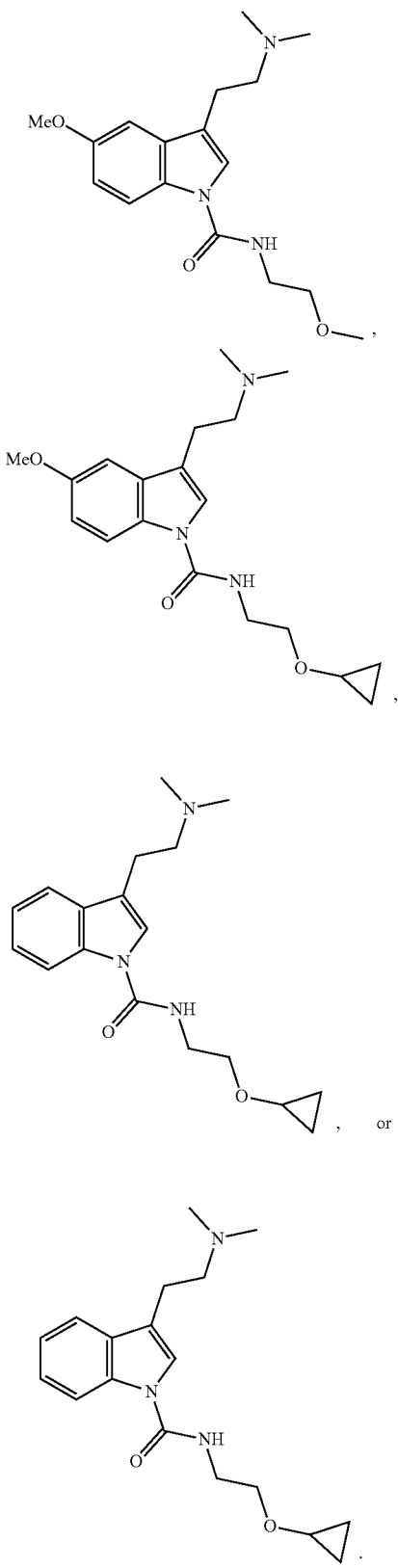

In some embodiments is a compound of Formula (I) having the structure of Formula (Ih), or a pharmaceutically acceptable salt thereof:

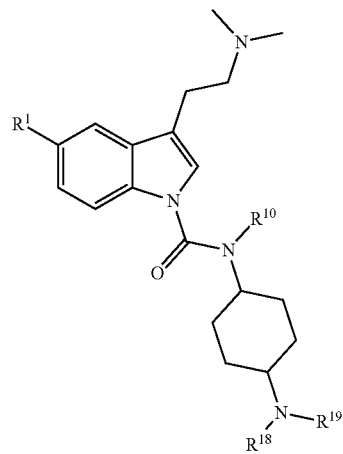

(Ih)

wherein:
R¹ is hydrogen or methoxy;
R¹⁰ is hydrogen, alkyl, heteroalkyl, or cycloalkyl, wherein each of alkyl, heteroalkyl, and cycloalkyl is unsubstituted or substituted with one or more $R^A$; and
each of R¹⁸ and R¹⁹ is independently hydrogen, alkyl, cycloalkyl, or heteroalkyl, wherein each alkyl, cycloalkyl, or heterocyclylalkyl is independently unsubstituted or substituted with one or more $R^B$; or R¹⁸ and R¹⁹ together with the atom to which they are attached form a heterocyclylalkyl ring that is unsubstituted or substituted with one or more $R^B$.

In some embodiments is a compound of Formula (Ih), or a pharmaceutically acceptable salt or solvate thereof, wherein R¹⁰ is hydrogen. In some embodiments is a compound of Formula (Ih), or a pharmaceutically acceptable salt or solvate thereof, wherein R¹⁰ is hydrogen, methyl, ethyl, n-propyl, or isopropyl. In some embodiments is a compound of Formula (Ih), or a pharmaceutically acceptable salt or solvate thereof, wherein R¹⁰ is CH₂CH₂OMe or CH₂CH₂SO₂Me.

In some embodiments is a compound of Formula (Ih), or a pharmaceutically acceptable salt or solvate thereof, wherein each of R¹⁸ and R¹⁹ is independently methyl, ethyl, n-propyl, isopropyl, cyclopropyl, tert-butyl, CH₂CH₂OMe, or CH₂CH₂SO₂Me. In some embodiments is a compound of Formula (Ih), or a pharmaceutically acceptable salt or solvate thereof, wherein R¹⁸ is hydrogen, and R¹⁹ is methyl, ethyl, n-propyl, isopropyl, cyclopropyl, tert-butyl, CH₂CH₂OMe, or CH₂CH₂SO₂Me. In some embodiments is a compound of Formula (Ih), or a pharmaceutically acceptable salt or solvate thereof, wherein each of R¹⁸ and R¹⁹ is methyl, ethyl, n-propyl, isopropyl, cyclopropyl, tert-butyl, CH₂CH₂OMe, or CH₂CH₂SO₂Me.

In some embodiments is a compound of Formula (Ih), or a pharmaceutically acceptable salt or solvate thereof, wherein R¹⁸ and R¹⁹ together with the atom to which they are attached form a heterocyclylalkyl ring. In some embodiments is a compound of Formula (Ih), or a pharmaceutically acceptable salt or solvate thereof, wherein R's and R¹⁹ together with the atom to which they are attached form a azetidine ring, a morpholine ring, a pyrrolidine ring, or a piperidine ring, each of which is substituted or unsubstituted. In some embodiments is a compound of Formula (Ih), or a pharmaceutically acceptable salt or solvate thereof, wherein R¹⁸ and R¹⁹ together with the atom to which they are attached form a azetidine ring, a morpholine ring, a pyrrolidine ring, or a piperidine ring.
In some embodiments is a compound of Formula (I) or (Ih), or a pharmaceutically acceptable salt or solvate thereof, wherein the compound is:
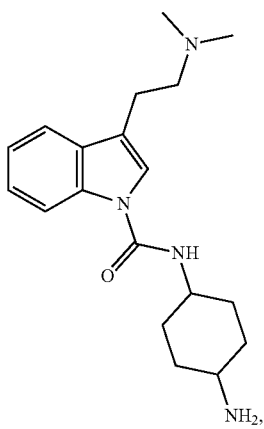
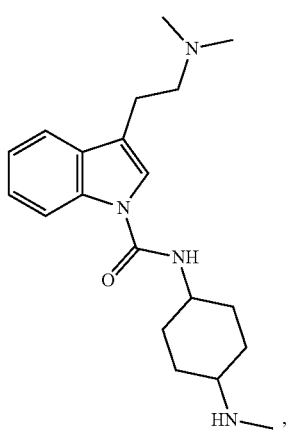
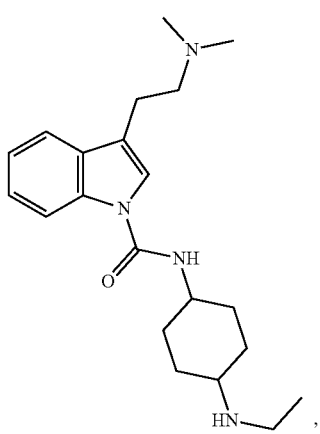
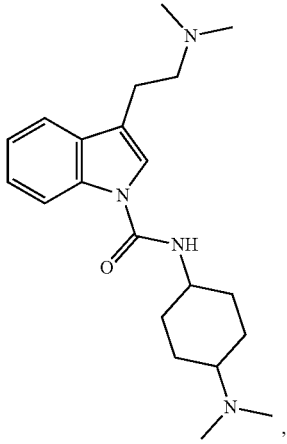
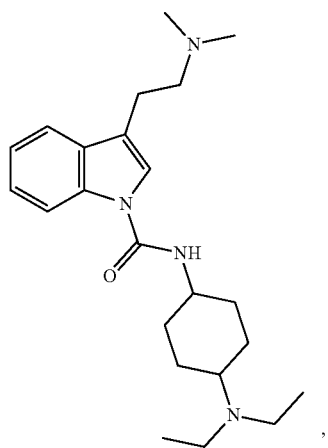
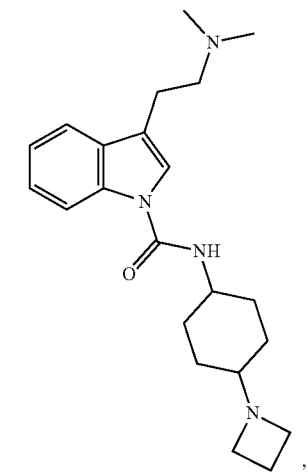

79
-continued
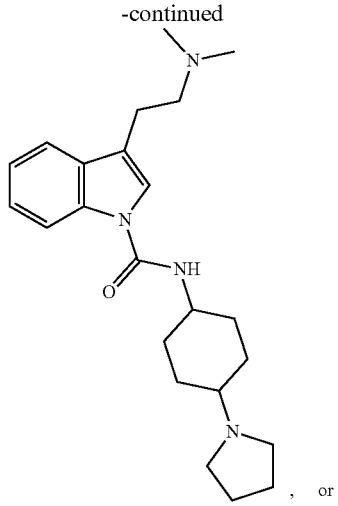
, or
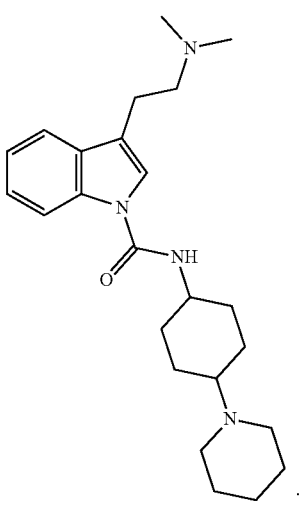 [SMILES: CN(C)CCc1cn(C(=O)NC2CCC(N3CCCCC3)CC2)c2ccccc12]
.
In some embodiments is a compound of Formula (I) or (Ih), or a pharmaceutically acceptable salt or solvate thereof, wherein the compound is:
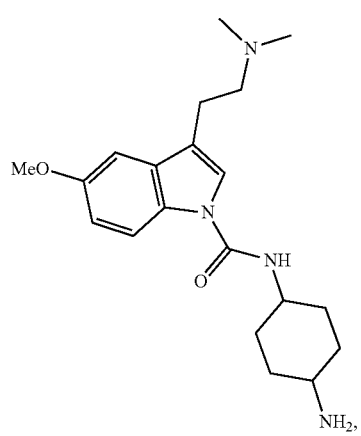
80
-continued
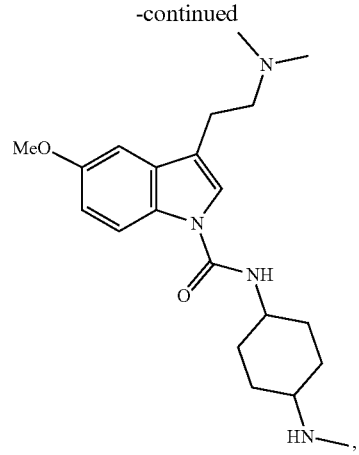
,
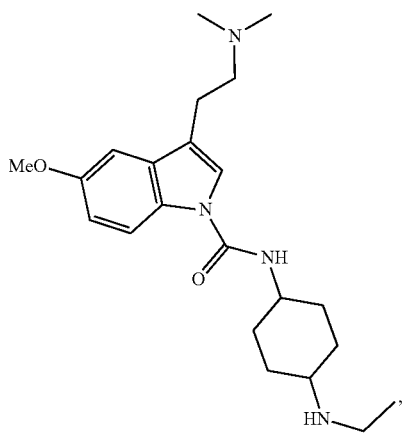
,
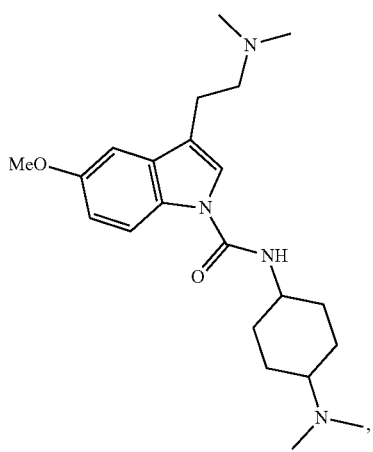
, -continued

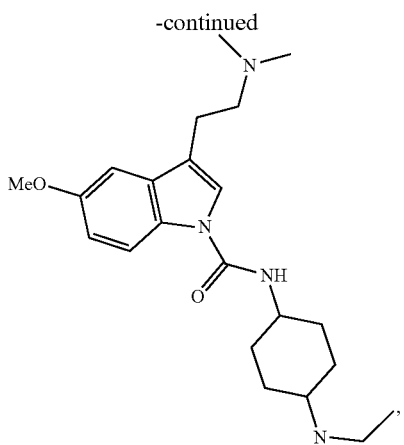

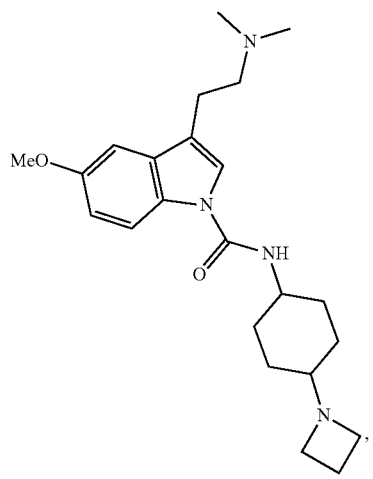

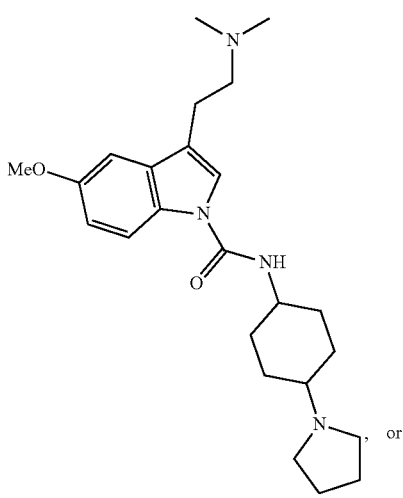

-continued

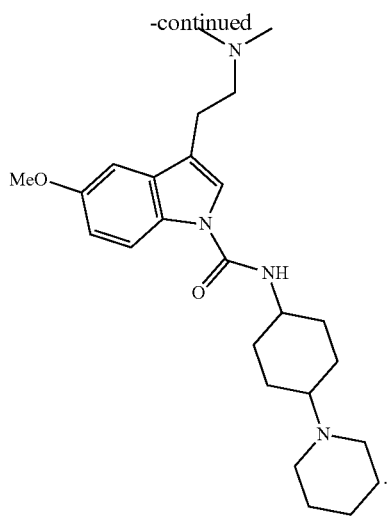

In some embodiments is a compound of Formula (I) having the structure of Formula (Ii), or a pharmaceutically acceptable salt thereof:

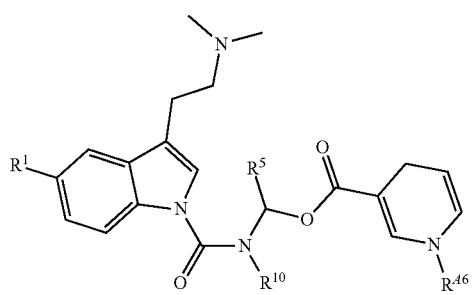

(Ii)

wherein:
R$^1$ is hydrogen or methoxy; and
each of R$^5$ and R$^{10}$ is independently hydrogen, alkyl, heteroalkyl, or cycloalkyl, wherein each alkyl, heteroalkyl, and cycloalkyl is independently unsubstituted or substituted with one or more R$^4$; and
R$^{46}$ is independently hydrogen, alkyl, heteroalkyl, or cycloalkyl, wherein each of alkyl, heteroalkyl, or cycloalkyl is unsubstituted or substituted with one or more alkyl, aryl, halogen, —OR$^3$, —NR(R$^{18}$)R$^{19}$, —C(O)R$^{14}$, —OC(O)R$^{15}$, —OC(O)OR$^{16}$, or —OC(O)N(R$^{18}$)R$^{19}$.

In some embodiments is a compound of Formula (Ii), or a pharmaceutically acceptable salt or solvate thereof, wherein R$^5$ is alkyl. In some embodiments is a compound of Formula (Ii), or a pharmaceutically acceptable salt or solvate thereof, wherein R$^5$ is unsubstituted alkyl. In some embodiments is a compound of Formula (Ii), or a pharmaceutically acceptable salt or solvate thereof, wherein R$^5$ is methyl, ethyl, or isopropyl. In some embodiments is a compound of Formula (Ii), or a pharmaceutically acceptable salt or solvate thereof, wherein R$^5$ is hydrogen, methyl, ethyl, or isopropyl. In some embodiments is a compound of Formula (Ii), or a pharmaceutically acceptable salt or solvate thereof, wherein R$^{46}$ is hydrogen. In some embodiments is a compound of Formula (Ii), or a pharmaceutically acceptable salt or solvate thereof, wherein R$^{46}$ is alkyl. In some embodiments is a compound of Formula (Ii), or a pharmaceutically acceptable salt or solvate thereof, wherein $R^{46}$ is methyl, ethyl, n-propyl, isopropyl, n-butyl, or benzyl. In some embodiments is a compound of Formula (Ii), or a pharmaceutically acceptable salt or solvate thereof, wherein $R^{46}$ is hydrogen, methyl, ethyl, n-propyl, isopropyl, n-butyl, or benzyl. In some embodiments is a compound of Formula (Ii), or a pharmaceutically acceptable salt or solvate thereof, wherein $R^5$ is alkyl, and $R^{46}$ is hydrogen, methyl, ethyl, n-propyl, isopropyl, n-butyl, or benzyl. In some embodiments is a compound of Formula (Ii), or a pharmaceutically acceptable salt or solvate thereof, wherein $R^5$ is unsubstituted alkyl, and $R^{46}$ is hydrogen, methyl, ethyl, n-propyl, isopropyl, n-butyl, or benzyl. In some embodiments is a compound of Formula (Ii), or a pharmaceutically acceptable salt or solvate thereof, wherein $R^5$ is hydrogen, and $R^{46}$ is hydrogen, methyl, ethyl, n-propyl, isopropyl, n-butyl, or benzyl.

In some embodiments is a compound of Formula (Ii), or a pharmaceutically acceptable salt or solvate thereof, wherein $R^{10}$ is hydrogen. In some embodiments is a compound of Formula (Ii), or a pharmaceutically acceptable salt or solvate thereof, wherein $R^{10}$ is alkyl. In some embodiments is a compound of Formula (Ii), or a pharmaceutically acceptable salt or solvate thereof, wherein $R^{10}$ is hydrogen, methyl, ethyl, n-propyl, or isopropyl. In some embodiments is a compound of Formula (Ii), or a pharmaceutically acceptable salt or solvate thereof, wherein $R^{10}$ is $CH_2CH_2OMe$ or $CH_2CH_2SO_2Me$.

In some embodiments is a compound of Formula (Ii), or a pharmaceutically acceptable salt or solvate thereof, wherein each of $R^5$, $R^{10}$, and $R^{46}$ is independently hydrogen, alkyl, heteroalkyl, or cycloalkyl. In some embodiments is a compound of Formula (Ii), or a pharmaceutically acceptable salt or solvate thereof, wherein each of $R^5$, $R^{10}$, and $R^{46}$ is independently hydrogen, alkyl, or cycloalkyl. In some embodiments is a compound of Formula (Ii), or a pharmaceutically acceptable salt or solvate thereof, wherein each of $R^5$, $R^{10}$, and $R^{46}$ is hydrogen. In some embodiments is a compound of Formula (Ii), or a pharmaceutically acceptable salt or solvate thereof, wherein each of $R^5$, $R^{10}$, and $R^{46}$ is independently hydrogen, methyl, ethyl, n-propyl, or isopropyl.

In some embodiments is a compound of Formula (Ii), or a pharmaceutically acceptable salt or solvate thereof, wherein the compound is:

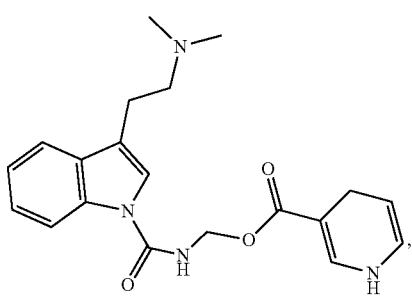

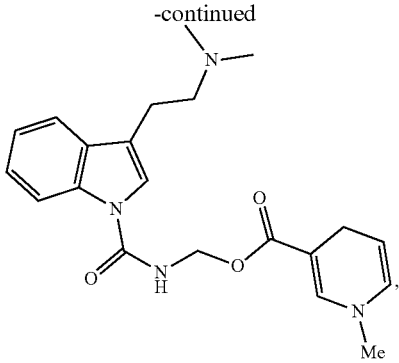

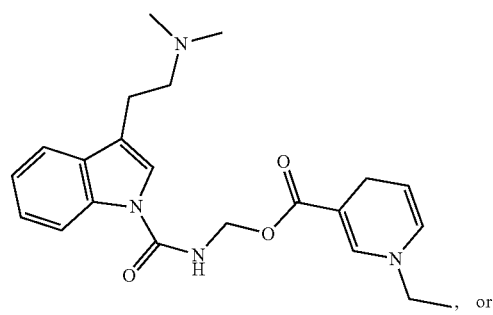

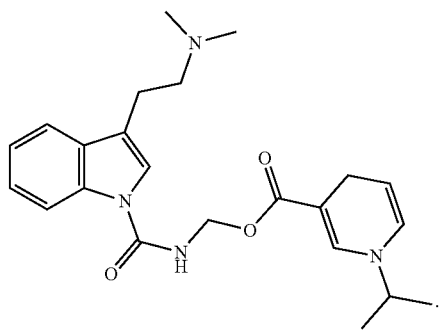

In some embodiments is a compound of Formula (Ii), or a pharmaceutically acceptable salt or solvate thereof, wherein the compound is:

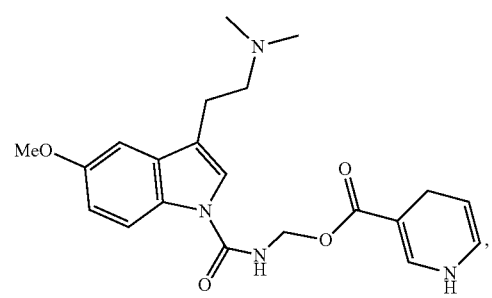

85
-continued

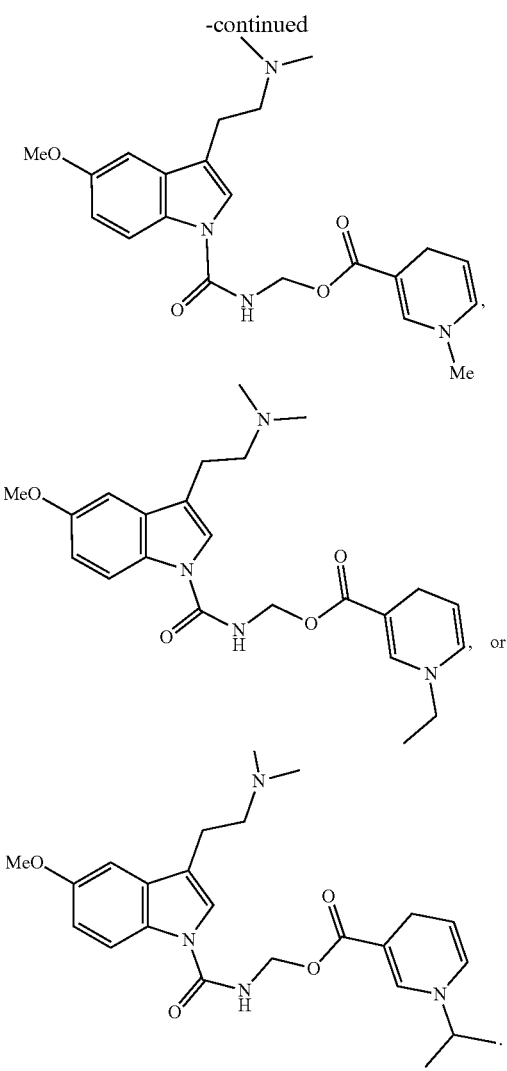

In some embodiments is a compound of Formula (I) having the structure of Formula (Ij), or a pharmaceutically acceptable salt thereof:

(Ij)

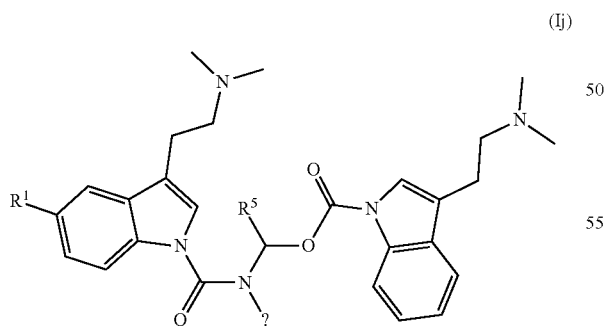

wherein $R^1$ is hydrogen or methoxy, and each of $R^5$ and $R^{10}$ is hydrogen, alkyl, or heteroalkyl, wherein each of alkyl and heteroalkyl is independently unsubstituted or substituted with one or more $R^4$.

In some embodiments is a compound of Formula (Ij), or a pharmaceutically acceptable salt or solvate thereof, wherein $R^5$ is hydrogen. In some embodiments is a compound of Formula (Ij), or a pharmaceutically acceptable salt or solvate thereof, wherein $R^5$ is alkyl. In some embodiments is a compound of Formula (Ij), or a pharmaceutically acceptable salt or solvate thereof, wherein $R^5$ is unsubstituted alkyl. In some embodiments is a compound of Formula (Ij), or a pharmaceutically acceptable salt or solvate thereof, wherein $R^5$ is methyl, ethyl, or isopropyl.

In some embodiments is a compound of Formula (Ij), or a pharmaceutically acceptable salt or solvate thereof, wherein $R^{10}$ is hydrogen. In some embodiments is a compound of Formula (Ij), or a pharmaceutically acceptable salt or solvate thereof, wherein $R^{10}$ is hydrogen, methyl, ethyl, n-propyl, or isopropyl. In some embodiments is a compound of Formula (Ij), or a pharmaceutically acceptable salt or solvate thereof, wherein $R^{10}$ is $CH_2CH_2OMe$ or $CH_2CH_2SO_2Me$.

In some embodiments is a compound of Formula (I) or (Ij), or a pharmaceutically acceptable salt or solvate thereof, wherein the compound is:

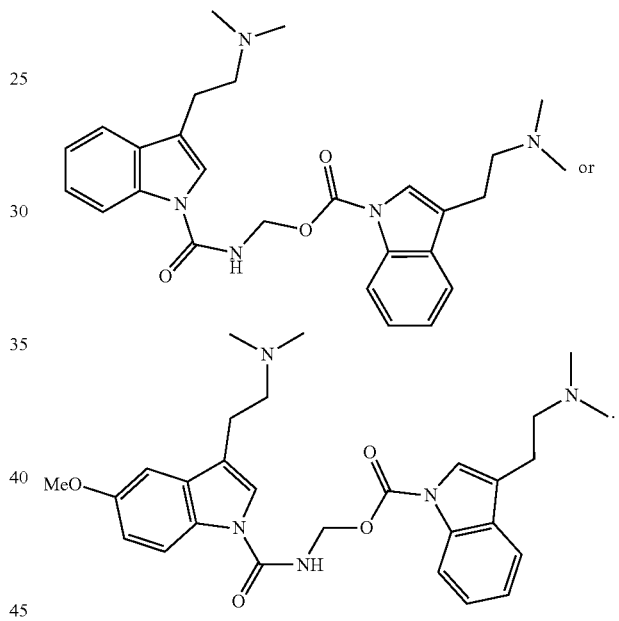

In some embodiments is a compound of Formula (I) having the structure of Formula (Ik), or a pharmaceutically acceptable salt thereof:

(Ik)

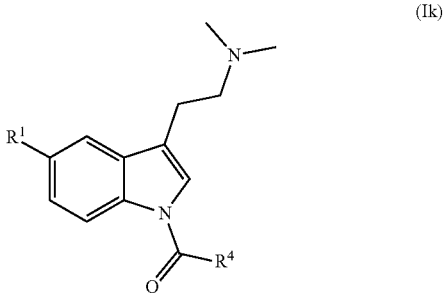

wherein $R^1$ is hydrogen or methoxy, and $R^4$ is alkyl, heterocyclylalkyl, aryl, heteroaryl, or heteroalkyl, each of which is unsubstituted or substituted with one or more $R^4$.

In some embodiments is a compound of Formula (Ik), or a pharmaceutically acceptable salt or solvate thereof, wherein R⁴ is heteroalkyl. In some embodiments is a compound of Formula (Ik), or a pharmaceutically acceptable salt or solvate thereof, wherein R⁴ is heterocyclylalkyl. In some embodiments is a compound of Formula (Ik), or a pharmaceutically acceptable salt or solvate thereof, wherein R¹ is hydrogen and R⁴ is heteroalkyl. In some embodiments is a compound of Formula (Ik), or a pharmaceutically acceptable salt or solvate thereof, wherein R¹ is hydrogen and R⁴ is heterocyclylalkyl. In some embodiments is a compound of Formula (Ik), or a pharmaceutically acceptable salt or solvate thereof, wherein R¹ is methoxy and R⁴ is heteroalkyl. In some embodiments is a compound of Formula (Ik), or a pharmaceutically acceptable salt or solvate thereof, wherein R¹ is methoxy and R⁴ is heterocyclylalkyl.

In some embodiments is a compound of Formula (Ik), or a pharmaceutically acceptable salt or solvate thereof, wherein R⁴ is alkyl. In some embodiments is a compound of Formula (Ik), or a pharmaceutically acceptable salt or solvate thereof, wherein R⁴ is $CH_2CF_3$. In some embodiments is a compound of Formula (Ik), or a pharmaceutically acceptable salt or solvate thereof, wherein R⁴ is unsubstituted alkyl. In some embodiments is a compound of Formula (Ik), or a pharmaceutically acceptable salt or solvate thereof, wherein R⁴ is methyl, ethyl, n-propyl, isopropyl, n-butyl, tert-butyl, 3-methyl-1-butyl, n-pentyl, n-hexyl, n-heptyl, n-octyl, or n-nonyl. In some embodiments is a compound of Formula (Ik), or a pharmaceutically acceptable salt or solvate thereof, wherein R⁴ is cycloalkyl. In some embodiments is a compound of Formula (Ik), or a pharmaceutically acceptable salt or solvate thereof, wherein R⁴ is unsubstituted cycloalkyl. In some embodiments is a compound of Formula (Ik), or a pharmaceutically acceptable salt or solvate thereof, wherein R⁴ is cyclopropyl, cyclobutyl, cyclohexyl, cycloheptyl, or cyclooctyl. In some embodiments is a compound of Formula (Ik), or a pharmaceutically acceptable salt or solvate thereof, wherein R⁴ is aryl. In some embodiments is a compound of Formula (Ik), or a pharmaceutically acceptable salt or solvate thereof, wherein R⁴ is phenyl. In some embodiments is a compound of Formula (Ik), or a pharmaceutically acceptable salt or solvate thereof, wherein R⁴ is heteroaryl. In some embodiments is a compound of Formula (Ik), or a pharmaceutically acceptable salt or solvate thereof, wherein R⁴ is 2-pyridyl, 3-pyridyl, 4-pyridyl, 2-pyrimidyl, 3-pyrimidyl, or 6-pyrimidyl.

In some embodiments is a compound of Formula (I) or (Ik), or a pharmaceutically acceptable salt or solvate thereof, wherein the compound is:

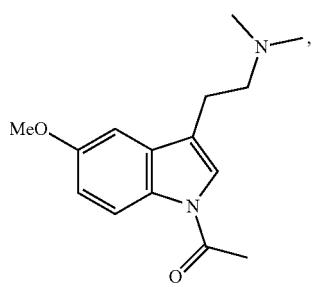

-continued

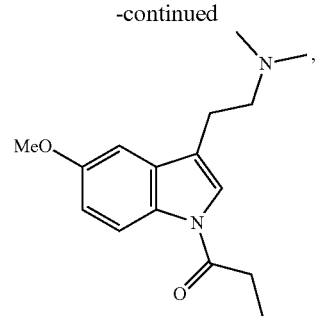

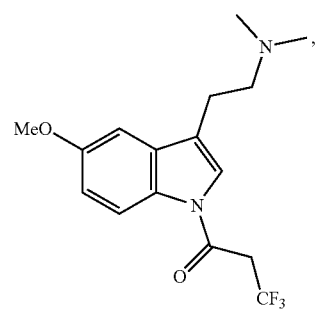

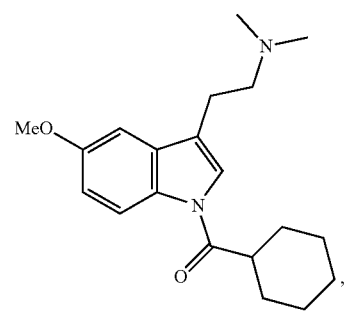

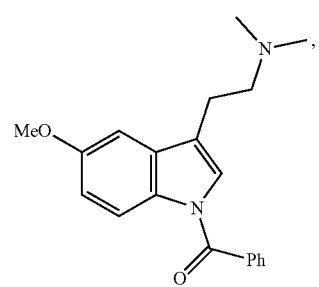

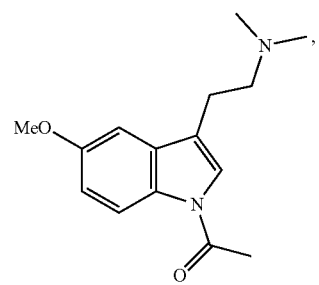

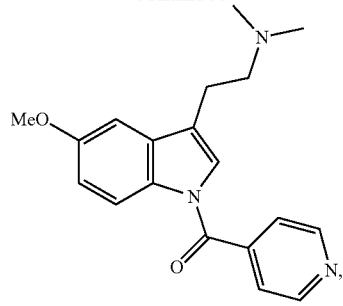,
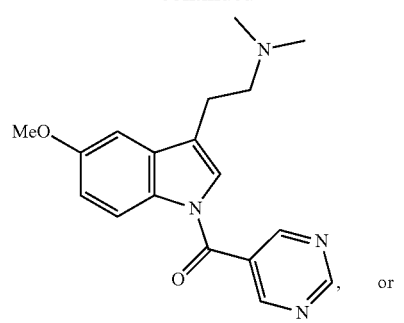 or
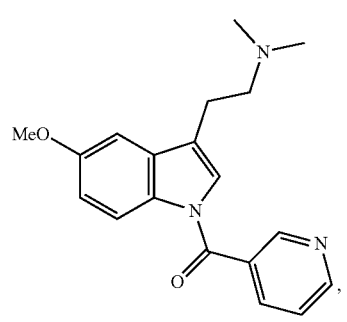,
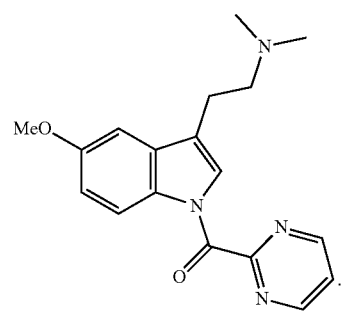.
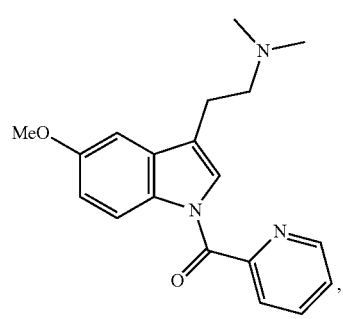,
In some embodiments is a compound of Formula (Ik), or a pharmaceutically acceptable salt or solvate thereof, wherein the compound is:
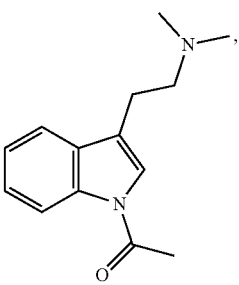, 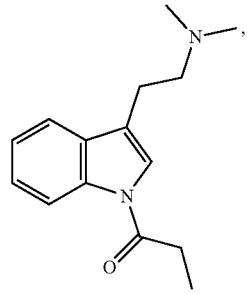,
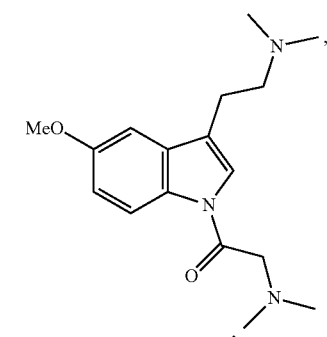,
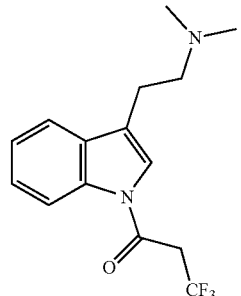, 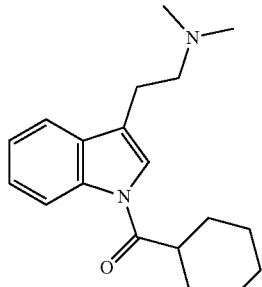,
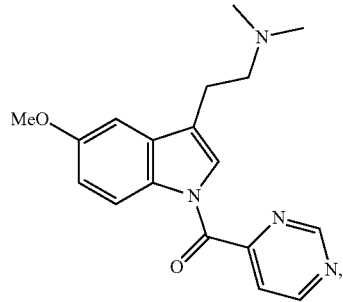,
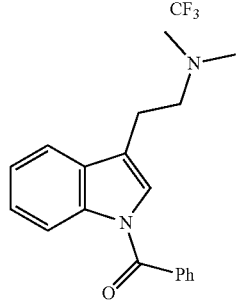, 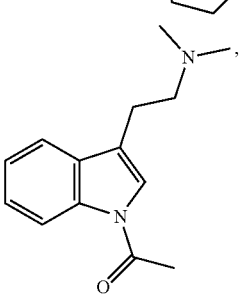,

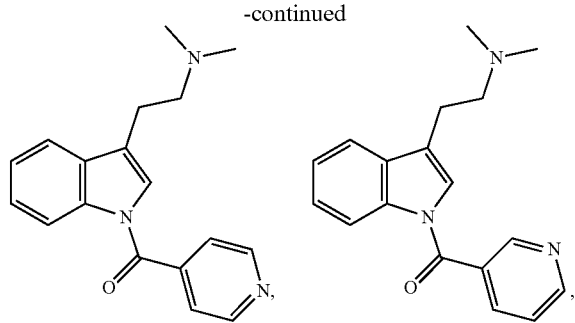

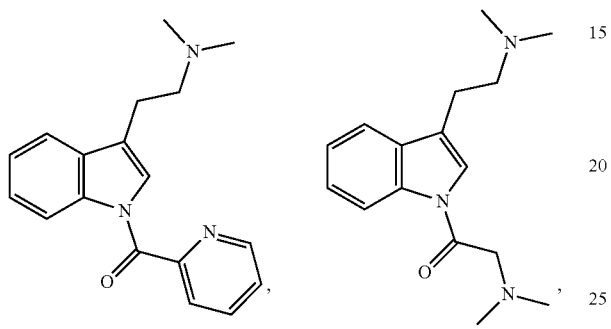

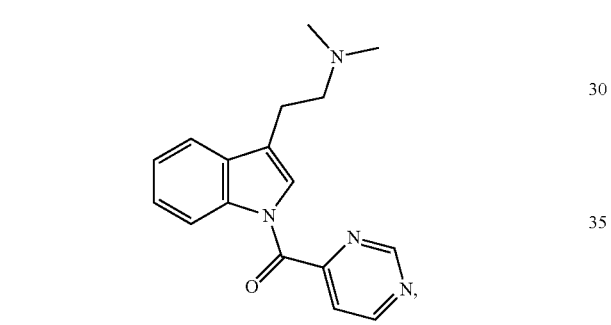

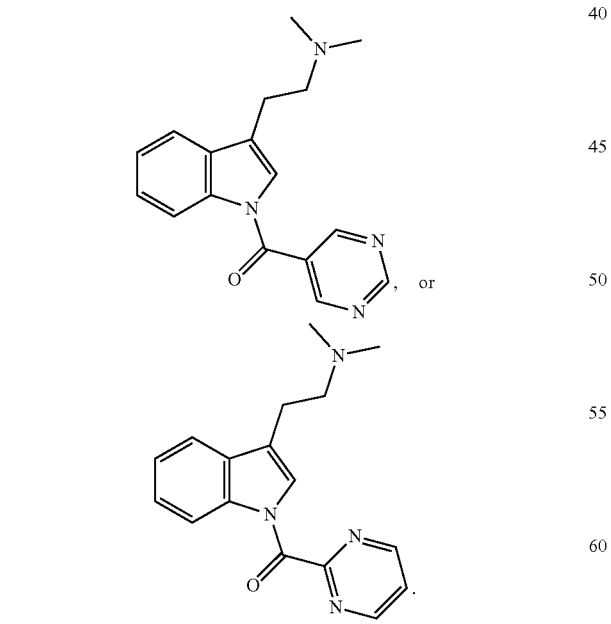

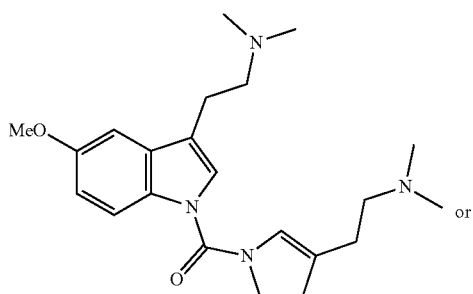

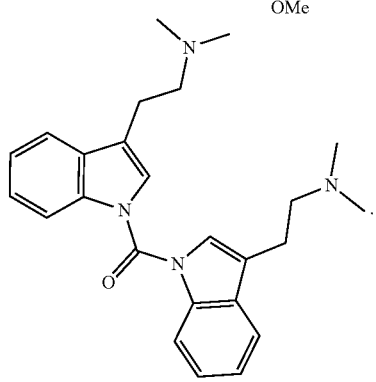

In some embodiments is a compound of Formula (I) or (Ik), or a pharmaceutically acceptable salt or solvate thereof, wherein the compound is:

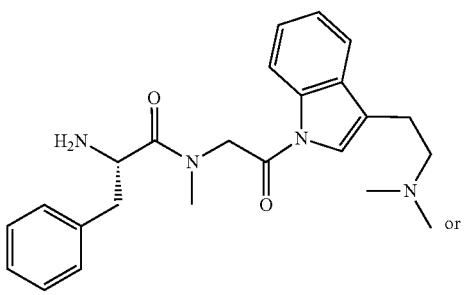

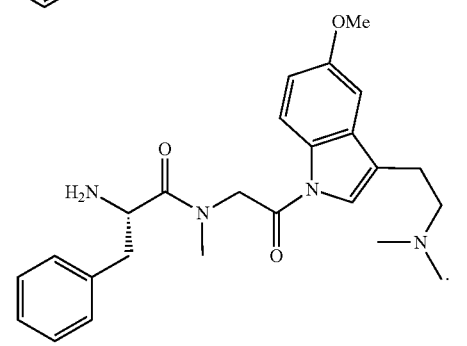

In some embodiments is a compound of Formula (I) or (Ik), or a pharmaceutically acceptable salt or solvate thereof, wherein the compound is:

In some embodiments is a compound of Formula (Ik), or a pharmaceutically acceptable salt or solvate thereof, wherein $R^4$ is heterocyclylalkyl. In some embodiments is a compound of Formula (Ik), or a pharmaceutically acceptable salt or solvate thereof, wherein $R^4$ is,

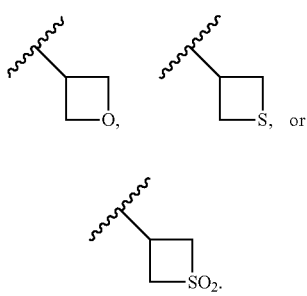

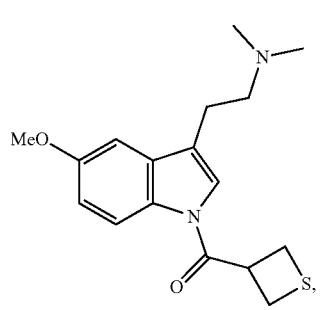

In some embodiments is a compound of Formula (Ik), or a pharmaceutically acceptable salt or solvate thereof, wherein the compound is:

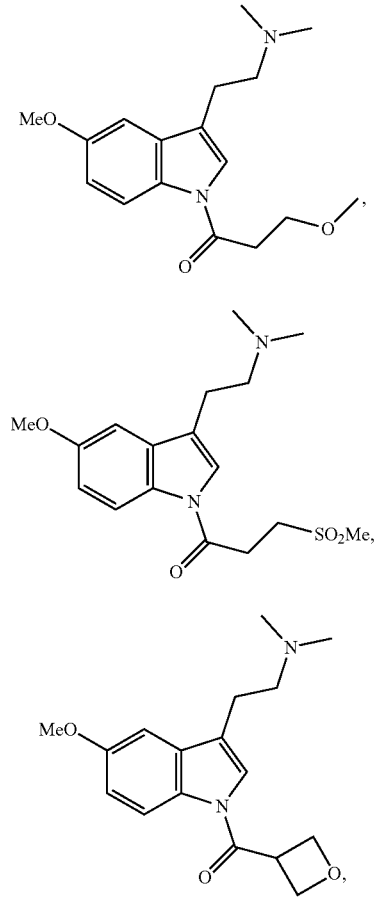

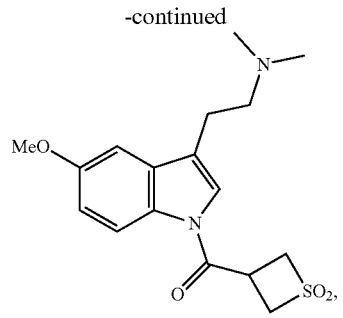

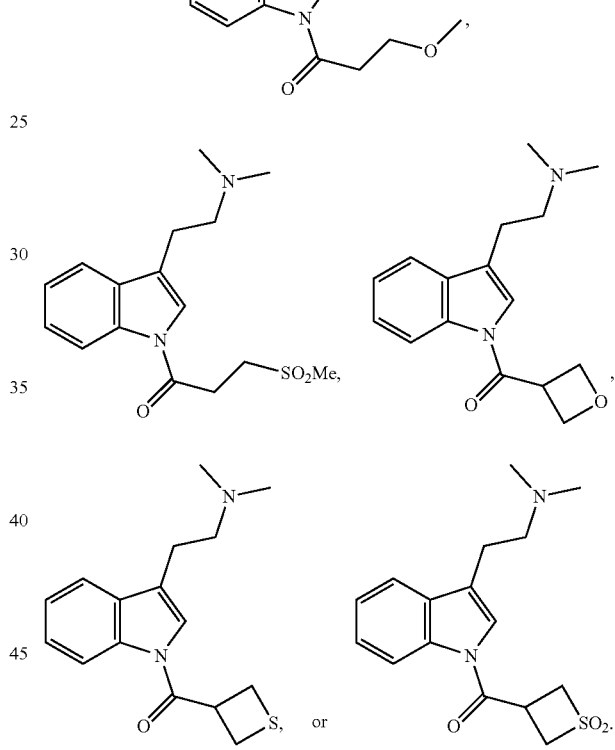

In some embodiments is a compound of Formula (Ik), or a pharmaceutically acceptable salt or solvate thereof, wherein $R^4$ is

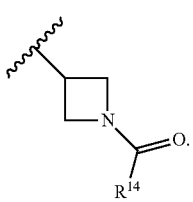

In some embodiments is a compound of Formula (Ik), or a pharmaceutically acceptable salt or solvate thereof, wherein $R^4$ is

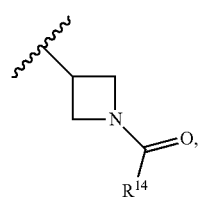

wherein R¹⁴ is alkyl, cycloalkyl, or aryl, each of which is independently unsubstituted or substituted with one or more $R^B$. In some embodiments is a compound of Formula (Ik), or a pharmaceutically acceptable salt or solvate thereof, wherein R⁴ is

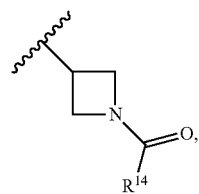

wherein R¹⁴ is methyl, ethyl, n-propyl, isopropyl, or CH₂CH₂OMe. In some embodiments is a compound of Formula (Ik), or a pharmaceutically acceptable salt or solvate thereof, wherein R⁴ is

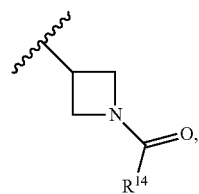

wherein R¹⁴ is phenyl.

In some embodiments is a compound of Formula (I) or (Ik), or a pharmaceutically acceptable salt or solvate thereof, wherein the compound is:

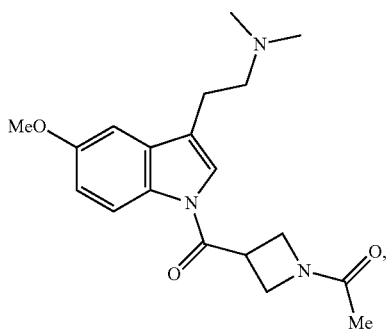

-continued

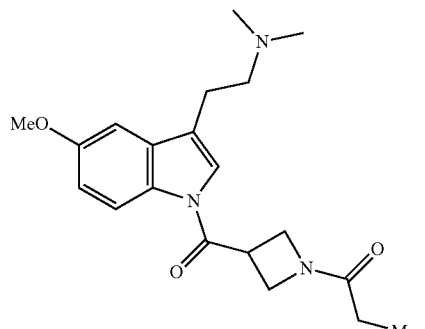

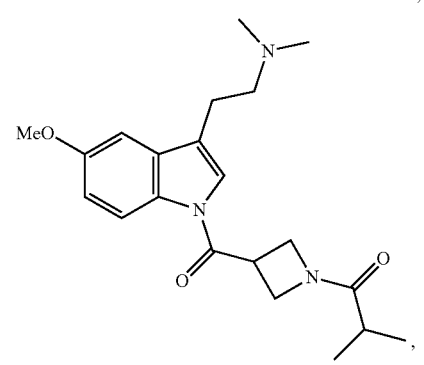

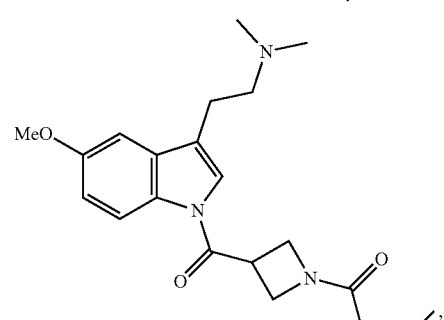

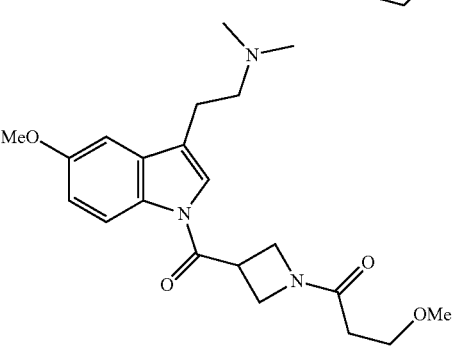

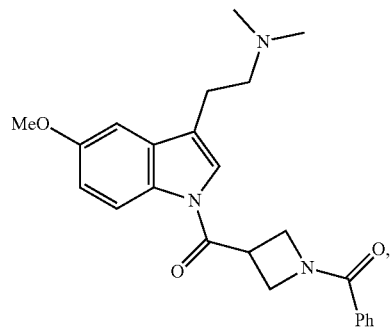

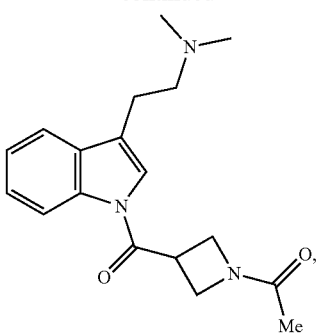

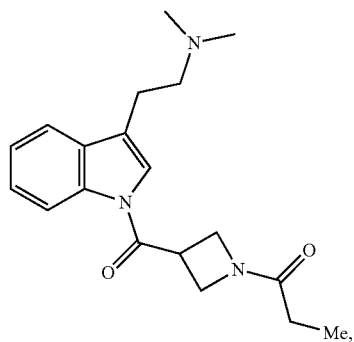

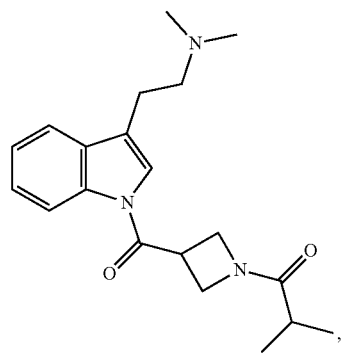

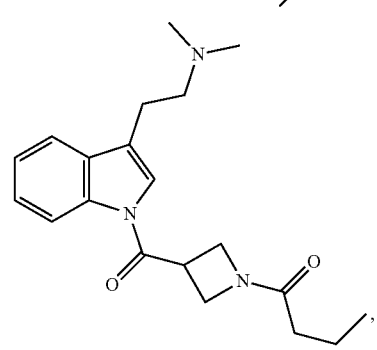

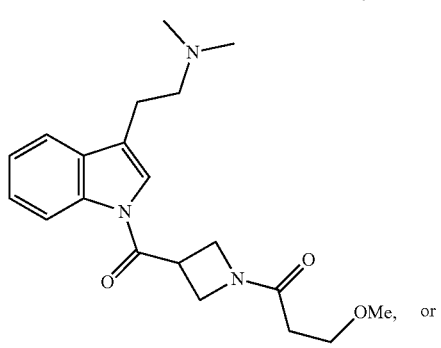

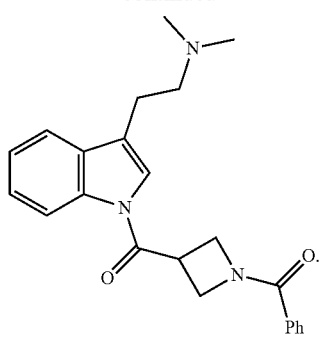

In some embodiments is a compound of Formula (Ik), or a pharmaceutically acceptable salt or solvate thereof, wherein R⁴ is

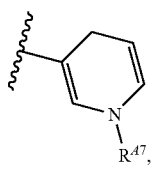

wherein $R^{47}$ is hydrogen or alkyl that is unsubstituted or substituted with one or more alkyl, aryl, halogen, —OR¹³, —NR(R¹⁸)R¹⁹, —C(O)R¹⁴, —OC(O)R¹⁵, —OC(O)OR¹⁶, or —OC(O)N(R¹⁸)R¹⁹. In some embodiments is a compound of Formula (Ik), or a pharmaceutically acceptable salt or solvate thereof, wherein R⁴ is

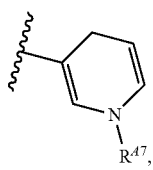

wherein $R^7$ is hydrogen. In some embodiments is a compound of Formula (Ik), or a pharmaceutically acceptable salt or solvate thereof, wherein R⁴ is

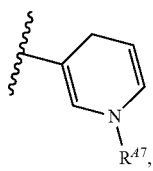

wherein $R^{47}$ is alkyl that is unsubstituted or substituted with one or more alkyl, aryl, halogen, —OR¹³, —NR(R¹⁸)R¹⁹, —C(O)R¹⁴, —OC(O)R¹⁵, —OC(O)OR¹⁶, or —OC(O)N(R¹⁸)R¹⁹. In some embodiments is a compound of Formula (Ik), or a pharmaceutically acceptable salt or solvate thereof, wherein R⁴ is

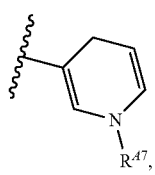

wherein R^{47} is unsubstituted alkyl. In some embodiments is a compound of Formula (Ik), or a pharmaceutically acceptable salt or solvate thereof, wherein $R^4$ is

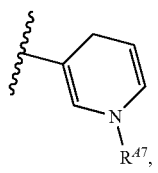

wherein $R^{47}$ is methyl, ethyl, n-propyl, isopropyl, or n-butyl. In some embodiments is a compound of Formula (Ik), or a pharmaceutically acceptable salt or solvate thereof, wherein $R^4$ is

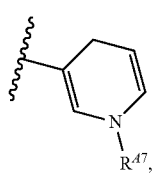

wherein $R^{47}$ is benzyl.

In some embodiments is a compound of Formula (Ik), or a pharmaceutically acceptable salt or solvate thereof, wherein the compound is:

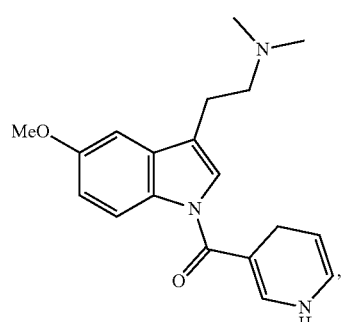

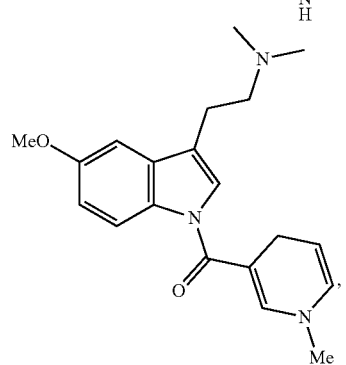

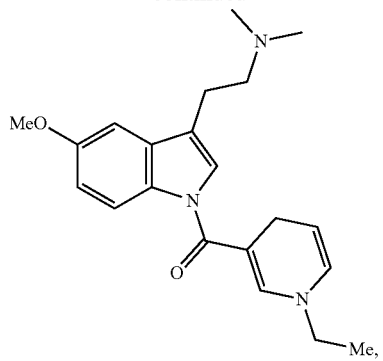

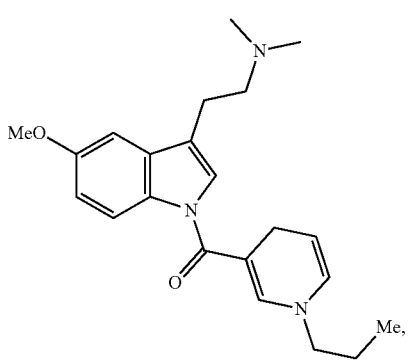

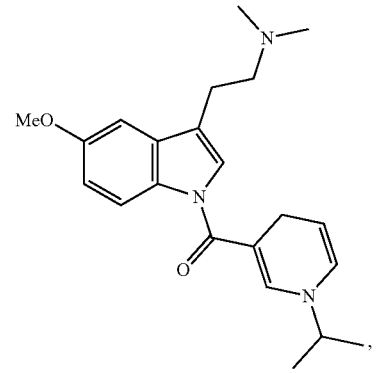

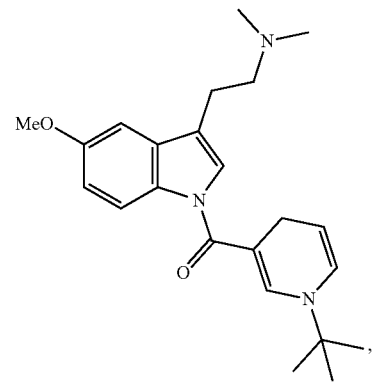

101
-continued
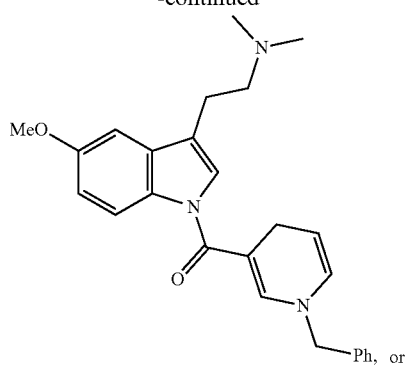
Ph, or
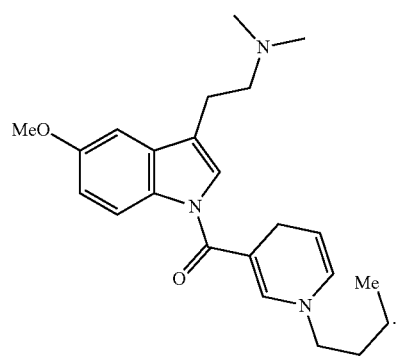
In some embodiments is a compound of Formula (Ik), or a pharmaceutically acceptable salt or solvate thereof, wherein the compound is:
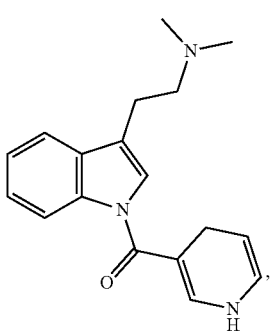
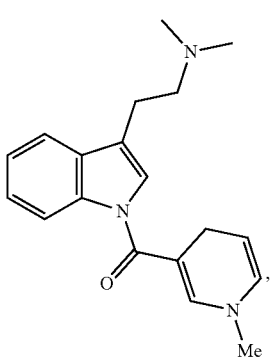
102
-continued
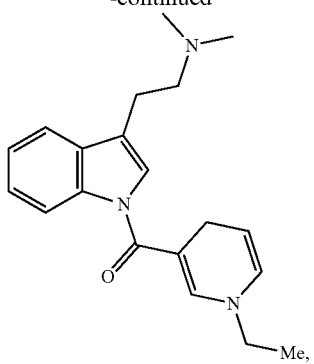
Me,
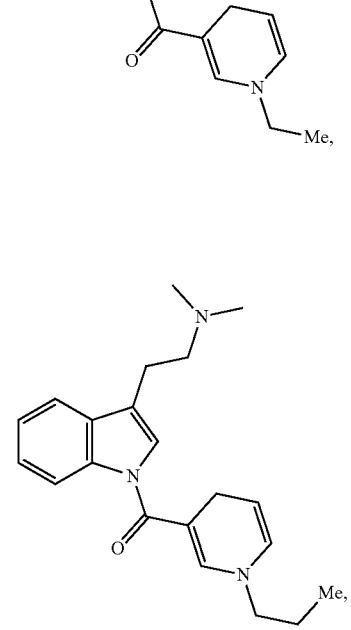
Me,
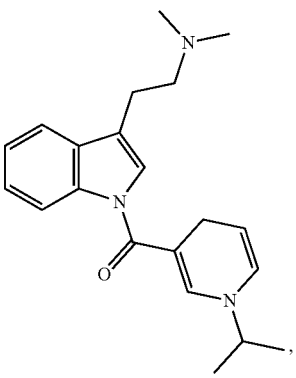
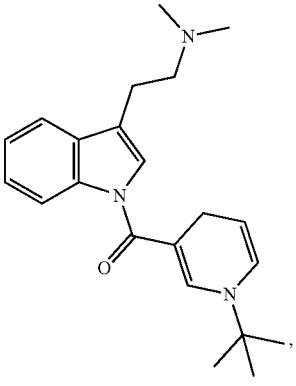

-continued

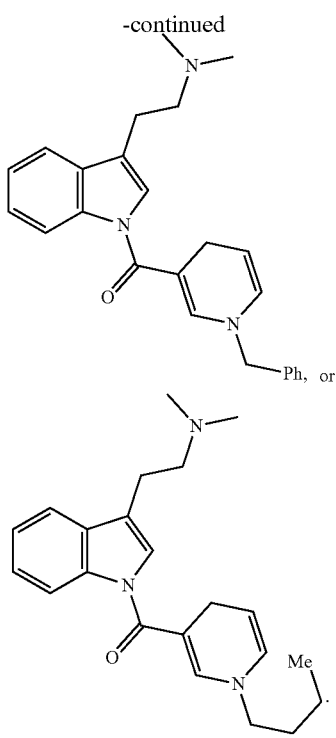

In some embodiments is a compound of Formula (I) or (Ik) having the structure of Formula (Ik1), or a pharmaceutically acceptable salt thereof:

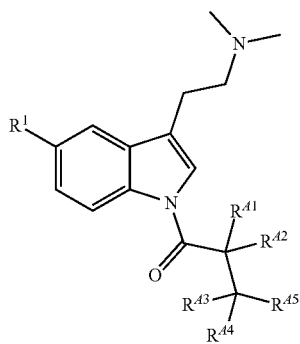

(Ik1)

wherein:
R$^1$ is methoxy or hydrogen;
each of R$^{A1}$, R$^{A2}$, R$^{A3}$, and R$^{A4}$ is independently hydrogen, alkyl, or an amino acid side chain, wherein each alkyl or amino acid side chain is independently unsubstituted or substituted with one or more alkyl, aryl, halogen, —OR$^{13}$, —NR(R$^{18}$)R$^{19}$, —C(O)R$^{14}$, —OC(O)R$^{15}$, —OC(O)OR$^{16}$, or —OC(O)N(R$^{18}$)R$^{19}$;
R$^{10}$ is hydrogen, alkyl, heteroalkyl, or cycloalkyl, wherein each of alkyl, heteroalkyl, and cycloalkyl is unsubstituted or substituted with one or more R$^A$; and
R$^{A5}$ is heteroalkyl, heterocyclylalkyl, heteroaryl, —C(O)OR$^{13}$, —N(R$^3$)C(O)OR$^{14}$, —N(R$^{13}$)C(O)R$^{14}$, —C(O)R$^{14}$, —OC(O)R$^{15}$, or —OC(O)OR$^{16}$, wherein each of heteroalkyl, heterocyclylalkyl, heteroaryl is unsubstituted or substituted with one or more alkyl, aryl, halogen, —OR$^{13}$, —NR(R$^{18}$)R$^{19}$, —C(O)R$^{14}$, —OC(O)R$^{15}$, —OC(O)OR$^{16}$, or —OC(O)N(R$^{18}$)R$^{19}$.

In some embodiments is a compound of Formula (Ik1), or a pharmaceutically acceptable salt or solvate thereof, wherein each of R$^{A1}$, R$^{A2}$, R$^{A3}$, and R$^{A4}$ is hydrogen. In some embodiments is a compound of Formula (Ik1), or a pharmaceutically acceptable salt or solvate thereof, wherein each of R$^{A1}$, R$^{A2}$, R$^{A3}$, and R$^{A4}$ is hydrogen or alkyl. In some embodiments is a compound of Formula (Ik1), or a pharmaceutically acceptable salt or solvate thereof, wherein each of R$^{A1}$, R$^{A2}$, R$^{A3}$, and R$^{A4}$ is hydrogen or unsubstituted alkyl. In some embodiments is a compound of Formula (Ik1), or a pharmaceutically acceptable salt or solvate thereof, wherein R$^{A5}$ is heteroalkyl or heterocyclylalkyl. In some embodiments is a compound of Formula (Ik1), or a pharmaceutically acceptable salt or solvate thereof, wherein R$^{A5}$ is heterocyclylalkyl. In some embodiments is a compound of Formula (Ik1), or a pharmaceutically acceptable salt or solvate thereof, wherein R$^{A5}$ is heteroalkyl. In some embodiments is a compound of Formula (Ik1), or a pharmaceutically acceptable salt or solvate thereof, wherein each of R$^{A1}$, R$^{A2}$, R$^{A3}$, and R$^{A4}$ is hydrogen, and R$^{A5}$ is alkoxy. In some embodiments is a compound of Formula (Ik1), or a pharmaceutically acceptable salt or solvate thereof, wherein each of R$^{A1}$, R$^{A2}$, R$^{A3}$, and R$^{A4}$ is hydrogen, and R$^{A5}$ is methoxy. In some embodiments is a compound of Formula (Ik1), or a pharmaceutically acceptable salt or solvate thereof, wherein each of R$^{A1}$, R$^{A2}$, R$^{A3}$, and R$^{A4}$ is hydrogen, and R$^{A5}$ is alkylsulfonyl. In some embodiments is a compound of Formula (Ik1), or a pharmaceutically acceptable salt or solvate thereof, wherein each of R$^{A1}$, R$^{A2}$, R$^{A3}$, and R$^{A4}$ is hydrogen, and R$^{A5}$ is methylsulfonyl.

In some embodiments is a compound of Formula (Ik1), or a pharmaceutically acceptable salt or solvate thereof, wherein R$^{A5}$ is —OC(O)R$^{15}$. In some embodiments is a compound of Formula (Ik1), or a pharmaceutically acceptable salt or solvate thereof, wherein R$^{A5}$ is —OC(O)R$^5$, wherein R$^{15}$ is alkyl, cycloalkyl, aryl, heteroaryl, heteroalkyl, or heterocyclylalkyl. In some embodiments is a compound of Formula (Ik1), or a pharmaceutically acceptable salt or solvate thereof, wherein R$^{A5}$ is —OC(O)R$^{15}$, wherein R$^{15}$ is alkyl. In some embodiments is a compound of Formula (Ik1), or a pharmaceutically acceptable salt or solvate thereof, wherein R$^{A5}$ is —OC(O)R$^5$, wherein R$^{15}$ is unsubstituted alkyl. In some embodiments is a compound of Formula (Ik1), or a pharmaceutically acceptable salt or solvate thereof, wherein R$^{A5}$ is —OC(O)R$^{15}$, wherein R$^{15}$ is methyl, ethyl, n-propyl, isopropyl n-butyl, tert-butyl, n-pentyl, or 3-methyl-1-butyl. In some embodiments is a compound of Formula (Ik1), or a pharmaceutically acceptable salt or solvate thereof, wherein R$^{A5}$ is —OC(O)R$^{15}$, wherein R$^{15}$ is aryl. In some embodiments is a compound of Formula (Ik1), or a pharmaceutically acceptable salt or solvate thereof, wherein R$^{A5}$ is —OC(O)R$^{15}$, wherein R$^{15}$ is unsubstituted aryl. In some embodiments is a compound of Formula (Ik1), or a pharmaceutically acceptable salt or solvate thereof, wherein R$^{A5}$ is —OC(O)R$^{15}$, wherein R$^{15}$ is phenyl. In some embodiments is a compound of Formula (Ik1), or a pharmaceutically acceptable salt or solvate thereof, wherein R$^{A5}$ is —OC(O)R$^{15}$, wherein R$^{15}$ is 2-pyridyl, 3-pyridyl, 4-pyridyl, 2-pyrimidyl, 4-pyrimidyl, 5-pyrimidyl, or 6-pyrimidyl.

In some embodiments is a compound of Formula (I) or (Ik) having the structure of Formula (Ik2), or a pharmaceutically acceptable salt thereof:

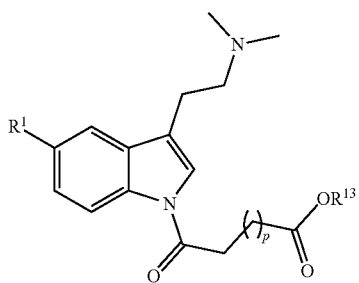

(Ik2)

wherein:
R¹ is methoxy or hydrogen;
R¹³ is hydrogen, alkyl, cycloalkyl, aryl, heteroaryl, heteroalkyl, or heterocyclylalkyl, wherein each of alkyl, cycloalkyl, aryl, heteroaryl, heteroalkyl, and heterocyclylalkyl is unsubstituted or substituted with one or more $R^B$; and
p is 0, 1, 2, 3, 4, 5, 6, 7, 8, 9, or 10.

In some embodiments is a compound of Formula (I), (Ik) or (Ik2), or a pharmaceutically acceptable salt or solvate thereof, wherein R¹³ is alkyl, cycloalkyl, aryl, heteroaryl, heteroalkyl, or heterocyclylalkyl. In some embodiments is a compound of Formula (I), (Ik) or (Ik2), or a pharmaceutically acceptable salt or solvate thereof, wherein R¹³ is hydrogen or alkyl. In some embodiments is a compound of Formula (I), (Ik) or (Ik2), or a pharmaceutically acceptable salt or solvate thereof, wherein R¹³ is hydrogen. In some embodiments is a compound of Formula (I), (Ik) or (Ik2), or a pharmaceutically acceptable salt or solvate thereof, wherein R¹³ is alkyl. In some embodiments is a compound of Formula (I), (Ik) or (Ik2), or a pharmaceutically acceptable salt or solvate thereof, wherein R¹³ is unsubstituted alkyl. In some embodiments is a compound of Formula (I), (Ik) or (Ik2), or a pharmaceutically acceptable salt or solvate thereof, wherein R¹³ is methyl, ethyl, n-propyl, isopropyl n-butyl, tert-butyl, n-pentyl, or 3-methyl-1-butyl. In some embodiments is a compound of Formula (I), (Ik) or (Ik2), or a pharmaceutically acceptable salt or solvate thereof, wherein R¹³ is hydrogen, methyl, ethyl, n-propyl, isopropyl n-butyl, tert-butyl, n-pentyl, or 3-methyl-1-butyl. In some embodiments is a compound of Formula (I), (Ik) or (Ik2), or a pharmaceutically acceptable salt or solvate thereof, wherein R¹³ is methyl. In some embodiments is a compound of Formula (I), (Ik) or (Ik2), or a pharmaceutically acceptable salt or solvate thereof, wherein R¹³ is hydrogen or methyl. In some embodiments is a compound of Formula (I), (Ik) or (Ik2), or a pharmaceutically acceptable salt or solvate thereof, wherein R¹³ is aryl. In some embodiments is a compound of Formula (I), (Ik) or (Ik2), or a pharmaceutically acceptable salt or solvate thereof, wherein R¹³ is unsubstituted aryl. In some embodiments is a compound of Formula (I), (Ik) or (Ik2), or a pharmaceutically acceptable salt or solvate thereof, wherein R¹³ is phenyl. In some embodiments is a compound of Formula (I), (Ik) or (Ik2), or a pharmaceutically acceptable salt or solvate thereof, wherein R¹³ is 2-pyridyl, 3-pyridyl, 4-pyridyl, 2-pyrimidyl, 4-pyrimidyl, 5-pyrimidyl, or 6-pyrimidyl. In some embodiments is a compound of Formula (I), (Ik) or (Ik2), or a pharmaceutically acceptable salt or solvate thereof, wherein p is 1, 2, 3, 4, or 5. In some embodiments is a compound of Formula (I), (Ik) or (Ik2), or a pharmaceutically acceptable salt or solvate thereof, wherein p is 1. In some embodiments is a compound of Formula (I), (Ik) or (Ik2), or a pharmaceutically acceptable salt or solvate thereof, wherein p is 2. In some embodiments is a compound of Formula (I), (Ik) or (Ik2), or a pharmaceutically acceptable salt or solvate thereof, wherein p is 3. In some embodiments is a compound of Formula (I), (Ik) or (Ik2), or a pharmaceutically acceptable salt or solvate thereof, wherein p is 4. In some embodiments is a compound of Formula (I), (Ik) or (Ik2), or a pharmaceutically acceptable salt or solvate thereof, wherein p is 5.

In some embodiments is a compound of Formula (Ik1), or a pharmaceutically acceptable salt or solvate thereof, wherein the compound is:

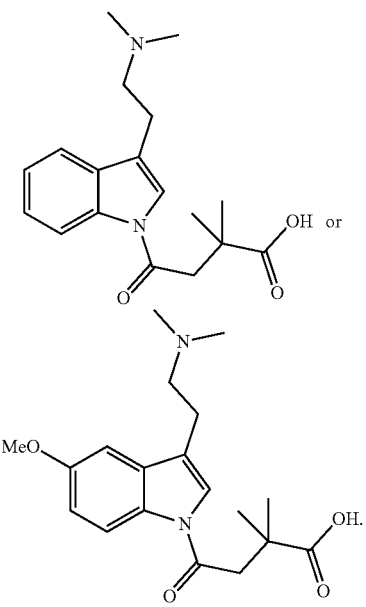

In some embodiments is a compound of Formula (Ik2), or a pharmaceutically acceptable salt or solvate thereof, wherein the compound is:

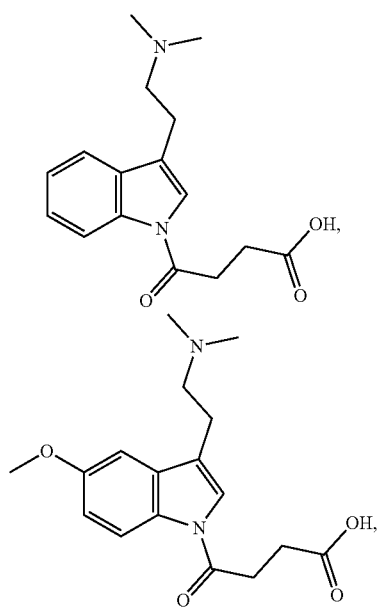

-continued

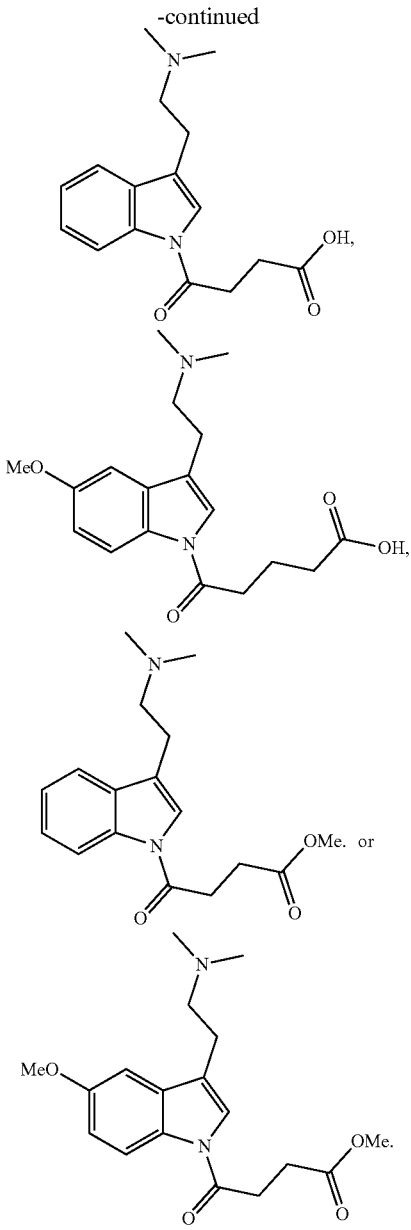

In some embodiments is a compound of Formula (I) or (Ik) having the structure of Formula (Ik3), or a pharmaceutically acceptable salt thereof:

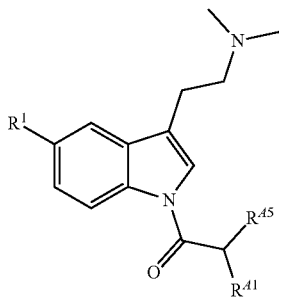

(Ik3)

wherein:

$R^1$ is methoxy or hydrogen;

$R^{41}$ is alkyl or an amino acid side chain, each of which is unsubstituted or substituted with one or more alkyl, aryl, halogen, $-OR^{13}$, $-NR(R^{18})R^{19}$, $-C(O)R^{14}$, $-OC(O)R^{15}$, $-OC(O)OR^{16}$, or $-OC(O)N(R^{18})R^{19}$; and $R^{45}$ is $-N(R^{18})R^{19}$ or $-N(R^{13})C(O)R^{14}$.

In some embodiments is a compound of Formula (Ik3), or a pharmaceutically acceptable salt or solvate thereof, wherein $R^{45}$ is $-N(R^{18})R^{19}$. In some embodiments is a compound of Formula (Ik3), or a pharmaceutically acceptable salt or solvate thereof, wherein $R^{41}$ is $-N(R^{18})R^{19}$, wherein each of $R^{18}$ and $R^{19}$ is hydrogen. In some embodiments is a compound of Formula (Ik3), or a pharmaceutically acceptable salt or solvate thereof, wherein $R^{45}$ is $-N(R^{18})R^{19}$, wherein $R^{19}$ is alkyl, cycloalkyl, or aryl. In some embodiments is a compound of Formula (Ik3), or a pharmaceutically acceptable salt or solvate thereof, wherein $R^{45}$ is $-N(R^{18})R^{19}$, wherein $R^{18}$ is hydrogen, and $R^{19}$ is alkyl, cycloalkyl, or aryl. In some embodiments is a compound of Formula (Ik3), or a pharmaceutically acceptable salt or solvate thereof, wherein $R^{45}$ is $-N(R^{18})R^{19}$, wherein $R^{18}$ is hydrogen, and $R^{19}$ is unsubstituted alkyl, unsubstituted cycloalkyl, or unsubstituted aryl. In some embodiments is a compound of Formula (Ik3), or a pharmaceutically acceptable salt or solvate thereof, wherein $R^{45}$ is $-N(R^{18})R^{19}$, wherein $R^{18}$ is hydrogen, and $R^{19}$ is methyl, ethyl, isopropyl, tert-butyl, or phenyl.

In some embodiments is a compound of Formula (Ik3), or a pharmaceutically acceptable salt or solvate thereof, wherein $R^{45}$ is $-N(R^{13})C(O)R^{14}$.

In some embodiments is a compound of Formula (Ik3), or a pharmaceutically acceptable salt or solvate thereof, wherein the compound is:

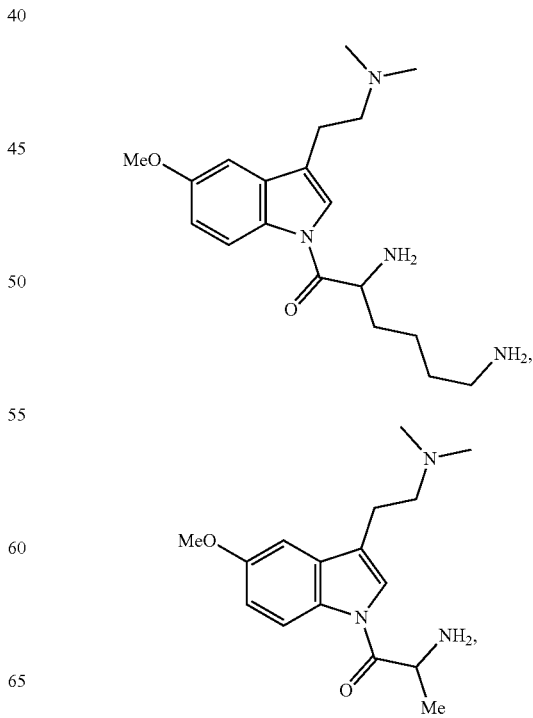

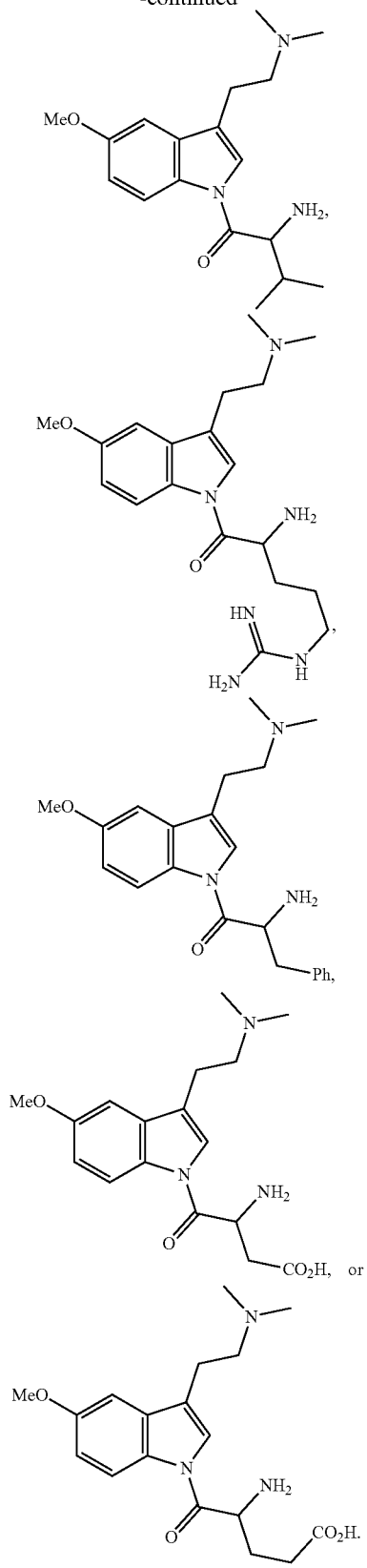
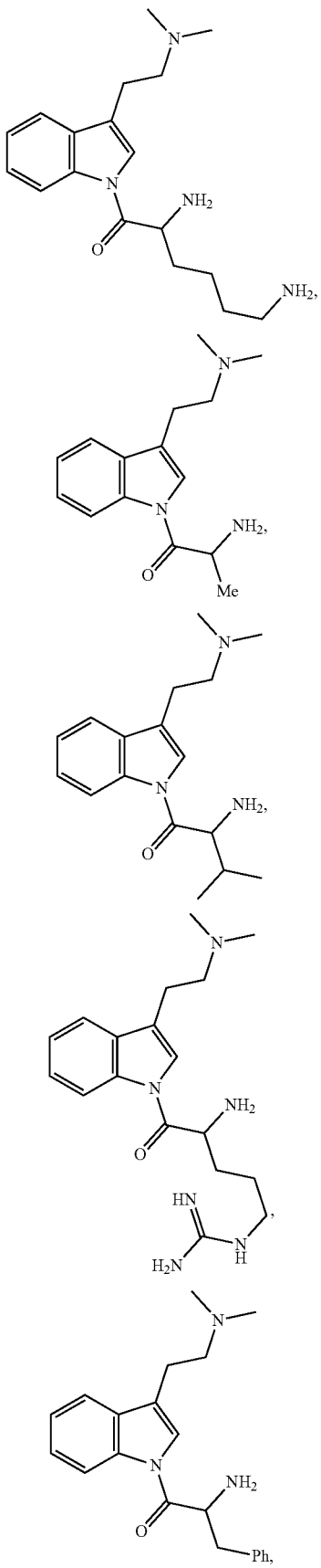
In some embodiments is a compound of Formula (Ik3), or a pharmaceutically acceptable salt or solvate thereof, wherein the compound is:

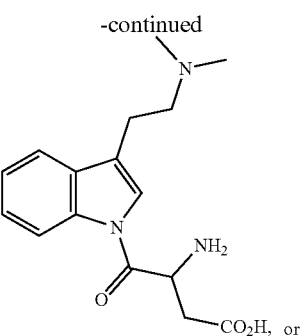
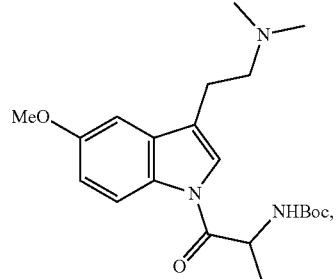
In some embodiments is a compound of Formula (Ik3), or a pharmaceutically acceptable salt or solvate thereof, wherein the compound is:
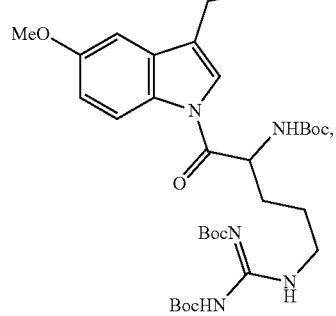
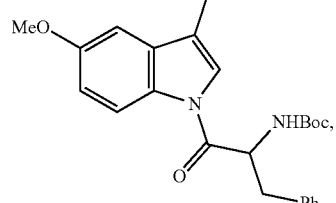
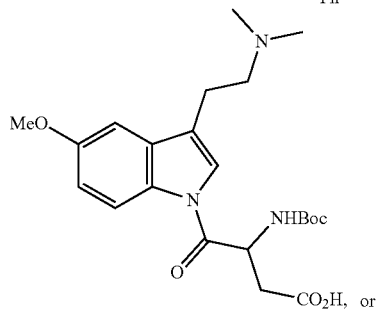
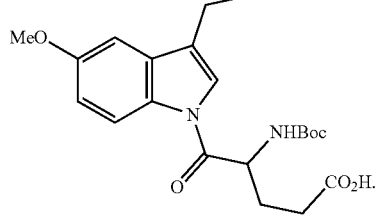
In some embodiments is a compound of Formula (Ik3), or a pharmaceutically acceptable salt or solvate thereof, wherein the compound is:

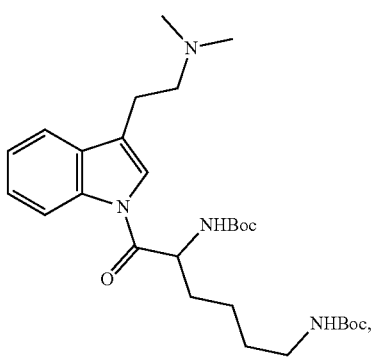

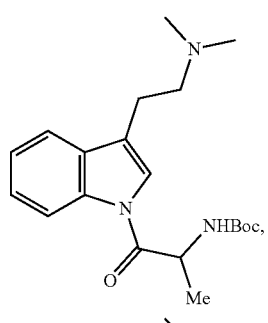

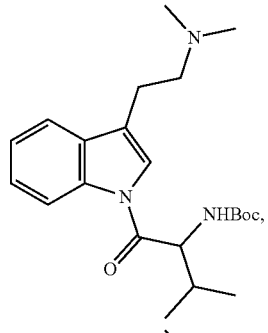

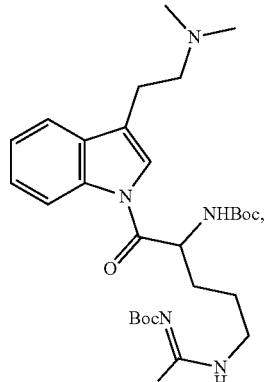

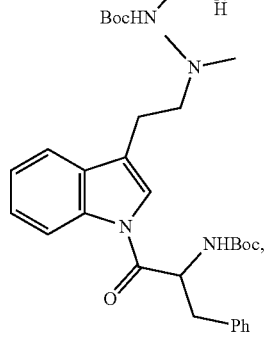

-continued

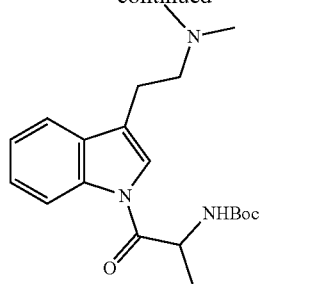

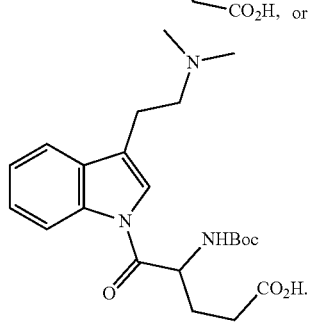

In some embodiments is a compound of Formula (I) having the structure of Formula (I1), or a pharmaceutically acceptable salt thereof:

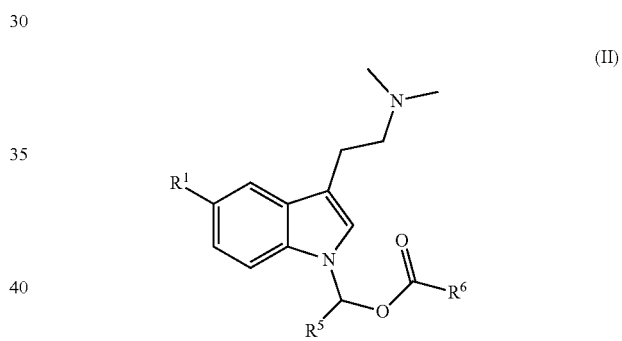

(II)

wherein:
$R^1$ is methoxy or hydrogen;
$R^5$ is hydrogen, alkyl, or cycloalkyl, wherein each of alkyl or cycloalkyl is unsubstituted or substituted with one or more $R^4$; and
$R^6$ is alkyl, cycloalkyl, heterocyclylalkyl, or heteroalkyl, wherein each of alkyl, cycloalkyl, heterocyclylalkyl, or heteroalkyl is unsubstituted or substituted with one or more $R^4$.

In some embodiments is a compound of Formula (I) or (I1), or a pharmaceutically acceptable salt or solvate thereof, wherein $R^6$ is methyl, ethyl, isopropyl, tert-butyl, 2-dimethylaminoethyl, or cyclopropyl. In some embodiments is a compound of Formula (I) or (I1), or a pharmaceutically acceptable salt or solvate thereof, wherein $R^1$ is hydrogen, $R^5$ is hydrogen, and $R^6$ is methyl, ethyl, isopropyl, tert-butyl, 2-dimethylaminoethyl, or cyclopropyl. In some embodiments is a compound of Formula (I) or (I1), or a pharmaceutically acceptable salt or solvate thereof, wherein $R^1$ is methoxy, $R^5$ is hydrogen, and $R^6$ is methyl, ethyl, isopropyl, tert-butyl, 2-dimethylaminoethyl, or cyclopropyl. In some embodiments is a compound of Formula (I) or (I1), or a pharmaceutically acceptable salt or solvate thereof, wherein $R^1$ is hydrogen, $R^5$ is hydrogen, and $R^6$ is tert-butyl. In some embodiments is a compound of Formula (I) or (I1), or a pharmaceutically acceptable salt or solvate thereof, R⁵ is hydrogen. In some embodiments is a compound of Formula (I) or (I1), or a pharmaceutically acceptable salt or solvate thereof, wherein R¹ is methoxy, R⁵ is hydrogen, and R⁶ is tert-butyl.

In some embodiments is a compound of Formula (I) or (I1), or a pharmaceutically acceptable salt or solvate thereof, wherein the compound is:

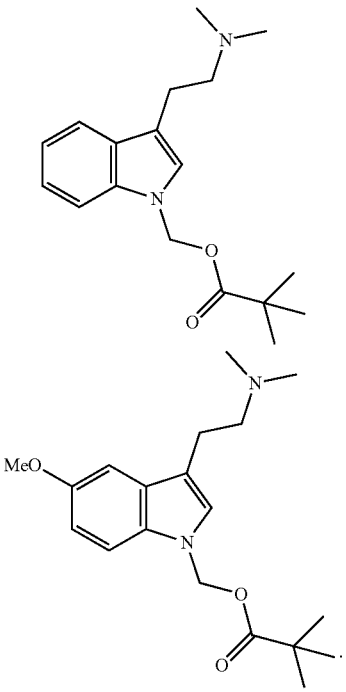

In some embodiments is a compound of Formula (I) having the structure of Formula (Im), or a pharmaceutically acceptable salt thereof:

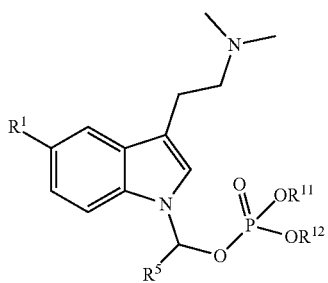

(Im)

wherein:
R¹ is methoxy or hydrogen;
R⁵ hydrogen, alkyl, cycloalkyl, or heteroalkyl, wherein each of alkyl, cycloalkyl, and heteroalkyl is unsubstituted or substituted with one or more $R^A$; and
each of R¹¹ and R¹² is independently hydrogen, cycloalkyl, aryl, heteroaryl, or alkyl, wherein each of alkyl, cycloalkyl, and heteroalkyl is independently unsubstituted or substituted with one or more $R^A$.

In some embodiments is a compound of Formula (I) or (Im), or a pharmaceutically acceptable salt or solvate thereof, wherein each of R¹¹ and R¹² is independently cycloalkyl, aryl, heteroaryl, or alkyl. In some embodiments is a compound of Formula (I) or (Im), or a pharmaceutically acceptable salt or solvate thereof, wherein R¹¹ is hydrogen and R¹² is cycloalkyl, aryl, heteroaryl, or alkyl. In some embodiments is a compound of Formula (I) or (Im), or a pharmaceutically acceptable salt or solvate thereof, wherein R¹¹ is hydrogen and R¹² is alkyl. In some embodiments is a compound of Formula (I) or (Im), or a pharmaceutically acceptable salt or solvate thereof, wherein R¹¹ is hydrogen and R¹² is tert-butyl. In some embodiments is a compound of Formula (I) or (Im), or a pharmaceutically acceptable salt or solvate thereof, wherein R⁵ is hydrogen or alkyl. In some embodiments is a compound of Formula (I) or (Im), or a pharmaceutically acceptable salt or solvate thereof, wherein R⁵ is hydrogen, unsubstituted alkyl, unsubstituted cycloalkyl, unsubstituted heteroalkyl, or alkyl substituted with heteroaryl. In some embodiments is a compound of Formula (I) or (Im), or a pharmaceutically acceptable salt or solvate thereof, wherein each of R¹¹ and R¹² is independently selected from unsubstituted alkyl, unsubstituted cycloalkyl, unsubstituted aryl, unsubstituted heteroaryl, unsubstituted alkyl, or alkyl substituted with aryl or heteroaryl. In some embodiments is a compound of Formula (I) or (Im), or a pharmaceutically acceptable salt or solvate thereof, wherein R¹¹ is hydrogen, and R¹² is cycloalkyl, aryl, heteroaryl, or alkyl. In some embodiments is a compound of Formula (I) or (Im), or a pharmaceutically acceptable salt or solvate thereof, wherein R¹ is hydrogen, and R¹² is alkyl. In some embodiments is a compound of Formula (I) or (Im), or a pharmaceutically acceptable salt or solvate thereof, wherein each of R¹¹ and R¹² is alkyl. In some embodiments is a compound of Formula (I) or (Im), or a pharmaceutically acceptable salt or solvate thereof, wherein each of R¹¹ and R¹² is unsubstituted alkyl. In some embodiments is a compound of Formula (I) or (Im), or a pharmaceutically acceptable salt or solvate thereof, wherein each of R¹¹ and R¹² is alkyl substituted with —OC(O)R⁵. In some embodiments is a compound of Formula (I) or (Im), or a pharmaceutically acceptable salt or solvate thereof, wherein each of R¹¹ and R¹² is alkyl substituted with —OC(O)R⁵, wherein each R¹⁵ is alkyl, cycloalkyl, heterocyclylalkyl, aryl, or heteroaryl. In some embodiments is a compound of Formula (I) or (Im), or a pharmaceutically acceptable salt or solvate thereof, wherein each of R¹¹ and R¹² is alkyl substituted with —OC(O)R¹⁵, wherein each R⁵ is unsubstituted alkyl, unsubstituted cycloalkyl, unsubstituted heterocyclylalkyl, unsubstituted aryl, or unsubstituted heteroaryl. In some embodiments is a compound of Formula (I) or (Im), or a pharmaceutically acceptable salt or solvate thereof, wherein each of R¹¹ and R¹² is alkyl substituted with —OC(O)R¹⁵, wherein each R¹⁵ is heterocyclylalkyl substituted with alkyl or arylalkyl.

In some embodiments is a compound of Formula (I) or (Im), or a pharmaceutically acceptable salt or solvate thereof, wherein R⁴ is hydrogen. In some embodiments is a compound of Formula (I) or (Im), or a pharmaceutically acceptable salt or solvate thereof, wherein R⁵ is hydrogen and each of R¹¹ and R¹² is alkyl, heterocyclylalkyl, or cycloalkyl. In some embodiments is a compound of Formula (I) or (Im), or a pharmaceutically acceptable salt or solvate thereof, wherein R⁵ is hydrogen. In some embodiments is a compound of Formula (I) or (Im), or a pharmaceutically acceptable salt or solvate thereof, wherein R⁵ is hydrogen and each of R¹¹ and R¹² is alkyl. In some embodiments is a compound of Formula (I) or (Im), or a pharmaceutically acceptable salt or solvate thereof, wherein R⁵ is hydrogen and each of R¹ and R¹² is unsubstituted alkyl. In some embodiments is a compound of Formula (I) or (Im), or a pharmaceutically acceptable salt or solvate thereof, wherein R¹ is methoxy, R⁴ is hydrogen, and each of R¹¹ and R¹² is unsubstituted alkyl. In some embodiments is a compound of Formula (I) or (Im), or a pharmaceutically acceptable salt or solvate thereof, wherein R¹ is hydrogen, R⁵ is hydrogen, and each of R¹¹ and R¹² is unsubstituted alkyl. In some embodiments is a compound of Formula (I) or (Im), or a pharmaceutically acceptable salt or solvate thereof, wherein R¹ is methoxy, R⁵ is hydrogen, and each of R¹¹ and R¹² is tert-butyl. In some embodiments is a compound of Formula (I) or (Im), or a pharmaceutically acceptable salt or solvate thereof, wherein R¹ is hydrogen, R⁵ is hydrogen, and each of R¹¹ and R¹² is tert-butyl.

In some embodiments is a compound of Formula (I) or (Im), or a pharmaceutically acceptable salt or solvate thereof, wherein each of R¹¹ and R¹² is

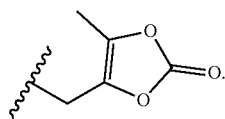 [SMILES: *Cc1oc(=O)oc1C]

In some embodiments is a compound of Formula (I) or (Im), or a pharmaceutically acceptable salt or solvate thereof, wherein each of R¹¹ and R¹² is methyl, ethyl, n-propyl, isopropyl, n-butyl, tert-butyl, n-pentyl, n-hexyl, or 3-methyl-1-butyl. In some embodiments is a compound of Formula (I) or (Im), or a pharmaceutically acceptable salt or solvate thereof, wherein each of R¹¹ and R¹² is cyclopropyl, cyclobutyl, cyclopentyl, cyclohexyl, or cycloheptyl. In some embodiments is a compound of Formula (I) or (Im), or a pharmaceutically acceptable salt or solvate thereof, wherein each of R¹¹ and R¹² is phenyl. In some embodiments is a compound of Formula (I) or (Im), or a pharmaceutically acceptable salt or solvate thereof, wherein each of R¹¹ and R¹² is 2-pyridyl, 3-pyridyl, 4-pyridyl, 2-pyrimidyl, 4-pyrimidyl, 5-pyrimidyl, or 6-pyrimidyl. In some embodiments is a compound of Formula (I) or (Im), or a pharmaceutically acceptable salt or solvate thereof, wherein each of R¹¹ and R¹² is 4-nitrophenyl. In some embodiments is a compound of Formula (I) or (Im), or a pharmaceutically acceptable salt or solvate thereof, wherein each of R¹¹ and R¹² is benzyl.

In some embodiments is a compound of Formula (I) or (Im) having the structure of Formula (Im1), or a pharmaceutically acceptable salt thereof:

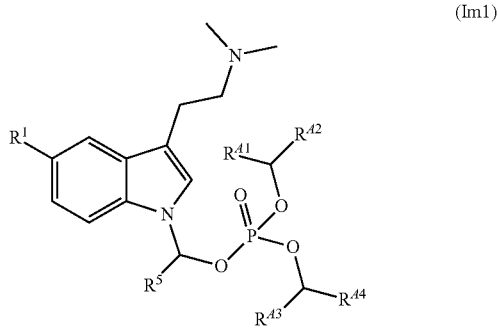

(Im1)

wherein:
R¹ is methoxy or hydrogen;
each of R^{A1}, R^{A3}, and R⁶ is independently hydrogen, alkyl, or cycloalkyl; and
each of R^{A2} and R^{A4} is independently alkyl, heteroalkyl, cycloalkyl, heterocyclylalkyl, aryl, or heteroaryl, —OC(O)R¹⁵, or —OC(O)OR¹⁶,
wherein each alkyl, heteroalkyl, cycloalkyl, heterocyclylalkyl, aryl, and heteroaryl is independently unsubstituted or substituted with one or more alkyl, aryl, halogen, —OR¹³, —NR(R¹⁸)R¹⁹, —C(O)R¹⁴, —OC(O)R¹⁵, —OC(O)OR¹⁶, or —OC(O)N(R¹⁸)R¹⁹.

In some embodiments is a compound of Formula (Im1), or a pharmaceutically acceptable salt or solvate thereof, wherein each of R^{A1}, R^{A3}, and R⁵ is independently hydrogen, methyl, ethyl, isopropyl, or tert-butyl. In some embodiments is a compound of Formula (Im1), or a pharmaceutically acceptable salt or solvate thereof, wherein R⁵ is hydrogen. In some embodiments is a compound of Formula (Im1), or a pharmaceutically acceptable salt or solvate thereof, wherein each of R^{A1} and R^{A3} is hydrogen.

In some embodiments is a compound of Formula (Im1), or a pharmaceutically acceptable salt or solvate thereof, wherein each of R^{A2} and R^{A4} is —OC(O)R⁵. In some embodiments is a compound of Formula (Im1), or a pharmaceutically acceptable salt or solvate thereof, wherein each of R^{A2} and R^{A4} is —OC(O)R⁵; and each of R^{A1}, R^{A3}, and R⁴ is independently hydrogen, methyl, ethyl, isopropyl, or tert-butyl. In some embodiments is a compound of Formula (Im1), or a pharmaceutically acceptable salt or solvate thereof, wherein each R¹⁵ is alkyl, cycloalkyl, aryl, or heteroaryl. In some embodiments is a compound of Formula (Im1), or a pharmaceutically acceptable salt or solvate thereof, wherein each of R^{A2} and R^{A4} is —OC(O)R¹⁵; each of R^{A1}, R^{A3}, and R⁵ is independently hydrogen, methyl, ethyl, isopropyl, or tert-butyl; and each R¹⁵ is alkyl, cycloalkyl, aryl, or heteroaryl. In some embodiments is a compound of Formula (Im1), or a pharmaceutically acceptable salt or solvate thereof, wherein each of R^{A2} and R^{A4} is —OC(O)R⁵; each of R^{A1}, R^{A3}, and R⁵ is independently hydrogen, methyl, ethyl, isopropyl, or tert-butyl; and each R¹⁵ is methyl, ethyl, n-propyl, n-butyl, n-pentyl, n-hexyl, isopropyl, tert-butyl, 3-methyl-1-butyl, cyclopropyl, or cyclobutyl. In some embodiments is a compound of Formula (Im1), or a pharmaceutically acceptable salt or solvate thereof, wherein each of R^{A2} and R^{A4} is —OC(O)R¹⁵; each of R^{A1}, R^{A3}, and R⁵ is hydrogen; and each R¹⁵ is methyl, ethyl, n-propyl, n-butyl, n-pentyl, n-hexyl, isopropyl, tert-butyl, 3-methyl-1-butyl, cyclopropyl, or cyclobutyl. In some embodiments is a compound of Formula (Im1), or a pharmaceutically acceptable salt or solvate thereof, wherein each of R^{A2} and R^{A4} is —OC(O)R⁵; each of R^{A1}, R^{A3}, and R⁵ is independently hydrogen, methyl, ethyl, isopropyl, or tert-butyl; and each R¹⁵ is phenyl or 4-nitrophenyl. In some embodiments is a compound of Formula (Im1), or a pharmaceutically acceptable salt or solvate thereof, wherein each of R^{A2} and R^{A4} is —OC(O)R⁵; each of R^{A1}, R^{A3}, and R⁵ is hydrogen; and each R¹⁵ is phenyl or 4-nitrophenyl. In some embodiments is a compound of Formula (Im1), or a pharmaceutically acceptable salt or solvate thereof, wherein each of R^{A2} and R^{A4} is —OC(O)R¹⁵; each of R^{A1}, R^{A3}, and R⁵ is independently hydrogen, methyl, ethyl, isopropyl, or tert-butyl; and each R¹⁵ is benzyl. In some embodiments is a compound of Formula (Im1), or a pharmaceutically acceptable salt or solvate thereof, wherein each of R^{A2} and R^{A4} is —OC(O)R¹⁵; each of R⁴, R^{A3}, and R⁵ is hydrogen; and each R¹⁵ is benzyl. In some embodiments is a compound of Formula (Im1), or a pharmaceutically acceptable salt or solvate thereof, wherein each of R^{A2} and R^{A4} is —OC(O)R¹⁵; each of $R^{41}$, $R^{43}$, and $R^5$ is independently hydrogen, methyl, ethyl, isopropyl, or tert-butyl; and each $R^{15}$ is 2-pyridyl, 3-pyridyl, 4-pyridyl, 2-pyrimidyl, or 4-pyrimidyl. In some embodiments is a compound of Formula (Im1), or a pharmaceutically acceptable salt or solvate thereof, wherein each of $R^{42}$ and $R^{44}$ is —OC(O)$R^5$; each of $R^{41}$, $R^{43}$, and $R^5$ is hydrogen; and each $R^{15}$ is 2-pyridyl, 3-pyridyl, 4-pyridyl, 2-pyrimidyl, or 4-pyrimidyl.

In some embodiments is a compound of Formula (Im1), or a pharmaceutically acceptable salt or solvate thereof, wherein each of $R^{42}$ and $R^{44}$ is —OC(O)O$R^{16}$. In some embodiments is a compound of Formula (Im1), or a pharmaceutically acceptable salt or solvate thereof, wherein each of $R^{42}$ and $R^{44}$ is —OC(O)O$R^{16}$; and each of $R^{41}$, $R^{43}$, and $R^5$ is independently hydrogen, methyl, ethyl, isopropyl, or tert-butyl. In some embodiments is a compound of Formula (Im1), or a pharmaceutically acceptable salt or solvate thereof, wherein each of $R^{42}$ and $R^{44}$ is —OC(O)O$R^{16}$; each of $R^{41}$, $R^{43}$, and $R^5$ is independently hydrogen, methyl, ethyl, isopropyl, or tert-butyl; and each $R^{16}$ is alkyl, cycloalkyl, aryl, or heteroaryl. In some embodiments is a compound of Formula (Im1), or a pharmaceutically acceptable salt or solvate thereof, wherein each of $R^{42}$ and $R^{44}$ is —OC(O)O$R^{16}$; each of $R^{41}$, $R^{43}$, and $R^5$ is independently hydrogen, methyl, ethyl, isopropyl, or tert-butyl; and each $R^{16}$ is methyl, ethyl, n-propyl, n-butyl, n-pentyl, n-hexyl, isopropyl, tert-butyl, 3-methyl-1-butyl, cyclopropyl, or cyclobutyl. In some embodiments is a compound of Formula (Im1), or a pharmaceutically acceptable salt or solvate thereof, wherein each of $R^{42}$ and $R^{44}$ is —OC(O)O$R^{16}$; each of $R^{41}$, $R^{43}$, and $R^5$ is hydrogen; and each $R^{16}$ is methyl, ethyl, n-propyl, n-butyl, n-pentyl, n-hexyl, isopropyl, tert-butyl, 3-methyl-1-butyl, cyclopropyl, or cyclobutyl. In some embodiments is a compound of Formula (Im1), or a pharmaceutically acceptable salt or solvate thereof, wherein each of $R^{42}$ and $R^{44}$ is —OC(O)O$R^{16}$; each of $R^{41}$, $R^{43}$, and $R^5$ is hydrogen; and each $R^{16}$ is isopropyl. In some embodiments is a compound of Formula (Im1), or a pharmaceutically acceptable salt or solvate thereof, wherein each $R^{42}$ and $R^{44}$ is —OC(O)O$R^{16}$; each of $R^{41}$, $R^{43}$, and $R^5$ is independently hydrogen, methyl, ethyl, isopropyl, or tert-butyl; and each $R^{16}$ is phenyl or 4-nitrophenyl. In some embodiments is a compound of Formula (Im1), or a pharmaceutically acceptable salt or solvate thereof, wherein each $R^{42}$ and $R^{44}$ is —OC(O)O$R^{16}$; each of $R^{41}$, $R^{43}$, and $R^5$ is hydrogen; and each $R^{16}$ is phenyl or 4-nitrophenyl. In some embodiments is a compound of Formula (Im1), or a pharmaceutically acceptable salt or solvate thereof, wherein each of $R^{42}$ and $R^{44}$ is —OC(O)O$R^{16}$; each of $R^{41}$, $R^{43}$, and $R^5$ is independently hydrogen, methyl, ethyl, isopropyl, or tert-butyl; and each $R^{16}$ is benzyl. In some embodiments is a compound of Formula (Im1), or a pharmaceutically acceptable salt or solvate thereof, wherein each of $R^{42}$ and $R^{44}$ is —OC(O)O$R^{16}$; each of $R^{41}$, $R^{43}$, and $R^5$ is hydrogen; and each $R^{16}$ is benzyl. In some embodiments is a compound of Formula (Im1), or a pharmaceutically acceptable salt or solvate thereof, wherein each of $R^{42}$ and $R^{44}$ is —OC(O)O$R^{16}$; each of $R^{41}$, $R^{43}$, and $R^5$ is independently hydrogen, methyl, ethyl, isopropyl, or tert-butyl; and each $R^{16}$ is 2-pyridyl, 3-pyridyl, 4-pyridyl, 2-pyrimidyl, or 4-pyrimidyl. In some embodiments is a compound of Formula (Im1), or a pharmaceutically acceptable salt or solvate thereof, wherein each of $R^{42}$ and $R^{44}$ is —OC(O)O$R^{16}$; each $R^{41}$, $R^{43}$, and $R^5$ is hydrogen; and each $R^{16}$ is 2-pyridyl, 3-pyridyl, 4-pyridyl, 2-pyrimidyl, or 4-pyrimidyl.

In some embodiments is a compound of Formula (I), (Im), or (Im1), or a pharmaceutically acceptable salt or solvate thereof, wherein the compound is:

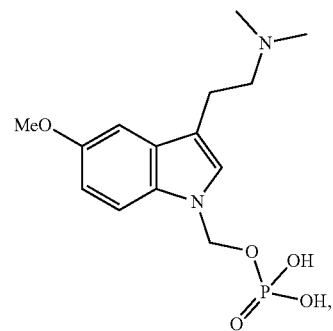

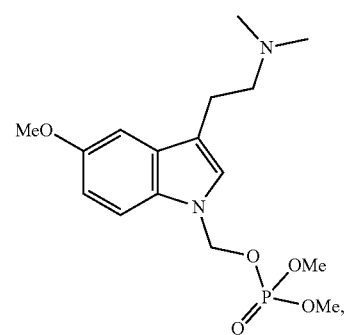

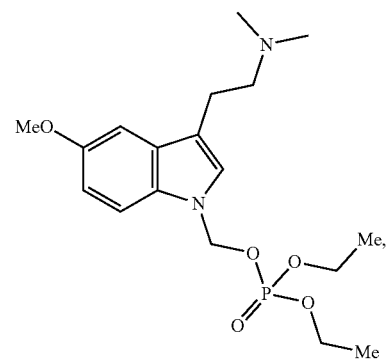

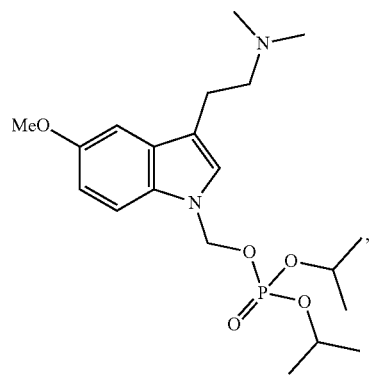

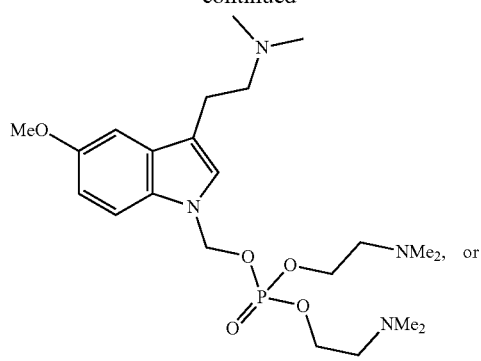
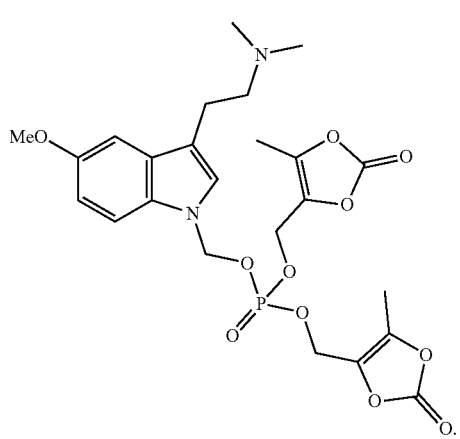 [SMILES: COc1ccc2c(c1)c(CCN(C)C)cn2COP(=O)(OCc1oc(=O)oc1C)OCc1oc(=O)oc1C]
In some embodiments is a compound of Formula (I), (Im), or (Im1), or a pharmaceutically acceptable salt or solvate thereof, wherein the compound is:
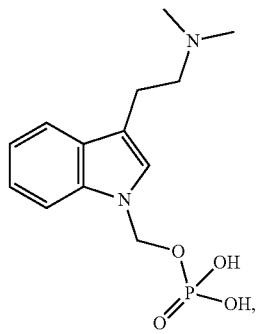
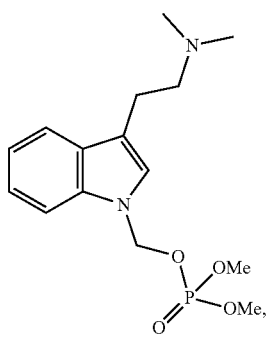
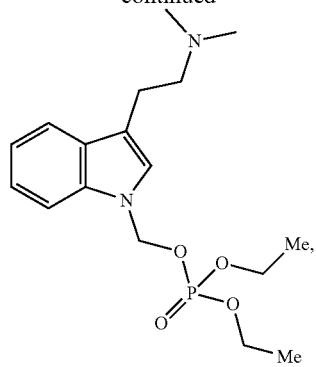
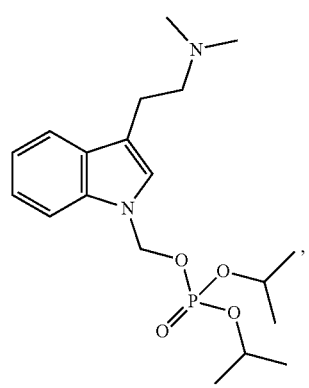
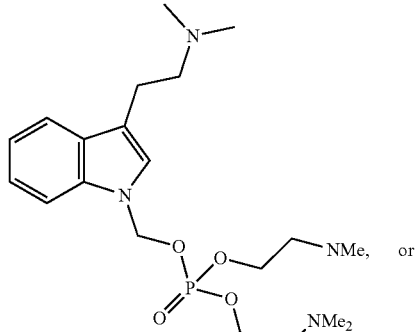
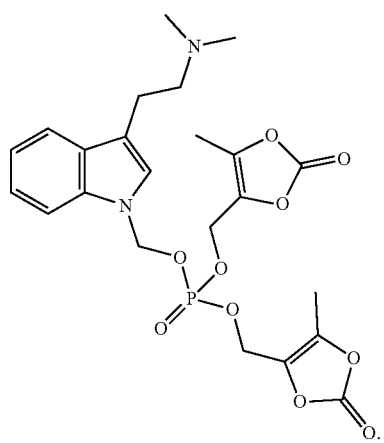 [SMILES: Cc1oc(=O)oc1COP(=O)(OCc1oc(=O)oc1C)OCn1cc(CCN(C)C)c2ccccc21]
In some embodiments is a compound of Formula (I), (Im), or (Im1), or a pharmaceutically acceptable salt or solvate thereof, wherein the compound is:

123
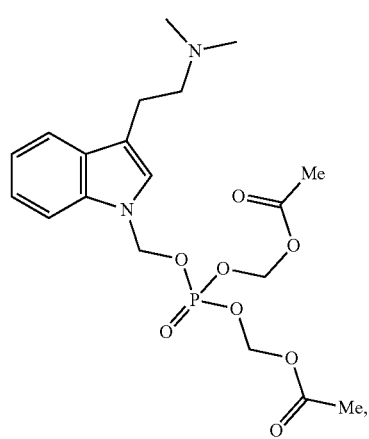
124
-continued
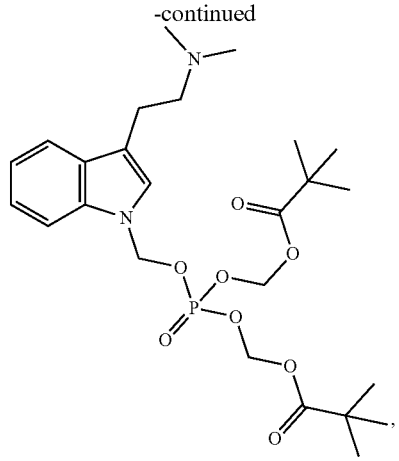
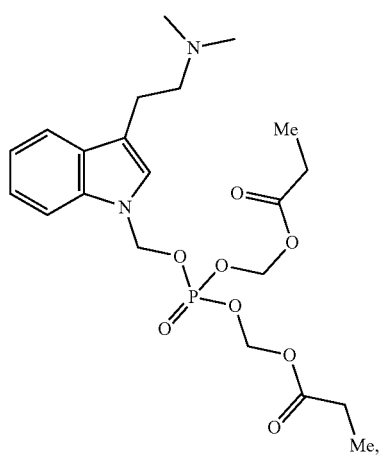
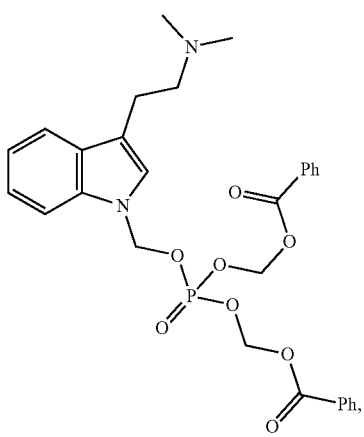
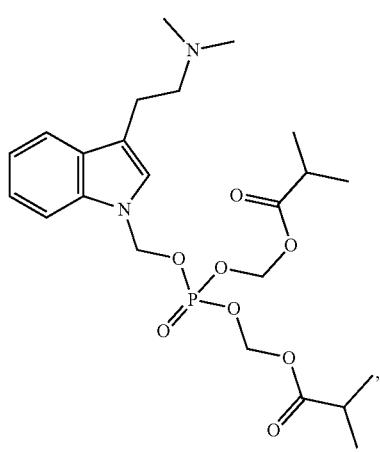
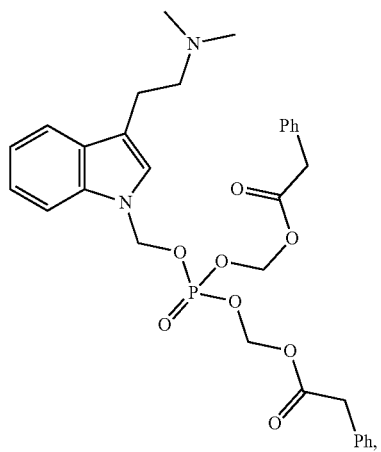

125
-continued
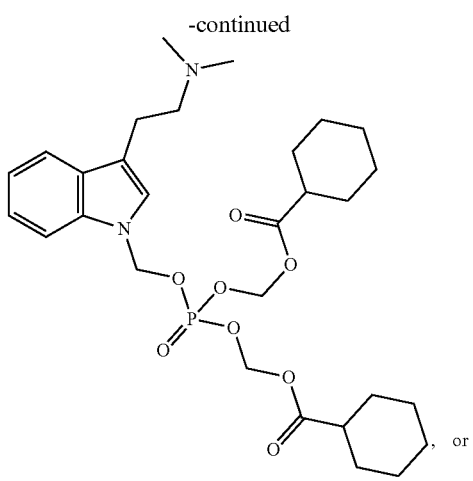, or
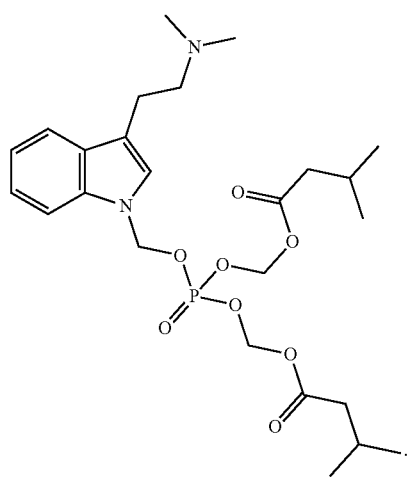
In some embodiments is a compound of Formula (I), (Im), or (Im1), or a pharmaceutically acceptable salt or solvate thereof, wherein the compound is:
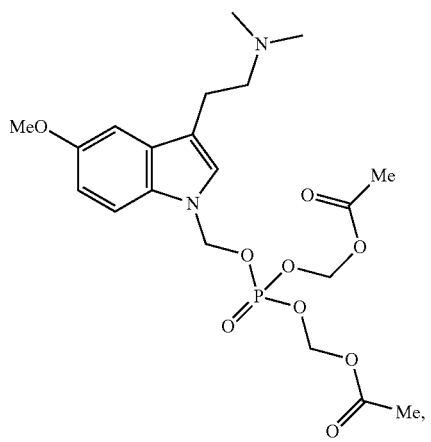
126
-continued
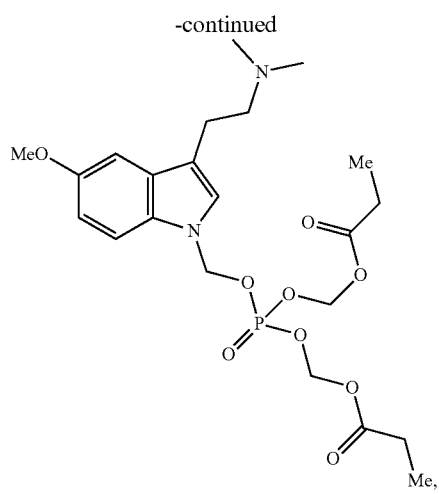
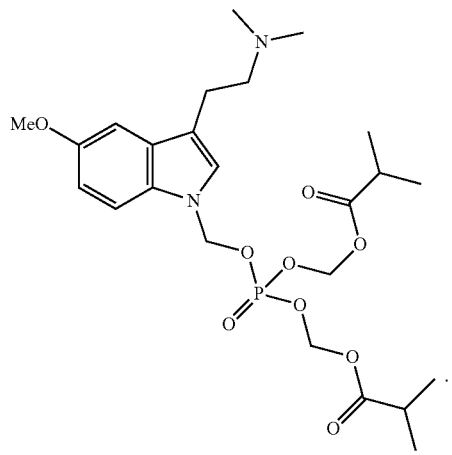
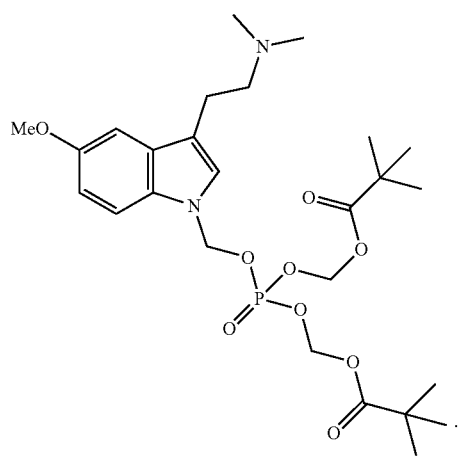

127
-continued
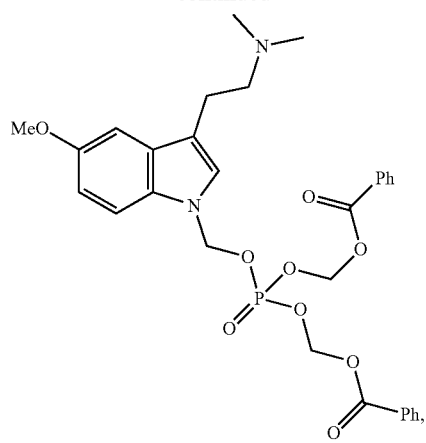
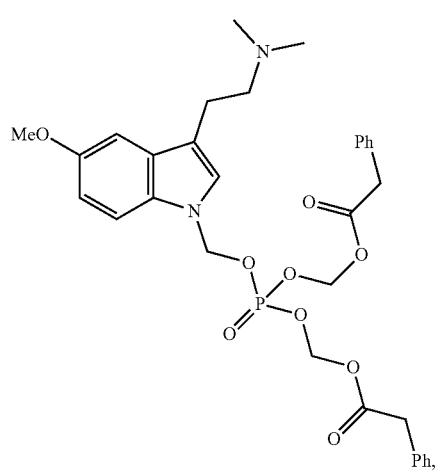
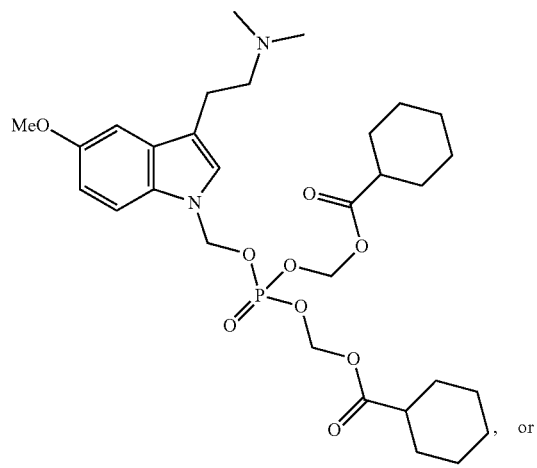, or
128
-continued
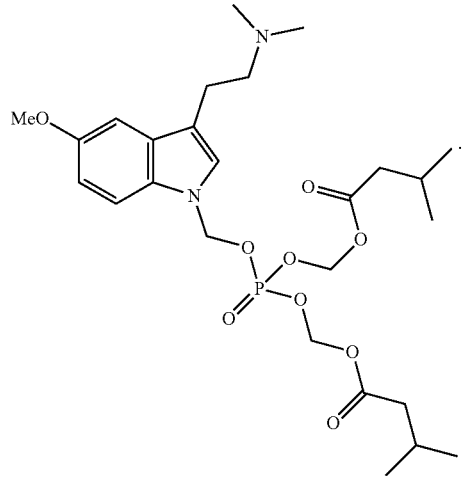
In some embodiments is a compound of Formula (I), (Im), or (Im1), or a pharmaceutically acceptable salt or solvate thereof, wherein the compound is:
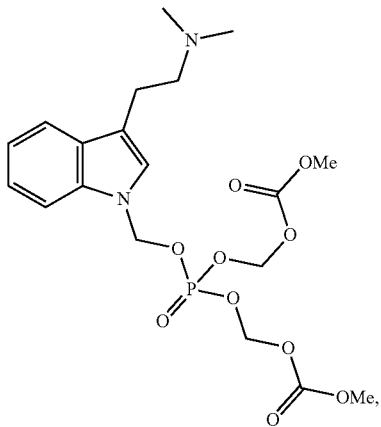
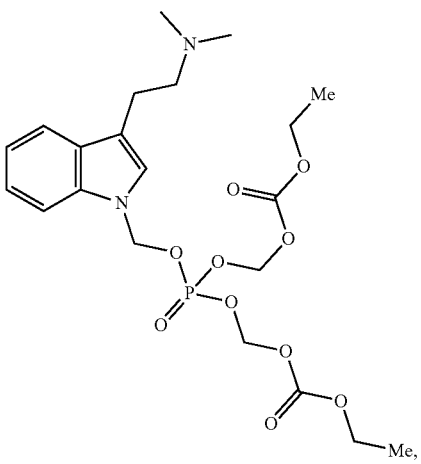

129
-continued
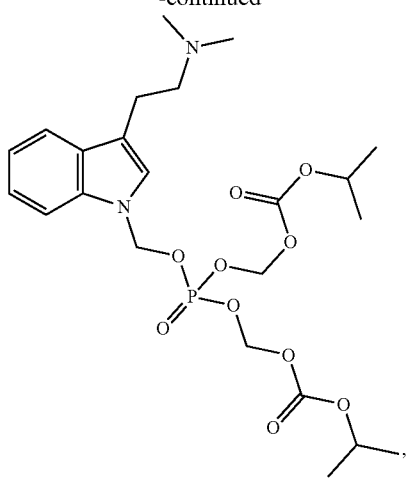
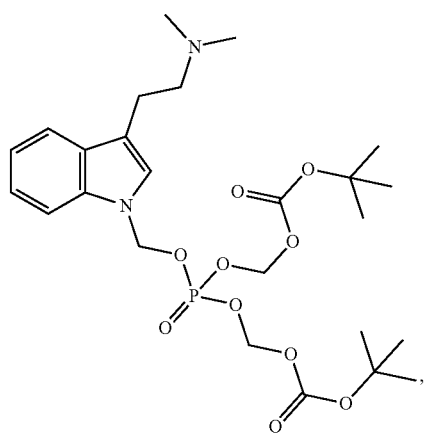
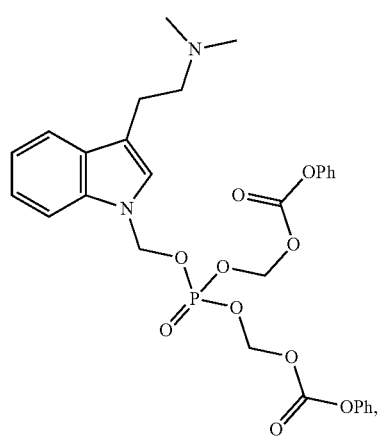
130
-continued
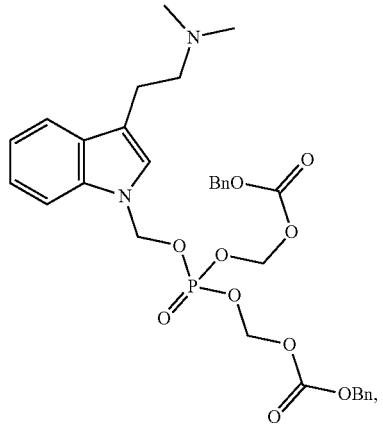
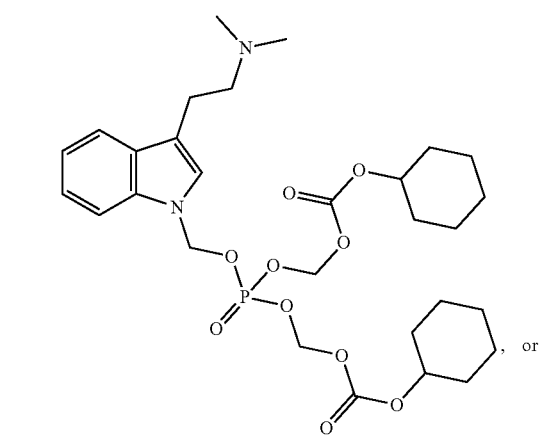, or
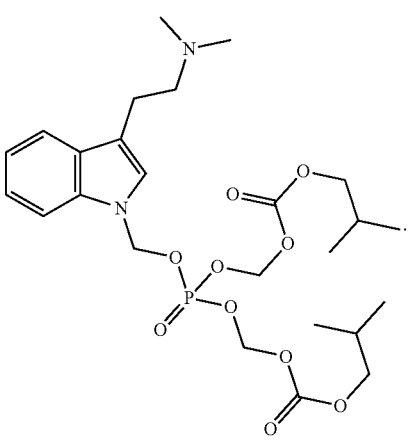
In some embodiments is a compound of Formula (I), (Im), or (Im1), or a pharmaceutically acceptable salt or solvate thereof, wherein the compound is:

131
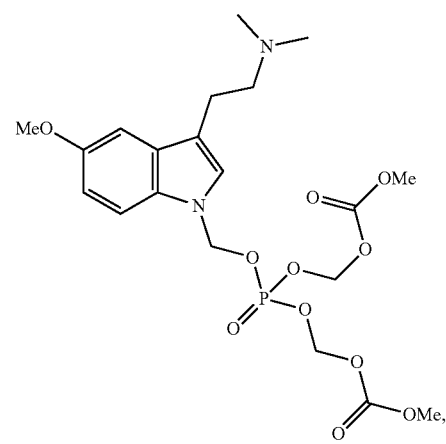
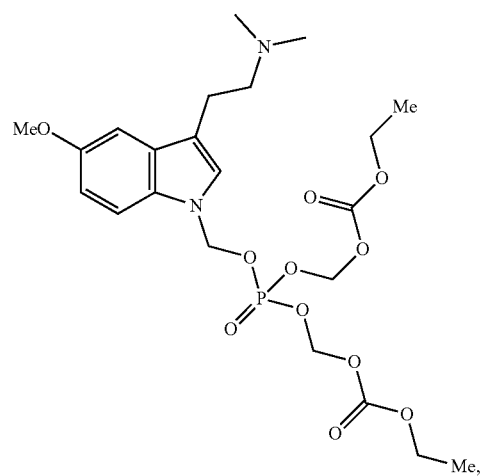
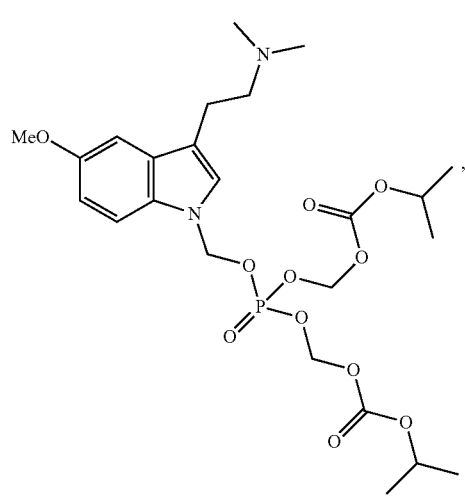
132
-continued
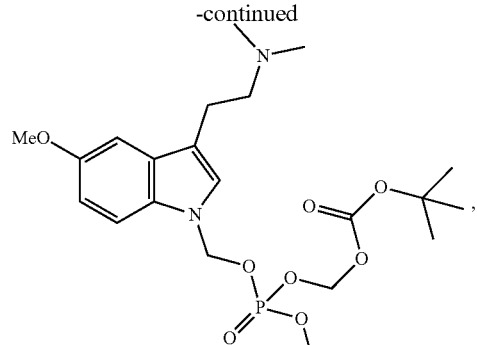
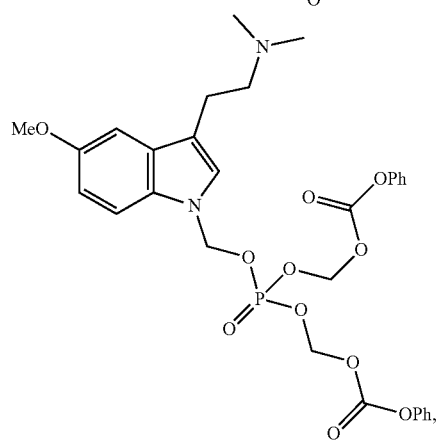
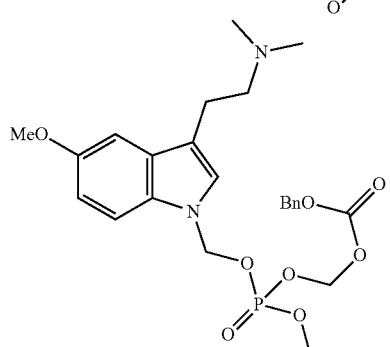
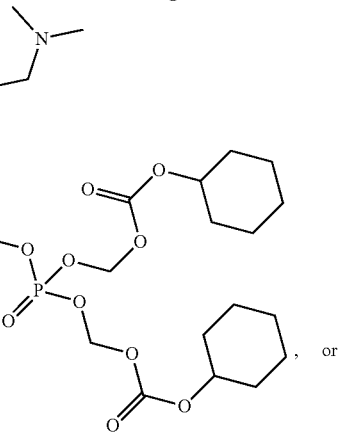

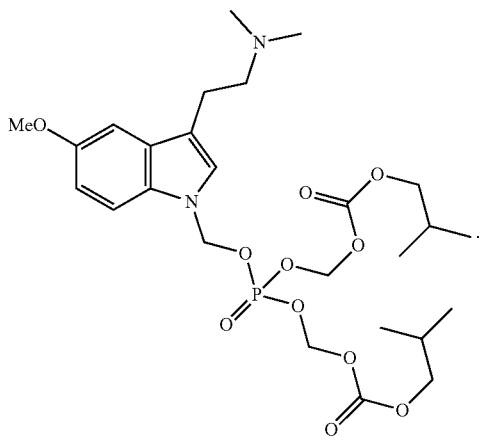

In some embodiments is a compound of Formula (I), (Im), or (Im1), or a pharmaceutically acceptable salt or solvate thereof, wherein the compound is:

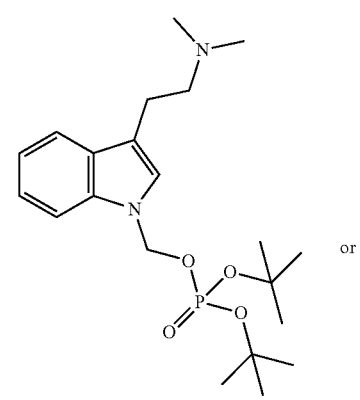 or

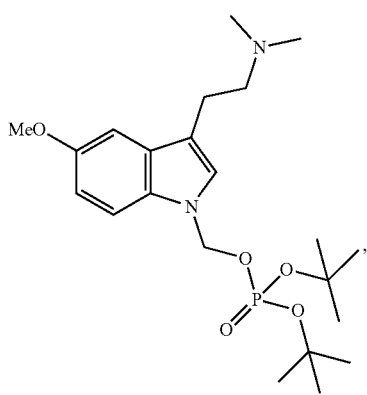

In some embodiments is a compound of Formula (I), (Im), or (Im1) having the structure of Formula (Im1a), or a pharmaceutically acceptable salt thereof:

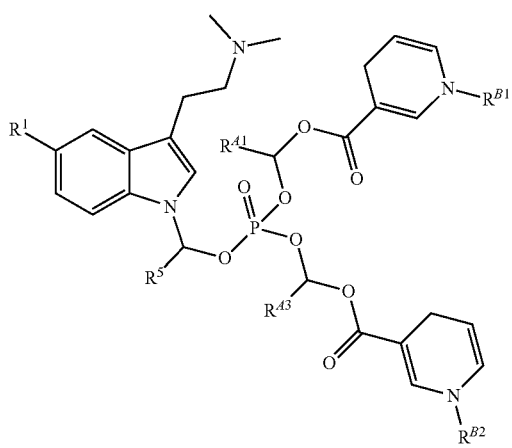

wherein:

$R^1$ is methoxy or hydrogen;

each of $R^{A1}$, $R^{A3}$, and $R^5$ is independently hydrogen, alkyl, or cycloalkyl, wherein each of alkyl and cycloalkyl is independently unsubstituted or substituted with one or more alkyl, aryl, halogen, —$OR^{13}$, —$NR(R^{18})R^{19}$, —$C(O)R^{14}$, —$OC(O)R^{15}$, —$OC(O)OR^{16}$, or —$OC(O)N(R^{18})R^{19}$; and each of $R^{B1}$ and $R^{B2}$ is independently hydrogen or alkyl that is unsubstituted or substituted with one or more halogen, amino, cyano, hydroxyl, alkyl, acetyl, or benzoyl.

In some embodiments is a compound of Formula (Im1a), or a pharmaceutically acceptable salt or solvate thereof, wherein each of $R^{B1}$ and $R^{B2}$ is independently hydrogen, methyl, ethyl, n-propyl, isopropyl, n-butyl, tert-butyl, pentan-3-yl, or benzyl. In some embodiments is a compound of Formula (Im1a), or a pharmaceutically acceptable salt or solvate thereof, wherein each of $R^{A1}$, $R^{A3}$, and $R^5$ is independently hydrogen, methyl, ethyl, isopropyl, or tert-butyl. In some embodiments is a compound of Formula (Im1a), or a pharmaceutically acceptable salt or solvate thereof, wherein each of $R^{A1}$, $R^{A3}$, and $R^5$ is hydrogen. In some embodiments is a compound of Formula (Im1a), or a pharmaceutically acceptable salt or solvate thereof, wherein each of $R^A$, $R^{A3}$, and $R^5$ is independently hydrogen, methyl, ethyl, isopropyl, or tert-butyl; and each of RBI and $R^{B2}$ is hydrogen, methyl, ethyl, n-propyl, isopropyl, n-butyl, tert-butyl, pentan-3-yl, or benzyl.

In some embodiments is a compound of Formula (I), (Im), (Im1), or (Im1a), or a pharmaceutically acceptable salt or solvate thereof, wherein the compound is:

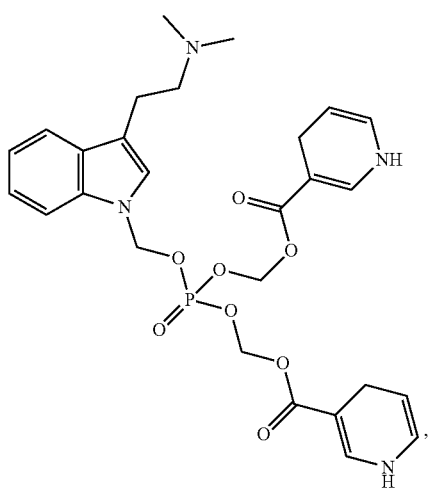
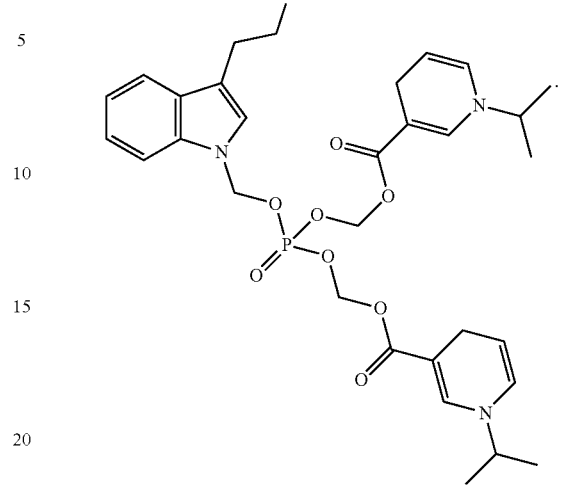
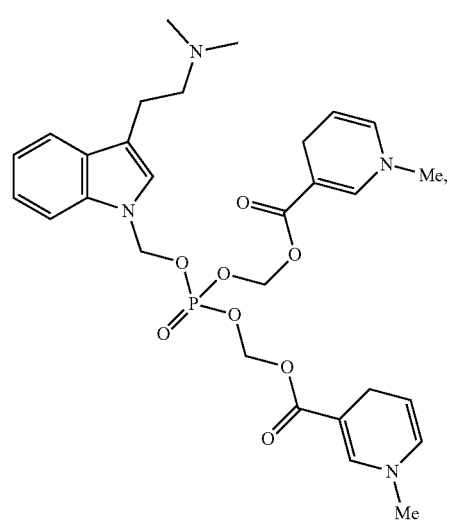
In some embodiments is a compound of Formula (I), (Im), (Im1), or (Im1a), or a pharmaceutically acceptable salt or solvate thereof, wherein the compound is:
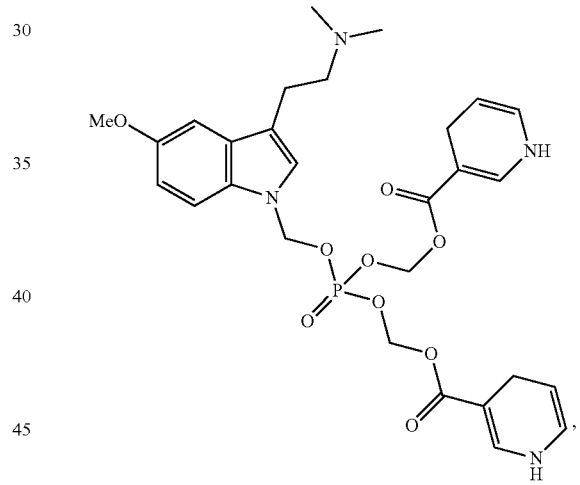
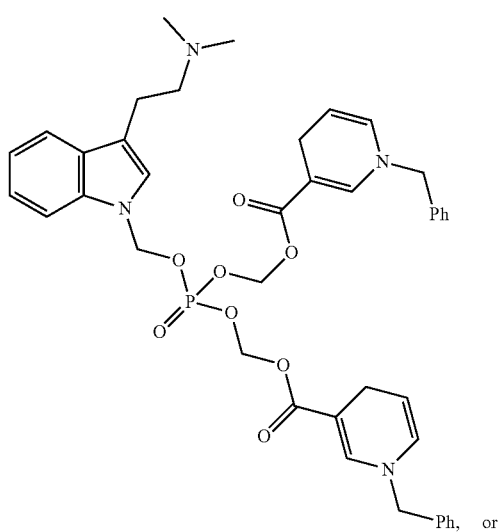
, or
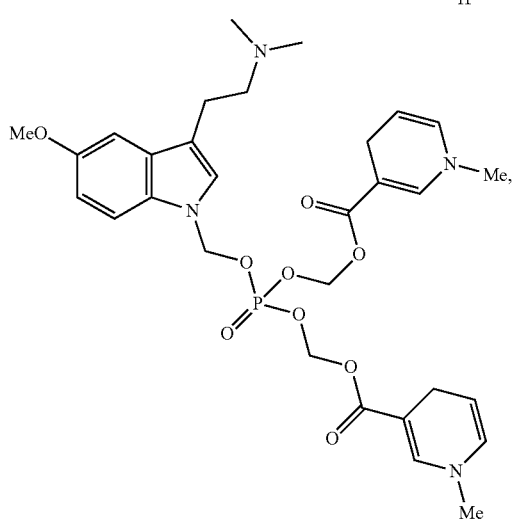

-continued

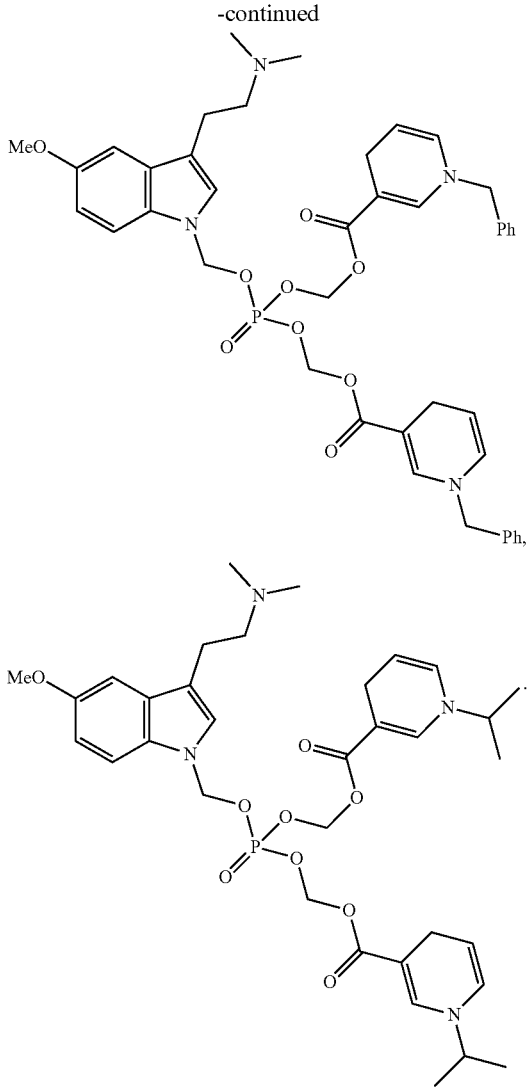

In some embodiments is a compound of Formula (I) having the structure of Formula (In), or a pharmaceutically acceptable salt thereof:

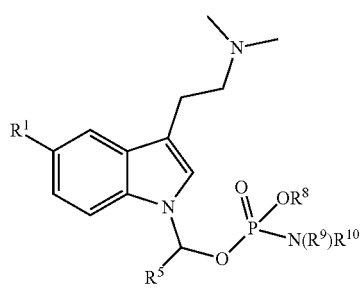

(In)

wherein:

R$^1$ is methoxy or hydrogen;

R$^5$ is hydrogen, alkyl, or cycloalkyl;

R$^8$ is hydrogen, alkyl, cycloalkyl, aryl, heterocyclylalkyl, or heteroaryl; and each of R$^9$ and R$^{10}$ is independently hydrogen or alkyl, wherein each cycloalkyl, aryl, heterocyclylalkyl, and heteroaryl is independently unsubstituted or substituted with one or more R$^A$.

In some embodiments is a compound of Formula (I) or (In), or a pharmaceutically acceptable salt or solvate thereof, wherein R$^5$ is alkyl. In some embodiments is a compound of Formula (I) or (In), or a pharmaceutically acceptable salt or solvate thereof, wherein R$^5$ is hydrogen. In some embodiments is a compound of Formula (I) or (In), or a pharmaceutically acceptable salt or solvate thereof, wherein R$^5$ is hydrogen or unsubstituted alkyl. In some embodiments is a compound of Formula (I) or (In), or a pharmaceutically acceptable salt or solvate thereof, wherein R$^5$ is hydrogen, methyl, ethyl, or tert-butyl. In some embodiments is a compound of Formula (I) or (In), or a pharmaceutically acceptable salt or solvate thereof, wherein R$^8$ is alkyl, cycloalkyl, aryl, heterocyclylalkyl, or heteroaryl. In some embodiments is a compound of Formula (I) or (In), or a pharmaceutically acceptable salt or solvate thereof, wherein R$^8$ is hydrogen. In some embodiments is a compound of Formula (I) or (In), or a pharmaceutically acceptable salt or solvate thereof, wherein R$^8$ is alkyl or cycloalkyl. In some embodiments is a compound of Formula (I) or (In), or a pharmaceutically acceptable salt or solvate thereof, wherein R$^8$ is unsubstituted alkyl or unsubstituted cycloalkyl. In some embodiments is a compound of Formula (I) or (In), or a pharmaceutically acceptable salt or solvate thereof, wherein R$^8$ is methyl, ethyl, n-propyl, n-butyl, n-pentyl, n-hexyl, isopropyl, tert-butyl, cyclopropyl, cyclobutyl, cyclopentyl, cyclohexyl, or cycloheptyl. In some embodiments is a compound of Formula (I) or (In), or a pharmaceutically acceptable salt or solvate thereof, wherein R$^8$ is phenyl. In some embodiments is a compound of Formula (I) or (In), or a pharmaceutically acceptable salt or solvate thereof, wherein R$^8$ is 4-nitrophenyl. In some embodiments is a compound of Formula (I) or (In), or a pharmaceutically acceptable salt or solvate thereof, wherein R$^8$ is benzyl. In some embodiments is a compound of Formula (I) or (In), or a pharmaceutically acceptable salt or solvate thereof, wherein R$^8$ is 2-pyridyl, 3-pyridyl, 4-pyridyl, 2-pyrimidyl, or 4-pyrimidyl. In some embodiments is a compound of Formula (I) or (In), or a pharmaceutically acceptable salt or solvate thereof, wherein R$^9$ is hydrogen. In some embodiments is a compound of Formula (I) or (In), or a pharmaceutically acceptable salt or solvate thereof, wherein R$^9$ is hydrogen, and R$^{10}$ is alkyl.

In some embodiments is a compound of Formula (I) or (In) having the structure of Formula (In1), or a pharmaceutically acceptable salt thereof:

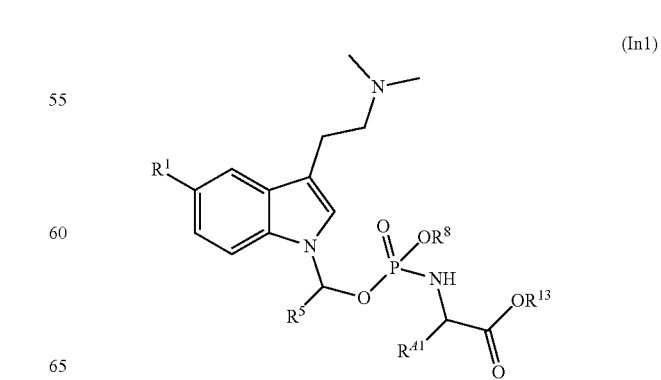

(In1)

wherein:
R¹ is methoxy or hydrogen;
R^{A1} is hydrogen, alkyl, or cycloalkyl, wherein each of alkyl and cycloalkyl is unsubstituted or substituted with alkyl, aryl, halogen, —OR$^{13}$, —NR(R$^{18}$)R$^{19}$, —C(O)R$^{14}$, —OC(O)R$^{15}$, —OC(O)OR$^{16}$, or —OC(O)N(R$^{18}$)R$^{19}$;
each of R$^5$ and R$^8$ is hydrogen, alkyl, cycloalkyl, aryl, heterocyclylalkyl, or heteroaryl, wherein alkyl, cycloalkyl, aryl, heterocyclylalkyl, and heteroaryl is independently unsubstituted or substituted with one or more R$^A$; and
R$^{13}$ is hydrogen or alkyl that is unsubstituted or substituted with one or more R$^B$.

In some embodiments is a compound of Formula (In1), or a pharmaceutically acceptable salt or solvate thereof, wherein each of R$^5$ and R$^{A1}$ is hydrogen or alkyl. In some embodiments is a compound of Formula (In1), or a pharmaceutically acceptable salt or solvate thereof, wherein each of R$^5$ and R$^{A1}$ is hydrogen or unsubstituted alkyl. In some embodiments is a compound of Formula (In1), or a pharmaceutically acceptable salt or solvate thereof, wherein each of R$^5$ and R$^{A1}$ is hydrogen, methyl, ethyl, or tert-butyl. In some embodiments is a compound of Formula (In1), or a pharmaceutically acceptable salt or solvate thereof, wherein each of R$^5$ and R$^{A1}$ is hydrogen. In some embodiments is a compound of Formula (In1), or a pharmaceutically acceptable salt or solvate thereof, wherein R$^8$ is alkyl or cycloalkyl. In some embodiments is a compound of Formula (In1), or a pharmaceutically acceptable salt or solvate thereof, wherein R$^8$ is unsubstituted alkyl or unsubstituted cycloalkyl. In some embodiments is a compound of Formula (In1), or a pharmaceutically acceptable salt or solvate thereof, wherein R$^8$ is methyl, ethyl, n-propyl, n-butyl, n-pentyl, n-hexyl, isopropyl, tert-butyl, cyclopropyl, cyclobutyl, cyclopentyl, cyclohexyl, or cycloheptyl. In some embodiments is a compound of Formula (In1), or a pharmaceutically acceptable salt or solvate thereof, wherein R$^8$ is phenyl. In some embodiments is a compound of Formula (In1), or a pharmaceutically acceptable salt or solvate thereof, wherein R$^8$ is 4-nitrophenyl. In some embodiments is a compound of Formula (In1), or a pharmaceutically acceptable salt or solvate thereof, wherein R$^8$ is benzyl. In some embodiments is a compound of Formula (In1), or a pharmaceutically acceptable salt or solvate thereof, wherein R$^8$ is 2-pyridyl, 3-pyridyl, 4-pyridyl, 2-pyrimidyl, or 4-pyrimidyl. In some embodiments is a compound of Formula (In1), or a pharmaceutically acceptable salt or solvate thereof, wherein R$^{13}$ is alkyl. In some embodiments is a compound of Formula (In1), or a pharmaceutically acceptable salt or solvate thereof, wherein R$^{13}$ is unsubstituted alkyl. In some embodiments is a compound of Formula (In1), or a pharmaceutically acceptable salt or solvate thereof, wherein R$^{13}$ is methyl, ethyl, n-propyl, isopropyl, n-butyl, tert-butyl, or —CH$_2$CH(Et)$_2$. In some embodiments is a compound of Formula (In1), or a pharmaceutically acceptable salt or solvate thereof, wherein each of R$^5$ and R$^{A1}$ is hydrogen or alkyl; and R$^3$ is methyl, ethyl, n-propyl, isopropyl, n-butyl, tert-butyl, or —CH$_2$CH(Et)$_2$. In some embodiments is a compound of Formula (In1), or a pharmaceutically acceptable salt or solvate thereof, wherein each of R$^5$ and R$^{A1}$ is hydrogen or unsubstituted alkyl; and R$^{13}$ is methyl, ethyl, n-propyl, isopropyl, n-butyl, tert-butyl, or —CH$_2$CH(Et)$_2$. In some embodiments is a compound of Formula (In1), or a pharmaceutically acceptable salt or solvate thereof, wherein each of R$^5$ and R$^{A1}$ is hydrogen; and R$^{13}$ is methyl, ethyl, n-propyl, isopropyl, n-butyl, tert-butyl, or —CH$_2$CH(Et)$_2$.

In some embodiments is a compound of Formula (I), (In), or (In1), or a pharmaceutically acceptable salt or solvate thereof, wherein the compound is:

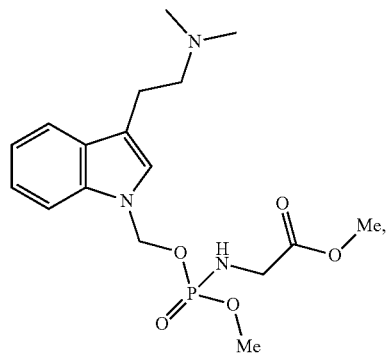

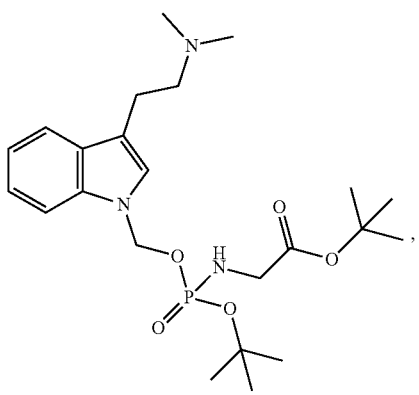

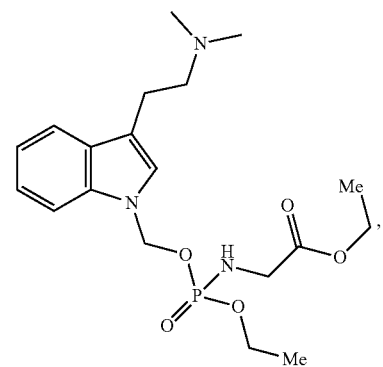

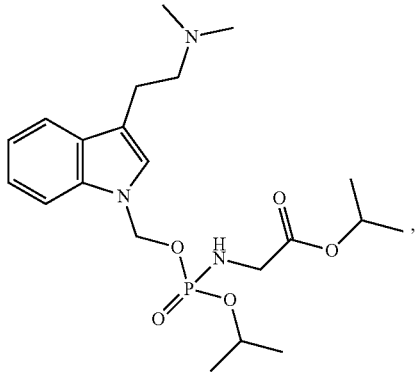

-continued
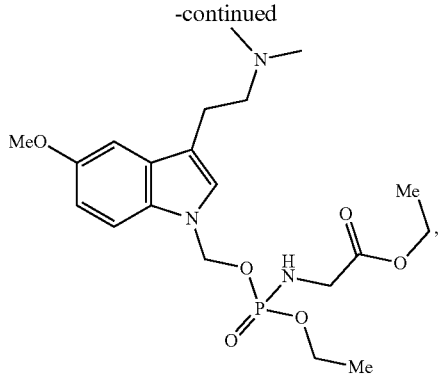
, or
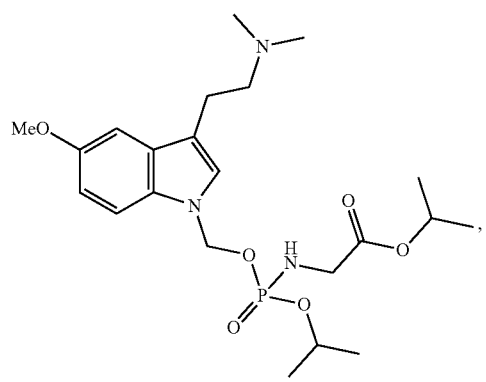
In some embodiments is a compound of Formula (I), (In), or (In1), or a pharmaceutically acceptable salt or solvate thereof, wherein the compound is:
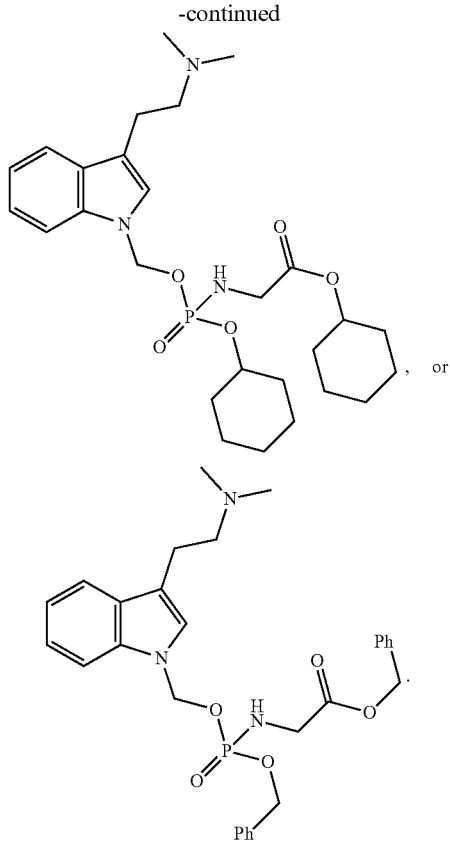
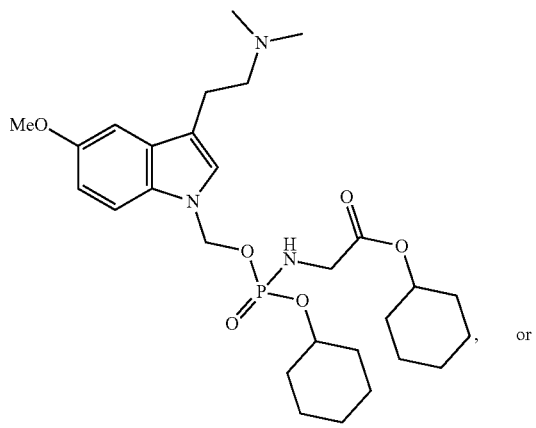
, or
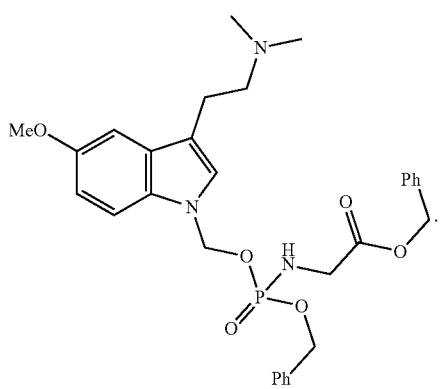 [SMILES: COc1ccc2c(c1)c(CCN(C)C)cn2COP(=O)(NCC(=O)OCc1ccccc1)OCc1ccccc1]
In some embodiments is a compound of Formula (I) having the structure of Formula (Io), or a pharmaceutically acceptable salt thereof:

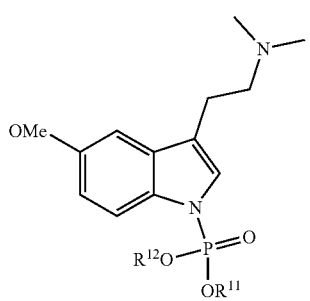
(Io)

wherein:
R¹ is methoxy or hydrogen; and
each of R¹¹ and R¹² is independently selected from hydrogen, cycloalkyl, aryl, heteroaryl, or alkyl, wherein each cycloalkyl, aryl, heteroaryl, and alkyl is independently unsubstituted or substituted with one or more R⁴, or R¹¹ and R¹² together with the atoms to which they are attached form a heterocyclylalkyl ring that is unsubstituted or substituted with one or more R⁴.

In some embodiments is a compound of Formula (I) or (Io), or a pharmaceutically acceptable salt or solvate thereof, wherein each of R¹¹ and R¹² is independently selected from cycloalkyl, aryl, heteroaryl, or alkyl; or R¹¹ and R¹² together with the atom to which they are attached form a heterocyclylalkyl ring. In some embodiments is a compound of Formula (I) or (Lo), or a pharmaceutically acceptable salt or solvate thereof, wherein each of R¹¹ and R¹² is independently selected from unsubstituted alkyl, unsubstituted cycloalkyl, unsubstituted aryl, unsubstituted heteroaryl, unsubstituted alkyl, or alkyl substituted with aryl or heteroaryl. In some embodiments is a compound of Formula (I) or (Io), or a pharmaceutically acceptable salt or solvate thereof, wherein R¹¹ is hydrogen, and R¹² is alkyl, cycloalkyl, aryl, heteroaryl, or alkyl. In some embodiments is a compound of Formula (I) or (Io), or a pharmaceutically acceptable salt or solvate thereof, wherein each of R¹¹ and R¹² is alkyl. In some embodiments is a compound of Formula (I) or (Io), or a pharmaceutically acceptable salt or solvate thereof, wherein each of R¹¹ and R¹² is alkyl. In some embodiments is a compound of Formula (I) or (Io), or a pharmaceutically acceptable salt or solvate thereof, wherein each of R¹¹ and R¹² is unsubstituted alkyl. In some embodiments is a compound of Formula (I) or (Io), or a pharmaceutically acceptable salt or solvate thereof, wherein each of R¹¹ and R¹² is alkyl substituted with —OC(O)R¹⁵. In some embodiments is a compound of Formula (I) or (Io), or a pharmaceutically acceptable salt or solvate thereof, wherein each of R¹¹ and R¹² is alkyl substituted with —OC(O)R¹⁵, wherein each R¹⁵ is alkyl, cycloalkyl, heterocyclylalkyl, aryl, or heteroaryl. In some embodiments is a compound of Formula (I) or (Io), or a pharmaceutically acceptable salt or solvate thereof, wherein each of R¹¹ and R¹² is alkyl substituted with —OC(O)R¹⁵, wherein each R¹⁵ is unsubstituted alkyl, unsubstituted cycloalkyl, unsubstituted heterocyclylalkyl, unsubstituted aryl, or unsubstituted heteroaryl. In some embodiments is a compound of Formula (I) or (Io), or a pharmaceutically acceptable salt or solvate thereof, wherein each of R¹¹ and R¹² is alkyl substituted with —OC(O)R¹⁵, wherein each R¹⁵ is heterocyclylalkyl substituted with alkyl or arylalkyl.

In some embodiments is a compound of Formula (I) or (Io), or a pharmaceutically acceptable salt or solvate thereof, wherein each of R¹¹ and R¹² is alkyl, heterocyclylalkyl, or cycloalkyl. In some embodiments is a compound of Formula (I) or (Io), or a pharmaceutically acceptable salt or solvate thereof, wherein each of R¹¹ and R¹² is alkyl. In some embodiments is a compound of Formula (I) or (Io), or a pharmaceutically acceptable salt or solvate thereof, wherein each of R¹¹ and R¹² is unsubstituted alkyl. In some embodiments is a compound of Formula (I) or (Io), or a pharmaceutically acceptable salt or solvate thereof, wherein R¹ is methoxy, and each of R¹¹ and R¹² is unsubstituted alkyl. In some embodiments is a compound of Formula (I) or (Io), or a pharmaceutically acceptable salt or solvate thereof, wherein R¹ is hydrogen, and each of R¹¹ and R¹² is unsubstituted alkyl. In some embodiments is a compound of Formula (I) or (Io), or a pharmaceutically acceptable salt or solvate thereof, wherein R¹ is methoxy, and each of R¹¹ and R¹² is tert-butyl. In some embodiments is a compound of Formula (I) or (Io), or a pharmaceutically acceptable salt or solvate thereof, wherein R¹ is hydrogen, and each of R¹¹ and R¹² is tert-butyl.

In some embodiments is a compound of Formula (I) or (Io), or a pharmaceutically acceptable salt or solvate thereof, wherein each of R¹¹ and R¹² is

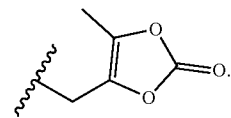 [SMILES: *Cc1oc(=O)oc1C]

In some embodiments is a compound of Formula (I) or (Io), or a pharmaceutically acceptable salt or solvate thereof, wherein each of R¹¹ and R¹² is methyl, ethyl, n-propyl, isopropyl, n-butyl, tert-butyl, n-pentyl, n-hexyl, or 3-methyl-1-butyl. In some embodiments is a compound of Formula (I) or (Io), or a pharmaceutically acceptable salt or solvate thereof, wherein each of R¹¹ and R¹² is cyclopropyl, cyclobutyl, cyclopentyl, cyclohexyl, or cycloheptyl. In some embodiments is a compound of Formula (I) or (Io), or a pharmaceutically acceptable salt or solvate thereof, wherein each of R¹¹ and R¹² is phenyl. In some embodiments is a compound of Formula (I) or (Jo), or a pharmaceutically acceptable salt or solvate thereof, wherein each of R¹¹ and R¹² is 2-pyridyl, 3-pyridyl, 4-pyridyl, 2-pyrimidyl, 4-pyrimidyl, 5-pyrimidyl, or 6-pyrimidyl. In some embodiments is a compound of Formula (I) or (Io), or a pharmaceutically acceptable salt or solvate thereof, wherein each of R¹¹ and R¹² is 4-nitrophenyl. In some embodiments is a compound of Formula (I) or (Io), or a pharmaceutically acceptable salt or solvate thereof, wherein each of R¹¹ and R¹² is benzyl.

In some embodiments is a compound of Formula (I) or (Io) having the structure of Formula (Io1), or a pharmaceutically acceptable salt thereof:

(Io1)

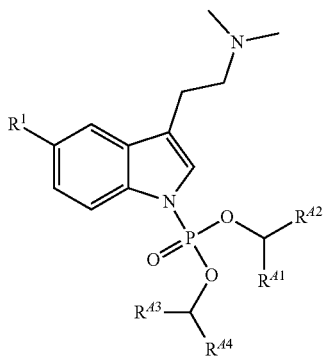

wherein:
R¹ is methoxy or hydrogen;
each of $R^{41}$ and $R^{43}$ is independently hydrogen, alkyl, or cycloalkyl; and
each of $R^{42}$ and $R^{44}$ is independently alkyl, heteroalkyl, or cycloalkyl, heterocyclylalkyl, aryl, heteroaryl, —OC(O)R⁵, or —OC(O)OR¹⁶,
wherein each alkyl, heteroalkyl, cycloalkyl, heterocyclylalkyl, aryl, and heteroaryl is independently unsubstituted or substituted with one or more alkyl, aryl, halogen, —OR¹³, —NR(R¹⁸)R¹⁹, —C(O)R¹⁴, —OC(O)R⁵, —OC(O)OR¹⁶, or —OC(O)N(R¹⁸)R¹⁹.

In some embodiments is a compound of Formula (Io1), or a pharmaceutically acceptable salt or solvate thereof, wherein each of $R^{41}$ and $R^{43}$ is independently hydrogen, methyl, ethyl, isopropyl, or tert-butyl. In some embodiments is a compound of Formula (Io1), or a pharmaceutically acceptable salt or solvate thereof, wherein each of $R^{41}$ and $R^{43}$ is hydrogen.

In some embodiments is a compound of Formula (Io1), or a pharmaceutically acceptable salt or solvate thereof, wherein each of $R^{42}$ and $R^{44}$ is —OC(O)R¹⁵. In some embodiments is a compound of Formula (Io1), or a pharmaceutically acceptable salt or solvate thereof, wherein each of $R^{42}$ and $R^{44}$ is —OC(O)R⁵; and each of $R^{41}$ and $R^{43}$ is independently hydrogen, methyl, ethyl, isopropyl, or tert-butyl. In some embodiments is a compound of Formula (Io1), or a pharmaceutically acceptable salt or solvate thereof, wherein each of $R^{42}$ and $R^{44}$ is —OC(O)R¹⁵; each of $R^{41}$ and $R^{43}$ is independently hydrogen, methyl, ethyl, isopropyl, or tert-butyl; and each R⁵ is alkyl, cycloalkyl, aryl, or heteroaryl. In some embodiments is a compound of Formula (Io1), or a pharmaceutically acceptable salt or solvate thereof, wherein each of $R^{42}$ and $R^{44}$ is —OC(O)R¹⁵; each of $R^{41}$ and $R^{43}$ is independently hydrogen, methyl, ethyl, isopropyl, or tert-butyl; and each R¹⁵ is methyl, ethyl, n-propyl, n-butyl, n-pentyl, n-hexyl, isopropyl, tert-butyl, 3-methyl-1-butyl, cyclopropyl, or cyclobutyl. In some embodiments is a compound of Formula (Io1), or a pharmaceutically acceptable salt or solvate thereof, wherein each of $R^{42}$ and $R^{44}$ is —OC(O)R¹⁵; each of $R^{41}$ and $R^{43}$ is hydrogen; and each R⁵ is methyl, ethyl, n-propyl, n-butyl, n-pentyl, n-hexyl, isopropyl, tert-butyl, 3-methyl-1-butyl, cyclopropyl, or cyclobutyl. In some embodiments is a compound of Formula (Io1), or a pharmaceutically acceptable salt or solvate thereof, wherein each of $R^{42}$ and $R^{44}$ is —OC(O)R⁵; each of $R^{41}$ and $R^{43}$ is independently hydrogen, methyl, ethyl, isopropyl, or tert-butyl; and each R¹⁵ is phenyl or 4-nitrophenyl. In some embodiments is a compound of Formula (Io1), or a pharmaceutically acceptable salt or solvate thereof, wherein each of $R^{42}$ and $R^{44}$ is —OC(O)R¹⁵; each of $R^{41}$ and $R^{43}$ is hydrogen; and each R¹⁵ is phenyl or 4-nitrophenyl. In some embodiments is a compound of Formula (Io1), or a pharmaceutically acceptable salt or solvate thereof, wherein each of $R^{42}$ and $R^{44}$ is —OC(O)R¹⁵; each of $R^{41}$ and $R^{43}$ is independently hydrogen, methyl, ethyl, isopropyl, or tert-butyl; and each R¹⁵ is benzyl. In some embodiments is a compound of Formula (Io1), or a pharmaceutically acceptable salt or solvate thereof, wherein each of $R^{42}$ and $R^{44}$ is —OC(O)R⁵; each of $R^{41}$ and $R^{43}$ is hydrogen; and each R¹⁵ is benzyl. In some embodiments is a compound of Formula (Io1), or a pharmaceutically acceptable salt or solvate thereof, wherein each of $R^{42}$ and $R^{44}$ is —OC(O)R¹⁵; each of $R^{41}$ and $R^{43}$ is independently hydrogen, methyl, ethyl, isopropyl, or tert-butyl; and each R¹⁵ is 2-pyridyl, 3-pyridyl, 4-pyridyl, 2-pyrimidyl, or 4-pyrimidyl. In some embodiments is a compound of Formula (Io1), or a pharmaceutically acceptable salt or solvate thereof, wherein each of $R^{42}$ and $R^{44}$ is —OC(O)R¹⁵; each of $R^{41}$ and $R^{43}$ is hydrogen; and each R¹⁵ is 2-pyridyl, 3-pyridyl, 4-pyridyl, 2-pyrimidyl, or 4-pyrimidyl.

In some embodiments is a compound of Formula (Io1), or a pharmaceutically acceptable salt or solvate thereof, wherein each of $R^{42}$ and $R^{44}$ is —OC(O)OR¹⁶. In some embodiments is a compound of Formula (Io1), or a pharmaceutically acceptable salt or solvate thereof, wherein each of $R^{42}$ and $R^{44}$ is —OC(O)OR¹⁶; and each of $R^{41}$ and $R^{43}$ is independently hydrogen, methyl, ethyl, isopropyl, or tert-butyl. In some embodiments is a compound of Formula (Io1), or a pharmaceutically acceptable salt or solvate thereof, wherein each of $R^{42}$ and $R^{44}$ is —OC(O)OR¹⁶; each of $R^{41}$ and $R^{43}$ is independently hydrogen, methyl, ethyl, isopropyl, or tert-butyl; and each R¹⁶ is alkyl, cycloalkyl, aryl, or heteroaryl. In some embodiments is a compound of Formula (Io1), or a pharmaceutically acceptable salt or solvate thereof, wherein each of $R^{42}$ and $R^{44}$ is —OC(O)OR¹⁶; each of $R^{41}$ and $R^{43}$ is independently hydrogen, methyl, ethyl, isopropyl, or tert-butyl; and each R¹⁶ is methyl, ethyl, n-propyl, n-butyl, n-pentyl, n-hexyl, isopropyl, tert-butyl, 3-methyl-1-butyl, cyclopropyl, or cyclobutyl. In some embodiments is a compound of Formula (Io1), or a pharmaceutically acceptable salt or solvate thereof, wherein each of $R^{42}$ and $R^{44}$ is —OC(O)OR¹⁶; each of $R^{41}$ and $R^{43}$ is hydrogen; and each R¹⁶ is methyl, ethyl, n-propyl, n-butyl, n-pentyl, n-hexyl, isopropyl, tert-butyl, 3-methyl-1-butyl, cyclopropyl, or cyclobutyl. In some embodiments is a compound of Formula (Io1), or a pharmaceutically acceptable salt or solvate thereof, wherein each $R^{42}$ and $R^{44}$ is —OC(O)OR¹⁶; each of $R^{41}$ and $R^{43}$ is independently hydrogen, methyl, ethyl, isopropyl, or tert-butyl; and each R¹⁶ is phenyl or 4-nitrophenyl. In some embodiments is a compound of Formula (Io1), or a pharmaceutically acceptable salt or solvate thereof, wherein each $R^{42}$ and $R^{44}$ is —OC(O)OR¹⁶; each of $R^{41}$ and $R^{43}$ is hydrogen; and each R¹⁶ is phenyl or 4-nitrophenyl. In some embodiments is a compound of Formula (Io1), or a pharmaceutically acceptable salt or solvate thereof, wherein each of $R^{42}$ and $R^{44}$ is —OC(O)OR¹⁶; each $R^{41}$ and $R^{43}$ is independently hydrogen, methyl, ethyl, isopropyl, or tert-butyl; and each R¹⁶ is benzyl. In some embodiments is a compound of Formula (Io1), or a pharmaceutically acceptable salt or solvate thereof, wherein each of $R^{42}$ and $R^{44}$ is —OC(O)OR¹⁶; each of $R^{41}$ and $R^{43}$ is hydrogen; and each R¹⁶ is benzyl. In some embodiments is a compound of Formula (Io1), or a pharmaceutically acceptable salt or solvate thereof, wherein each of $R^{42}$ and $R^{44}$ is —OC(O)OR¹⁶; each of $R^{41}$ and $R^{43}$ is independently hydrogen, methyl, ethyl, isopropyl, or tert-butyl; and each $R^{16}$ is 2-pyridyl, 3-pyridyl, 4-pyridyl, 2-pyrimidyl, or 4-pyrimidyl. In some embodiments is a compound of Formula (Io1), or a pharmaceutically acceptable salt or solvate thereof, wherein each of $R^{42}$ and $R^{44}$ is —OC(O)OR$^{16}$; each $R^{41}$ and $R^{43}$ is hydrogen; and each $R^{16}$ is 2-pyridyl, 3-pyridyl, 4-pyridyl, 2-pyrimidyl, or 4-pyrimidyl.

In some embodiments is a compound of Formula (I), (Jo), or (Io1), or a pharmaceutically acceptable salt or solvate thereof, wherein the compound is:

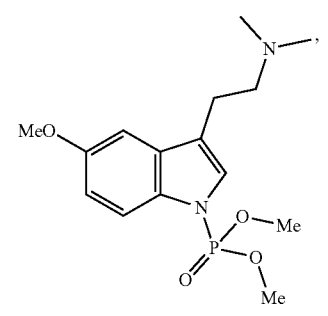

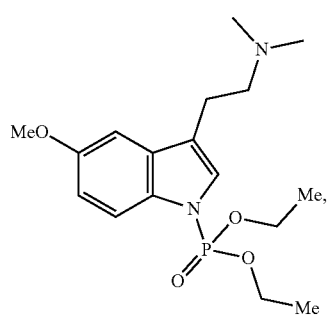

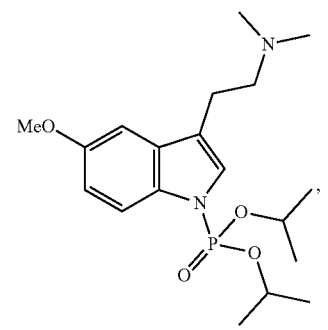

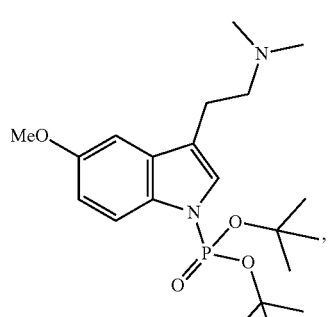

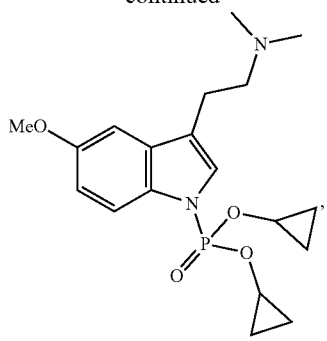

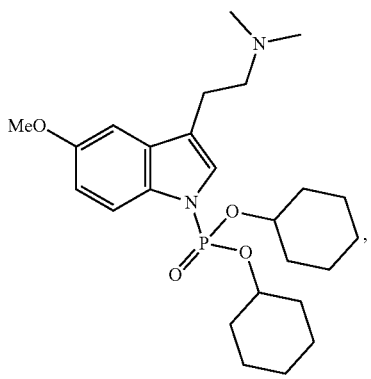

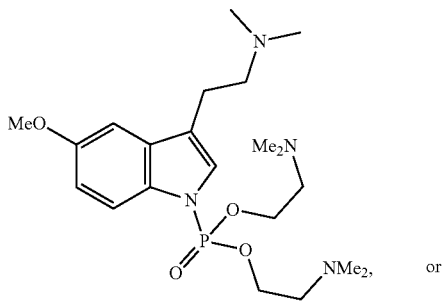

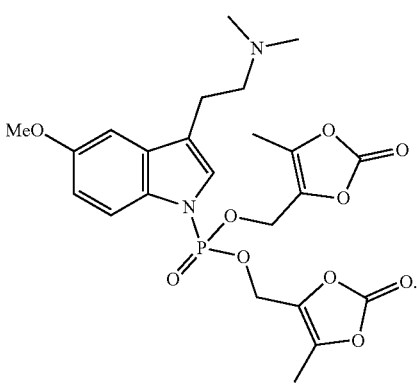

In some embodiments is a compound of Formula (I), (Io), or (Io1), or a pharmaceutically acceptable salt or solvate thereof, wherein:

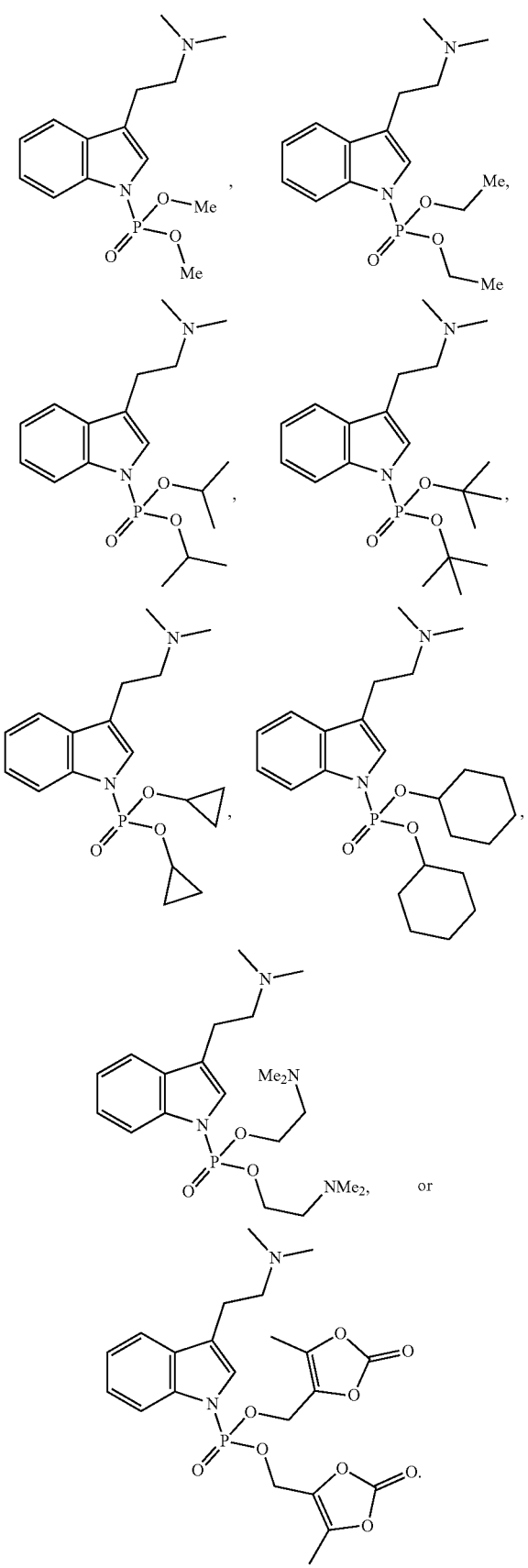

In some embodiments is a compound of Formula (I) or (Io) having the structure of Formula (Io2), or a pharmaceutically acceptable salt thereof:

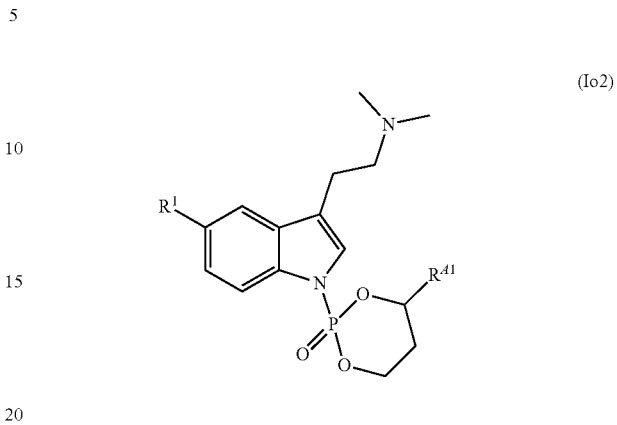

(Io2)

wherein $R^1$ is methoxy or hydrogen; and $R^{41}$ is aryl or heteroaryl, each of which is unsubstituted or substituted with one or more alkyl, aryl, halogen, —$OR^{13}$, —$NR(R^{18})R^{19}$, —$C(O)R^{14}$, —$OC(O)R^{15}$, —$OC(O)OR^{16}$, or —$OC(O)N(R^{18})R^{19}$.

In some embodiments is a compound of Formula (Io2), or a pharmaceutically acceptable salt or solvate thereof, wherein $R^{41}$ is aryl. In some embodiments is a compound of Formula (Io2), or a pharmaceutically acceptable salt or solvate thereof, wherein $R^{41}$ is aryl substituted with halogen. In some embodiments is a compound of Formula (Io2), or a pharmaceutically acceptable salt or solvate thereof, wherein $R^{41}$ is

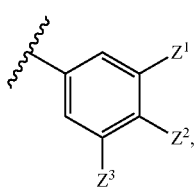

wherein each of $Z^1$, $Z^2$, and $Z^3$ is independently hydrogen or halogen. In some embodiments is a compound of Formula (Io2), or a pharmaceutically acceptable salt or solvate thereof, wherein $R^{41}$ is

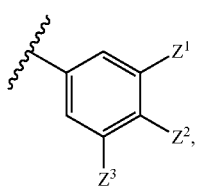

wherein each of $Z^1$, $Z^2$, and $Z^3$ is independently hydrogen, fluoro, chloro, bromo, or iodo. In some embodiments is a compound of Formula (Io2), or a pharmaceutically acceptable salt or solvate thereof, wherein $R^{41}$ is 151
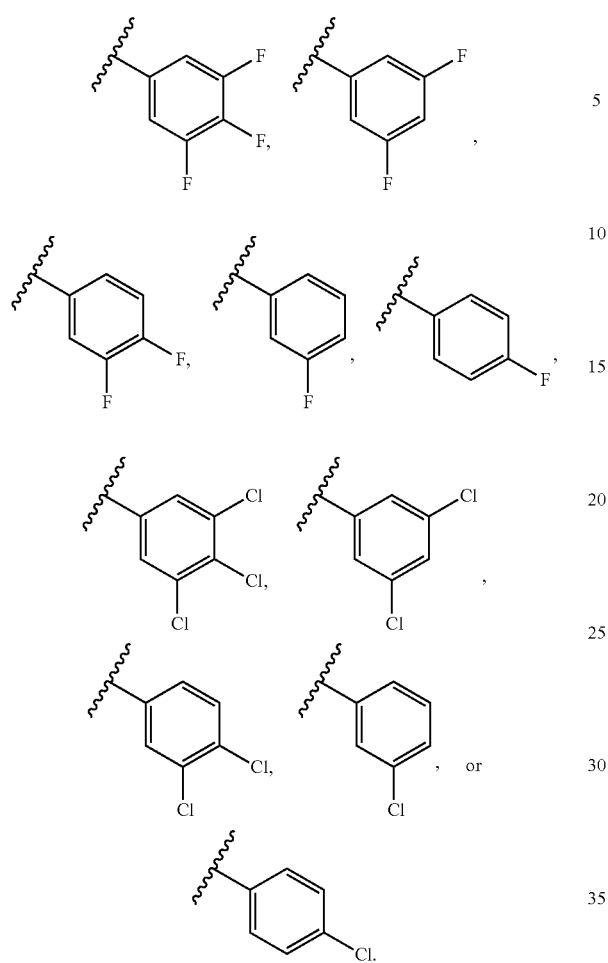
In some embodiments is a compound of Formula (Io2), or a pharmaceutically acceptable salt or solvate thereof, wherein the compound is:
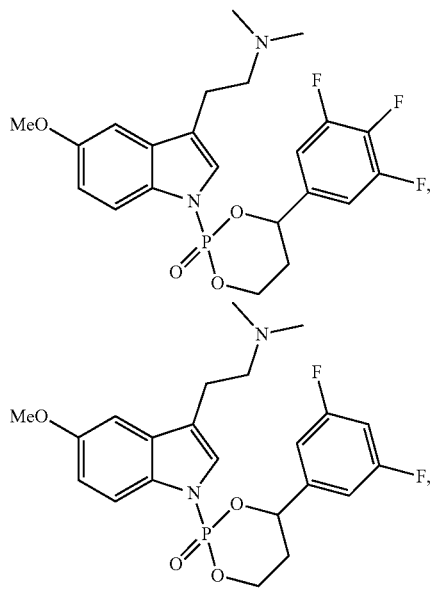
152
-continued
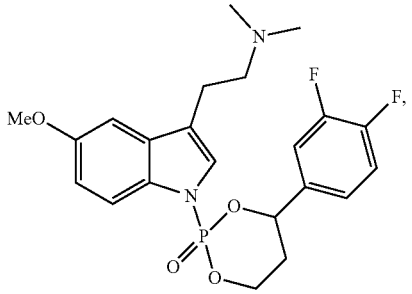
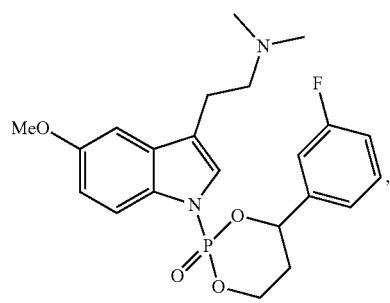
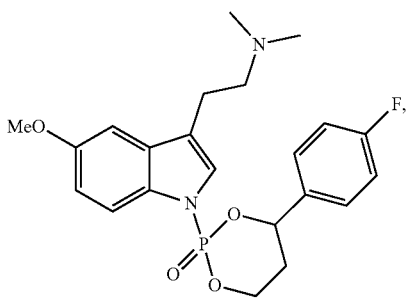
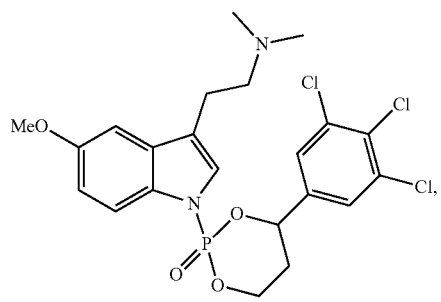
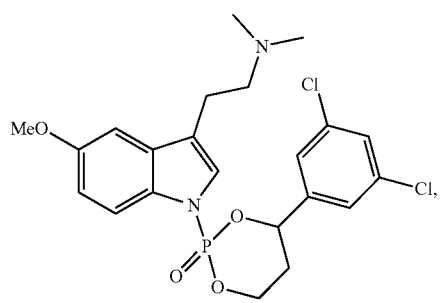

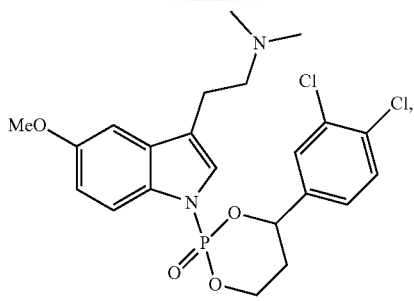
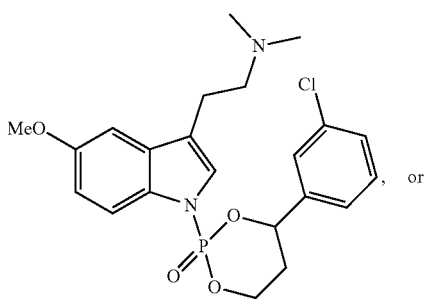
, or
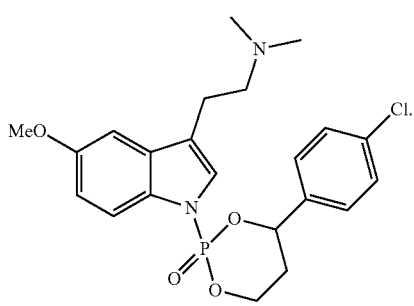
In some embodiments is a compound of Formula (Io2), or a pharmaceutically acceptable salt or solvate thereof, wherein the compound is:
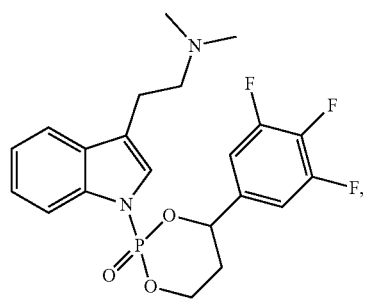
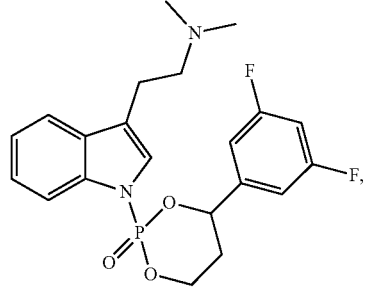
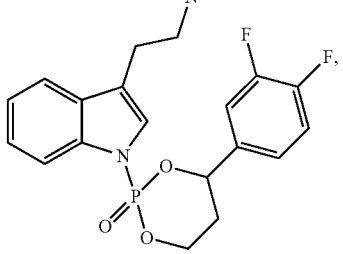
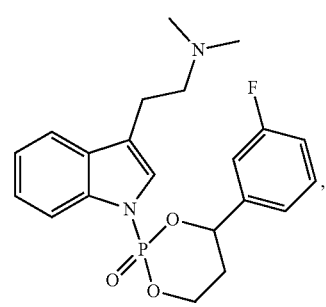
,
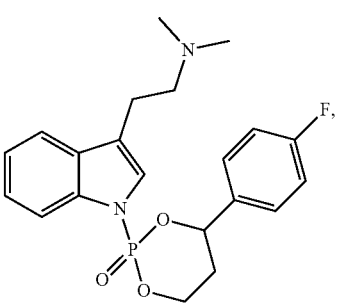
,
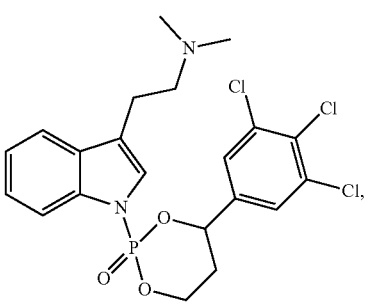
,
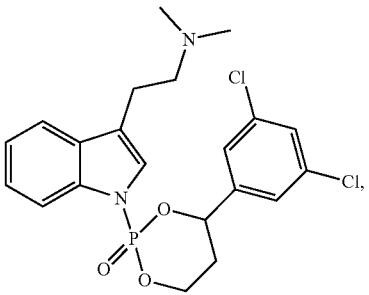
,

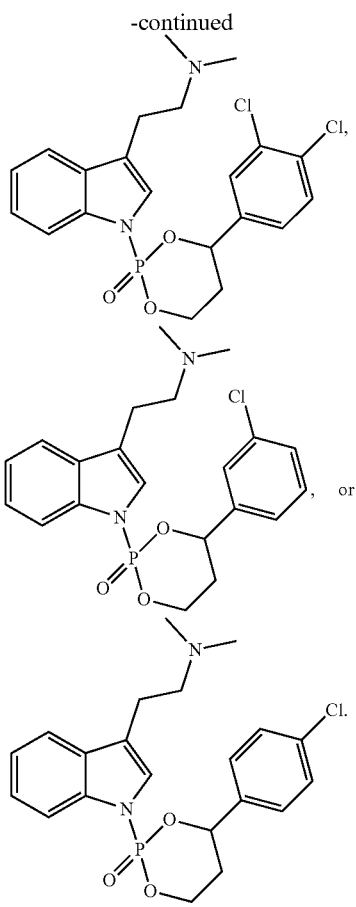

In some embodiments is a compound of Formula (I), (Io), or (Io1), having the structure of Formula (Io1a), or a pharmaceutically acceptable salt thereof:

(Io1a)

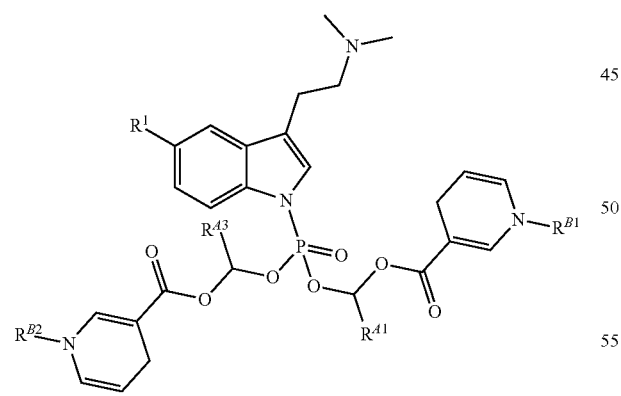

wherein:
R$^1$ is methoxy or hydrogen;
each of R$^{A1}$ and R$^{A3}$ is independently hydrogen, alkyl, or cycloalkyl, wherein each alkyl and cycloalkyl is independently unsubstituted or substituted with one or more alkyl, aryl, halogen, —OR$^{13}$, —NR(R$^{18}$)R$^{19}$, —C(O)R$^{14}$, —OC(O)R$^{15}$, —OC(O)OR$^{16}$, or —OC(O)N(R$^{18}$)R$^{19}$; and each of R$^{B1}$ and R$^{B2}$ is independently hydrogen or alkyl that is unsubstituted or substituted with one or more halogen, amino, cyano, hydroxyl, alkyl, acetyl, or benzoyl.

In some embodiments is a compound of Formula (Io1a), or a pharmaceutically acceptable salt or solvate thereof, wherein each of R$^{B1}$ and R$^{B2}$ is independently hydrogen, methyl, ethyl, n-propyl, isopropyl, n-butyl, tert-butyl, pentan-3-yl, or benzyl. In some embodiments is a compound of Formula (Io1a), or a pharmaceutically acceptable salt or solvate thereof, wherein each of R$^{A1}$ and R$^{A3}$ is independently hydrogen, methyl, ethyl, isopropyl, or tert-butyl. In some embodiments is a compound of Formula (Io1a), or a pharmaceutically acceptable salt or solvate thereof, wherein each of R$^A$ and R$^{A3}$ is independently hydrogen. In some embodiments is a compound of Formula (Io1a), or a pharmaceutically acceptable salt or solvate thereof, wherein each of R$^{A1}$ and R$^{A3}$ is independently hydrogen, methyl, ethyl, isopropyl, or tert-butyl; and each of RBI and R$^{B2}$ is hydrogen, methyl, ethyl, n-propyl, isopropyl, n-butyl, tert-butyl, pentan-3-yl, or benzyl.

In some embodiments is a compound of Formula (Io1a), or a pharmaceutically acceptable salt or solvate thereof, wherein the compound is:

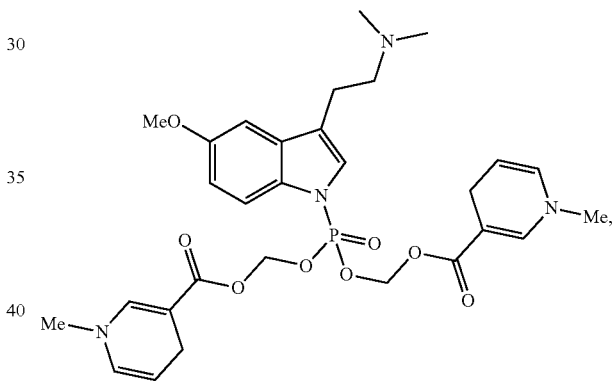

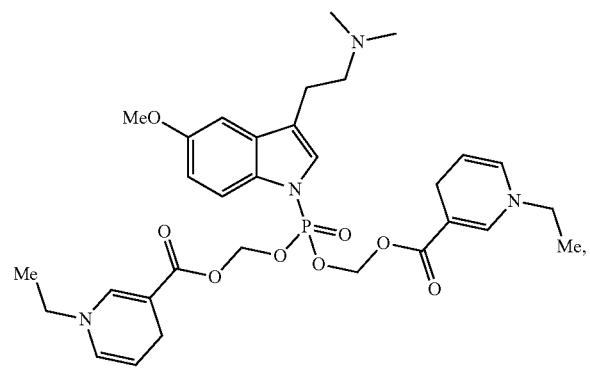

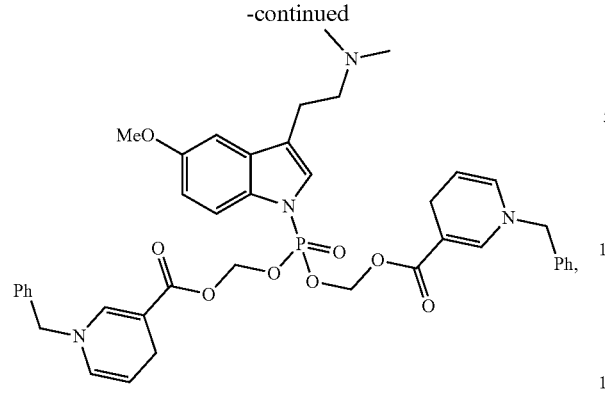
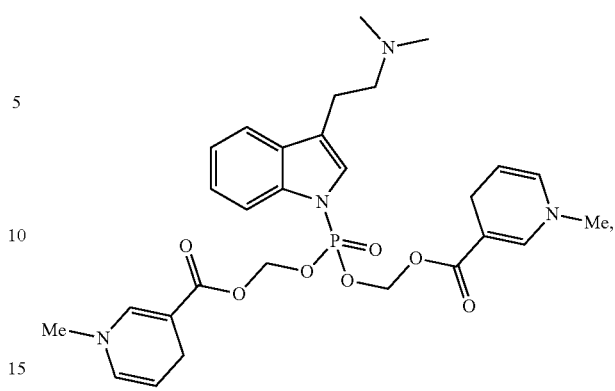
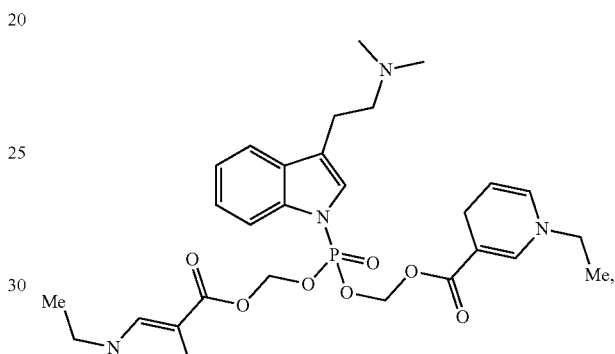
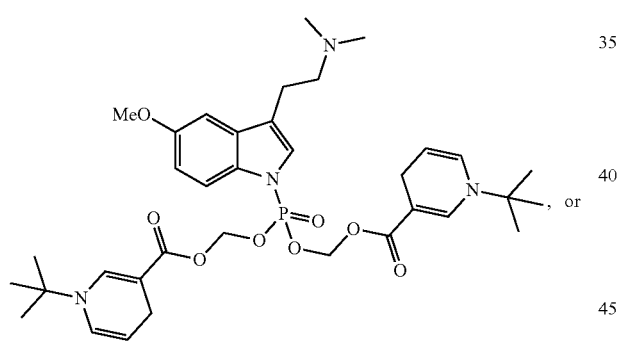
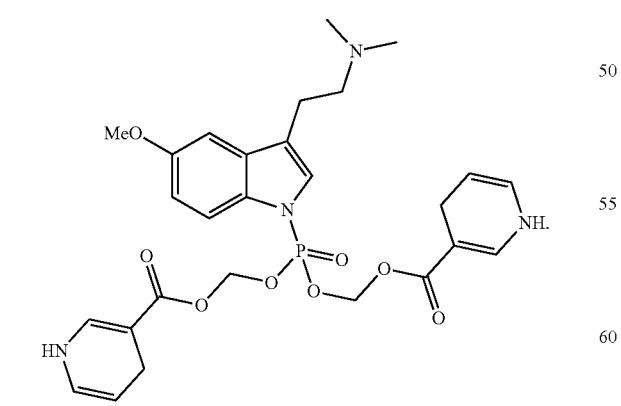
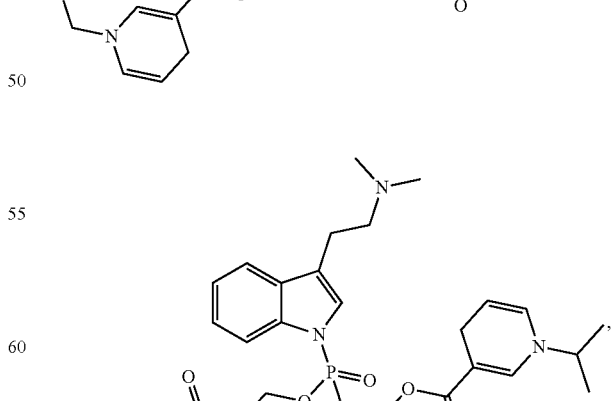
In some embodiments is a compound of Formula (Iola), or a pharmaceutically acceptable salt or solvate thereof, wherein the compound is:

-continued

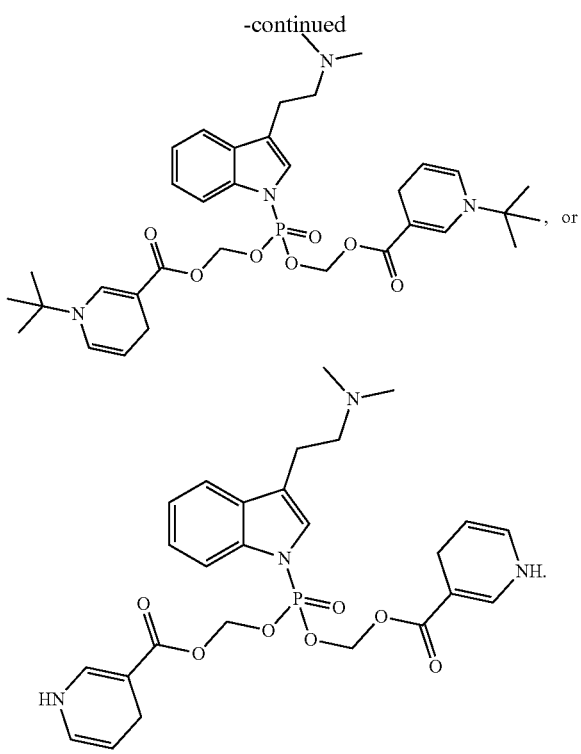

In some embodiments is a compound of Formula (I) having the structure of Formula (Ip), or a pharmaceutically acceptable salt thereof:

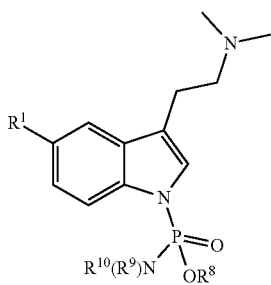
(Ip)

wherein:
R$^1$ is methoxy or hydrogen;
R$^8$ is alkyl, cycloalkyl, aryl, heterocyclylalkyl, or heteroaryl; and
each of R$^9$ and R$^{10}$ is independently hydrogen or alkyl, wherein each alkyl, cycloalkyl, aryl, heterocyclylalkyl, and heteroaryl is independently unsubstituted or substituted with one or more R$^A$.

In some embodiments is a compound of Formula (I) or (Ip), or a pharmaceutically acceptable salt or solvate thereof, wherein R$^8$ is alkyl or cycloalkyl. In some embodiments is a compound of Formula (I) or (Ip), or a pharmaceutically acceptable salt or solvate thereof, wherein R$^8$ is unsubstituted alkyl or unsubstituted cycloalkyl. In some embodiments is a compound of Formula (I) or (Ip), or a pharmaceutically acceptable salt or solvate thereof, wherein R$^8$ is methyl, ethyl, n-propyl, n-butyl, n-pentyl, n-hexyl, isopropyl, tert-butyl, cyclopropyl, cyclobutyl, cyclopentyl, cyclohexyl, or cycloheptyl. In some embodiments is a compound of Formula (I) or (Ip), or a pharmaceutically acceptable salt or solvate thereof, wherein R$^8$ is aryl. In some embodiments is a compound of Formula (I) or (Ip), or a pharmaceutically acceptable salt or solvate thereof, wherein R$^8$ is phenyl. In some embodiments is a compound of Formula (I) of (Ip), or a pharmaceutically acceptable salt or solvate thereof, wherein R$^8$ is 4-nitrophenyl. In some embodiments is a compound of Formula (I) or (Ip), or a pharmaceutically acceptable salt or solvate thereof, wherein R$^9$ is benzyl. In some embodiments is a compound of Formula (I) or (Ip), or a pharmaceutically acceptable salt or solvate thereof, wherein R$^8$ is 2-pyridyl, 3-pyridyl, 4-pyridyl, 2-pyrimidyl, or 4-pyrimidyl. In some embodiments is a compound of Formula (I) or (Ip), or a pharmaceutically acceptable salt or solvate thereof, wherein R$^9$ is hydrogen. In some embodiments is a compound of Formula (I) or (Ip), or a pharmaceutically acceptable salt or solvate thereof, wherein R$^9$ is hydrogen, and R$^{10}$ is alkyl.

In some embodiments is a compound of Formula (I) or (Ip) having the structure of Formula (Ip1), or a pharmaceutically acceptable salt thereof:

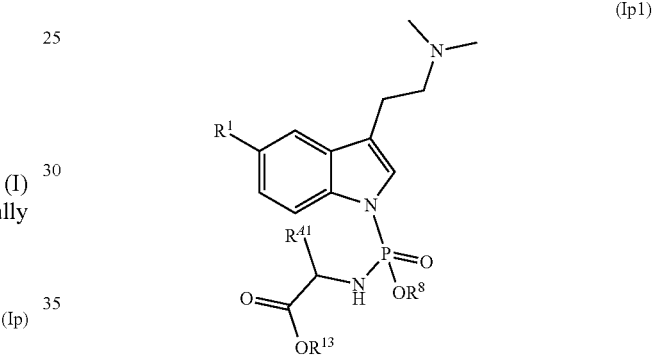
(Ip1)

wherein:
R$^1$ is methoxy or hydrogen;
R$^{41}$ is hydrogen, alkyl, or cycloalkyl, wherein each of alkyl and cycloalkyl is unsubstituted or substituted with one or more alkyl, aryl, halogen, —OR$^{13}$, —NR(R$^{18}$)R$^{19}$, —C(O)R$^{14}$, —OC(O)R$^{15}$, —OC(O)OR$^{16}$, or —OC(O)N(R$^{18}$)R$^{19}$;
R$^8$ is hydrogen, alkyl, cycloalkyl, aryl, heterocyclylalkyl, or heteroaryl, wherein each alkyl, cycloalkyl, aryl, heterocyclylalkyl, and heteroaryl is unsubstituted or substituted with one or more R$^A$; and
R$^{13}$ is hydrogen or alkyl that is unsubstituted or substituted with one or more R$^B$.

In some embodiments is a compound of Formula (Ip1), or a pharmaceutically acceptable salt or solvate thereof, wherein R$^{41}$ is hydrogen or alkyl. In some embodiments is a compound of Formula (Ip1), or a pharmaceutically acceptable salt or solvate thereof, wherein R$^{41}$ is hydrogen or unsubstituted alkyl. In some embodiments is a compound of Formula (Ip1), or a pharmaceutically acceptable salt or solvate thereof, wherein R$^{41}$ is hydrogen, methyl, ethyl, or tert-butyl. In some embodiments is a compound of Formula (Ip1), or a pharmaceutically acceptable salt or solvate thereof, wherein R$^{41}$ is hydrogen. In some embodiments is a compound of Formula (Ip1), or a pharmaceutically acceptable salt or solvate thereof, wherein R$^8$ is alkyl or cycloalkyl. In some embodiments is a compound of Formula (Ip1), or a pharmaceutically acceptable salt or solvate thereof, wherein R$^8$ is unsubstituted alkyl or unsubstituted cycloalkyl. In some embodiments is a compound of Formula (Ip1), or a pharmaceutically acceptable salt or solvate thereof, wherein $R^8$ is methyl, ethyl, n-propyl, n-butyl, n-pentyl, n-hexyl, isopropyl, tert-butyl, cyclopropyl, cyclobutyl, cyclopentyl, cyclohexyl, or cycloheptyl. In some embodiments is a compound of Formula (Ip1), or a pharmaceutically acceptable salt or solvate thereof, wherein $R^8$ is phenyl. In some embodiments is a compound of Formula (Ip1), or a pharmaceutically acceptable salt or solvate thereof, wherein $R^8$ is 4-nitrophenyl. In some embodiments is a compound of Formula (Ip1), or a pharmaceutically acceptable salt or solvate thereof, wherein $R^8$ is benzyl. In some embodiments is a compound of Formula (Ip1), or a pharmaceutically acceptable salt or solvate thereof, wherein $R^8$ is 2-pyridyl, 3-pyridyl, 4-pyridyl, 2-pyrimidyl, or 4-pyrimidyl. In some embodiments is a compound of Formula (Ip1), or a pharmaceutically acceptable salt or solvate thereof, wherein $R^{13}$ is alkyl. In some embodiments is a compound of Formula (Ip1), or a pharmaceutically acceptable salt or solvate thereof, wherein $R^{13}$ is unsubstituted alkyl. In some embodiments is a compound of Formula (Ip1), or a pharmaceutically acceptable salt or solvate thereof, wherein $R^{13}$ is methyl, ethyl, n-propyl, isopropyl, n-butyl, tert-butyl, or —CH$_2$CH(Et)$_2$. In some embodiments is a compound of Formula (Ip1), or a pharmaceutically acceptable salt or solvate thereof, wherein $R^{41}$ is hydrogen or unsubstituted alkyl; and $R^{13}$ is methyl, ethyl, n-propyl, isopropyl, n-butyl, tert-butyl, or —CH$_2$CH(Et)$_2$. In some embodiments is a compound of Formula (Ip1), or a pharmaceutically acceptable salt or solvate thereof, wherein $R^{41}$ is hydrogen; and $R^{13}$ is methyl, ethyl, n-propyl, isopropyl, n-butyl, tert-butyl, or —CH$_2$CH(Et)$_2$.

In some embodiments is a compound of Formula (Ip1), or a pharmaceutically acceptable salt or solvate thereof, wherein the compound is:

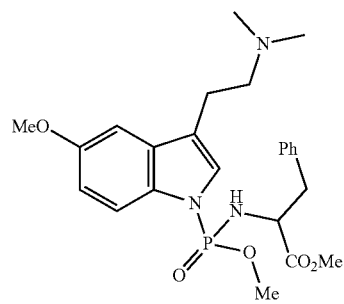

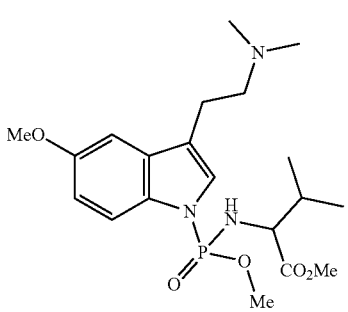

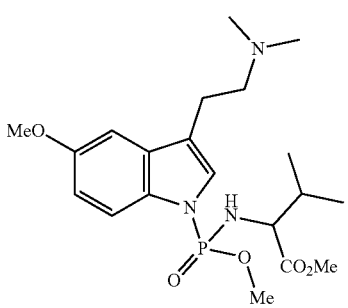

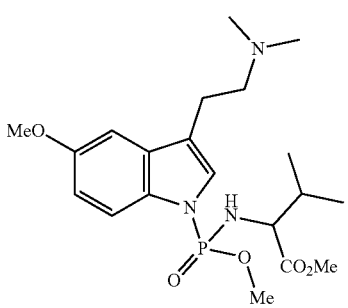

-continued

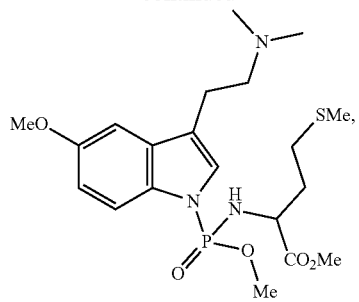

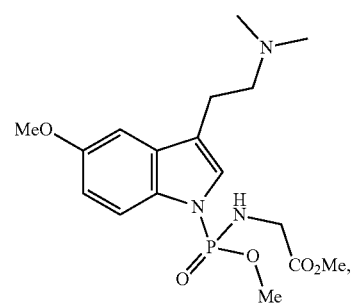

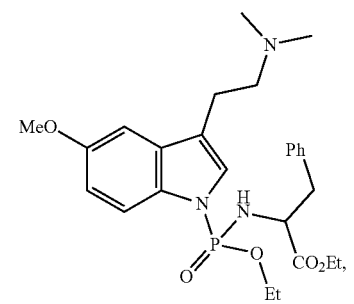

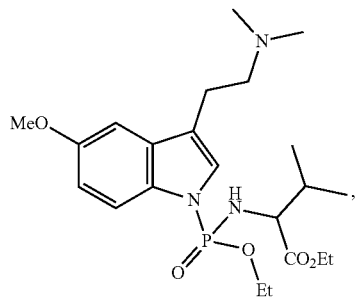

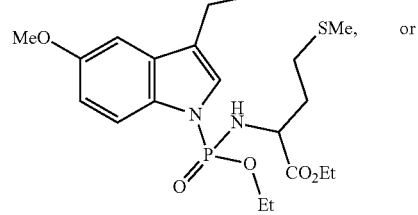

or

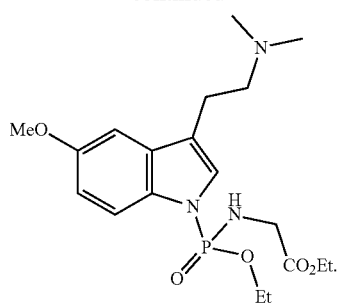
In some embodiments is a compound of Formula (Ip1), or a pharmaceutically acceptable salt or solvate thereof, wherein the compound is:
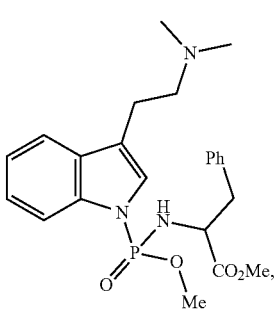
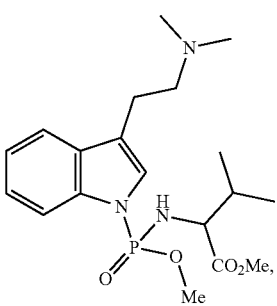
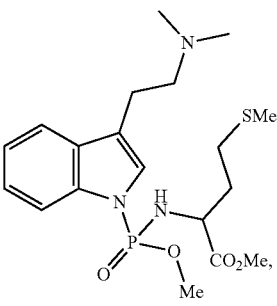
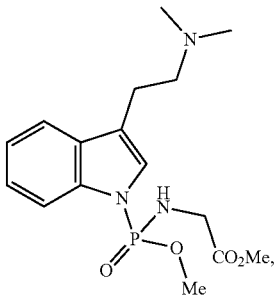
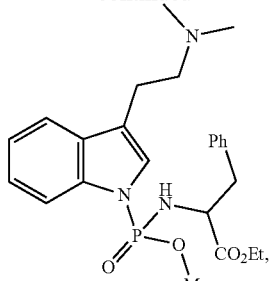
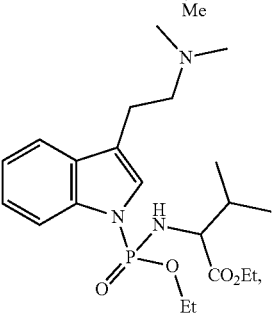
In some embodiments is a compound of Formula (I) having the structure of Formula (Iq), or a pharmaceutically acceptable salt thereof:
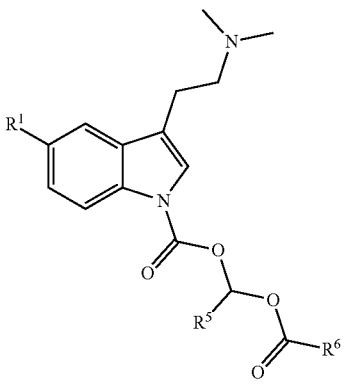

wherein:
R$^1$ is methoxy or hydrogen;
R$^5$ is hydrogen, alkyl, or cycloalkyl; and
R$^6$ is alkyl, cycloalkyl, heteroalkyl, heterocyclylalkyl, aryl, or heteroaryl,
wherein each alkyl, cycloalkyl, heteroalkyl, heterocyclylalkyl, aryl, and heteroaryl is independently unsubstituted or substituted with one or more R$^4$.

In some embodiments is a compound of Formula (I) or (Iq), or a pharmaceutically acceptable salt or solvate thereof, wherein R$^5$ is hydrogen or alkyl. In some embodiments is a compound of Formula (I) or (Iq), or a pharmaceutically acceptable salt or solvate thereof, wherein R$^5$ is alkyl. In some embodiments is a compound of Formula (I) or (Iq), or a pharmaceutically acceptable salt or solvate thereof, wherein R$^5$ is hydrogen or unsubstituted alkyl. In some embodiments is a compound of Formula (I) or (Iq), or a pharmaceutically acceptable salt or solvate thereof, wherein R$^5$ is hydrogen. In some embodiments is a compound of Formula (I) or (Iq), or a pharmaceutically acceptable salt or solvate thereof, wherein R$^6$ is alkyl, cycloalkyl, heterocyclylalkyl, aryl, or heteroaryl. In some embodiments is a compound of Formula (I) or (Iq), or a pharmaceutically acceptable salt or solvate thereof, wherein R$^6$ is alkyl. In some embodiments is a compound of Formula (I) or (Iq), or a pharmaceutically acceptable salt or solvate thereof, wherein R$^6$ is heterocyclylalkyl. In some embodiments is a compound of Formula (I) or (Iq), or a pharmaceutically acceptable salt or solvate thereof, wherein R$^6$ is heteroalkyl. In some embodiments is a compound of Formula (I) or (Iq), or a pharmaceutically acceptable salt or solvate thereof, wherein R$^6$ is unsubstituted alkyl, unsubstituted cycloalkyl, unsubstituted heterocyclylalkyl, unsubstituted aryl, or unsubstituted heteroaryl. In some embodiments is a compound of Formula (I) or (Iq), or a pharmaceutically acceptable salt or solvate thereof, wherein R$^6$ is alkyl. In some embodiments is a compound of Formula (I) or (Iq), or a pharmaceutically acceptable salt or solvate thereof, wherein R$^6$ is heteroalkyl. In some embodiments is a compound of Formula (I) or (Iq), or a pharmaceutically acceptable salt or solvate thereof, wherein R$^6$ is heterocyclylalkyl substituted with arylalkyl. In some embodiments is a compound of Formula (I) or (Iq), or a pharmaceutically acceptable salt or solvate thereof, wherein R$^5$ is methyl, isopropyl, tert-butyl, or —CH(Et)$_2$.

In some embodiments is a compound of Formula (I) or (Iq), or a pharmaceutically acceptable salt or solvate thereof, wherein R$^5$ is hydrogen, and R$^6$ is alkyl. In some embodiments is a compound of Formula (I) or (Iq), or a pharmaceutically acceptable salt or solvate thereof, wherein R$^5$ is alkyl, and R$^6$ is alkyl. In some embodiments is a compound of Formula (I) or (Iq), or a pharmaceutically acceptable salt or solvate thereof, wherein R$^5$ is hydrogen, and R$^6$ is unsubstituted alkyl. In some embodiments is a compound of Formula (I) or (Iq), or a pharmaceutically acceptable salt or solvate thereof, wherein R$^5$ is unsubstituted alkyl, and R$^6$ is unsubstituted alkyl. In some embodiments is a compound of Formula (I) or (Iq), or a pharmaceutically acceptable salt or solvate thereof, wherein R$^6$ is methyl, ethyl, isopropyl, tert-butyl, or cyclopropyl. In some embodiments is a compound of Formula (I) or (Iq), or a pharmaceutically acceptable salt or solvate thereof, wherein R$^5$ is hydrogen, and R$^6$ is methyl, ethyl, isopropyl, tert-butyl, or cyclopropyl. In some embodiments is a compound of Formula (I) or (Iq), or a pharmaceutically acceptable salt or solvate thereof, wherein R$^5$ is hydrogen, and R$^6$ is tert-butyl. In some embodiments is a compound of Formula (I) or (Iq), or a pharmaceutically acceptable salt or solvate thereof, wherein R$^1$ is hydrogen, R$^5$ is hydrogen, and R$^6$ is tert-butyl. In some embodiments is a compound of Formula (I) or (Iq), or a pharmaceutically acceptable salt or solvate thereof, wherein R$^1$ is methoxy, R$^5$ is hydrogen, and R$^6$ is tert-butyl.

In some embodiments is a compound of Formula (I) or (Iq), or a pharmaceutically acceptable salt or solvate thereof, wherein R$^6$ is alkyl. In some embodiments is a compound of Formula (I) or (Iq), or a pharmaceutically acceptable salt or solvate thereof, wherein R$^6$ is unsubstituted alkyl. In some embodiments is a compound of Formula (I) or (Iq), or a pharmaceutically acceptable salt or solvate thereof, wherein R$^6$ is cycloalkyl. In some embodiments is a compound of Formula (I) or (Iq), or a pharmaceutically acceptable salt or solvate thereof, wherein R$^6$ is methyl, ethyl, n-propyl, tert-butyl, 3-methyl-1-butyl, n-pentyl, n-hexyl, cyclopropyl, cyclobutyl, cyclopentyl, cyclohexyl, or cycloheptyl. In some embodiments is a compound of Formula (I) or (Iq), or a pharmaceutically acceptable salt or solvate thereof, wherein R$^6$ is phenyl. In some embodiments is a compound of Formula (I) or (Iq), or a pharmaceutically acceptable salt or solvate thereof, wherein R$^6$ is 4-nitrophenyl. In some embodiments is a compound of Formula (I) or (Iq), or a pharmaceutically acceptable salt or solvate thereof, wherein R$^6$ is benzyl. In some embodiments is a compound of Formula (I) or (Iq), or a pharmaceutically acceptable salt or solvate thereof, wherein R$^6$ is heteroaryl. In some embodiments is a compound of Formula (I) or (Iq), or a pharmaceutically acceptable salt or solvate thereof, wherein R$^6$ is 2-pyridyl, 3-pyridyl, 4-pyridyl, 2-pyrimidyl, or 4-pyrimidyl.

In some embodiments is a compound of Formula (I) or (Iq), or a pharmaceutically acceptable salt or solvate thereof, wherein R$^6$ is heteroalkyl. In some embodiments is a compound of Formula (I) or (Iq), or a pharmaceutically acceptable salt or solvate thereof, wherein R$^6$ is CH$_2$CH$_2$OMe or CH$_2$CH$_2$SO$_2$Me. In some embodiments is a compound of Formula (I) or (Iq), or a pharmaceutically acceptable salt or solvate thereof, wherein R$^6$ is —(CH$_2$)$_r$CO$_2$H, wherein r is 1, 2, 3, 4, 5, or 6. In some embodiments is a compound of Formula (I) or (Iq), or a pharmaceutically acceptable salt or solvate thereof, wherein R$^6$ is —(CH$_2$)$_s$CO$_2$R$^{13}$, wherein s is 1, 2, 3, 4, 5, or 6. In some embodiments is a compound of Formula (I) or (Iq), or a pharmaceutically acceptable salt or solvate thereof, wherein R$^6$ is —(CH$_2$)$_s$CO$_2$R$^{13}$, wherein R$^{13}$ is alkyl. In some embodiments is a compound of Formula (I) or (Iq), or a pharmaceutically acceptable salt or solvate thereof, wherein R$^6$ is —(CH$_2$)$_s$CO$_2$R$^{13}$, wherein R$^{13}$ is unsubstituted alkyl. In some embodiments is a compound of Formula (I) or (Iq), or a pharmaceutically acceptable salt or solvate thereof, wherein R$^6$ is —(CH$_2$)$_s$CO$_2$R$^{13}$, wherein R$^{13}$ is methyl, ethyl, n-propyl, isopropyl, n-butyl, tert-butyl, or —CH(Et)$_2$.

In some embodiments is a compound of Formula (I) or (Iq), or a pharmaceutically acceptable salt or solvate thereof, wherein R$^6$ is —CH(R$^{41}$)NH$_2$, wherein R$^{41}$ is hydrogen, alkyl, heteroalkyl, or an amino acid side chain. In some embodiments is a compound of Formula (I) or (Iq), or a pharmaceutically acceptable salt or solvate thereof, wherein R$^6$ is —CH(R$^{41}$)NH$_2$, wherein R$^{41}$ is an amino acid side chain. In some embodiments is a compound of Formula (I) or (Iq), or a pharmaceutically acceptable salt or solvate thereof, wherein R$^6$ is —CH(R$^{41}$)NH$_2$, wherein R$^{41}$ is methyl, ethyl, n-propyl, isopropyl, tert-butyl, CH(Me)Et, CH$_2$CH(Me)$_2$, or CH$_2$CH$_2$SMe. In some embodiments is a compound of Formula (I) or (Iq), or a pharmaceutically acceptable salt or solvate thereof, wherein R$^6$ is —CH(R$^{41}$)NH$_2$, wherein R$^{41}$ is benzyl.

In some embodiments is a compound of Formula (I) or (Iq), or a pharmaceutically acceptable salt or solvate thereof, wherein the compound is:
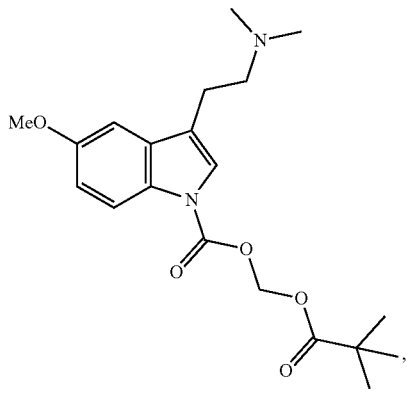
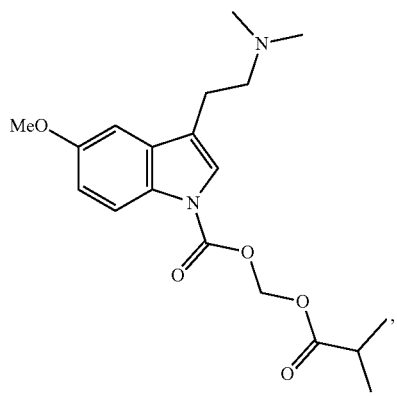
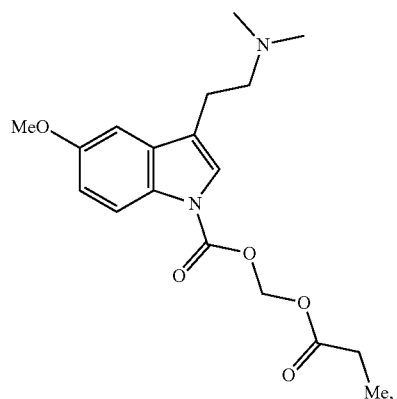
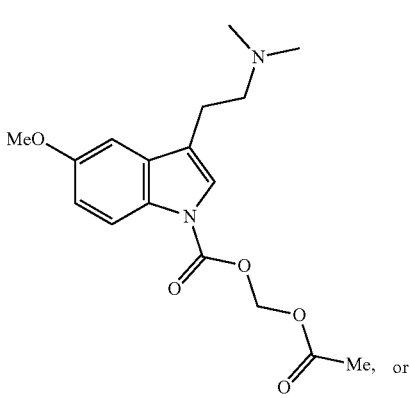
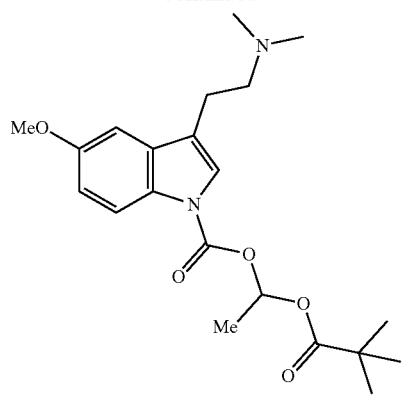
In some embodiments is a compound of Formula (I) or (Iq), or a pharmaceutically acceptable salt or solvate thereof, wherein the compound is:
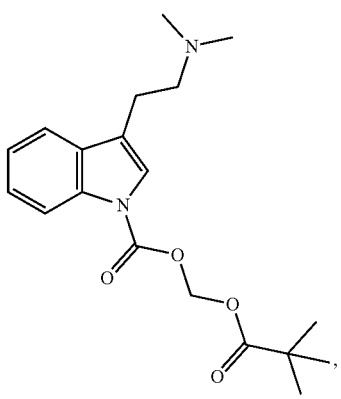
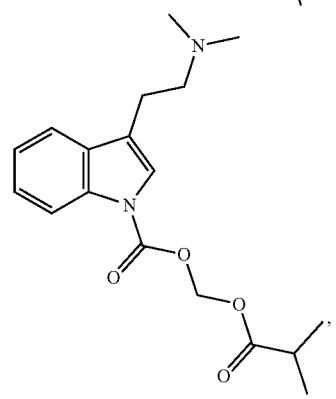
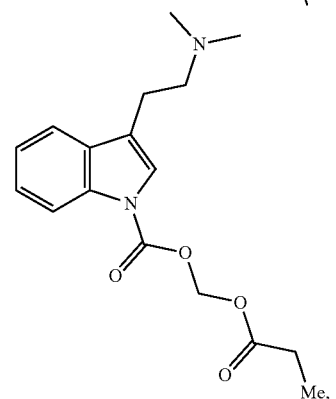

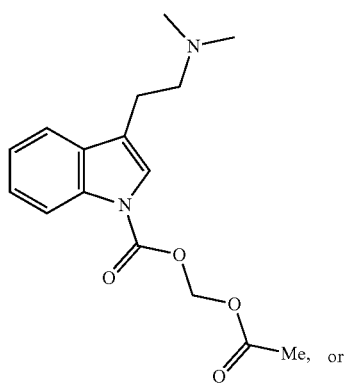
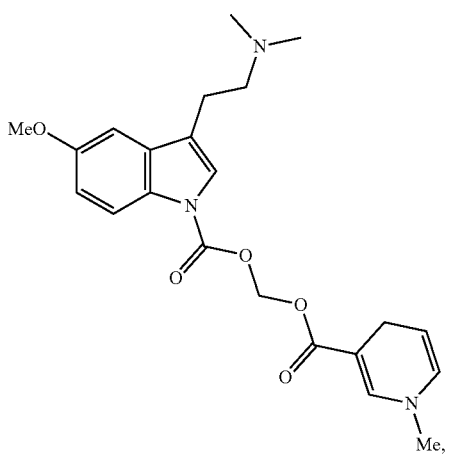
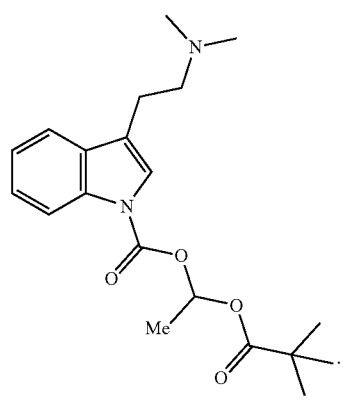
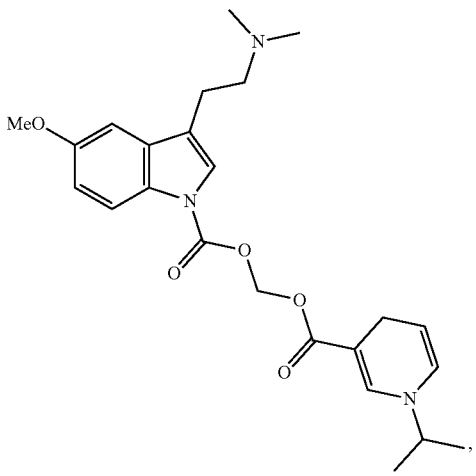
In some embodiments is a compound of Formula (I) or (Iq), or a pharmaceutically acceptable salt or solvate thereof, wherein the compound is:
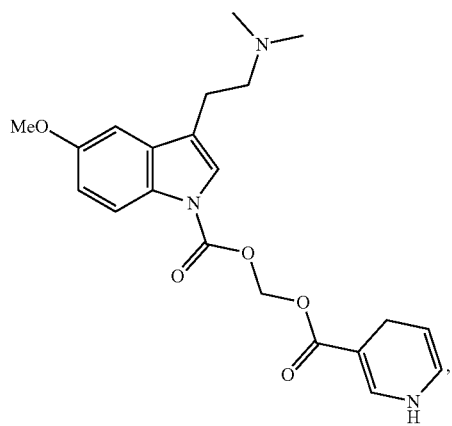
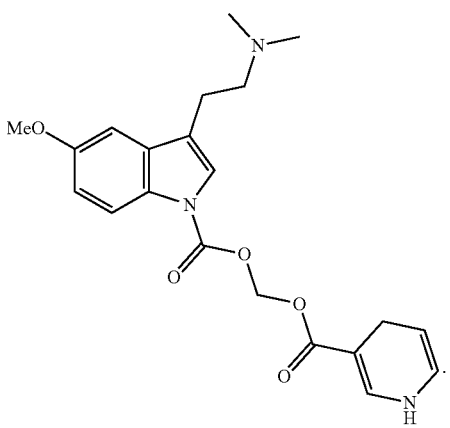 [SMILES: COc1ccc2c(c1)c(CCN(C)C)cn2C(=O)OCOC(=O)C1=CNC=CC1]
In some embodiments is a compound of Formula (I) or (Iq), or a pharmaceutically acceptable salt or solvate thereof, wherein the compound is:

171
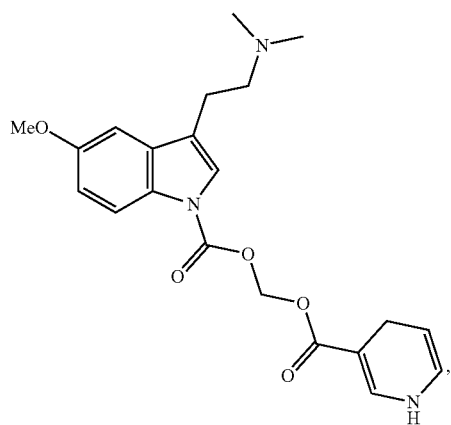
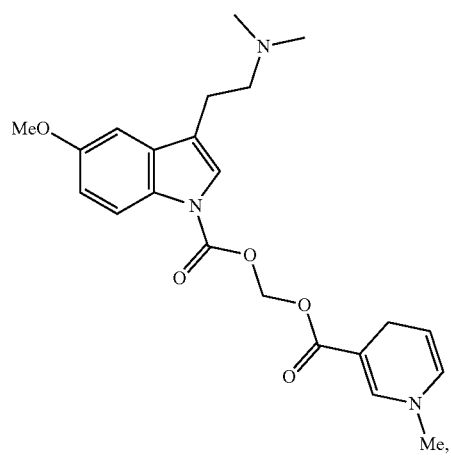
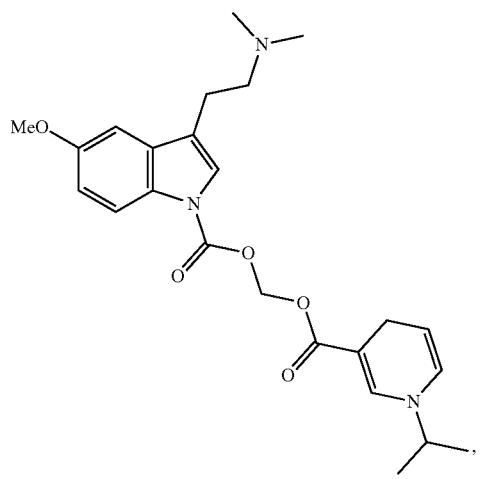
172
-continued
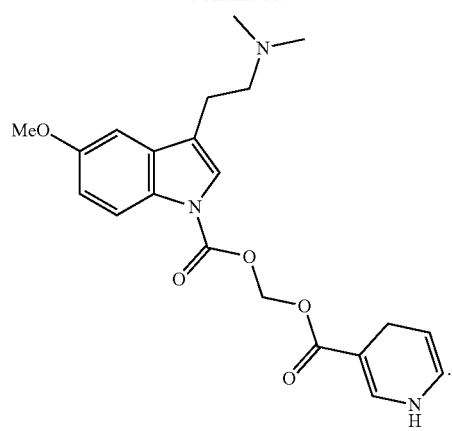
In some embodiments is a compound of Formula (I) or (Iq), or a pharmaceutically acceptable salt or solvate thereof, wherein the compound is:
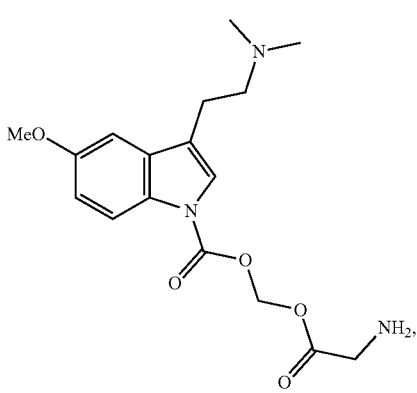
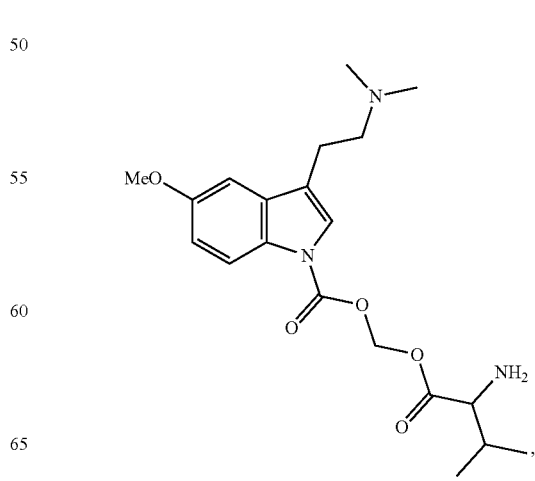

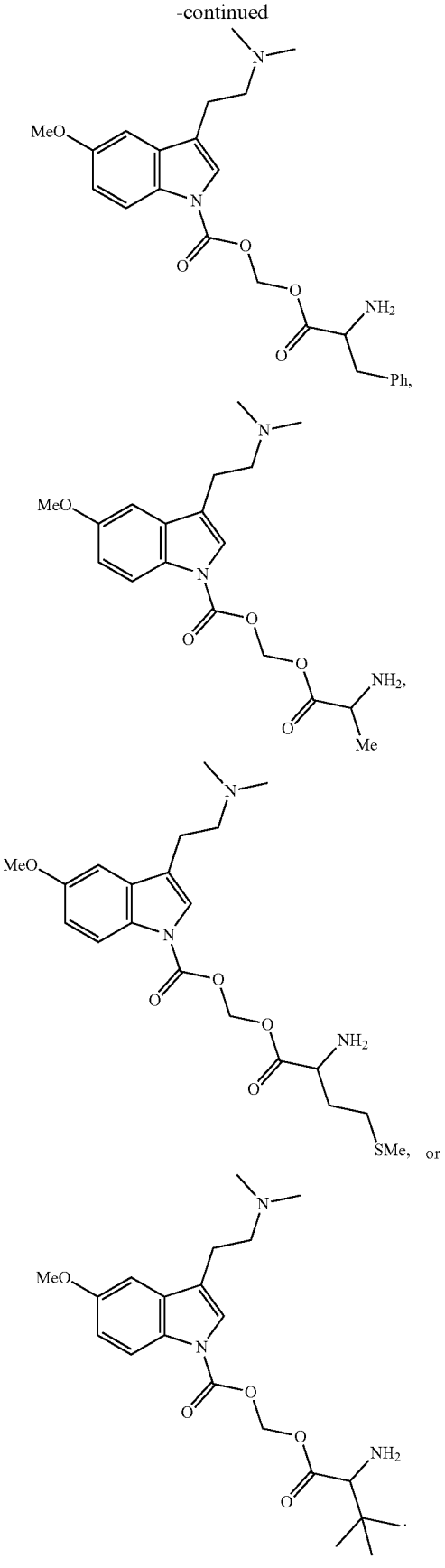
In some embodiments is a compound of Formula (I) or (Iq), or a pharmaceutically acceptable salt or solvate thereof, wherein the compound is:
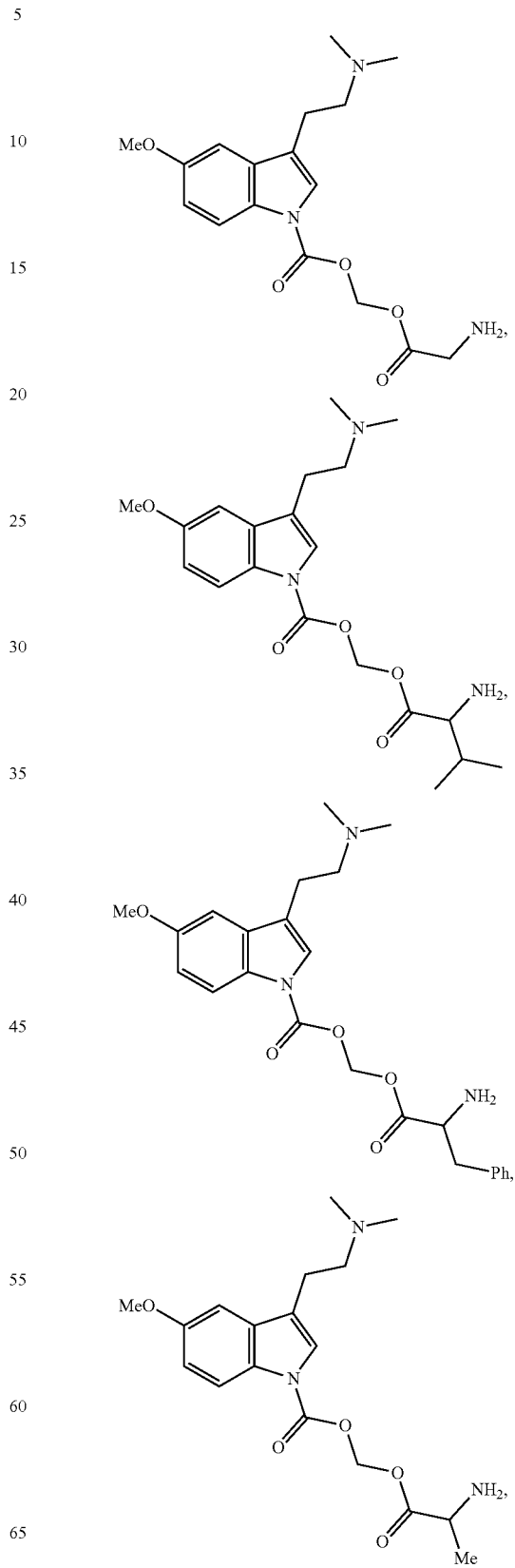

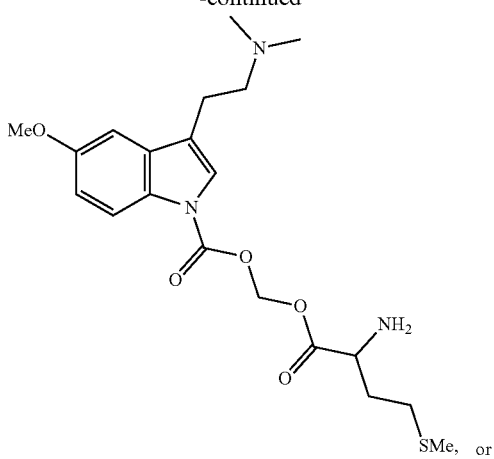

SMe, or

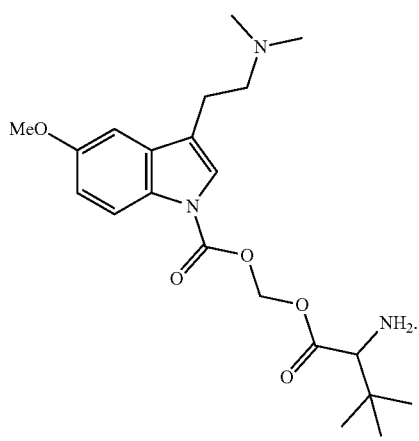

In some embodiments is a compound of Formula (I) or (Iq) having the structure of Formula (Iq1), or a pharmaceutically acceptable salt thereof:

(Iq1)

wherein:
R¹ is methoxy or hydrogen;
R⁵ is hydrogen, alkyl, or cycloalkyl, wherein each of alkyl and cycloalkyl is unsubstituted or substituted with one or more $R^4$; and Q¹ is

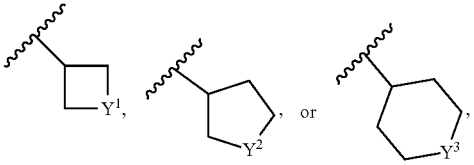

wherein
each of $Y^1$, $Y^2$, or $Y^3$ is independently —O—, —S—, —S(O)—, —S(O)$_2$—, —N(R¹)—, or —NC(O)$R^{Y2}$, wherein each of $R^{Y1}$ and $R^{Y2}$ is independently hydrogen, alkyl, heteroalkyl, or heteroaryl.

In some embodiments is a compound of Formula (Iq1), or a pharmaceutically acceptable salt or solvate thereof, wherein each of $Y^1$, $Y^2$, or $Y^3$ is —N($R^{Y1}$)—. In some embodiments is a compound of Formula (Iq1), or a pharmaceutically acceptable salt or solvate thereof, wherein each of $Y^1$, $Y^2$, or $Y^3$ is —N($R^{Y1}$)—, wherein $R^{Y1}$ is hydrogen. In some embodiments is a compound of Formula (Iq1), or a pharmaceutically acceptable salt or solvate thereof, wherein each of $Y^1$, $Y^2$, or $Y^3$ is —N($R^{Y1}$)— or —NC(O)$R^{Y2}$, wherein each of $R^{Y1}$ and $R^{Y2}$ is independently methyl, ethyl, n-propyl, isopropyl, n-butyl, tert-butyl, CH(Et)$_2$, CH$_2$CH$_2$OMe, CH$_2$CH$_2$SO$_2$Me, or CH$_2$CF$_3$. In some embodiments is a compound of Formula (Iq1), or a pharmaceutically acceptable salt or solvate thereof, wherein each of $Y^1$, $Y^2$, or $Y^3$ is —N($R^{Y1}$)— or —NC(O)$R^{Y2}$, wherein each of $R^{Y1}$ and $R^{Y2}$ is phenyl. In some embodiments is a compound of Formula (Iq1), or a pharmaceutically acceptable salt or solvate thereof, wherein each of $Y^1$, $Y^2$, or $Y^3$ is —N($R^{Y1}$)— or —NC(O)$R^{Y2}$, wherein each of $R^{Y1}$ and $R^{Y2}$ is benzyl. In some embodiments is a compound of Formula (Iq1), or a pharmaceutically acceptable salt or solvate thereof, wherein each of $Y^1$, $Y^2$, or $Y^3$ is —N($R^{Y1}$)— or —NC(O)$R^{Y2}$, wherein each of $R^{Y1}$ and $R^{Y2}$ is independently 2-pyridyl, 3-pyridyl, or 4-pyridyl.

In some embodiments is a compound of Formula (Iq) or (Iq1), or a pharmaceutically acceptable salt or solvate thereof, wherein the compound is:

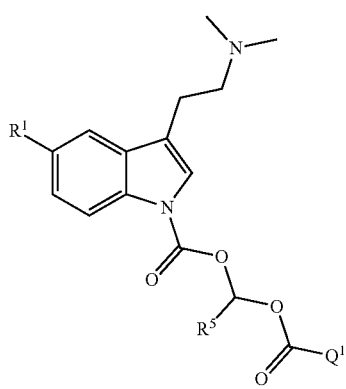

-continued
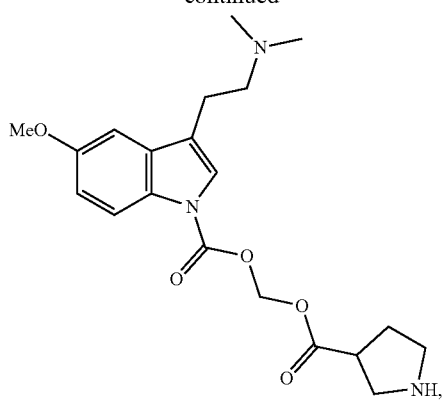
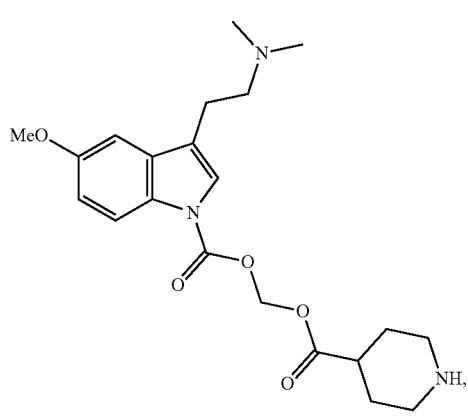
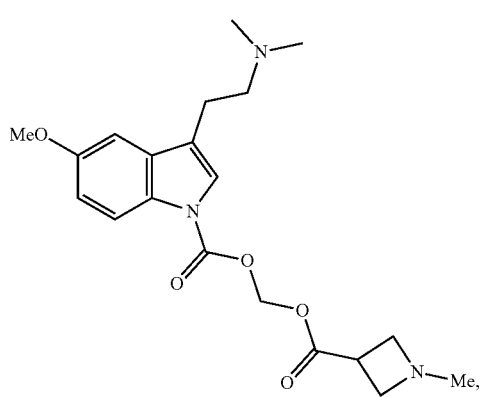
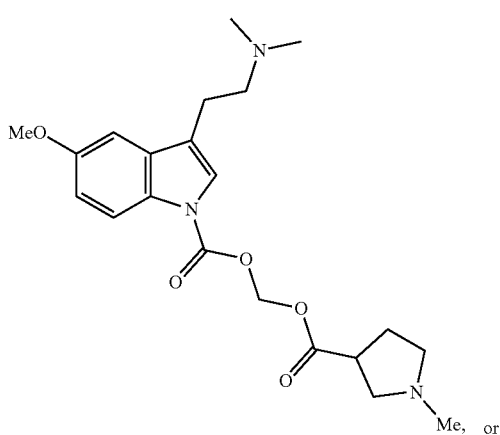
Me, or
-continued
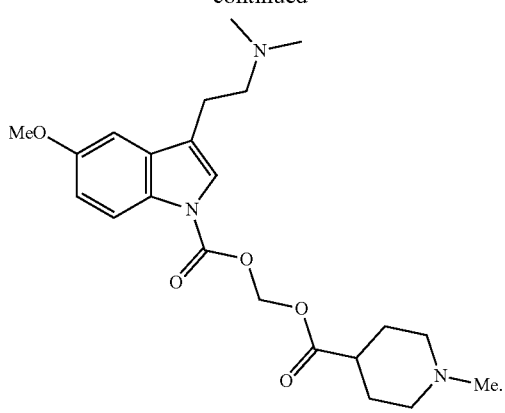
In some embodiments is a compound of Formula (Iq) or (Iq1), or a pharmaceutically acceptable salt or solvate thereof, wherein the compound is:
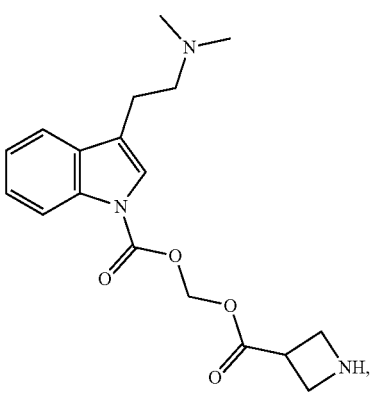
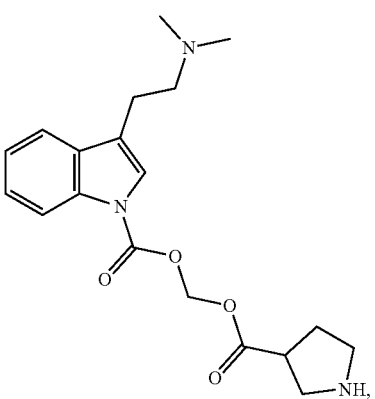

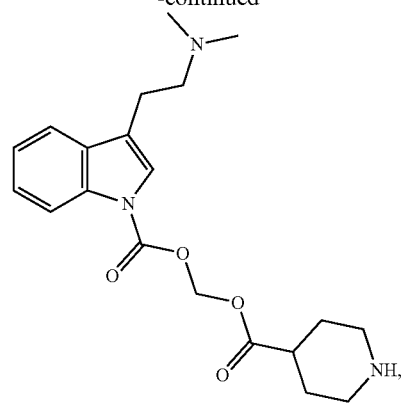
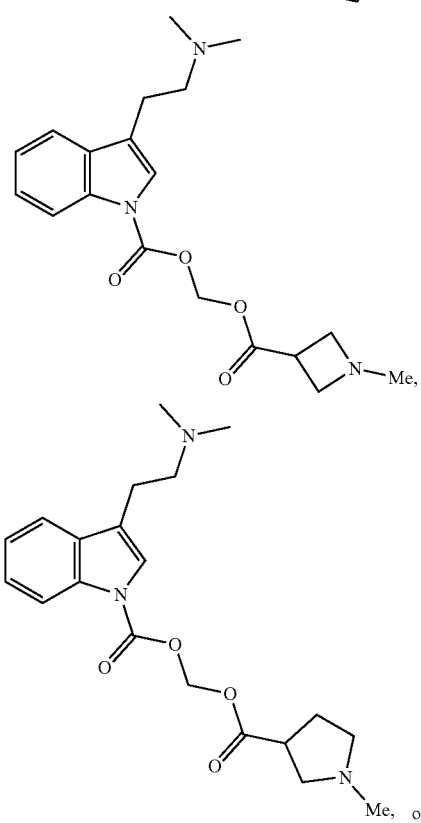
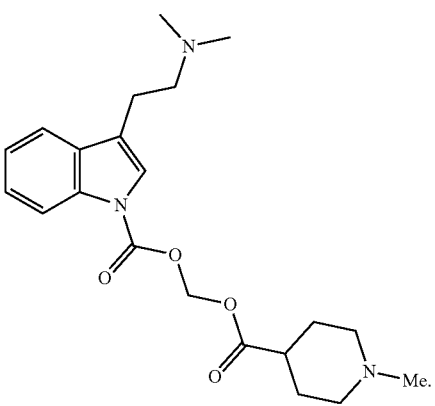
In some embodiments is a compound of Formula (Iq) or (Iq1), or a pharmaceutically acceptable salt or solvate thereof, wherein the compound is:
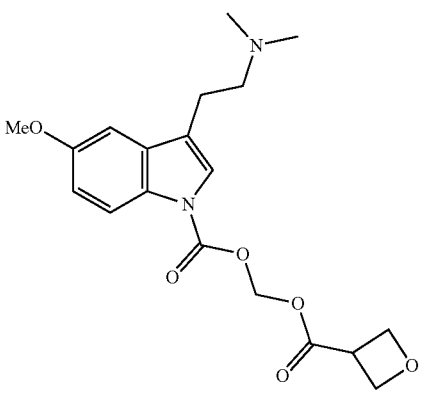
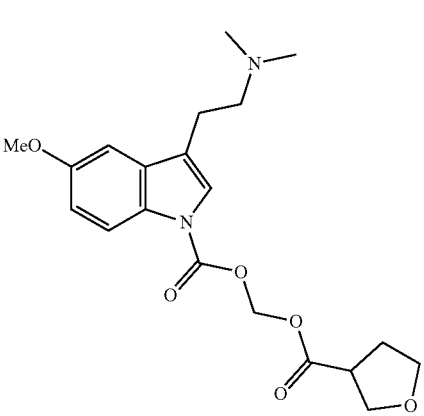
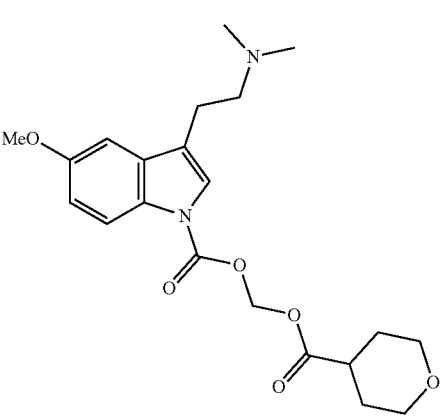
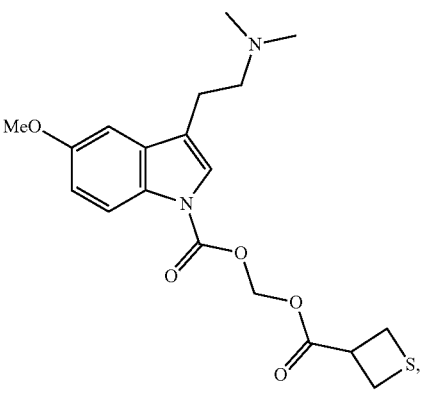

-continued

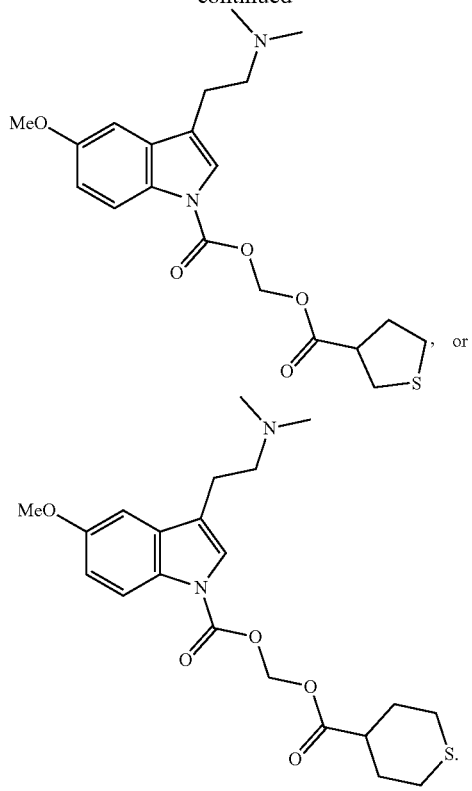

, or

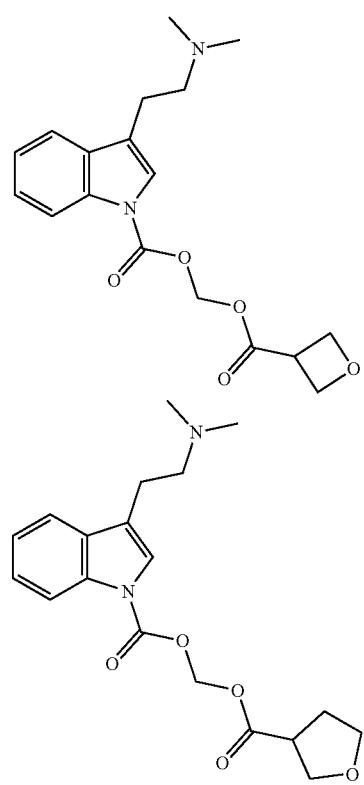

In some embodiments is a compound of Formula (Iq) or (Iq1), or a pharmaceutically acceptable salt or solvate thereof, wherein the compound is:

-continued

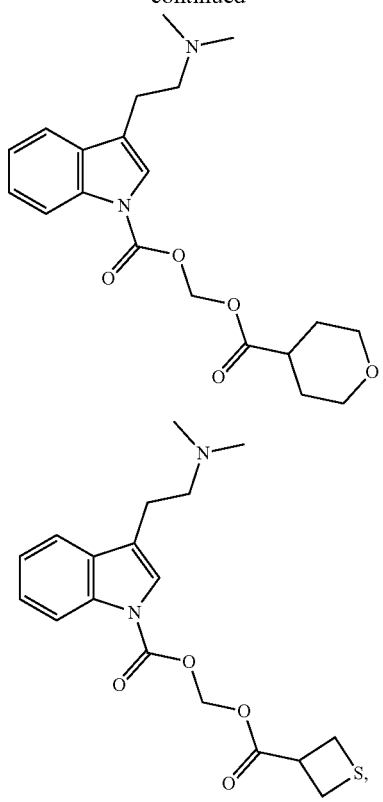

In some embodiments is a compound of Formula (Iq1), or a pharmaceutically acceptable salt or solvate thereof, wherein each of $Y^1$, $Y^2$, or $Y^3$ is —N($R^{Y1}$)— or —NC(O)$R^{Y2}$, wherein each of $R^{Y1}$ and $R^{Y2}$ is independently

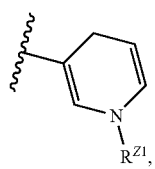

wherein R$^{Z1}$ is hydrogen or alkyl. In some embodiments is a compound of Formula (Iq1), or a pharmaceutically acceptable salt or solvate thereof, wherein each of Y$^1$, Y$^2$, or Y$^3$ is —N(R$^{Y1}$)— or —NC(O)R$^{Y2}$, wherein each of R$^{Y1}$ and R$^{Y2}$ is independently

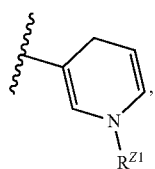

wherein R$^{Z1}$ is methyl, ethyl, n-propyl, isopropyl, n-butyl, tert-butyl, or CH(Et)$_2$. In some embodiments is a compound of Formula (Iq1), or a pharmaceutically acceptable salt or solvate thereof, wherein each of Y$^1$, Y$^2$, or Y$^3$ is —N(R$^{Y1}$)— or —NC(O)R$^{Y2}$, wherein each of R$^{Y1}$ and R$^{Y2}$ is independently

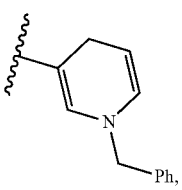

wherein R$^{Z1}$ is benzyl.

In some embodiments is a compound of Formula (Iq1), or a pharmaceutically acceptable salt or solvate thereof, wherein the compound is:

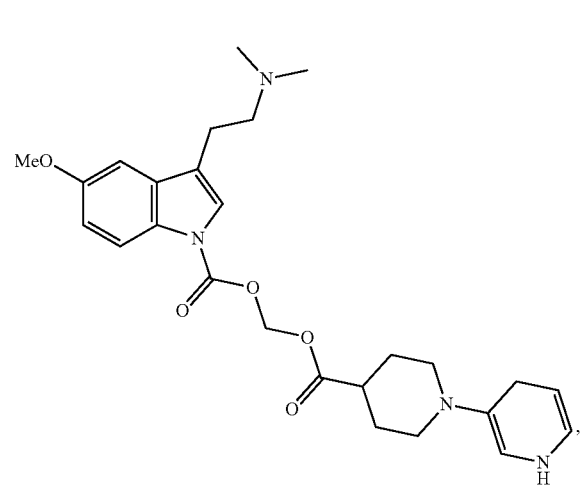

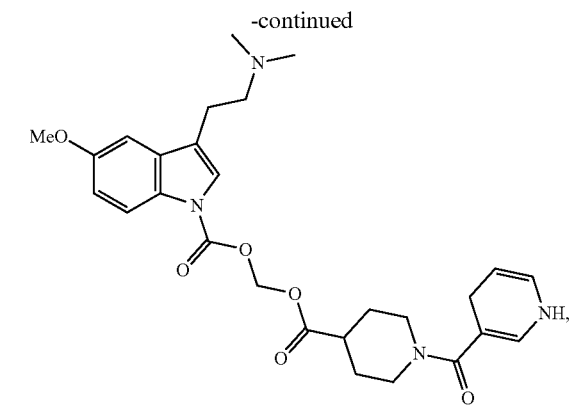

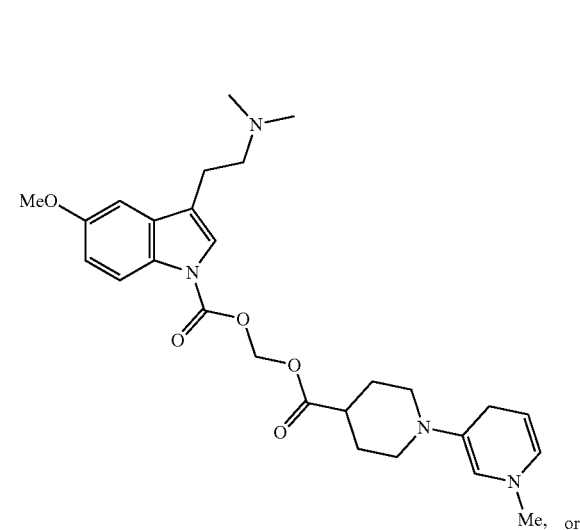

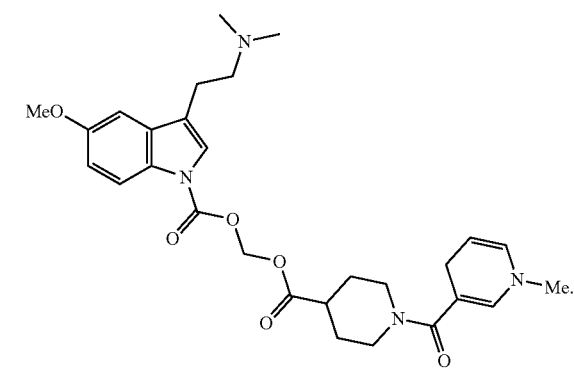

In some embodiments is a compound of Formula (Iq1), or a pharmaceutically acceptable salt or solvate thereof, wherein the compound is:

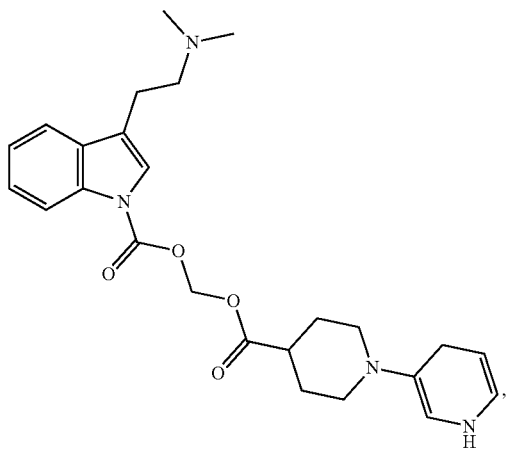

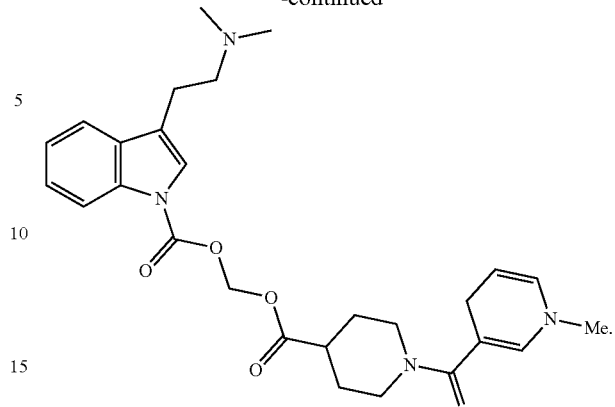

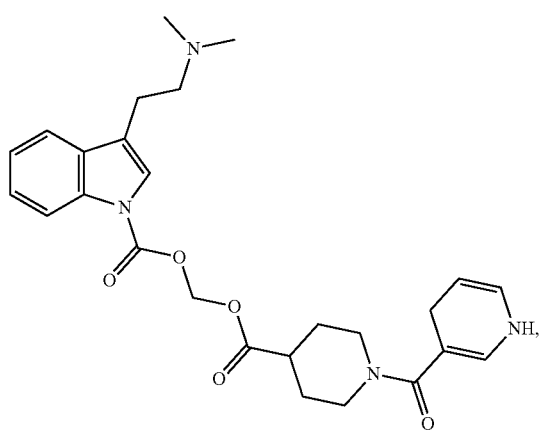

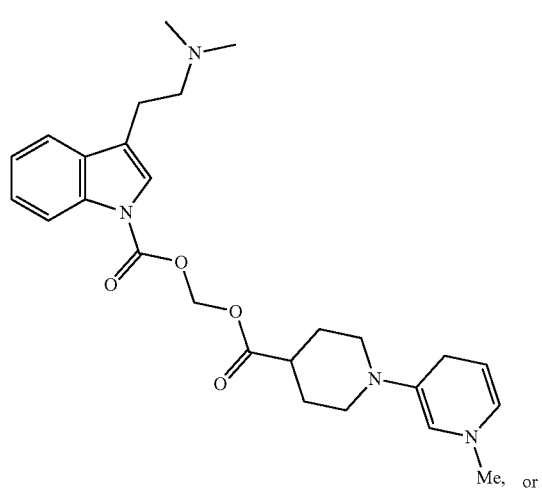

In some embodiments is a compound of Formula (I) having the structure of Formula (Ir), or a pharmaceutically acceptable salt thereof:

(Ir)

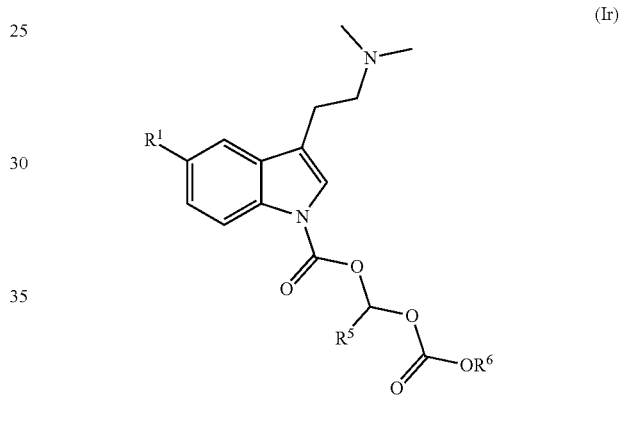

wherein:
$R^1$ is methoxy or hydrogen;
$R^5$ is hydrogen, alkyl, or cycloalkyl; and
$R^6$ is alkyl, cycloalkyl, heteroalkyl, heterocyclylalkyl, aryl, or heteroaryl,
wherein each alkyl, cycloalkyl, heteroalkyl, heterocyclylalkyl, aryl, and heteroaryl is independently unsubstituted or substituted with one or more $R^4$.

In some embodiments is a compound of Formula (I) or (Ir), or a pharmaceutically acceptable salt or solvate thereof, wherein $R^5$ is hydrogen or alkyl. In some embodiments is a compound of Formula (I) or (Ir), or a pharmaceutically acceptable salt or solvate thereof, wherein $R^5$ is alkyl. In some embodiments is a compound of Formula (I) or (Ir), or a pharmaceutically acceptable salt or solvate thereof, wherein $R^5$ is hydrogen. In some embodiments is a compound of Formula (I) or (Ir), or a pharmaceutically acceptable salt or solvate thereof, wherein $R^5$ is hydrogen or unsubstituted alkyl. In some embodiments is a compound of Formula (I) or (Ir), or a pharmaceutically acceptable salt or solvate thereof, wherein $R^5$ is hydrogen. In some embodiments is a compound of Formula (I) or (Ir), or a pharmaceutically acceptable salt or solvate thereof, wherein $R^6$ is alkyl, cycloalkyl, heterocyclylalkyl, aryl, or heteroaryl. In some embodiments is a compound of Formula (I) or (Ir), or a pharmaceutically acceptable salt or solvate thereof, wherein $R^6$ is alkyl. In some embodiments is a compound of Formula (I) or (Ir), or a pharmaceutically acceptable salt or solvate thereof, wherein R⁶ is heteroalkyl. In some embodiments is a compound of Formula (I) or (Ir), or a pharmaceutically acceptable salt or solvate thereof, wherein R⁶ is unsubstituted alkyl, unsubstituted cycloalkyl, unsubstituted heterocyclylalkyl, unsubstituted aryl, or unsubstituted heteroaryl. In some embodiments is a compound of Formula (I) or (Ir), or a pharmaceutically acceptable salt or solvate thereof, wherein R⁶ is alkyl. In some embodiments is a compound of Formula (I) or (Ir), or a pharmaceutically acceptable salt or solvate thereof, wherein R⁶ is heteroalkyl. In some embodiments is a compound of Formula (I) or (Ir), or a pharmaceutically acceptable salt or solvate thereof, wherein R⁶ is heterocyclylalkyl substituted with arylalkyl. In some embodiments is a compound of Formula (I) or (Ir), or a pharmaceutically acceptable salt or solvate thereof, wherein R⁵ is methyl, ethyl, isopropyl, tert-butyl, or —CH(Et)₂.

In some embodiments is a compound of Formula (I) or (Ir), or a pharmaceutically acceptable salt or solvate thereof, wherein R⁵ is hydrogen, and R⁶ is alkyl. In some embodiments is a compound of Formula (I) or (Ir), or a pharmaceutically acceptable salt or solvate thereof, wherein R⁵ is alkyl, and R⁶ is alkyl. In some embodiments is a compound of Formula (I) or (Ir), or a pharmaceutically acceptable salt or solvate thereof, wherein R⁵ is hydrogen, and R⁶ is unsubstituted alkyl. In some embodiments is a compound of Formula (I) or (Ir), or a pharmaceutically acceptable salt or solvate thereof, wherein R⁵ is unsubstituted alkyl, and R⁶ is unsubstituted alkyl. In some embodiments is a compound of Formula (I) or (Ir), or a pharmaceutically acceptable salt or solvate thereof, wherein R⁵ is unsubstituted alkyl, and R⁶ is heterocyclylalkyl. In some embodiments is a compound of Formula (I) or (Ir), or a pharmaceutically acceptable salt or solvate thereof, wherein R⁶ is methyl, ethyl, n-propyl, isopropyl, tert-butyl, 3-methyl-1-butyl, n-pentyl, n-hexyl, cyclopropyl, cyclobutyl, cyclopentyl, cyclohexyl, or cycloheptyl. In some embodiments is a compound of Formula (I) or (Ir), or a pharmaceutically acceptable salt or solvate thereof, wherein R⁶ is aryl. In some embodiments is a compound of Formula (I) or (Ir), or a pharmaceutically acceptable salt or solvate thereof, wherein R⁶ is phenyl. In some embodiments is a compound of Formula (I) or (Ir), or a pharmaceutically acceptable salt or solvate thereof, wherein R⁶ is heterocyclylalkyl. In some embodiments is a compound of Formula (I) or (Ir), or a pharmaceutically acceptable salt or solvate thereof, wherein R⁶ is oxetan-3-yl or azetindin-3-yl. In some embodiments is a compound of Formula (I) or (Ir), or a pharmaceutically acceptable salt or solvate thereof, wherein R⁶ is heteroaryl. In some embodiments is a compound of Formula (I) or (Ir), or a pharmaceutically acceptable salt or solvate thereof, wherein R⁶ is 2-pyridyl, 3-pyridyl, 4-pyridyl, 2-pyrimidyl, or 4-pyyrimidyl. In some embodiments is a compound of Formula (I) or (Ir), or a pharmaceutically acceptable salt or solvate thereof, wherein R⁶ is benzyl. In some embodiments is a compound of Formula (I) or (Ir), or a pharmaceutically acceptable salt or solvate thereof, wherein R⁶ is

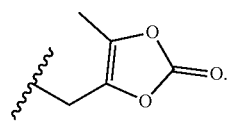 [SMILES: *Cc1oc(=O)oc1C]

In some embodiments is a compound of Formula (I) or (Ir), or a pharmaceutically acceptable salt or solvate thereof, wherein the compound is:

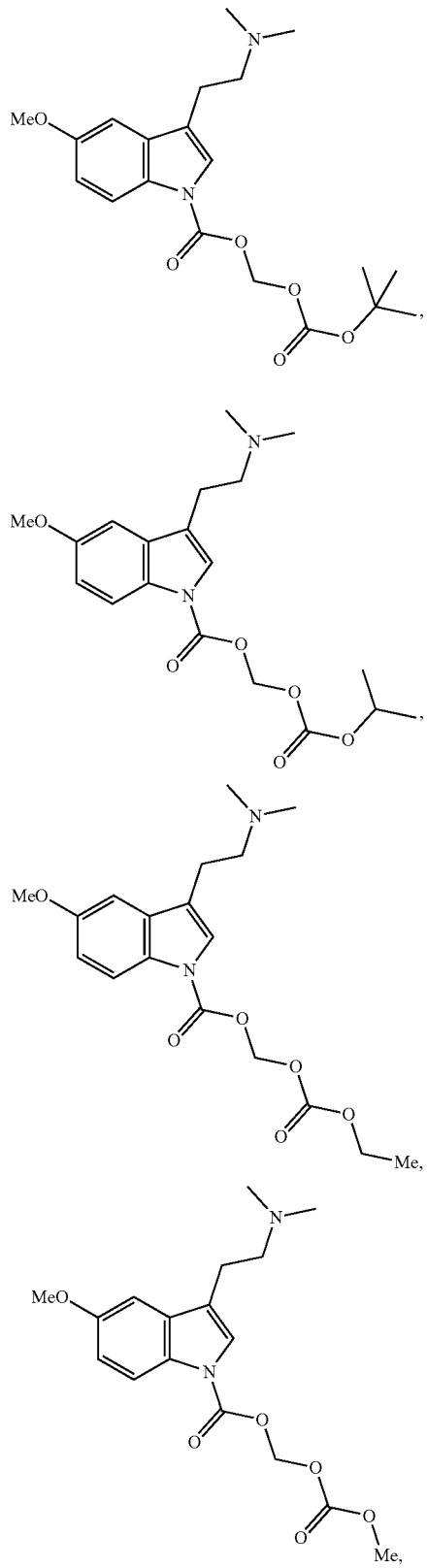

189
-continued
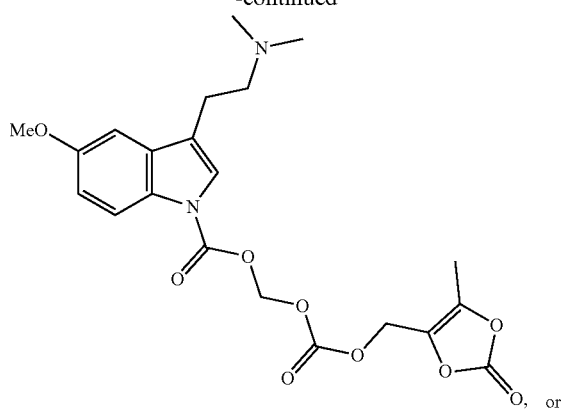
, or
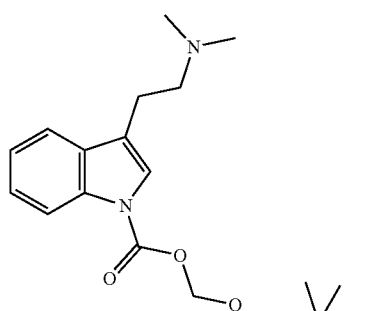
In some embodiments is a compound of Formula (I) or (Ir), or a pharmaceutically acceptable salt or solvate thereof, wherein the compound is:
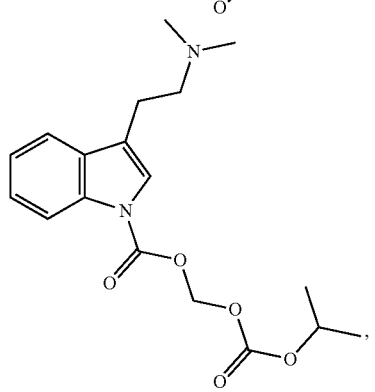
;
190
-continued
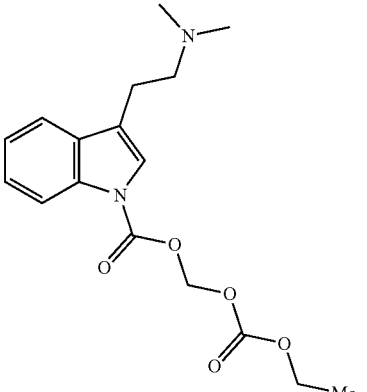
,
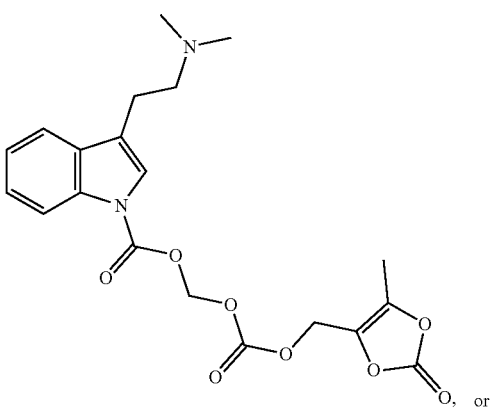
, or
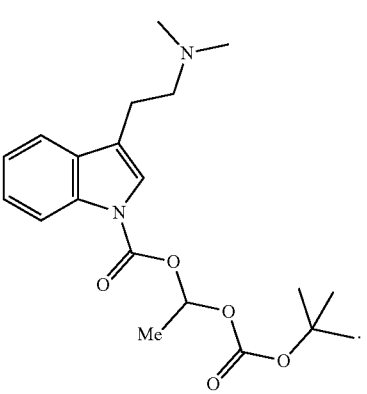
.
In some embodiments is a compound of Formula (I) or (Ir) having the structure of Formula (Ir1), or a pharmaceutically acceptable salt thereof:

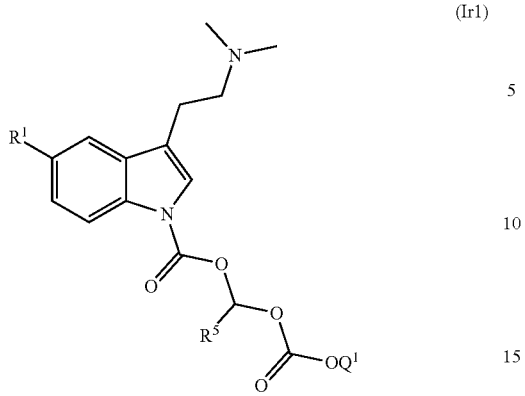

(Ir1)

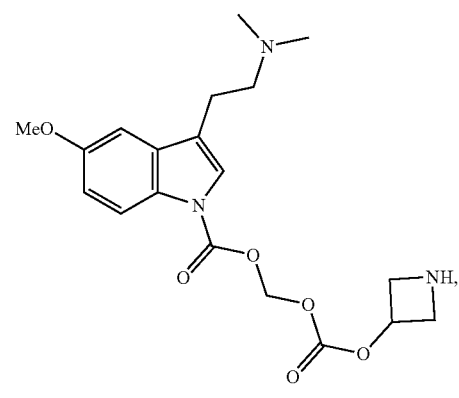

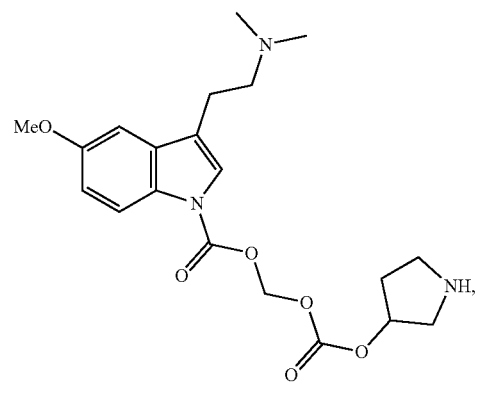

wherein:
R¹ is methoxy or hydrogen;
R⁵ is hydrogen, alkyl, or cycloalkyl, wherein each of alkyl and cycloalkyl is unsubstituted or substituted with one or more R⁴; and
Q¹ is

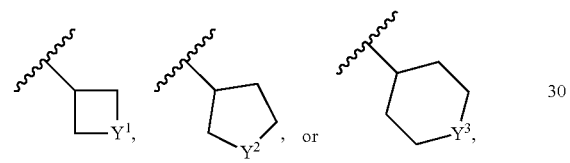

wherein
each of $Y^1$, $Y^2$, or $Y^3$ is independently —O—, —S—, —S(O)—, —S(O)$_2$—, —N(R$^{Y1}$)—, or —NC(O)R$^{Y2}$, wherein each of R$^{Y1}$ and R$^{Y2}$ is independently hydrogen, alkyl, heteroalkyl, or heteroaryl.

In some embodiments is a compound of Formula (Ir1), or a pharmaceutically acceptable salt or solvate thereof, wherein each of $Y^1$, $Y^2$, or $Y^3$ is —N(R$^{Y1}$)—. In some embodiments is a compound of Formula (Ir1), or a pharmaceutically acceptable salt or solvate thereof, wherein each of $Y^1$, $Y^2$, or $Y^3$ is —N(R$^{Y1}$)—, wherein R$^{Y1}$ is hydrogen. In some embodiments is a compound of Formula (Ir1), or a pharmaceutically acceptable salt or solvate thereof, wherein each of $Y^1$, $Y^2$, or $Y^3$ is —N(R$^{Y1}$)— or —NC(O)R$^{Y2}$, wherein each of R$^{Y1}$ and R² is independently methyl, ethyl, n-propyl, isopropyl, n-butyl, tert-butyl, CH(Et)$_2$, CH$_2$CH$_2$OMe, CH$_2$CH$_2$SO$_2$Me, or CH$_2$CF$_3$. In some embodiments is a compound of Formula (Ir1), or a pharmaceutically acceptable salt or solvate thereof, wherein each of $Y^1$, $Y^2$, or $Y^3$ is —N(R$^{Y1}$)— or —NC(O)R$^{Y2}$, wherein each of R$^{Y1}$ and R$^{Y2}$ is phenyl. In some embodiments is a compound of Formula (Ir1), or a pharmaceutically acceptable salt or solvate thereof, wherein each of $Y^1$, $Y^2$, or $Y^3$ is —N(R$^{Y1}$)— or —NC(O)R$^{Y2}$, wherein each of R$^{Y1}$ and R$^{Y2}$ is benzyl. In some embodiments is a compound of Formula (Ir1), or a pharmaceutically acceptable salt or solvate thereof, wherein each of $Y^1$, $Y^2$, or $Y^3$ is —N(R$^{Y1}$)— or —NC(O)R$^{Y2}$, wherein each of R$^{Y1}$ and R$^{Y2}$ is independently 2-pyridyl, 3-pyridyl, or 4-pyridyl.

In some embodiments is a compound of Formula (I) or (Ir), or a pharmaceutically acceptable salt or solvate thereof, wherein the compound is:

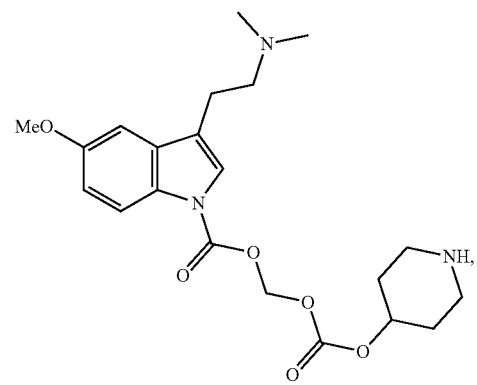

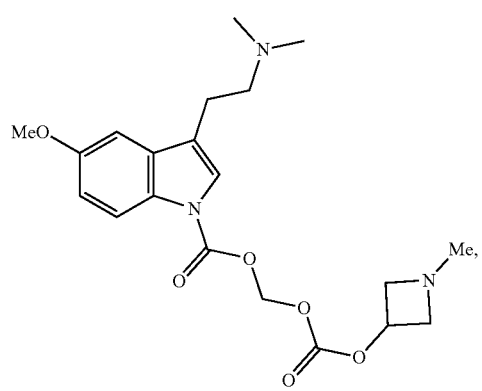

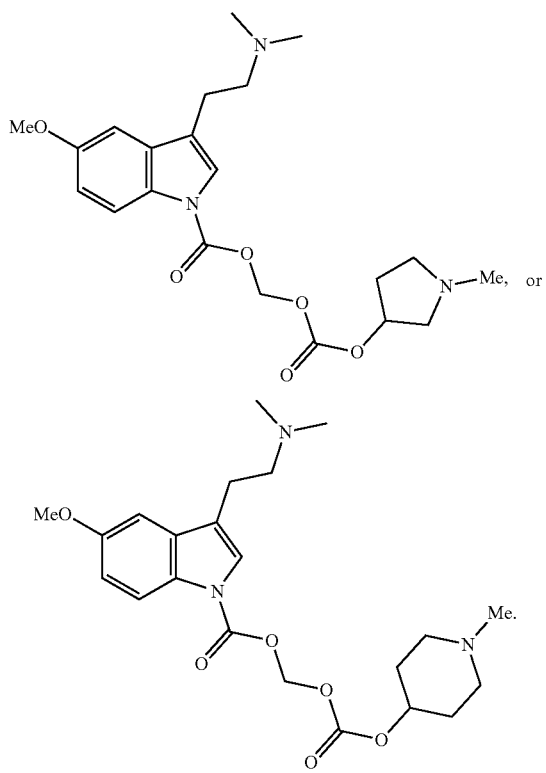
In some embodiments is a compound of Formula (I) or (Ir), or a pharmaceutically acceptable salt or solvate thereof, wherein the compound is:
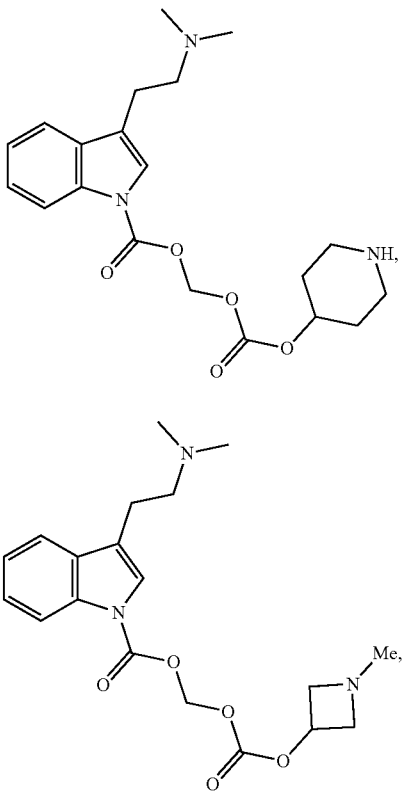
In some embodiments is a compound of Formula (I) or (Ir), or a pharmaceutically acceptable salt or solvate thereof, wherein the compound is:

195
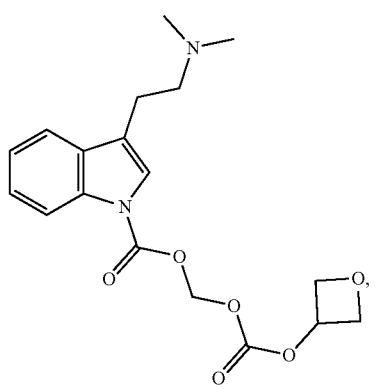
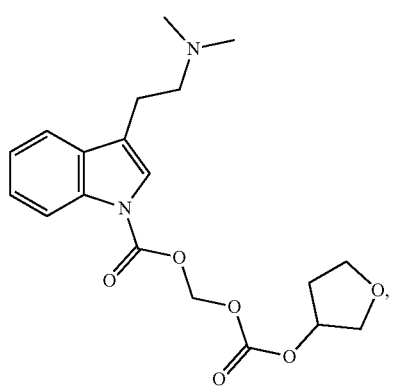
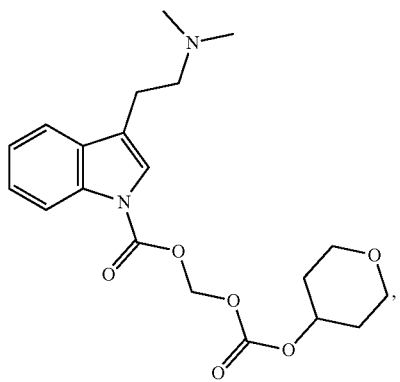
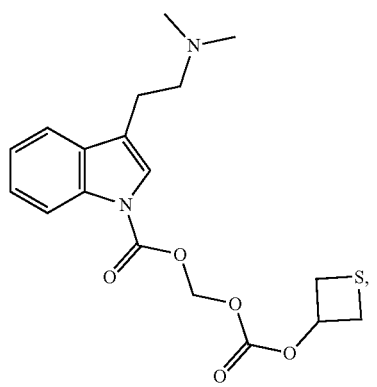
196
-continued
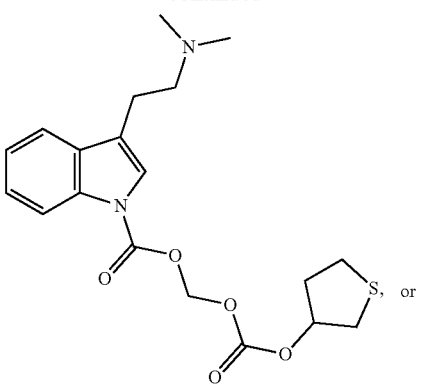
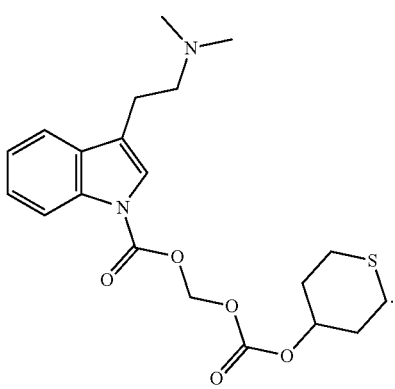
In some embodiments is a compound of Formula (I) or (Ir), or a pharmaceutically acceptable salt or solvate thereof, wherein the compound is:
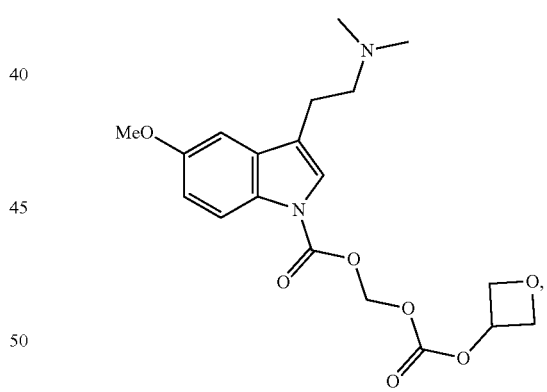
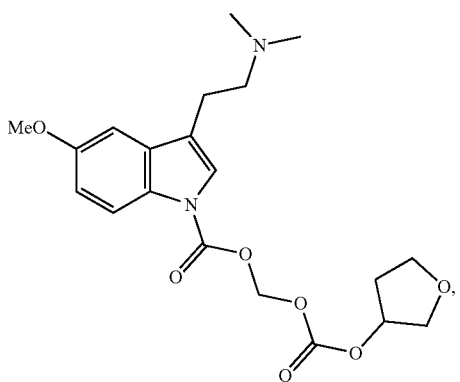

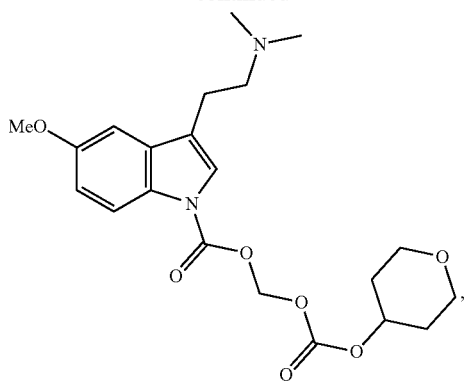

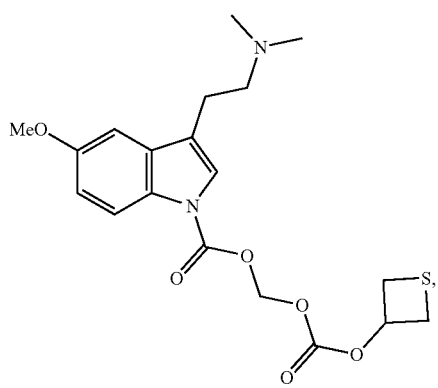

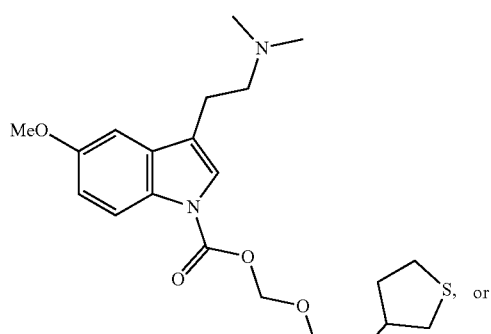

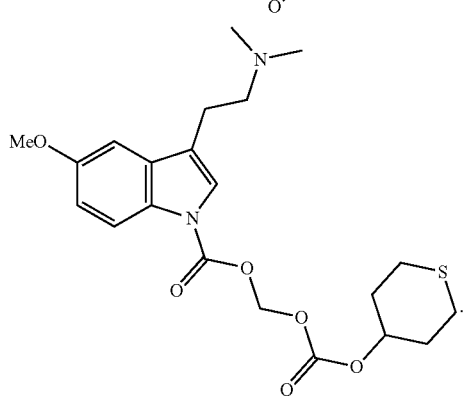

In some embodiments is a compound of Formula (Ir1), or a pharmaceutically acceptable salt or solvate thereof, wherein each of $Y^1$, $Y^2$, or $Y^3$ is —N(R$^{Y1}$)— or —NC(O)R$^{Y2}$, wherein each of R$^{Y1}$ and R$^{Y2}$ is independently

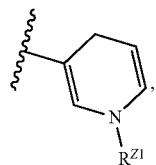

wherein R$^{Z1}$ is hydrogen or alkyl. In some embodiments is a compound of Formula (Ir1), or a pharmaceutically acceptable salt or solvate thereof, wherein each of $Y^1$, $Y^2$, or $Y^3$ is —N(R$^{Y1}$)— or —NC(O)R$^{Y2}$, wherein each of R$^{Y1}$ and R$^{Y2}$ is independently

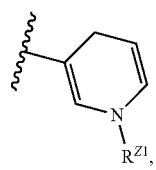

wherein R$^{Z1}$ is methyl, ethyl, n-propyl, isopropyl, n-butyl, tert-butyl, or CH(Et)$_2$. In some embodiments is a compound of Formula (Ir1), or a pharmaceutically acceptable salt or solvate thereof, wherein each of $Y^1$, $Y^2$, or $Y^3$ is —N(R$^{Y1}$)— or —NC(O)R$^{Y2}$, wherein each of R$^{Y1}$ and R$^{Y2}$ is independently

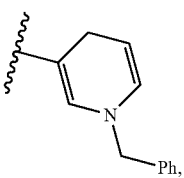 [SMILES: *C1=CN(Cc2ccccc2)C=CC1]

In some embodiments is a compound of Formula (Ir1), or a pharmaceutically acceptable salt or solvate thereof, wherein the compound is:

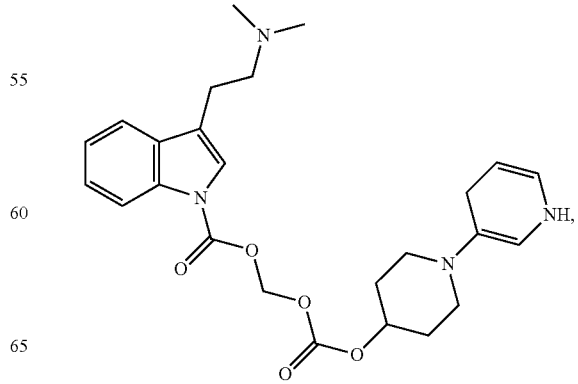

199

-continued

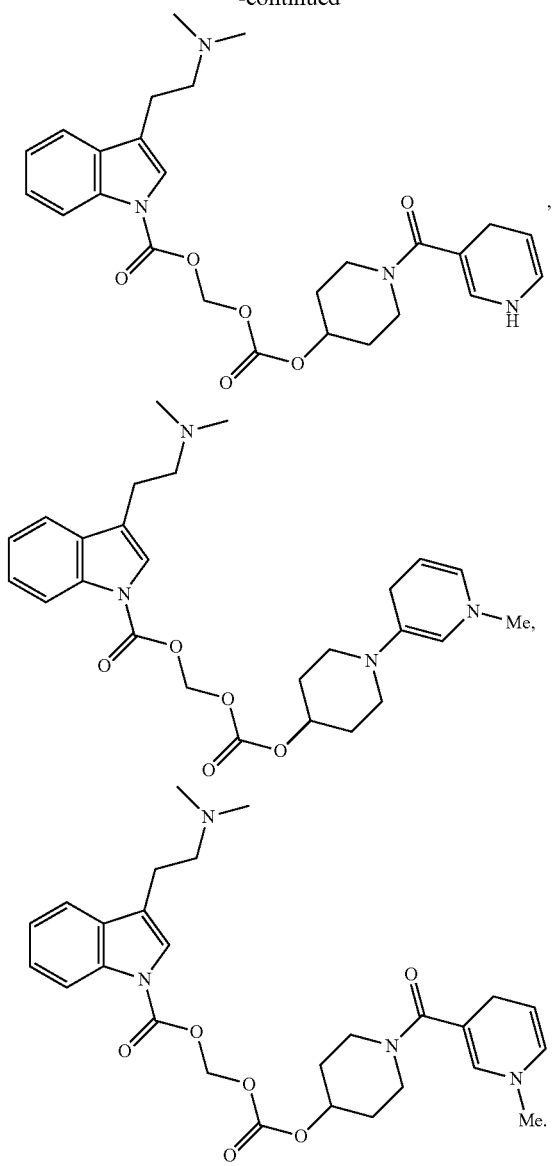

In some embodiments is a compound of Formula (Ir1), or a pharmaceutically acceptable salt or solvate thereof, wherein the compound is:

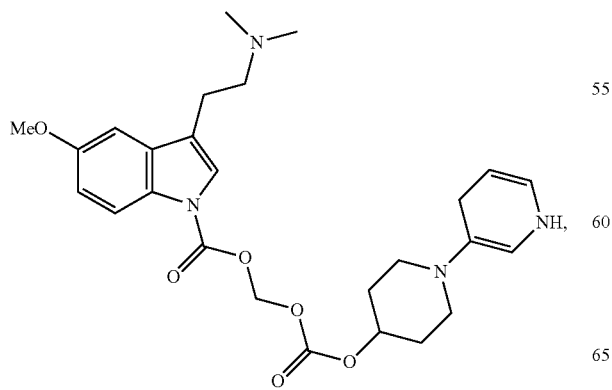

200

-continued

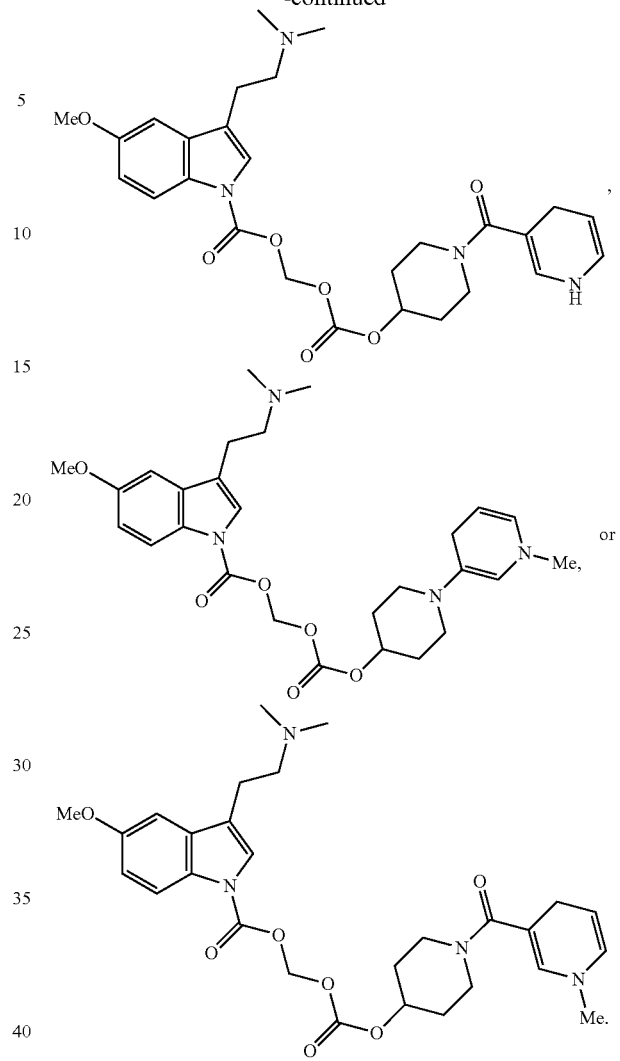

In some embodiments is a compound of Formula (I) having the structure of Formula (Is), or a pharmaceutically acceptable salt thereof:

(Is)

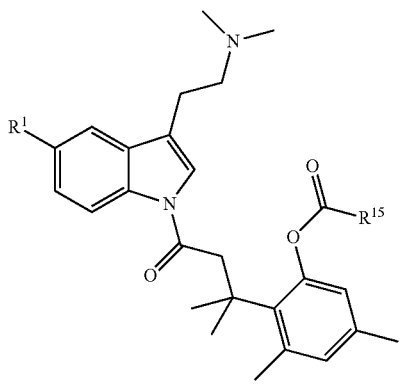

wherein $R^1$ is hydrogen or methoxy, and $R^5$ is alkyl, heteroalkyl, cycloalkyl, aryl, or heteroaryl, each of which is unsubstituted or substituted with one or more $R^B$.

In some embodiments is a compound of Formula (I) or (Is), or a pharmaceutically acceptable salt or solvate thereof, wherein $R^{15}$ is alkyl. In some embodiments is a compound of Formula (I) or (Is), or a pharmaceutically acceptable salt or solvate thereof, wherein $R^{15}$ is unsubstituted alkyl. In some embodiments is a compound of Formula (I) or (Is), or a pharmaceutically acceptable salt or solvate thereof, wherein $R^{15}$ is methyl, ethyl, n-propyl, isopropyl, n-butyl, or tert-butyl. In some embodiments is a compound of Formula (I) or (Is), or a pharmaceutically acceptable salt or solvate thereof, wherein $R^{15}$ is cycloalkyl. In some embodiments is a compound of Formula (I) or (Is), or a pharmaceutically acceptable salt or solvate thereof, wherein $R^{15}$ is cyclopropyl. In some embodiments is a compound of Formula (I) or (Is), or a pharmaceutically acceptable salt or solvate thereof, wherein $R^{15}$ is heteroalkyl. In some embodiments is a compound of Formula (I) or (Is), or a pharmaceutically acceptable salt or solvate thereof, wherein $R^{15}$ is —CH[CH(Me)$_2$]NH$_2$. In some embodiments is a compound of Formula (I) or (Is), or a pharmaceutically acceptable salt or solvate thereof, wherein $R^{15}$ is —(CH$_2$)$_q$CO$_2$H, wherein q is 1, 2, 3, 4, 5, or 6. In some embodiments is a compound of Formula (I) or (Is), or a pharmaceutically acceptable salt or solvate thereof, wherein $R^{15}$ is phenyl. In some embodiments is a compound of Formula (I) or (Is), or a pharmaceutically acceptable salt or solvate thereof, wherein $R^{15}$ is 2-pyridyl, 3-pyridyl, 4-pyridyl, 2-pyrimidyl, 4-pyrimidyl, 5-pyrimidyl, or 6-pyrimidyl. In some embodiments is a compound of Formula (I) or (Is), or a pharmaceutically acceptable salt or solvate thereof, wherein $R^{15}$ is methyl, ethyl, isopropyl, or tert-butyl. In some embodiments is a compound of Formula (I) or (Is), or a pharmaceutically acceptable salt or solvate thereof, wherein $R^{15}$ is methyl. In some embodiments is a compound of Formula (I) or (Is), or a pharmaceutically acceptable salt or solvate thereof, wherein $R^1$ is hydrogen, and $R^5$ is methyl. In some embodiments is a compound of Formula (I) or (Is), or a pharmaceutically acceptable salt or solvate thereof, wherein $R^1$ is methoxy, and $R^{15}$ is methyl.

In some embodiments is a compound of Formula (I) or (Is), or a pharmaceutically acceptable salt or solvate thereof, wherein the compound is:

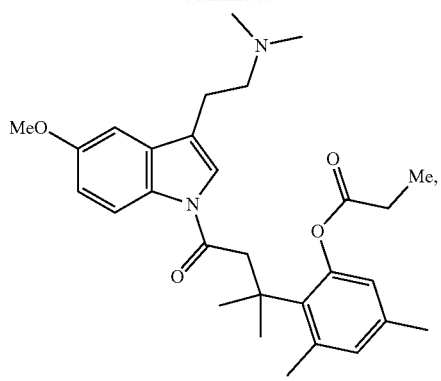

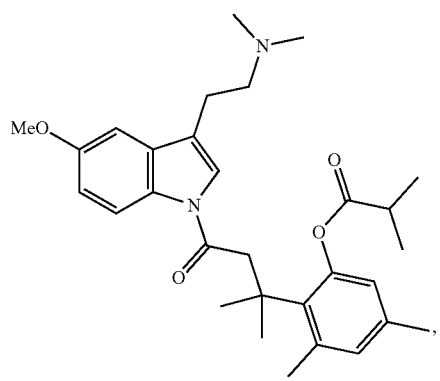

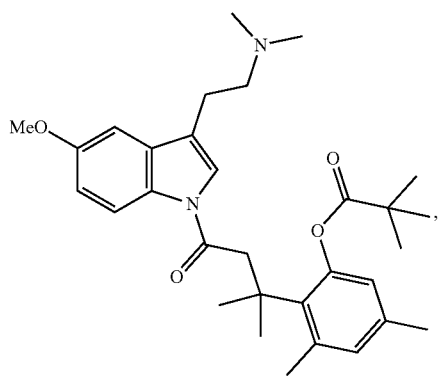

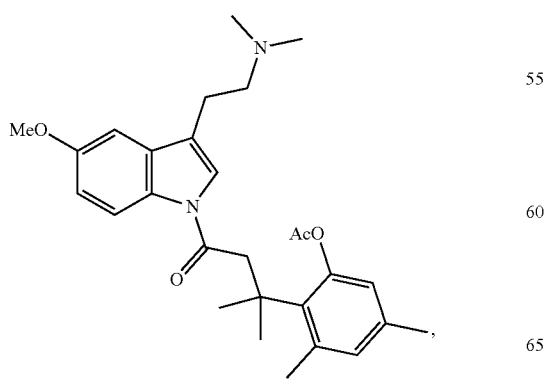

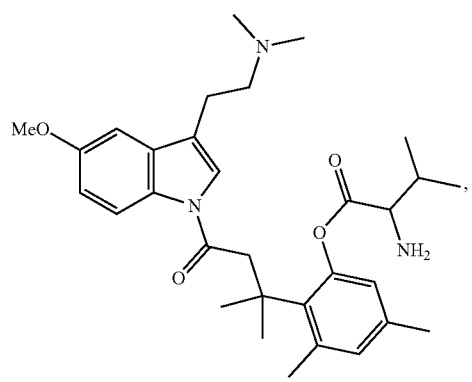

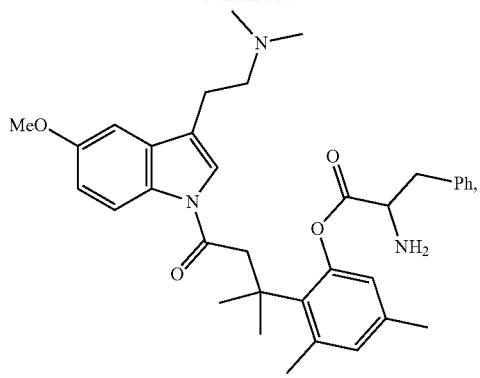
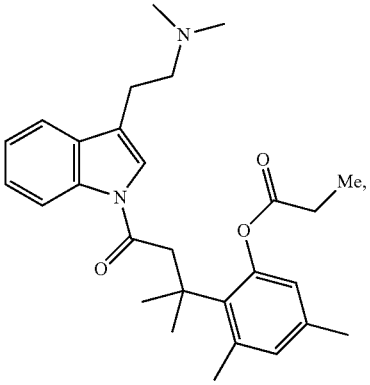
In some embodiments is a compound of Formula (I) or (Is), or a pharmaceutically acceptable salt or solvate thereof, wherein the compound is:
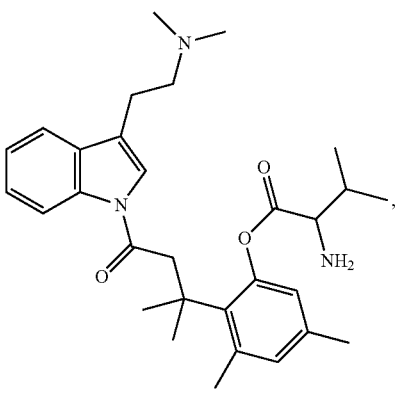

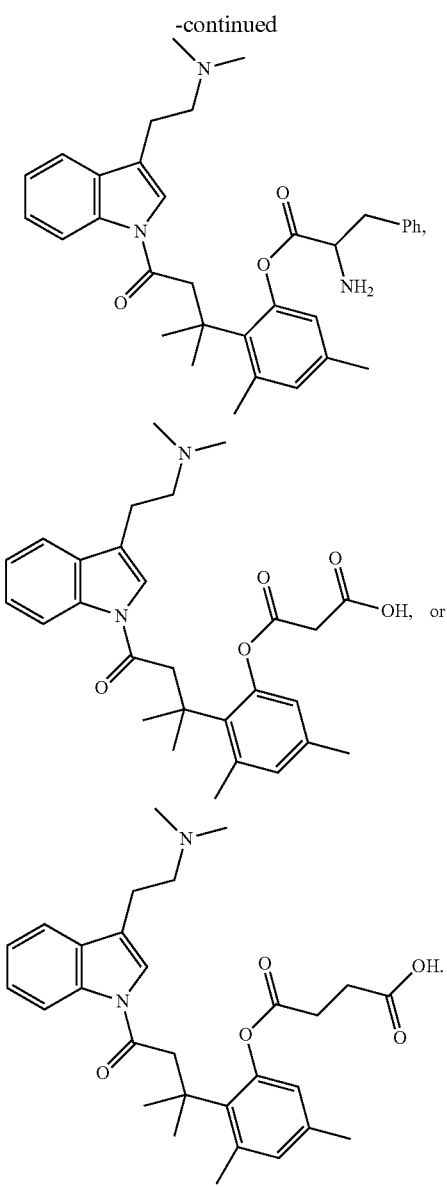

In some embodiments is a compound of Formula (I) having the structure of Formula (It), or a pharmaceutically acceptable salt thereof:

(It)

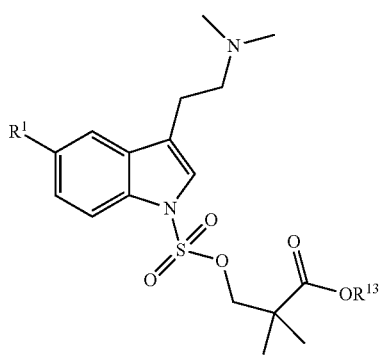

wherein $R^1$ is hydrogen or methoxy, and $R^{13}$ is alkyl, cycloalkyl, heterocyclylalkyl, aryl, or heteroaryl, each of which is unsubstituted or substituted with one or more $R^B$.

In some embodiments is a compound of Formula (I) or (It), or a pharmaceutically acceptable salt or solvate thereof, wherein $R^{13}$ is alkyl. In some embodiments is a compound of Formula (I) or (It), or a pharmaceutically acceptable salt or solvate thereof, wherein $R^{13}$ is unsubstituted alkyl. In some embodiments is a compound of Formula (I) or (It), or a pharmaceutically acceptable salt or solvate thereof, wherein $R^{13}$ is methyl, ethyl, isopropyl, tert-butyl, n-butyl, n-pentyl, n-hexyl, n-heptyl, or n-octyl. In some embodiments is a compound of Formula (I) or (It), or a pharmaceutically acceptable salt or solvate thereof, wherein $R^{13}$ is cycloalkyl. In some embodiments is a compound of Formula (I) or (It), or a pharmaceutically acceptable salt or solvate thereof, wherein $R^{13}$ is cyclopropyl, cyclobutyl, cyclopentyl, cyclohexyl, or cycloheptyl. In some embodiments is a compound of Formula (I) or (It), or a pharmaceutically acceptable salt or solvate thereof, wherein $R^3$ is heteroalkyl. In some embodiments is a compound of Formula (I) or (It), or a pharmaceutically acceptable salt or solvate thereof, wherein $R^{13}$ is —CH$_2$CH$_2$OMe, CH$_2$CH$_2$SO$_2$Me, or CH$_2$CH$_2$NMe$_2$. In some embodiments is a compound of Formula (I) or (It), or a pharmaceutically acceptable salt or solvate thereof, wherein $R^{13}$ is (CH$_2$)$_u$CO$_2$H, wherein u is 1, 2, 3, 4, 5, or 6. In some embodiments is a compound of Formula (I) or (It), or a pharmaceutically acceptable salt or solvate thereof, wherein $R^{13}$ is aryl. In some embodiments is a compound of Formula (I) or (It), or a pharmaceutically acceptable salt or solvate thereof, wherein $R^{13}$ is phenyl. In some embodiments is a compound of Formula (I) or (It), or a pharmaceutically acceptable salt or solvate thereof, wherein $R^{13}$ is heteroaryl. In some embodiments is a compound of Formula (I) or (It), or a pharmaceutically acceptable salt or solvate thereof, wherein $R^{13}$ is 2-pyridyl, 3-pyridyl, 4-pyridyl, 2-pyrimidyl, 4-pyrimidyl, 5-pyrimidyl, or 6-pyrimidyl. In some embodiments is a compound of Formula (I) or (It), or a pharmaceutically acceptable salt or solvate thereof, wherein $R^{13}$ is heterocyclylalkyl. In some embodiments is a compound of Formula (I) or (It), or a pharmaceutically acceptable salt or solvate thereof, wherein $R^{13}$ is oxetan-3-yl or azetidine-3-yl. In some embodiments is a compound of Formula (I) or (It), or a pharmaceutically acceptable salt or solvate thereof, wherein $R^{13}$ is

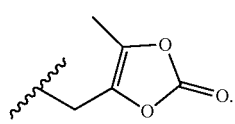 [SMILES: *Cc1oc(=O)oc1C]

In some embodiments is a compound of Formula (I) or (It), or a pharmaceutically acceptable salt or solvate thereof, wherein $R^{13}$ is

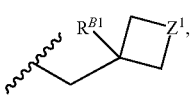

wherein $R^{B1}$ is hydrogen or alkyl, and $Z^1$ is —O—, —S—, —S(O)—, —S(O)$_2$—, or —N($R^{C1}$)—, wherein $R^{C1}$ is hydrogen, alkyl, acetyl, or benzoyl. In some embodiments is a compound of Formula (I) or (It), or a pharmaceutically acceptable salt or solvate thereof, wherein $R^{13}$ is

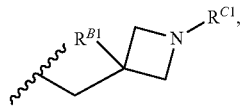

wherein $R^{C1}$ is alkyl. In some embodiments is a compound of Formula (I) or (It), or a pharmaceutically acceptable salt or solvate thereof, wherein $R^{13}$ is

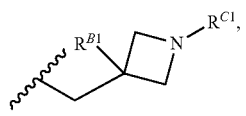

wherein $R^{C1}$ is methyl, acetyl, or benzoyl. In some embodiments is a compound of Formula (I) or (It), or a pharmaceutically acceptable salt or solvate thereof, wherein $R^{13}$ is

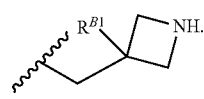

In some embodiments is a compound of Formula (I) or (It), or a pharmaceutically acceptable salt or solvate thereof, wherein $R^{13}$ is

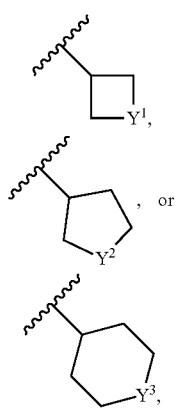

wherein each of $Y^1$, $Y^2$, or $Y^3$ is independently —O—, —S—, —S(O)—, —S(O)$_2$—, or —N($R^{B2}$)—, wherein each $R^{B2}$ is independently hydrogen, alkyl, acetyl, or benzoyl. In some embodiments is a compound of Formula (I) or (It), or a pharmaceutically acceptable salt or solvate thereof, wherein $R^{13}$ is

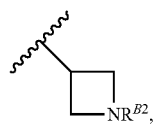

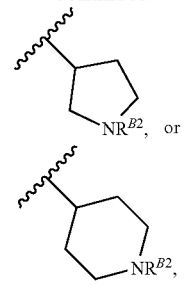

wherein $R^{B2}$ is alkyl. In some embodiments is a compound of Formula (I) or (It), or a pharmaceutically acceptable salt or solvate thereof, wherein $R^{13}$ is

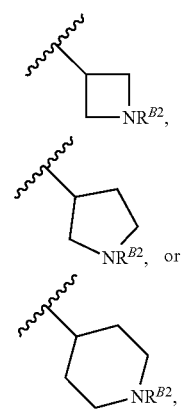

wherein $R^{B2}$ is unsubstituted alkyl. In some embodiments is a compound of Formula (I) or (It), or a pharmaceutically acceptable salt or solvate thereof, wherein $R^{13}$ is

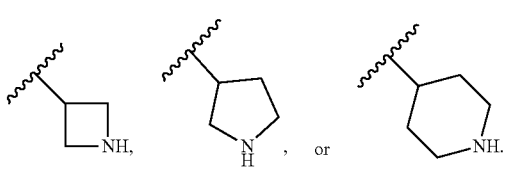 [SMILES: *C1CNC1 ; *C1CCNC1 ; *C1CCNCC1]

wherein each $R^{B2}$ independently is methyl, acetyl, or benzoyl. In some embodiments is a compound of Formula (I) or (It), or a pharmaceutically acceptable salt or solvate thereof, wherein $R^{13}$ is In some embodiments is a compound of Formula (I) or (It), or a pharmaceutically acceptable salt or solvate thereof, wherein $R^{13}$ is —CH$_2$CH$_2$R$^{B3}$, wherein $R^{B3}$ is heteroaryl or heterocyclylalkyl. In some embodiments is a compound of Formula (I) or (It), or a pharmaceutically acceptable salt or solvate thereof, wherein $R^{13}$ is —CH$_2$CH$_2$R$^{B3}$, wherein $R^{B3}$ is heterocyclylalkyl. In some embodiments is a compound of Formula (I) or (It), or a pharmaceutically acceptable salt or solvate thereof, wherein $R^{13}$ is —$CH_2CH_2R^{B3}$, wherein $R^{B3}$ is
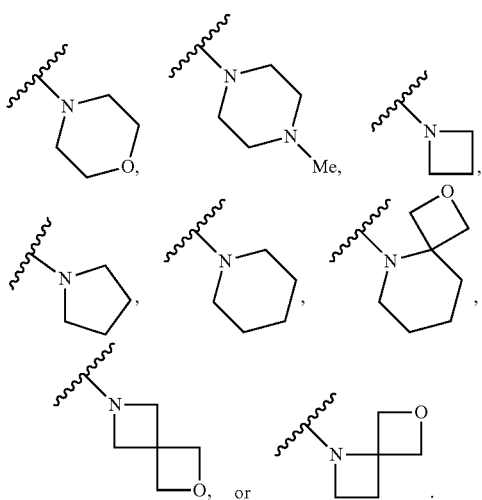
In some embodiments is a compound of Formula (I) or (It), or a pharmaceutically acceptable salt or solvate thereof, wherein the compound is:
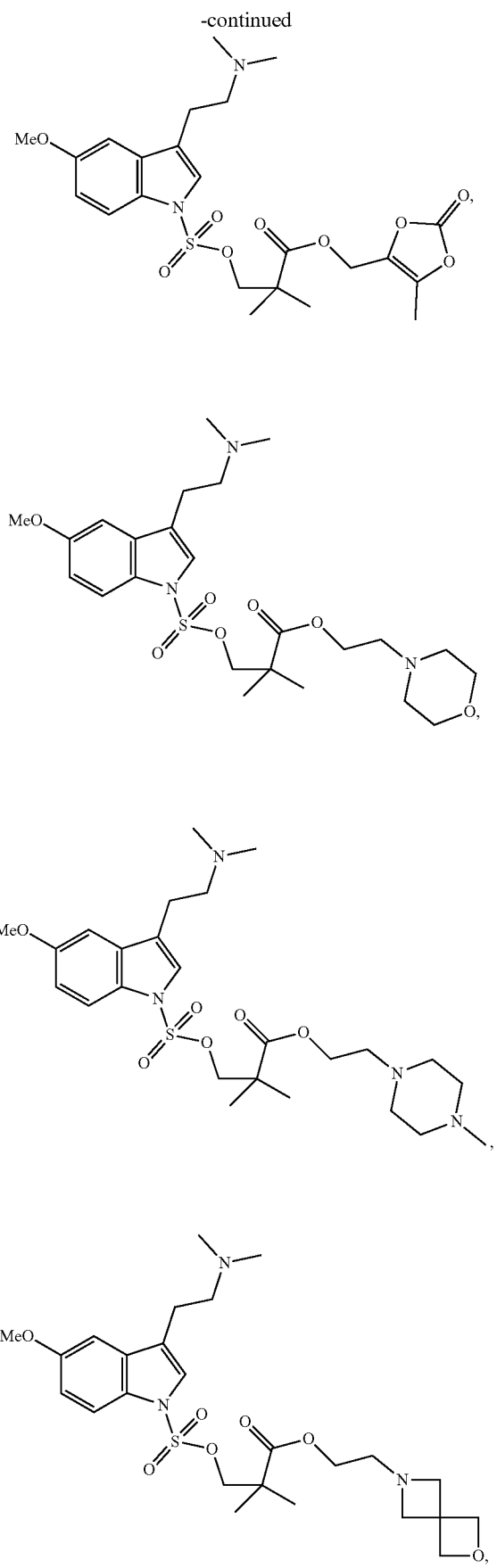

211
-continued
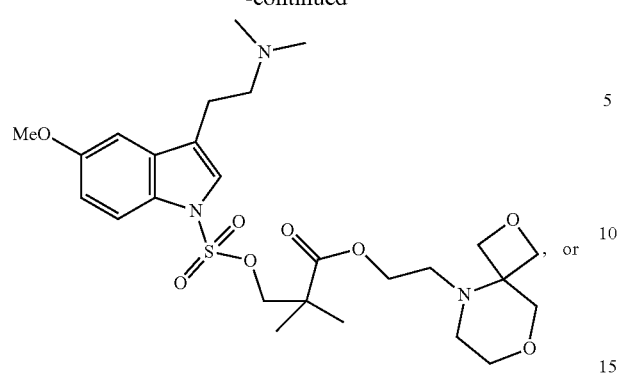
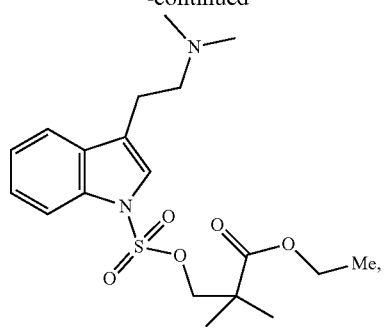
212
-continued
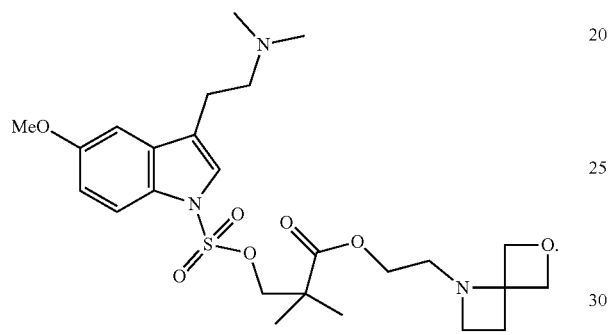
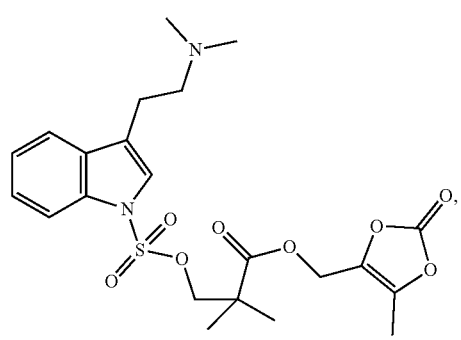
In some embodiments is a compound of Formula (I) or (It), or a pharmaceutically acceptable salt or solvate thereof, wherein the compound is:
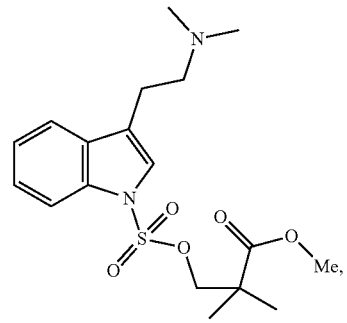
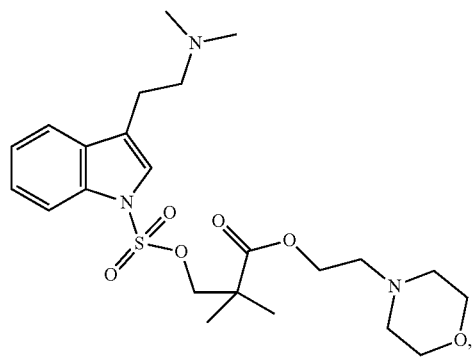
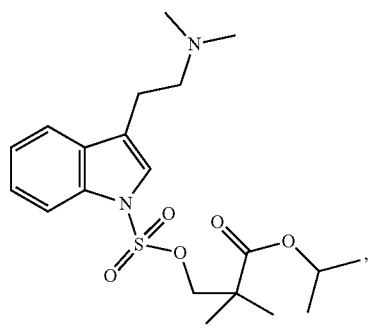
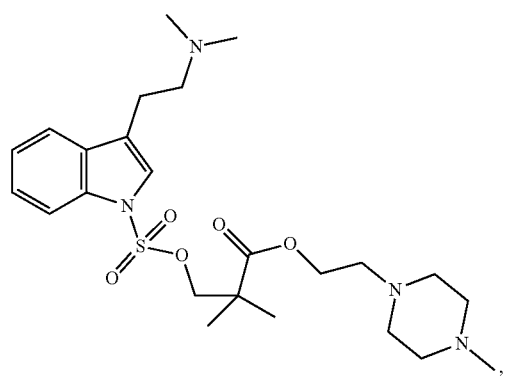

213
-continued
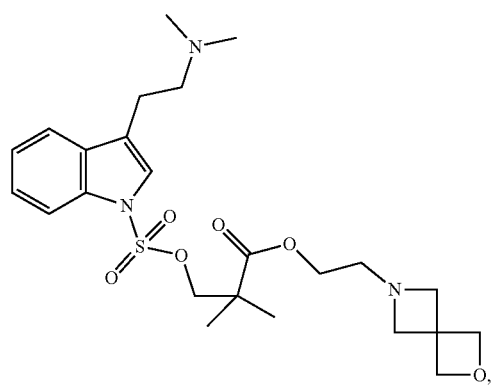
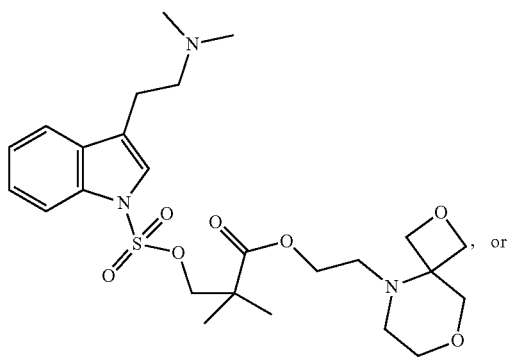
, or
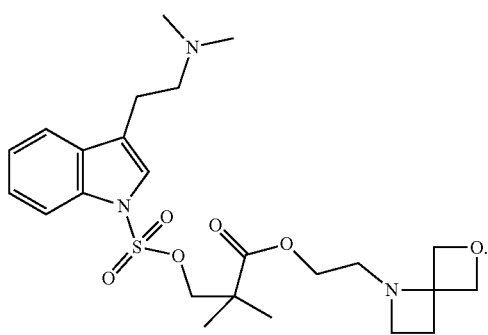
In some embodiments is a compound of Formula (I) or (It), or a pharmaceutically acceptable salt or solvate thereof, wherein the compound is:
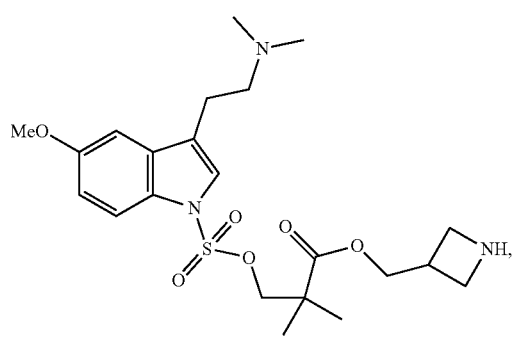
214
-continued
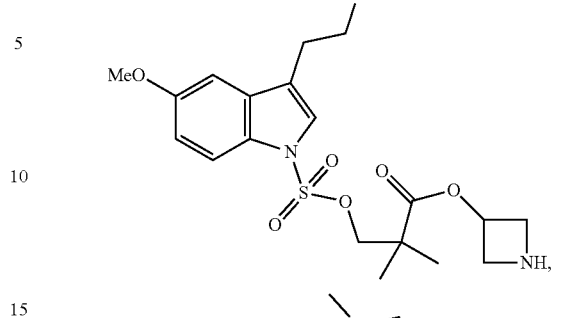
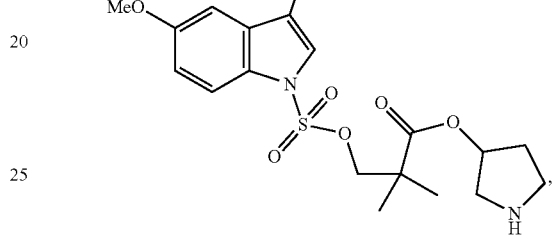
,
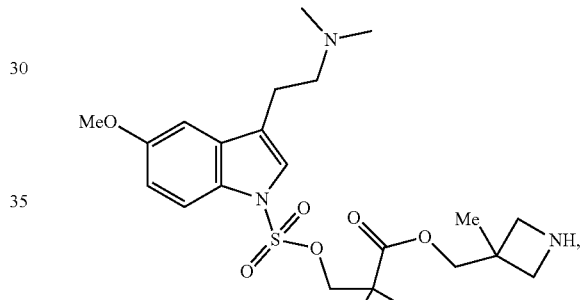
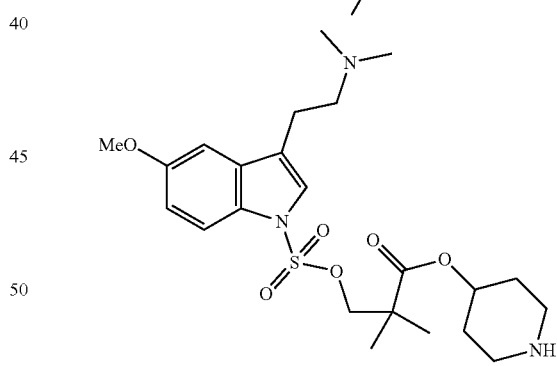
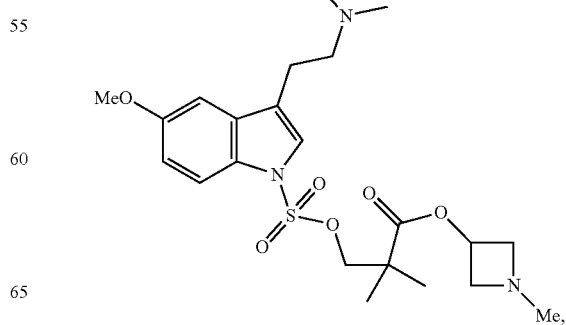

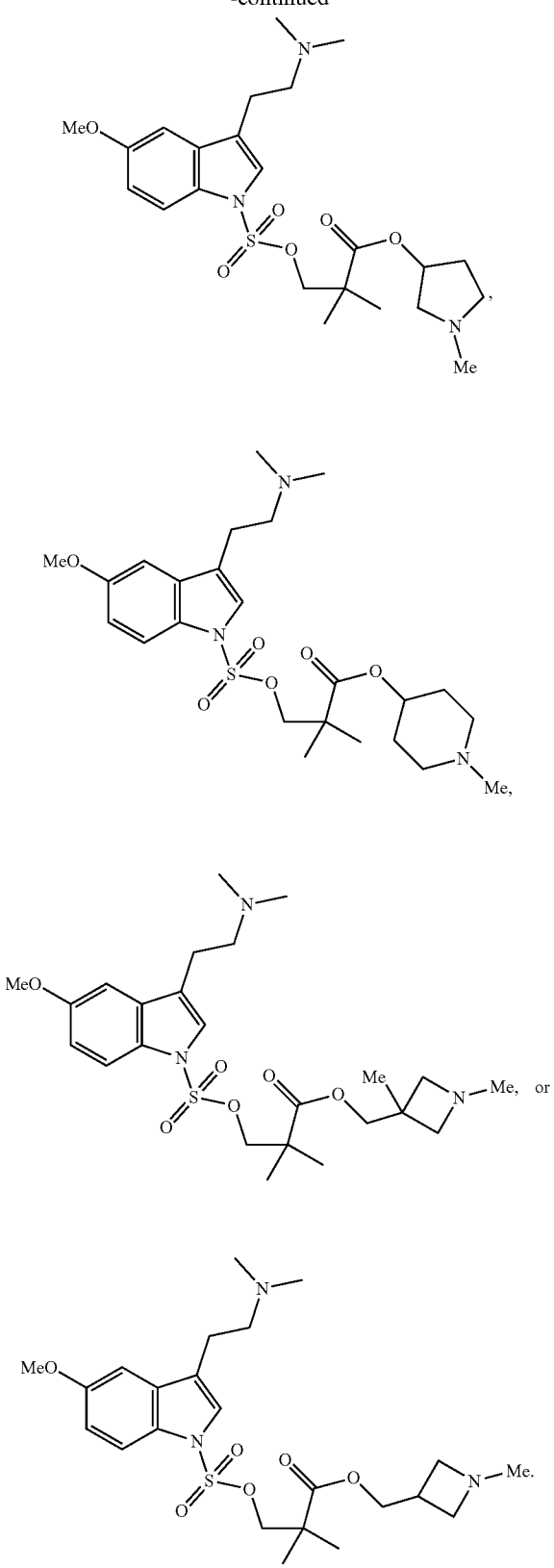
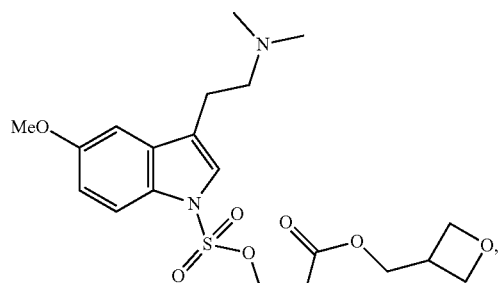
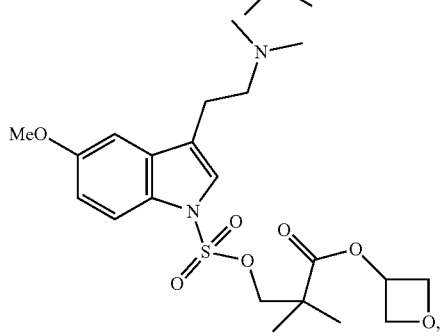

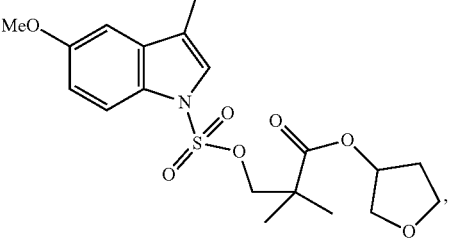
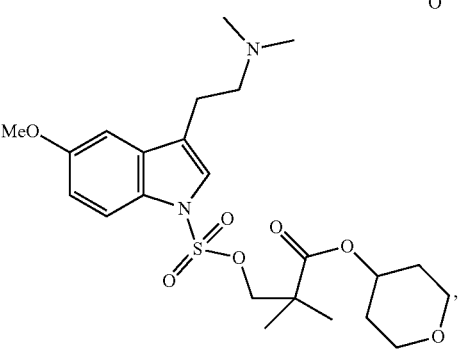
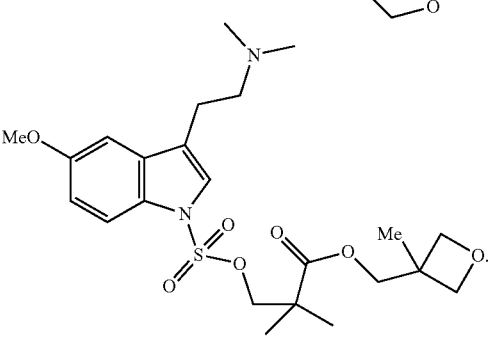
In some embodiments is a compound of Formula (I) or (It), or a pharmaceutically acceptable salt or solvate thereof, wherein the compound is:
In some embodiments is a compound of Formula (I) or (It), or a pharmaceutically acceptable salt or solvate thereof, wherein the compound is:

217
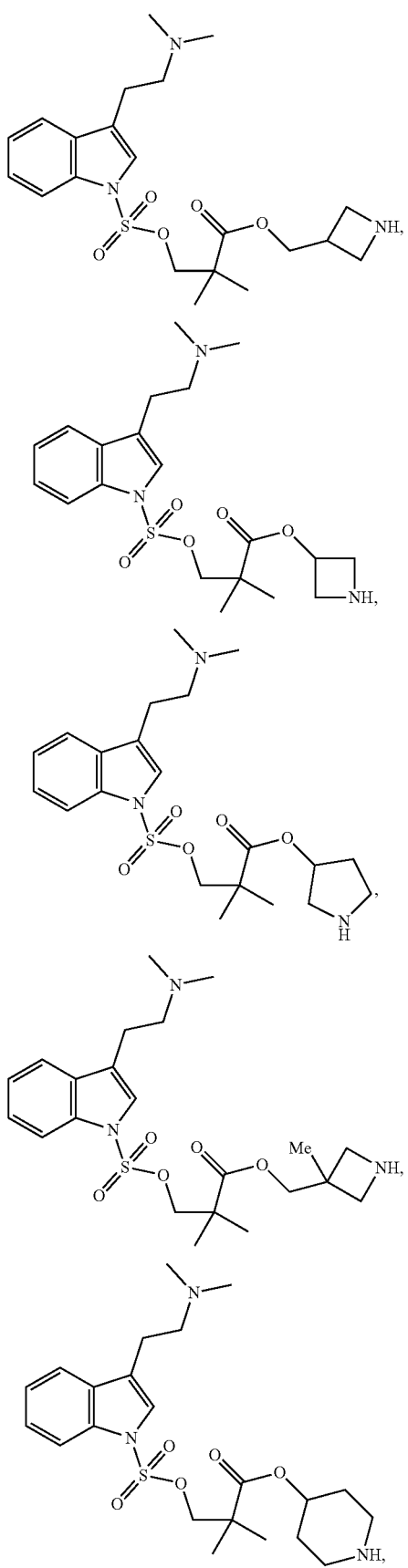
218
-continued
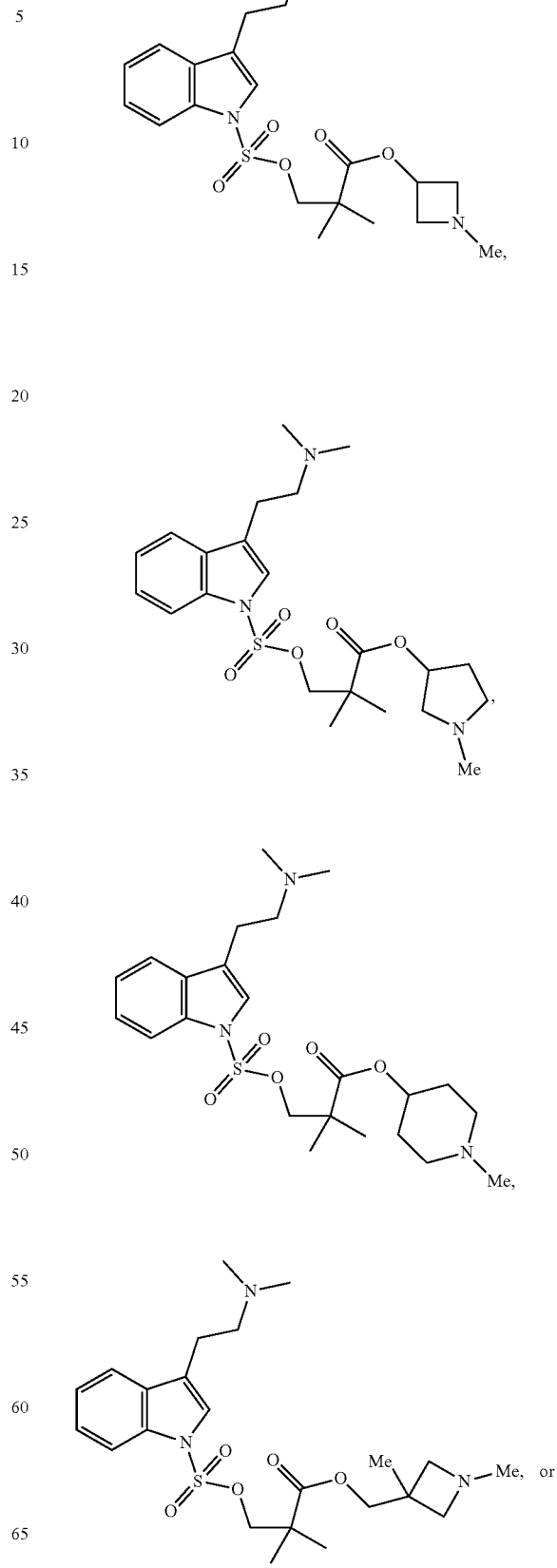

-continued

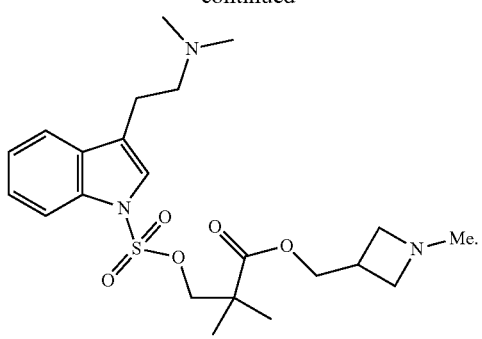

In some embodiments is a compound of Formula (I) or (It), or a pharmaceutically acceptable salt or solvate thereof, wherein the compound is:

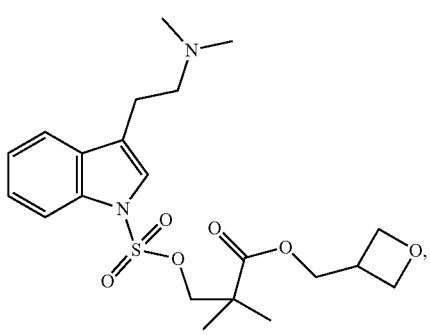

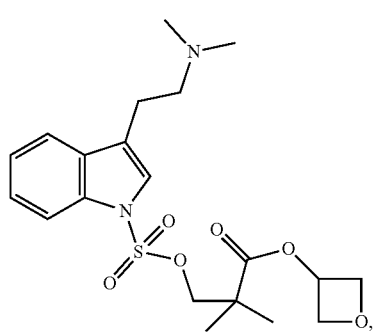

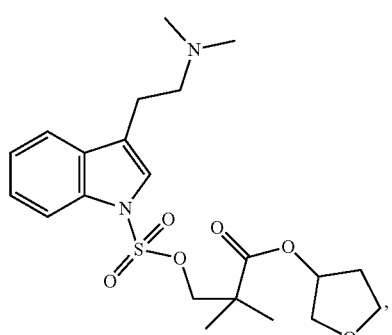

-continued

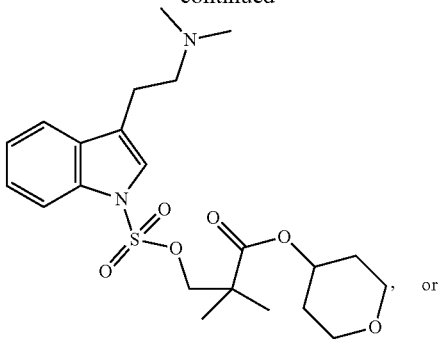

or

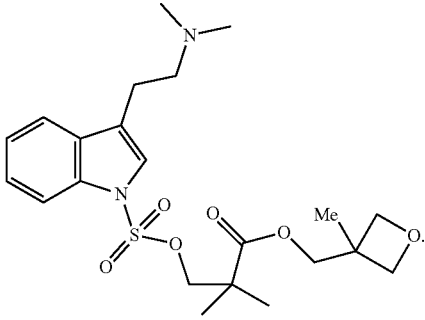

In some embodiments is a compound of Formula (I) having the structure of Formula (Iu), or a pharmaceutically acceptable salt thereof:

(Iu)

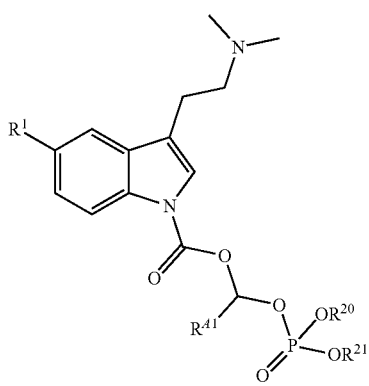

wherein:
R$^1$ is hydrogen or methoxy;
R$^{41}$ is hydrogen, alkyl, or cycloalkyl, wherein each of alkyl and cycloalkyl is unsubstituted or substituted with one or more alkyl, aryl, halogen, —OR$^{13}$, —NR(R$^{18}$)R$^{19}$, —C(O)R$^{14}$, —OC(O)R$^{15}$, —OC(O)OR$^{16}$, or —OC(O)N(R$^{18}$)R$^{19}$; and
each of R$^{20}$ and R$^{21}$ is independently hydrogen, alkyl, cycloalkyl, aryl, heterocyclylalkyl, or heteroaryl, wherein each of alkyl, cycloalkyl, aryl, heterocyclylalkyl, and heteroaryl is independently unsubstituted or substituted with one or more R$^B$, or R$^{20}$ and R$^{21}$ together with the atoms to which they are attached form a heterocyclylalkyl ring that is unsubstituted or substituted with one or more R$^B$.

In some embodiments is a compound of Formula (Iu), or a pharmaceutically acceptable salt or solvate thereof, wherein R$^{41}$ is alkyl. In some embodiments is a compound of Formula (Iu), or a pharmaceutically acceptable salt or solvate thereof, wherein $R^4$ is unsubstituted alkyl. In some embodiments is a compound of Formula (Iu), or a pharmaceutically acceptable salt or solvate thereof, wherein $R^{41}$ is methyl, ethyl, isopropyl, or tert-butyl. In some embodiments is a compound of Formula (Iu), or a pharmaceutically acceptable salt or solvate thereof, wherein $R^{41}$ is hydrogen. In some embodiments is a compound of Formula (Iu), or a pharmaceutically acceptable salt or solvate thereof, wherein $R^{41}$ is methyl. In some embodiments is a compound of Formula (Iu), or a pharmaceutically acceptable salt or solvate thereof, wherein $R^{41}$ is hydrogen. In some embodiments is a compound of Formula (Iu), or a pharmaceutically acceptable salt or solvate thereof, wherein $R^{41}$ is methyl, ethyl, isopropyl, —CH(Et)$_2$, or tert-butyl.

In some embodiments is a compound of Formula (Iu), or a pharmaceutically acceptable salt or solvate thereof, wherein each of $R^{20}$ and $R^{21}$ is alkyl. In some embodiments is a compound of Formula (Iu), or a pharmaceutically acceptable salt or solvate thereof, wherein each of $R^{20}$ and $R^{21}$ is independently unsubstituted alkyl. In some embodiments is a compound of Formula (Iu), or a pharmaceutically acceptable salt or solvate thereof, wherein each of $R^{20}$ and $R^{21}$ is independently methyl, ethyl, n-propyl, isopropyl, tert-butyl, 3-methyl-1-butyl, n-pentyl, or n-hexyl. In some embodiments is a compound of Formula (Iu), or a pharmaceutically acceptable salt or solvate thereof, wherein each of $R^{20}$ and $R^{21}$ is benzyl. In some embodiments is a compound of Formula (Iu), or a pharmaceutically acceptable salt or solvate thereof, wherein each of $R^{20}$ and $R^{21}$ is independently

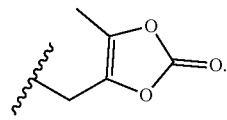 [SMILES: *Cc1oc(=O)oc1C]

In some embodiments is a compound of Formula (Lu), or a pharmaceutically acceptable salt or solvate thereof, wherein each of $R^{20}$ and $R^{21}$ is phenyl. In some embodiments is a compound of Formula (Iu), or a pharmaceutically acceptable salt or solvate thereof, wherein each of $R^{20}$ and $R^{21}$ is independently cycloalkyl. In some embodiments is a compound of Formula (Iu), or a pharmaceutically acceptable salt or solvate thereof, wherein each of $R^{20}$ and $R^{21}$ is independently cyclopropyl, cyclobutyl, cyclopentyl, cyclohexyl, or cycloheptyl. In some embodiments is a compound of Formula (Iu), or a pharmaceutically acceptable salt or solvate thereof, wherein each of $R^{20}$ and $R^{21}$ is independently heteroaryl. In some embodiments is a compound of Formula (Iu), or a pharmaceutically acceptable salt or solvate thereof, wherein each of $R^{20}$ and $R^{21}$ is independently 2-pyridyl, 3-pyridyl, 4-pyridyl, 2-pyrimidyl, or 4-pyrimidyl. In some embodiments is a compound of Formula (Lu), or a pharmaceutically acceptable salt or solvate thereof, $R^{20}$ is hydrogen, and $R^{21}$ is alkyl, alkyl, heteroalkyl, cycloalkyl, heterocyclylalkyl, aryl, heteroaryl, or hydrogen, wherein alkyl, heteroalkyl, cycloalkyl, heterocyclylalkyl, aryl, or heteroaryl.

In some embodiments is a compound of Formula (Iu), or a pharmaceutically acceptable salt or solvate thereof, wherein each of $R^{20}$ and $R^{21}$ is independently alkyl or cycloalkyl. In some embodiments is a compound of Formula (Iu), or a pharmaceutically acceptable salt or solvate thereof, wherein each of $R^{20}$ and $R^{21}$ is independently unsubstituted alkyl, and $R^{41}$ is hydrogen. In some embodiments is a compound of Formula (Iu), or a pharmaceutically acceptable salt or solvate thereof, wherein each of $R^{20}$ and $R^{21}$ is independently unsubstituted alkyl, and $R^1$ is methyl. In some embodiments is a compound of Formula (Iu), or a pharmaceutically acceptable salt or solvate thereof, wherein each of $R^{20}$ and $R^{21}$ is tert-butyl, $R^{41}$ is hydrogen, and $R^1$ is methoxy. In some embodiments is a compound of Formula (Iu), or a pharmaceutically acceptable salt or solvate thereof, wherein each of $R^{20}$ and $R^{21}$ is tert-butyl, $R^{41}$ is hydrogen, and $R^1$ is hydrogen.

In some embodiments is a compound of Formula (Iu), or a pharmaceutically acceptable salt or solvate thereof, wherein the compound is:

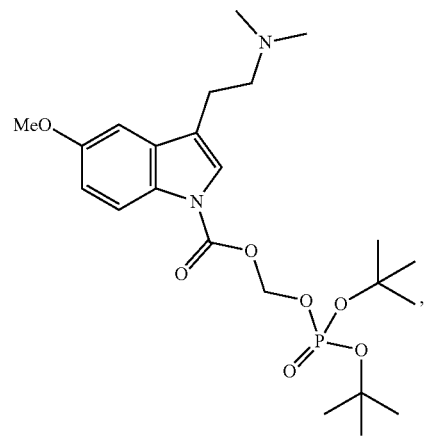

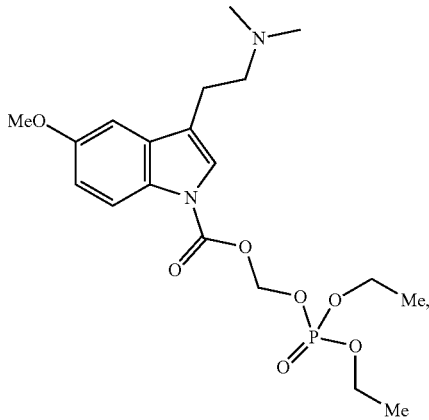

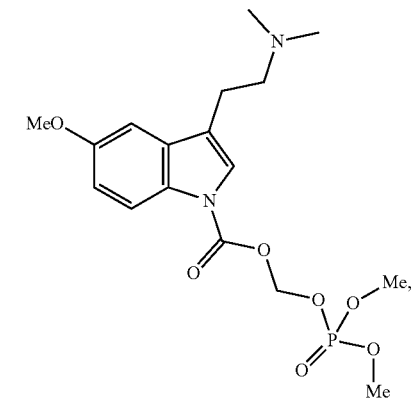

223
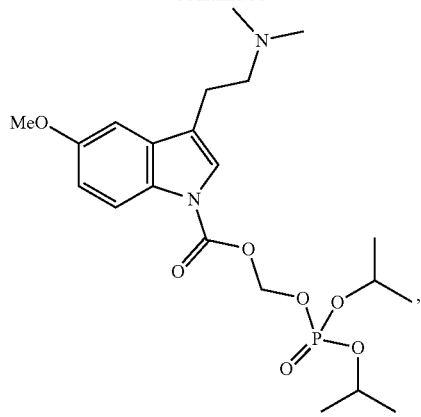
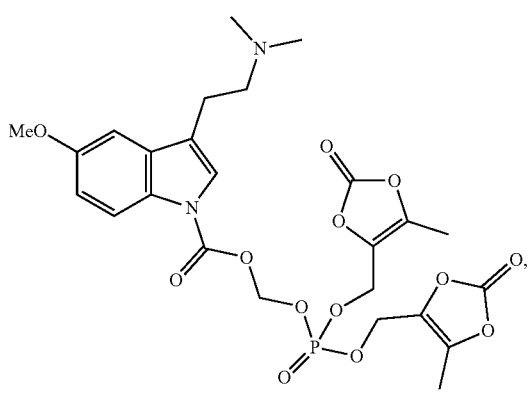
, or
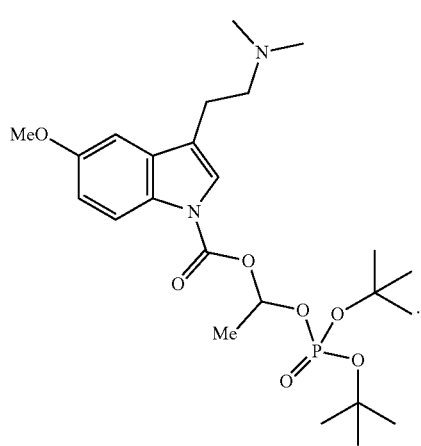
224
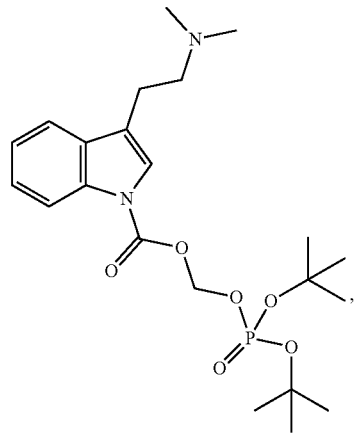
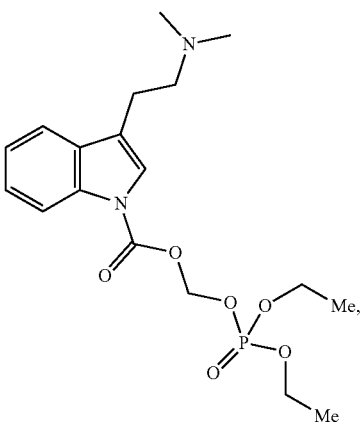
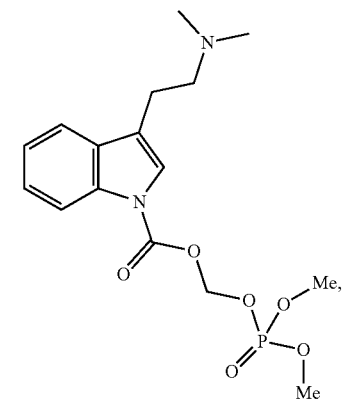
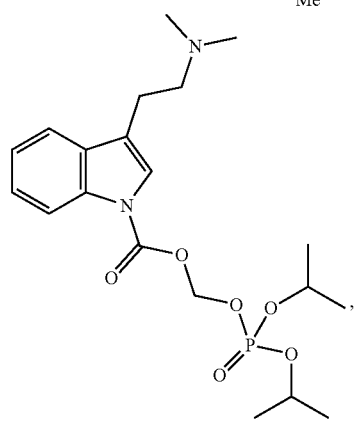
In some embodiments is a compound of Formula (Iu), or a pharmaceutically acceptable salt or solvate thereof, wherein the compound is:

225
-continued

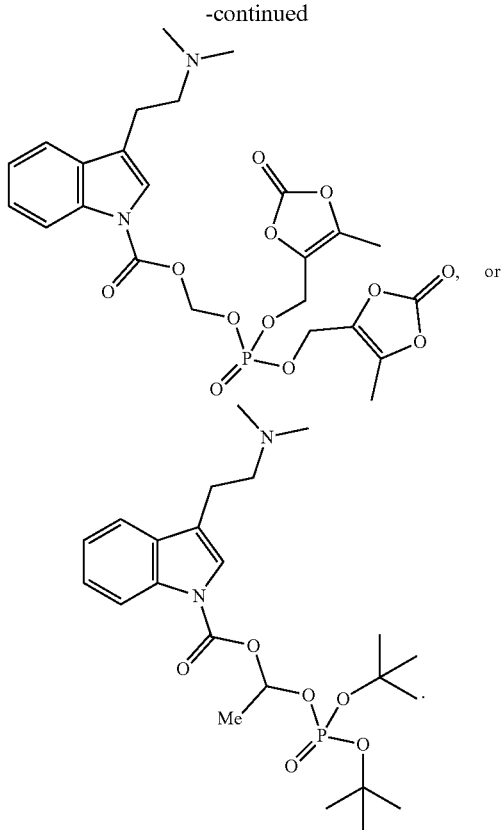

In some embodiments is a compound of Formula (I) having the structure of Formula (Iv), or a pharmaceutically acceptable salt thereof:

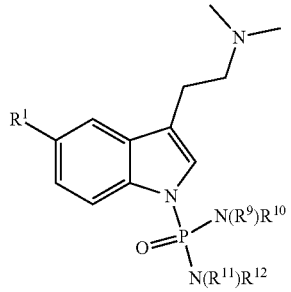

(Iv)

wherein:
R$^1$ is hydrogen or methoxy;
each of R$^9$ and R$^{10}$ is independently alkyl, heteroalkyl, cycloalkyl, heterocyclylalkyl, aryl, heteroaryl, or hydrogen, wherein each alkyl, heteroalkyl, cycloalkyl, heterocyclylalkyl, aryl, and heteroaryl is independently unsubstituted or substituted with one or more R$^A$, or R$^9$ and R$^{10}$ together with the atom to which they are attached form a heterocyclylalkyl ring that is unsubstituted or substituted with one or more R$^A$; and
each of R$^{11}$ and R$^{12}$ is independently alkyl, heteroalkyl, cycloalkyl, heterocyclylalkyl, aryl, heteroaryl, or hydrogen, wherein each alkyl, heteroalkyl, cycloalkyl, heterocyclylalkyl, aryl, and heteroaryl is independently unsubstituted or substituted with one or more R$^A$, or

226

R$^{11}$ and R$^{12}$ together with the atoms to which they are attached form a heterocyclylalkyl ring that is unsubstituted or substituted with one or more R$^A$.

In some embodiments is a compound of Formula (Iv), or a pharmaceutically acceptable salt or solvate thereof, wherein each of R$^9$ and R$^{10}$ is independently alkyl, heteroalkyl, cycloalkyl, heterocyclylalkyl, aryl, heteroaryl, or hydrogen, wherein each alkyl, heteroalkyl, cycloalkyl, heterocyclylalkyl, aryl, and heteroaryl is independently unsubstituted or substituted with one or more R$^A$. In some embodiments is a compound of Formula (Iv), or a pharmaceutically acceptable salt or solvate thereof, wherein each of R$^{11}$ and R$^{12}$ is independently alkyl, heteroalkyl, cycloalkyl, heterocyclylalkyl, aryl, heteroaryl, or hydrogen, wherein each alkyl, heteroalkyl, cycloalkyl, heterocyclylalkyl, aryl, and heteroaryl is independently unsubstituted or substituted with one or more R$^A$. In some embodiments is a compound of Formula (Iv), or a pharmaceutically acceptable salt or solvate thereof, wherein each of R$^9$, R$^{10}$, R$^{11}$, and R$^{12}$ is independently alkyl, cycloalkyl, or hydrogen, wherein each alkyl and cycloalkyl is independently unsubstituted or substituted with one or more R$^A$. In some embodiments is a compound of Formula (Iv), or a pharmaceutically acceptable salt or solvate thereof, wherein each of R$^9$, R$^{10}$, R$^{11}$, and R$^{12}$ is independently hydrogen, methyl, ethyl, isopropyl, n-propyl, isobutyl, tert-butyl, or n-butyl. In some embodiments is a compound of Formula (Iv), or a pharmaceutically acceptable salt or solvate thereof, wherein each of R$^9$, R$^{10}$, R$^{11}$, and R$^{12}$ is methyl.

In some embodiments is a compound of Formula (Iv), or a pharmaceutically acceptable salt or solvate thereof, wherein the compound is:

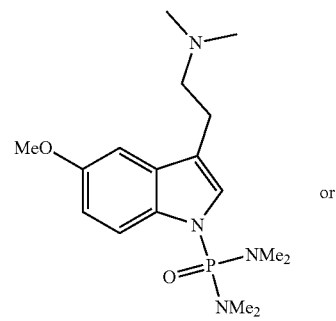

or

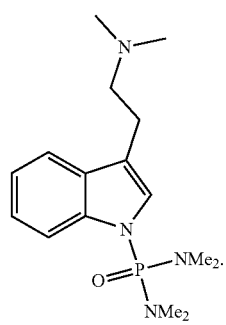

In some embodiments, the compound of Formula (I) having the structure of Formula (Iw), or a pharmaceutically acceptable salt thereof:

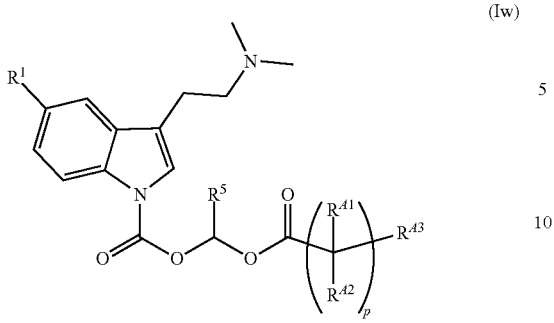

(Iw)

wherein:
R¹ is hydrogen or methoxy; each $R^{41}$ and $R^{42}$ is independently hydrogen, alkyl, or cycloalkyl, wherein each alkyl and cycloalkyl is independently unsubstituted or substituted with one or more alkyl, aryl, halogen, —OR¹³, —NR(R¹⁸)R¹⁹, —C(O)R¹⁴, —OC(O)R¹⁵, —OC(O)OR¹⁶, or —OC(O)N(R¹⁸)R¹⁹;
$R^{43}$ is —OR¹³, —N(R¹⁸)R¹⁹, —C(O)OR¹³, —N(R¹³)C(O)OR¹⁴, —N(R¹³)C(O)R¹⁴, —C(O)R¹⁴, —OC(O) R¹⁵, —OC(O)OR¹⁶, —OP(O)OR¹⁷[N(R¹⁸)R¹⁹], —C(O)N(R¹⁸)R¹⁹, —OC(O)N(R¹⁸)R¹⁹, or —OP(O)OR²⁰ (OR²¹), and
p is 1, 2, 3, 4, 5, 6, 7, 8, 9, or 10.

In some embodiments is a compound of Formula (Iw), or a pharmaceutically acceptable salt or solvate thereof, wherein each $R^{41}$ and $R^{42}$ is independently hydrogen, alkyl, or cycloalkyl. In some embodiments is a compound of Formula (Iw), or a pharmaceutically acceptable salt or solvate thereof, wherein each $R^{41}$ and $R^{42}$ is independently hydrogen, unsubstituted alkyl, or unsubstituted cycloalkyl. In some embodiments is a compound of Formula (Iw), or a pharmaceutically acceptable salt or solvate thereof, wherein each $R^{41}$ and $R^{42}$ is independently hydrogen.

In some embodiments is a compound of Formula (Iw), or a pharmaceutically acceptable salt or solvate thereof, wherein $R^{43}$ is —C(O)OR¹³, —N(R^{D3})C(O)OR¹⁴, —N(R¹³)C(O)R¹⁴, or —C(O)R¹⁴. In some embodiments is a compound of Formula (Iw), or a pharmaceutically acceptable salt or solvate thereof, wherein $R^{43}$ is —C(O)OR¹³. In some embodiments is a compound of Formula (Iw), or a pharmaceutically acceptable salt or solvate thereof, wherein $R^{43}$ is —C(O)OR¹³, wherein R¹³ is hydrogen or alkyl that is unsubstituted or substituted with one or more $R^B$. In some embodiments is a compound of Formula (Iw), or a pharmaceutically acceptable salt or solvate thereof, wherein $R^{43}$ is —C(O)OR¹³, wherein R¹³ is hydrogen or alkyl that is unsubstituted. In some embodiments is a compound of Formula (Iw), or a pharmaceutically acceptable salt or solvate thereof, wherein $R^{43}$ is —C(O)OR¹³, wherein R¹³ is hydrogen, methyl, ethyl, n-propyl, isopropyl, n-butyl, isobutyl, or tert-butyl. In some embodiments is a compound of Formula (Iw), or a pharmaceutically acceptable salt or solvate thereof, wherein $R^{43}$ is —C(O)OR¹³, wherein R¹³ is hydrogen or tert-butyl.

In some embodiments is a compound of Formula (Iw), or a pharmaceutically acceptable salt or solvate thereof, wherein p is 1, 2, 3, 4, or 5. In some embodiments is a compound of Formula (Iw), or a pharmaceutically acceptable salt or solvate thereof, wherein p is 2, 3, 4, or 5.

In some embodiments is a compound of Formula (Iv), or a pharmaceutically acceptable salt or solvate thereof, wherein the compound is:

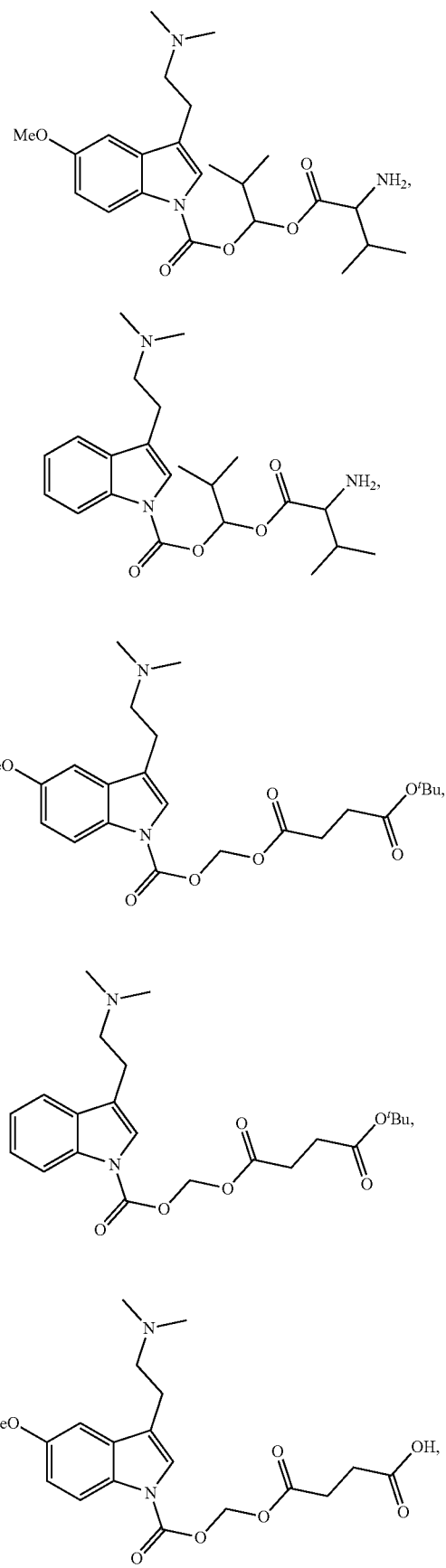

229
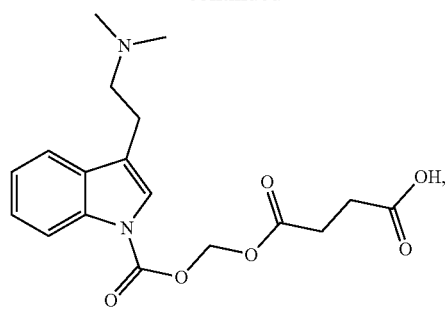
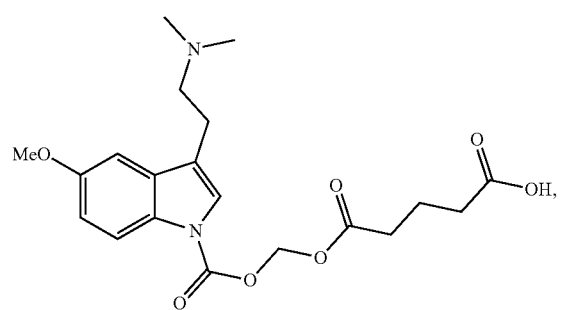
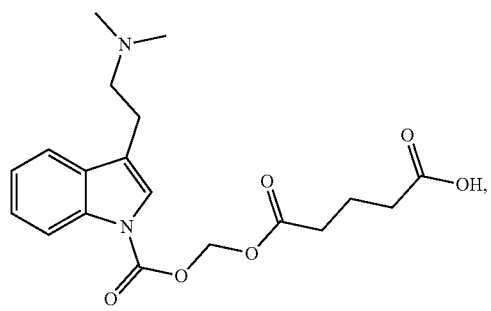
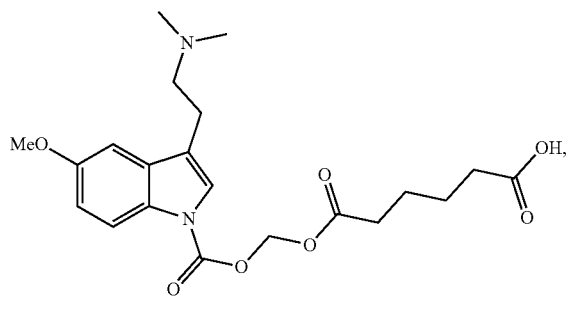
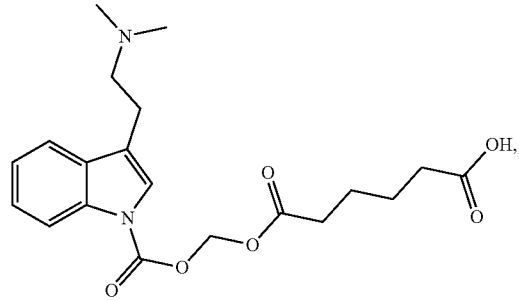
230
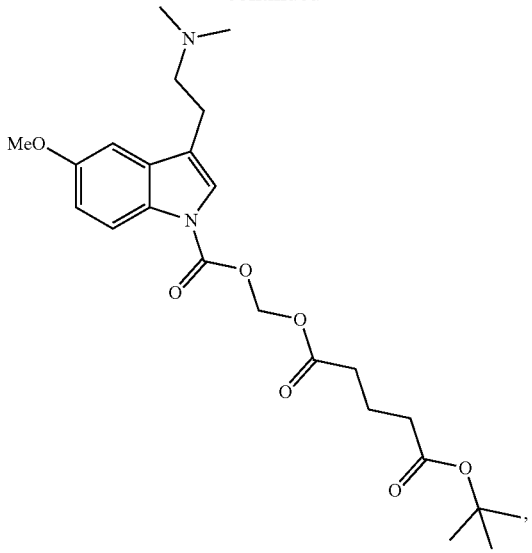
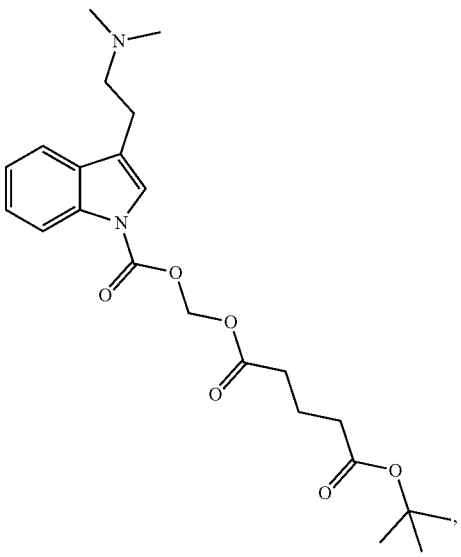
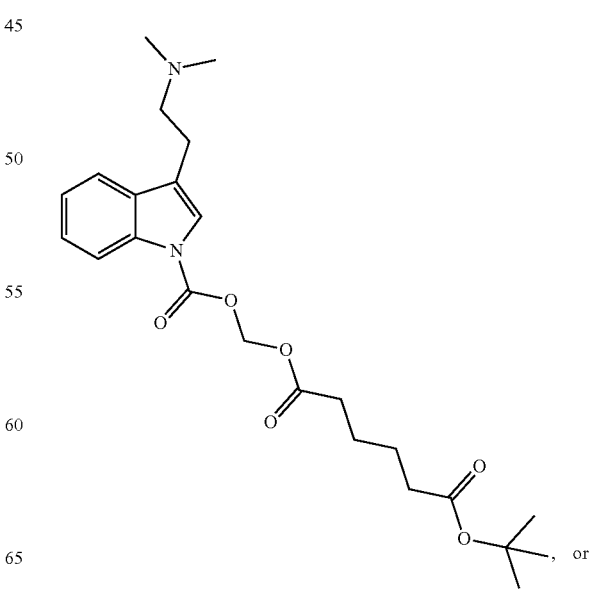
or

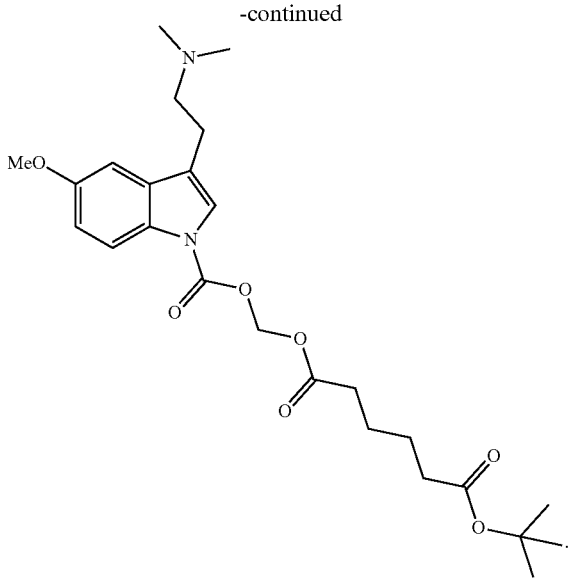

In some embodiments is a compound of Formula (I), (Ia), (Ib), (Ib-1) (Ib1), (Ic), (Id), (Ie), (If), (If1), (Ig), (Ih), (Ii), (Ij), (Ik), (Ik1), (Ik2), (Ik3), (Il), (Im), (Im1), (Im1a), (In), (In1), (Jo), (Io1), (Io2), (Io1a), (Ip) (Ip1), (Iq), (Iq1), (Ir), (Ir1), (Is), (It), (Iu), (Iv), or (Iw), or a pharmaceutically acceptable salt thereof, wherein $R^1$ is methoxy. In some embodiments is a compound of Formula (I), (Ia), (Ib), (Ib-1) (Ib1), (Ic), (Id), (Ie), (If), (If1), (Ig), (Ih), (Ii), (Ij), (Ik), (Ik1), (Ik2), (Ik3), (Il), (Im), (Im1), (Im1a), (In), (In1), (Io), (Io1), (Io2), (Io1a), (Ip) (Ip1), (Iq), (Iq1), (Ir), (Ir1), (Is), (It), (Iu), (Iv), or (Iw), or a pharmaceutically acceptable salt thereof, wherein $R^1$ is hydrogen.

In some embodiments is a compound of Formula (I), or a pharmaceutically acceptable salt or solvate thereof, wherein $R^4$ is hydrogen or alkyl. In some embodiments is a compound of Formula (I), or a pharmaceutically acceptable salt or solvate thereof, wherein $R^4$ is alkyl. In some embodiments is a compound of Formula (I), or a pharmaceutically acceptable salt or solvate thereof, wherein $R^4$ is hydrogen or unsubstituted alkyl. In some embodiments is a compound of Formula (I), or a pharmaceutically acceptable salt or solvate thereof, wherein $R^4$ is hydrogen. In some embodiments is a compound of Formula (I), or a pharmaceutically acceptable salt or solvate thereof, wherein $R^4$ is unsubstituted alkyl.

In some embodiments is a compound of Formula (I), or a pharmaceutically acceptable salt or solvate thereof, wherein $R^5$ is hydrogen or alkyl. In some embodiments is a compound of Formula (I), or a pharmaceutically acceptable salt or solvate thereof, wherein $R^5$ is alkyl. In some embodiments is a compound of Formula (I), or a pharmaceutically acceptable salt or solvate thereof, wherein $R^5$ is hydrogen or unsubstituted alkyl. In some embodiments is a compound of Formula (I), or a pharmaceutically acceptable salt or solvate thereof, wherein $R^5$ is hydrogen. In some embodiments is a compound of Formula (I), or a pharmaceutically acceptable salt or solvate thereof, wherein $R^5$ is unsubstituted alkyl.

In some embodiments is a compound of Formula (I), or a pharmaceutically acceptable salt or solvate thereof, wherein $R^2$ is —C(O)OCH($R^5$)OC(O)$R^6$. In some embodiments is a compound of Formula (I), or a pharmaceutically acceptable salt or solvate thereof, wherein $R^2$ is —C(O)OCH($R^5$)OC(O)$R^6$, wherein $R^5$ is hydrogen or alkyl. In some embodiments is a compound of Formula (I), or a pharmaceutically acceptable salt or solvate thereof, wherein $R^2$ is —C(O)OCH($R^5$)OC(O)$R^6$, wherein $R^5$ is hydrogen or unsubstituted alkyl. In some embodiments is a compound of Formula (I), or a pharmaceutically acceptable salt or solvate thereof, wherein $R^2$ is —C(O)OCH$_2$OC(O)$R^6$. In some embodiments is a compound of Formula (I), or a pharmaceutically acceptable salt or solvate thereof, wherein $R^2$ is —C(O)OCH($R^5$)OC(O)$R^6$, wherein $R^6$ is alkyl, cycloalkyl, heterocyclylalkyl, aryl, or heteroaryl. In some embodiments is a compound of Formula (I), or a pharmaceutically acceptable salt or solvate thereof, wherein $R^2$ is —C(O)OCH($R^5$)OC(O)$R^6$, wherein $R^6$ is alkyl. In some embodiments is a compound of Formula (I), or a pharmaceutically acceptable salt or solvate thereof, wherein $R^2$ is —C(O)OCH($R^5$)OC(O)$R^6$, wherein $R^6$ is heteroalkyl. In some embodiments is a compound of Formula (I), or a pharmaceutically acceptable salt or solvate thereof, wherein $R^2$ is —C(O)OCH($R^5$)OC(O)$R^6$, wherein $R^6$ is unsubstituted alkyl, unsubstituted cycloalkyl, unsubstituted heterocyclylalkyl, unsubstituted aryl, or unsubstituted heteroaryl. In some embodiments is a compound of Formula (I), or a pharmaceutically acceptable salt or solvate thereof, wherein $R^2$ is —C(O)OCH($R^5$)OC(O)$R^6$, wherein $R^6$ is alkyl. In some embodiments is a compound of Formula (I), or a pharmaceutically acceptable salt or solvate thereof, wherein $R^2$ is —C(O)OCH($R^5$)OC(O)$R^6$, wherein $R^6$ is heteroalkyl. In some embodiments is a compound of Formula (I), or a pharmaceutically acceptable salt or solvate thereof, wherein $R^2$ is —C(O)OCH($R^5$)OC(O)$R^6$, wherein $R^6$ is heterocyclylalkyl substituted with arylalkyl.

In some embodiments is a compound of Formula (I), or a pharmaceutically acceptable salt or solvate thereof, wherein $R^2$ is —C(O)OCH($R^5$)OC(O)O$R^6$. In some embodiments is a compound of Formula (I), or a pharmaceutically acceptable salt or solvate thereof, wherein $R^2$ is —C(O)OCH$_2$OC(O)O$R^6$. In some embodiments is a compound of Formula (I), or a pharmaceutically acceptable salt or solvate thereof, wherein $R^2$ is —C(O)OCH($R^5$)OC(O)O$R^6$, wherein $R^5$ is alkyl. In some embodiments is a compound of Formula (I), or a pharmaceutically acceptable salt or solvate thereof, wherein $R^2$ is —C(O)OCH($R^5$)OC(O)O$R^6$, wherein $R^5$ is hydrogen or unsubstituted alkyl. In some embodiments is a compound of Formula (I), or a pharmaceutically acceptable salt or solvate thereof, wherein $R^2$ is —C(O)OCH($R^5$)OC(O)O$R^6$, wherein $R^6$ is heteroalkyl. In some embodiments is a compound of Formula (I), or a pharmaceutically acceptable salt or solvate thereof, wherein $R^2$ is —C(O)OCH($R^5$)OC(O)O$R^6$, wherein $R^6$ is alkyl, heteroalkyl, cycloalkyl, or heterocyclylalkyl. In some embodiments is a compound of Formula (I), or a pharmaceutically acceptable salt or solvate thereof, wherein $R^2$ is —C(O)OCH($R^5$)OC(O)O$R^6$, wherein $R^6$ is heterocyclylalkyl substituted with alkyl, heteroalkyl, or arylalkyl. In some embodiments is a compound of Formula (I), or a pharmaceutically acceptable salt or solvate thereof, wherein $R^2$ is —C(O)OCH($R^5$)OC(O)O$R^6$, wherein $R^6$ is unsubstituted heteroalkyl. In some embodiments is a compound of Formula (I), or a pharmaceutically acceptable salt or solvate thereof, wherein $R^2$ is —C(O)OCH($R^5$)OC(O)O$R^6$, wherein $R^6$ is unsubstituted alkyl, unsubstituted heteroalkyl, unsubstituted cycloalkyl, or unsubstituted heterocyclylalkyl. In some embodiments is a compound of Formula (I), or a pharmaceutically acceptable salt or solvate thereof, wherein $R^2$ is —C(O)OCH($R^5$)OC(O)O$R^6$, wherein $R^6$ is heterocyclylalkyl substituted with alkyl, heteroalkyl, or arylalkyl. In some embodiments is a compound of Formula (I), or a pharmaceutically acceptable salt or solvate thereof, wherein $R^2$ is —C(O)OCH($R^5$)OC(O)O$R^6$, wherein $R^6$ is heterocyclylalkyl that is unsubstituted.

In some embodiments is a compound of Formula (I), or a pharmaceutically acceptable salt or solvate thereof, wherein $R^2$ is —C(O)N($R^9$)$R^{10}$. In some embodiments is a compound of Formula (I), or a pharmaceutically acceptable salt or solvate thereof, wherein $R^2$ is —C(O)N($R^9$)$R^{10}$, wherein each of $R^9$ and $R^{10}$ is independently alkyl. In some embodiments is a compound of Formula (I), or a pharmaceutically acceptable salt or solvate thereof, wherein $R^2$ is —C(O)N($R^9$)$R^{10}$, wherein each of $R^9$ and $R^{10}$ is independently alkyl that is unsubstituted. In some embodiments is a compound of Formula (I), or a pharmaceutically acceptable salt or solvate thereof, wherein $R^2$ is —C(O)N(H)$R^{10}$, wherein $R^{10}$ is alkyl. In some embodiments is a compound of Formula (I), or a pharmaceutically acceptable salt or solvate thereof, wherein $R^2$ is —C(O)N(H)$R^{10}$, wherein $R^{10}$ is alkyl that is unsubstituted. In some embodiments is a compound of Formula (I), or a pharmaceutically acceptable salt or solvate thereof, wherein $R^2$ is —C(O)N($R^9$)$R^{10}$, wherein each of $R^9$ and $R^{10}$ is independently alkyl substituted with —N($R^{18}$)$R^{19}$ or —C(O)O$R^3$. In some embodiments is a compound of Formula (I), or a pharmaceutically acceptable salt or solvate thereof, wherein $R^2$ is —C(O)N($R^9$)$R^{10}$, wherein $R^9$ is unsubstituted alkyl, and $R^{10}$ is alkyl substituted with —N($R^{18}$)$R^{19}$ or —C(O)O$R^{13}$. In some embodiments is a compound of Formula (I), or a pharmaceutically acceptable salt or solvate thereof, wherein $R^2$ is —C(O)N(H)$R^{10}$, wherein $R^{10}$ is alkyl substituted with —N($R^{18}$)$R^{19}$ or —C(O)O$R^{13}$. In some embodiments is a compound of Formula (I), or a pharmaceutically acceptable salt or solvate thereof, wherein $R^2$ is —C(O)N($R^9$)$R^{10}$, wherein $R^9$ is alkyl, and $R^{10}$ is alkyl substituted with —N($R^{18}$)$R^{19}$, wherein each of $R^{18}$ and $R^{19}$ is alkyl. In some embodiments is a compound of Formula (I), or a pharmaceutically acceptable salt or solvate thereof, wherein $R^2$ is —C(O)N($R^9$)$R^{10}$, wherein $R^9$ is alkyl, and $R^{10}$ is alkyl substituted with —N($R^{18}$)$R^{19}$, wherein each of $R^{18}$ and $R^{19}$ is alkyl that is unsubstituted. In some embodiments is a compound of Formula (I), or a pharmaceutically acceptable salt or solvate thereof, wherein $R^2$ is —C(O)N($R^9$)$R^{10}$, wherein $R^9$ is unsubstituted alkyl, and $R^{10}$ is alkyl substituted with —N($R^{18}$)$R^{19}$, wherein each of $R^{18}$ and $R^{19}$ is alkyl that is unsubstituted. In some embodiments is a compound of Formula (I), or a pharmaceutically acceptable salt or solvate thereof, wherein $R^2$ is —C(O)N(H)$R^{10}$, wherein $R^{10}$ is alkyl substituted with —N($R^{18}$)$R^{19}$, wherein each of $R^{18}$ and $R^{19}$ is alkyl that is unsubstituted. In some embodiments is a compound of Formula (I), or a pharmaceutically acceptable salt or solvate thereof, wherein $R^2$ is —C(O)N($R^9$)$R^{10}$, wherein $R^9$ is alkyl, and $R^{10}$ is alkyl substituted with —C(O)O$R^{13}$, wherein $R^{13}$ is alkyl or hydrogen. In some embodiments is a compound of Formula (I), or a pharmaceutically acceptable salt or solvate thereof, wherein $R^2$ is —C(O)N($R^9$)$R^{10}$, wherein $R^9$ is alkyl, and $R^{10}$ is alkyl substituted with —C(O)O$R^{13}$, wherein $R^{13}$ is alkyl that is unsubstituted, or hydrogen. In some embodiments is a compound of Formula (I), or a pharmaceutically acceptable salt or solvate thereof, wherein $R^2$ is —C(O)N(H)$R^{10}$, wherein $R^{10}$ is alkyl substituted with —C(O)O$R^{13}$, wherein $R^{13}$ is alkyl that is unsubstituted, or hydrogen. In some embodiments is a compound of Formula (I), or a pharmaceutically acceptable salt or solvate thereof, wherein $R^2$ is —C(O)N($R^9$)$R^{10}$, wherein each of $R^9$ and $R^{10}$ is independently alkyl substituted with —C(O)OH. In some embodiments is a compound of Formula (I), or a pharmaceutically acceptable salt or solvate thereof, wherein $R^2$ is —C(O)N($R^9$)$R^{10}$, wherein $R^9$ is alkyl, and $R^{10}$ is alkyl substituted with —C(O)OH. In some embodiments is a compound of Formula (I), or a pharmaceutically acceptable salt or solvate thereof, wherein $R^2$ is C(O)N(H)$R^{10}$, wherein $R^{10}$ is alkyl substituted with —C(O)OH.

In some embodiments is a compound of Formula (I), or a pharmaceutically acceptable salt or solvate thereof, wherein $R^2$ is —C(O)N($R^9$)$R^{10}$. In some embodiments is a compound of Formula (I), or a pharmaceutically acceptable salt or solvate thereof, wherein $R^2$ is —C(O)N($R^9$)$R^{10}$, wherein $R^9$ is hydrogen, aryl, heteroaryl, alkyl, or heteroalkyl. In some embodiments is a compound of Formula (I), or a pharmaceutically acceptable salt or solvate thereof, wherein $R^2$ is —C(O)N($R^9$)$R^{10}$, wherein $R^{10}$ is alkyl or heteroalkyl. In some embodiments is a compound of Formula (I), or a pharmaceutically acceptable salt or solvate thereof, wherein $R^2$ is —C(O)N($R^9$)$R^{10}$, wherein $R^9$ is hydrogen, unsubstituted aryl, unsubstituted heteroaryl, unsubstituted alkyl, or unsubstituted heteroalkyl. In some embodiments is a compound of Formula (I), or a pharmaceutically acceptable salt or solvate thereof, wherein $R^2$ is —C(O)N($R^9$)$R^{10}$, wherein $R^9$ is hydrogen, aryl, heteroaryl, alkyl, or heteroalkyl, each of which is substituted with heteroalkyl. In some embodiments is a compound of Formula (I), or a pharmaceutically acceptable salt or solvate thereof, wherein $R^2$ is —C(O)N($R^9$)$R^{10}$, wherein $R^9$ is hydrogen, aryl, heteroaryl, alkyl, or heteroalkyl, each of which is substituted with heterocyclylalkyl. In some embodiments is a compound of Formula (I), or a pharmaceutically acceptable salt or solvate thereof, wherein $R^2$ is —C(O)N($R^9$)$R^{10}$, wherein $R^9$ is hydrogen, aryl, heteroaryl, alkyl, or heteroalkyl, each of which is substituted with cycloalkyl. In some embodiments is a compound of Formula (I), or a pharmaceutically acceptable salt or solvate thereof, wherein $R^2$ is —C(O)N($R^9$)$R^{10}$, wherein $R^9$ is hydrogen, aryl, heteroaryl, alkyl, or heteroalkyl, each of which is substituted with heteroalkyl that is unsubstituted. In some embodiments is a compound of Formula (I), or a pharmaceutically acceptable salt or solvate thereof, wherein $R^2$ is —C(O)N($R^9$)$R^{10}$, wherein $R^9$ is hydrogen, aryl, heteroaryl, alkyl, or heteroalkyl, each of which is substituted with heterocyclylalkyl that is unsubstituted. In some embodiments is a compound of Formula (I), or a pharmaceutically acceptable salt or solvate thereof, wherein $R^2$ is —C(O)N($R^9$)$R^{10}$, wherein $R^9$ is hydrogen, aryl, heteroaryl, alkyl, or heteroalkyl, each of which is substituted with cycloalkyl that is unsubstituted. In some embodiments is a compound of Formula (I), or a pharmaceutically acceptable salt or solvate thereof, wherein $R^2$ is —C(O)N($R^9$)$R^{10}$, wherein $R^9$ is hydrogen, aryl, heteroaryl, alkyl, or heteroalkyl, each of which is substituted with heteroalkyl. In some embodiments is a compound of Formula (I), or a pharmaceutically acceptable salt or solvate thereof, wherein $R^2$ is —C(O)N($R^9$)$R^{10}$, wherein $R^9$ is hydrogen, aryl, heteroaryl, alkyl, or heteroalkyl, each of which is substituted with heterocyclylalkyl. In some embodiments is a compound of Formula (I), or a pharmaceutically acceptable salt or solvate thereof, wherein $R^2$ is —C(O)N($R^9$)$R^{10}$, wherein $R^9$ is hydrogen, aryl, heteroaryl, alkyl, or heteroalkyl, each of which is substituted with cycloalkyl substituted with alkyl. In some embodiments is a compound of Formula (I), or a pharmaceutically acceptable salt or solvate thereof, wherein $R^2$ is —C(O)N($R^9$)$R^{10}$, wherein $R^9$ is hydrogen, aryl, heteroaryl, alkyl, or heteroalkyl, each of which is substituted with —OC(O)$R^{15}$. In some embodiments is a compound of Formula (I), or a pharmaceutically acceptable salt or solvate thereof, wherein $R^2$ is —C(O)N($R^9$)$R^{10}$, wherein $R^9$ is hydrogen, aryl, heteroaryl, alkyl, or heteroalkyl, each of which is substituted with —OC(O)R$^5$, wherein R$^{15}$ is hydrogen, alkyl, aryl, or heteroaryl. In some embodiments is a compound of Formula (I), or a pharmaceutically acceptable salt or solvate thereof, wherein R$^2$ is —C(O)N(R$^9$)R$^{10}$, wherein R$^9$ is hydrogen, aryl, heteroaryl, alkyl, or heteroalkyl, each of which is substituted with —OC(O)R$^{15}$, wherein R$^{15}$ is hydrogen, unsubstituted alkyl, unsubstituted aryl, or unsubstituted heteroaryl.

In some embodiments is a compound of Formula (I), or a pharmaceutically acceptable salt or solvate thereof, wherein R$^2$ is —C(O)N(R$^9$)R$^{10}$, wherein R$^9$ is hydrogen, alkyl, cycloalkyl, or heteroalkyl. In some embodiments is a compound of Formula (I), or a pharmaceutically acceptable salt or solvate thereof, wherein R$^2$ is —C(O)N(R$^9$)R$^{10}$, wherein R$^9$ is hydrogen, unsubstituted alkyl, unsubstituted cycloalkyl, or unsubstituted heteroalkyl. In some embodiments is a compound of Formula (I), or a pharmaceutically acceptable salt or solvate thereof, wherein R$^2$ is —C(O)N(R$^9$)R$^{10}$, wherein R$^{10}$ is alkyl or heteroalkyl. In some embodiments is a compound of Formula (I), or a pharmaceutically acceptable salt or solvate thereof, wherein R$^2$ is —C(O)N(R$^9$)R$^{10}$, wherein R$^{10}$ is alkyl or heteroalkyl, each of which is substituted with —N(R$^{13}$)C(O)R$^{14}$, wherein each of R$^3$ and R$^{14}$ is independently hydrogen, aryl, heteroaryl, alkyl, or heteroalkyl. In some embodiments is a compound of Formula (I), or a pharmaceutically acceptable salt or solvate thereof, wherein R$^2$ is —C(O)N(R$^9$)R$^{10}$, wherein R$^{10}$ is alkyl or heteroalkyl, each of which is substituted with —C(O)N(R$^{18}$)R$^{19}$, wherein each of R$^{18}$ and R$^{19}$ is independently hydrogen, aryl, heteroaryl, alkyl, or heteroalkyl. In some embodiments is a compound of Formula (I), or a pharmaceutically acceptable salt or solvate thereof, wherein R$^2$ is —C(O)N(R$^9$)R$^{10}$, wherein R$^{10}$ is alkyl or heteroalkyl, each of which is substituted with —N(R$^{13}$)C(O)R$^{14}$, wherein each of R$^3$ and R$^{14}$ is independently hydrogen, unsubstituted aryl, unsubstituted heteroaryl, unsubstituted alkyl, or unsubstituted heteroalkyl. In some embodiments is a compound of Formula (I), or a pharmaceutically acceptable salt or solvate thereof, wherein R$^2$ is —C(O)N(R$^9$)R$^{10}$, wherein R$^{10}$ is alkyl or heteroalkyl, each of which is substituted with —C(O)N(R$^{18}$)R$^{19}$, wherein each of R$^{18}$ and R$^{19}$ is independently hydrogen, unsubstituted aryl, unsubstituted heteroaryl, unsubstituted alkyl, or unsubstituted heteroalkyl.

In some embodiments is a compound of Formula (I), or a pharmaceutically acceptable salt or solvate thereof, wherein R$^2$ is —C(O)N(R$^9$)R$^{10}$, wherein R$^9$ is hydrogen, alkyl, cycloalkyl, or heteroalkyl. In some embodiments is a compound of Formula (I), or a pharmaceutically acceptable salt or solvate thereof, wherein R$^2$ is —C(O)N(R$^9$)R$^{10}$, wherein R$^9$ is hydrogen, unsubstituted alkyl, unsubstituted cycloalkyl, or unsubstituted heteroalkyl. In some embodiments is a compound of Formula (I), or a pharmaceutically acceptable salt or solvate thereof, wherein R$^2$ is —C(O)N(R$^9$)R$^{10}$, wherein R$^{10}$ is cycloalkyl substituted with —N(R$^{18}$)R$^{19}$, wherein each of R$^{18}$ and R$^{19}$ is hydrogen, alkyl, heteroalkyl, or cycloalkyl. In some embodiments is a compound of Formula (I), or a pharmaceutically acceptable salt or solvate thereof, wherein R$^2$ is —C(O)N(R$^9$)R$^{10}$, wherein R$^{10}$ is cycloalkyl substituted with —N(R$^{18}$)R$^{19}$, wherein each of R's and R$^{19}$ is hydrogen, unsubstituted alkyl, unsubstituted heteroalkyl, or unsubstituted cycloalkyl. In some embodiments is a compound of Formula (I), or a pharmaceutically acceptable salt or solvate thereof, wherein R$^2$ is —C(O)N(R$^9$)R$^{10}$, wherein R$^{10}$ is cycloalkyl substituted with —N(R$^{18}$)R$^{19}$, wherein R$^{18}$ and R$^{19}$ together with the atom to which they are attached form a heterocyclylalkyl ring that is unsubstituted.

In some embodiments is a compound of Formula (I), or a pharmaceutically acceptable salt or solvate thereof, wherein R$^2$ is —C(O)N(R$^9$)R$^{10}$, wherein R$^9$ is hydrogen, alkyl, cycloalkyl, or heteroalkyl. In some embodiments is a compound of Formula (I), or a pharmaceutically acceptable salt or solvate thereof, wherein R$^2$ is —C(O)N(R$^9$)R$^{10}$, wherein R$^9$ is hydrogen, unsubstituted alkyl, unsubstituted cycloalkyl, or unsubstituted heteroalkyl. In some embodiments is a compound of Formula (I), or a pharmaceutically acceptable salt or solvate thereof, wherein R$^2$ is —C(O)N(R$^9$)R$^{10}$, wherein R$^{10}$ is alkyl substituted with —OC(O)N(R$^{18}$)R$^{19}$, wherein R$^{18}$ and R$^{19}$ together with the atom to which they are attached form a heteroaryl ring or a heterocyclylalkyl ring, each of which is substituted with alkyl, heteroalkyl, or cycloalkyl. In some embodiments is a compound of Formula (I), or a pharmaceutically acceptable salt or solvate thereof, wherein R$^2$ is —C(O)N(R$^9$)R$^{10}$, wherein R$^{10}$ is alkyl substituted with —OC(O)R$^5$, wherein R$^{15}$ is heterocyclylalkyl substituted with alkyl or arylalkyl.

In some embodiments is a compound of Formula (I), or a pharmaceutically acceptable salt or solvate thereof, wherein R$^2$ is —C(O)R$^4$, wherein R$^4$ is alkyl, heteroalkyl, heterocyclylalkyl, or cycloalkyl. In some embodiments is a compound of Formula (I), or a pharmaceutically acceptable salt or solvate thereof, wherein R$^2$ is —C(O)R$^4$, wherein R$^4$ is unsubstituted alkyl, unsubstituted heteroalkyl, unsubstituted heterocyclylalkyl, or unsubstituted cycloalkyl. In some embodiments is a compound of Formula (I), or a pharmaceutically acceptable salt or solvate thereof, wherein R$^2$ is —C(O)R$^4$, wherein R$^4$ is heterocyclylalkyl substituted with aryl or arylalkyl. In some embodiments is a compound of Formula (I), or a pharmaceutically acceptable salt or solvate thereof, wherein R$^2$ is —C(O)R$^4$, wherein R$^4$ is heterocyclylalkyl substituted with aryl, heterocyclylalkyl, or arylalkyl. In some embodiments is a compound of Formula (I), or a pharmaceutically acceptable salt or solvate thereof, wherein R$^2$ is —C(O)R$^4$, wherein R$^4$ is heterocyclylalkyl substituted with heterocyclylalkyl.

In some embodiments is a compound of Formula (Iu), or a pharmaceutically acceptable salt or solvate thereof, wherein the compound is:

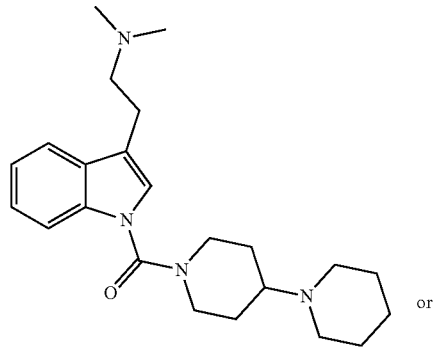 or

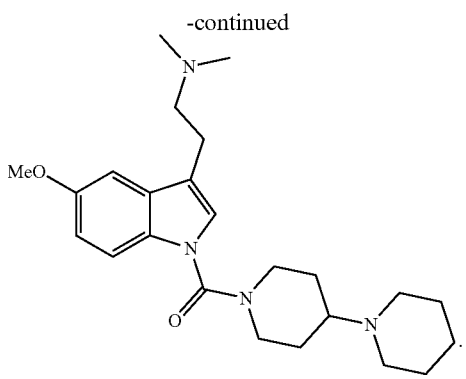

In some embodiments is a compound of Formula (I), or a pharmaceutically acceptable salt or solvate thereof, wherein $R^2$ is —C(O)$R^4$, wherein $R^4$ is alkyl substituted with —C(O)O$R^{13}$. In some embodiments is a compound of Formula (I), or a pharmaceutically acceptable salt or solvate thereof, wherein $R^2$ is —C(O)$R^4$, wherein $R^4$ is alkyl substituted with —C(O)O$R^{13}$, wherein $R^3$ is hydrogen, alkyl, cycloalkyl, aryl, or heteroaryl. In some embodiments is a compound of Formula (I), or a pharmaceutically acceptable salt or solvate thereof, wherein $R^2$ is —C(O)$R^4$, wherein $R^4$ is alkyl substituted with —C(O)O$R^{13}$, wherein $R^{13}$ is hydrogen, unsubstituted alkyl, unsubstituted cycloalkyl, unsubstituted aryl, or unsubstituted heteroaryl. In some embodiments is a compound of Formula (I), or a pharmaceutically acceptable salt or solvate thereof, wherein $R^2$ is —C(O)$R^4$, wherein $R^4$ is alkyl substituted with —OC(O)$R^{15}$, wherein $R^{15}$ is alkyl, cycloalkyl, heteroaryl, or heterocyclylalkyl. In some embodiments is a compound of Formula (I), or a pharmaceutically acceptable salt or solvate thereof, wherein $R^2$ is —C(O)$R^4$, wherein $R^4$ is alkyl substituted with —OC(O)$R^{15}$, wherein $R^{15}$ is alkyl, cycloalkyl, heteroaryl, or heterocyclylalkyl. In some embodiments is a compound of Formula (I), or a pharmaceutically acceptable salt or solvate thereof, wherein $R^2$ is —C(O)$R^4$, wherein $R^4$ is alkyl substituted with —OC(O)$R^{15}$, wherein $R^{15}$ is unsubstituted alkyl, unsubstituted cycloalkyl, unsubstituted heteroaryl, or unsubstituted heterocyclylalkyl. In some embodiments is a compound of Formula (I), or a pharmaceutically acceptable salt or solvate thereof, wherein $R^2$ is —C(O)$R^4$, wherein $R^4$ is alkyl substituted with —OC(O)$R^{15}$, wherein $R^{15}$ is heterocyclylalkyl substituted with alkyl. In some embodiments is a compound of Formula (I), or a pharmaceutically acceptable salt or solvate thereof, wherein $R^2$ is —C(O)$R^4$, wherein $R^4$ is alkyl substituted with —N($R^{13}$)C(O)$R^4$, wherein $R^{13}$ is alkyl, cycloalkyl, or hydrogen; and $R^{14}$ is alkyl, aryl, or heteroaryl. In some embodiments is a compound of Formula (I), or a pharmaceutically acceptable salt or solvate thereof, wherein $R^2$ is —C(O)$R^4$, wherein $R^4$ is alkyl substituted with —N($R^{13}$)C(O)$R^4$, wherein $R^{13}$ is unsubstituted alkyl, unsubstituted cycloalkyl, or hydrogen; and $R^{14}$ is unsubstituted alkyl, unsubstituted aryl, or unsubstituted heteroaryl. In some embodiments is a compound of Formula (I), or a pharmaceutically acceptable salt or solvate thereof, wherein $R^2$ is —C(O)$R^4$, wherein $R^4$ is alkyl substituted with —NH$_2$. In some embodiments is a compound of Formula (I), or a pharmaceutically acceptable salt or solvate thereof, wherein $R^2$ is —C(O)$R^4$, wherein $R^4$ is alkyl substituted with aryl, wherein the aryl is substituted with alkyl or —OC(O)O$R^{16}$. In some embodiments is a compound of Formula (I), or a pharmaceutically acceptable salt or solvate thereof, wherein $R^2$ is —C(O)$R^4$, wherein $R^4$ is alkyl substituted with aryl, wherein the aryl is substituted with alkyl or —OC(O)O$R^{16}$, wherein $R^{16}$ is alkyl, heteroalkyl, cycloalkyl, aryl, or heteroaryl. In some embodiments is a compound of Formula (I), or a pharmaceutically acceptable salt or solvate thereof, wherein $R^2$ is —C(O)$R^4$, wherein $R^4$ is alkyl substituted with aryl, wherein the aryl is substituted with alkyl or —OC(O)O$R^{16}$, wherein $R^{10}$ is unsubstituted alkyl, unsubstituted heteroalkyl, unsubstituted cycloalkyl, unsubstituted aryl, or unsubstituted heteroaryl.

In some embodiments is a compound of Formula (I), or a pharmaceutically acceptable salt or solvate thereof, wherein $R^2$ is —C(O)$R^4$, wherein $R^4$ is heterocyclylalkyl substituted with C(O)$R^{14}$. In some embodiments is a compound of Formula (I), or a pharmaceutically acceptable salt or solvate thereof, wherein $R^2$ is —C(O)$R^4$, wherein $R^4$ is heterocyclylalkyl substituted with C(O)$R^{14}$, wherein $R^{14}$ is alkyl, heteroalkyl, cycloalkyl, or aryl. In some embodiments is a compound of Formula (I), or a pharmaceutically acceptable salt or solvate thereof, wherein $R^2$ is —C(O)$R^4$, wherein $R^4$ is heterocyclylalkyl substituted with C(O)$R^{14}$, wherein $R^{14}$ is unsubstituted alkyl, unsubstituted heteroalkyl, unsubstituted cycloalkyl, or unsubstituted aryl.

In some embodiments is a compound of Formula (I) or a pharmaceutically acceptable salt thereof, wherein $R^2$ is —P(O)O$R^{11}$ (O$R^{12}$) or CH($R^5$)OP(O)O$R^{11}$ (O$R^{12}$), wherein $R^{11}$ is hydrogen, and $R^{12}$ is alkyl, heteroalkyl, cycloalkyl, heterocyclylalkyl, aryl, or heteroaryl, wherein alkyl, heteroalkyl, cycloalkyl, heterocyclylalkyl, aryl, or heteroaryl is unsubstituted or substituted with one or more $R^A$. In some embodiments is a compound of Formula (I) or a pharmaceutically acceptable salt thereof, wherein $R^2$ is —P(O)O$R^{11}$ (O$R^{12}$) or CH($R^5$)OP(O)O$R^{11}$ (O$R^{12}$), wherein $R^{11}$ is hydrogen, and $R^{12}$ is alkyl that is unsubstituted or substituted with one or more $R^A$.

In some embodiments is a compound of Formula (I) or (Iu), or a pharmaceutically acceptable salt thereof, wherein $R^{20}$ is hydrogen, and $R^{21}$ is alkyl, alkyl, heteroalkyl, cycloalkyl, heterocyclylalkyl, aryl, heteroaryl, or hydrogen, wherein alkyl, heteroalkyl, cycloalkyl, heterocyclylalkyl, aryl, or heteroaryl is unsubstituted or substituted with one or more $R^B$, or $R^{20}$ and $R^{21}$ together with the atoms to which they are attached form a heterocyclylalkyl ring that is unsubstituted or substituted with one or more $R^B$. In some embodiments is a compound of Formula (I) or (Iu) or a pharmaceutically acceptable salt thereof, wherein $R^{20}$ is hydrogen, and $R^{21}$ is alkyl that is unsubstituted or substituted with one or more $R^B$.

In some embodiments is a compound of Formula (I), or a pharmaceutically acceptable salt thereof, wherein $R^2$ is —CH($R^5$)OC(O)O$R^6$. In some embodiments is a compound of Formula (I), or a pharmaceutically acceptable salt thereof, wherein $R^2$ is —CH($R^5$)OC(O)O$R^6$, wherein each of $R^5$ and $R^6$ is independently hydrogen, alkyl, heteroalkyl, cycloalkyl, heterocyclylalkyl, aryl, or heteroaryl, wherein each alkyl, heteroalkyl, cycloalkyl, heterocyclylalkyl, aryl, and heteroaryl is independently unsubstituted or substituted with one or more $R^A$. In some embodiments is a compound of Formula (I), or a pharmaceutically acceptable salt thereof, wherein $R^2$ is —CH($R^5$)OC(O)O$R^6$, wherein each of $R^5$ and $R^6$ is independently hydrogen or alkyl that is unsubstituted or substituted with one or more $R^A$. In some embodiments is a compound of Formula (I), or a pharmaceutically acceptable salt thereof, wherein $R^2$ is —CH($R^5$)OC(O)O$R^6$, wherein $R^5$ is hydrogen and $R^6$ is hydrogen or alkyl that is unsubstituted or substituted with one or more $R^A$. In some embodiments is a compound of Formula (I), or a pharmaceutically acceptable salt thereof, wherein $R^2$ is —CH($R^5$)

OC(O)OR$^6$, wherein R$^5$ is hydrogen and R$^6$ is methyl, ethyl, n-propyl, isopropyl, isobutyl, tert-butyl, or n-butyl. In some embodiments is a compound of Formula (I), or a pharmaceutically acceptable salt thereof, wherein R$^2$ is —CH(R$^5$)OC(O)OR$^6$, wherein R$^5$ is hydrogen and R$^6$ is ethyl.

In some embodiments is a compound of Formula (I), or a pharmaceutically acceptable salt or solvate thereof, wherein R$^2$ is —CH(R$^5$)OP(O)OR$^{11}$ (OR$^{12}$). In some embodiments is a compound of Formula (I), or a pharmaceutically acceptable salt or solvate thereof, wherein R$^2$ is —CH(R$^5$)OP(O)OR$^{11}$ (OR$^{12}$), wherein R$^5$ is hydrogen, alkyl, cycloalkyl, or heteroalkyl. In some embodiments is a compound of Formula (I), or a pharmaceutically acceptable salt or solvate thereof, wherein R$^2$ is —CH(R$^5$)OP(O)OR$^{11}$ (OR$^{12}$), wherein R$^5$ is hydrogen, unsubstituted alkyl, unsubstituted cycloalkyl, unsubstituted heteroalkyl, or alkyl substituted with heteroaryl. In some embodiments is a compound of Formula (I), or a pharmaceutically acceptable salt or solvate thereof, wherein R$^2$ is —CH(R$^5$)OP(O)OR$^{11}$ (OR$^{12}$), wherein each of R$^{11}$ and R$^{12}$ is independently selected from alkyl, cycloalkyl, aryl, heteroaryl, or alkyl. In some embodiments is a compound of Formula (I), or a pharmaceutically acceptable salt or solvate thereof, wherein R$^2$ is —CH(R$^5$)OP(O)OR$^{11}$ (OR$^{12}$), wherein each of R$^{11}$ and R$^{12}$ is independently selected from unsubstituted alkyl, unsubstituted cycloalkyl, unsubstituted aryl, unsubstituted heteroaryl, unsubstituted alkyl, or alkyl substituted with aryl or heteroaryl. In some embodiments is a compound of Formula (I), or a pharmaceutically acceptable salt or solvate thereof, wherein R$^2$ is —CH(R$^5$)OP(O)OR$^{11}$ (OR$^{12}$), wherein each of R$^{11}$ and R$^{12}$ is alkyl. In some embodiments is a compound of Formula (I), or a pharmaceutically acceptable salt or solvate thereof, wherein R$^2$ is —CH(R$^5$)OP(O)OR$^{11}$ (OR$^{12}$), wherein each of R$^{11}$ and R$^{12}$ is unsubstituted alkyl. In some embodiments is a compound of Formula (I), or a pharmaceutically acceptable salt or solvate thereof, wherein R$^2$ is —CH(R$^5$)OP(O)OR$^{11}$(OR$^{12}$), wherein each of R$^{11}$ and R$^{12}$ is alkyl substituted with —OC(O)R$^{15}$. In some embodiments is a compound of Formula (I), or a pharmaceutically acceptable salt or solvate thereof, wherein R$^2$ is —CH(R$^5$)OP(O)OR$^{11}$ (OR$^{12}$), wherein each of R$^{11}$ and R$^{12}$ is alkyl substituted with —OC(O)R", wherein each R$^{15}$ is alkyl, cycloalkyl, heterocyclylalkyl, aryl, or heteroaryl. In some embodiments is a compound of Formula (I), or a pharmaceutically acceptable salt or solvate thereof, wherein R$^2$ is —CH(R$^5$)OP(O)OR$^{11}$ (OR$^{12}$), wherein each of R$^{11}$ and R$^{12}$ is alkyl substituted with —OC(O)R$^{15}$, wherein each R$^{15}$ is unsubstituted alkyl, unsubstituted cycloalkyl, unsubstituted heterocyclylalkyl, unsubstituted aryl, or unsubstituted heteroaryl. In some embodiments is a compound of Formula (I), or a pharmaceutically acceptable salt or solvate thereof, wherein R$^2$ is —CH(R$^5$)OP(O)OR$^{11}$ (OR$^{12}$), wherein each of R$^{11}$ and R$^{12}$ is alkyl substituted with —OC(O)R$^{15}$, wherein each R$^{15}$ is heterocyclylalkyl substituted with alkyl or arylalkyl.

In some embodiments is a compound of Formula (I), or a pharmaceutically acceptable salt or solvate thereof, wherein R$^2$ is —CH(R$^5$)OP(O)OR$^8$[N(R$^9$)R$^{10}$]. In some embodiments is a compound of Formula (I), or a pharmaceutically acceptable salt or solvate thereof, wherein R$^2$ is —CH(R$^5$)OP(O)OR$^8$[N(R$^9$)R$^{10}$], wherein R$^5$ is hydrogen, alkyl, cycloalkyl, heteroalkyl, or alkyl substituted with heteroaryl. In some embodiments is a compound of Formula (I), or a pharmaceutically acceptable salt or solvate thereof, wherein R$^2$ is —CH(R$^5$)OP(O)OR$^8$[N(R$^9$)R$^{10}$], wherein R$^4$ is hydrogen, unsubstituted alkyl, unsubstituted cycloalkyl, unsubstituted heteroalkyl, or alkyl substituted with heteroaryl. In some embodiments is a compound of Formula (I), or a pharmaceutically acceptable salt or solvate thereof, wherein R$^2$ is —CH(R$^5$)OP(O)OR$^8$[N(R$^9$)R$^{10}$], wherein R$^8$ is alkyl, cycloalkyl, aryl, heteroaryl, alkyl, or alkyl substituted with aryl or heteroaryl; R$^9$ is hydrogen; and R$^{12}$ is alkyl substituted with —C(O)OR$^{13}$. In some embodiments is a compound of Formula (I), or a pharmaceutically acceptable salt or solvate thereof, wherein R$^2$ is —CH(R$^5$)OP(O)OR$^8$[N(R$^9$)R$^{10}$], wherein R$^8$ is unsubstituted alkyl, unsubstituted cycloalkyl, unsubstituted aryl, unsubstituted heteroaryl, unsubstituted alkyl, or alkyl substituted with aryl or heteroaryl; R$^9$ is hydrogen; and R$^{12}$ is alkyl substituted with —C(O)OR$^{13}$. In some embodiments is a compound of Formula (I), or a pharmaceutically acceptable salt or solvate thereof, wherein R$^{13}$ is alkyl. In some embodiments is a compound of Formula (I), or a pharmaceutically acceptable salt or solvate thereof, wherein R$^2$ is —CH(R$^5$)OP(O)OR$^8$[N(R$^9$)R$^{10}$], wherein R$^{12}$ is alkyl substituted with —C(O)OR$^{13}$, wherein R$^{13}$ is unsubstituted alkyl.

In some embodiments is a compound of Formula (I), or a pharmaceutically acceptable salt or solvate thereof, wherein R$^2$ is —P(O)OR$^{11}$ (OR$^{12}$). In some embodiments is a compound of Formula (I), or a pharmaceutically acceptable salt or solvate thereof, wherein R$^2$ is —P(O)OR$^{11}$ (OR$^{12}$), wherein each of R$^{11}$ and R$^{12}$ is alkyl. In some embodiments is a compound of Formula (I), or a pharmaceutically acceptable salt or solvate thereof, wherein R$^2$ is —P(O)OR$^{11}$ (OR$^{12}$), wherein each of R$^{11}$ and R$^{12}$ is unsubstituted alkyl. In some embodiments is a compound of Formula (I), or a pharmaceutically acceptable salt or solvate thereof, wherein R$^2$ is —P(O)OR$^{11}$ (OR$^{12}$), wherein each of R$^{11}$ and R$^{12}$ is alkyl substituted with —C(O)OR$^{13}$. In some embodiments is a compound of Formula (I), or a pharmaceutically acceptable salt or solvate thereof, wherein R$^2$ is —P(O)OR$^{11}$ (OR$^{12}$), wherein R$^3$ is alkyl, cycloalkyl, aryl, or heteroaryl. In some embodiments is a compound of Formula (I), or a pharmaceutically acceptable salt or solvate thereof, wherein R$^2$ is —P(O)OR$^{11}$ (OR$^{12}$), wherein R$^{13}$ is unsubstituted alkyl, unsubstituted cycloalkyl, unsubstituted aryl, or unsubstituted heteroaryl. In some embodiments is a compound of Formula (I), or a pharmaceutically acceptable salt or solvate thereof, wherein R$^2$ is —P(O)OR$^{11}$ (OR$^{12}$), wherein each of R$^{11}$ and R$^{12}$ is alkyl substituted with —OC(O)R$^{15}$. In some embodiments is a compound of Formula (I), or a pharmaceutically acceptable salt or solvate thereof, wherein R$^2$ is —P(O)OR$^{11}$ (OR$^{12}$), wherein each of R$^{11}$ and R$^{12}$ is alkyl substituted with —OC(O)R$^{15}$, wherein R$^5$ is alkyl, cycloalkyl, heteroaryl, or heterocyclylalkyl. In some embodiments is a compound of Formula (I), or a pharmaceutically acceptable salt or solvate thereof, wherein R$^2$ is —P(O)OR$^{11}$ (OR$^{12}$), wherein each of R$^{11}$ and R$^{12}$ is alkyl substituted with —OC(O)R$^{15}$, wherein R$^5$ is unsubstituted alkyl, unsubstituted cycloalkyl, unsubstituted heteroaryl, or unsubstituted heterocyclylalkyl. In some embodiments is a compound of Formula (I), or a pharmaceutically acceptable salt or solvate thereof, wherein R$^2$ is —P(O)OR$^{11}$ (OR$^{12}$), wherein each of R$^{11}$ and R$^{12}$ is alkyl substituted with —OC(O)R$^{15}$, wherein R$^{15}$ is heterocyclylalkyl substituted with alkyl or arylalkyl. In some embodiments is a compound of Formula (I), or a pharmaceutically acceptable salt or solvate thereof, wherein R$^2$ is —P(O)OR$^{11}$ (OR$^{12}$), wherein each of R$^{11}$ and R$^{12}$ is alkyl substituted with —OC(O)OR$^{16}$, wherein R$^{16}$ is alkyl, cycloalkyl, heteroaryl, or heterocyclylalkyl. In some embodiments is a compound of Formula (I), or a pharmaceutically acceptable salt or solvate thereof, wherein R$^2$ is —P(O)OR$^{11}$ (OR$^{12}$), wherein each of R$^{11}$ and R$^{12}$ is alkyl substituted with —OC(O)OR$^{16}$, wherein R$^{16}$ is unsubstituted alkyl, unsubstituted cycloalkyl, unsubstituted heteroaryl, or unsubstituted heterocyclylalkyl.

In some embodiments is a compound of Formula (I), or a pharmaceutically acceptable salt or solvate thereof, wherein $R^2$ is —P(O)OR$^{11}$ (OR$^{12}$), wherein $R^{11}$ and $R^{12}$ together with the atom to which they are attached form a heterocyclylalkyl ring. In some embodiments is a compound of Formula (I), or a pharmaceutically acceptable salt or solvate thereof, wherein $R^2$ is —P(O)OR$^{11}$ (OR$^{12}$), wherein $R^{11}$ and $R^{12}$ together with the atom to which they are attached form a heterocyclylalkyl ring that is unsubstituted. In some embodiments is a compound of Formula (I), or a pharmaceutically acceptable salt or solvate thereof, wherein $R^2$ is —P(O)OR$^{11}$ (OR$^{12}$), wherein $R^{11}$ and $R^{12}$ together with the atom to which they are attached form a heterocyclylalkyl ring that is substituted with aryl. In some embodiments is a compound of Formula (I), or a pharmaceutically acceptable salt or solvate thereof, wherein $R^2$ is —P(O)OR$^{11}$ (OR$^{12}$), wherein $R^{11}$ and $R^{12}$ together with the atom to which they are attached form a heterocyclylalkyl ring that is substituted with unsubstituted aryl. In some embodiments is a compound of Formula (I), or a pharmaceutically acceptable salt or solvate thereof, wherein $R^2$ is —P(O)OR$^{11}$ (OR$^{12}$), wherein $R^{11}$ and $R^{12}$ together with the atom to which they are attached form a heterocyclylalkyl ring that is substituted with aryl, wherein the aryl is substituted with halogen.

In some embodiments is a compound of Formula (I), or a pharmaceutically acceptable salt or solvate thereof, wherein $R^2$ is —P(O)OR$^8$[N(R$^9$)R$^{10}$]. In some embodiments is a compound of Formula (I), or a pharmaceutically acceptable salt or solvate thereof, wherein $R^2$ is —P(O)OR$^8$[N(R$^9$)R$^{10}$], wherein $R^8$ is alkyl, aryl, or heteroaryl. In some embodiments is a compound of Formula (I), or a pharmaceutically acceptable salt or solvate thereof, wherein $R^2$ is —P(O)OR$^8$[N(R$^9$)R$^{10}$], wherein $R^8$ is unsubstituted alkyl, unsubstituted aryl, or unsubstituted heteroaryl. In some embodiments is a compound of Formula (I), or a pharmaceutically acceptable salt or solvate thereof, wherein $R^2$ is —P(O)OR$^8$[N(R$^9$)R$^{10}$], wherein each of $R^9$ and $R^{10}$ are independently selected from hydrogen or alkyl. In some embodiments is a compound of Formula (I), or a pharmaceutically acceptable salt or solvate thereof, wherein $R^2$ is —P(O)OR$^8$[N(R$^9$)R$^{10}$], wherein $R^8$ is unsubstituted alkyl, unsubstituted aryl, or unsubstituted heteroaryl, $R^9$ is hydrogen, and $R^{10}$ is alkyl. In some embodiments is a compound of Formula (I), or a pharmaceutically acceptable salt or solvate thereof, wherein $R^2$ is —P(O)OR$^8$[N(R$^9$)R$^{10}$], wherein $R^8$ is unsubstituted alkyl, unsubstituted aryl, or unsubstituted heteroaryl, $R^9$ is hydrogen, and $R^{10}$ is alkyl substituted with —C(O)R$^{14}$. In some embodiments is a compound of Formula (I), or a pharmaceutically acceptable salt or solvate thereof, wherein $R^2$ is —P(O)OR$^8$[N(R$^9$)R$^{10}$], wherein $R^{10}$ is alkyl substituted with —C(O)R$^{14}$, wherein $R^{14}$ is hydrogen or alkyl. In some embodiments is a compound of Formula (I), or a pharmaceutically acceptable salt or solvate thereof, wherein $R^{14}$ is unsubstituted alkyl.

In some embodiments is a compound of Formula (I), or a pharmaceutically acceptable salt or solvate thereof, wherein $R^2$ is —S(O)$_2$OR$^7$. In some embodiments is a compound of Formula (I), or a pharmaceutically acceptable salt or solvate thereof, wherein $R^2$ is —S(O)$_2$OR$^7$, wherein $R^7$ is alkyl. In some embodiments is a compound of Formula (I), or a pharmaceutically acceptable salt or solvate thereof, wherein $R^2$ is —S(O)$_2$OR$^7$, wherein $R^7$ is alkyl substituted with —C(O)R$^{14}$. In some embodiments is a compound of Formula (I), or a pharmaceutically acceptable salt or solvate thereof, wherein $R^7$ is alkyl substituted with —C(O)R$^{14}$, wherein $R^{14}$ is alkyl, heteroalkyl, cycloalkyl, heterocyclylalkyl, aryl, or heteroaryl. In some embodiments is a compound of Formula (I), or a pharmaceutically acceptable salt or solvate thereof, wherein $R^2$ is —S(O)$_2$OR$^7$, wherein $R^7$ is alkyl substituted with —C(O)R$^{14}$. In some embodiments is a compound of Formula (I), or a pharmaceutically acceptable salt or solvate thereof, wherein $R^7$ is alkyl substituted with —C(O)R$^{14}$, wherein $R^{14}$ is heterocyclylalkyl. In some embodiments is a compound of Formula (I), or a pharmaceutically acceptable salt or solvate thereof, wherein $R^2$ is —S(O)$_2$OR$^7$, wherein $R^7$ is alkyl substituted with —C(O)R$^{14}$. In some embodiments is a compound of Formula (I), or a pharmaceutically acceptable salt or solvate thereof, wherein $R^7$ is alkyl substituted with —C(O)R$^{14}$, wherein $R^{14}$ is heterocyclylalkyl substituted with alkyl, —C(O)CH$_3$, or C(O)Ph.

In some embodiments is a compound of Formula ((I), (Ia), (Ib), (Ib-1) (Ib1), (Ic), (Id), (Ie), (If), (If1), (Ig), (Ih), (Ii), (Ij), (Ik), (Ik1), (Ik2), (Ik3), (Il), (Im), (Im1), (Im1a), (In), (In1), (Io), (Io1), (Io2), (Io1a), (Ip) (Ip1), (Iq), (Iq1), (Ir), (Ir1), (Is), (It), (Iu), (Iv), or (Iw), or a pharmaceutically acceptable salt thereof, wherein $R^1$ is hydrogen. In some embodiments is a compound of Formula (I), (Ia), (Ib), (Ib-1) (Ib1), (Ic), (Id), (Ie), (If), (If1), (Ig), (Ih), (Ii), (Ij), (Ik), (Ik1), (Ik2), (Ik3), (Il), (Im), (Im1), (Im1a), (In), (In1), (Io), (Io1), (Io2), (Io1a), (Ip) (Ip1), (Iq), (Iq1), (Ir), (Ir1), (Is), (It), (Iu), (Iv), or (Iw), or a pharmaceutically acceptable salt thereof, wherein $R^1$ is methoxy.

In some embodiments is a compound of Formula (I), or a pharmaceutically acceptable salt or solvate thereof, wherein $R^2$ is —C(O)OR$^3$, wherein $R^3$ is alkyl substituted with —OP(O)OR$^{20}$ (OR$^{21}$). In some embodiments is a compound of Formula (I), or a pharmaceutically acceptable salt or solvate thereof, wherein $R^2$ is —C(O)OR$^3$, wherein $R^3$ is alkyl substituted with —OP(O)OR$^{20}$ (OR$^{21}$), wherein each of $R^{20}$ and $R^{21}$ is independently alkyl, cycloalkyl, aryl, heterocyclylalkyl, or heteroaryl. In some embodiments is a compound of Formula (I), or a pharmaceutically acceptable salt or solvate thereof, wherein $R^2$ is —C(O)OR$^3$, wherein $R^3$ is alkyl substituted with —OP(O)OR$^{20}$ (OR$^{21}$), wherein each of $R^{20}$ and $R^{21}$ is independently alkyl. In some embodiments is a compound of Formula (I), or a pharmaceutically acceptable salt or solvate thereof, wherein $R^2$ is —C(O)OR$^3$, wherein $R^3$ is alkyl substituted with —OP(O)OR$^{20}$ (OR$^{21}$), wherein each of $R^{20}$ and $R^{21}$ is independently unsubstituted alkyl, unsubstituted cycloalkyl, unsubstituted aryl, unsubstituted heterocyclylalkyl, or unsubstituted heteroaryl. In some embodiments is a compound of Formula (I), or a pharmaceutically acceptable salt or solvate thereof, wherein $R^2$ is —C(O)OR$^3$, wherein $R^3$ is alkyl substituted with —OP(O)OR$^{20}$ (OR$^{21}$), wherein each of $R^{20}$ and $R^{21}$ is independently unsubstituted alkyl.

In another aspect, the present disclosure provides a pharmaceutically acceptable composition comprising a compound according to any of Formula (I), (Ia), (Ib), (Ib-1) (Ib1), (Ic), (Id), (Ie), (If), (If1), (Ig), (Ih), (Ii), (Ij), (Ik), (Ik1), (Ik2), (Ik3), (Il), (Im), (Im1), (Im1a), (In), (In1), (Io), (Io1), (Io2), (Io1a), (Ip) (Ip1), (Iq), (Iq1), (Ir), (Ir1), (Is), (It), (Iu), (Iv), or (Iw), or a pharmaceutically acceptable salt thereof, and a pharmaceutically acceptable excipient, carrier, adjuvant, or vehicle.

Pharmaceutical compositions of the present disclosure can comprise racemic, scalemic, or diastereomerically enriched mixtures of any compound described herein comprising a stereogenic center.

Selected compounds of the disclosure with corresponding simplified molecular-input line-entry system (SMILES) strings are provided in TABLE 1.
TABLE 1
| Cpd | Structure SMILES* |
|---|---|
| 1 | 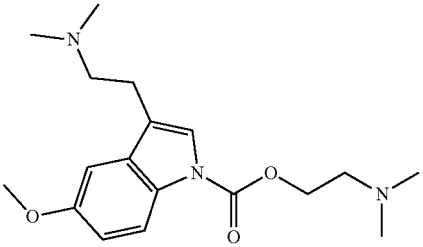<br>CN(CCC1=CN(C2=C1C=C(OC)C=C2)C(OCCN(C)C)=O)C |
| 2 | 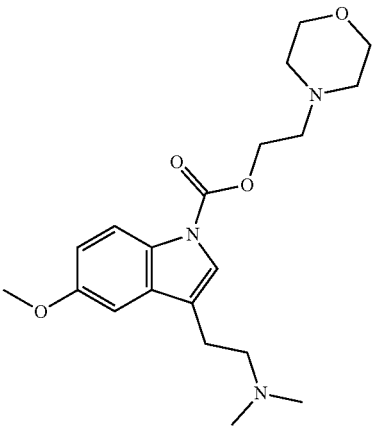 [SMILES: COc1ccc2c(c1)c(CCN(C)C)cn2C(=O)OCCN1CCOCC1]<br>CN(CCC1=CN(C2=C1C=C(OC)C=C2)C(OCCN3CCOCC3)=O)C |
| 3 | 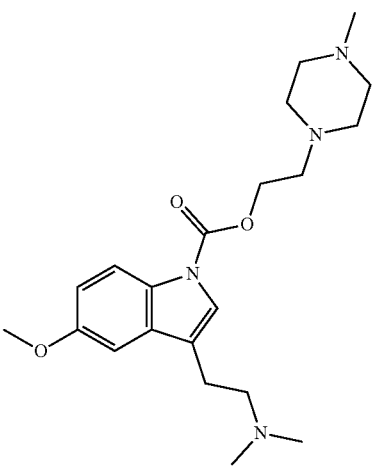 [SMILES: COc1ccc2c(c1)c(CCN(C)C)cn2C(=O)OCCN1CCN(C)CC1]<br>CN(CCC1=CN(C2=C1C=C(OC)C=C2)C(OCCN3CCN(CC3)C)=O)C |

TABLE 1-continued
| Cpd | Structure SMILES* |
|---|---|
| 4 | 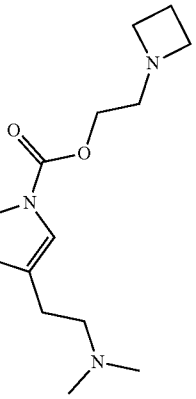<br>CN(CCC1=CN(C2=C1C=C(OC)C=C2)C(OCCN3CCC3)=O)C |
| 5 | <br>CN(CCC1=CN(C2=C1C=C(OC)C=C2)C(OCCN3CCCC3)=O)C |
| 6 | <br>CN(CCC1=CN(C2=C1C=C(OC)C=C2)C(OCCN3CCCCC3)=O)C |

TABLE 1-continued

| Cpd | Structure SMILES* |
|---|---|
| 7 | CN(CCC1=CN(C2=C1C=C(OC)C=C2)C(OCCN3CCCCC34COC4)=O)C |
| 8 | CN(CCC1=CN(C2=C1C=C(OC)C=C2)C(OCCN3CC4(C3)COC4)=O)C |
| 9 | CN(CCC1=CN(C2=C1C=C(OC)C=C2)C(OCCN3CCC34COC4)=O)C |

TABLE 1-continued

| Cpd | Structure SMILES* |
|---|---|
| 10 | CN(CCC1=CN(C2=C1C=CC=C2)C(OCCN(C)C)=O)C |
| 11 | CN(CCC1=CN(C2=C1C=C(OC)C=C2)C(OCCN3CCOCC3)=O)C |
| 12 | CN(CCC1=CN(C2=C1C=CC=C2)C(OCCN3CCN(CC3)C)=O)C |

TABLE 1-continued
| Cpd | Structure SMILES* |
|---|---|
| 13 | 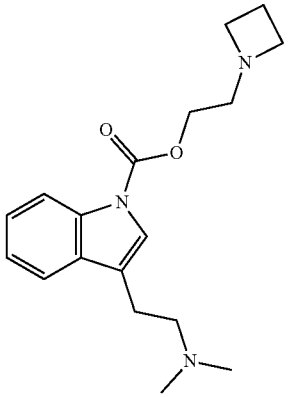 [SMILES: CN(C)CCc1cn(C(=O)OCCN2CCC2)c2ccccc12]
CN(CCC1=CN(C2=C1C=CC=C2)C(OCCN3CCC3)=O)C |
| 14 | 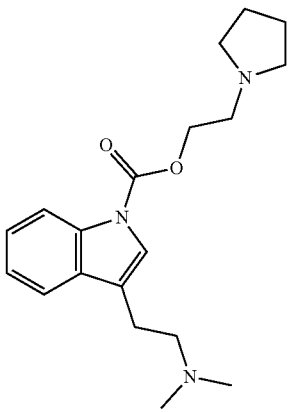 [SMILES: CN(C)CCc1cn(C(=O)OCCN2CCCC2)c2ccccc12]
CN(CCC1=CN(C2=C1C=CC=C2)C(OCCN3CCCC3)=O)C |
| 15 | 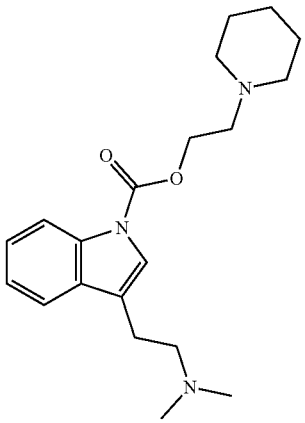 [SMILES: CN(C)CCc1cn(C(=O)OCCN2CCCCC2)c2ccccc12]
CN(CCC1=CN(C2=C1C=CC=C2)C(OCCN3CCCCC3)=O)C |

| Cpd | Structure<br>SMILES* |
|---|---|
| 16 | 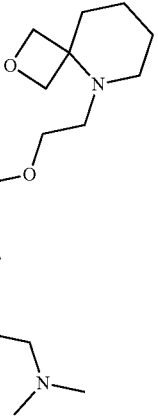<br>CN(CCC1=CN(C2=C1C=CC=C2)C(OCCN3CCCCC34COC4)=O)C |
| 17 | 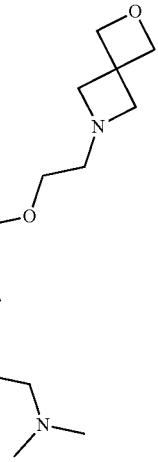<br>CN(CCC1=CN(C2=C1C=CC=C2)C(OCCN3CCC4(C3)COC4)=O)C |
| 18 | 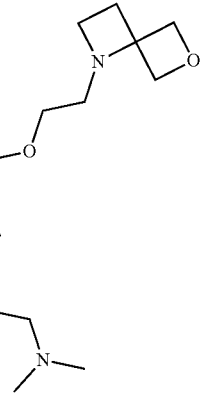<br>CN(CCC1=CN(C2=C1C=CC=C2)C(OCCN3CCC34COC4)=O)C |

TABLE 1-continued

| Cpd | Structure SMILES* |
|---|---|

19

CN(CCC1=CN(C2=C1C=C(OC)C=C2)C(OCC)=O)C

20

CN(CCC1=CN(C2=C1C=CC=C2)C(OCC)=O)C

21

CN(CCC1=CN(C2=C1C=C(OC)C=C2)C(OCC(OC3=O)=C(O3)C)=O)C

22

CN(CCC1=CN(C2=C1C=C(OC)C=C2)C(OCCOC)=O)C

TABLE 1-continued

| Cpd | Structure SMILES* |
|---|---|
| 23 | CN(CCC1=CN(C2=C1C=C(OC)C=C2)C(OCCOC3CC3)=O)C |
| 24 | CN(CCC1=CN(C2=C1C=CC=C2)C(OCC(OC3=O)=C(O3)C)=O)C |
| 25 | CN(CCC1=CN(C2=C1C=CC=C2)C(OCCOC)=O)C |
| 26 | CN(CCC1=CN(C2=C1C=CC=C2)C(OCCOC3CC3)=O)C |

TABLE 1-continued

| Cpd | Structure SMILES* |
|---|---|
| 27 | CN(CCC1=CN(C2=C1C=CC=C2)C(OCOC(N3C4=C(C(CCN(C)C)=C3)C=C3)C=CC=C4)=O)=O)C |
| 28 | CN(CCC1=CN(C2=C1C=C(OC)C=C2)C(OCOC(N3C4=C(C(CCN(C)C)=C3)C=CC=C4)=O)=O)C |
| 29 | CN(CCC1=CN(C2=C1C=CC=C2)C(OC3CCC(CC3)N)=O)C |
| 30 | CN(CCC1=CN(C2=C1C=CC=C2)C(OC3CCC(CC3)NC)=O)C |

TABLE 1-continued
| Cpd | Structure SMILES* |
|---|---|
| 31 | 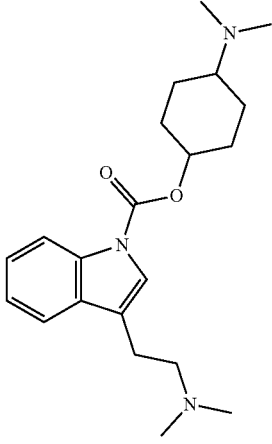 [SMILES: CN(C)CCc1cn(C(=O)OC2CCC(N(C)C)CC2)c2ccccc12]<br>CN(CCC1=CN(C2=C1C=CC=C2)C(OC3CCC(CC3)N(C)C)=O)C |
| 32 | 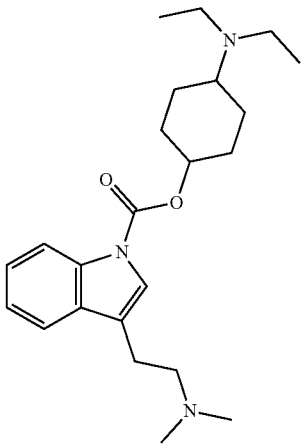 [SMILES: CCN(CC)C1CCC(OC(=O)n2cc(CCN(C)C)c3ccccc32)CC1]<br>CN(CCC1=CN(C2=C1C=CC=C2)C(OC3CCC(CC3)N(CC)CC)=O)C |
| 33 | 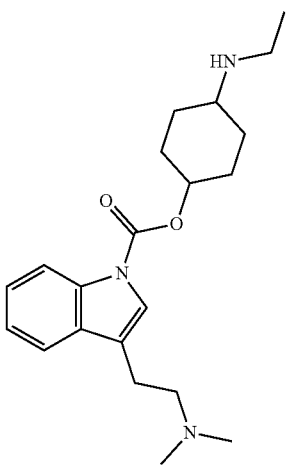 [SMILES: CCNC1CCC(OC(=O)n2cc(CCN(C)C)c3ccccc32)CC1]<br>CN(CCC1=CN(C2=C1C=CC=C2)C(OC3CCC(CC3)NCC)=O)C |

TABLE 1-continued
| Cpd | Structure SMILES* |
|---|---|
| 34 | 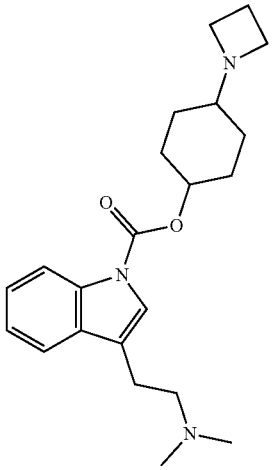 [SMILES: CN(C)CCc1cn(C(=O)OC2CCC(N3CCC3)CC2)c2ccccc12]<br>CN(CCC1=CN(C2=C1C=CC=C2)C(OC3CCC(CC3)N4CCC4)=O)C |
| 35 | 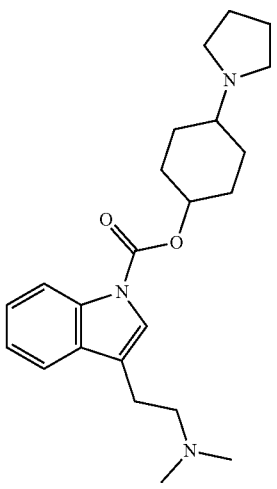 [SMILES: CN(C)CCc1cn(C(=O)OC2CCC(N3CCCC3)CC2)c2ccccc12]<br>CN(CCC1=CN(C2=C1C=CC=C2)C(OC3CCC(CC3)N4CCCC4)=O)C |
| 36 | 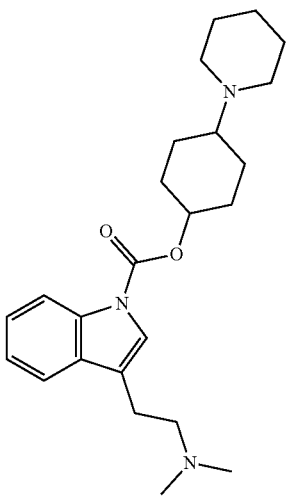 [SMILES: CN(C)CCc1cn(C(=O)OC2CCC(N3CCCCC3)CC2)c2ccccc12]<br>CN(CCC1=CN(C2=C1C=CC=C2)C(OC3CCC(CC3)N4CCCCC4)=O)C |

TABLE 1-continued

| Cpd | Structure SMILES* |
|---|---|
| 37 | CN(CCC1=CN(C2=C1C=C(OC)C=C2)C(OC3CCC(CC3)N)=O)C |
| 38 | CN(CCC1=CN(C2=C1C=C(OC)C=C2)C(OC3CCC(CC3)NC)=O)C |
| 39 | CN(CCC1=CN(C2=C1C=C(OC)C=C2)C(OC3CCC(CC3)N(C)C)=O)C |

TABLE 1-continued

| Cpd | Structure SMILES* |
|---|---|
| 40 | CN(CCC1=CN(C2=C1C=C(OC)C=C2)C(OC3CCC(CC3)N(CC)CC)=O)C |
| 41 | CN(CCC1=CN(C2=C1C=C(OC)C=C2)C(OC3CCC(CC3)NCC)=O)C |
| 42 | CN(CCC1=CN(C2=C1C=C(OC)C=C2)C(OC3CCC(CC3)N4CCC4)=O)C |

TABLE 1-continued

| Cpd | Structure SMILES* |
|---|---|
| 43 | CN(CCC1=CN(C2=C1C=C(OC)C=C2)C(OC3CCC(CC3)N4CCCC4)=O)C |
| 44 | CN(CCC1=CN(C2=C1C=C(OC)C=C2)C(OC3CCC(CC3)N4CCCCC4)=O)C |
| 45 | CN(CCC1=CN(C2=C1C=CC=C2)C(OCOC(C3=CNC=CC3)=O)=O)C |

TABLE 1-continued
| Cpd | Structure SMILES* |
|---|---|
46
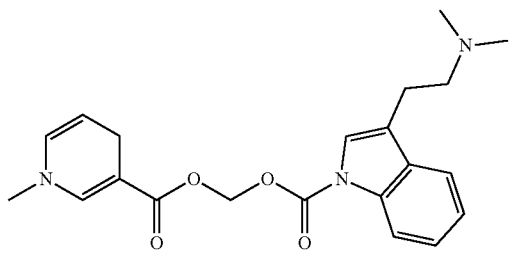
CN(CCC1=CN(C2=C1C=CC=C2)C(OCOC(C3=CN(C)C=CC3)=O)=O)C
47
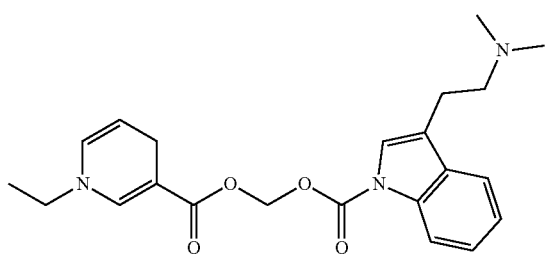 [SMILES: CCN1C=CCC(C(=O)OCOC(=O)n2cc(CCN(C)C)c3ccccc32)=C1]
CN(CCC1=CN(C2=C1C=CC=C2)C(OCOC(C3=CN(C=CC3)CC)=O)=O)C
48
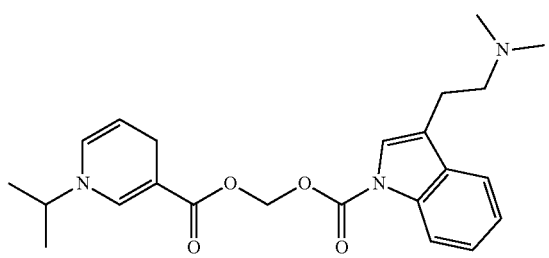 [SMILES: CC(C)N1C=CCC(C(=O)OCOC(=O)n2cc(CCN(C)C)c3ccccc32)=C1]
CN(CCC1=CN(C2=C1C=CC=C2)C(OCOC(C3=CN(=CC3)C(C)C)=O)=O)C
49
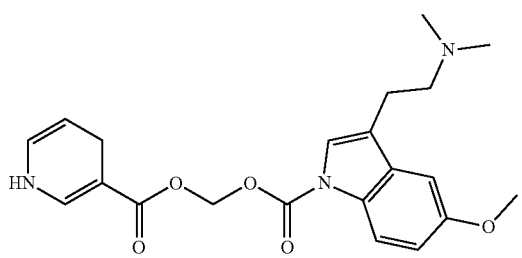 [SMILES: COc1ccc2c(c1)c(CCN(C)C)cn2C(=O)OCOC(=O)C1=CNC=CC1]
CN(CCC1=CN(C2=C1C=C(OC)C=C2)C(OCOC(C3=CNC=CC3)=O)=O)C
50
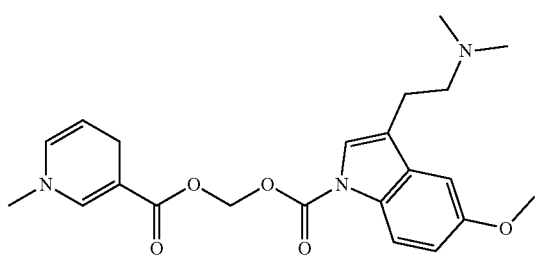
CN(CCC1=CN(C2=C1C=C(OC)C=C2)C(OCOC(C3=CN(C)C=CC3)=O)=O)C TABLE 1-continued
| Cpd | Structure SMILES* |
|---|---|
51
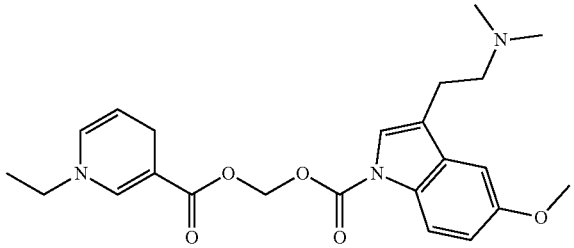 [SMILES: CCN1C=CCC(C(=O)OCOC(=O)n2cc(CCN(C)C)c3cc(OC)ccc32)=C1]
CN(CCC1=CN(C2=C1C=C(OC)C=C2)C(OCOC(C3=CN(C=CC3)CC)=O)=O)C
52
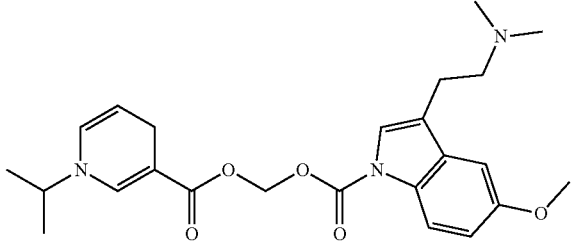
CN(CCC1=CN(C2=C1C=C(OC)C=C2)C(OCOC(C3=CN(C=CC3)C(C)C)=O)=O)C
53
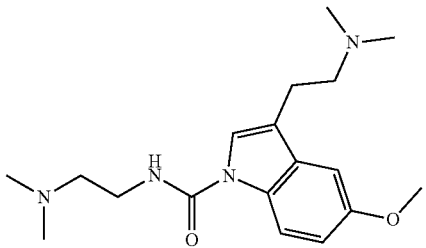
CN(CCC1=CN(C2=C1C=C(OC)C=C2)C(NCCN(C)C)=O)C
54
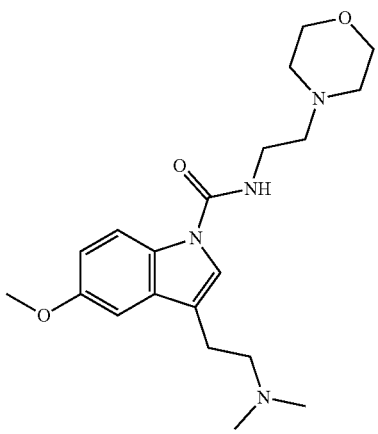 [SMILES: COc1ccc2c(c1)c(CCN(C)C)cn2C(=O)NCCN1CCOCC1]
CN(CCC1=CN(C2=C1C=C(OC)C=C2)C(NCCN3CCOCC3)=O)C TABLE 1-continued
| Cpd | Structure SMILES* |
|---|---|
55
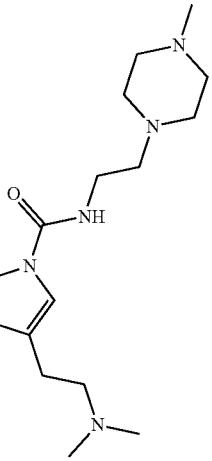
CN(CCC1=CN(C2=C1C=C(OC)C=C2)C(NCCN3CCN(CC3)C)=O)C
56
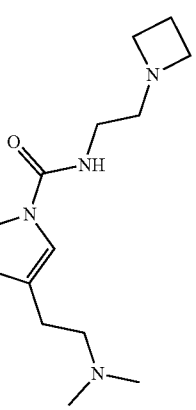
CN(CCC1=CN(C2=C1C=C(OC)C=C2)C(NCCN3CCC3)=O)C
57
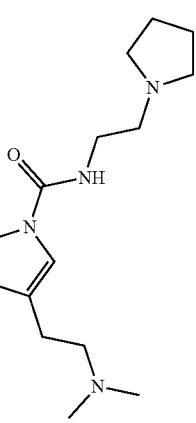
CN(CCC1=CN(C2=C1C=C(OC)C=C2)C(NCCN3CCCC3)=O)C TABLE 1-continued

| Cpd | Structure SMILES* |
|---|---|
| 58 | CN(CCC1=CN(C2=C1C=C(OC)C=C2)C(NCCN3CCCCC3)=O)C |
| 59 | CN(CCC1=CN(C2=C1C=C(OC)C=C2)C(NCCN3CCCCC34COC4)=O)C |
| 60 | CN(CCC1=CN(C2=C1C=C(OC)C=C2)C(NCCN3CC4(C3)COC4)=O)C |

TABLE 1-continued

| Cpd | Structure SMILES* |
|---|---|
| 61 | CN(CCC1=CN(C2=C1C=C(OC)C=C2)C(NCCN3CCC34COC4)=O)C |
| 62 | CN(CCC1=CN(C2=C1C=CC=C2)C(NCCN(C)C)=O)C |
| 63 | CN(CCC1=CN(C2=C1C=C(OC)C=C2)C(NCCN3CCOCC3)=O)C |

TABLE 1-continued

| Cpd | Structure SMILES* |
|---|---|
| 64 | CN(CCC1=CN(C2=C1C=CC=C2)C(NCCN3CCN(CC3)C)=O)C |
| 65 | CN(CCC1=CN(C2=C1C=CC=C2)C(NCCN3CCC3)=O)C |
| 66 | CN(CCC1=CN(C2=C1C=CC=C2)C(NCCN3CCC3)=O)C |

TABLE 1-continued
| Cpd | Structure SMILES* |
|---|---|
| 67 | 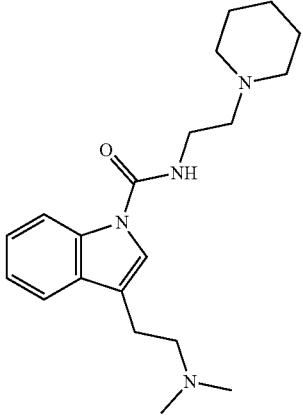 [SMILES: CN(C)CCc1cn(C(=O)NCCN2CCCCC2)c2ccccc12]<br>CN(CCC1=CN(C2=C1C=CC=C2)C(NCCN3CCCCC3)=O)C |
| 68 | 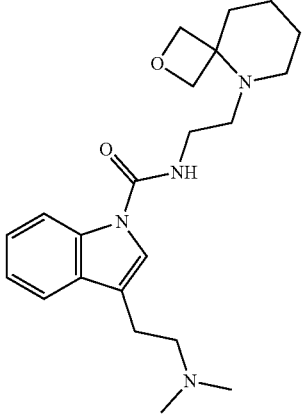 [SMILES: CN(C)CCc1cn(C(=O)NCCN2CCCCC23COC3)c2ccccc12]<br>CN(CCC1=CN(C2=C1C=CC=C2)C(NCCN3CCCCC34COC4)=O)C |
| 69 | 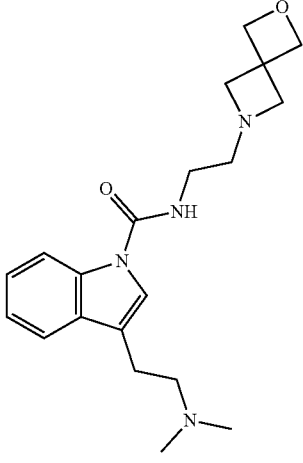 [SMILES: CN(C)CCc1cn(C(=O)NCCN2CC3(COC3)C2)c2ccccc12]<br>CN(CCC1=CN(C2=C1C=CC=C2)C(NCCN3CC4(C3)COC4)=O)C |

TABLE 1-continued

| Cpd | Structure SMILES* |
|---|---|
| 70 | CN(CCC1=CN(C2=C1C=CC=C2)C(NCCN3CCC34COC4)=O)C |
| 71 | CN(CCC1=CN(C2=C1C=C(OC)C=C2)C(NCC)=O)C |
| 72 | CN(CCC1=CN(C2=C1C=CC=C2)C(NCC)=O)C |
| 73 | CN(CCC1=CN(C2=C1C=C(OC)C=C2)C(NCC(OC3=O)=C(O3)C)=O)C |

TABLE 1-continued

| Cpd | Structure SMILES* |
|---|---|

74

CN(CCC1=CN(C2=C1C=C(OC)C=C2)C(NCCOC)=O)C

75

CN(CCC1=CN(C2=C1C=C(OC)C=C2)C(NCCOC3CC3)=O)C

76

CN(CCC1=CN(C2=C1C=CC=C2)C(NCC(OC3=O)=C(O3)C)=O)C

77

CN(CCC1=CN(C2=C1C=CC=C2)C(NCCOC)=O)C

| Cpd | Structure SMILES* |
|---|---|
78
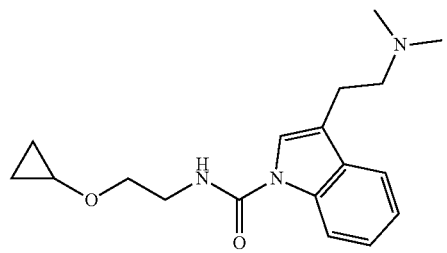 [SMILES: CN(C)CCc1cn(C(=O)NCCOC2CC2)c2ccccc12]
CN(CCC1=CN(C2=CC=CC=C2)C(NCCOC3CC3)=O)C
79
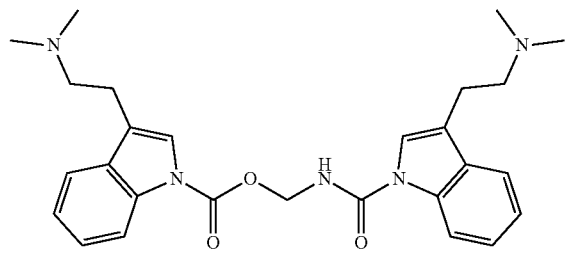
CN(CCC1=CN(C2=C1C=CC=C2)C(NCOC(N3C4=C(C(CCN(C)C)=C3)C=CC=C4)=O)=O)C
80
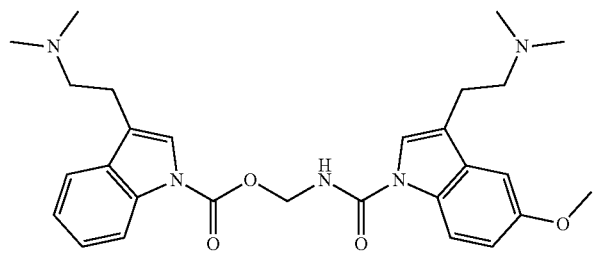
CN(CCC1=CN(C2=C1C=C(OC)C=C2)C(NCOC(N3C4=C(C(CCN(C)C)=C3)C=CC=C4)=O)=O)C
81
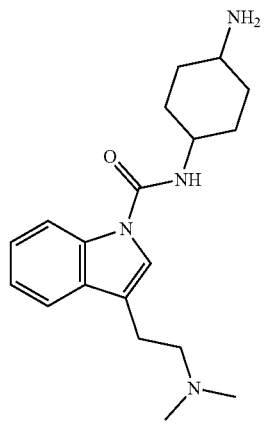 [SMILES: CN(C)CCc1cn(C(=O)NC2CCC(N)CC2)c2ccccc12]
CN(CCC1=CN(C2=C1C=CC=C2)C(NC3CCC(CC3)N)=O)C TABLE 1-continued

| Cpd | Structure SMILES* |
|---|---|
| 82 | CN(CCC1=CN(C2=C1C=CC=C2)C(NC3CCC(CC3)NC)=O)C |
| 83 | CN(CCC1=CN(C2=C1C=CC=C2)C(NC3CCC(CC3)N(C)C)=O)C |
| 84 | CN(CCC1=CN(C2=C1C=CC=C2)C(NC3CCC(CC3)N(CC)CC)=O)C |

TABLE 1-continued

| Cpd | Structure SMILES* |
|---|---|
| 85 | CN(CCC1=CN(C2=C1C=CC=C2)C(NC3CCC(CC3)NCC)=O)C |
| 86 | CN(CCC1=CN(C2=C1C=CC=C2)C(NC3CCC(CC3)N4CCC4)=O)C |
| 87 | CN(CCC1=CN(C2=C1C=CC=C2)C(NC3CCC(CC3)N4CCCC4)=O)C |

TABLE 1-continued

| Cpd | Structure SMILES* |
|---|---|
| 88 | CN(CCC1=CN(C2=C1C=CC=C2)C(NC3CCC(CC3)N4CCCCC4)=O)C |
| 89 | CN(CCC1=CN(C2=C1C=C(OC)C=C2)C(NC3CCC(CC3)N)=O)C |
| 90 | CN(CCC1=CN(C2=C1C=C(OC)C=C2)C(NC3CCC(CC3)NC)=O)C |

TABLE 1-continued
| Cpd | Structure SMILES* |
|---|---|
| 91 | 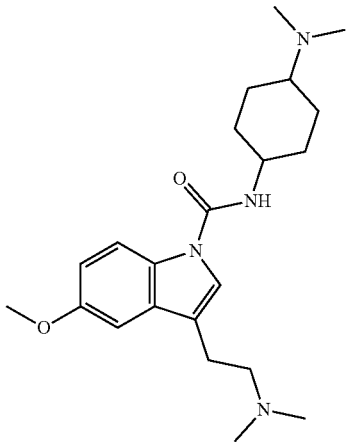
CN(CCC1=CN(C2=C1C=C(OC)C=C2)C(NC3CCC(CC3)N(C)C)=O)C |
| 92 | 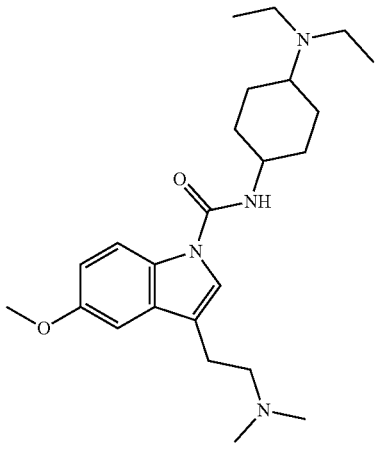 [SMILES: CCN(CC)C1CCC(NC(=O)n2cc(CCN(C)C)c3cc(OC)ccc32)CC1]
CN(CCC1=CN(C2=C1C=C(OC)C=C2)C(NC3CCC(CC3)N(CC)CC)=O)C |
| 93 | 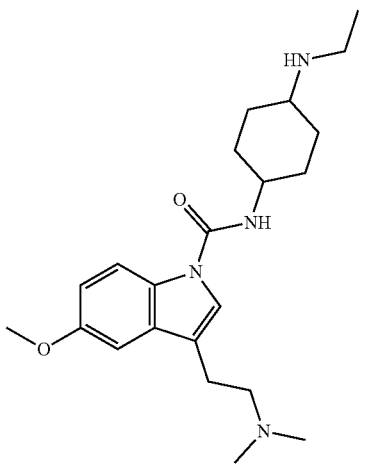 [SMILES: CCNC1CCC(NC(=O)n2cc(CCN(C)C)c3cc(OC)ccc32)CC1]
CN(CCC1=CN(C2=C1C=C(OC)C=C2)(C(NC3CCC(CC3)NCC)=O)C |

TABLE 1-continued
| Cpd | Structure SMILES* |
|---|---|
| 94 | 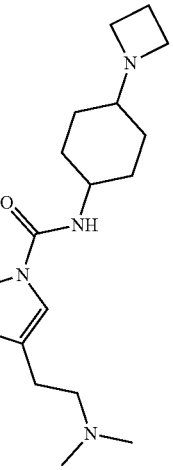<br>CN(CCC1=CN(C2=C1C=C(OC)C=C2)C(NC3CCC(CC3)N4CCC4)=O)C |
| 95 | 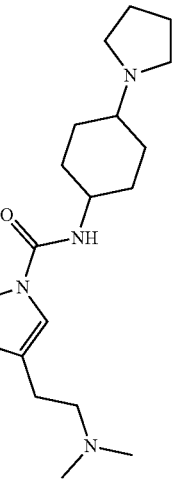<br>CN(CCC1=CN(C2=C1C=C(OC)C=C2)C(NC3CCC(CC3)N4CCCC4)=O)C |
| 96 | 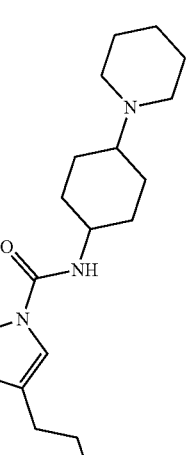<br>CN(CCC1=CN(C2=C1C=C(OC)C=C2)C(NC3CCC(CC3)N4CCCCC4)=O)C |

TABLE 1-continued

| Cpd | Structure SMILES* |
|---|---|
| 97 | CN(CCC1=CN(C2=C1C=CC=C2)C(NCOC(C3=CNC=CC3)=O)=O)C |
| 98 | CN(CCC1=CN(C2=C1C=CC=C2)C(NCOC(C3=CN(C)C=CC3)=O)=O)C |
| 99 | CN(CCC1=CN(C2=C1C=CC=C2)C(NCOC(C3=CN(C=CC3)CC=O)=O)C |
| 100 | CN(CCC1=CN(C2=C1C=CC=C2)C(NCOC(C3=CN(C=CC3)C(C)C)=O)=O)C |
| 101 | CN(CCC1=CN(C2=C1C=C(OC)C=C2)C(NCOC(C3=CNC=CC3)=O)=O)C |

TABLE 1-continued
| Cpd | Structure SMILES* |
|---|---|
| 102 | 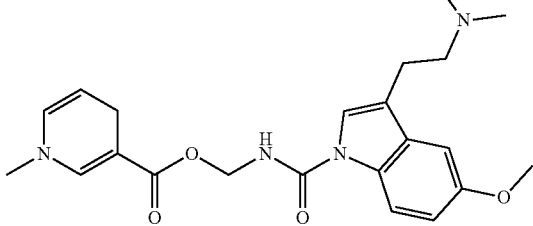<br>CN(CCC1=CN(C2=C1C=C(OC)C=C2)C(NCOC(C3=CN(OC=CC3)=O)=O)C |
| 103 | 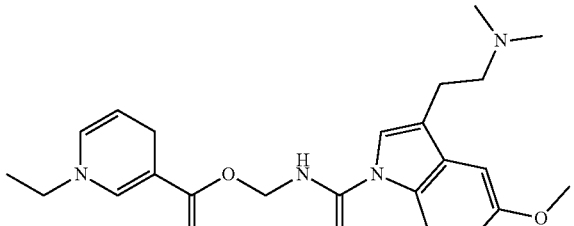<br>CN(CCC1=CN(C2=C1C=C(OC)C=C2)C(NCOC(C3=CN(C=CC3)CC)=O)=O)C |
| 104 | 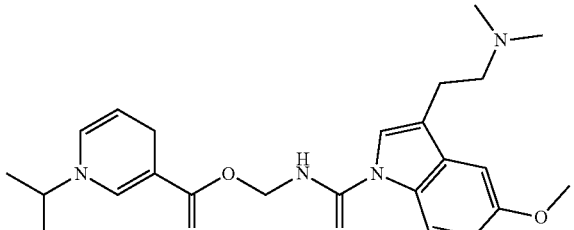<br>CN(CCC1=CN(C2=C1C=C(OC)C=C2)C(NCOC(C3=CN(C=CC3)C(C)C)=O)=O)C |
| 105 | 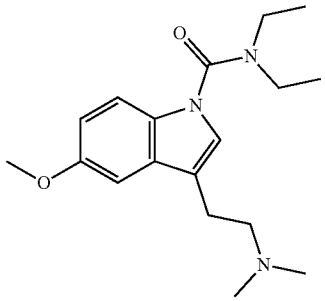 [SMILES: CCN(CC)C(=O)n1cc(CCN(C)C)c2cc(OC)ccc21]<br>CN(CCC1=CN(C2=C1C=C(OC)C=C2)C(N(CC)CC)=O)C |
| 106 | 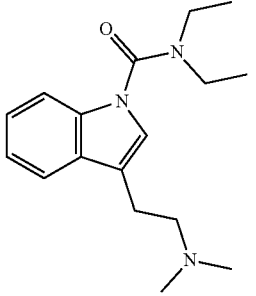 [SMILES: CCN(CC)C(=O)n1cc(CCN(C)C)c2ccccc21]<br>CN(CCC1=CN(C2=C1C=CC=C2)C(N(CC)CC)=O)C |

TABLE 1-continued

| Cpd | Structure SMILES* |
|---|---|
| 107 | CN(CCC1=CN(C2=C1C=C(OC)C=C2)C(C)=O)C |
| 108 | CN(CCC1=CN(C2=C1C=C(OC)C=C2)C(CC=O)C |
| 109 | CN(CCC1=CN(C2=C1C=C(OC)C=C2)C(C3CCCCC3)=O)C |
| 110 | CN(CCC1=CN(C2=C1C=C(OC)C=C2)C(C3=CC=CC=C3)=O)C |

| Cpd | Structure SMILES* |
|---|---|
| 111 | CN(CCC1=CN(C2=C1C=C(OC)C=C2)C(C)=O)C |
| 112 | CN(CCC1=CN(C2=C1C=C(OC)C=C2)C(C3=CC=NC=C3)=O)C |
| 113 | CN(CCC1=CN(C2=C1C=C(OC)C=C2)C(C3=CC=CN=N3)=O)C |
| 114 | CN(CCC1=CN(C2=C1C=C(OC)C=C2)C(C3=CC=CC=N3)=O)C |

TABLE 1-continued
| Cpd | Structure SMILES* |
|---|---|
| 115 | 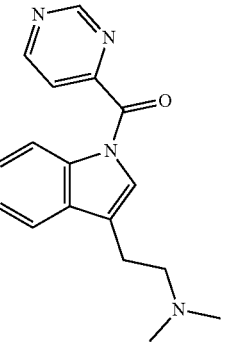<br>CN(CCC1=CN(C2=C1C=C(OC)C=C2)C(C3=CC=NC=N3)=O)C |
| 116 | 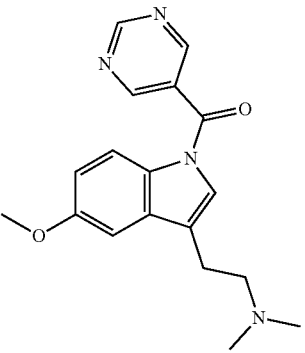<br>CN(CCC1=CN(C2=C1C=C(OC)C=C2)C(C3=CN=CN=C3)=O)C |
| 117 | 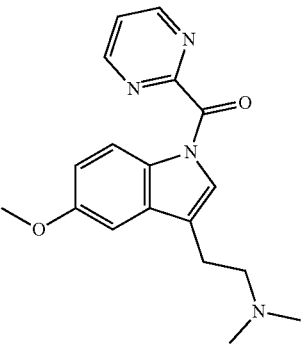<br>CN(CCC1=CN(C2=C1C=C(OC)C=C2)C(C3=NC=CC=N3)=O)C |
| 118 | 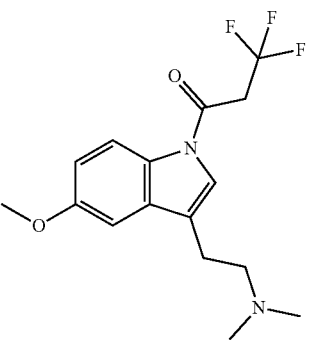 [SMILES: COc1ccc2c(c1)c(CCN(C)C)cn2C(=O)CC(F)(F)F]<br>CN(CCC1=CN(C2=C1C=C(OC)C=C2)C(CC(F)(F)F)=O)C |

TABLE 1-continued

| Cpd | Structure SMILES* |
|---|---|
| 119 | CN(CCC1=CN(C2=C1C=CC=C2)C(C)=O)C |
| 120 | CN(CCC1=CN(C2=C1C=CC=C2)C(CC)=O)C |
| 121 | CN(CCC1=CN(C2=C1C=CC=C2)C(C3CCCCC3)=O)C |
| 122 | CN(CCC1=CN(C2=C1C=CC=C2)C(C3=CC=CC=C3)=O)C |

TABLE 1-continued

| Cpd | Structure SMILES* |
|---|---|
| 123 | CN(CCC1=CN(C2=C1C=CC=C2)C(C)=O)C |
| 124 | CN(CCC1=CN(C2=C1C=CC=C2)C(C3=CC=NC=C3)=O)C |
| 125 | CN(CCC1=CN(C2=C1C=CC=C2)C(C3=CC=CN=C3)=O)C |
| 126 | CN(CCC1=CN(C2=C1C=CC=C2)C(C3=CC=CC=N3)=O)C |

TABLE 1-continued
| Cpd | Structure SMILES* |
|---|---|
| 127 | 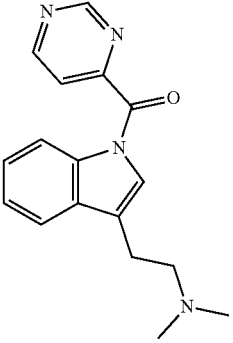 [SMILES: CN(C)CCc1cn(C(=O)c2ccncn2)c2ccccc12]<br>CN(CCC1=CN(C2=C1C=CC=C2)C(C3=CC=NC=N3)=O)C |
| 128 | 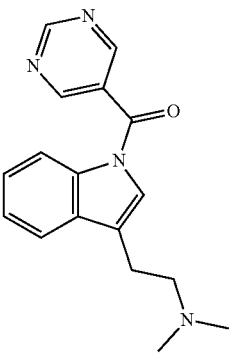 [SMILES: CN(C)CCc1cn(C(=O)c2cncnc2)c2ccccc12]<br>CN(CCC1=CN(C2=C1C=CC=C2)C(C3=CN=CN=C3)=O)C |
| 129 | 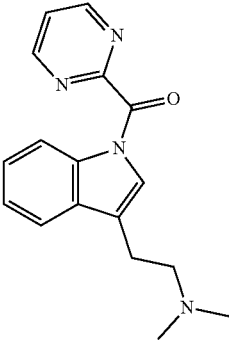 [SMILES: CN(C)CCc1cn(C(=O)c2ncccn2)c2ccccc12]<br>CN(CCC1=CN(C2=C1C=CC=C2)C(C3=NC=CC=N3)=O)C |
| 130 | 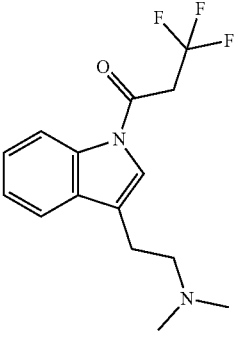 [SMILES: CN(C)CCc1cn(C(=O)CC(F)(F)F)c2ccccc12]<br>CN(CCC1=CN(C2=C1C=CC=C2)C(CC(F)(F)F)=O)C |

TABLE 1-continued

| Cpd | Structure SMILES* |
|---|---|
| 131 | CN(CCC1=CN(C2=C1C=C(OC)C=C2)C(CCOC)=O)C |
| 132 | CN(CCC1=CN(C2=C1C=C(OC)C=C2)C(C3COC3)=O)C |
| 133 | CN(CCC1=CN(C2=C1C=C(OC)C=C2)C(C3CSC3)=O)C |
| 134 | CN(CCC1=CN(C2=C1C=C(OC)C=C2)C(C3CS(C3)(=O)=O)=O)C |

TABLE 1-continued

| Cpd | Structure SMILES* |
|---|---|
| 135 | CN(CCC1=CN(C2=C1C=C(OC)C=C2)C(CCS(=O)(C)=O)=O)C |
| 136 | CN(CCC1=CN(C2=C1C=CC=C2)C(CCOC)=O)C |
| 137 | CN(CCC1=CN(C2=C1C=CC=C2)C(C3COC3)=O)C |
| 138 | CN(CCC1=CN(C2=C1C=CC=C2)C(C3CSC3)=O)C |

TABLE 1-continued

| Cpd | Structure SMILES* |
|---|---|

139

CN(CCC1=CN(C2=C1C=CC=C2)C(C3CS(C3)(=O)=O)=O)C

140

CN(CCC1=CN(C2=C1C=CC=C2)C(CCS(=O)(C)=O)=O)C

141

CN(CCC1=CN(C2=C1C=C(OC)C=C2)C(C3CN(C3)C(C)=O)=O)C

TABLE 1-continued
| Cpd | Structure SMILES* |
|---|---|
| 142 | 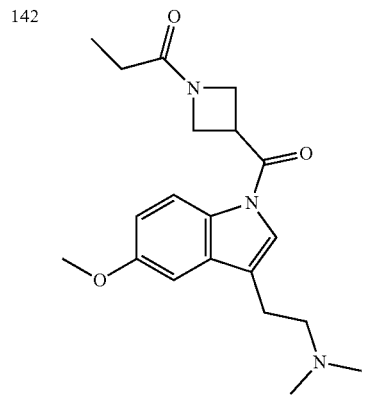<br>CN(CCC1=CN(C2=C1C=C(OC)C=C2)C(C3CN(C3)C(CC)=O)=O)C |
| 143 | 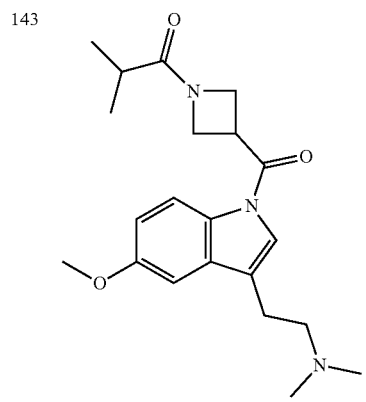<br>CN(CCC1=CN(C2=C1C=C(OC)C=C2)C(C3CN(C3)C(C(C)C)=O)=O)C |
| 144 | 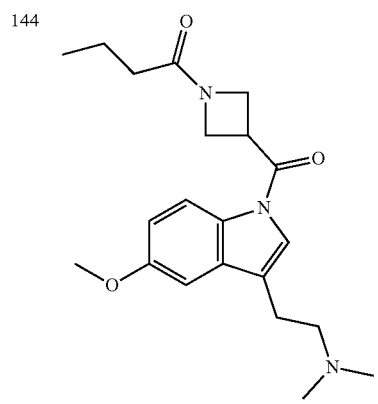<br>CN(CCC1=CN(C2=C1C=C(OC)C=C2)C(C3CN(C3)C(CCC)=O)=O)C |

TABLE 1-continued

| Cpd | Structure SMILES* |
|---|---|
| 145 | CN(CCC1=CN(C2=C1C=C(OC)C=C2)C(C3CN(C3)C(CCOC)=O)=O)C |
| 146 | CN(CCC1=CN(C2=C1C=C(OC)C=C2)C(C3CN(C3)C(C4=CC=CC=C4)=O)=O)C |
| 147 | CN(CCC1=CN(C2=C1C=CC=C2)C(C3CN(C3)C(C)=O)=O)C |

TABLE 1-continued

| Cpd | Structure SMILES* |
|---|---|

148

CN(CCC1=CN(C2=C1C=CC=C2)C(C3CN(C3)C(CC)=O)=O)C

149

CN(CCC1=CN(C2=C1C=CC=C2)C(C3CN(C3)C(C(C)C)=O)=O)C

150

CN(CCC1=CN(C2=C1C=CC=C2)C(C3CN(C3)C(CCC)=O)=O)C

TABLE 1-continued

| Cpd | Structure SMILES* |
|---|---|
| 151 | CN(CCC1=CN(C2=C1C=CC=C2)C(C3CN(C3)C(CCOC)=O)=O)C |
| 152 | CN(CCC1=CN(C2=C1C=CC=C2)C(C3CN(C3)C(C4=CC=CC=C4)=O)=O)C |
| 153 | CN(CCC1=CN(C2=C1C=C(OC)C=C2)C(C3=CNC=CC3)=O)C |

TABLE 1-continued

| Cpd | Structure SMILES* |
|---|---|
| 154 | CN(C)CCc1=CN(C(=O)C2=CN(C)CC=C2)c2cc(OC)ccc12 |

CN(CCC1=CN(C2=C1C=C(OC)C=C2)C(C3=CN(C)C=CC3)=O)C

| 155 | |

CN(CCC1=CN(C2=C1C=C(OC)C=C2)C(C3=CN(C=CC3)CC)=O)C

| 156 | |

CN(CCC1=CN(C2=C1C=C(OC)C=C2)C(C3=CN(C=CC3)CCC)=O)C

| 157 | |

CN(CCC1=CN(C2=C1C=C(OC)C=C2)C(C3=CN(C=CC3)C(C)C)=O)C

TABLE 1-continued
| Cpd | Structure SMILES* |
|---|---|
158 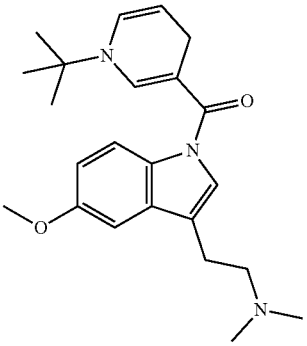
CN(CCC1=CN(C2=C1C=C(OC)C=C2)C(C3=CN(C=CC3)C(C)(C)C)=O)C
159 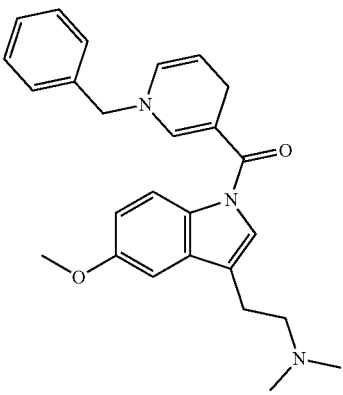 [SMILES: COc1ccc2c(c1)c(CCN(C)C)cn2C(=O)C1=CN(Cc2ccccc2)C=CC1]
CN(CCC1=CN(C2=C1C=C(OC)C=C2)C(C3=CN(C=CC3)CC4=CC=CC=C4)=O)C
160 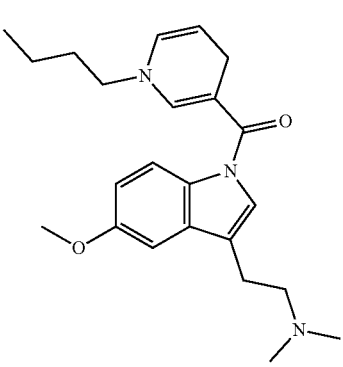 [SMILES: CCCCN1C=CCC(C(=O)n2cc(CCN(C)C)c3cc(OC)ccc32)=C1]
CN(CCC1=CN(C2=C1C=C(OC)C=C2)C(C3=CN(C=CC3)CCCC)=O)C TABLE 1-continued
| Cpd | Structure SMILES* |
|---|---|
| 161 | 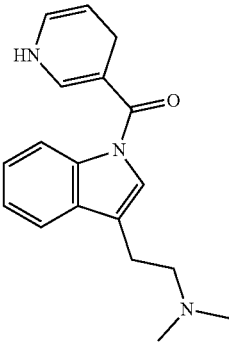 [SMILES: CN(C)CCc1cn(C(=O)C2=CNC=CC2)c2ccccc12]<br>CN(CCC1=CN(C2=C1C=CC=C2)C(C3=CNC=CC3)=O)C |
| 162 | 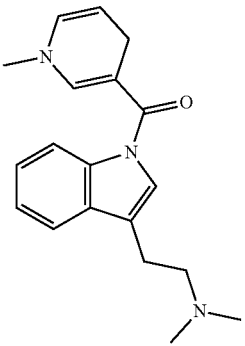<br>CN(CCC1=CN(C2=C1C=CC=C2)C(C3CN(C)C=CC3)=O)C |
| 163 | 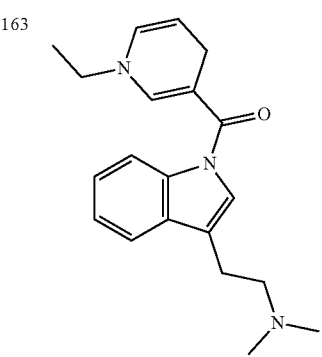<br>CN(CCC1=CN(C2=C1C=CC=C2)C(C3=CN(C=CC3)CC)=O)C |
| 164 | 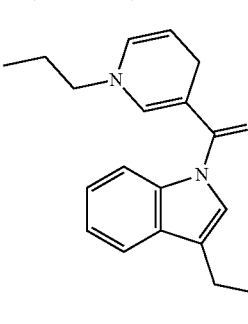<br>CN(CCC1=CN(C2=C1C=CC=C2)C(C3=CN(C=CC3)CCC)=O)C |

TABLE 1-continued
| Cpd | Structure SMILES* |
|---|---|
| 165 | 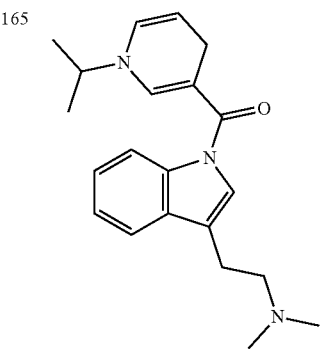<br>CN(CCC1=CN(C2=C1C=CC=C2)C(C3=CN(C=CC3)C(C)C)=O)C |
| 166 | 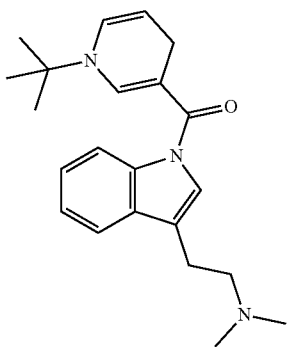 [SMILES: CN(C)CCc1cn(C(=O)C2=CN(C(C)(C)C)C=CC2)c2ccccc12]<br>CN(CCC1=CN(C2=C1C=CC=C2)C(C3=CN(C=CC3)C(C)(C)C)=O)C |
| 167 | 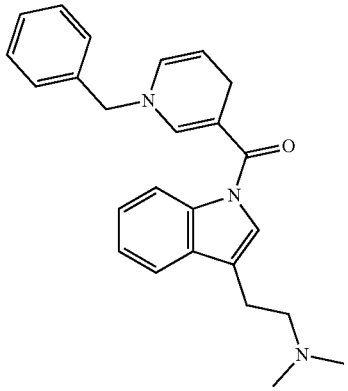 [SMILES: CN(C)CCc1cn(C(=O)C2=CN(Cc3ccccc3)C=CC2)c2ccccc12]<br>CN(CCC1=CN(C2=C1C=CC=C2)C(C3=CN(C=CC3)CC4=CC=CC=C4)=O)C |

TABLE 1-continued

| Cpd | Structure SMILES* |
|---|---|

168

CN(CCC1=CN(C2=C1C=CC=C2)C(C3=CN(C=CC3)CCCC)=O)C

169

CN(CCC1=CN(C2=C1C=C(OC)C=C2)C(N3C4=C(C(CCN(C)C)=C3)C=C(OC)C=C4)=O)C

170

CN(CCC1=CN(C2=C1C=CC=C2)C(N3C4=C(C(CCN(C)C)=C3)C=CC=C4)=O)C

TABLE 1-continued

| Cpd | Structure SMILES* |
|---|---|

171

CN(CCC1=CN(C2=C1C=C(OC)C=C2)C(C(N)CCCCN)=O)C

172

CN(CCC1=CN(C2=C1C=C(OC)C=C2)C(C(C)N)=O)C

173

CN(CCC1=CN(C2=C1C=C(OC)C=C2)C(C(N)C(C)C)=O)C

174

CN(CCC1=CN(C2=C1C=C(OC)C=C2)C(C(N)CCCNC(N)=N)=O)C

TABLE 1-continued
| Cpd | Structure SMILES* |
|---|---|
175
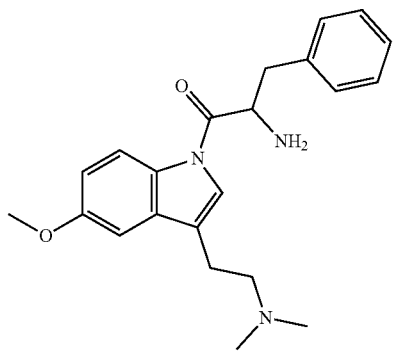 [SMILES: COc1ccc2c(c1)c(CCN(C)C)cn2C(=O)C(N)Cc1ccccc1]
CN(CCC1=CN(C2=C1C=C(OC)C=C2)C(C(N)CC3=CC=CC=C3)=O)C
176
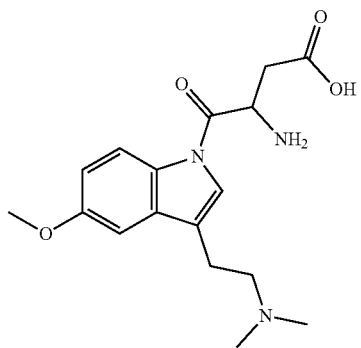 [SMILES: COc1ccc2c(c1)c(CCN(C)C)cn2C(=O)C(N)CC(=O)O]
CN(CCC1=CN(C2=C1C=C(OC)C=C2)C(C(N)CC(O)=O)=O)C
177
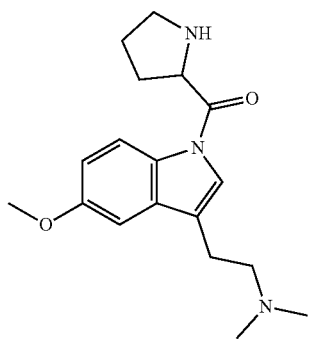
CN(CCC1=CN(C2=C1C=C(OC)C=C2)C(C3CCCN3)=O)C
178
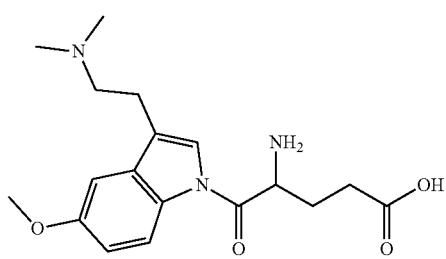 [SMILES: COc1ccc2c(c1)c(CCN(C)C)cn2C(=O)C(N)CCC(=O)O]
CN(CCC1=CN(C2=C1C=C(OC)C=C2)C(C(N)CCC(O)=O)=O)C TABLE 1-continued
| Cpd | Structure SMILES* |
|---|---|
| 179 | 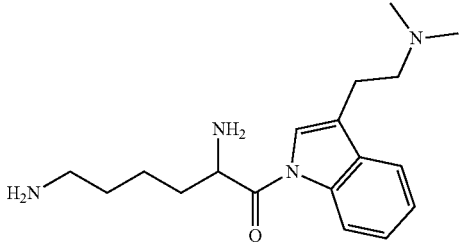 [SMILES: CN(C)CCc1cn(C(=O)C(N)CCCCN)c2ccccc12]
CN(CCC1=CN(C2=C1C=CC=C2)C(C(N)CCCCN)=O)C |
| 180 | 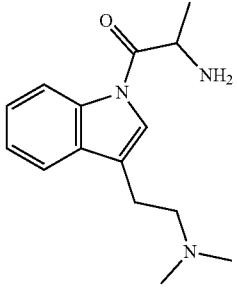 [SMILES: CC(N)C(=O)n1cc(CCN(C)C)c2ccccc21]
CN(CCC1=CN(C2=C1C=CC=C2)C(C(C)N)=O)C |
| 181 | 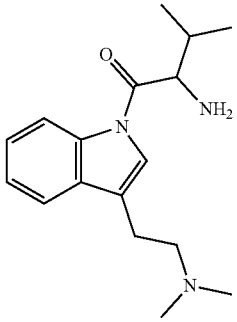 [SMILES: CC(C)C(N)C(=O)n1cc(CCN(C)C)c2ccccc21]
CN(CCC1=CN(C2=C1C=CC=C2)C(C(N)C(C)C)=O)C |
| 182 | 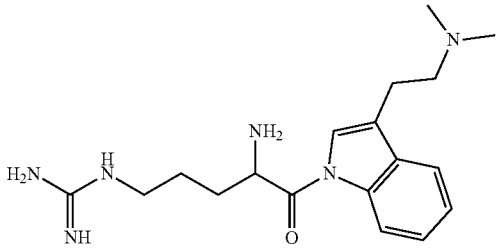 [SMILES: CN(C)CCc1cn(C(=O)C(N)CCCNC(=N)N)c2ccccc12]
CN(CCC1=CN(C2=C1C=CC=C2)C(C(N)CCCNC(N)=N)=O)C |

TABLE 1-continued

| Cpd | Structure SMILES* |
|---|---|
| 183 | CN(CCC1=CN(C2=C1C=CC=C2)C(C(N)CC3=CC=CC=C3)=O)C |
| 184 | CN(CCC1=CN(C2=C1C=CC=C2)C(C(N)CC(O)=O)=O)C |
| 185 | CN(CCC1=CN(C2=C1C=CC=C2)C(C3CCCN3)=O)C |
| 186 | CN(CCC1=CN(C2=C1C=CC=C2)C(C(N)CCC(O)=O)=O)C |

TABLE 1-continued

| Cpd | Structure SMILES* |
|---|---|
| 187 | CN(C)CC1=CN(C2=C1C=CC=C2)COC(C(C)(C)C)=O)C |
| 188 | CN(C)CC1=CN(C2=C1C=C(OC)C=C2)COC(C(C)(C)C)=O)C |
| 189 | CN(C)CC1=CN(C2=C1C=C(OC)C=C2)COP(OCC)(OCC)=O)C |
| 190 | CN(C)CC1=CN(C2=C1C=C(OC)C=C2)COP(OC(C)C)(OC(C)C)=O)C |

TABLE 1-continued

| Cpd | Structure SMILES* |
|---|---|
| 191 | CN(CCC1=CN(C2=C1C=C(OC)C=C2)COP(OCCN(C)C)(OCCN(C)C)=O)C |
| 192 | CN(CCC1=CN(C2=C1C=C(OC)C=C2)COP(O)(O)=O)C |
| 193 | CN(CCC1=CN(C2=C1C=C(OC)C=C2)COP(OCC(OC3=O)=C(O3)C)(OCC(OC4=O)=C(O4)C)=O)C |
| 194 | CN(CCC1=CN(C2=C1C=C(OC)C=C2)COP(OC)(OC)=O)C |

TABLE 1-continued

| Cpd | Structure SMILES* |
|---|---|
| 195 | CN(CCC1=CN(C2=C1C=CC=C2)COP(OCC)(OCC)=O)C |
| 196 | CN(CCC1=CN(C2=C1C=CC=C2)COP(OC(C)C)(OC(C)C)=O)C |
| 197 | CN(CCC1=CN(C2=C1C=CC=C2)COP(OCCN(C)C)(OCCN(C)C)=O)C |
| 198 | CN(CCC1=CN(C2=C1C=CC=C2)COP(O)(O)=O)C |

TABLE 1-continued
| Cpd | Structure SMILES* |
|---|---|
199
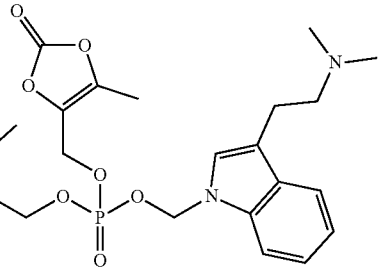
CN(CCC1=CN(C2=C1C=CC=C2)COP(OCC(OC3=O)=C(O3)C)(OCC(OC4=O)=C(O4)C)=O)C
200
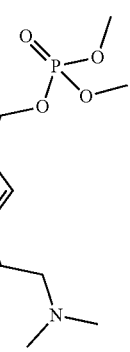
CN(CCC1=CN(C2=C1C=CC=C2)COP(OC)(OC)=O)C
201
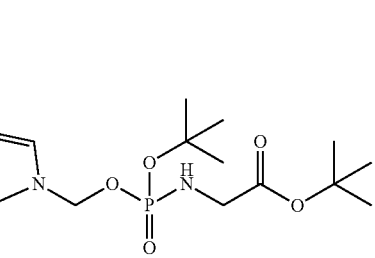
CN(CCC1=CN(C2=C1C=CC=C2)COP(OC(C)(C)C)(NCC(OC(C)(C)C)=O)=O)C
202
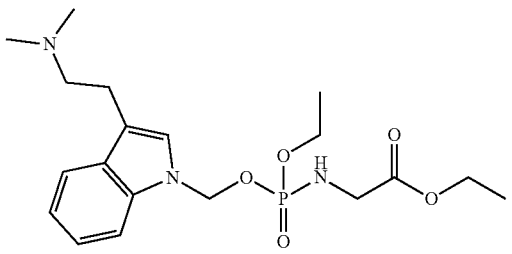 [SMILES: CCOC(=O)CNP(=O)(OCC)OCn1cc(CCN(C)C)c2ccccc21]
CN(CCC1=CN(C2=C1C=CC=C2)COP(OCC)(NCC(OCC)=O)=O)C
203
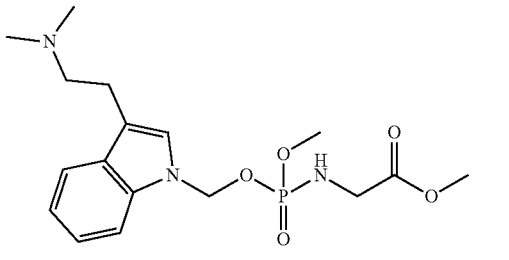
CN(CCC1=CN(C2=C1C=CC=C2)COP(OC)(NCC(OC)=O)=O)C TABLE 1-continued
| Cpd | Structure SMILES* |
|---|---|
204
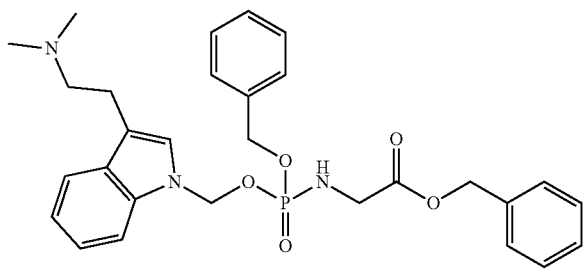 [SMILES: CN(C)CCc1cn(COP(=O)(NCC(=O)OCc2ccccc2)OCc2ccccc2)c2ccccc12]
CN(CCC1=CN(C2=C1C=CC=C2)COP(OCC3=CC=CC=C3)(NCC(OCC4=CC=CC=C4)=O)=O)C
205
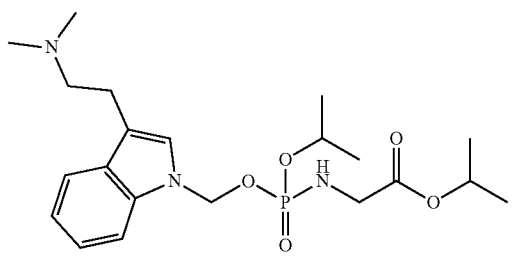 [SMILES: CC(C)OC(=O)CNP(=O)(OCn1cc(CCN(C)C)c2ccccc21)OC(C)C]
CN(CCC1=CN(C2=C1C=CC=C2)COP(OC(C)C)(NCC(OC(C)C)=O)=O)C
206
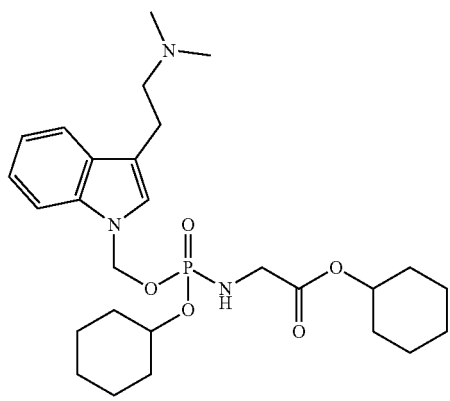 [SMILES: CN(C)CCc1cn(COP(=O)(NCC(=O)OC2CCCCC2)OC2CCCCC2)c2ccccc12]
CN(CCC1=CN(C2=C1C=CC=C2)COP(OC3CCCCC3)(NCC(OC4CCCCC4)=O)=O)C
207
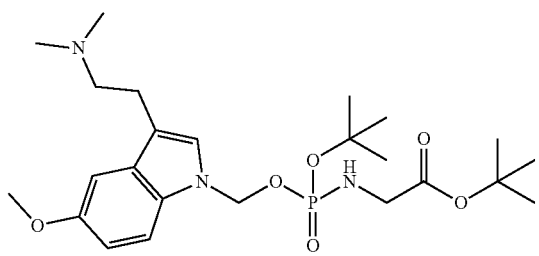 [SMILES: COc1ccc2c(c1)c(CCN(C)C)cn2COP(=O)(NCC(=O)OC(C)(C)C)OC(C)(C)C]
CN(CCC1=CN(C2=C1C=C(OC)C=C2)COP(OC(C)(C)C)(NCC(OC(C)(C)C)=O)=O)C TABLE 1-continued

| Cpd | Structure SMILES* |
|---|---|

208

CN(CCC1=CN(C2=C1C=C(OC)C=C2)COP(OCC)(NCC(OCC)=O)=O)C

209

CN(CCC1=CN(C2=C1C=C(OC)C=C2)COP(OC)(NCC(OC)=O)=O)C

210

CN(CCC1=CN(C2=C1C=C(OC)C=C2)COP(OCC3=CC=CC=C3)(NCC(OCC4=CC=CC=C4)=O)=O)C

211

CN(CCC1=CN(C2=C1C=C(OC)C=C2)COP(OC(C)C)(NCC(OC(C)C)=O)=O) C

| Cpd | Structure SMILES* |
|---|---|
| 212 | 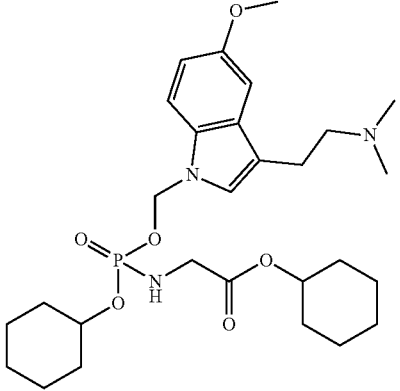 [SMILES: COc1ccc2c(c1)c(CCN(C)C)cn2COP(=O)(NCC(=O)OC1CCCCC1)OC1CCCCC1]
CN(CCC1=CN(C2=C1C=C(OC)C=C2)COP(OC3CCCCC3)(NCC(OC4CCCCC4)=O)=O)C |
| 213 | 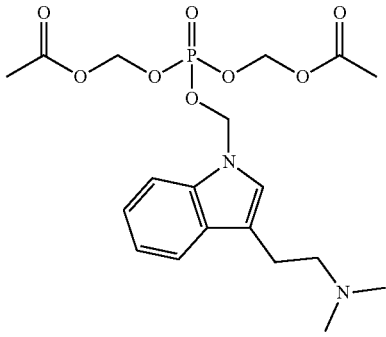 [SMILES: CC(=O)OCOP(=O)(OCOC(C)=O)OCn1cc(CCN(C)C)c2ccccc21]
CN(CCC1=CN(C2=C1C=CC=C2)COP(OCOC(C)=O)(OCOC(C)=O)=O)C |
| 214 | 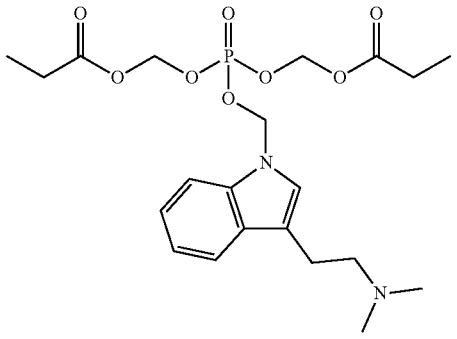 [SMILES: CCC(=O)OCOP(=O)(OCOC(=O)CC)OCn1cc(CCN(C)C)c2ccccc21]
CN(CCC1=CN(C2=C1C=CC=C2)COP(OCOC(CC)=O)(OCOC(CC)=O)=O)C |
| 215 | 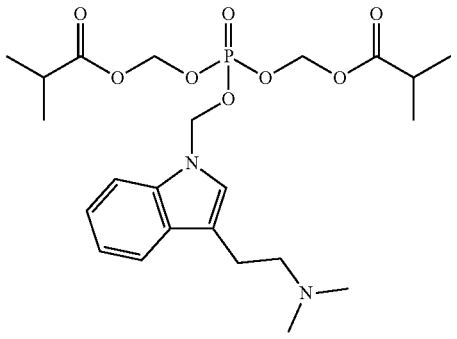 [SMILES: CC(C)C(=O)OCOP(=O)(OCOC(=O)C(C)C)OCn1cc(CCN(C)C)c2ccccc21]
CN(CCC1=CN(C2=C1C=CC=C2)COP(OCOC(C(C)C)=O)(OCOC(C(C)C)=O)=O)C |

TABLE 1-continued
| Cpd | Structure SMILES* |
|---|---|
| 216 | 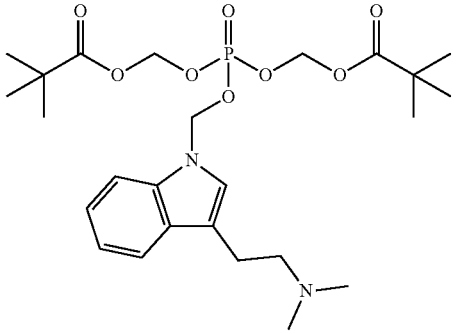 [SMILES: CN(C)CCc1cn(COP(=O)(OCOC(=O)C(C)(C)C)OCOC(=O)C(C)(C)C)c2ccccc12]<br>CN(CCC1=CN(C2=C1C=CC=C2)COP(OCOC(C(C)(C)C)=O)(OCOC(C(C)(C)C)=O)=O)C |
| 217 | 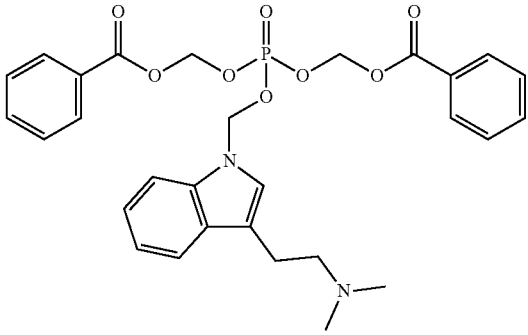 [SMILES: CN(C)CCc1cn(COP(=O)(OCOC(=O)c2ccccc2)OCOC(=O)c2ccccc2)c2ccccc12]<br>CN(CCC1=CN(C2=C1C=CC=C2)COP(OCOC(C3=CC=CC=C3)=O)(OCOC(C4=CC=CC=C4)=O)=O)C |
| 218 | 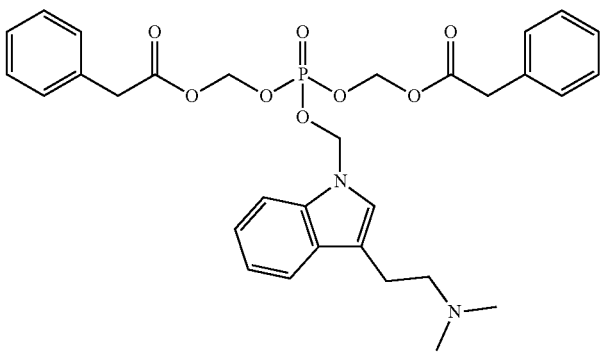 [SMILES: CN(C)CCc1cn(COP(=O)(OCOC(=O)Cc2ccccc2)OCOC(=O)Cc2ccccc2)c2ccccc12]<br>CN(CCC1=CN(C2=C1C=CC=C2)COP(OCOC(CC3=CC=CC=C3)=O)(OCOC(CC4=CC=CC=C4)=O)=O)C |
| 219 | 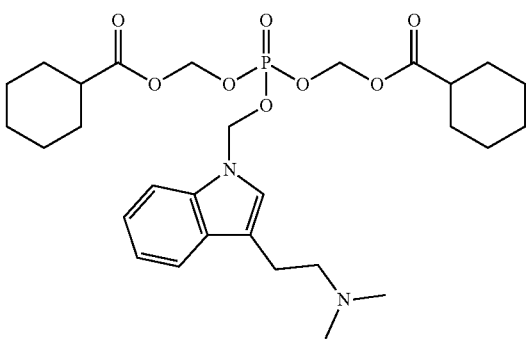 [SMILES: CN(C)CCc1cn(COP(=O)(OCOC(=O)C2CCCCC2)OCOC(=O)C2CCCCC2)c2ccccc12]<br>CN(CCC1=CN(C2=C1C=CC=C2)COP(OCOC(C3CCCCC3)=O)(OCOC(C4CCCCC4)=O)=O)C |

TABLE 1-continued

| Cpd | Structure SMILES* |
|---|---|
| 220 | CN(CCC1=CN(C2=C1C=CC=C2)COP(OCOC(CC(C)C)=O)(OCOC(CC(C)C)=O)=O)C |
| 221 | CN(CCC1=CN(C2=C1C=C(OC)C=C2)COP(OCOC(C)=O)(OCOC(C)=O)=O)C |
| 222 | CN(CCC1=CN(C2=C1C=C(OC)C=C2)COP(OCOC(CC)=O)(OCOC(CC)=O)=O)C |
| 223 | CN(CCC1=CN(C2=C1C=C(OC)C=C2)COP(OCOC(C(C)C)=O)(OCOC(C(C)C)=O)=O)C |

TABLE 1-continued

| Cpd | Structure SMILES* |
|---|---|
| 224 | CN(CCC1=CN(C2=C1C=C(OC)C=C2)COP(OCOC(C(C)(C)C)=O)(OCOC(C(C)(C)C)=O)=O)C |
| 225 | CN(CCC1=CN(C2=C1C=C(OC)C=C2)COP(OCOC(C3=CC=CC=C3)=O)(OCOC(C4=CC=CC=C4)=O)=O)C |
| 226 | CN(CCC1=CN(C2=C1C=C(OC)C=C2)COP(OCOC(CC3=CC=CC=C3)=O)(OCOC(CC4=CC=CC=C4)=O)=O)C |
| 227 | CN(CCC1=CN(C2=C1C=C(OC)C=C2)COP(OCOC(C3CCCCC3)=O)(OCOC(C4CCCCC4)=O)=O)C |

TABLE 1-continued

| Cpd | Structure SMILES* |
|---|---|
| 228 | CN(CCC1=CN(C2=C1C=C(OC)C=C2)COP(OCOC(CC(C)C)=O)(OCOC(CC(C)C)=O)=O)C |
| 229 | CN(CCC1-CN(C2=C1C-CC-C2)COP(OCOC(OC)=O)(OCOC(OC)=O)=O)C |
| 230 | CN(CCC1=CN(C2=C1C=CC=C2)COP(OCOC(OCC)=O)(OCOC(OCC)=O)=O)C |
| 231 | CN(CCC1=CN(C2=C1C=CC=C2)COP(OCOC(OC(C)C)=O)(OCOC(OC(C)C)=O)=O)C |

TABLE 1-continued
| Cpd | Structure SMILES* |
|---|---|
| 232 | 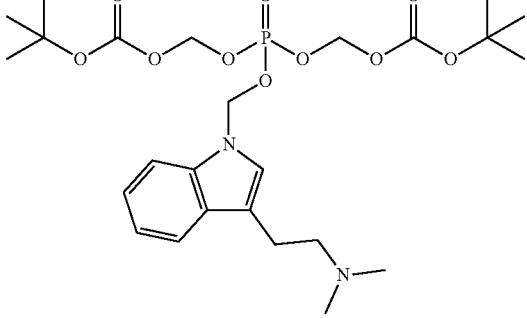
CN(CCC1=CN(C2=C1C=CC=C2)COP(OCOC(OC(C)(C)C)=O)(OCOC(OC(C)(C)C)=O)=O)C |
| 233 | 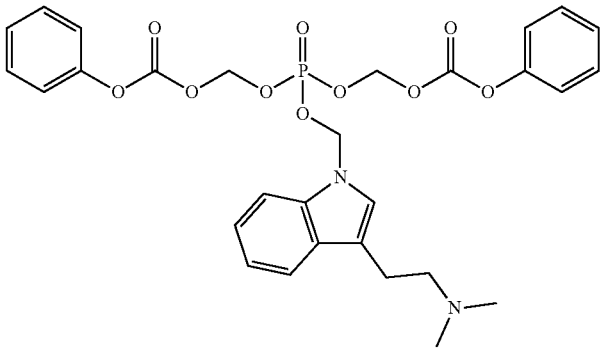 [SMILES: CN(C)CCc1cn(COP(=O)(OCOC(=O)Oc2ccccc2)OCOC(=O)Oc2ccccc2)c2ccccc12]
CN(CCC1=CN(C2=C1C=CC=C2)COP(OCOC(OC3=CC=CC=C3)=O)(OCOC(OC4=CC=CC=C4)=O)=O)C |
| 234 | 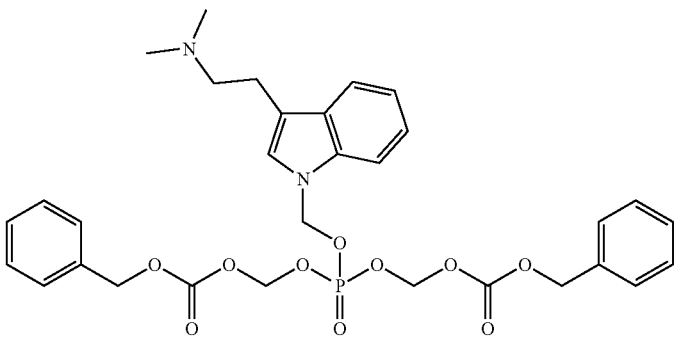 [SMILES: CN(C)CCc1cn(COP(=O)(OCOC(=O)OCc2ccccc2)OCOC(=O)OCc2ccccc2)c2ccccc12]
CN(CCC1=CN(C2=C1C=CC=C2)COP(OCOC(OCC3=CC=CC=C3)=O)(OCOC(OCC4=CC=CC=C4)=O)=O)C |
| 235 | 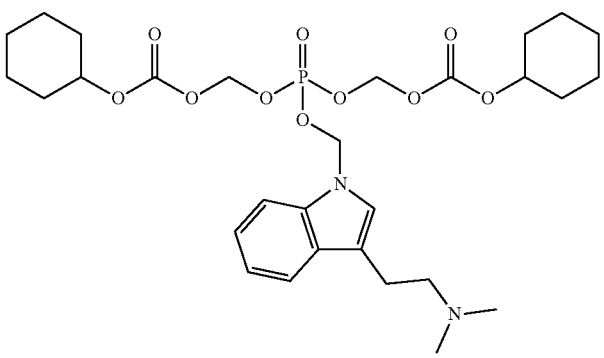 [SMILES: CN(C)CCc1cn(COP(=O)(OCOC(=O)OC2CCCCC2)OCOC(=O)OC2CCCCC2)c2ccccc12]
CN(CCC1=CN(C2=C1C=CC=C2)COP(OCOC(OC3CCCCC3)=O)(OCOC(OC4CCCCC4)=O)=O)C |

TABLE 1-continued

| Cpd | Structure SMILES* |
|---|---|
| 236 | CN(C)CCc1=CN(C2=C1C=CC=C2)COP(OCOC(OCC(C)C)=O)(OCOC(OCC(C)C)=O)=O)C |
| 237 | CN(C)CCc1=CN(C2=C1C=C(OC)C=C2)COP(OCOC(OC)=O)(OCOC(OC)=O)=O)C |
| 238 | CN(C)CCc1=CN(C2=C1C=C(OC)C=C2)COP(OCOC(OCC)=O)(OCOC(OCC)=O)=O)C |
| 239 | CN(C)CCc1=CN(C2=C1C=C(OC)C=C2)COP(OCOC(OC(C)C)=O)(OCOC(OC(C)C)=O)=O)C |

TABLE 1-continued

| Cpd | Structure SMILES* |
|---|---|
| 240 | CN(C)CCc1=cn(c2=c1c=c(OC)c=c2)COP(OCOC(OC(C)(C)C)=O)(OCOC(OC(C)(C)C)=O)=O)C |
| 241 | CN(C)CCc1=cn(c2=c1c=c(OC)c=c2)COP(OCOC(OC3=CC=CC=C3)=O)(OCOC(OC4=CC=CC=C4)=O)=O)C |
| 242 | CN(C)CCc1=cn(c2=c1c=c(OC)c=c2)COP(OCOC(OCC3=CC=CC=C3)=O)(OCOC(OCC4=CC=CC=C4)=O)=O)C |
| 243 | CN(C)CCc1=cn(c2=c1c=c(OC)c=c2)COP(OCOC(OC3CCCCC3)=O)(OCOC(OC4CCCCC4)=O)=O)C |

TABLE 1-continued

| Cpd | Structure SMILES* |
|---|---|
| 244 | CN(CCC1=CN(C2=C1C=C(OC)C=C2)COP(OCOC(OCC(C)C)=O)(OCOC(OCC(C)C)=O)=O)C |
| 245 | CN(CCC1=CN(C2=C1C=CC=C2)COP(OCOC(C3=CNC=CC3)=O)(OCOC(C4=CNC=CC4)=O)=O)C |
| 246 | CN(CCC1=CN(C2=C1C=CC=C2)COP(OCOC(C3=CN(C)C=CC3)=O)(OCOC(C4=CN(C)C=CC4)=O)=O)C |
| 247 | CN(CCC1=CN(C2=C1C=CC=C2)COP(OCOC(C3=CN(C=CC3)CC4=CC=CC=C4)=O)(OCOC(C5=CN(C=CC5)CC6=CC=CC=C6)=O)=O)C |

TABLE 1-continued
| Cpd | Structure SMILES* |
|---|---|
248
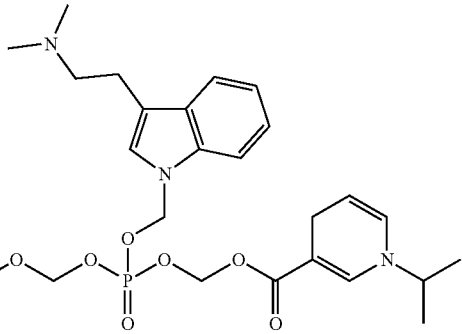
CN(CCC1=CN(C2=C1C=CC=C2)COP(OCOC(C3=CN(C=CC3)C(C)C)=O)(OCOC(C4=CN(C=CC4)C(C)C)=O)=O)C
249
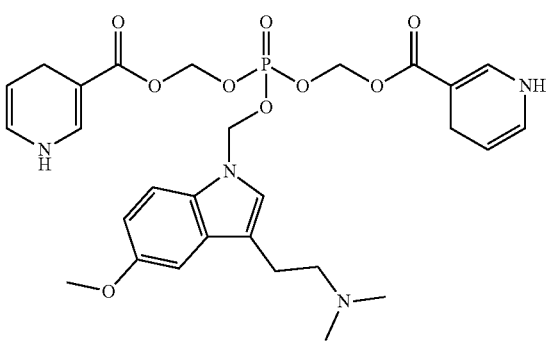 [SMILES: COc1ccc2c(c1)c(CCN(C)C)cn2COP(=O)(OCOC(=O)C1=CNC=CC1)OCOC(=O)C1=CNC=CC1]
CN(CCC1=CN(C2=C1C=C(OC)C=C2)COP(OCOC(C3=CNC=CC3)=O)(OCOC(C4=CNC=CC4)=O)=O)C
250
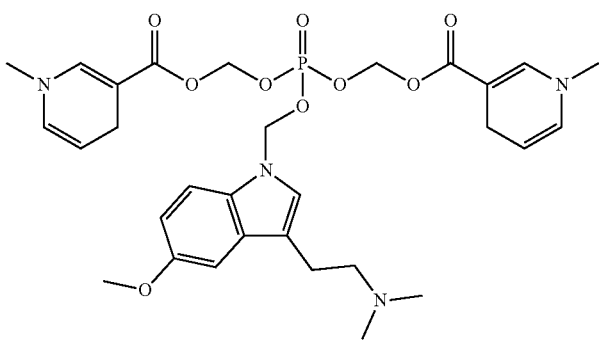
CN(CCC1=CN(C2=C1C=C(OC)C=C2)COP(OCOC(C3=CN(C)C=CC3)=O)(OCCC(C4=CN(C)C=CC4)=O)=O)C
251
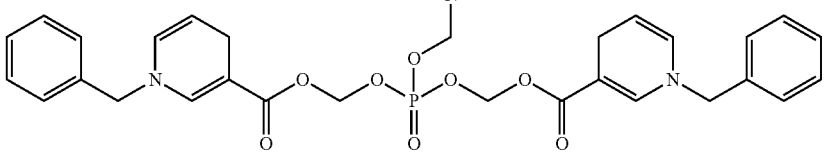
CN(CCC1=CN(C2=C1C=C(OC)C=C2)COP(OCOC(C3=CN(C=CC3)CC4=CC=CC=C4)=O)(OCOC(C5=CN(C=CC5)CC6=CC=CC=C6)=O)=O)C TABLE 1-continued
| Cpd | Structure SMILES* |
|---|---|
252
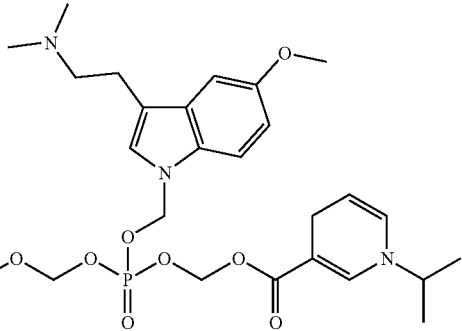
CN(CCC1=CN(C2=C1C=C(OC)C=C2)COP(OCOC(C3=CN(C=CC3)C(C)C)=O)(OCOC(C4=CN(C=CC4)C(C)C)=O)=O)C
253
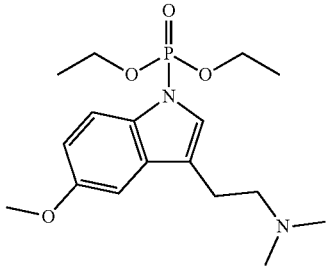
CN(CCC1=CN(C2=C1C=C(OC)C=C2)P(OCC)(OCC)=O)C
254
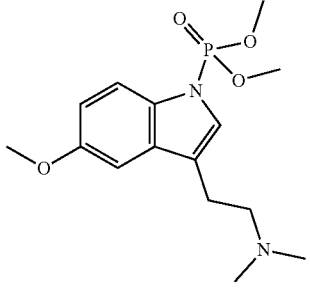
CN(CCC1=CN(C2=C1C=C(OC)C=C2)P(OC)(OC)=O)C
255
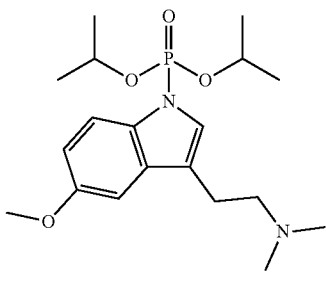
CN(CCC1=CN(C2=C1C=C(OC)C=C2)P(OC)(C)C)(OC(C)C)=O)C TABLE 1-continued

| Cpd | Structure SMILES* |
|---|---|
| 256 | CN(CCC1=CN(C2=C1C=C(OC)C=C2)P(OC(C)(C)C)(OC(C)(C)C)=O)C |
| 257 | CN(CCC1=CN(C2=C1C=C(OC)C=C2)P(OC3CCCCC3)(OC4CCCCC4)=O)C |
| 258 | CN(CCC1=CN(C2=C1C=C(OC)C=C2)P(OC3CC3)(OC4CC4)=O)C |
| 259 | CN(CCC1=CN(C2=C1C=C(OC)C=C2)P(OCCN(C)C)(OCCN(C)C)=O)C |

TABLE 1-continued

| Cpd | Structure SMILES* |
|---|---|

260

CN(CCC1=CN(C2=C1C=C(OC)C=C2)P(OCC3=C(OC(O3)=O)C)(OCC(OC4=O)=C(O4)C)=O)C

261

CN(CCC1=CN(C2=C1C=CC=C2)P(OCC)(OCC)=O)C

262

CN(CCC1=CN(C2=C1C=CC=C2)P(OC)(OC)=O)C

263

CN(CCC1=CN(C2=C1C=CC=C2)P(OC(C)C)(OC(C)C)=O)C

TABLE 1-continued

| Cpd | Structure SMILES* |
|---|---|

264

CN(CCC1=CN(C2=C1C=CC=C2)P(OC(C)(C)(OC(C)(C)C)=O)C

265

CN(CCC1=CN(C2=C1C=CC=C2)P(OC3CCCCC3)(OC4CCCCC4)=O)C

266

CN(CCC1=CN(C2=C1C=CC=C2)P(OC3CC3)(OC4CC4)=O)C

267

CN(CCC1=CN(C2=C1C=CC=C2)P(OCCN(C)C)(OCCN(C)C)=O)C

TABLE 1-continued
| Cpd | Structure SMILES* |
|---|---|
268 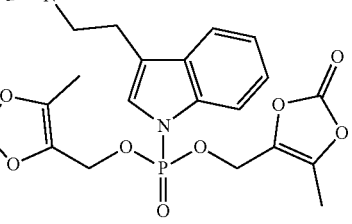
CN(CCC1=CN(C2=C1C=CC=C2)P(OCC3=C(OC(O3)=O)C)(OCC(OC4=O)=C(O4)C)=O)C
269 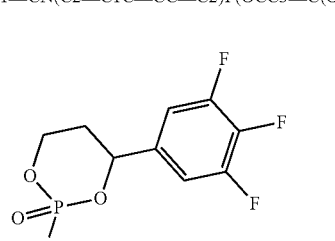
CN(CCC1=CN(C2=CC=CC=C21)P3(OCCC(O3)C4=CC(F)=C(C(F)=C4)F)=O)C
270 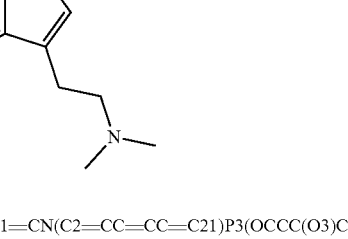
CN(CCC1=CN(C2=CC=CC=C21)P3(OCCC(O3)C4=CC(F)=CC(F)=C4)=O)C TABLE 1-continued
| Cpd | Structure SMILES* |
|---|---|
271
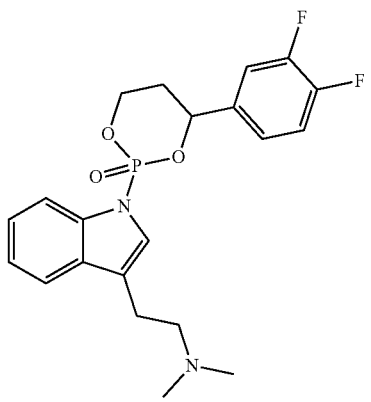 [SMILES: CN(C)CCc1cn(P2(=O)OCCC(c3ccc(F)c(F)c3)O2)c2ccccc12]
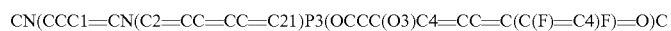
CN(CCC1=CN(C2=CC=CC=C21)P3(OCCC(O3)C4=CC=C(C(F)=C4)F)=O)C
272
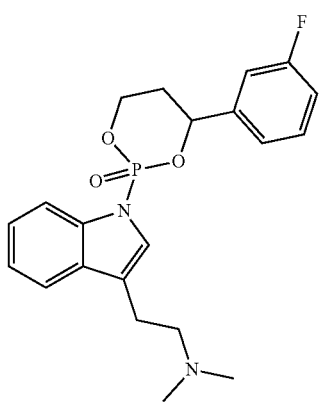 [SMILES: CN(C)CCc1cn(P2(=O)OCCC(c3cccc(F)c3)O2)c2ccccc12]
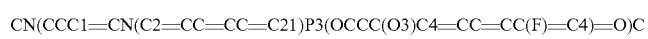
CN(CCC1=CN(C2=CC=CC=C21)P3(OCCC(O3)C4=CC=CC(F)=C4)=O)C
273
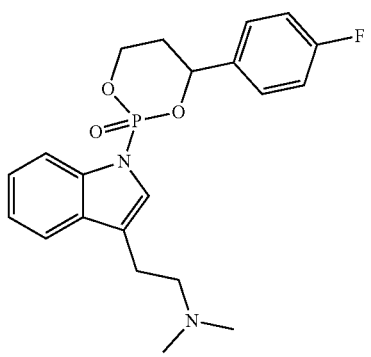 [SMILES: CN(C)CCc1cn(P2(=O)OCCC(c3ccc(F)cc3)O2)c2ccccc12]
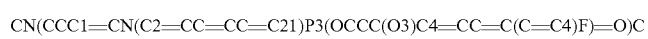
CN(CCC1=CN(C2=CC=CC=C21)P3(OCCC(O3)C4=CC=C(C=C4)F)=O)C TABLE 1-continued
| Cpd | Structure SMILES* |
|---|---|
| 274 | 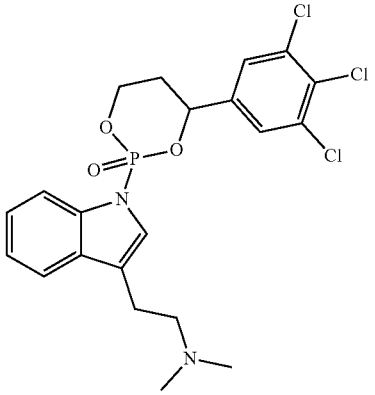 [SMILES: CN(C)CCc1cn(P2(=O)OCCC(c3cc(Cl)c(Cl)c(Cl)c3)O2)c2ccccc12]
CN(CCC1=CN(C2=CC=CC=C21)P3(OCCC(O3)C4=CC(Cl)=C(C(Cl)=C4)Cl)=O)C |
| 275 | 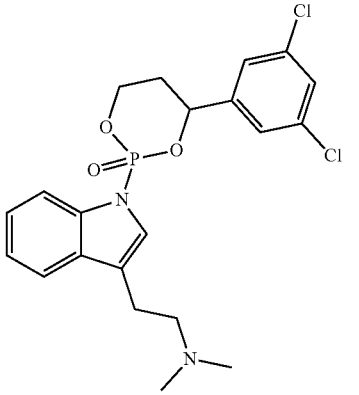 [SMILES: CN(C)CCc1cn(P2(=O)OCCC(c3cc(Cl)cc(Cl)c3)O2)c2ccccc12]
CN(CCC1=CN(C2=CC=CC=C21)P3(OCCC(O3)C4=CC(Cl)=CC(Cl)=C4)=O)C |
| 276 | 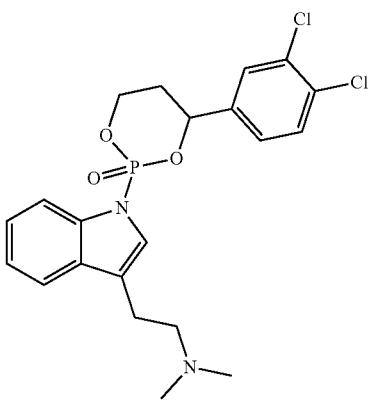 [SMILES: CN(C)CCc1cn(P2(=O)OCCC(c3ccc(Cl)c(Cl)c3)O2)c2ccccc12]
CN(CCC1=CN(C2=CC=CC=C21)P3(OCCC(O3)C4=CC=C(C(Cl)=C4)Cl)=O)C |

TABLE 1-continued

| Cpd | Structure SMILES* |
|---|---|

277

CN(CCC1=CN(C2=CC=CC=C21)P3(OCCC(O3)C4=CC=CC(Cl)=C4)=O)C

278

CN(CCC1=CN(C2=CC=CC=C21)P3(OCCC(O3)C4=CC=C(C=C4)Cl)=O)C

279

CN(CCC1=CN(C2=CC=C(OC)C=C21)P3(OCCC(O3)C4=CC(F)=C(C(F)=C4)F)=O)C

TABLE 1-continued

| Cpd | Structure SMILES* |
|---|---|

280

CN(CCC1=CN(C2=CC=C(OC)C=C21)P3(OCCC(O3)C4=CC(F)=CC(F)=C4)=O)C

281

CN(CCC1=CN(C2=CC=C(OC)C=C21)P3(OCCC(O3)C4=CC=C(C(F)=C4)F)=O)C

282

CN(CCC1=CN(C2=CC=C(OC)C=C21)P3(OCCC(O3)C4=CC=CC(F)=C4)=O)C

TABLE 1-continued

| Cpd | Structure SMILES* |
|---|---|
| 283 | CN(CCC1=CN(C2=CC=C(OC)C=C21)P3(OCCC(O3)C4=CC=C(C=C4)F)=O)C |
| 284 | CN(CCC1=CN(C2=CC=C(OC)C=C21)P3(OCCC(O3)C4=CC(Cl)=C(C(Cl)=C4)Cl)=O)C |
| 285 | CN(CCC1=CN(C2=CC=C(OC)C=C21)P3(OCCC(O3)C4=CC(Cl)=CC(Cl)=C4)=O)C |

TABLE 1-continued
| Cpd | Structure SMILES* |
|---|---|
| 286 | 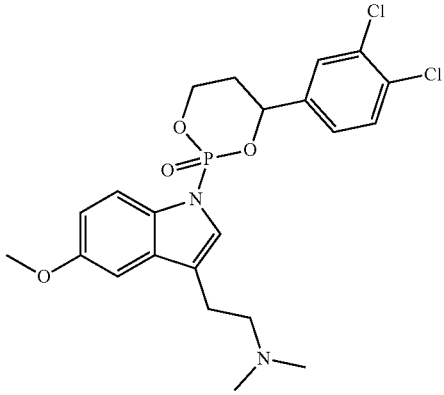
CN(CCC1=CN(C2=CC=C(OC)C=C21)P3(OCCC(O3)C4=CC=C(C(Cl)=C4)Cl)=O)C |
| 287 | 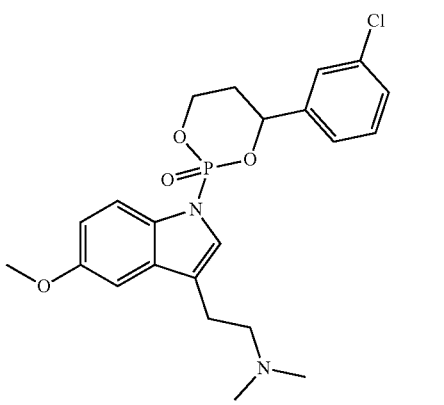 [SMILES: COc1ccc2c(c1)c(CCN(C)C)cn2P1(=O)OCCC(c2cccc(F)c2)O1]
CN(CCC1=CN(C2=CC=C(OC)C=C21)P3(OCCC(O3)C4=CC=CC(Cl)=C4)=O)C |
| 288 | 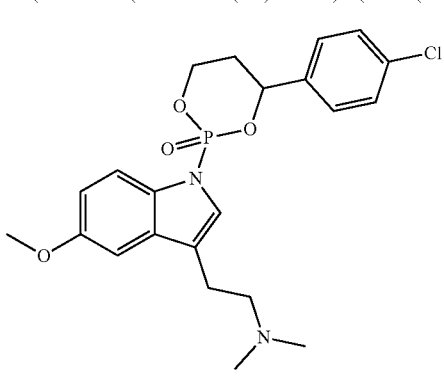
CN(CCC1=CN(C2=CC=C(OC)C=C21)P3(OCCC(O3)C4=CC=C(C=C4)Cl)=O)C |
| 289 | 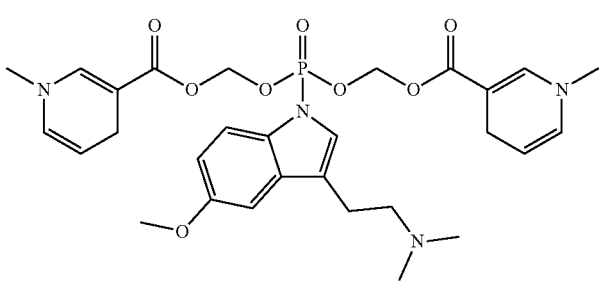
CN(CCC1=CN(C2=CC=C(OC)C=C21)P(OCOC(C3=CN(C)C=CC3)=O)(OCOC(C4=CN(C)C=CC4)=O)=O)C |

TABLE 1-continued

Cpd | Structure
SMILES*

290

CN(CCC1=CN(C2=CC=C(OC)C=C21)P(OCOC(C3=CN(C=CC3)CC)=O)(OCOC(C4=CN(C=CC4)CC)=O)=O)C

291

CN(CCC1=CN(C2=CC=C(OC)C=C21)P(OCOC(C3=CN(C=CC3)CC4=CC=CC=C4)=O)(OCOC(C5=CN(C=CC5)CC6=CC=CC=C6)=O)=O)C

292

CN(CCC1=CN(C2=CC=C(OC)C=C21)P(OCOC(C3=CN(C=CC3)C(C)C)=O)(OCOC(C4=CN(C=CC4)C(C)C)=O)=O)C

293

CN(CCC1=CN(C2=CC=C(OC)C=C21)P(OCOC(C3=CNC=CC3)=O)(OCOC(C4=CNC=CC4)=O)=O)C

TABLE 1-continued
| Cpd | Structure SMILES* |
|---|---|
294
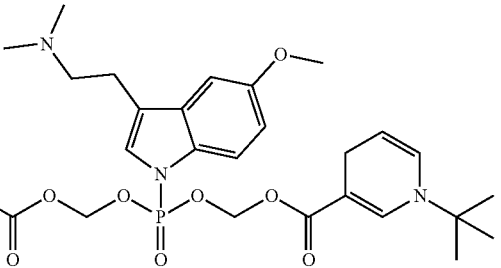
CN(CCC1=CN(C2=CC=C(OC)C=C21)P(OCOC(C3=CN(C=CC3)C(C)(C)C)=O)(OCOC(C4=CN(C=CC4)C(C)(C)C)=O)=O)C
295
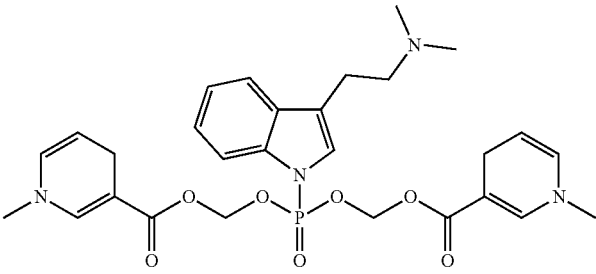
CN(CCC1=CN(C2=CC=CC=C21)P(OCOC(C3=CN(C)C=CC3)=O)(OCOC(C4=CN(C)C=CC4)=O)=O)C
296
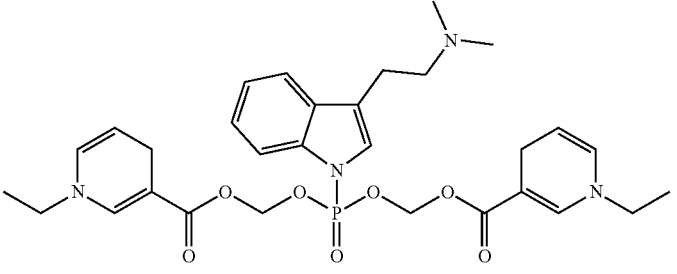 [SMILES: CCN1C=CCC(C(=O)OCOP(=O)(OCOC(=O)C2=CN(CC)C=CC2)n2cc(CCN(C)C)c3ccccc32)=C1]
CN(CCC1=CN(C2=CC=CC=C21)P(OCOC(C3=CN(C=CC3)CC)=O)(OCOC(C4=CN(C=CC4)CC)=O)=O)C
297
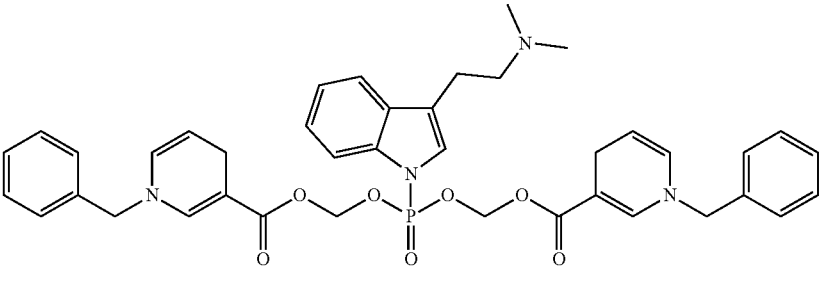 [SMILES: CN(C)CCc1cn(P(=O)(OCOC(=O)C2=CN(Cc3ccccc3)C=CC2)OCOC(=O)C2=CN(Cc3ccccc3)C=CC2)c2ccccc12]
CN(CCC1=CN(C2=CC=CC=C21)P(OCOC(C3=CN(C=CC3)CC4=CC=CC=C4)=O)(OCOC(C5=CN(C=CC5)CC6=CC=CC=C6)=O)=O)C
298
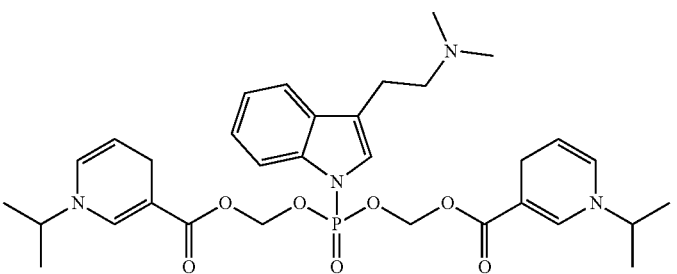 [SMILES: CC(C)N1C=CCC(C(=O)OCOP(=O)(OCOC(=O)C2=CN(C(C)C)C=CC2)n2cc(CCN(C)C)c3ccccc32)=C1]

TABLE 1-continued
| Cpd | Structure SMILES* |
|---|---|
| | CN(CCC1=CN(C2=CC=CC=C21)P(OCOC(C3=CN(C=CC3)C(C)C)=O)(OCOC(C4=CN(C=CC4)C(C)C)=O)=O)C |
| 299 | 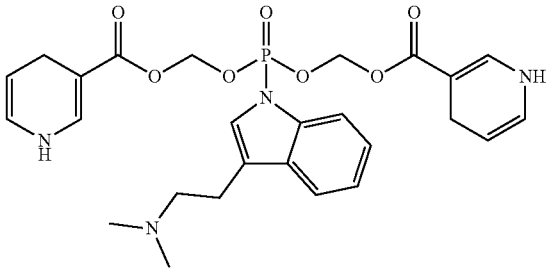 [SMILES: CN(C)CCc1cn(P(=O)(OCOC(=O)C2=CNC=CC2)OCOC(=O)C2=CNC=CC2)c2ccccc12] |
| | CN(CCC1=CN(C2=CC=CC=C21)P(OCOC(C3=CNC=CC3)=O)(OCOC(C4=CNC=CC4)=O)=O)C |
| 300 | 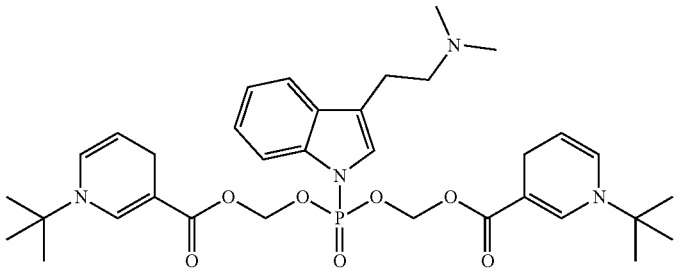 [SMILES: CN(C)CCc1cn(P(=O)(OCOC(=O)C2=CN(C(C)(C)C)C=CC2)OCOC(=O)C2=CN(C(C)(C)C)C=CC2)c2ccccc12] |
| | CN(CCC1=CN(C2=CC=CC=C21)P(OCOC(C3=CN(C=CC3)C(C)(C)C)=O)(OCOC(C4=CN(C=CC4)C(C)(C)C)=O)=O)C |
| 301 | 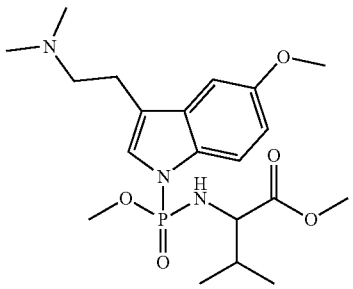 |
| | CN(CCC1=CN(C2=C1C=C(OC)C=C2)P(OC)(NC(C(OC)=O)C(C)C)=O)C |
| 302 | 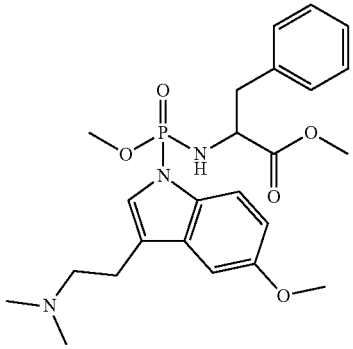 [SMILES: COC(=O)C(Cc1ccccc1)NP(=O)(OC)n1cc(CCN(C)C)c2cc(OC)ccc21] |
| | CN(CCC1=CN(C2=C1C=C(OC)C=C2)P(OC)(NC(C(OC)=O)CC3=CC=CC=C3)=O)C |

TABLE 1-continued

| Cpd | Structure SMILES* |
|---|---|
| 303 | CN(CCC1=CN(C2=C1C=C(OC)C=C2)P(OC)(NC(C(OC)=O)CCSC)=O)C |
| 304 | CN(CCC1=CN(C2=C1C=C(OC)C=C2)P(OC)(NCC(OC)=O)=O)C |
| 305 | CN(CCC1=CN(C2=C1C=C(OC)C=C2)P(OCC)(NC(C(OCC)=O)C(C)C)=O)C |
| 306 | CN(CCC1=CN(C2=C1C=C(OC)C=C2)P(OCC)(NC(C(OCC)=O)CC3=CC=CC=C3)=O)C |

TABLE 1-continued
| Cpd | Structure SMILES* |
|---|---|
307
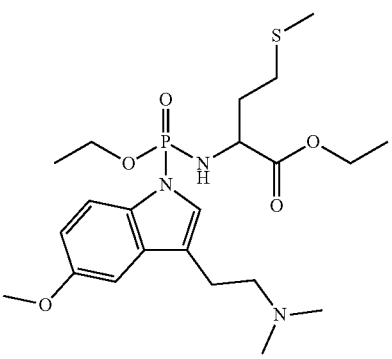 [SMILES: CCOC(=O)C(CCSC)NP(=O)(OCC)n1cc(CCN(C)C)c2cc(OC)ccc21]
CN(CCC1=CN(C2=C1C=C(OC)C=C2)P(OCC)(NC(C(OCC)=O)CCSC)=O)C
308
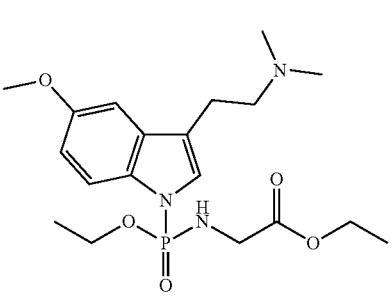 [SMILES: CCOC(=O)CNP(=O)(OCC)n1cc(CCN(C)C)c2cc(OC)ccc21]
CN(CCC1=CN(C2=C1C=C(OC)C=C2)P(OCC)(NCC(OCC)=O)=O)C
309
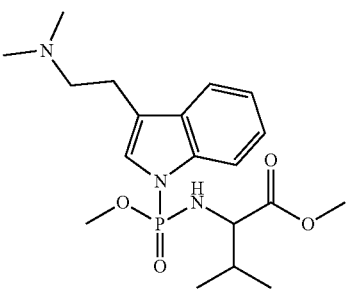
CN(CCC1=CN(C2=C1C=CC=C2)P(OC)(NC(C(OC)=O)C(C)C)=O)C
310
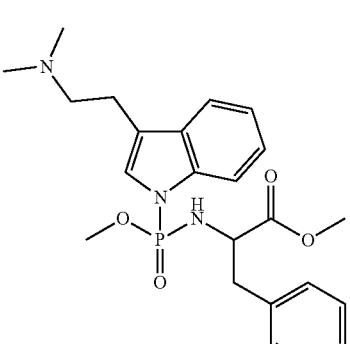
CN(CCC1=CN(C2=C1C=CC=C2)P(OC)(NC(C(OC)=O)CC3=CC=CC=C3)=O)C TABLE 1-continued
| Cpd | Structure SMILES* |
|---|---|
311
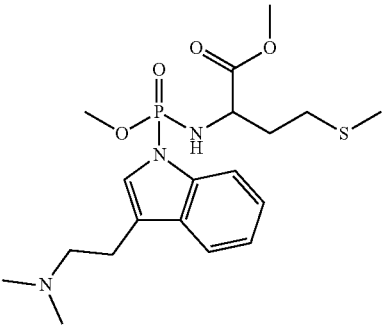
CN(CCC1=CN(C2=C1C=CC=C2)P(OC)(NC(C(OC)=O)CCSC)=O)C
312
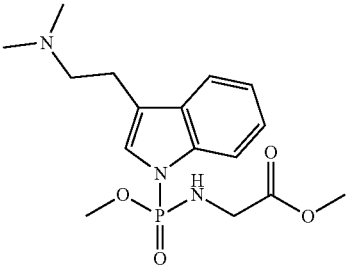
CN(CCC1=CN(C2=C1C=CC=C2)P(OC)(NCC(OC)=O)=O)C
313
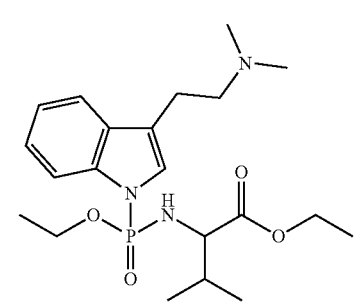 [SMILES: CCOC(=O)C(NP(=O)(OCC)n1cc(CCN(C)C)c2ccccc21)C(C)C]
CN(CCC1=CN(C2=C1C=CC=C2)P(OCC)(NC(C(OCC)=O)C(C)C)=O)C
314
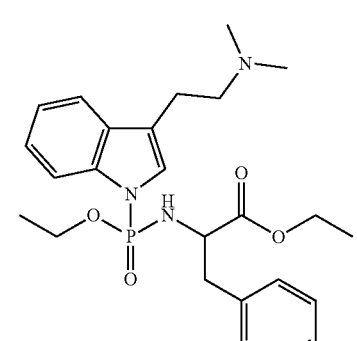
CN(CCC1=CN(C2=C1C=CC=C2)P(OCC)(NC(C(OCC)=O)CC3=CC=CC=C3)=O)C TABLE 1-continued

| Cpd | Structure SMILES* |
|---|---|

315

CN(CCC1=CN(C2=C1C=CC=C2)P(OCC)(NC(C(OCC)=O)CCSC)=O)C

316

CN(CCC1=CN(C2=C1C=CC=C2)P(OCC)(NCC(OCC)=O)=O)C

317

CN(CCC1=CN(C2=C1C=C(OC)C=C2)C(OCOC(C(C)(C)C)=O)=O)C

318

CN(CCC1=CN(C2=C1C=C(OC)C=C2)C(OCOC(C(C)C)=O)=O)C

TABLE 1-continued

| Cpd | Structure SMILES* |
|---|---|
| 319 | CN(C)CCC1=CN(C2=C1C=C(OC)C=C2)C(OCOC(CC)=O)=O)C |
| 320 | CN(C)CCC1=CN(C2=C1C=C(OC)C=C2)C(OCOC(C)=O)=O)C |
| 321 | CN(C)CCC1=CN(C2=C1C=C(OC)C=C2)C(OCOC(C3CNC3)=O)=O)C |
| 322 | CN(C)CCC1=CN(C2=C1C=C(OC)C=C2)C(OCOC(C3CNCC3)=O)=O)C |
| 323 | CN(C)CCC1=CN(C2=C1C=C(OC)C=C2)C(OCOC(C3CCNCC3)=O)=O)C |

TABLE 1-continued

| Cpd | Structure SMILES* |
|---|---|
| 324 | CN(CCC1=CN(C2=C1C=C(OC)C=C2)C(OCOC(C3=CNC=CC3)=O)=O)C |
| 325 | CN(CCC1=CN(C2=C1C=C(OC)C=C2)C(OCOC(C3COC3)=O)=O)C |
| 326 | CN(CCC1=CN(C2=C1C=C(OC)C=C2)C(OCOC(C3COCC3)=O)=O)C |
| 327 | CN(CCC1=CN(C2=C1C=C(OC)C=C2)C(OCOC(C3CCOCC3)=O)=O)C |
| 328 | CN(CCC1=CN(C2=C1C=C(OC)C=C2)C(OCOC(C3CSC3)=O)=O)C |

TABLE 1-continued

| Cpd | Structure SMILES* |
|---|---|
| 329 | CN(CCC1=CN(C2=C1C=C(OC)C=C2)C(OCOC(C3CSCC3)=O)=O)C |
| 330 | CN(CCC1=CN(C2=C1C=C(OC)C=C2)C(OCOC(C3CCSCC3)=O)=O)C |
| 331 | CN(CCC1=CN(C2=C1C=C(OC)C=C2)C(OCOC(C3CN(C)C3)=O)=O)C |
| 332 | CN(CCC1=CN(C2=C1C=C(OC)C=C2)C(OCOC(C3CN(C)CC3)=O)=O)C |
| 333 | CN(CCC1=CN(C2=C1C=C(OC)C=C2)C(OCOC(C3CCN(C)CC3)=O)=O)C |

TABLE 1-continued

| Cpd | Structure SMILES* |
|---|---|
| 334 | CN(CCC1=CN(C2=C1C=C(OC)C=C2)C(OCOC(C3=CN(C)C=CC3)=O)=O)C |
| 335 | CN(CCC1=CN(C2=C1C=C(OC)C=C2)C(OCOC(C3CCN(CC3)C4=CNC=CC4)=O)=O)C |
| 336 | CN(CCC1=CN(C2=C1C=C(OC)C=C2)C(OCOC(C3CCN(CC3)C(C4=CNC=CC4)=O)=O)=O)C |
| 337 | CN(CCC1=CN(C2=C1C=CC=C2)C(OCOC(C(C)(C)C)=O)=O)C |
| 338 | CN(CCC1=CN(C2=C1C=CC=C2)C(OCOC(C(C)C)=O)=O)C |

TABLE 1-continued

| Cpd | Structure SMILES* |
|---|---|
| 339 | CN(CCC1=CN(C2=C1C=CC=C2)C(OCOC(CC)=O)=O)C |
| 340 | CN(CCC1=CN(C2=C1C=CC=C2)C(OCOC(C)=O)=O)C |
| 341 | CN(CCC1=CN(C2=C1C=CC=C2)C(OCOC(C3CNC3)=O)=O)C |
| 342 | CN(CCC1=CN(C2=C1C=CC=C2)C(OCOC(C3CNCC3)=O)=O)C |
| 343 | CN(CCC1=CN(C2=C1C=CC=C2)C(OCOC(C3CCNCC3)=O)=O)C |

TABLE 1-continued

| Cpd | Structure SMILES* |
|---|---|
| 344 | CN(CCC1=CN(C2=C1C=CC=C2)C(OCOC(C3=CNC=CC3)=O)=O)C |
| 345 | CN(CCC1=CN(C2=C1C=CC=C2)C(OCOC(C3COC3)=O)=O)C |
| 346 | CN(CCC1=CN(C2=C1C=CC=C2)C(OCOC(C3COCC3)=O)=O)C |
| 347 | CN(CCC1=CN(C2=C1C=CC=C2)C(OCOC(C3CCOCC3)=O)=O)C |
| 348 | CN(CCC1=CN(C2=C1C=CC=C2)C(OCOC(C3CSC3)=O)=O)C |

TABLE 1-continued

| Cpd | Structure SMILES* |
|---|---|
| 349 | CN(CCC1=CN(C2=C1C=CC=C2)C(OCOC(C3CSCC3)=O)=O)C |
| 350 | CN(CCC1=CN(C2=C1C=CC=C2)C(OCOC(C3CCSCC3)=O)=O)C |
| 351 | CN(CCC1=CN(C2=C1C=CC=C2)C(OCOC(C3CN(C)C3)=O)=O)C |
| 352 | CN(CCC1=CN(C2=C1C=CC=C2)C(OCOC(C3CN(C)CC3)=O)=O)C |
| 353 | CN(CCC1=CN(C2=C1C=CC=C2)C(OCOC(C3CCN(C)CC3)=O)=O)C |

TABLE 1-continued

| Cpd | Structure SMILES* |
|---|---|
| 354 | CN(CCC1=CN(C2=C1C=CC=C2)C(OCOC(C3=CN(C)C=CC3)=O)=O)C |
| 355 | CN(CCC1=CN(C2=C1C=CC=C2)C(OCOC(C3CCN(CC3)C4=CNC=CC4)=O)=O)C |
| 356 | CN(CCC1=CN(C2=C1C=CC=C2)C(OCOC(C3CCN(CC3)C(C4=CNC=CC4)=O)=O)=O)C |
| 357 | CN(CCC1=CN(C2=C1C=C(OC)C=C2)C(OCOC(CN)=O)=O)C |
| 358 | CN(CCC1=CN(C2=C1C=C(OC)C=C2)C(OCOC(C(C(C)C)N)=O)=O)C |

TABLE 1-continued

| Cpd | Structure SMILES* |
|---|---|
| 359 | CN(CCC1=CN(C2=C1C=C(OC)C=C2)C(OCOC(C(CC3=CC=CC=C3)N)=O)=O)C |
| 360 | CN(CCC1=CN(C2=C1C=C(OC)C=C2)C(OCOC(C(C)N)=O)=O)C |
| 361 | CN(CCC1=CN(C2=C1C=C(OC)C=C2)C(OCOC(C(CCSC)N)=O)=O)C |
| 362 | CN(CCC1=CN(C2=C1C=C(OC)C=C2)C(OCOC(C(C(C)(C)C)N)=O)=O)C |
| 363 | CN(CCC1=CN(C2=C1C=CC=C2)C(OCOC(CN)=O)=O)C |

TABLE 1-continued
| Cpd | Structure SMILES* |
|---|---|
| 364 | 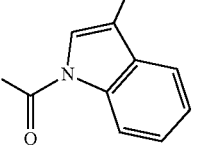<br>CN(CCC1=CN(C2=C1C=CC=C2)C(OCOC(C(C(C)C)N)=O)=O)C |
| 365 | 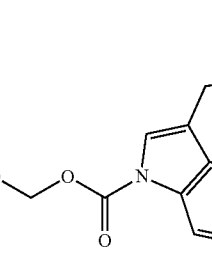<br>CN(CCC1=CN(C2=C1C=CC=C2)C(OCOC(C(CC3=CC=CC=C3)N)=O)=O)C |
| 366 | 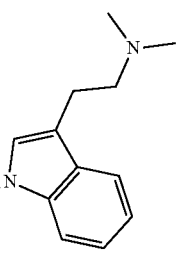<br>CN(CCC1=CN(C2=C1C=CC=C2)C(OCOC(C(C)N)=O)=O)C |
| 367 | 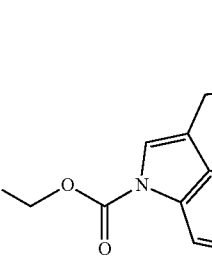<br>CN(CCC1=CN(C2=C1C=CC=C2)C(OCOC(C(CCSC)N)=O)=O)C |
| 368 | 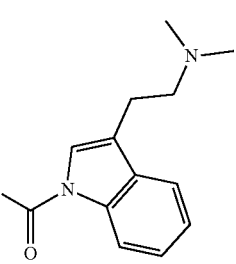<br>CN(CCC1=CN(C2=C1C=CC=C2)C(OCOC(C(C(C)(C)C)N)=O)=O)C |

TABLE 1-continued

| Cpd | Structure SMILES* |
|---|---|
| 369 | CN(C)CCc1cn(C(=O)OCOC(=O)OC(C)(C)C)c2cc(OC)ccc12<br>CN(CCC1=CN(C2=C1C=C(OC)C=C2)C(OCOC(OC(C)(C)C)=O)=O)C |
| 370 | CN(CCC1=CN(C2=C1C=C(OC)C=C2)C(OCOC(OC(C)C)=O)=O)C |
| 371 | CN(CCC1=CN(C2=C1C=C(OC)C=C2)C(OCOC(OCC)=O)=O)C |
| 372 | CN(CCC1=CN(C2=C1C=C(OC)C=C2)C(OCOC(OC)=O)=O)C |
| 373 | CN(CCC1=CN(C2=C1C=C(OC)C=C2)C(OCOC(OC3CNC3)=O)=O)C |

TABLE 1-continued

| Cpd | Structure SMILES* |
|---|---|
| 374 | CN(CCC1=CN(C2=C1C=C(OC)C=C2)C(OCOC(OC3CNCC3)=O)=O)C |
| 375 | CN(CCC1=CN(C2=C1C=C(OC)C=C2)C(OCOC(OC3CCNCC3)=O)=O)C |
| 376 | CN(CCC1=CN(C2=C1C=C(OC)C=C2)C(OCOC(OC3CN(C)C3)=O)=O)C |
| 377 | CN(CCC1=CN(C2=C1C=C(OC)C=C2)C(OCOC(OC3CN(C)CC3)=O)=O)C |
| 378 | CN(CCC1=CN(C2=C1C=C(OC)C=C2)C(OCOC(OC3CCN(C)CC3)=O)=O)C |

TABLE 1-continued
| Cpd | Structure SMILES* |
|---|---|
| 379 | 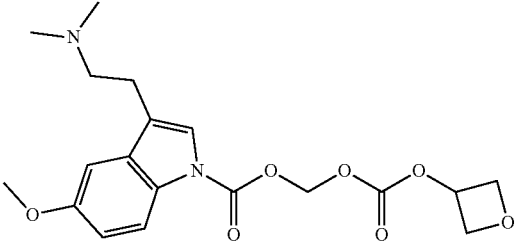 [SMILES: COc1ccc2c(c1)c(CCN(C)C)cn2C(=O)OCOC(=O)OC1COC1]<br>CN(CCC1=CN(C2=C1C=C(OC)C=C2)C(OCOC(OC3COC3)=O)=O)C |
| 380 | 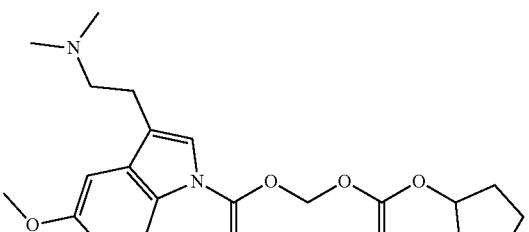<br>CN(CCC1=CN(C2=C1C=C(OC)C=C2)C(OCOC(OC3COCC3)=O)=O)C |
| 381 | 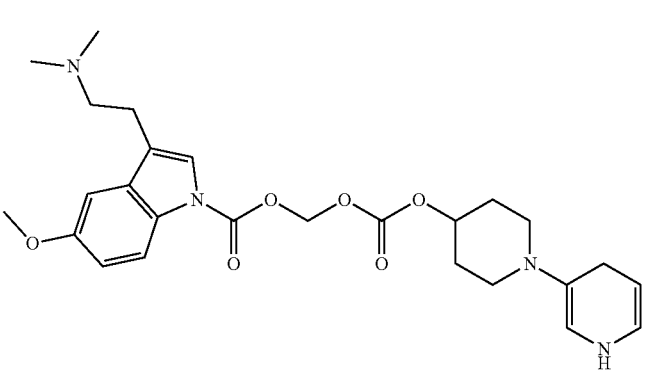 [SMILES: COc1ccc2c(c1)c(CCN(C)C)cn2C(=O)OCOC(=O)OC1CCN(C2=CNC=CC2)CC1]<br>CN(CCC1=CN(C2=C1C=C(OC)C=C2)C(OCOC(OC3CCN(CC3)C4=CNC=CC4)=O)=O)C |
| 382 | 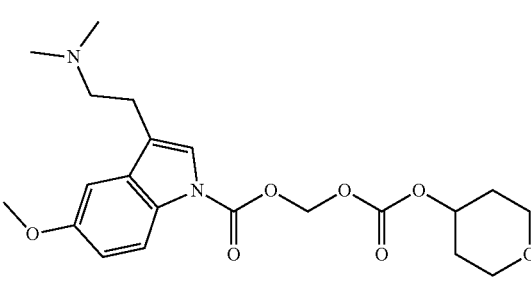 [SMILES: COc1ccc2c(c1)c(CCN(C)C)cn2C(=O)OCOC(=O)OC1CCSCC1]<br>CN(CCC1=CN(C2=C1C=C(OC)C=C2)C(OCOC(OC3CCOCC3)=O)=O)C |

TABLE 1-continued

| Cpd | Structure SMILES* |
|---|---|
| 383 | CN(CCC1=CN(C2=C1C=C(OC)C=C2)C(OCOC(OC3CCN(CC3)C(C4=CNC=CC4)=O)=O)=O)C |
| 384 | CN(CCC1=CN(C2=C1C=C(OC)C=C2)C(OCOC(OC3CSC3)=O)=O)C |
| 385 | CN(CCC1=CN(C2=C1C=C(OC)C=C2)C(OCOC(OC3CSCC3)=O)=O)C |
| 386 | CN(CCC1=CN(C2=C1C=C(OC)C=C2)C(OCOC(OC3CCSCC3)=O)=O)C |
| 387 | CN(CCC1=CN(C2=C1C=CC=C2)C(OCOC(OC(C)(C)C)=O)=O)C |

TABLE 1-continued

| Cpd | Structure SMILES* |
|---|---|
| 388 | CN(CCC1=CN(C2=C1C=CC=C2)C(OCOC(OC(C)C)=O)=O)C |
| 389 | CN(CCC1=CN(C2=C1C=CC=C2)C(OCOC(OCC)=O)=O)C |
| 390 | CN(CCC1=CN(C2=C1C=CC=C2)C(OCOC(OC)=O)=O)C |
| 391 | CN(CCC1=CN(C2=C1C=CC=C2)C(OCOC(OC3CNC3)=O)=O)C |
| 392 | CN(CCC1=CN(C2=C1C=CC=C2)C(OCOC(OC3CNCC3)=O)=O)C |

TABLE 1-continued

| Cpd | Structure SMILES* |
|---|---|
| 393 | CN(CCC1=CN(C2=C1C=CC=C2)C(OCOC(OC3CCNCC3)=O)=O)C |
| 394 | CN(CCC1=CN(C2=C1C=CC=C2)C(OCOC(OC3CN(C)C3)=O)=O)C |
| 395 | CN(CCC1=CN(C2=C1C=CC=C2)C(OCOC(OC3CN(C)CC3)=O)=O)C |
| 396 | CN(CCC1=CN(C2=C1C=CC=C2)C(OCOC(OC3CCN(C)CC3)=O)=O)C |
| 397 | CN(CCC1=CN(C2=C1C=CC=C2)C(OCOC(OC3COC3)=O)=O)C |

| Cpd | Structure<br>SMILES* |
|---|---|
| 398 | 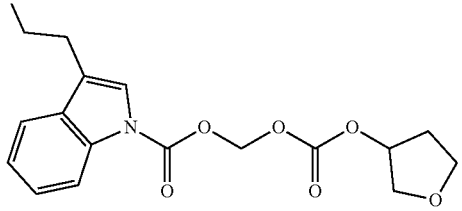<br>CN(C)CCC1=CN(C2=C1C=CC=C2)C(OCOC(OC3COCC3)=O)=O |
| 399 | 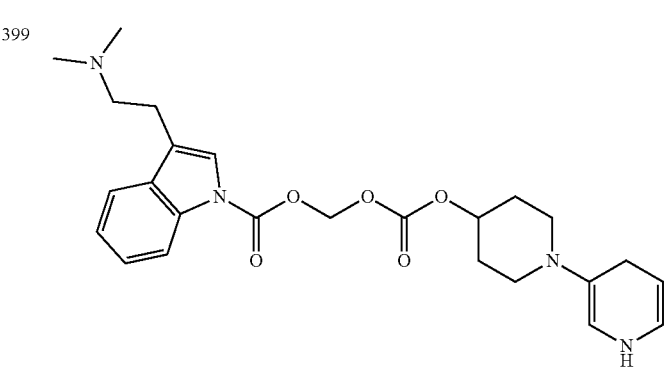<br>CN(C)CCC1=CN(C2=C1C=CC=C2)C(OCOC(OC3CCN(CC3)C4=CNC=CC4)=O)=O |
| 400 | 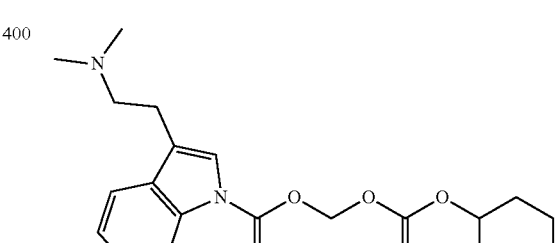<br>CN(C)CCC1=CN(C2=C1C=CC=C2)C(OCOC(OC3CCOCC3)=O)=O |
| 401 | 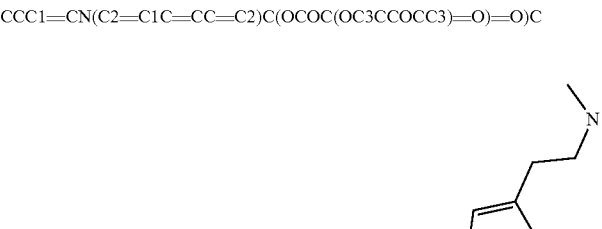<br>CN(C)CCC1=CN(C2=C1C=CC=C2)C(OCOC(OC3CCN(CC3)C(C4=CNC=CC4)=O)=O)=O |

TABLE 1-continued

| Cpd | Structure SMILES* |
|---|---|

402

CN(CCC1=CN(C2=C1C=CC=C2)C(OCOC(OC3CSC3)=O)=O)C

403

CN(CCC1=CN(C2=C1C=CC=C2)C(OCOC(OC3CSCC3)=O)=O)C

404

CN(CCC1=CN(C2=C1C=CC=C2)C(OCOC(OC3CCSCC3)=O)=O)C

405

CN(CCC1=CN(C2=C1C=C(OC)C=C2)C(CC(C)(C3=C(C=C(C=C3OC(C)=O)C)C)C)=O)C

TABLE 1-continued
| Cpd | Structure SMILES* |
|---|---|
| 406 | 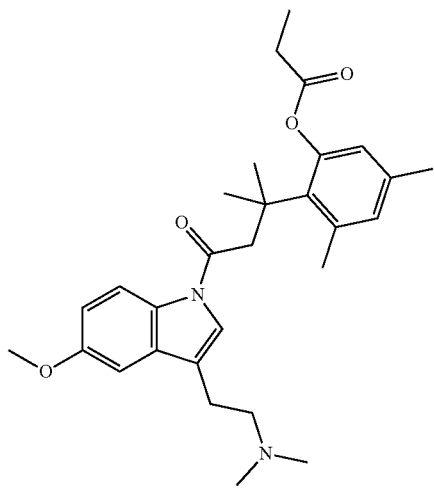 |
| | CN(CCC1=CN(C2=C1C=C(OC)C=C2)C(CC(C)(C3=C(C=C(C=C3OC(CC)=O)C)C)C)=O)C |
| 407 | 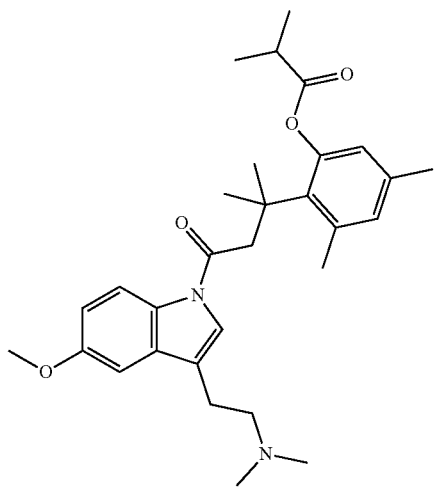 |
| | CN(CCC1=CN(C2=C1C=C(OC)C=C2)C(CC(C)(C3=C(C=C(C=C3OC(C(C)C)=O)C)C)C)=O)C |

TABLE 1-continued

| Cpd | Structure SMILES* |
|---|---|

408

CN(CCC1=CN(C2=C1C=C(OC)C=C2)C(CC(C)(C3=C(C=C(C=C3OC(C(C)(C)C)=O)C)C)C)=O)C

409

CN(CCC1=CN(C2=C1C=C(OC)C=C2)C(CC(C)(C3=C(C=C(C=C3OC(C(C(C)C)N)=O)C)C)C)=O)C

410

CN(CCC1=CN(C2=C1C=C(OC)C=C2)C(CC(C)(C3=C(C=C(C=C3OC(CCC(O)=O)=O)C)C)C)=O)C

TABLE 1-continued

| Cpd | Structure SMILES* |
|---|---|
| 411 | CN(CCC1=CN(C2=C1C=C(OC)C=C2)C(CC(C)(C3=C(C=C(C=C3OC(CC(O)=O)=O)C)C)C)=O)C |
| 412 | CN(CCC1=CN(C2=C1C=C(OC)C=C2)C(CC(C)(C3=C(C=C(C=C3OC(C(CC4=CC=CC=C4)N)=O)C)C)C)=O)C |

TABLE 1-continued

| Cpd | Structure SMILES* |
|---|---|
| 413 | CN(CCC1=CN(C2=C1C=CC=C2)C(CC(C)(C3=C(C=C(C=C3OC(C)=O)C)C)C)=O)C |
| 414 | CN(CCC1=CN(C2=C1C=CC=C2)C(CC(C)(C3=C(C=C(C=C3OC(CC)=O)C)C)C)=O)C |
| 415 | CN(CCC1=CN(C2=C1C=CC=C2)C(CC(C)(C3=C(C=C(C=C3OC(C(C)C)=O)C)C)C)=O)C |

TABLE 1-continued

| Cpd | Structure SMILES* |
|---|---|
| 416 | CN(CCC1=CN(C2=C1C=CC=C2)C(CC(C)(C)C3=C(C=C(C=C3OC(C(C)(C)C)=O)C)C)C)=O)C |
| 417 | CN(CCC1=CN(C2=C1C=CC=C2)C(CC(C)(C)C3=C(C=C(C=C3OC(C(C(C)C)N)=O)C)C)C)=O)C |
| 418 | CN(CCC1=CN(C2=C1C=CC=C2)C(CC(C)(C)C3=C(C=C(C=C3OC(CCC(O)=O)=O)C)C)C)=O)C |

TABLE 1-continued
| Cpd | Structure SMILES* |
|---|---|
| 419 | 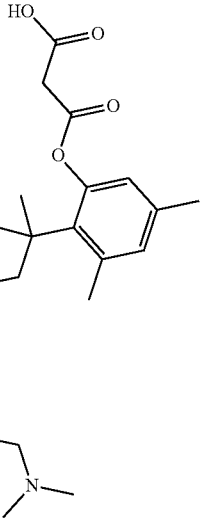<br>CN(CCC1=CN(C2=C1C=CC=C2)C(CC(C)(C3=C(C=C(C=C3OC(CC(O)=O)=O)C)C)=O)C |
| 420 | 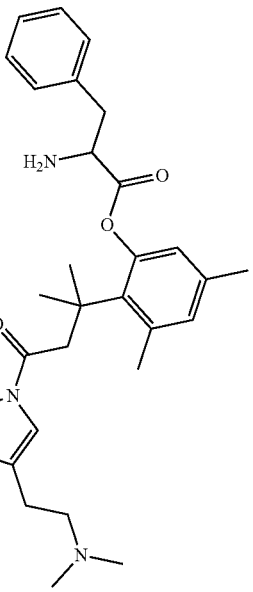<br>CN(CCC1=CN(C2=C1C=CC=C2)C(CC(C)(C3=C(C=C(C=C3OC(C(CC4=CC=CC=C4)N)=O)C)C)=O)C |
| 421 | 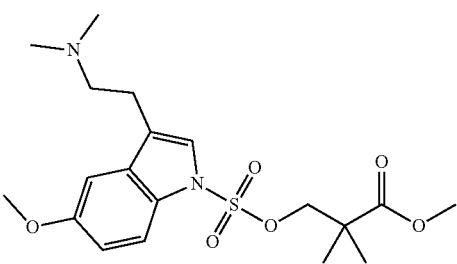<br>CN(CCC1=CN(C2=C1C=C(OC)C=C2)S(OCC(C(OC)=O)(C)C)(=O)=O)C |

TABLE 1-continued
| Cpd | Structure SMILES* |
|---|---|
| 422 | 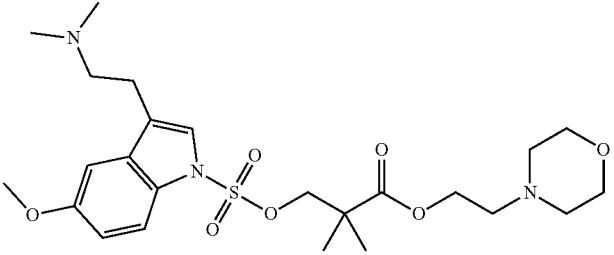 [SMILES: COc1ccc2c(c1)c(CCN(C)C)cn2S(=O)(=O)OCC(C)(C)C(=O)OCCN1CCOCC1]<br>CN(CCC1=CN(C2=C1C=C(OC)C=C2)S(OCC(C)(C)C(OCCN3CCOCC3)=O)(=O)=O)C |
| 423 | 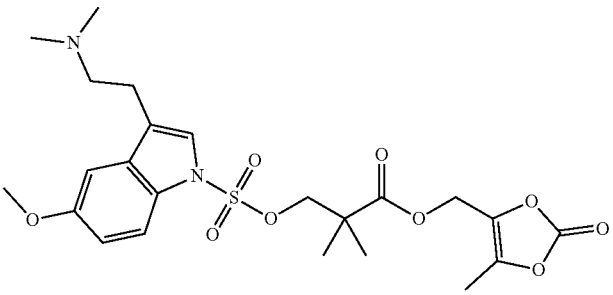 [SMILES: COc1ccc2c(c1)c(CCN(C)C)cn2S(=O)(=O)OCC(C)(C)C(=O)OCc1oc(=O)oc1C]<br>CN(CCC1=CN(C2=C1C=C(OC)C=C2)S(OCC(C(OCC3=C(OC(O3)=O)C)=O)(C)C)(=O)=O)C |
| 424 | 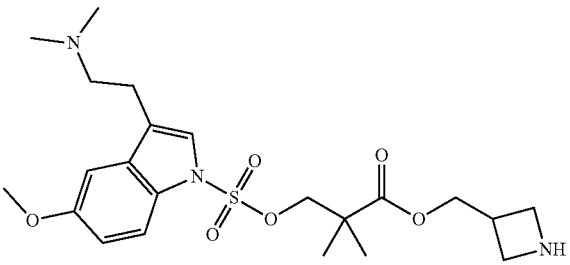 [SMILES: COc1ccc2c(c1)c(CCN(C)C)cn2S(=O)(=O)OCC(C)(C)C(=O)OCC1CNC1]<br>CN(CCC1=CN(C2=C1C=C(OC)C=C2)S(OCC(C(OCC3CNC3)=O)(C)C)(=O)=O)C |
| 425 | 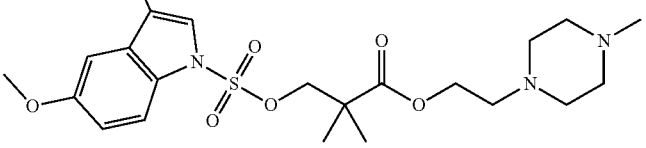<br>CN(CCC1=CN(C2=C1C=C(OC)C=C2)S(OCC(C)(C)C(OCCN3CCN(CC3)C)=O)(=O)=O)C |
| 426 | 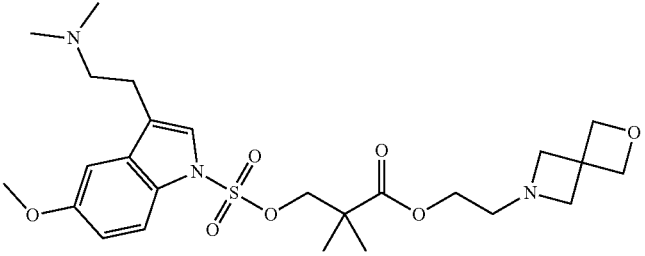 [SMILES: COc1ccc2c(c1)c(CCN(C)C)cn2S(=O)(=O)OCC(C)(C)C(=O)OCCN1CC2(COC2)C1]<br>CN(CCC1=CN(C2=C1C=C(OC)C=C2)S(OCC(C)(C)C(OCCN3CC4(C3)COC4)=O)(=O)=O)C |

TABLE 1-continued

| Cpd | Structure SMILES* |
|---|---|
| 427 | CN(CCC1=CN(C2=C1C=C(OC)C=C2)S(OCC(C)(C)C(OCCN3CCOCC34COC4)=O)(=O)=O)C |
| 428 | CN(CCC1=CN(C2=C1C=C(OC)C=C2)S(OCC(C)(C)C(OCCN3CCC34COC4)=O)(=O)=O)C |
| 429 | CN(CCC1=CN(C2=C1C=C(OC)C=C2)S(OCC(C(OC3CNC3)=O)(C)C)(=O)=O)C |
| 430 | CN(CCC1=CN(C2=C1C=C(OC)C=C2)S(OCC(C(OC3CNCC3)=O)(C)C)(=O)=O)C |
| 431 | CN(CCC1=CN(C2=C1C=C(OC)C=C2)S(OCC(C(OC3CCNCC3)=O)(C)C)(=O)=O)C |

TABLE 1-continued

| Cpd | Structure SMILES* |
|---|---|
| 432 | CN(CCC1=CN(C2=C1C=C(OC)C=C2)S(OCC(C(OC(C)C)=O)(C)C)(=O)=O)C |
| 433 | CN(CCC1=CN(C2=C1C=C(OC)C=C2)S(OCC(C(OCC)=O)(C)C)(=O)=O)C |
| 434 | CN(CCC1=CN(C2=C1C=C(OC)C=C2)S(OCC(C(OCC3(C)CNC3)=O)(C)C)(=O)=O)C |
| 435 | CN(CCC1=CN(C2=C1C=C(OC)C=C2)S(OCC(C(OCC3CN(C)C3)=O)(C)C)(=O)=O)C |
| 436 | CN(CCC1=CN(C2=C1C=C(OC)C=C2)S(OCC(C(OC3CN(C)C3)=O)(C)C)(=O)=O)C |

TABLE 1-continued
| Cpd | Structure SMILES* |
|---|---|
| 437 | 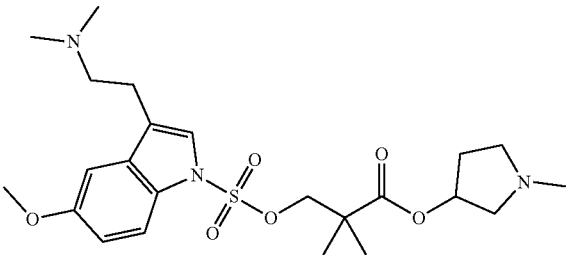
CN(CCC1=CN(C2=C1C=C(OC)C=C2)S(OCC(C(OC3CN(C)CC3)=O)(C)C)(=O)=O)C |
| 438 | 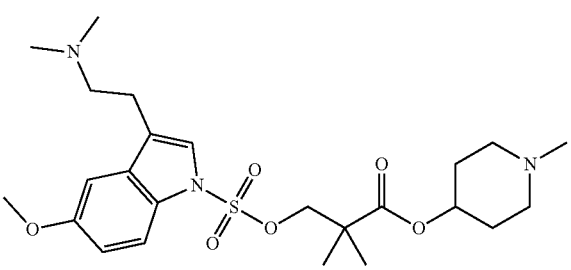
CN(CCC1=CN(C2=C1C=C(OC)C=C2)S(OCC(C(OC3CCN(C)CC3)=O)(C)C)(=O)=O)C |
| 439 | 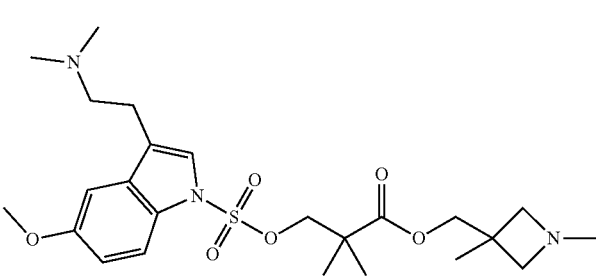
CN(CCC1=CN(C2=C1C=C(OC)C=C2)S(OCC(C(OCC3(C)CN(C)C3)=O)(C)C)(=O)=O)C |
| 440 | 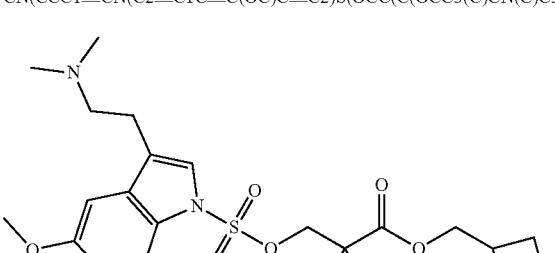
CN(CCC1=CN(C2=C1C=C(OC)C=C2)S(OCC(C(OCC3COC3)=O)(C)C)(=O)=O)C |
| 441 | 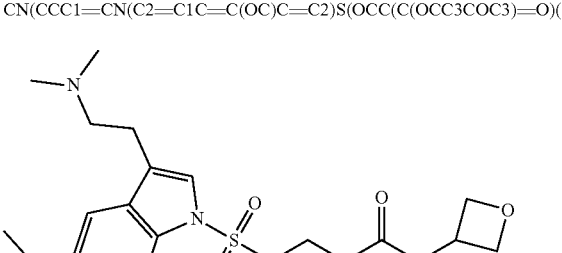
CN(CCC1=CN(C2=C1C=C(OC)C=C2)S(OCC(C(OC3COC3)=O)(C)C)(=O)=O)C |

TABLE 1-continued

| Cpd | Structure SMILES* |
|---|---|
| 442 | CN(CCC1=CN(C2=C1C=C(OC)C=C2)S(OCC(C(OC3COCC3)=O)(C)C)(=O)=O)C |
| 443 | CN(CCC1=CN(C2=C1C=C(OC)C=C2)S(OCC(C(OC3CCOCC3)=O)(C)C)(=O)=O)C |
| 444 | CN(CCC1=CN(C2=C1C=C(OC)C=C2)S(OCC(C(OCC3(C)COC3)=O)(C)C)(=O)=O)C |
| 445 | CN(CCC1=CN(C2=C1C=CC=C2)S(OCC(C(OC)=O)(C)C)(=O)=O)C |
| 446 | CN(CCC1=CN(C2=C1C=CC=C2)S(OCC(C)(C)C(OCCN3CCOCC3)=O)(=O)=O)C |

TABLE 1-continued

| Cpd | Structure SMILES* |
|---|---|
| 447 | CN(CCC1=CN(C2=C1C=CC=C2)S(OCC(C(OCC3=C(OC(O3)=O)C)=O)(C)C)(=O)=O)C |
| 448 | CN(CCC1=CN(C2=C1C=CC=C2)S(OCC(C(OCC3CNC3)=O)(C)C)(=O)=O)C |
| 449 | CN(CCC1=CN(C2=C1C=CC=C2)S(OCC(C)(C)C(OCCN3CCN(CC3)C)=O)(=O)=O)C |
| 450 | CN(CCC1=CN(C2=C1C=CC=C2)S(OCC(C)(C)C(OCCN3CC4(C3)COC4)=O)(=O)=O)C |
| 451 | CN(CCC1=CN(C2=C1C=CC=C2)S(OCC(C)(C)C(OCCN3CCOCC34COC4)=O)(=O)=O)C |

TABLE 1-continued
| Cpd | Structure SMILES* |
|---|---|
| 452 | 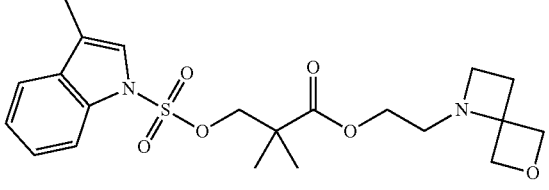<br>CN(CCC1=CN(C2=C1C=CC=C2)S(OCC(C)(C)C(OCCN3CCC34COC4)=O)(=O)=O)C |
| 453 | 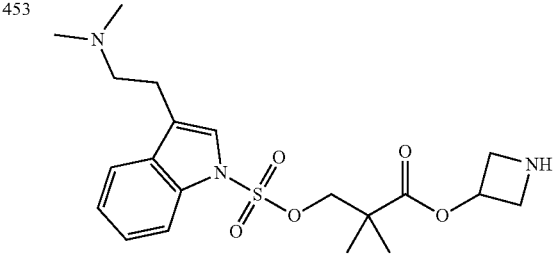<br>CN(CCC1=CN(C2=C1C=CC=C2)S(OCC(C(OC3CNC3)=O)(C)C)(=O)=O)C |
| 454 | 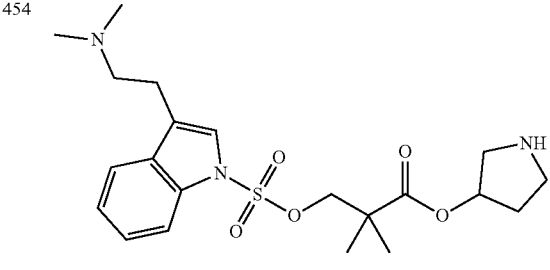<br>CN(CCC1=CN(C2=C1C=CC=C2)S(OCC(C(OC3CNCC3)=O)(C)C)(=O)=O)C |
| 455 | 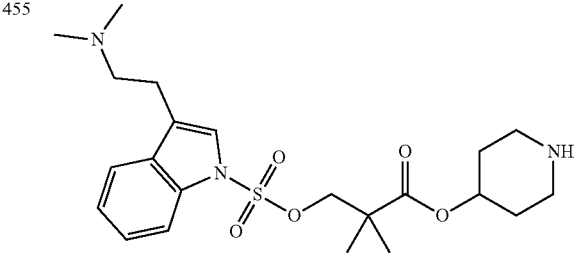<br>CN(CCC1=CN(C2=C1C=CC=C2)S(OCC(C(OC3CCNCC3)=O)(C)C)(=O)=O)C |
| 456 | 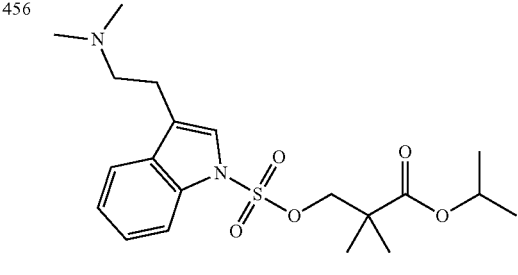<br>CN(CCC1=CN(C2=C1C=CC=C2)S(OCC(C(OC(C)C)=O)(C)C)(=O)=O)C |

TABLE 1-continued

| Cpd | Structure SMILES* |
|---|---|
| 457 | CN(CCC1=CN(C2=C1C=CC=C2)S(OCC(C(OCC)=O)(C)C)(=O)=O)C |
| 458 | CN(CCC1=CN(C2=C1C=CC=C2)S(OCC(C(OCC3(C)CNC3)=O)(C)C)(=O)=O)C |
| 459 | CN(CCC1=CN(C2=C1C=CC=C2)S(OCC(C(OCC3CN(C)C3)=O)(C)C)(=O)=O)C |
| 460 | CN(CCC1=CN(C2=C1C=CC=C2)S(OCC(C(OC3CN(C)C3)=O)(C)C)(=O)=O)C |
| 461 | CN(CCC1=CN(C2=C1C=CC=C2)S(OCC(C(OC3CN(C)CC3)=O)(C)C)(=O)=O)C |

TABLE 1-continued
| Cpd | Structure SMILES* |
|---|---|
| 462 | 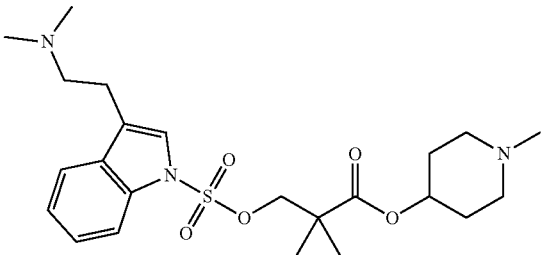<br>CN(CCC1=CN(C2=C1C=CC=C2)S(OCC(C(OC3CCN(C)CC3)=O)(C)C)(=O)=O)C |
| 463 | 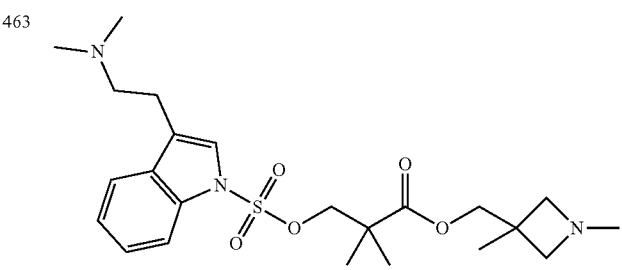<br>CN(CCC1=CN(C2=C1C=CC=C2)S(OCC(C(OCC3(C)CN(C)C3)=O)(C)C)(=O)=O)C |
| 464 | 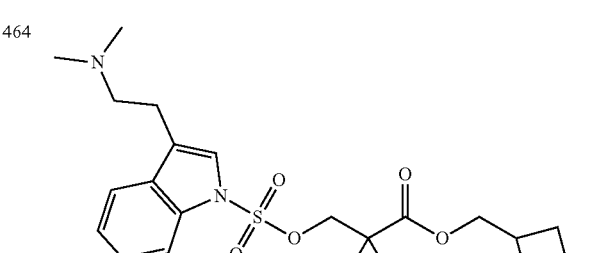<br>CN(CCC1=CN(C2=C1C=CC=C2)S(OCC(C(OCC3COC3)=O)(C)C)(=O)=O)C |
| 465 | 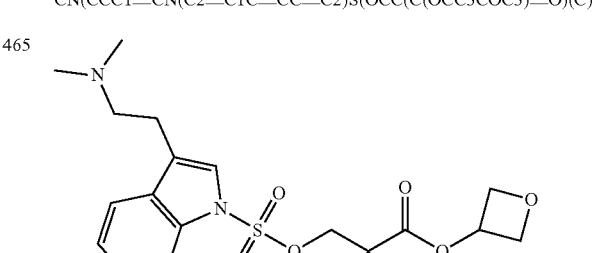<br>CN(CCC1=CN(C2=C1C=CC=C2)S(OCC(C(OC3COC3)=O)(C)C)(=O)=O)C |
| 466 | 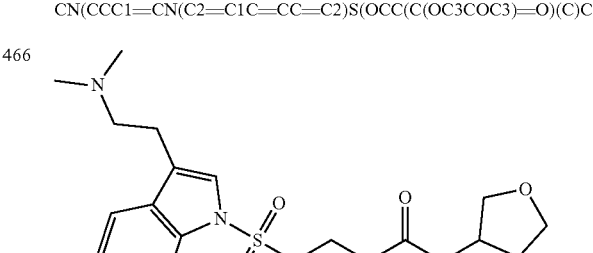<br>CN(CCC1=CN(C2=C1C=CC=C2)S(OCC(C(OC3COCC3)=O)(C)C)(=O)=O)C |

TABLE 1-continued
| Cpd | Structure SMILES* |
|---|---|
| 467 | 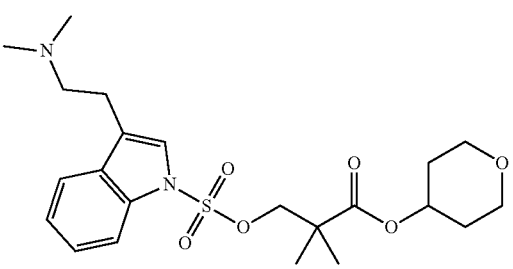 [SMILES: CN(C)CCc1cn(S(=O)(=O)OCC(C)(C)C(=O)OC2CCOCC2)c2ccccc12]<br>CN(C)CCC1=CN(C2=C1C=CC=C2)S(OCC(C(OC3CCOCC3)=O)(C)C)(=O)=O |
| 468 | 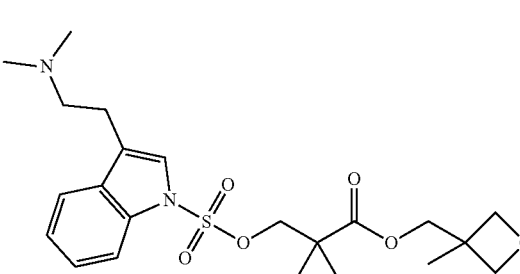<br>CN(C)CCC1=CN(C2=C1C=CC=C2)S(OCC(C(OCC3(C)COC3)=O)(C)C)(=O)=O |
| 469 | 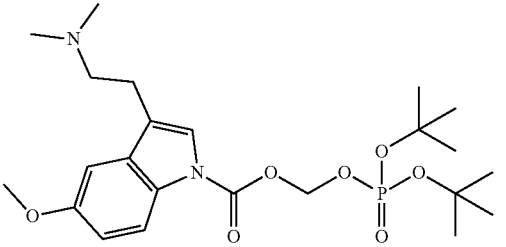 [SMILES: COc1ccc2c(c1)c(CCN(C)C)cn2C(=O)OCOP(=O)(OC(C)(C)C)OC(C)(C)C]<br>CN(C)CCC1=CN(C2=C1C=C(OC)C=C2)C(OCOP(OC(C)(C)C)(OC(C)(C)C)=O)=O |
| 470 | 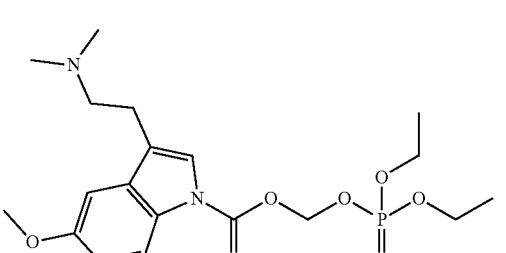<br>CN(C)CCC1=CN(C2=C1C=C(OC)C=C2)C(OCOP(OCC)(OCC)=O)=O |
| 471 | 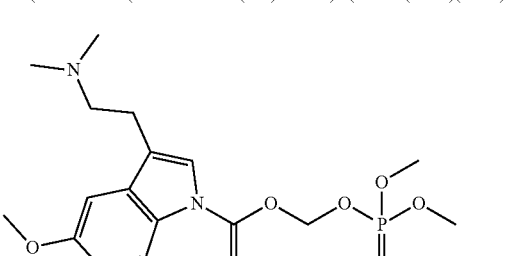<br>CN(C)CCC1=CN(C2=C1C=C(OC)C=C2)C(OCOP(OC)(OC)=O)=O |

| Cpd | Structure SMILES* |
|---|---|
| 472 | CN(CCC1=CN(C2=C1C=C(OC)C=C2)C(OCOP(OC(C)C)(OC(C)C)=O)=O)C |
| 473 | CN(CCC1=CN(C2=C1C=C(OC)C=C2)C(OCOP(OCC3=C(OC(O3)=O)C)(OCC4=C(OC(O4)=O)C)=O)=O)C |
| 474 | CN(CCC1=CN(C2=C1C=CC=C2)C(OCOP(OC(C)(C)C)(OC(C)(C)C)=O)=O)C |
| 475 | CN(CCC1=CN(C2=C1C=CC=C2)C(OCOP(OCC)(OCC)=O)=O)C |
| 476 | CN(CCC1=CN(C2=C1C=CC=C2)C(OCOP(OC)(OC)-O)=O)C |

TABLE 1-continued

| Cpd | Structure SMILES* |
|---|---|
| 477 | CN(C)CCc1=CN(C2=C1C=CC=C2)C(OCOP(OC(C)C)(OC(C)C)=O)=O |
| 478 | CN(C)CCc1=CN(C2=C1C=CC=C2)C(OCOP(OCC3=C(OC(O3)=O)C)(OCC4=C(OC(O4)=O)C)=O)=O |
| 479 | CN(C)CCc1=CN(C2=C1C=C(OC)C=C2)C(OC(C)OP(OC(C)(C)C)(OC(C)(C)C)=O)=O |
| 480 | CN(C)CCc1=CN(C2=C1C=CC=C2)C(OC(C)OP(OC(C)(C)C)(OC(C)(C)C)=O)=O |
| 481 | CN(C)CCc1=CN(C2=C1C=CC=C2)C(OC(C)OC(OC(C)(C)C)=O)=O |

| Cpd | Structure
SMILES* |
|---|---|
| 482 | CN(CCC1=CN(C2=C1C=C(OC)C=C2)C(OC(C)OC(OC(C)(C)C)=O)=O)C |
| 483 | CN(CCC1=CN(C2=C1C=CC=C2)C(OC(OC(C)=O)C)=O)C |
| 484 | CN(CCC1=CN(C2=C1C=C(OC)C=C2)C(OC(OC(C)=O)C)=O)C |
| 485 | CN(CCC1=CN(C2=C1C=C(OC)C=C2)COP(OC(C)OC(OC(C)(C)C)=O)(OC(C)OC(OC(C)(C)C)=O)=O)C |

TABLE 1-continued
| Cpd | Structure SMILES* |
|---|---|
| 486 | 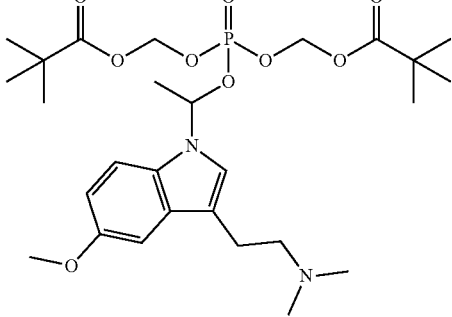<br>CN(CCC1=CN(C2=C1C=C(OC)C=C2)C(C)OP(OCOC(C(C)(C)C)=O)(OCOC(C(C)(C)C)=O)=O)C |
| 487 | 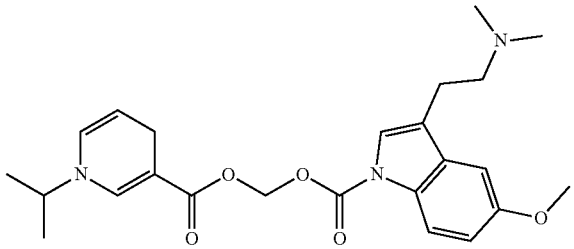<br>CN(CCC1=CN(C2=C1C=C(OC)C=C2)C(OCOC(C3=CN(C=CC3)C(C)C)=O)=O)C |
| 488 | 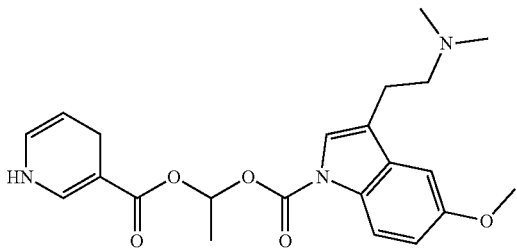<br>CN(CCC1=CN(C2=C1C=C(OC)C=C2)C(OC(C)OC(C3=CNC=CC3)=O)=O)C |
| 489 | 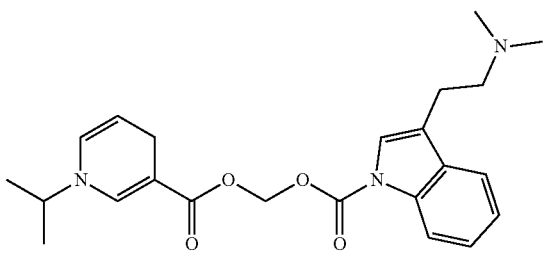 [SMILES: CC(C)N1C=CCC(C(=O)OCOC(=O)n2cc(CCN(C)C)c3ccccc32)=C1]<br>CN(CCC1=CN(C2=C1C=CC=C2)C(OCOC(C3=CN(C=CC3)C(C)C)=O)=O)C |
| 490 | 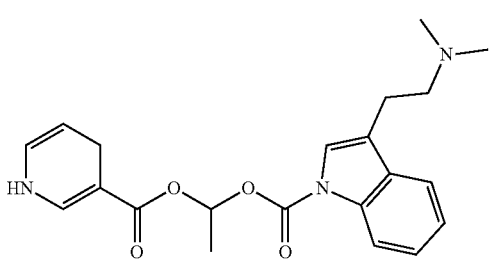<br>CN(CCC1=CN(C2=C1C=CC=C2)C(OC(C)OC(C3=CNC=CC3)=O)=O)C |

TABLE 1-continued

| Cpd | Structure SMILES* |
|---|---|

491

CN(CCC1=CN(C2=C1C=C(OC)C=C2)C(OCOC(C3CCN(CC3)C4=CN(C)C=CC4=O)=O)C

492

CN(CCC1=CN(C2=C1C=C(OC)C=C2)C(OCOC(C3CCN(CC3)C(C4=CN(C)C=CC4)=O)=O)=O)C

493

CN(CCC1=CN(C2=C1C=CC=C2)C(OCOC(C3CCN(CC3)C4=CN(C)C=CC4=O)=O)C

494

CN(CCC1=CN(C2=C1C=CC=C2)C(OCOC(C3CCN(CC3)C(C4=CN(C)C=CC4)=O)=O)=O)C

495

CN(CCC1=CN(C2=C1C=CC=C2)C(OCOC(OCC(OC3=O)=C(O3)C)=O)=O)C

TABLE 1-continued

| Cpd | Structure SMILES* |
|---|---|
| 496 | CN(CCC1=CN(C2=C1C=C(OC)C=C2)C(OCOC(OCC(OC3=O)=C(O3)C)=O)=O)C |
| 497 | CN(CCC1=CN(C2=C1C=CC=C2)C(OCOC(OC3CCN(CC3)C4=CN(C)C=CC4)=O)=O)C |
| 498 | CN(CCC1=CN(C2=C1C=CC=C2)C(OCOC(OC3CCN(CC3)C(C4=CN(C)C=CC4)=O)=O)=O)C |
| 499 | CN(CCC1=CN(C2=C1C=C(OC)C=C2)C(OCOC(OC3CCN(CC3)C4=CN(C)C=CC4)=O)=O)C |

TABLE 1-continued
| Cpd | Structure SMILES* |
|---|---|
| 500 | 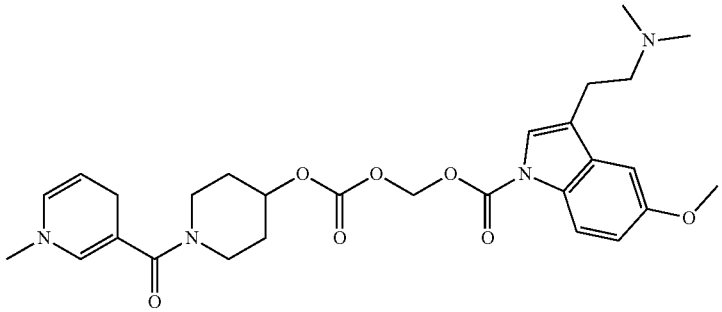<br>CN(CCC1=CN(C2=C1C=C(OC)C=C2)C(OCOC(OC3CCN(CC3)C(C4=CN(C)C=CC4)=O)=O)=O)C |
| 501 | 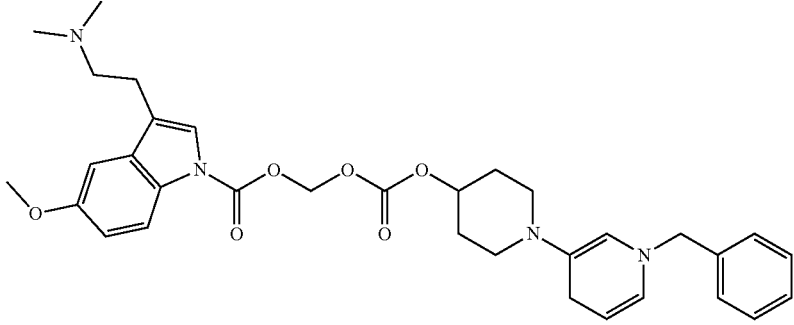 [SMILES: COc1ccc2c(c1)c(CCN(C)C)cn2C(=O)OCOC(=O)OC1CCN(C2=CN(Cc3ccccc3)C=CC2)CC1]<br>CN(CCC1=CN(C2=C1C=C(OC)C=C2)C(OCOC(OC3CCN(CC3)C4=CN(C=CC4)CC5=CC=CC=C5)=O)=O)C |
| 502 | 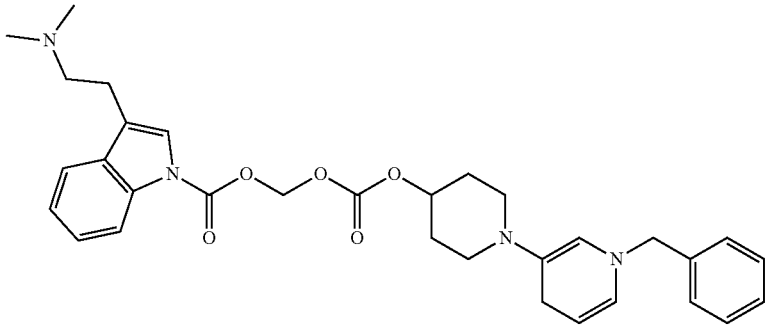 [SMILES: CN(C)CCc1cn(C(=O)OCOC(=O)OC2CCN(C3=CN(Cc4ccccc4)C=CC3)CC2)c2ccccc12]<br>O=C(N(C1=C2C=CC=C1)C=C2CCN(C)C)OCOC(OC3CCN(CC3)C4=CN(C=CC4)CC5=CC=CC=C5)=O |
| 503 | 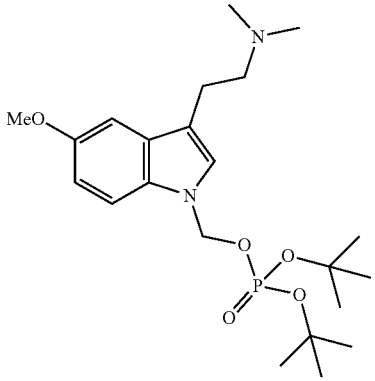 [SMILES: COc1ccc2c(c1)c(CCN(C)C)cn2COP(=O)(OC(C)(C)C)OC(C)(C)C]<br>CN(C)CCC1=CN(COP(OC(C)(C)C)(OC(C)(C)C)=O)C2=C1C=C(OC)C=C2 |

TABLE 1-continued

| Cpd | Structure SMILES* |
|---|---|
| 504 | CN(C)CCC1=CN(COP(OC(C)(C)C)(OC(C)(C)C)=O)C2=C1C=CC=C2 |
| 505 | CN(C)CCC1=CN(COP(O)(OC)=O)C2=C1C=C(OC)C=C2 |
| 506 | CN(C)CCC1=CN(COP(O)(OCC)=O)C2=C1C=C(OC)C=C2 |
| 507 | CN(C)CCC1=CN(COP(O)(OC(C)C)=O)C2=C1C=C(OC)C=C2 |

TABLE 1-continued
| Cpd | Structure SMILES* |
|---|---|
| 508 | 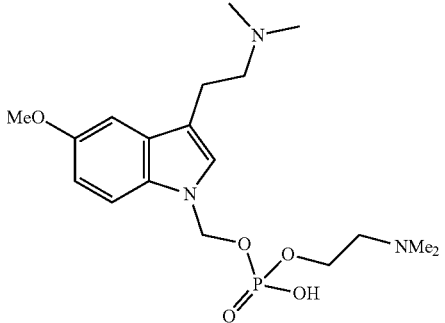 [SMILES: COc1ccc2c(c1)c(CCN(C)C)cn2COP(=O)(O)OCCN(C)C]
CN(C)CCC1=CN(COP(O)(OCCN(C)C)=O)C2=C1C=C(OC)C=C2 |
| 509 | 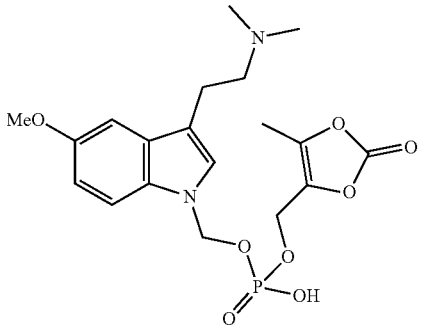 [SMILES: COc1ccc2c(c1)c(CCN(C)C)cn2COP(=O)(O)OCc1oc(=O)oc1C]
CN(C)CCC1=CN(COP(O)(OCC(O2)=C(C)OC2=O)=O)C3=C1C=C(OC)C=C3 |
| 510 | 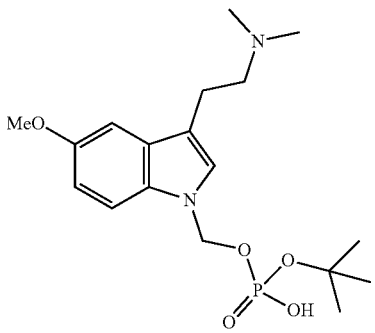 [SMILES: COc1ccc2c(c1)c(CCN(C)C)cn2COP(=O)(O)OC(C)(C)C]
CN(C)CCC1=CN(COP(O)(OC(C)(C)C)=O)C2=C1C=C(OC)C=C2 |
| 511 | 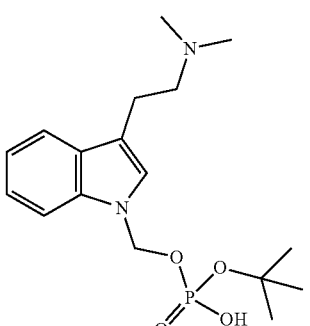
CN(C)CCC1=CN(COP(O)(OC(C)(C)C)=O)C2=C1C=CC=C2 |

TABLE 1-continued

| Cpd | Structure SMILES* |
|---|---|
| 512 | CN(C)CCC1=CN(COP(O)(OC)=O)C2=C1C=CC=C2 |
| 513 | CN(C)CCC1=CN(COP(O)(OCC)=O)C2=C1C=CC=C2 |
| 514 | CN(C)CCC1=CN(COP(O)(OC(C)C)=O)C2=C1C=CC=C2 |
| 515 | CN(C)CCC1=CN(COP(O)(OCCN(C)C)=O)C2=C1C=CC=C2 |

TABLE 1-continued
| Cpd | Structure SMILES* |
|---|---|
| 516 | 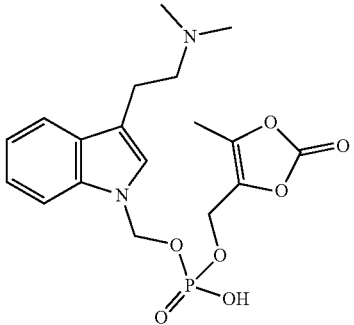 [SMILES: Cc1oc(=O)oc1COP(=O)(O)OCn1cc(CCN(C)C)c2ccccc21]
CN(C)CCC1=CN(COP(O)(OCC(O2)=C(C)OC2=O)=O)C3=C1C=CC=C3 |
| 517 | 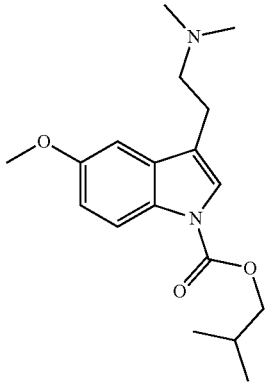 [SMILES: COc1ccc2c(c1)c(CCN(C)C)cn2C(=O)OCC(C)C]
COC1=CC=C(N(C(OCC(C)C)=O)C=C2CCN(C)C)C2=C1 |
| 518 | 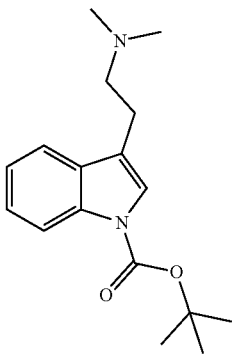 [SMILES: CN(C)CCc1cn(C(=O)OC(C)(C)C)c2ccccc12]
CN(C)CCC1=CN(C(OC(C)(C)C)=O)C2=CC=CC=C21 |
| 519 | 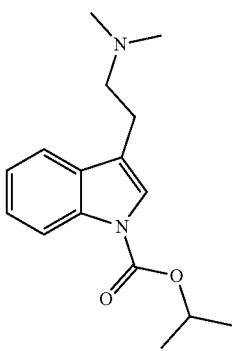 [SMILES: CC(C)OC(=O)n1cc(CCN(C)C)c2ccccc21]
CN(C)CCC1=CN(C(OC(C)C)=O)C2=CC=CC=C21 |

TABLE 1-continued
| Cpd | Structure SMILES* |
|---|---|
520 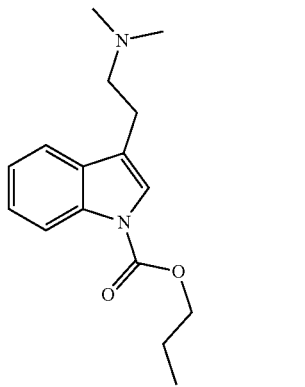 [SMILES: CCCOC(=O)n1cc(CCN(C)C)c2ccccc21]
CN(C)CCC1=CN(C(OCCC)=O)C2=CC=CC=C21
521 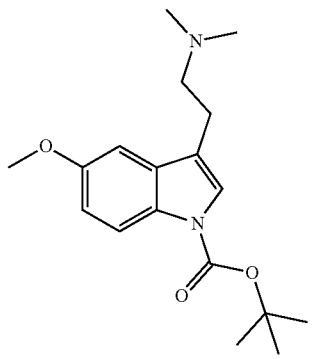 [SMILES: COc1ccc2c(c1)c(CCN(C)C)cn2C(=O)OC(C)(C)C]
COC1=CC=C(N(C(OC(C)(C)C)=O)C=C2CCN(C)C)C2=C1
522 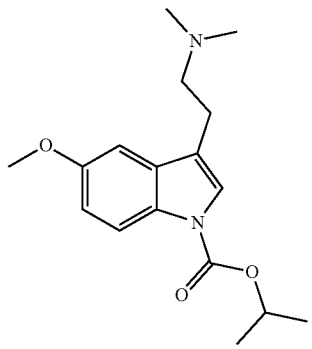 [SMILES: COc1ccc2c(c1)c(CCN(C)C)cn2C(=O)OC(C)C]
COC1=CC=C(N(C(OC(C)C)=O)C=C2CCN(C)C)C2=C1

TABLE 1-continued

| Cpd | Structure SMILES* |
|---|---|
| 523 | COC1=CC=C(N(C(OCCC)=O)C=C2CCN(C)C)C2=C1 |
| 524 | CN(C)CCC1=CN(C(OCC(C)C)=O)C2=CC=CC=C21 |
| 525 | CN(C)CCC1=CN(C(N(C)C)=O)C2=CC=CC=C21 |
| 526 | CN(C)CCC1=CN(C(N(C)C)=O)C2=CC=C(OC)C=C21 HCO₂H |

TABLE 1-continued

| Cpd | Structure SMILES* |
|---|---|

529

CN(C)CCC1=CN(C(CCC(O)=O)=O)C2=C1C=CC=C2

530

CN(C)CCC1=CN(C(CCC(O)=O)=O)C2=C1C=C(OC)C=C2

531

CN(C)CCC1=CN(C(CCC(O)=O)=O)C2=C1C=CC=C2

532

CN(C)CCC1=CN(C(CCCC(O)=O)=O)C2=C1C=C(OC)C=C2

TABLE 1-continued

| Cpd | Structure SMILES* |
|---|---|

533

CN(C)CCC1=CN(C(CCC(OC)=O)=O)C2=CC=CC=C21

534

CN(C)CCC1=CN(C(CCC(OC)=O)=O)C2=CC=C(OC)C=C21

535

CN(C)CCC1=CN(C([C@@H](NC(OC(C)(C)C)=O)CCCCNC(OC(C)(C)C)=O)=O)C2=CC=CC=C21

536

CN(C)CCC1=CN(C([C@@H](NC(OC(C)(C)C)=O)CCCCNC(OC(C)(C)C)=O)=O)C2=CC=C(OC)C=C21

TABLE 1-continued

| Cpd | Structure SMILES* |
|---|---|
| 537 | C(C)CCC1=CN(C([C@@H](N)CCCCN)=O)C2=CC=CC=C21 |
| 538 | CN(C)CCC1=CN(C([C@@H](N)CCCCN)=O)C2=CC=C(OC)C=C21 |
| 539 | CN(C)CCC1=CN(C([C@@H](NC(OC(C)(C)C)=O)C)=O)C2=CC=CC=C21 |
| 540 | CN(C)CCC1=CN(C([C@@H](N)C)=O)C2=CC=CC=C21 |

TABLE 1-continued

| Cpd | Structure SMILES* |
|---|---|
| 541 | CN(C)CCC1=CN(C([C@@H](NC(OC(C)(C)C)=O)C)=O)C2=CC=C(OC)C=C21 |
| 542 | 2 HCl<br>CN(C)CCC1=CN(C([C@@H](N)C)=O)C2=CC=C(OC)C=C21 |
| 543 | CN(C)CCC1=CN(C([C@H](CC2=CC=CC=C2)NC(OC(C)(C)C)=O)=O)C3=CC=CC=C31 |
| 544 | CN(C)CCC1=CN(C([C@H](C(C)C)NC(OC(C)(C)C)=O)=O)C2=CC=CC=C21 |

TABLE 1-continued
| Cpd | Structure SMILES* |
|---|---|
| 545 | 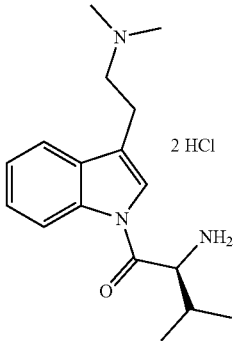 [SMILES: CC(C)[C@H](N)C(=O)n1cc(CCN(C)C)c2ccccc21]
CN(C)CCC1=CN(C([C@H](C(C)C)N)=O)C2=CC=CC=C21 |
| 546 | 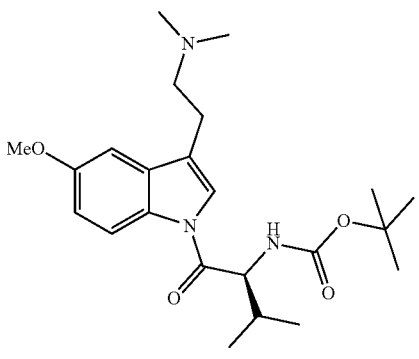 [SMILES: COc1ccc2c(c1)c(CCN(C)C)cn2C(=O)[C@@H](NC(=O)OC(C)(C)C)C(C)C]
CN(C)CCC1=CN(C([C@H](C(C)C)NC(OC(C)(C)C)=O)=O)C2=CC=C(OC)C=C21 |
| 547 | 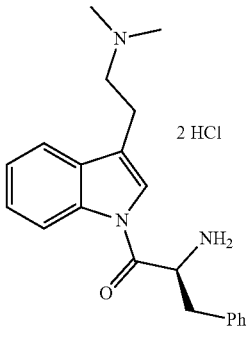 [SMILES: CN(C)CCc1cn(C(=O)[C@@H](N)Cc2ccccc2)c2ccccc12]
CN(C)CCC1=CN(C([C@H](CC2=CC=CC=C2)N)=O)C3=CC=CC=C31 |
| 548 | 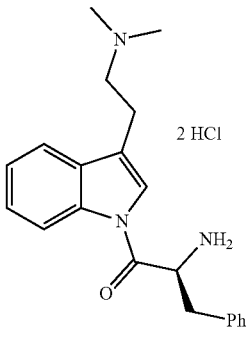 [SMILES: CN(C)CCc1cn(C(=O)[C@@H](N)Cc2ccccc2)c2ccccc12]
CN(C)CCC1=CN(C([C@H](CC2=CC=CC=C2)N)=O)C3=CC=CC=C31 |

TABLE 1-continued

| Cpd | Structure SMILES* |
|---|---|
| 549 | CN(C)CCC1=CN(C([C@H](CC2=CC=CC=C2)NC(OC(C)(C)C)=O)=O)C3=CC=C(OC)C=C31 |
| 550 | CN(C)CCC1=CN(C([C@H](CC2=CC=CC=C2)N)=O)C3=CC=C(OC)C=C31 ·2HCl |
| 551 | CN(C)CCC1=CN(C(CN(C)C)=O)C2=CC=CC=C21 ·HCl |
| 552 | CN(C)CCC1=CN(C(CN(C)C)=O)C2=CC=C(OC)C=C21 ·HCO₂H |

TABLE 1-continued

| Cpd | Structure SMILES* |
|---|---|

553

O=C(N(C)CC(N1C=C(CCN(C)C)C2=C1C=CC=C2)=O)[C@H](CC3=CC=CC=C3)N

554

O=C(N(C)CC(N1C=C(CCN(C)C)C2=C1C=CC(OC)=C2)=O)[C@H](CC3=CC=CC=C3)N

555

CN(C)CCC1=CN(C(OCC(C)(C)COC(C(C)(C)C)=O)=O)C2=CC=C(OC)C=C21

556

CN(C)CCC1=CN(C(OCC(C)(C)COC(C(C)(C)C)=O)=O)C2=CC=CC=C21

TABLE 1-continued
| Cpd | Structure SMILES* |
|---|---|
557
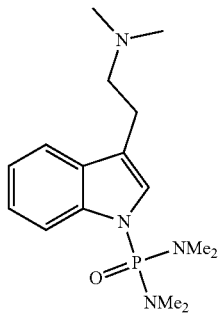 [SMILES: CN(C)CCc1cn(P(=O)(N(C)C)N(C)C)c2ccccc12]
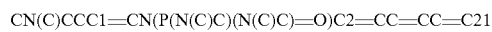
CN(C)CCC1=CN(P(N(C)C)(N(C)C)=O)C2=CC=CC=C21
558
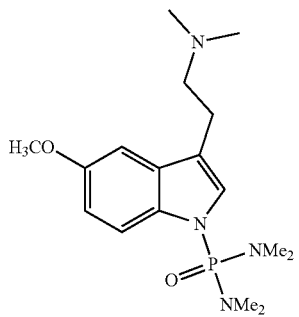 [SMILES: COc1ccc2c(c1)c(CCN(C)C)cn2P(=O)(N(C)C)N(C)C]
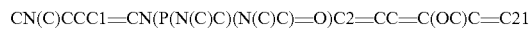
CN(C)CCC1=CN(P(N(C)C)(N(C)C)=O)C2=CC=C(OC)C=C21
559
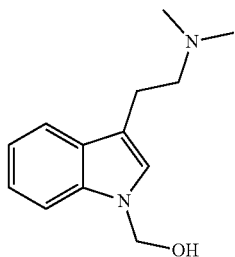 [SMILES: CN(C)CCc1cn(CO)c2ccccc12]
CN(C)CCC1=CN(CO)C2=CC=CC=C21
560
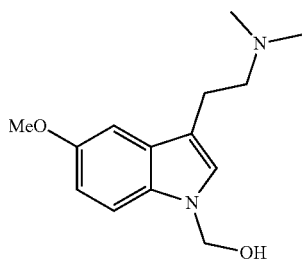 [SMILES: COc1ccc2c(c1)c(CCN(C)C)cn2CO]
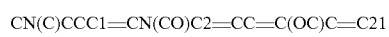
CN(C)CCC1=CN(CO)C2=CC=C(OC)C=C21

TABLE 1-continued

| Cpd | Structure SMILES* |
|---|---|
| 561 | CN(C)CCC1=CN(COC(OCC)=O)C2=CC=CC=C21 |
| 562 | CN(C)CCC1=CN(COC(OCC)=O)C2=CC=C(OC)C=C21 |
| 563 | O=C(OC(C(C)C)OC([C@H](C(C)C)N)=O)N1C2=CC=C(OC)C=C2C(CCN(C)C)=C1 |
| 564 | O=C(OC(C(C)C)OC([C@H](C(C)C)N)=O)N1C2=CC=CC=C2C(CCN(C)C)=C1 |

TABLE 1-continued
| Cpd | Structure SMILES* |
|---|---|
| 565 | 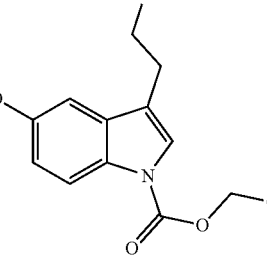
CN(C)CCC1=CN(C(OCOC(CCC(OC(C)(C)C)=O)=O)=O)C2=CC=C(OC)C=C21 |
| 566 | 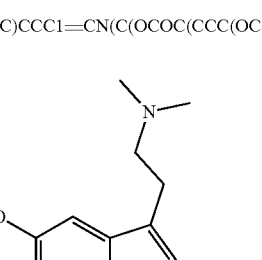
CN(C)CCC1=CN(C(OCOC(CCC(O)=O)=O)=O)C2=CC=C(OC)C=C21 |
| 567 | 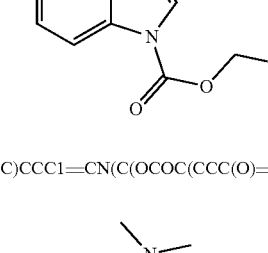
CN(C)CCC1=CN(C(OCOC(CCCC(O)=O)=O)=O)C2=CC=C(OC)C=C21 |
| 568 | 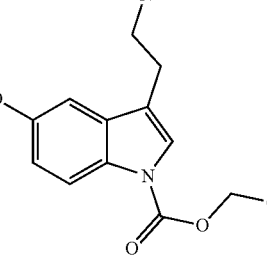
CN(C)CCC1=CN(C(OCOC(CCCCC(O)=O)=O)=O)C2=CC=C(OC)C=C21 |

TABLE 1-continued
| Cpd | Structure SMILES* |
|---|---|
| 569 | 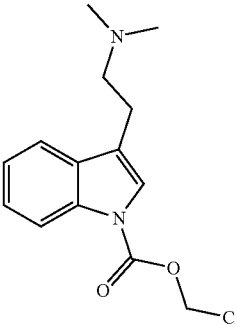<br>CN(C)CCC1=CN(C(OCCl)=O)C2=CC=CC=C21 |
| 570 | 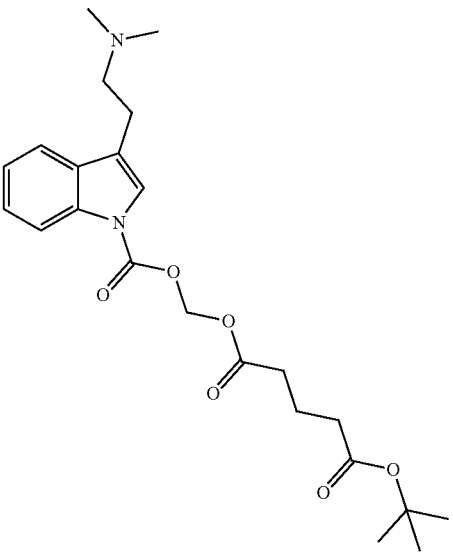 [SMILES: CN(C)CCc1cn(C(=O)OCOC(=O)CCCC(=O)OC(C)(C)C)c2ccccc12]<br>CN(C)CCC1=CN(C(OCOC(CCCC(OC(C)(C)C)=O)=O)=O)C2=CC=CC=C21 |
| 571 | 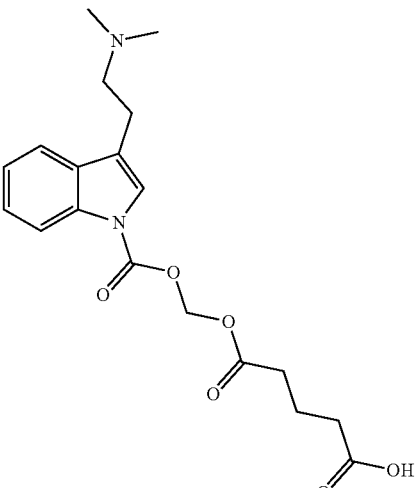<br>CN(C)CCC1=CN(C(OCOC(CCCC(O)=O)=O)=O)C2=CC=CC=C21 |

TABLE 1-continued
| Cpd | Structure SMILES* |
|---|---|
| 572 | 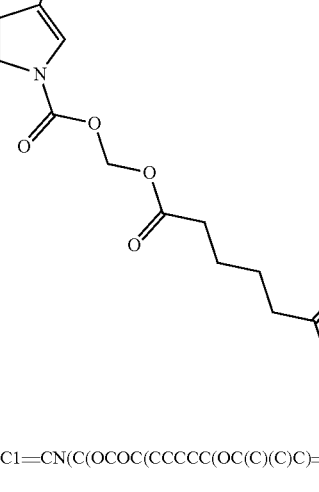
CN(C)CCC1=CN(C(OCOC(CCCCC(OC(C)(C)C)=O)=O)=O)C2=CC=CC=C21 |
| 573 | 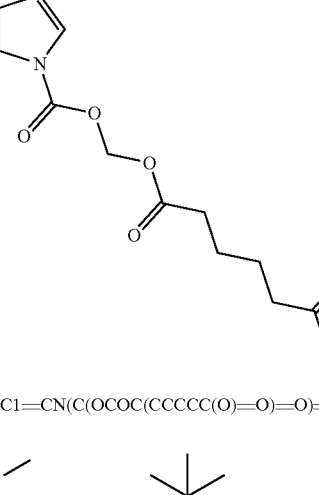
CN(C)CCC1=CN(C(OCOC(CCCCC(O)=O)=O)=O)C2=CC=CC=C21 |
| 574 | 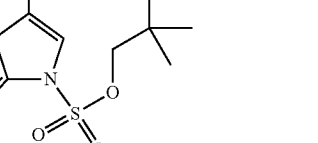
CN(C)CCC1=CN(S(=O)(OCC(C)(C)C(OC(C)(C)C)=O)=O)C2=CC=CC=C21 |

TABLE 1-continued

| Cpd | Structure SMILES* |
|---|---|
| 575 | CN(C)CCC1=CN(S(=O)(OCC(C)(C)C(OC(C)(C)C)=O)=O)C2=CC=C(OC)C=C21 |
| 576 | CN(C)CCC1=CN(C(CC(C)(C(O)=O)C)=O)C2=CC=CC=C21 |
| 577 | CN(C)CCC1=CN(C(CC(C)(C(O)=O)C)=O)C2=CC=C(OC)C=C21 |

*SMILES strings of the corresponding freebase are provided for all compounds that are salts. In some embodiments, the compound described herein is a compound selected from Table 1.

*SMILES strings of the corresponding freebase are provided for all compounds that are salts.

In some embodiments, the compound described herein is a compound selected from Table 1.

In some embodiment, the compound described herein a compound selected from Table 1A below.

TABLE 1A

| Compound | Structure | Chemical Name |
|---|---|---|
| 20 | 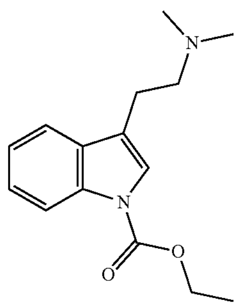 [SMILES: CCOC(=O)n1cc(CCN(C)C)c2ccccc21] | Ethyl 3-[2-(dimethylamino)-ethyl]indole-1-carboxylate |
| 19 | 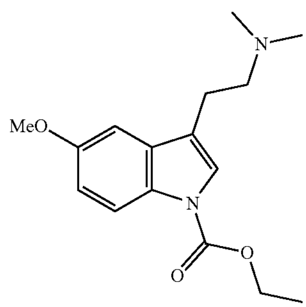 [SMILES: CCOC(=O)n1cc(CCN(C)C)c2cc(OC)ccc21] | Ethyl 3-[2-(dimethylamino)-ethyl]-5-methoxy-indole-1-carboxylate |
| 263 | 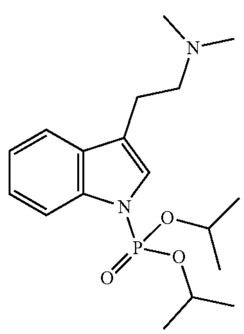 [SMILES: CC(C)OP(=O)(OC(C)C)n1cc(CCN(C)C)c2ccccc21] | 2-(1-Diisopropoxyphosphor-ylindol-3-yl)-N,N-dimethyl-ethanamine |
| 255 | 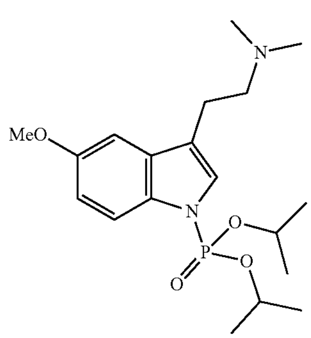 [SMILES: COc1ccc2c(c1)c(CCN(C)C)cn2P(=O)(OC(C)C)OC(C)C] | 2-(1-Diisopropoxyphosphor-yl-5-methoxy-indol-3-yl)-N,N-dimethyl-ethanamine |

TABLE 1A-continued
| Compound | Structure | Chemical Name |
|---|---|---|
| 511 | 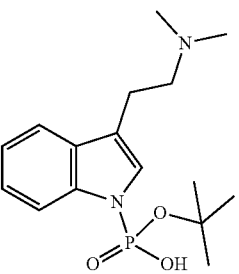 [SMILES: CN(C)CCc1cn(P(=O)(O)OC(C)(C)C)c2ccccc12] | Tert-butyl [3-[2-(dimethyl-amino)ethyl]indol-1-yl]-methyl hydrogen |
| 510 | 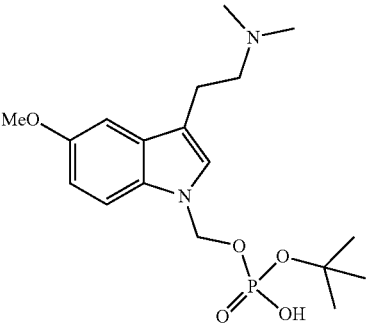 [SMILES: COc1ccc2c(c1)c(CCN(C)C)cn2COP(=O)(O)OC(C)(C)C] | Terf-butyl [3-[2-(dimethyl-amino)ethyl]-5-methoxy-indol-1-yl] methyl hydrogen phosphate |
| 517 | 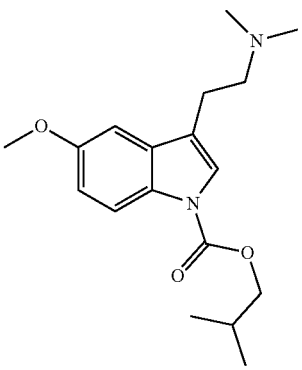 | Isobutyl 3-[2-(dimethyl-amino)ethyl]-6-methoxy-indole-1-carboxylate |
| 518 | 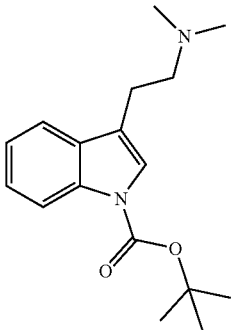 [SMILES: CN(C)CCc1cn(C(=O)OC(C)(C)C)c2ccccc12] | tert-butyl 3-[2-(dimethyl-amino)ethyl]indole-1-carboxylate |

TABLE 1A-continued

| Compound | Structure | Chemical Name |
|---|---|---|
| 519 | 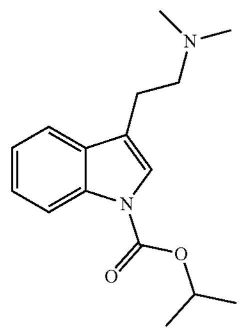 [SMILES: CC(C)OC(=O)n1cc(CCN(C)C)c2ccccc21] | isopropyl 3-[2-(dimethyl-amino)ethyl]indole-1-carboxylate |
| 520 | 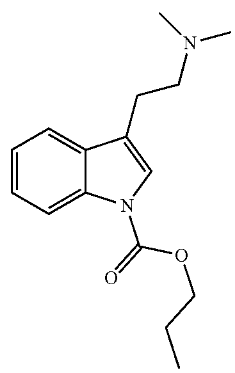 [SMILES: CCCOC(=O)n1cc(CCN(C)C)c2ccccc21] | propyl 3-[2-(dimethylamino)-ethyl]indole-1-carboxylate |
| 521 | 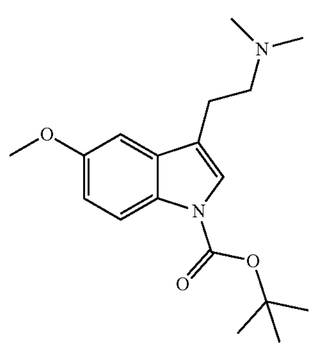 [SMILES: COc1ccc2c(c1)c(CCN(C)C)cn2C(=O)OC(C)(C)C] | tert-butyl 3-[2-(dimethyl-amino)ethyl]-5-methoxy-indole-1-carboxylate |
| 522 | 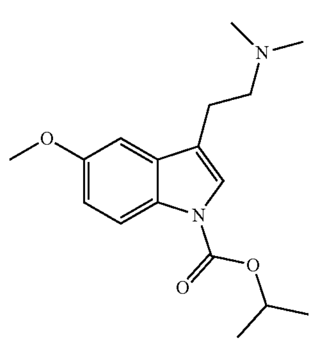 [SMILES: COc1ccc2c(c1)c(CCN(C)C)cn2C(=O)OC(C)C] | isopropyl 3-[2-(dimethyl-amino)ethyl]-5-methoxy-indole-1-carboxylate |

TABLE 1A-continued

| Compound | Structure | Chemical Name |
|---|---|---|
| 523 | 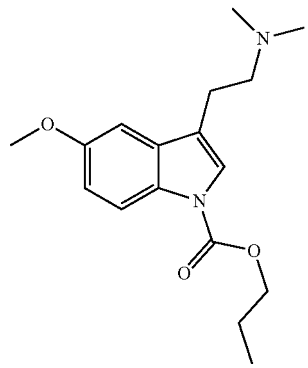 | propyl 3-[2-(dimethylamino)-ethyl]-5-methoxy-indole-1-carboxylate |
| 524 | 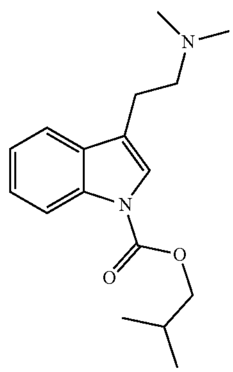 [SMILES: CC(C)COC(=O)n1cc(CCN(C)C)c2ccccc21] | isobutyl 3-[2-(dimethylamino)ethyl]indole-1-carboxylate[a] |
| 119 | 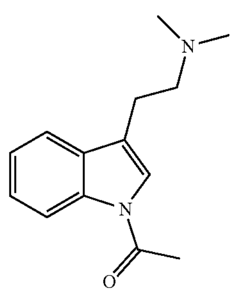 [SMILES: CC(=O)n1cc(CCN(C)C)c2ccccc21] | 1-[3-[2-(dimethylamino)-ethyl]indol-1-yl]ethenone |
| 122 | 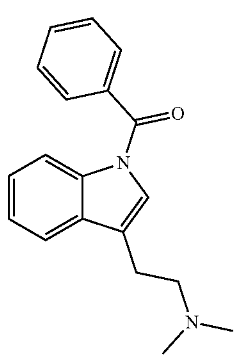 [SMILES: CN(C)CCc1cn(C(=O)c2ccccc2)c2ccccc12] | [3-[2-(dimethylamino)ethyl]-indol-1-yl]-phenyl-methanone |

TABLE 1A-continued

| Compound | Structure | Chemical Name |
|---|---|---|
| 120 | 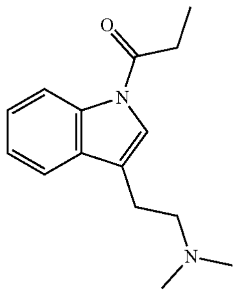 [SMILES: CCC(=O)n1cc(CCN(C)C)c2ccccc21] | 1-[3-[2-(dimethylamino)-ethyl]indol-1-yl]propan-1-one |
| 108 | 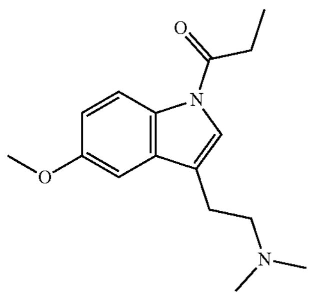 | 1-[3-[2-(dimethylamino)-ethyl]-5-methoxy-indol-1-yl]propan-1-one |
| 110 | 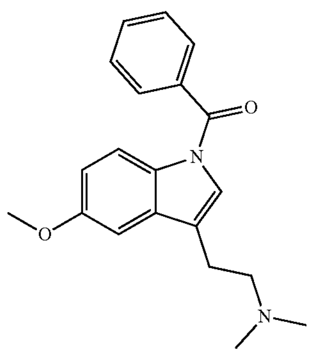 | [3-[2-(dimethylamino)ethyl]-5-methoxy-indol-1-yl]-phenyl-methanone |
| 107 | 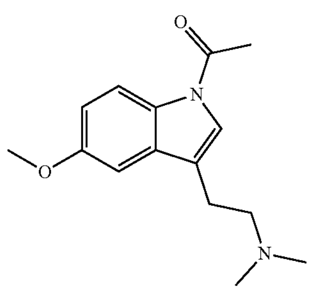 | 1-[3-[2-(dimethylamino)ethyl]-5-methoxy-indol-1-yl]ethanone |
| 525 | 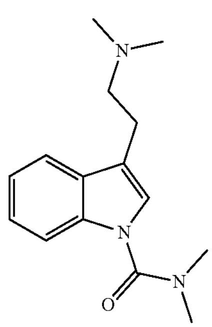 [SMILES: CN(C)CCc1cn(C(=O)N(C)C)c2ccccc12] | 3-[2-(dimethylamino)ethyl]-N,N-dimethyl-indole-1-carboxamide |

TABLE 1A-continued
| Compound | Structure | Chemical Name |
|---|---|---|
| 526 | 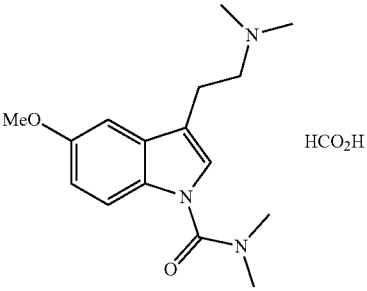 [SMILES: COc1ccc2c(c1)c(CCN(C)C)cn2C(=O)N(C)C ; "HCO2H"] | 3-(2-(dimethylamino)ethyl)-5-methoxy-N,N-dimethyl-1H-indole-1-carboxamide formate |
| 88 | 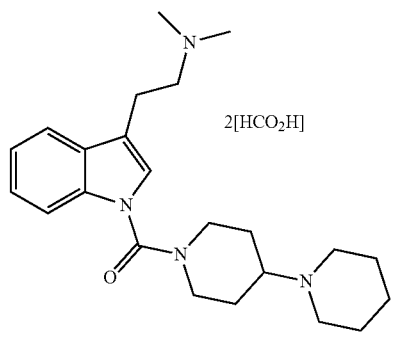 [SMILES: CN(C)CCc1cn(C(=O)N2CCC(N3CCCCC3)CC2)c2ccccc12] | [1,4'-Bipiperidin]-1'-yl(3-(2-(dimethylamino)ethyl)-1H-indol-1-yl)methanone di-formate |
| 96 | 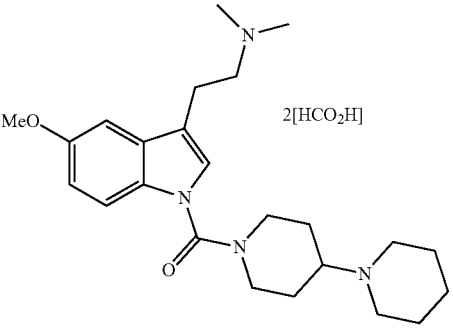 [SMILES: COc1ccc2c(c1)c(CCN(C)C)cn2C(=O)N1CCC(N2CCCCC2)CC1] | [1,4'-bipiperidin]-1'-yl(3-(2-(dimethylamino)ethyl)-5-methoxy-1H-indol-1-yl)-methanone di-formate |
| 413 | 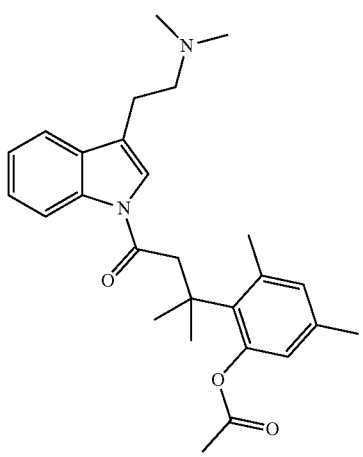 [SMILES: CC(=O)Oc1cc(C)cc(C)c1C(C)(C)CC(=O)n1cc(CCN(C)C)c2ccccc21] | 2-(4-(3-(2-(dimethylamino)-ethyl)-1H-indol-1-yl)-2-methyl-4-oxobutan-2-yl)-3,5-dimethylphenyl acetate |

TABLE 1A-continued

| Compound | Structure | Chemical Name |
| --- | --- | --- |
| 405 | 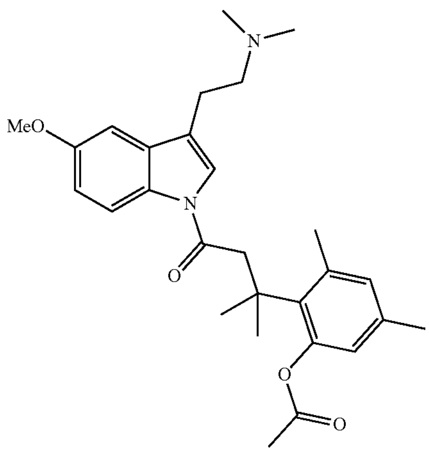 [SMILES: COc1ccc2c(c1)c(CCN(C)C)cn2C(=O)CC(C)(C)c1c(C)cc(C)cc1OC(C)=O] | 2-(4-(3-(2-(dimethylamino)-ethyl)-5-methoxy-1H-indol-1-yl)-2-methyl-4-oxobutan-2-yl)-3,5-dimethylphenyl |
| 25 | 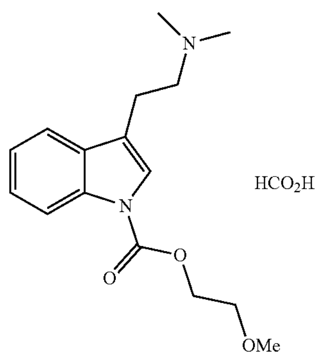 [SMILES: COCCOC(=O)n1cc(CCN(C)C)c2ccccc21 ; "HCO2H"] | 2-Methoxyethyl 3-(2-(dimethylamino)ethyl)-1H-indole-1-carboxylate formate |
| 22 | 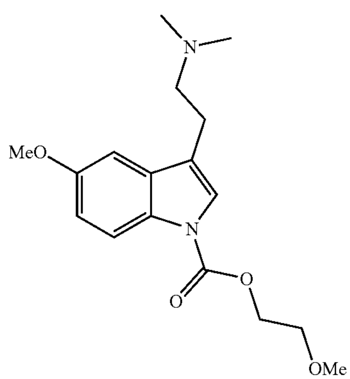 [SMILES: COCCOC(=O)n1cc(CCN(C)C)c2cc(OC)ccc21] | 2-Methoxyethyl 3-(2-(dimethylamino)ethyl)-5-methoxy-1H-indole-1-carboxylate formate |
| 529 | 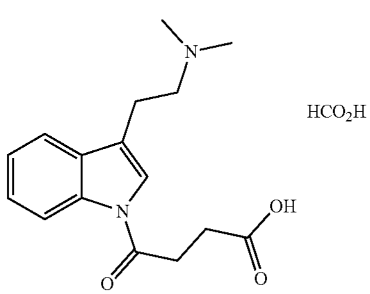 [SMILES: CN(C)CCc1cn(C(=O)CCC(=O)O)c2ccccc12 ; "HCO2H"] | 4-(3-(2-(dimethylamino)-ethyl)-1H-indol-1-yl)-4-oxo-butanoic acid formate salt |

TABLE 1A-continued

| Compound | Structure | Chemical Name |
|---|---|---|
| 530 | 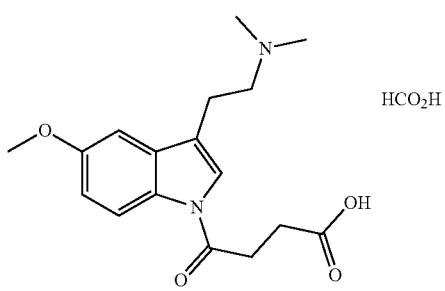 [SMILES: COc1ccc2c(c1)c(CCN(C)C)cn2C(=O)CCC(=O)O ; "HCO2H"] | 4-(3-(2-(dimethylamino)-ethyl)-5-methoxy-1H-indol-1-yl)-4-oxobutanoic acid formate salt |
| 531 | 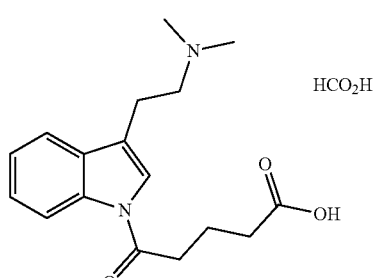 | 5-(3-(2-(dimethylamino)-ethyl)-1H-indol-1-yl)-5-oxo-pentanoic acid formate salt |
| 532 | 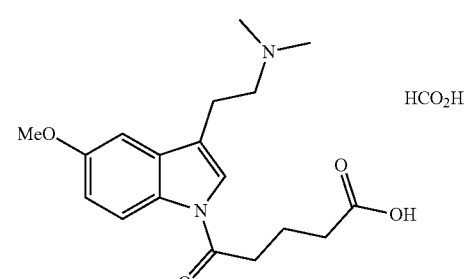 | 5-(3-(2-(dimethylamino)-ethyl)-5-methoxy-1H/-indol-1-yl)-5-oxopentanoic acid formate salt |
| 369 | 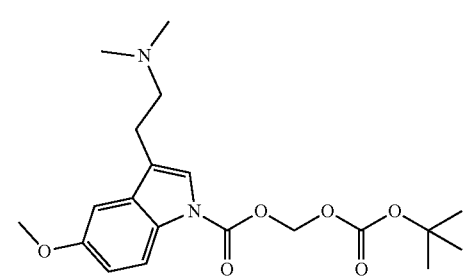 [SMILES: COc1ccc2c(c1)c(CCN(C)C)cn2C(=O)OCOC(=O)OC(C)(C)C] | (Pivaloyloxy)methyl 3-(2-(dimethylamino)ethyl)-5-methoxy-1H-indole-1-carboxylate |
| 387 | 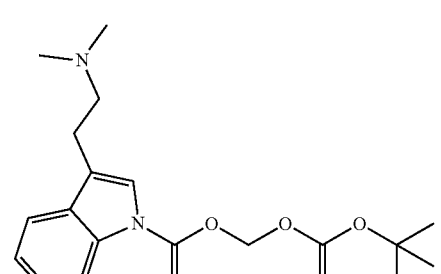 | (Pivaloyloxy)methyl 3-(2-(dimethylamino)ethyl)-1H-indole-1-carboxylate diformat |

TABLE 1A-continued

| Compound | Structure | Chemical Name |
| --- | --- | --- |
| 533 | 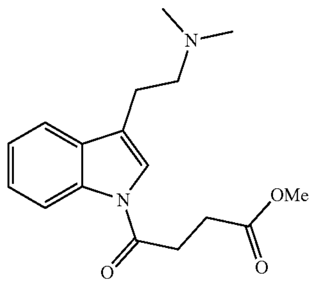 [SMILES: COC(=O)CCC(=O)n1cc(CCN(C)C)c2ccccc21] | Methyl 4-(3-(2-(dimethyl-amino)ethyl)-1H-indol-1-yl)-4-oxobutanoate |
| 534 | 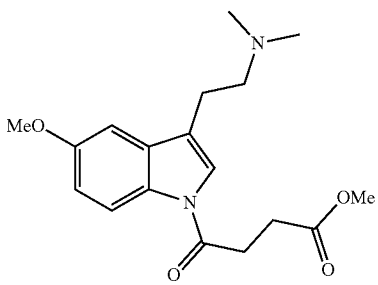 [SMILES: COC(=O)CCC(=O)n1cc(CCN(C)C)c2cc(OC)ccc21] | Methyl 4-(3-(2-(dimethyl-amino)ethyl)-5-methoxy-1H-indol-1-yl)-4-oxobutanoate |
| 535 | 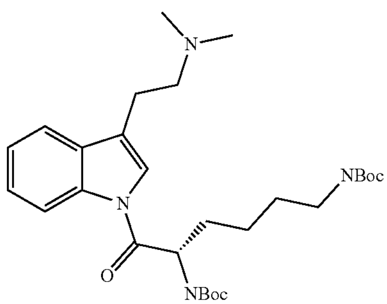 | (S)-di-tert-butyl (6-(3-(2-(dimethylamino)ethyl)-1H-indol-1-yl)-6-oxohexane-1,5-diyl)dicarbamate |
| 536 | 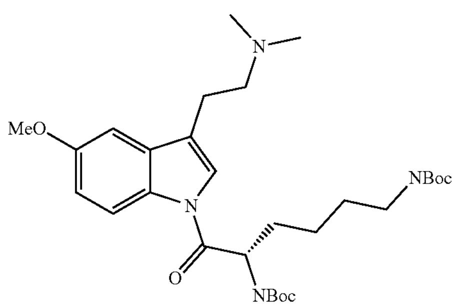 | (S)-di-tert-butyl (6-(3-(2-(dimethylamino)ethyl)-5-methoxy-1H-indol-1-yl)-6-oxohexane-1,5-diyl)-dicarbamate |
| 537 | 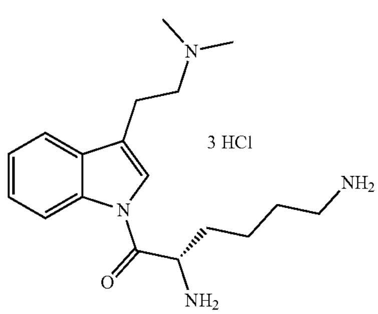 [SMILES: CN(C)CCc1cn(C(=O)[C@@H](N)CCCCN)c2ccccc12] | (S)-2,6-diamino-1-(3-(2-(dimethylamino)ethyl-1H-indol-1-yl)hexan-1-one trihydrochloride |

TABLE 1A-continued

| Compound | Structure | Chemical Name |
|---|---|---|
| 538 | 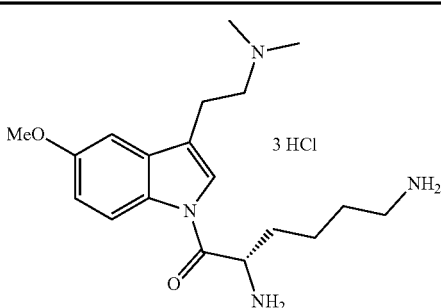 | (S)-2,6-diamino-1-(3-(2-(dimethylamino)ethyl)-5-methoxy-1H-indol-1-yl)-hexan-1-one trihydrochloride |
| 539 | 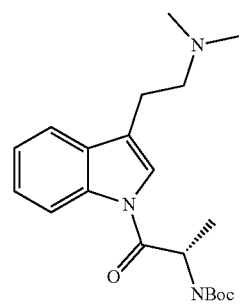 | (S)-tert-butyl (1-(3-(2-(dimethylamino)ethyl)-1H-indol-1-yl)-1-oxopropan-2-yl)carbamate |
| 540 | 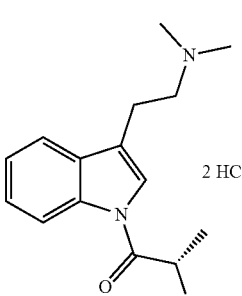 | (S)-2-amino-1-(3-(2-(dimethylamino)ethyl)-1H-indol-1-yl)propan-1-one dihydrochloride |
| 541 | 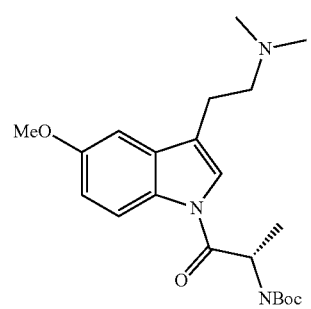 | (S)-tert-butyl (1-(3-(2-(dimethylamino)ethyl)-5-methoxy-1H-indol-1-yl)-1-oxopropan-2-yl)carbamate |
| 542 | 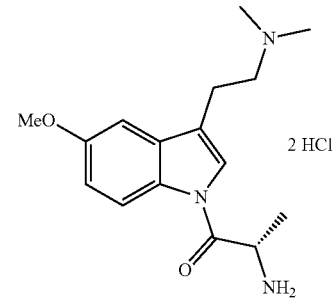 [SMILES: COc1ccc2c(c1)c(CCN(C)C)cn2C(=O)[C@H](C)N] | (S)-2-amino-1-(3-(2-(dimethylamino)ethyl)-5-methoxy-1H-indol-1-yl)propan-1-one dihydrochloride |

| Compound | Structure | Chemical Name |
|---|---|---|
| 543 | 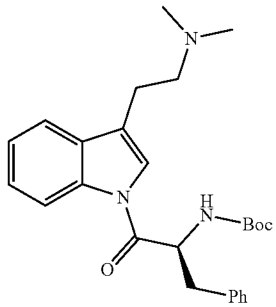 [SMILES: CN(C)CCc1cn(C(=O)[C@H](Cc2ccccc2)NC(=O)OC(C)(C)C)c2ccccc12] | (S)-tert-butyl (1-(3-(2-(dimethylamino)ethyl)-1H-indol-1-yl)-1-oxo-3-phenyl-propan-2-yl)carbamate |
| 544 | 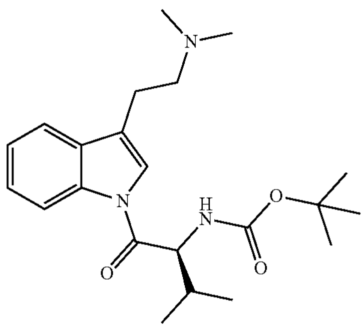 [SMILES: CC(C)[C@H](NC(=O)OC(C)(C)C)C(=O)n1cc(CCN(C)C)c2ccccc21] | (S)-tert-butyl (1-(3-(2-(dimethylamino)ethyl)-1H-indol-1-yl)-3-methyl-1-oxo-butan-2-yl)carbamate |
| 545 | 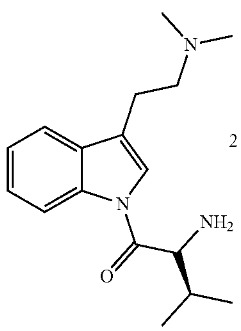 | (S)-2-amino-1-(3-(2-(dimethylamino)ethyl)-1H-indol-1-yl)-3-methylbutan-1-one dihydrochloride |
| 546 | 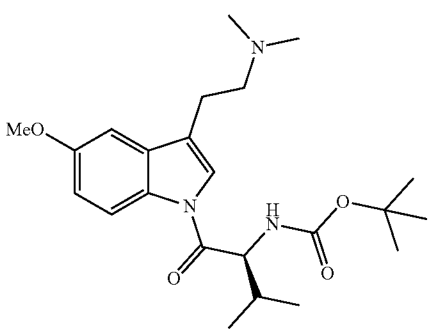 [SMILES: COc1ccc2c(c1)c(CCN(C)C)cn2C(=O)[C@@H](NC(=O)OC(C)(C)C)C(C)C] | (S)-tert-butyl (1-(3-(2-(dimethylamino)ethyl)-5-methoxy-1H-indol-1-yl)-3-methyl-1-oxobutan-2-yl)-carbamate |
| 547 | 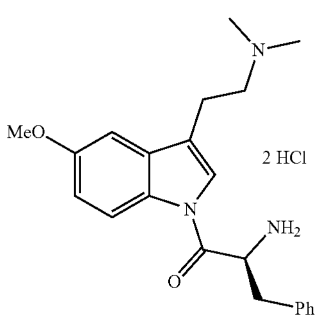 [SMILES: COc1ccc2c(c1)c(CCN(C)C)cn2C(=O)[C@@H](N)Cc1ccccc1] | (S)-2-amino-1-(3-(2-(dimethylamino)ethyl)-5-methoxy-1H-indol-1-yl)-3-methyl-butan-1-one bis-hydrochloride |

TABLE 1A-continued

| Compound | Structure | Chemical Name |
|---|---|---|
| 548 | 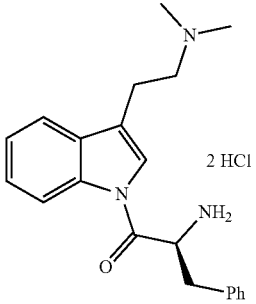 [SMILES: CN(C)CCc1cn(C(=O)[C@@H](N)Cc2ccccc2)c2ccccc12] | (S)-2-amino-1-(3-(2-(dimethylamino)ethyl)-1H-indol-1-yl)-3-phenylpropan-1-one bis-hydrochloride |
| 549 | 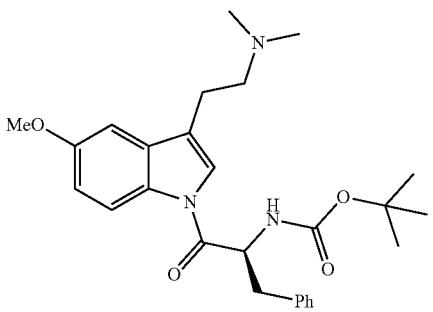 [SMILES: COc1ccc2c(c1)c(CCN(C)C)cn2C(=O)[C@H](Cc1ccccc1)NC(=O)OC(C)(C)C] | (S)-tert-butyl (1-(3-(2-(dimethylamino)ethyl)-5-methoxy-1H-indol-1-yl)-1-oxo-3-phenylpropan-2-yl)-carbamate |
| 550 | 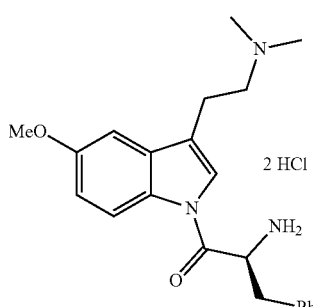 | (S)-2-amino-1-(3-(2-(dimethylamino)ethyl)-5-methoxy-1H-indol-1-yl)-3-phenylpropan-1-one bis-hydrochloride |
| 551 | 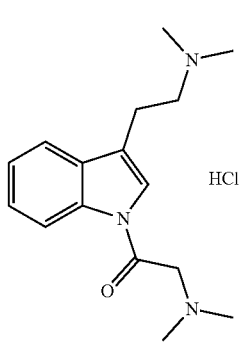 [SMILES: CN(C)CCc1cn(C(=O)CN(C)C)c2ccccc12 ; Cl] | 2-(Dimethylamino)-1-(3-(2-(dimethylamino)ethyl)-1H-indol-1-yl)ethan-1-one hydrochloride |
| 552 | 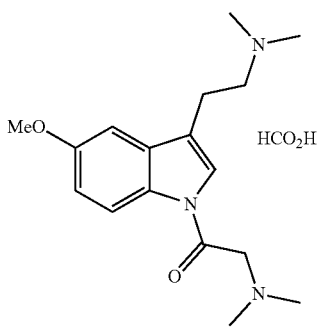 [SMILES: COc1ccc2c(c1)c(CCN(C)C)cn2C(=O)CN(C)C ; "HCO2H"] | 2-(Dimethylamino)-1-(3-(2-(dimethylamino)ethyl)-5-methoxy-1H-indol-1-yl)ethan-1-one formate |

TABLE 1A-continued

| Compound | Structure | Chemical Name |
|---|---|---|
| 553 | 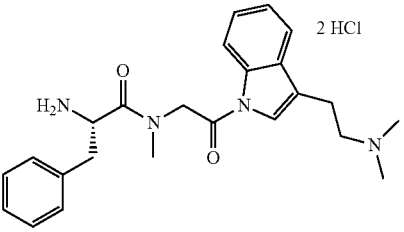 [SMILES: CN(C)CCc1cn(C(=O)CN(C)C(=O)[C@@H](N)Cc2ccccc2)c2ccccc12] | (S)-2-amino-N-(2-(3-(2-(dimethylamino)ethyl)-1H-indol-1-yl)-2-oxoethyl)-N-methyl-3-phenylpropan-amide bis-hydrochloride |
| 554 | 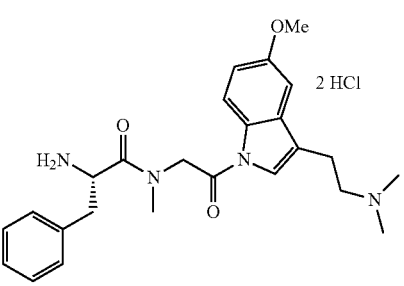 [SMILES: COc1ccc2c(c1)c(CCN(C)C)cn2C(=O)CN(C)C(=O)[C@@H](N)Cc1ccccc1] | (S)-2-amino-N-(2-(3-(2-(dimethylamino)ethyl)-5-methoxy-1H-indol-1-yl)-2-oxoethyl)-N-methyl-3-phen-ylpropanamide bis-hydro-chloride |
| 555 | 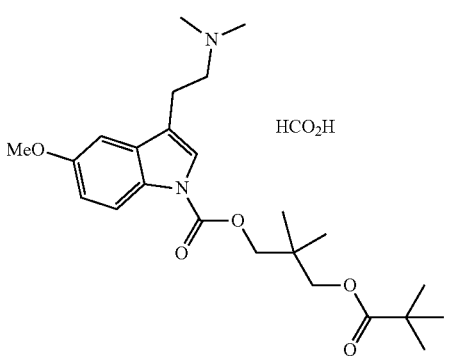 [SMILES: COc1ccc2c(c1)c(CCN(C)C)cn2C(=O)OCC(C)(C)COC(=O)C(C)(C)C ; "HCO2H"] | 2,2-dimethyl-3-(pivaloyloxy)-propyl 3-(2-(dimethylamino)-ethyl)-5-methoxy-1H-indole-1-carboxylate formate |
| 556 | 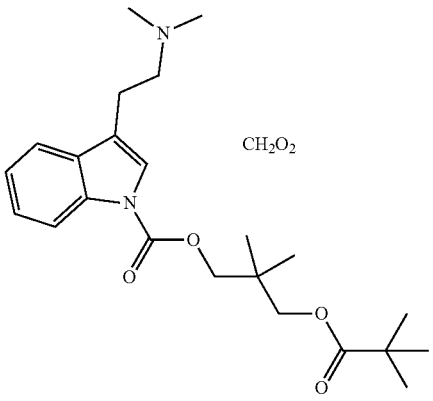 [SMILES: CN(C)CCc1cn(C(=O)OCC(C)(C)COC(=O)C(C)(C)C)c2ccccc12 ; "CH2O2"] | 2,2-Dimethyl-3-(pivaloyloxy)-propyl 3-(2-(dimethylamino)-ethyl)-1H-indole-1-carbox-ylate formate |
| 557 | 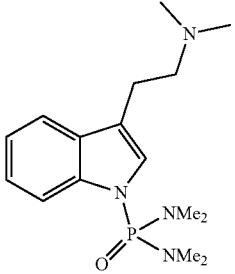 [SMILES: CN(C)CCc1cn(P(=O)(N(C)C)N(C)C)c2ccccc12] | 2-(1-di(dimethylamino)-phosphoryl-indol-3-yl)-N,N-dimethyl-ethanamine |

TABLE 1A-continued
| Compound | Structure | Chemical Name |
|---|---|---|
| 558 | 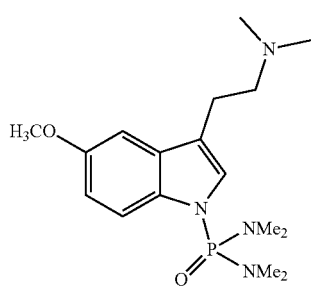 [SMILES: COc1ccc2c(c1)c(CCN(C)C)cn2P(=O)(N(C)C)N(C)C] | 2-(1-di(dimethylamino)-phosphoryl-5-methoxy-indol-3-yl)-N,N-dimethyl-ethan-amine |
| 170 | 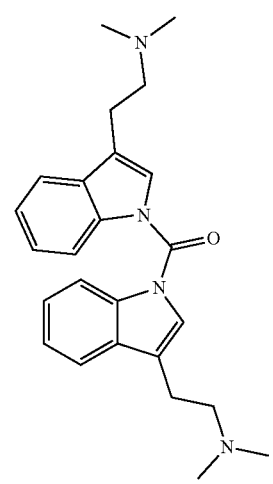 [SMILES: CN(C)CCc1cn(C(=O)n2cc(CCN(C)C)c3ccccc32)c2ccccc12] | bis(3-(2-(Dimethylamino)-ethyl)-1H-indol-1-yl)-methanone di-formate |
| 169 | 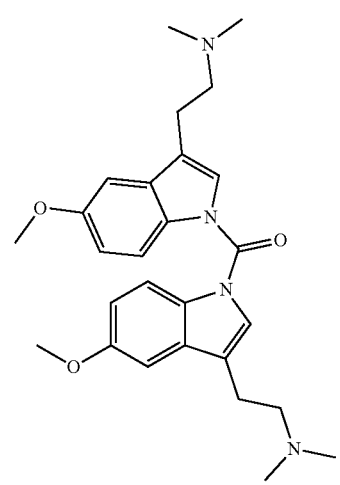 | bis(3-(2-(Dimethylamino)-ethyl)-5-methoxy-1H-indol-1-yl)methanone di-formate |
| 559 | 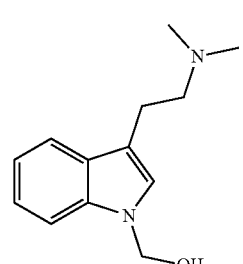 | (3-(2-(Dimethylamino)ethyl)-1H-indol-1-yl)methanol |

TABLE 1A-continued

| Compound | Structure | Chemical Name |
| --- | --- | --- |
| 560 | 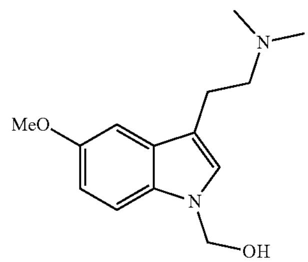 [SMILES: COc1ccc2c(c1)c(CCN(C)C)cn2CO] | (3-(2-(Dimethylamino)ethyl)-5-methoxy-1H-indol-1-yl)-methanol |
| 187 | 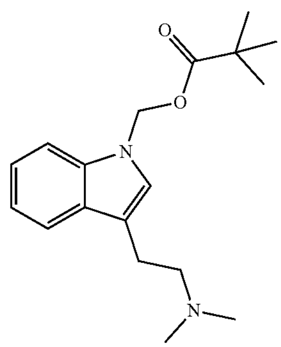 [SMILES: CN(C)CCc1cn(COC(=O)C(C)(C)C)c2ccccc12] | (3-(2-(dimethylamino)ethyl)-1H-indol-1-yl)methyl pivalate |
| 188 | 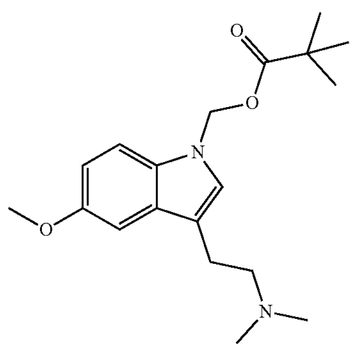 [SMILES: COc1ccc2c(c1)c(CCN(C)C)cn2COC(=O)C(C)(C)C] | (3-(2-(Dimethylamino)ethyl)-5-methoxy-1H-indol-1-yl)-methyl pivalate |
| 561 | 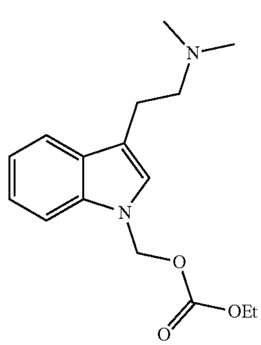 [SMILES: CCOC(=O)OCn1cc(CCN(C)C)c2ccccc21] | (3-(2-(Dimethylamino)ethyl)-1H-indol-1-yl)methyl ethyl carbonate |

TABLE 1A-continued

| Compound | Structure | Chemical Name |
|---|---|---|
| 562 | 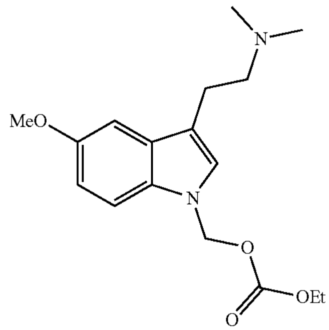 [SMILES: CCOC(=O)OCn1cc(CCN(C)C)c2cc(OC)ccc21] | (3-(2-(Dimethylamino)ethyl)-5-methoxy-1H-indol-1-yl)-methyl ethyl carbonate |
| 264 | 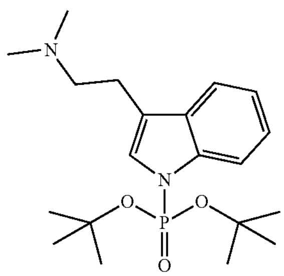 [SMILES: CN(C)CCc1cn(P(=O)(OC(C)(C)C)OC(C)(C)C)c2ccccc12] | Di-tert-butyl ((3-(2-(dimethylamino)ethyl)-1H-indol-1-yl)methyl) phosphate |
| 256 | 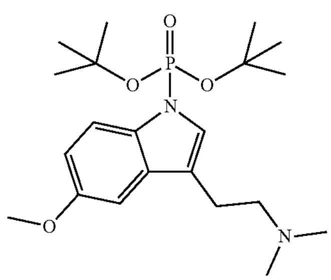 | Di-tert-butyl ((3-(2-(dimethylamino)ethyl)-5-methoxy-1H-indol-1-yl)methyl)phosphate |
| 563 | 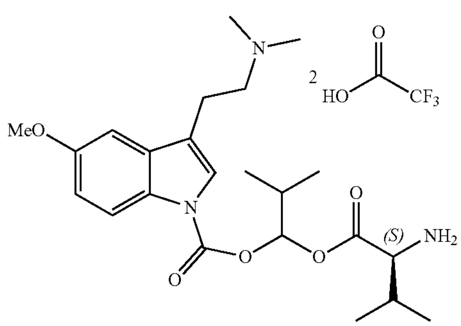 | 1-(((S)-2-amino-3-methylbutanoyl)oxy)-2-methylpropyl 3-(2-(dimethylamino)ethyl)-5-methoxy-1H-indole-1-carboxylate di-trifluoroacetate |
| 564 | 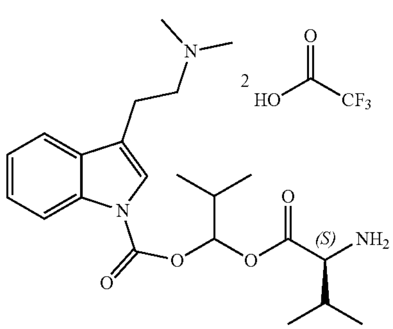 | 1-(((S)-2-amino-3-methylbutanoyl)oxy)-2-methylpropyl 3-(2-(dimethylamino)ethyl)-1H-indole-1-carboxylate di-trifluoroacetate |

TABLE 1A-continued

| Compound | Structure | Chemical Name |
| --- | --- | --- |
| 565 | 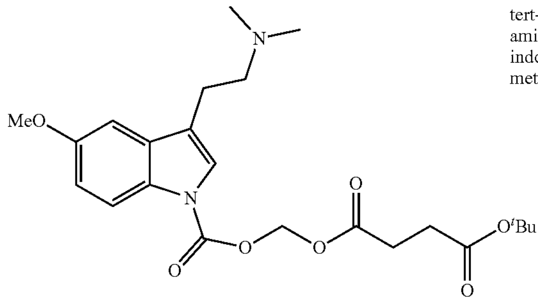 [SMILES: COc1ccc2c(c1)c(CCN(C)C)cn2C(=O)OCOC(=O)CCC(=O)OC(C)(C)C] | tert-Butyl (((3-(2-(dimethyl-amino)ethyl)-5-methoxy-1H-indole-1-carbonyl)oxy)-methyl)succinate |
| 566 | 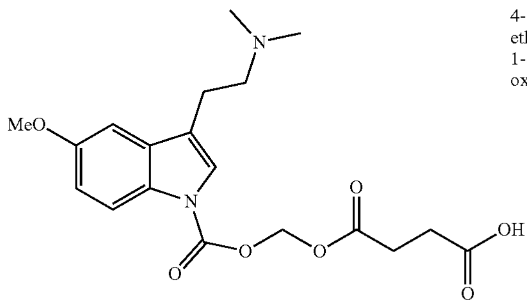 [SMILES: COc1ccc2c(c1)c(CCN(C)C)cn2C(=O)OCOC(=O)CCC(=O)O] | 4-(((3-(2-(Dimethylamino)-ethyl)-5-methoxy-1H-indole-1-carbonyl)oxy)methoxy)-4-oxobutanoic acid |
| 567 | 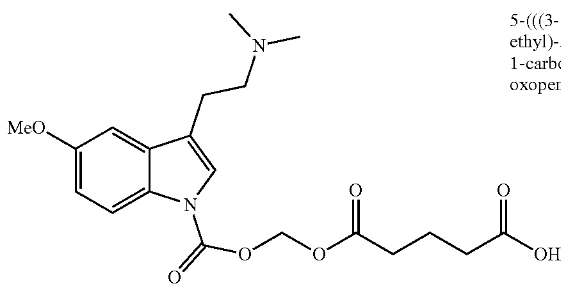 [SMILES: COc1ccc2c(c1)c(CCN(C)C)cn2C(=O)OCOC(=O)CCCC(=O)O] | 5-(((3-(2-(Dimethylamino)-ethyl)-5-methoxy-1H-indole-1-carbonyl)oxy)methoxy)-5-oxopentanoic acid |
| 568 | 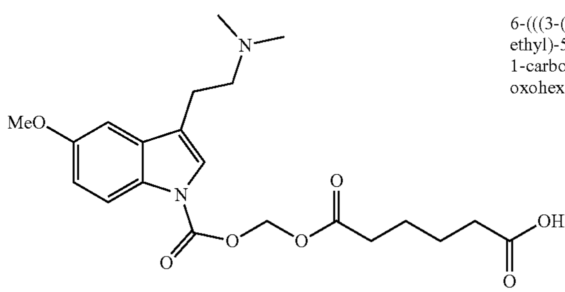 [SMILES: COc1ccc2c(c1)c(CCN(C)C)cn2C(=O)OCOC(=O)CCCCC(=O)O] | 6-(((3-(2-(Dimethylamino)-ethyl)-5-methoxy-1H-indole-1-carbonyl)oxy)methoxy)-6-oxohexanoic acid |
| 569 | 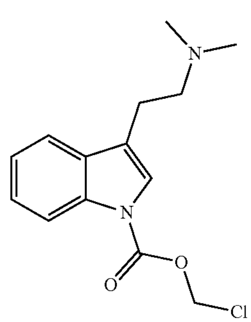 [SMILES: CN(C)CCc1cn(C(=O)OCCl)c2ccccc12] | Chloromethyl 3-(2-(dimethyl-amino)ethyl)-1H-indole-1-carboxylate |

TABLE 1A-continued

| Compound | Structure | Chemical Name |
| --- | --- | --- |
| 570 | 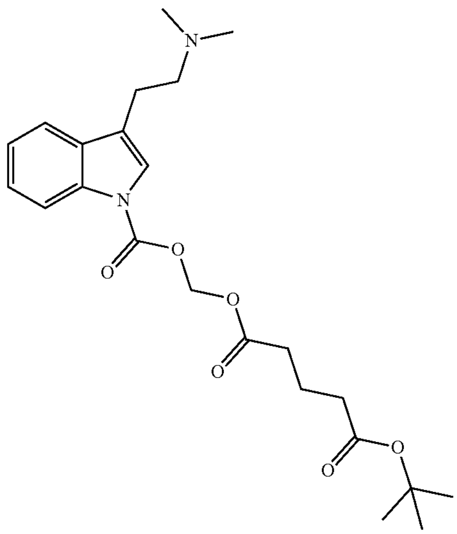 [SMILES: CN(C)CCc1cn(C(=O)OCOC(=O)CCCC(=O)OC(C)(C)C)c2ccccc12] | tert-Butyl (((3-(2-(dimethyl-amino)ethyl)-1H-indole-1-carbonyl)oxy)methyl) glutarate |
| 571 | 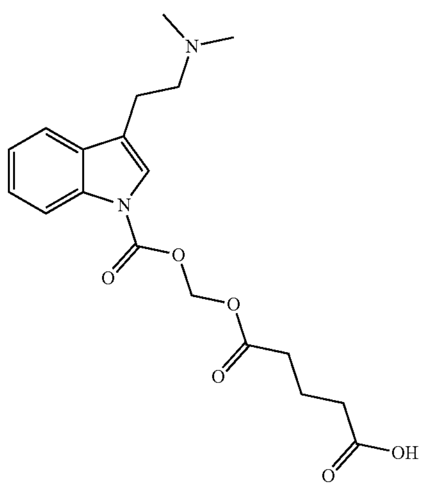 [SMILES: CN(C)CCc1cn(C(=O)OCOC(=O)CCCC(=O)O)c2ccccc12] | 5-(((3-(2-(dimethylamino)-ethyl)-1H-indole-1-carbonyl)-oxy)methoxy)-5-oxopentanoic acid |
| 572 | 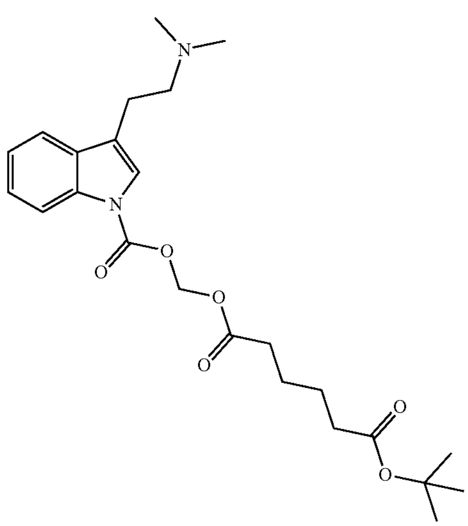 [SMILES: CN(C)CCc1cn(C(=O)OCOC(=O)CCCCC(=O)OC(C)(C)C)c2ccccc12] | tert-Butyl (((3-(2-(dimethyl-amino)ethyl)-1H-indole-1-carbonyl)oxy)methyl) adipate |

TABLE 1A-continued
| Compound | Structure | Chemical Name |
|---|---|---|
| 573 | 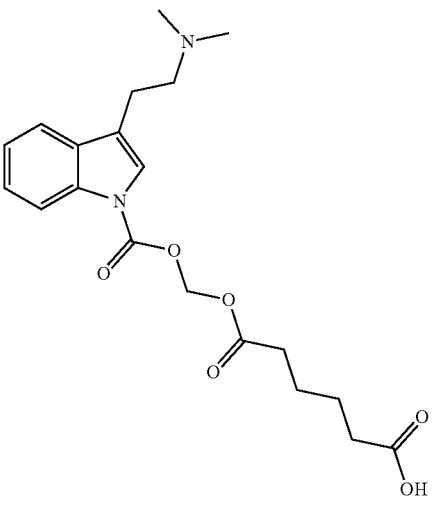 [SMILES: CN(C)CCc1cn(C(=O)OCOC(=O)CCCCC(=O)O)c2ccccc12] | 6-(((3-(2-(Dimethylamino)-ethyl)-1H-indole-1-carbonyl)-oxy)methoxy)-6-oxohexanoic acid |
| 574 | 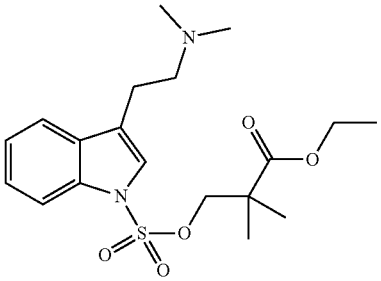 [SMILES: CCOC(=O)C(C)(C)COS(=O)(=O)n1cc(CCN(C)C)c2ccccc21] | Ethyl 3-(((3-(2-(dimethyl-amino)ethyl)-1H-indol-1-yl)-sulfonyl)oxy)-2,2-dimethyl-propanoate |
| 575 | 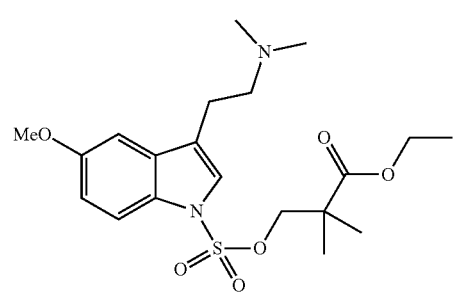 [SMILES: CCOC(=O)C(C)(C)COS(=O)(=O)n1cc(CCN(C)C)c2cc(OC)ccc21] | Ethyl 3-(((3-(2-(dimethyl-amino)ethyl)-5-methoxy-1H-indol-1-yl)sulfonyl)oxy)-2,2-dimethylpropanoate |
| 576 | 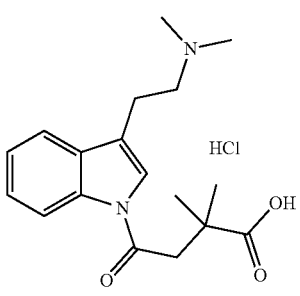 [SMILES: CN(C)CCc1cn(C(=O)CC(C)(C)C(=O)O)c2ccccc12 ; Cl] | 4-(3-(2-(dimethylamino)-ethyl)-1H-indol-1-yl)-2,2-dimethyl-4-oxobutanoic acid HCl salt |

TABLE 1A-continued

| Compound | Structure | Chemical Name |
|---|---|---|
| 577 | 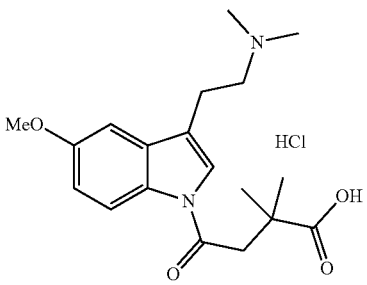 [SMILES: COc1ccc2c(c1)c(CCN(C)C)cn2C(=O)CC(C)(C)C(=O)O ; Cl] | 4-(3-(2-(dimethylamino)-ethyl)-5-methoxy-1H-indol-1-yl)-2,2-dimethyl-4-oxo-butanoic acid HCl salt |

Methods of Treatment.

In yet another aspect, the present disclosure provides a method of treating or preventing a disease, disorder, or condition in which an increased level of a tryptamine psychedelic such as DMT is beneficial, comprising administering to a subject in need thereof an effective amount of a compound of Formula (I), (Ia), (Ib), (Ib-1) (Ib1), (Ic), (Id), (Ie), (If), (If1), (Ig), (Ih), (Ii), (Ij), (Ik), (Ik1), (Ik2), (Ik3), (Il), (Im), (Im1), (Im1a), (In), (In1), (Io), (Io1), (Io2), (Io1a), (Ip) (Ip1), (Iq), (Iq1), (Ir), (Ir1), (Is), (It), (Iu), (Iv), or (Iw), or a pharmaceutically acceptable salt thereof. In some embodiments, the condition comprises post-traumatic stress disorder, major depression, schizophrenia, Alzheimer's disease, frontotemporal dementia, Parkinson's disease, Parkinson's dementia, dementia, Lewy body dementia, multiple system atrophy, or substance abuse. In some embodiments, the condition comprises musculoskeletal pain disorder including fibromyalgia, muscle pain, joint stiffness, osteoarthritis, rheumatoid arthritis, muscle cramps. In some embodiments, the present disclosure provides a method of treating a disease of women's reproductive health including premenstrual dysphoric disorder (PMDD), premenstrual syndrome (PMS), post-partum depression, and menopause. The compounds of the present invention can also be used to treat any brain disease.

In some embodiments, a compound disclosed herein has activity as a 5-$HT_{2A}$ modulator. In some embodiments a compound disclosed herein elicits a biological response by activating the 5-$HT_{2A}$ receptor (e.g., allosteric modulation or modulation of a biological target that activates the 5-$HT_{2A}$ receptor). 5-$HT_{2A}$ agonism has been correlated with the promotion of neural plasticity. 5-$HT_{2A}$ antagonists abrogate the neuritogenesis and spinogenesis effects of hallucinogenic compounds with 5-$HT_{2A}$ agonist activity, for example, DMT, LSD, and DOI. In some embodiments, a compound disclosed herein is a 5-$HT_{2A}$ modulator and promotes neural plasticity (e.g., cortical structural plasticity). In some embodiments, a compound disclosed herein is a selective 5-$HT_{2A}$ modulator and promotes neural plasticity (e.g., cortical structural plasticity). Promotion of neural plasticity can include, for example, increased dendritic spine growth, increased synthesis of synaptic proteins, strengthened synaptic responses, increased dendritic arbor complexity, increased dendritic branch content, increased spinogenesis, increased neuritogenesis, or any combination thereof. In some embodiments, increased neural plasticity includes increased cortical structural plasticity in the anterior parts of the brain.

In some embodiments, the 5-$HT_{2A}$ modulators (e.g., 5-$HT_{2A}$ agonists) are non-hallucinogenic. In some embodiments, non-hallucinogenic 5-$HT_{2A}$ modulators (e.g., 5-$HT_{2A}$ agonists) are used to treat neurological diseases, which modulators do not elicit dissociative side-effects. In some embodiments, the hallucinogenic potential of the compounds described herein is assessed in vitro. In some embodiments, the hallucinogenic potential assessed in vitro of the compounds described herein is compared to the hallucinogenic potential assessed in vitro of hallucinogenic homologs. In some embodiments, the compounds described herein elicit less hallucinogenic potential in vitro than the hallucinogenic homologs.

In some embodiments, serotonin receptor modulators, such as modulators of serotonin receptor 2A (5-$HT_{2A}$ modulators, e.g., 5-$HT_{2A}$ agonists), are used to treat a brain disorder. In some embodiments, a compound of the present disclosure functions as a 5-$HT_{2A}$ agonist alone, or in combination with a second therapeutic agent that also is a 5-$HT_{2A}$ modulator. In such cases the second therapeutic agent can be an agonist or an antagonist. In some instances, it may be helpful administer a 5-$HT_{2A}$ antagonist in combination with a compound of the present disclosure to mitigate undesirable effects of 5-$HT_{2A}$ agonism, such as potential hallucinogenic effects. Serotonin receptor modulators useful as second therapeutic agents for combination therapy as described herein are known to those of skill in the art and include, without limitation, MDL-11,939, eplivanserin (SR-46,349), ketanserin, ritanserin, altanserin, acepromazine, mianserin, mirtazapine, quetiapine, SB204741, SB206553, SB242084, LY272015, SB243213, blonanserin, SB200646, RS102221, nefazodone, MDL-100,907, pimavanserin, flibanserin, nelotanserin and lorcaserin. In some embodiments, the serotonin receptor modulator used as a second therapeutic is pimavanserin or a pharmaceutically acceptable salt, solvate, metabolite, derivative, or prodrug thereof. In some embodiments, the serotonin receptor modulator is administered prior administration of a compound disclosed herein, such as about three or about hours prior administration of the compound. In some embodiments, the serotonin receptor modulator is administered at most about one hour prior to the compound. In some embodiments, the second therapeutic agent is a serotonin receptor modulator. In some embodiments, the serotonin receptor modulator is provided at a dose of from about 10 mg to about 350 mg. In some embodiments, the serotonin receptor modulator is provided at a dose of from about 20 mg to about 200 mg. In some embodiments, the serotonin receptor modulator is provided at a dose of from about 10 mg to about 100 mg. In certain such embodiments, a compound of the present disclosure is provided at a dose of from about 10 mg to about 100 mg, or from about 20 to about 200 mg, or from about 15 to about 300 mg, and the serotonin receptor modulator is provided at a dose of about 10 mg to about 100 mg.

In some embodiments, non-hallucinogenic 5-HT$_{2A}$ modulators (e.g., 5-HT$_{2A}$ agonists) are used to treat neurological diseases. In some embodiments, the neurological diseases comprise decreased neural plasticity, decreased cortical structural plasticity, decreased 5-HT$_{2A}$ receptor content, decreased dendritic arbor complexity, loss of dendritic spines, decreased dendritic branch content, decreased spinogenesis, decreased neuritogenesis, retraction of neurites, or any combination thereof.

In some embodiments, non-hallucinogenic 5-HT$_{2A}$ modulators (e.g., 5-HT$_{2A}$ agonists) are used for increasing neuronal plasticity. In some embodiments, non-hallucinogenic 5-HT$_{2A}$ modulators (e.g., 5-HT$_{2A}$ agonists) are used for treating a brain disorder. In some embodiments, non-hallucinogenic 5-HT$_{2A}$ modulators (e.g., 5-FIT$_{2A}$ agonists) are used for increasing at least one of translation, transcription, or secretion of neurotrophic factors.

In some embodiments, a compound herein is given to patients in a low dose that is lower than would produce noticeable psychedelic effects but high enough to provide a therapeutic benefit. This dose range is predicted to be between 200 μg (micrograms) and 2 mg.

In some embodiments, a compound described herein is used to treat a neurological disease. For example, a compound provided herein can exhibit, anti-addictive properties, antidepressant properties, anxiolytic properties, or a combination thereof. In some embodiments, the neurological disease is a neuropsychiatric disease. In some embodiments, the neuropsychiatric disease is a mood or anxiety disorder. In some embodiments, the neurological disease is a migraine, headaches (e.g., cluster headache), post-traumatic stress disorder (PTSD), anxiety, depression, neurodegenerative disorder, Alzheimer's disease, Parkinson's disease, psychological disorder, treatment resistant depression, suicidal ideation, major depressive disorder, bipolar disorder, schizophrenia, stroke, traumatic brain injury, and addiction (e.g., substance use disorder). In some embodiments, the neurological disease is a migraine or cluster headache. In some embodiments, the neurological disease is a neurodegenerative disorder, Alzheimer's disease, or Parkinson's disease. In some embodiments, the neurological disease is a psychological disorder, treatment resistant depression, suicidal ideation, major depressive disorder, bipolar disorder, schizophrenia, post-traumatic stress disorder (PTSD), addiction (e.g., substance use disorder), depression, or anxiety. In some embodiments, the neuropsychiatric disease is a psychological disorder, treatment resistant depression, suicidal ideation, major depressive disorder, bipolar disorder, schizophrenia, post-traumatic stress disorder (PTSD), addiction (e.g., substance use disorder), depression, or anxiety. In some embodiments, the neuropsychiatric disease or neurological disease is post-traumatic stress disorder (PTSD), addiction (e.g., substance use disorder), schizophrenia, depression, or anxiety. In some embodiments, the neuropsychiatric disease or neurological disease is addiction (e.g., substance use disorder). In some embodiments, the neuropsychiatric disease or neurological disease is depression. In some embodiments, the neuropsychiatric disease or neurological disease is anxiety. In some embodiments, the neuropsychiatric disease or neurological disease is post-traumatic stress disorder (PTSD). In some embodiments, the neurological disease is stroke or traumatic brain injury. In some embodiments, the neuropsychiatric disease or neurological disease is schizophrenia.

In some embodiments, a compound of the present disclosure is used for increasing neuronal plasticity. In some embodiments, a compound described herein is used for treating a brain disorder. In some embodiments, a compound described herein is used for increasing translation, transcription, or secretion of neurotrophic factors.

A compound disclosed herein can also be useful for increasing neuronal plasticity in a subject. As used herein, "neuronal plasticity" can refer to the ability of the brain to change structure and/or function throughout a subject's life. New neurons can be produced and integrated into the central nervous system throughout the subject's life. Increasing neuronal plasticity can include, but is not limited to, promoting neuronal growth, promoting neuritogenesis, promoting synaptogenesis, promoting dendritogenesis, increasing dendritic arbor complexity, increasing dendritic spine density, and increasing excitatory synapsis in the brain. In some embodiments, increasing neuronal plasticity comprises promoting neuronal growth, promoting neuritogenesis, promoting synaptogenesis, promoting dendritogenesis, increasing dendritic arbor complexity, and increasing dendritic spine density.

In some embodiments, increasing neuronal plasticity by treating a subject with a compound the present disclosure can treat neurodegenerative disorder, Alzheimer's, Parkinson's disease, psychological disorder, depression, addiction, anxiety, post-traumatic stress disorder, treatment resistant depression, suicidal ideation, major depressive disorder, bipolar disorder, schizophrenia, stroke, traumatic brain injury, or substance use disorder.

In some embodiments, the present disclosure provides a method for increasing neuronal plasticity, comprising contacting a neuronal cell with a compound of the present disclosure. In some embodiments, increasing neuronal plasticity improves a brain disorder described herein.

In some embodiments, a compound disclosed herein is used to increase neuronal plasticity and has, for example, anti-addictive properties, antidepressant properties, anxiolytic properties, or a combination thereof. In some embodiments, decreased neuronal plasticity is associated with a neuropsychiatric disease. In some embodiments, the neuropsychiatric disease is a mood or anxiety disorder. In some embodiments, the neuropsychiatric disease includes, for example, migraine, cluster headache, post-traumatic stress disorder (PTSD), schizophrenia, anxiety, depression, and addiction (e.g., substance abuse disorder). Brain disorders can include, for example, migraines, addiction (e.g., substance use disorder), depression, and anxiety.

In some embodiments, the experiment or assay to determine increased neuronal plasticity derived from the administration of any compound of the present disclosure is a phenotypic assay, a dendritogenesis assay, a spinogenesis assay, a synaptogenesis assay, a Sholl analysis, a concentration-response experiment, a 5-HT$_{2A}$ agonist assay, a 5-HT$_{2A}$ antagonist assay, a 5-HT$_{2A}$ binding assay, or a 5-HT$_{2A}$ blocking experiment (e.g., ketanserin blocking experiments). In some embodiments, the experiment or assay to determine the hallucinogenic potential of any compound of the present disclosure is a mouse head-twitch response (HTR) assay.

In some embodiments, the condition is a musculoskeletal pain disorder including fibromyalgia, muscle pain, joint stiffness, osteoarthritis, rheumatoid arthritis, muscle cramps. In some embodiments, the present disclosure provides a method of treating a disease of women's reproductive health including premenstrual dysphoric disorder (PMDD), premenstrual syndrome (PMS), post-partum depression, and menopause. In some embodiments, the present disclosure provides a method of treating a brain disorder, including administering to a subject in need thereof, a therapeutically effective amount of a compound of the present disclosure. In some embodiments, the present disclosure provides a method of treating a brain disorder with combination therapy, including administering to a subject in need thereof, a therapeutically effective amount of a compound of the present disclosure and at least one additional therapeutic agent.

In some embodiments, a compound of the present disclosure is used to treat brain disorders. In some embodiments, the compound has, for example, anti-addictive properties, antidepressant properties, anxiolytic properties, or a combination thereof. In some embodiments, the brain disorder is a neuropsychiatric disease. In some embodiments, the neuropsychiatric disease is a mood or anxiety disorder. In some embodiments, brain disorders include, for example, migraine, cluster headache, post-traumatic stress disorder (PTSD), anxiety, depression, panic disorder, suicidality, schizophrenia, and addiction (e.g., substance abuse disorder). In some embodiments, brain disorders include, for example, migraines, addiction (e.g., substance use disorder), depression, and anxiety.

In some embodiments, the present disclosure provides a method of treating a brain disorder, comprising administering to a subject in need thereof a therapeutically effective amount of a compound disclosed herein. In some embodiments, the brain disorder is a neurodegenerative disorder, Alzheimer's disease, Parkinson's disease, a psychological disorder, depression, addiction, anxiety, post-traumatic stress disorder, treatment resistant depression, suicidal ideation, major depressive disorder, bipolar disorder, schizophrenia, stroke, traumatic brain injury, or a substance use disorder.

In some embodiments, the brain disorder is a neurodegenerative disorder, Alzheimer's disease or Parkinson's disease. In some embodiments, the brain disorder is a psychological disorder, depression, addiction, anxiety, or a post-traumatic stress disorder. In some embodiments, the brain disorder is depression. In some embodiments, the brain disorder is addiction. In some embodiments, the brain disorder is treatment resistant depression, suicidal ideation, major depressive disorder, bipolar disorder, schizophrenia, stroke, traumatic brain injury or substance use disorder. In some embodiments, the brain disorder is treatment resistant depression, suicidal ideation, major depressive disorder, bipolar disorder, schizophrenia, or substance use disorder. In some embodiments, the brain disorder is stroke or traumatic brain injury. In some embodiments, the brain disorder is treatment resistant depression, suicidal ideation, major depressive disorder, bipolar disorder, or substance use disorder. In some embodiments, the brain disorder is schizophrenia. In some embodiments, the brain disorder is alcohol use disorder.

In some embodiments, the method further comprises administering one or more additional therapeutic agent. Non-limiting examples of additional therapeutics suitable for administration with a compound of the present disclosure can include lithium, olanzapine (Zyprexa), quetiapine (Seroquel), risperidone (Risperdal), aripiprazole (Abilify), ziprasidone (Geodon), clozapine (Clozaril), divalproex sodium (Depakote), lamotrigine (Lamictal), valproic acid (Depakene), carbamazepine (Equetro), topiramate (Topamax), levomilnacipran (Fetzima), duloxetine (Cymbalta, Yentreve), venlafaxine (Effexor), citalopram (Celexa), fluvoxamine (Luvox), escitalopram (Lexapro), fluoxetine (Prozac), paroxetine (Paxil), sertraline (Zoloft), clomipramine (Anafranil), amitriptyline (Elavil), desipramine (Norpramin), imipramine (Tofranil), nortriptyline (Pamelor), phenelzine (Nardil), tranylcypromine (Parnate), diazepam (Valium), alprazolam (Xanax), or clonazepam (Klonopin).

In some embodiments, the additional therapeutic agent is a monoamine oxidase inhibitor (MAOI), which can be, for example, moclobemide, caroxazone (Surodil, Timostenil), brofaromine (Consonar), methylene blue, pirlindole (Pirazidol), minaprine (Cantor), metralindole (Inkazan), eprobemide, tetrindole, harmine, harmaline, amiflamine, befloxatone (MD-370,503), cimoxatone (MD-780,515), sercloremine (CGP-4718-A), esuprone, or CX157.

In some embodiments, the additional therapeutic agent is a phenethylamine, such as 3,4-methylene-dioxymethamphetamine (MDMA) and analogs thereof. Other suitable empathogenic agents for use in combination a compound of the present disclosure include, without limitation, N-Allyl-3,4-methylenedioxy-amphetamine (MDAL), N-Butyl-3,4-methylenedioxyamphetamine (MDBU), N-Benzyl-3,4-methylenedioxyamphetamine (MDBZ), N-Cyclopropylmethyl-3,4-methylenedioxyamphetamine (MDCPM), N,N-Dimethyl-3,4-methylenedioxyamphetamine (MDDM), N-Ethyl-3,4-methylenedioxyamphetamine (MDE; MDEA); N-(2-Hydroxyethyl)-3,4-methylenedioxy amphetamine (MDHOET), N-Isopropyl-3,4-methylenedioxyamphetamine (MDIP), N-Methyl-3,4-ethylenedioxyamphetamine (MDMC) N-Methoxy-3,4-methylenedioxyamphetamine (MDMEO), N-(2-Methoxyethyl)-3,4-methylenedioxyamphetamine (MDMEOET), alpha,alpha,N-Trimethyl-3,4-methylenedioxyphenethylamine (MDMP), 3,4-Methylenedioxy-N-methylphentermine N-Hydroxy-3,4-methylenedioxyamphetamine (MDOH), 3,4-Methylenedioxyphenethylamine (MDPEA), alpha,alpha-Dimethyl-3,4-methylenedioxyphenethylamine (MDPH; 3,4-methylenedioxyphentermine), N-Propargyl-3,4-methylenedioxyamphetamine (MDPL), Methylenedioxy-2-aminoindane (MDAI), 1,3-Benzodioxolyl-N-methylbutanamine (MBDB), N-methyl-1,3-benzodioxolylbutanamine, 3,4-methylenedioxy-N-methyl-α-ethylphenylethylamine, 3,4-Methylenedioxyamphetamine (MDA), Methylone (3,4-methylenedioxy-N-methylcathinone), Ethylone (3,4-methylenedioxy-N-ethylcathinone), GHB or Gamma Hydroxybutyrate or sodium oxybate, N-Propyl-3,4-methylenedioxyamphetamine (MDPR), and the like.

In some embodiments, a compound of the present disclosure is used in combination with the standard of care therapy for a neurological disease described herein. Non-limiting examples of the standard of care therapies, may include, for example, lithium, olanzapine, quetiapine, risperidone, aripiprazole, ziprasidone, clozapine, divalproex sodium, lamotrigine, valproic acid, carbamazepine, topiramate, levomilnacipran, duloxetine, venlafaxine, citalopram, fluvoxamine, escitalopram, fluoxetine, paroxetine, sertraline, clomipramine, amitriptyline, desipramine, imipramine, nortriptyline, phenelzine, tranylcypromine, diazepam, alprazolam, clonazepam, or any combination thereof. Nonlimiting examples of standard of care therapy for depression are sertraline, fluoxetine, escitalopram, venlafaxine, or aripiprazole. Non-limiting examples of standard of care therapy for depression are citralopram, escitalopram, fluoxetine, paroxetine, diazepam, or sertraline. Additional examples of standard of care therapeutics are known to those of ordinary skill in the art.

Methods of Increasing at Least One of Translation, Transcription, or Secretion of Neurotrophic Factors.

As used herein, the term "neurotrophic factor" can refer to a family of soluble peptides or proteins which support the survival, growth, and differentiation of developing and mature neurons. Increasing at least one of translation, transcription, or secretion of neurotrophic factors can be useful for, for example, increasing neuronal plasticity, promoting neuronal growth, promoting neuritogenesis, promoting synaptogenesis, promoting dendritogenesis, increasing dendritic arbor complexity, increasing dendritic spine density, and increasing excitatory synapsis in the brain. In some embodiments, increasing at least one of translation, transcription, or secretion of neurotrophic factors increases neuronal plasticity. In some embodiments, increasing at least one of translation, transcription, or secretion of neurotrophic factors promotes neuronal growth, promotes neuritogenesis, promotes synaptogenesis, promotes dendritogenesis, increases dendritic arbor complexity, and/or increases dendritic spine density.

In some embodiments, a $5\text{-}HT_{2A}$ modulators (e.g., $5\text{-}HT_{2A}$ agonists) is used to increase at least one of translation, transcription, or secretion of neurotrophic factors. In some embodiments, a compound of the present disclosure is used to increase translation, transcription, or secretion of neurotrophic factors. In some embodiments, increasing translation, transcription or secretion of neurotrophic factors is sufficient for the treatment of migraine, headaches (e.g., cluster headache), post-traumatic stress disorder (PTSD), anxiety, depression, neurodegenerative disorder, Alzheimer's disease, Parkinson's disease, psychological disorder, treatment resistant depression, suicidal ideation, major depressive disorder, bipolar disorder, schizophrenia, stroke, traumatic brain injury, or addiction (e.g., substance use disorder).

An experiment or assay can be used to detect increased translation of neurotrophic factors, which can include, for example, ELISA, western blot, an immunofluorescence assay, a proteomic experiment, and mass spectrometry. In some embodiments, the experiment or assay used to detect increased transcription of neurotrophic factors is a gene expression assay, PCR, or microarray. In some embodiments, the experiment or assay used to detect increased secretion of neurotrophic factors is ELISA, western blot, an immunofluorescence assay, a proteomic experiment, or a mass spectrometry assay.

In some embodiments, the present disclosure provides a method for increasing translation, transcription, or secretion of neurotrophic factors, wherein the method comprises contacting a neuronal cell with a compound disclosed herein. Pharmacokinetics.

In yet another aspect, the present disclosure provides a method of treating a condition in a subject in need thereof, the method comprising administering to the subject a therapeutically-effective amount of a compound of Formula (I), (Ia), (Ib), (Ib-1) (Ib1), (Ic), (Id), (Ie), (If), (If1), (Ig), (Ih), (Ii), (Ij), (Ik), (Ik1), (Ik2), (Ik3), (Il), (Im), (Im1), (Im1a), (In), (In1), (Io), (Io1), (Io2), (Io1a), (Ip) (Ip1), (Iq), (Iq1), (Ir), (Ir1), (Is), (It), (Iu), (Iv), or (Iw), or a pharmaceutically acceptable salt thereof. In some embodiments, a plasma concentration of DMT in the subject is, for administration of a dose of about 10 mg/kg, from about 500 nM to about 2500 ng/mL at about 0.25 hours after the administration. In some embodiments, a plasma concentration of DMT in the subject is, for administration of a dose of about 10 mg/kg, from about 1400 nM to about 2500 ng/mL at about 0.5 hours after the administration. In some embodiments, a plasma concentration of DMT in the subject is, for administration of a dose of about 10 mg/kg, from about 1400 nM to about 2500 ng/mL at about 0.75 hours after the administration. In some embodiments, a plasma concentration of DMT in the subject is, for administration of a dose of about 10 mg/kg, from about 1100 nM to about 2500 ng/mL at about 1 hours after the administration. In some embodiments, a plasma concentration of DMT in the subject is, for administration of a dose of about 10 mg/kg, from about 600 nM to about 2500 ng/mL at about 2 hours after the administration. In some embodiments, a plasma concentration of DMT in the subject is, for administration of a dose of about 10 mg/kg, from about 50 nM to about 2500 ng/mL at about 4 hours after the administration. In some embodiments, a plasma concentration of DMT in the subject is, for administration of a dose of about 10 mg/kg, from about 500 nM to about 2500 ng/mL at about 0.25 hours after the administration. In some embodiments, a plasma concentration of DMT in the subject is, for administration of a dose of about 10 mg/kg, from about 1400 nM to about 1800 ng/mL at about 0.5 hours after the administration. In some embodiments, a plasma concentration of DMT in the subject is, for administration of a dose of about 10 mg/kg, from about 1400 nM to about 2400 ng/mL at about 0.75 hours after the administration. In some embodiments, a plasma concentration of DMT in the subject is, for administration of a dose of about 10 mg/kg, from about 1100 nM to about 1600 ng/mL at about 1 hours after the administration. In some embodiments, a plasma concentration of DMT in the subject is, for administration of a dose of about 10 mg/kg, from about 600 nM to about 1200 ng/mL at about 2 hours after the administration. In some embodiments, a plasma concentration of DMT in the subject is, for administration of a dose of about 10 mg/kg, from about 50 nM to about 1000 ng/mL at about 4 hours after the administration. In some embodiments, the administration is oral administration. In some embodiments, the subject is a rat. In some embodiments, the compound is a compound of Formula (I). In some embodiments, the subject is a rat. In some embodiments, the compound is a compound of Formula (I), wherein $R^3$ is cycloalkyl or alkyl. In some embodiments, the compound is a compound of Formula (I), wherein $R^1$ is hydrogen.

In yet another aspect, the present disclosure provides a method of treating a condition in a subject in need thereof, the method comprising administering to the subject a therapeutically-effective amount of a compound of Formula (I), (Ia), (Ib), (Ib-1) (Ib1), (Ic), (Id), (Ie), (If), (If1), (Ig), (Ih), (Ii), (Ij), (Ik), (Ik1), (Ik2), (Ik3), (Il), (Im), (Im1), (Im1a), (In), (In1), (Io), (Io1), (Io2), (Io1a), (Ip) (Ip1), (Iq), (Iq1), (Ir), (Ir1), (Is), (It), (Lu), (Iv), or (Iw), or a pharmaceutically acceptable salt thereof. In some embodiments, a plasma concentration of 5-OMe-DMT in the subject is, for administration of a dose of about 10 mg/kg, from about 50 nM to about 300 ng/mL at about 0.25 hours after the administration. In some embodiments, a plasma concentration of 5-OMe-DMT in the subject is, for administration of a dose of about 10 mg/kg, from about 100 nM to about 300 ng/mL at about 0.5 hours after the administration. In some embodiments, a plasma concentration of 5-OMe-DMT in the subject is, for administration of a dose of about 10 mg/kg, from about 100 nM to about 300 ng/mL at about 0.75 hours after the administration. In some embodiments, a plasma concentration of 5-OMe-DMT in the subject is, for administration of a dose of about 10 mg/kg, from about 100 nM to about 300 ng/mL at about 1 hours after the administration. In some embodiments, a plasma concentration of 5-OMe-DMT in the subject is, for administration of a dose of about 10 mg/kg, from about 30 nM to about 300 ng/mL at about 2 hours after the administration. In some embodiments, a plasma concentration of 5-OMe-DMT in the subject is, for administration of a dose of about 10 mg/kg, from about 1 nM to about 300 ng/mL at about 4 hours after the administration. In some embodiments, a plasma concentration of 5-OMe-DMT in the subject is, for administration of a dose of about 10 mg/kg, from about 50 nM to about 150 ng/mL at about 0.25 hours after the administration. In some embodiments, a plasma concentration of 5-OMe-DMT in the subject is, for administration of a dose of about 10 mg/kg, from about 100 nM to about 300 ng/mL at about 0.5 hours after the administration. In some embodiments, a plasma concentration of 5-OMe-DMT in the subject is, for administration of a dose of about 10 mg/kg, from about 100 nM to about 200 ng/mL at about 0.75 hours after the administration. In some embodiments, a plasma concentration of 5-OMe-DMT in the subject is, for administration of a dose of about 10 mg/kg, from about 100 nM to about 250 ng/mL at about 1 hours after the administration. In some embodiments, a plasma concentration of 5-OMe-DMT in the subject is, for administration of a dose of about 10 mg/kg, from about 30 nM to about 100 ng/mL at about 2 hours after the administration. In some embodiments, a plasma concentration of 5-OMe-DMT in the subject is, for administration of a dose of about 10 mg/kg, from about 1 nM to about 200 ng/mL at about 4 hours after the administration. In some embodiments, the administration is oral administration. In some embodiments, the subject is a rat. In some embodiments, the compound is a compound of Formula (I). In some embodiments, the subject is a rat. In some embodiments, the compound is a compound of Formula (I), wherein $R^3$ is cycloalkyl or alkyl. In some embodiments, the compound is a compound of Formula (I), wherein $R^1$ is methoxy.

EXAMPLES

The following examples are intended to illustrate the invention and are not to be construed as being limitations thereon. Temperatures are given in degrees centigrade. If not mentioned otherwise, all evaporations are performed in vacuo, preferably between about 15 mm Hg and 100 mm Hg (=20-133 mbar). The structure of final products, intermediates and starting materials is confirmed by standard analytical methods, e.g., MS and NMR. Abbreviations used are those conventional in the art. If not defined, the terms have their generally accepted meanings.

Example 1: Preparation of Selected Compounds and Intermediates

The following preparations of compounds and intermediates are given to enable those of skill in the art to more clearly understand and to practice the present disclosure. They should not be considered as limiting the scope of the disclosure, but merely as illustrative and representative thereof.

Abbreviation app apparent
Boc tert-butyl carbamate
Boc-Sar-OH Boc-sarcosine
br broad
CDCl$_3$ d$_3$-chloroform
d doublet
dd doublet of doublets
DCM dichloromethane
DIPEA diisopropylethylamine
DMA dimethylacetamide
DMAP 4-dimethylaminopyridine
DMF N,N-dimethylformamide
DMSO dimethyl sulfoxide
EtOAc ethyl acetate
HATU 1-[Bis(dimethylamino)methylene]-1H-1,2,3-triazolo[4,5-b]pyridinium 3-oxid hexafluorophosphate
HCl hydrochloric acid
h hextet; sextet
hr or hrs hour or hours
HPLC high pressure liquid chromatography
LC-MS liquid chromatography and mass spectrometry
MeOH MeOH
MeCN acetonitrile
MS mass spectrometry
m multiplet
min(s) minute(s)
mL milliliter(s)
μL microliter(s)
m/z mass to charge ratio
p pentet
q quartet
NaHCO$_3$ sodium hydrogen carbonate
Na$_2$SO$_4$ sodium sulfate
NMP N-methyl-2-pyrrolidone
NMR nuclear magnetic resonance
Rt retention time
s singlet
sar sarcosine
t triplet
tert tertiary
THF tetrahydrofiran Referring to the examples that follow, compounds of the preferred embodiments were synthesized using the methods described herein, or other methods, which are known in the art. The various starting materials, intermediates, and compounds of the preferred embodiments may be isolated and purified, where appropriate, using conventional techniques such as precipitation, filtration, crystallization, evaporation, distillation, and chromatography. Salts may be prepared from compounds by known salt-forming procedures. Unless otherwise stated, all starting materials are obtained from commercial suppliers and used without further purification.

General Conditions for Characterization:
NMR Analysis.

$^1$H, $^{13}$C, $^{19}$F and $^{31}$P NMR analyses were conducted on a Bruker™ Avance 400 MHz NMR spectrometer using deuterated chloroform or deuterated dimethyl sulfoxide as solvent. The shift (d) of each signal was measured in parts per million (ppm) relative the residual solvent peak, and the multiplicity reported together with the associated coupling constant (J), where applicable.

UPLC-MS Analysis Methodology.

UPLC-MS analysis was carried out on a Waters™ Acquity UPLC system consisting of an Acquity I-Class Sample Manager-FL, Acquity I-Class Binary Solvent Manager and an Acquity UPLC Column Manager. UV detection was afforded using an Acquity UPLC PDA detector (scanning from 210 to 400 nm), whilst mass detection was achieved using an Acquity QDa detector (mass scanning from 100-1250 Da; positive and negative modes simultaneously), and ELS detection was achieved using an Acquity UPLC ELS Detector. A Waters™ Acquity UPLC BEH C18 column (2.1×50 mm, 1.7 mm) was used to separate the analytes.

Samples were prepared by dissolution (with or without sonication) into 1 mL of 50% (v/v) MeCN in water. The resulting solutions were then filtered through a 0.2 mm syringe filter before submitting for analysis. All of the solvents, including formic acid and 36% ammonia solution, were purchased as the HPLC grade.

Conditions (Acidic 2 min).

0.1% v/v Formic acid in water [Eluent A]; 0.1% v/v Formic acid in MeCN [Eluent B]; flow rate 0.8 mL/min; column oven 50° C.; sample manager 20° C.; injection volume 2 mL and 1.5 minutes equilibration time between samples. Gradient parameters are provided in TABLE 2.

TABLE 2

| Time (min) | Eluent A (%) | Eluent B (%) |
|---|---|---|
| 0.00 | 95 | 5 |
| 0.25 | 95 | 5 |
| 1.25 | 5 | 95 |
| 1.55 | 5 | 95 |
| 1.65 | 95 | 5 |
| 2.00 | 95 | 5 |

Conditions (Acidic 4 min).

0.1% v/v formic acid in water [Eluent A]; 0.1% v/v formic acid in MeCN [Eluent B]; flow rate 0.8 mL/min; column oven 50° C.; sample manager 20° C.; injection volume 2 mL and 1.5 minutes equilibration time between samples. Gradient parameters are provided in TABLE 3.

TABLE 3

| Time (min) | Eluent A (%) | Eluent B (%) |
|---|---|---|
| 0.00 | 95 | 5 |
| 0.25 | 95 | 5 |
| 2.75 | 5 | 95 |
| 3.25 | 5 | 95 |
| 3.35 | 95 | 5 |
| 4.00 | 95 | 5 |

Conditions (Acidic 6 mini).

0.1% v/v formic acid in water [Eluent A]; 0.1% v/v formic acid in MeCN [Eluent B]; flow rate 0.8 mL/min; column oven 50° C.; sample manager 20° C.; injection volume 2 ml, and 1.5 minutes equilibration time between samples. Gradient parameters are provided in TABLE 4.

TABLE 4

| Time (min) | Eluent A (%) | Eluent B (%) |
|---|---|---|
| 0.00 | 95 | 5 |
| 0.30 | 95 | 5 |
| 6.00 | 5 | 95 |
| 6.10 | 95 | 5 |
| 7.00 | 95 | 5 |

Conditions (Basic 2 min).

0.1% ammonia in water [Eluent A]; 0.1% ammonia in MeCN [Eluent B]; flow rate 0.8 mU/min; column oven 50° C.; sample manager 20° C.; injection volume 2 mL and 1.5 minutes equilibration time between samples. Gradient parameters are provided in TABLE 5.

TABLE 5

| Time (min) | Eluent A (%) | Eluent B (%) |
|---|---|---|
| 0.00 | 95 | 5 |
| 0.25 | 95 | 5 |
| 1.25 | 5 | 95 |

TABLE 5-continued

| Time (min) | Eluent A (%) | Eluent B (%) |
|---|---|---|
| 1.55 | 5 | 95 |
| 1.65 | 95 | 5 |
| 2.00 | 95 | 5 |

Conditions (Basic 4 min).

0.1% ammonia in water [Eluent A]; 0.1% ammonia in MeCN [Eluent B]; flow rate 0.8 mL/min; column oven 50° C.; sample manager 20° C.; injection volume 2 mL and 1.5 minutes equilibration time between samples. Gradient parameters are provided in TABLE 6.

TABLE 6

| Time (min) | Eluent A (%) | Eluent B (%) |
|---|---|---|
| 0.00 | 95 | 5 |
| 0.25 | 95 | 5 |
| 2.75 | 5 | 95 |
| 3.25 | 5 | 95 |
| 3.35 | 95 | 5 |
| 4.00 | 95 | 5 |

Conditions (Basic 6 min).

0.1% ammonia in water [Eluent A]; 0.1% ammonia in MeCN [Eluent B]; flow rate 0.8 mL/min; column oven 50° C.; sample manager 20° C.; injection volume 2 mL and 1.5 minutes equilibration time between samples. Gradient parameters are provided in TABLE 7.

TABLE 7

| Time (min) | Eluent A (%) | Eluent B (%) |
|---|---|---|
| 0.00 | 95 | 5 |
| 0.30 | 95 | 5 |
| 6.00 | 5 | 95 |
| 6.10 | 95 | 5 |
| 7.00 | 95 | 5 |

Example 1-1: Dimethyl Tryptamine (DMT)

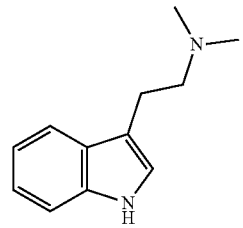

A solution of 4% sulfuric acid (0.16 M, 0.82 mL, 15.3 mmol) was heated to 55° C. and purged with nitrogen. Phenylhydrazine (1.50 g, 13.9 mmol) was added to the heated acidic solution, followed by dropwise addition of 4,4-dimethoxy-N,N-dimethyl-butan-1-amine (2.46 g, 15.3 mmol), while maintaining 55° C. The resulting solution was heated to reflux for 2 h and then cooled to room temperature. A solution of NaOH (10 g) in $H_2O$ (50 mL) was added slowly to the crude reaction mixture, which was then extracted with EtOAc (×3). The organic phases were combined, washed with brine, dried over $Na_2SO_4$, filtered, and concentrated to dryness under reduced pressure to produce an orange oil (2.1 g). The crude oil was purified by column chromatography on silica gel (40 g cartridge, 5-20% MeOH in acetone) to afford 2-(1H-indol-3-yl)-N,N-dimethyl-ethanamine (1.46 g, 53% yield) as a solid. $^1$H NMR (400 MHz, d$_6$-DMSO) δ 10.77 (s, 1H), 7.51 (ddt, J=7.9, 1.5, 0.9 Hz, 1H), 7.33 (dt, J=8.1, 1.0 Hz, 1H), 7.16-7.12 (m, 1H), 7.06 (ddd, J=8.2, 7.0, 1.2 Hz, 1H), 6.97 (ddd, J=7.9, 7.0, 1.1 Hz, 1H), 2.86-2.77 (m, 2H), 2.55-2.50 (m, 2H), 2.23 (s, 6H).

Example 1-2: 5-Methoxy Dimethyl Tryptamine (5-MeO-DMT)

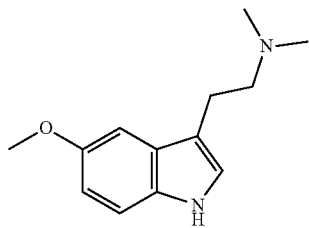

To a magnetically stirred solution of 4-methoxyphenyl-hydrazine hydrochloride (2.00 g, 11.5 mmol) in water (20 mL) at room temperature under an atmosphere of N$_2$ was added H$_2$SO$_4$ (0.67 mL, 12.6 mmol) dropwise while maintaining the temperature below 40° C. The solution was heated to 40° C. and stirred for 10 min. A mixture of 4,4-dimethoxy-N,N-dimethyl-butan-1-amine (2.20 mL, 12.0 mmol) in acetonitrile (10 mL) was added dropwise. The reaction was agitated at 40° C. for 1 h. The acetonitrile was removed under reduced pressure, and the resulting aqueous solution was washed with 2-MeTHF (2×30 mL). The aqueous phase was treated with NaOH (4 M, 9.00 mL, 1.60 g NaOH) to adjust the pH to ~11-12, and the product was extracted with 2-MeTHF (3×30 mL). The organic phases were combined and concentrated under reduced pressure to provide a brown oil, which was then purified by column chromatography on silica gel (20 g cartridge, 1-10% MeOH in acetone) to afford 2-(5-methoxy-1H-indol-3-yl)-N,N-dimethyl-ethanamine (1.70 g, 68% yield) as an oil. UPLC-MS (4 min, basic): rt=1.12 min; m/z=219.2 [M+H]$^+$; rt=1.12 min; m/z=219.2 [M+H]$^+$; —two peaks same product; $^1$H NMR (400 MHz, CDCl$_3$) δ 7.97 (s, 1H), 7.29 (dd, J=4.8, 1.4 Hz, 1H), 7.09 (d, J=2.4 Hz, 1H), 7.04 (d, J=2.3 Hz, 1H), 6.89 (dt, J=8.8, 1.9 Hz, 1H), 3.90 (s, 3H), 2.99-2.90 (m, 2H), 2.72-2.61 (m, 2H), 2.38 (s, 6H).

Example 1-3: Ethyl 3-[2-(dimethylamino)ethyl] indole-1-carboxylate (Compound 20)

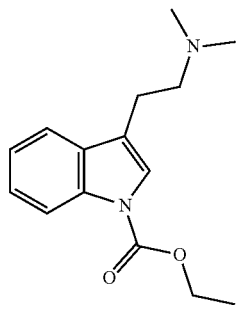 [SMILES: CCOC(=O)n1cc(CCN(C)C)c2ccccc21]

To a stirring solution of DMT (2-(1H-indol-3-yl)-N,N-dimethyl-ethanamine, 99 mg, 0.53 mmol) in THF (10 mL) at −78° C. was added sodium bis(trimethylsilyl)amide (2.0 M solution in THF, 0.53 mL, 1.05 mmol). The resulting solution was stirred at −78° C. for 15 min. Ethyl chloroformate (101 μL, 1.05 mmol) was added dropwise and stirred for a further 5 min at −78° C. The reaction mixture was allowed to warm to room temperature and then stirred for 18 h. Saturated brine was added followed by EtOAc. The organic phase was separated and the aqueous was extracted with EtOAc (×2). The organic phases were combined, washed with brine, dried over Na$_2$SO$_4$, filtered, and evaporated to provide an orange oil. The crude oil was purified by column chromatography on silica gel (4 g, 0 to 20% methanol in dichloromethane) to afford Compound 20 (ethyl 3-[2-(dimethylamino)ethyl]indole-1-carboxylate, 77 mg, 56% yield) as an oil. UPLC-MS (4 min, basic): rt=1.84 min; m/z=261.0 [M+H]$^+$; $^1$H NMR (400 MHz, CDCl$_3$) δ 8.00 (d, J=8.2 Hz, 1H), 7.39 (ddd, J=7.8, 1.4, 0.8 Hz, 1H), 7.28 (s, 1H), 7.18 (ddd, J=8.3, 7.2, 1.4 Hz, 1H), 7.15-7.06 (m, 1H), 4.32 (q, J=7.1 Hz, 2H), 2.79-2.69 (m, 2H), 2.59-2.46 (m, 2H), 2.21 (s, 6H), 1.31 (t, J=7.1 Hz, 3H); $^{13}$C NMR (101 MHz, CDCl$_3$) δ 151.0, 135.6, 130.6, 124.6, 122.7, 122.3, 119.4, 119.0, 115.3, 77.4, 77.0, 76.7, 63.0, 59.2, 45.4, 23.3, 14.5.

Example 1-4: Ethyl 3-[2-(dimethylamino)ethyl]-5-methoxy-indole-1-carboxylate (Compound 19)

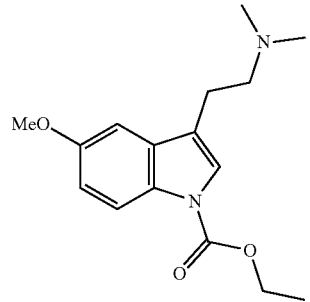 [SMILES: CCOC(=O)n1cc(CCN(C)C)c2cc(OC)ccc21]

To a stirring solution of 5-MeO DMT (2-(5-methoxy-1H-indol-3-yl)-N,N-dimethyl-ethanamine, 200 mg, 0.92 mmol) in THF (10 mL) at −78° C. was added sodium bis(trimethylsilyl)amide (2.0 M solution in THF, 0.69 mL, 1.37 mmol). The resulting solution was stirred at −78° C. for 15 min. Ethyl chloroformate (180 μL, 1.83 mmol) was added dropwise and stirred for a further 5 min at −78° C. The reaction mixture was allowed to warm to room temperature and then stirred for 18 h. The reaction mixture was then diluted with EtOAc (10 mL), washed with H$_2$O (10 ml), and extracted a second time with EtOAc (10 mL). The combined organic phases were washed with brine (10 mL), dried over Na$_2$SO$_4$, and concentrated under reduced pressure. The crude product was purified by column chromatography on silica gel (10 g, 50-100% EtOAc in heptane with 1% TEA over 10 CV, then 100% ethyl acetate with 1% TEA for 10 CV) to give Compound 19 (ethyl 3-[2-(dimethylamino)ethyl]-5-methoxy-indole-1-carboxylate, 115 mg, 43% yield) as an oil. UPLC-MS (4 min, basic): rt=1.79 min; m/z=291.2 [M+H]$^+$; 100%. $^1$H NMR (400 MHz, CDCl$_3$) δ 8.03 (s, 1H), 7.41 (s, 1H), 6.99 (d, J=2.4 Hz, 1H), 6.93 (dd, J=9.0, 2.5 Hz, 1H), 4.45 (q, J=7.1 Hz, 2H), 3.87 (s, 3H), 2.88-2.78 (m, 2H), 2.67-2.58 (m, 2H), 2.33 (s, 6H), 1.45 (t, J=7.1 Hz, 3H).

Example 1-5: 2-(1-Diisopropoxyphosphorylindol-3-yl)-N,N-dimethyl-ethanamine (Compound 263)

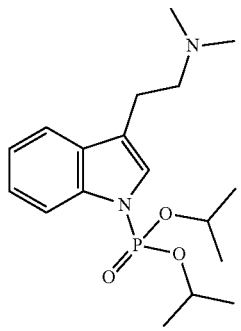 [SMILES: CC(C)OP(=O)(OC(C)C)n1cc(CCN(C)C)c2ccccc21]

To a stirring solution of DMT (2-(1H-indol-3-yl)-N,N-dimethyl-ethanamine, 200 mg, 1.06 mmol) in THF (10 mL) at −78° C. was added sodium bis(trimethylsilyl)amide (1.0 M solution in THF, 1.6 mL, 1.59 mmol). The mixture was stirred at −78° C. for 15 min, and 2-[chloro(isopropoxy)phosphoryl]oxypropane (0.100 mL, 0.6 mmol) was then added. The mixture allowed to warm to room temperature, stirred for 20 h, and concentrated under reduced pressure. The resulting residue was first purified by column chromatography on silica gel (12 g Si, 5 CV DCM+1% TEA, 10 CV 0-5% iso-propanol in DCM+1% TEA, 20 CV 10% iso-propanol in DCM+1% TEA), then further purified by preparative-HPLC to give Compound 263 (2-(1-diisopropoxy-phosphorylindol-3-yl)-N,N-dimethyl-ethanamine, 123 mg, 33% yield) as an oil. UPLC-MS (4 min, basic): rt=1.88 min, m/z=353.3 [M+H]$^+$; $^1$H NMR (400 MHz, CDCl$_3$) δ 7.71 (dt, J=8.2, 0.9 Hz, 1H), 7.57 (dtd, J=7.5, 1.6, 0.7 Hz, 1H), 7.28 (dd, J=7.1, 1.3 Hz, 1H), 7.25-7.19 (m, 2H), 4.63 (dp, J=7.5, 6.2 Hz, 2H), 2.92-2.86 (m, 2H), 2.68-2.60 (m, 2H), 2.33 (s, 6H), 1.41 (d, J=6.2 Hz, 6H), 1.10 (d, J=6.2 Hz, 6H); $^{31}$P NMR (162 MHz, CDCl$_3$) δ−5.27 (t, J=7.7 Hz).

Example 1-6: 2-(1-Diisopropoxyphosphoryl-5-methoxy-indol-3-yl)-N,N-dimethyl-ethanamine (Compound 255)

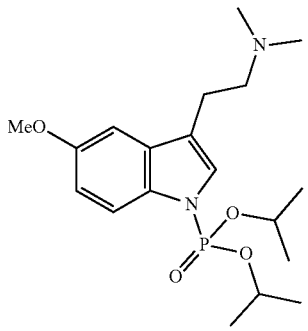 [SMILES: COc1ccc2c(c1)c(CCN(C)C)cn2P(=O)(OC(C)C)OC(C)C]

To a stirring solution of 5-MeO DMT (2-(5-methoxy-1H-indol-3-yl)-N,N-dimethyl-ethanamine, 228 mg, 1.04 mmol) in THF (10 mL) at −78° C. was added sodium bis(trimethylsilyl)amide (1.0 M solution in THF, 1.6 mL, 1.57 mmol), whereupon the mixture was stirred at −78° C. for 15 min. 2-[chloro(isopropoxy)phosphoryl]oxypropane (0.37 mL, 2.1 mmol) was then added, and the mixture allowed to warm to room temperature. The mixture was stirred at temperature for 20 h, quenched with iso-propanol (5 mL), and concentrated under reduced pressure. The residue was purified by column chromatography on silica gel (12 g Si, 5 CV DCM+1% TEA, 10 CV 0-5% iso-propanol in DCM+1% TEA, 20 CV 10% iso-propanol in DCM+1% TEA), and then further purified by preparative-HPLC to afford Compound 255 (2-(1-diisopropoxyphosphoryl-5-methoxy-indol-3-yl)-N,N-dimethyl-ethanamine, 65 mg, 16% yield) as an oil. UPLC-MS (4 min, basic): rt=1.82 min, m/z=383.3 [M+H]$^+$; $^1$H NMR (400 MHz, CDCl$_3$) δ 7.59 (d, J=8.9 Hz, 1H), 7.24 (dt, J=2.2, 1.1 Hz, 1H), 7.00 (t, J=2.0 Hz, 1H), 6.90 (dd, J=8.9, 2.5 Hz, 1H), 4.61 (dhept, J=7.5, 6.2 Hz, 2H), 3.86 (s, 3H), 2.89-2.81 (m, 2H), 2.67-2.58 (m, 2H), 2.34 (s, 6H), 1.40 (d, J=6.2 Hz, 6H), 1.10 (d, J=6.2 Hz, 6H).

Example 1-7: Tert-butyl [3-[2-(dimethylamino)ethyl]indol-1-yl]methyl hydrogen (Compound 511)

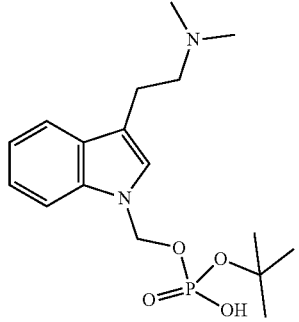 [SMILES: CN(C)CCc1cn(COP(=O)(O)OC(C)(C)C)c2ccccc12]

To a stirring solution of DMT (2-(1H-indol-3-yl)-N,N-dimethyl-ethanamine, 150 mg, 0.8 mmol) in DMSO (3 mL) at room temperature was added K$_2$CO$_3$, 325 mesh (440 mg, 3.2 mmol). The mixture was stirred at room temperature for 15 min, after which time di-tert-butyl chloromethyl phosphate (412 mg, 1.59 mmol) was added and the mixture stirred for 17 h. H$_2$O (2 mL) was then added, and the mixture was stirred for 21 h at rt. The resulting crude mixture was purified by reverse phase column chromatography (23 g, gradient of 10-50% MeCN in water with 0.1% NH$_4$OH) to afford Compound 511 (tert-butyl [3-[2-(dimethylamino)ethyl]indol-1-yl]methyl hydrogen phosphate, 219 mg, 78% yield) as a solid. UPLC-MS (2 min, basic): rt=0.74 min, m/z=355.1 [M+H]$^+$; 1H NMR (400 MHz, d$_6$-DMSO) δ 7.68 (dt, J=7.9, 1.1 Hz, 1H), 7.54 (dt, J=8.3, 0.9 Hz, 1H), 7.33 (s, 1H), 7.18 (ddd, J=8.2, 7.0, 1.2 Hz, 1H), 7.13-6.98 (m, 1H), 6.49 (s, 1H), 4.86 (dd, J=8.9, 3.4 Hz, 2H), 3.55-3.41 (m, 2H), 3.33 (s, 6H), 3.18 (td, J=8.0, 3.1 Hz, 2H), 3.08 (d, J=1.8 Hz, 6H), 1.31 (d, J=0.8 Hz, 9H); $^{31}$P NMR (162 MHz, d$_6$-DMSO) δ−6.09 (q, J=8.8 Hz).

Example 1-8: Tert-butyl [3-[2-(dimethylamino)ethyl]-5-methoxy-indol-1-yl]methyl hydrogen phosphate (Compound 510)

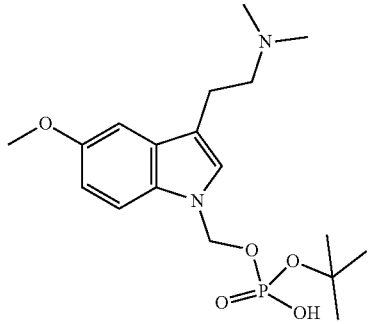 [SMILES: COc1ccc2c(c1)c(CCN(C)C)cn2COP(=O)(O)OC(C)(C)C]

To a stirring solution of 5-MeO DMT (2-(5-methoxy-1H-indol-3-yl)-N,N-dimethyl-ethanamine, 150 mg, 0.69 mmol) in DMSO (3 mL) at room temperature was added K2CO3, 325 mesh (380 mg, 2.75 mmol). The mixture was stirred at room temperature for 15 min, and then chloromethyl bis(2-methyl-2-propanyl) phosphate (356 mg, 1.37 mmol) was added. The resulting mixture was stirred at room temperature for 17 h, after which time H$_2$O (2 mL) was added and the mixture was stirred for a further 21 h at room temperature. The mixture was purified by reverse phase column chromatography (C18, 23 g, 10-50% MeCN in H$_2$O with 0.1% NH$_4$OH) to afford Compound 510 (tert-butyl [3-[2-(dimethylamino)ethyl]-5-methoxy-indol-1-yl]methyl hydrogen phosphate, 195 mg, 74% yield) as a solid. UPLC-MS (2 min, basic): rt=0.75 min, m/z=385.2 [M+H]$^+$; $^1$H NMR (400 MHz, d$_6$-DMSO) δ 7.44-7.14 (m, 3H), 6.83-6.70 (m, 1H), 5.41 (s, 1H), 4.85 (d, J=9.0 Hz, 2H), 3.80 (d, J=5.4 Hz, 3H), 3.50-3.41 (m, 2H), 3.14 (d, J=8.5 Hz, 2H), 3.07 (s, 6H), 1.30 (s, 9H); $^{31}$P NMR (162 MHz, d$_6$-DMSO) δ -5.99 (q, J=8.8 Hz).

Example 1-9: Isobutyl 3-[2-(dimethylamino)ethyl]-6-methoxy-indole-1-carboxylate (Compound 517)

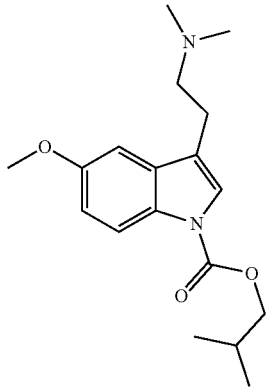 [SMILES: COc1ccc2c(c1)c(CCN(C)C)cn2C(=O)OCC(C)C]

To a stirring solution of 5-OMe-DMT (200 mg, 0.92 mmol) in THF (10 mL) at −78° C. was added NaHMDS, 1M in THF (1.4 mL, 1.4 mmol). The mixture was stirred at −78° C. for 15 min before isobutyl chloroformate (0.24 mL, 1.83 mmol) was added. The mixture was allowed to warm to rt and stirred for 30 min. The mixture was diluted with EtOAc (10 mL), washed with H$_2$O (10 mL), brine (10 mL), dried over Na$_2$SO$_4$, filtered and the filtrate was concentrated under reduced pressure. The crude residue was purified by column chromatography on silica gel (12 g cartridge) eluting with a gradient of EtOAc (50% to 100%; v/v) in hexane (with 1% NEt$_3$) to afford isobutyl 3-[2-(dimethylamino)ethyl]-6-methoxy-indole-1-carboxylate (Compound 517, 56 mg, 19% yield) as an oil. UPLC-MS (4 min, basic): rt=2.17 min, m/z=319.1 [M+H]$^+$; $^1$H NMR (400 MHz, CDCl$_3$) δ 7.96 (s, 1H), 7.34 (s, 1H), 6.92 (d, J=2.5 Hz, 1H), 6.87 (dd, J=9.0, 2.5 Hz, 1H), 4.12 (d, J=6.6 Hz, 2H), 3.80 (s, 3H), 2.81-2.72 (m, 2H), 2.60-2.51 (m, 2H), 2.27 (s, 6H), 2.15-2.00 (m, 1H), 0.98 (d, J=6.7 Hz, 6H).

The following compounds were made by analogous methods to that described for isobutyl 3-[2-(dimethylamino)ethyl]-6-methoxy-indole-1-carboxylate (Compound 517)

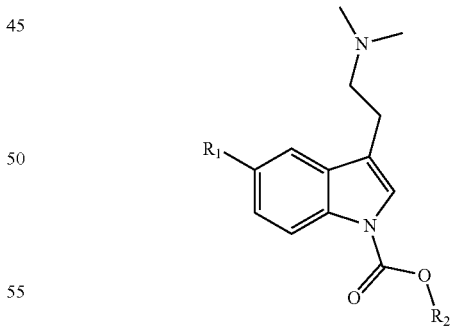

| Cpd | Name | R$_1$ | R$_2$ | UPLC-MS | $^1$H NMR |
|---|---|---|---|---|---|
| 518 | tert-butyl 3-[2-(dimethylamino)ethyl]indole-1-carboxylate | H | $^t$Bu | (4 min, basic): rt = 2.13 min, m/z = 289.1.1 [M + H]$^+$, 96% purity. | $^1$H NMR (400 MHz, CDCl$_3$) δ 8.15-8.08 (m, 1H), 7.53 (ddd, J = 7.7, 1.4, 0.8 Hz, 1H), 7.40 (s, 1H), 7.31 (ddd, J = 8.3, 7.2, 1.4 Hz, 1H), 7.23 (ddd, J = 8.2, 7.3, 1.1 |

| Cpd | Name | R₁ | R₂ | UPLC-MS | ¹H NMR |
|---|---|---|---|---|---|
| | | | | | Hz, 1H), 2.91-2.82 (m, 2H), 2.68-2.59 (m, 2H), 2.33 (s, 6H), 1.67 (s, 9H). |
| 519 | isopropyl 3-[2-(dimethylamino)ethyl]indole-1-carboxylate | H | ⁱPr | (4 min, basic): rt = 1.90 min, m/z = 275.1 [M + H]⁺, 97% purity. | ¹H NMR (400 MHz, CDCl₃) δ 8.15 (d, J = 8.2 Hz, 1H), 7.54 (ddd, J = 7.7, 1.4, 0.8 Hz, 1H), 7.47-7.36 (m, 1H), 7.32 (ddd, J = 8.4, 7.2, 1.3 Hz, 1H), 7.25 (td, J = 7.5, 1.1 Hz, 1H), 5.26 (hept, J = 6.3 Hz, 1H), 2.92-2.83 (m, 2H), 2.68-2.60 (m, 2H), 2.34 (s, 6H), 1.45 (d, J = 6.3 Hz, 6H). |
| 520 | propyl 3-[2-(dimethylamino)ethyl]indole-1-carboxylate | H | Pr | (4 min, basic): rt = 2.02 min, m/z = 275.1 [M + H]⁺, 96% purity. | ¹H NMR (400 MHz, CDCl₃) δ 8.15 (d, J = 8.0 Hz, 1H), 7.58-7.49 (m, 1H), 7.43 (s, 1H), 7.33 (ddd, J = 8.4, 7.2, 1.4 Hz, 1H), 7.25 (td, J = 7.5, 1.1 Hz, 1H), 4.38 (t, J = 6.7 Hz, 2H), 2.92-2.83 (m, 2H), 2.68-2.60 (m, 2H), 2.34 (s, 6H), 1.86 (h, J = 7.2 Hz, 2H), 1.07 (t, J = 7.4 Hz, 3H). |
| 521 | tert-butyl 3-[2-(dimethylamino)ethyl]-5-methoxy-indole-1-carboxylate | OMe | ᵗBu | (4 min, basic): rt = 2.10 min, m/z = 305.1 [M + H]⁺, 100% purity. | ¹H NMR (400 MHz, CDCl₃) δ 7.98 (s, 1H), 7.37 (s, 1H), 6.98 (d, J = 2.5 Hz, 1H), 6.91 (dd, J = 9.0, 2.5 Hz, 1H), 3.86 (s, 3H), 2.87-2.78 (m, 2H), 2.66-2.58 (m, 2H), 2.33 (s, 6H), 1.65 (s, 9H). |
| 522 | isopropyl 3-[2-(dimethylamino)ethyl]-5-methoxy-indole-1-carboxylate | OMe | ⁱPr | (4 min, basic): rt = 1.85 min, m/z = 305.1 [M + H]⁺, 100% purity. | ¹H NMR (400 MHz, CDCl₃) δ 8.02 (s, 1H), 7.40 (s, 1H), 6.99 (d, J = 2.5 Hz, 1H), 6.93 (dd, J = 8.9, 2.5 Hz, 1H), 5.23 (hept, J = 6.2 Hz, 1H), 3.87 (s, 3H), 2.88-2.79 (m, 2H), 2.67-2.58 (m, 2H), 2.34 (s, 6H), 1.44 (d, J = 6.2 Hz, 6H). |
| 523 | propyl 3-[2-(dimethylammo)ethyl]-5-methoxy-indole-1-carboxylate | OMe | n-Pr | (4 min, basic): rt = 2.00 min, m/z = 305.1 [M + H]⁺, 100% purity | ¹H NMR (400 MHz, CDCl₃) δ 8.02 (s, 1H), 7.41 (s, 1H), 6.99 (d, J = 2.5 Hz, 1H), 6.93 (dd, J = 8.9, 2.5 Hz, 1H), 4.36 (t, J = 6.7 Hz, 2H), 3.87 (s, 3H), 2.88-2.79 (m, 2H), 2.67-2.58 (m, 2H), 2.33 (s, 6H), 1.85 (h, J = 7.2 Hz, 2H), 1.06 (t, J = 7.4 Hz, 3H). |
| 524 | isobutyl 3-[2-(dimethylamino)ethyl]indole-1-carboxylate[a] | H | ⁱBu | (4 min, basic): rt = 2.19 min, m/z = 289.1.1 [M + H]⁺, 96% purity | ¹H NMR (400 MHz, CDCl₃) δ 8.06-8.00 (m, 1H), 7.46-7.39 (m, 1H), 7.36-7.28 (m, 1H), 7.21 (ddd, J = 8.3, 7.2, 1.4 Hz, 1H), 7.17-7.09 (m, 1H), 7.14 (s, 1H), 4.09 (d, J = 6.6 Hz, 2H), 2.80-2.71 (m, 2H), 2.56-2.48 (m, 2H), 2.22 (s, 6H), 2.02 (dh, J = 13.4, 6.7 Hz, 1H), 0.94 (d, J = 6.7 Hz, 6H). |

[a]Following chromatography, further purification was performed using reverse phase chromatography: C18 (23 g cartridge) eluting with a gradient of MeCN (0.1% NEt₃/formic acid) (5% to 98%; v/v) in water (0.1% NEt₃/formic acid)

Example 1-10: 1-[3-[2-(dimethylamino)ethyl]indol-1-yl]ethenone (Compound 119)

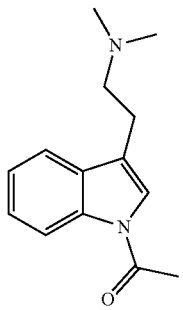 [SMILES: CC(=O)n1cc(CCN(C)C)c2ccccc21]

To a stirring solution of DMT (378 mg, 2.0 mmol) in THF (10 mL) at −78° C. was added NaHMDS, 1M solution in THF (3.0 mL, 3.0 mmol). The mixture was stirred at −78° C. for 15 min then AcCl (0.29 mL, 4.0 mmol) was added. The mixture allowed to warm up to rt and stirred overnight, then diluted with EtOAc (10 ml), washed with $H_2O$ (10 mL), brine (10 mL), dried over $Na_2SO_4$, filtered and the filtrate was concentrated under reduced pressure. The residue was purified by column chromatography on silica gel (4 g cartridge) eluting with a gradient of MeOH in DCM (0-10%) to afford 1-[3-[2-(dimethylamino)ethyl]indol-1-yl]ethanone (Compound 119, 52 mg, 11% yield) as an oil. UPLC-MS analysis (4 min, basic): rt=1.51 min, m/z=231.1 [M+H]$^+$; $^1$H NMR (400 MHz, CDCl$_3$) δ 8.34 (d, J=8.0 Hz, 1H), 7.51-7.41 (m, 11H), 7.28 (ddd, J=8.3, 7.2, 1.4 Hz, 1H), 7.21 (td, J=7.5, 1.1 Hz, 1H), 7.19 (s, 1H), 2.85-2.76 (m, 2H), 2.58 (dd, J=8.9, 6.8 Hz, 2H), 2.54 (s, 3H), 2.27 (s, 6H).

The following compounds were made by analogous methods to that described for isobutyl-[3-[2-(dimethylamino)ethyl]indol-1-yl]ethanone (Compound 119)

| Cpd | Name | R$_1$ | R$_2$ | UPLC-MS | 1H NMR |
|-----|------|-------|-------|---------|--------|
| 122 | [3-[2-(dimethylamino)ethyl]indol-1-yl]-phenyl-methanone | H | Ph | (4 min, basic): rt = 2.01 min, m/z = 293.1 [M + H]$^+$, 100% purity. | $^1$H NMR (400 MHz, CDCl$_3$) δ: 8.36 (d, J = 8.1 Hz, 1H), 7.75-7.70 (m, 2H), 7.63-7.49 (m, 4H), 7.41-7.30 (m, 2H), 7.13 (d, J = 1.3 Hz, 1H), 2.86 (dd, J = 9.3, 6.5 Hz, 2H), 2.66-2.57 (m, 2H), 2.32 (s, 6H). |
| 120 | 1-[3-[2-(dimethylamino)ethyl]indol-1-yl]propan-1-one | H | Et | (4 min, basic): rt = 1.77 min, m/z = 245.1 [M + H]$^+$, 100% purity. | $^1$H NMR (400 MHZ, DMSO-d$_6$) δ 8.35 (d, J = 8.0 Hz, 1H), 7.70 (d, J = 1.2 Hz, 1H), 7.61 (dd, J = 7.3, 1.4 Hz, 1H), 7.36-7.22 (m, 2H), 3.02 (q, J = 7.3 Hz, 2H), 2.86-2.76 (m, 2H), 2.58 (dd, J = 8.6, 6.8 Hz, 2H), 2.23 (s, 6H), 1.18 (t, J = 7.3 Hz, 3H). |
| 108 | 1-[3-[2-(dimethylamino)ethyl]-5-methoxy-indol-1-yl]propan-1-one | OMe | Et | (4 min, basic): rt = 1.66 min, m/z = 275.1 [M + H]$^+$, 100% purity. | |
| 110 | [3-[2-(dimethylamino)ethyl]-5-methoxy-indol-1-yl]-phenyl-methanone | OMe | Ph | (4 min, basic): rt = 1.93 min, m/z = 323.2 [M + H]$^+$, 100% purity. | $^1$H NMR (400 MHz, CDCl$_3$) δ 8.26 (d, J = 9.0 Hz, 1H), 7.73-7.67 (m, 2H), 7.62 (t, J = 7.4 Hz, 1H), 7.54 (dd, J = 8.2, 6.7 Hz, 2H), 7.18 (d, J = 2.4 Hz, 1H), 7.15 (s, 1H), 7.01 (dd, J = 9.0, 2.5 Hz, 1H), 3.93 (s, 3H), 3.23 (s, 2H), 3.11 (s, 2H), 2.76 (s, 6H). |
| 107 | 1-[3-[2-(dimethylamino)ethyl]-5-methoxy-indol-1-yl]ethanone | OMe | Me | (4 min, basic): rt = 1.48 min, m/z = 261.2 [M + H]$^+$, 96% purity. | $^1$H NMR (400 MHz, CDCl$_3$) δ 8.27 (d, J = 9.0 Hz, 1H), 7.18-7.08 (m, 1H), 6.95-6.86 (m, 2H), 3.80 (s, 3H), 2.80 (q, J = 7.2 Hz, 2H), 2.61 (dd, J = 8.9, 6.7 Hz, 2H), 2.52 (s, 2H), 2.31 (d, J = 2.6 Hz, 6H). |

Example 1-11: 3-[2-(dimethylamino)ethyl]-N,N-dimethyl-indole-1-carboxamide (Compound 525)

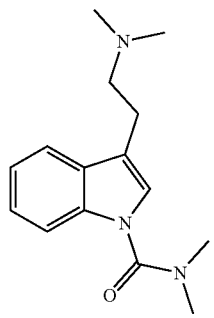

To a stirring solution of DMT (145 mg, 0.77 mmol) in THF (10 mL) at −78° C. was added NaHMDS, 1M solution in THF (1.2 mL, 1.2 mmol). The mixture was stirred at −78° C. for 15 min, then dimethyl carbamoyl chloride (166 mg, 1.54 mmol) was added. The mixture was allowed to warm to rt and stirred overnight, then diluted with EtOAc (10 mL), washed with H$_2$O (3×10 mL), dried over Na$_2$SO$_4$, filtered and the filtrate was concentrated under reduced pressure. The residue was purified by column chromatography on silica gel (4 g cartridge) eluting with a gradient of MeOH (0% to 10%; v/v) in DCM to afford 3-[2-(dimethylamino)ethyl]-N,N-dimethyl-indole-1-carboxamide (Compound 525, 59 mg, 30% yield) as an oil. UPLC-MS analysis (4 min, basic): rt=1.85 min, m/z=305.1 [M+H]$^+$; $^1$H NMR (400 MHz, CDCl$_3$) δ 7.61 (t, J=7.6 Hz, 2H), 7.32 (t, J=7.7 Hz, 1H), 7.28 (s, 1H), 7.26-7.21 (m, 1H), 3.34 (dd, J=10.3, 5.8 Hz, 2H), 3.22 (dd, J=10.2, 5.9 Hz, 2H), 3.09 (s, 6H), 2.81 (s, 6H).

A repeat experiment was additionally purified by reversed-phase chromatography, eluting with 0 to 100% acetonitrile in 0.1% formic acid. The pooled fractions were concentrated and lyophilised to give 3-(2-(dimethylamino)ethyl)-N,N-dimethyl-1H-indole-1-carboxamide formate (94 mg) as an oil. LC-MS (+ve mode): m/z=260.15 [M+H]$^+$; $^1$H NMR (300 MHz, CDCl$_3$) δ 8.43 (s, 1H, HCO), 7.53 (m, 2H, 2×ArH), 7.20 (m, 3H, 3×ArH), 3.11 (m, 4H, 2×CH$_2$), 3.02 (s, 6H, 2× NMe), 2.67 (s, 6H, 2× NMe); $^{13}$C NMR (75.5 MHz, CDCl$_3$) δ 167.7, 154.9, 135.8, 128.5, 142.1, 121.9, 118.7, 114.2, 113.8, 57.6, 43.0, 38.5, 21.0.

Example 1-12: 3-(2-(dimethylamino)ethyl)-5-methoxy-N,N-dimethyl-1H-indole-1-carboxamide formate (Compound 526)

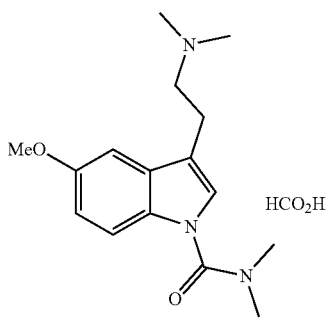 [SMILES: COc1ccc2c(c1)c(CCN(C)C)cn2C(=O)N(C)C ; "HCO2H"]

To a solution of 5-OMe-DMT (115 mg, 0.53 mmol) in THF (8 mL) at −78° C. under an atmosphere of N$_2$ was added NaHMDS, 1M in THF (1.06 mL, 1.06 mmol) and the mixture was stirred for 30 min at −78° C., then dimethylcarbamyl chloride (110 mg, 97 µL, 1.06 mmol) was added. The mixture was stirred at −78° C. for 20 min, then warmed to rt and stirred overnight. H$_2$O (1 mL) was added and the mixture was concentrated under reduced pressure. The residue was purified by column chromatography on silica gel, eluting with 0 to 50% MeOH in EtOAc (containing 0.1% Et$_3$N), then purified further by reverse-phase HPLC, eluting with 0 to 100% acetonitrile in 0.1% formic acid to give 3-(2-(dimethylamino)ethyl)-5-methoxy-N,N-dimethyl-1H-indole-1-carboxamide formate (Compound 526, 118 mg, 66%) as an oil. LC-MS (+ve mode): m/z=290.15 [M+H]$^+$; $^1$H NMR (300 MHz, CDCl$_3$) δ 8.43 (s, 1H, formate), 7.51 (d, J=9.0 Hz, 1H, ArH), 7.12 (s, 1H, ArH), 7.06 (d, J=2.4 Hz, 1H, ArH), 6.87 (dd, J=9.0, 2.5 Hz, 1H, ArH), 3.82 (s, 3H, OMe), 3.13 (s, 4H, 2×CH$_2$), 3.07 (s, 6H, 2×NMe), 2.66 (s, 6H, 2× NMe); $^{13}$C NMR (75.5 MHz, CDCl$_3$) δ 167.7, 155.5, 155.0, 130.7, 129.3, 124.6, 114.6, 114.0, 113.3, 101.2, 57.4, 56.0, 43.0, 38.5, 21.1.

Example 1-13: [1,4'-Bipiperidin]-1'-yl(3-(2-(dimethylamino)ethyl)-1H-indol-1-yl)methanone di-formate (di-formate salt of Compound 88)

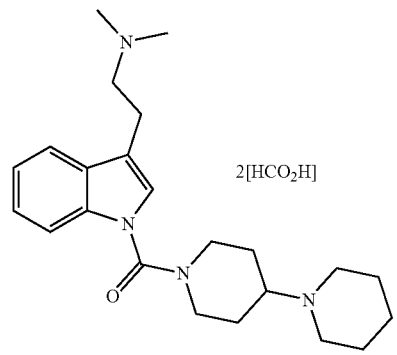 [SMILES: CN(C)CCc1cn(C(=O)N2CCC(N3CCCCC3)CC2)c2ccccc12]

To a solution of DMT (146 mg, 0.78 mmol) in THF (10 mL) at −78° C. under an atmosphere of N$_2$ was added NaHMDS, 1M in THF (3.1 mL, 3.1 mmol) and the mixture was stirred for 30 min at −78° C. 1-Chlorocarbonyl-4-piperidinopiperidine hydrochloride (414 mg, 1.55 mmol) was added, and the mixture was stirred at −78° C. for 20 min then warmed to rt and stirred overnight. H$_2$O (2 mL) was added and the mixture was concentrated under reduced pressure. The residue was purified by reverse-phase chromatography, eluting with 0 to 100% acetonitrile in 0.1% formic acid to give [1,4'-bipiperidin]-1'-yl(3-(2-(dimethylamino)ethyl)-1H-indol-1-yl)methanone di-formate (di-formate salt of Compound 88, 255 mg, 69%) as a semi-solid. LC-MS (+ve mode): m/z=383.25 [M+H]$^+$; $^1$H NMR (300 MHz, DMSO-d$_6$) δ 8.26 (s, 2H, 2×formate), 7.62 (m, 2H, 2×ArH), 7.38 (s, 1H, ArH), 7.27 (m, 1H, ArH), 7.17 (m, 1H, ArH), 3.94 (m, 2H, CH$_2$), 3.60 (m, 1H, CH), 3.06 (t, J=12.5 Hz, 2H, CH$_2$), 2.89 (m, 2H, CH$_2$), 2.76 (m, 2H, CH$_2$), 2.61 (m, 6H, 3×CH$_2$), 2.38 (s, 6H, 2×NMe), 1.54 (br, 6H, 3×CH$_2$), 1.42 (br, 4H, 2×CH$_2$); $^{13}$C NMR (75.5 MHz, DMSO-d$_6$) δ 164.6, 153.5, 135.8, 129.4, 124.7, 123.8, 121.7, 119.5, 116.5, 113.7, 61.9, 58.6, 50.0, 46.0, 44.7, 27.8, 26.0, 24.5, 22.2.

Example 1-14: [1,4'-bipiperidin]-1'-yl(3-(2-(dimethylamino)ethyl)-5-methoxy-1H-indol-1-yl)methanone di-formate (di-formate salt of Compound 96)

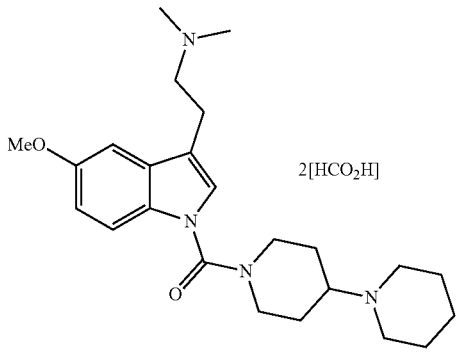 [SMILES: COc1ccc2c(c1)c(CCN(C)C)cn2C(=O)N1CCC(N2CCCCC2)CC1]

To a mixture of 5-methoxy-N,N-dimethyltryptamine (169 mg, 0.78 mmol) in THF (10 mL) at −78° C. under an atmosphere of N₂ was added NaHMDS, 1M in THF (3.1 mL, 3.1 mmol) and the mixture was stirred for 30 min at −78° C. 1-Chlorocarbonyl-4-piperidinopiperidine HCl (414 mg, 1.55 mmol) was added, the mixture was stirred at −78° C. for 20 min, then warmed to rt and stirred overnight. H₂O (2 mL) was added and the mixture was concentrated under reduced pressure. The residue was purified by reversed-phase chromatography, eluting with 0 to 100% acetonitrile in 0.1% formic acid to give [1,4'-bipiperidin]-1'-yl(3-(2-(dimethylamino)ethyl)-5-methoxy-1H-indol-1-yl)methanone di-formate (di-formate salt of Compound 96, 311 mg, 62%) as a semi-solid. LC-MS (+ve mode): m/z=413.30 [M+H]⁺; ¹H NMR (300 MHz, DMSO-d₆) δ 8.25 (s, 2H, 2×formate), 7.51 (d, J=8.9 Hz, 1H, ArH), 7.33 (s, 1H, ArH), 7.10 (d, J=2.5 Hz, 1H, ArH), 6.88 (dd, J=8.9, 2.5 Hz, 1H, ArH), 3.92 (m, 2H, CH₂), 3.80 (s, 3H, OMe), 3.02 (t, J=12.5 Hz, 2H, CH₂), 2.87 (m, 2H, CH₂), 2.78 (m, 2H, CH₂), 2.63 (m, 4H, 2×CH₂), 2.40 (s, 6H, 2×NMe), 1.82 (d, J=12.6 Hz, 2H, CH₂), 1.47 (m, 8H, 4×CH₂); ¹³C NMR (75.5 MHz, DMSO-d₆) δ 164.6, 155.2, 153.7, 130.6, 130.1, 125.2, 116.3, 114.6, 113.0, 102.0, 61.9, 58.3, 55.9, 50.0, 46.0, 44.5, 27.8, 25.9, 25.0, 22.1.

Example 1-15: 2-(4-(3-(2-(dimethylamino)ethyl)-1H-indol-1-yl)-2-methyl-4-oxobutan-2-yl)-3,5-dimethylphenyl acetate (Compound 413)

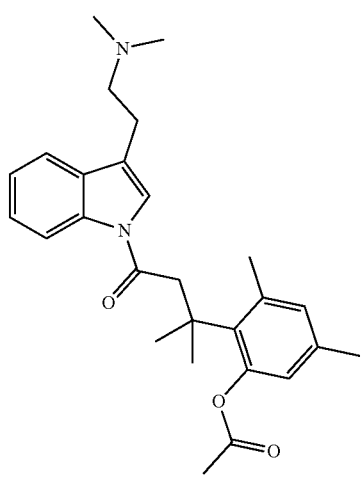 [SMILES: CC(=O)Oc1cc(C)cc(C)c1C(C)(C)CC(=O)n1cc(CCN(C)C)c2ccccc21]

Step 1: 2-(4-Chloro-2-methyl-4-oxobutan-2-yl)-3,5-dimethylphenyl acetate

To a mixture of 3-(2-acetoxy-4,6-dimethylphenyl)-3-methylbutyric acid (0.56 g, 2.12 mmol) in DCM (2.1 mL) at 0° C. under an atmosphere of N₂ was added oxalyl chloride (268 mg, 0.18 mL, 2.12 mmol). The mixture was warmed to rt and stirred for 2 h 45 min, then concentrated under reduced pressure to give 2-(4-chloro-2-methyl-4-oxobutan-2-yl)-3,5-dimethylphenyl acetate as an oil, which was used directly in the next step.

Step 2: 2-(4-(3-(2-(dimethylamino)ethyl)-1H-indol-1-yl)-2-methyl-4-oxobutan-2-yl)-3,5-dimethylphenyl acetate To a solution of DMT (100 mg, 0.53 mmol) in THF (10 mL) at −78° C. under an atmosphere of N₂ was added NaHMDS, 1M in THF (1.06 mL, 1.06 mmol) and the mixture was stirred for 30 min at −78° C. 2-(4-Chloro-2-methyl-4-oxobutan-2-yl)-3,5-dimethylphenyl acetate solution, 1M in THF (1.06 mL, 1.06 mmol) was added and the mixture was stirred at −78° C. for 20 min, then warmed to rt and stirred overnight. H₂O (2 mL) was added and the mixture was concentrated under reduced pressure. The residue was purified by reversed-phase HPLC, eluting with 0 to 100% acetonitrile in 0.1% formic acid to give the product (56 mg). A further batch was prepared on the same scale to afford 79 mg of material.

The combined materials from batches 1 and 2 (135 mg) were purified by column 1) chromatography on silica gel (MeOH/EtOAc (containing 0.1% triethylamine), 0:1 to 1) to afford 2-(4-(3-(2-(dimethylamino)ethyl)-1H-indol-1-yl)-2-methyl-4-oxobutan-2-yl)-3,5-dimethylphenyl acetate (Compound 413, 67 mg, 15% based on the two batches) as an oil. LC-MS (+ve mode): m/z=435.25 [M+H]⁺; ¹H NMR (300 MHz, CDCl₃) δ 8.41 (d, J=7.8 Hz, 1H, ArH), 7.50 (m, 1H, ArH), 7.28 (m, 3H, 3×ArH), 6.83 (d, J=2.1 Hz, 1H, ArH), 6.55 (d, J=2.0 Hz, 1H, ArH), 3.41 (s, 2H, CH₂), 2.91 (m, 2H, CH₂), 2.69 (m, 2H, CH₂), 2.55 (s, 3H, COMe), 2.41 (s, 6H, 2×NMe), 2.24 (s, 3H, ArMe), 2.19 (s, 3H, ArMe), 1.67 (s, 6H, 2×CMe); ¹³C NMR (75.5 MHz, CDCl₃) δ 170.0, 169.3, 149.2, 138.0, 136.3, 136.0, 133.9, 132.7, 130.3, 125.1, 123.3, 123.1, 122.0, 119.6, 118.6, 117.0, 60.4, 58.9, 45.1, 39.2, 31.6, 25.6, 23.0, 21.8, 20.3, 17.7.

Example 1-16: 2-(4-(3-(2-(dimethylamino)ethyl)-5-methoxy-1H-indol-1-yl)-2-methyl-4-oxobutan-2-yl)-3,5-dimethylphenyl (Compound 405)

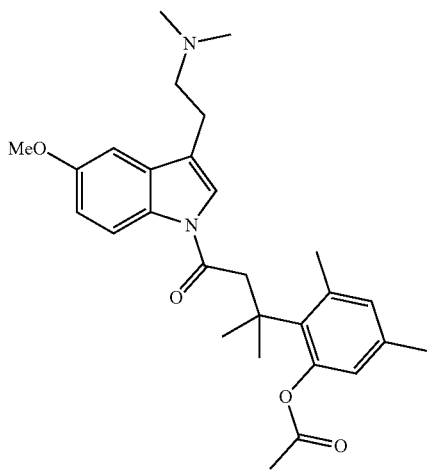 [SMILES: COc1ccc2c(c1)c(CCN(C)C)cn2C(=O)CC(C)(C)c1c(C)cc(C)cc1OC(C)=O]

Compound 405 was prepared using the procedure similar to that in Example 1-15 for Compound 413, afforded as a semi-solid (71 mg, 14% yield). LC-MS (+ve mode): m/z=465.25 [M+H]$^+$; $^1$H NMR (300 MHz, CDCl$_3$) δ 8.21 (d, J=9.0 Hz, 1H, ArH), 7.19 (s, 1H, ArH), 6.96 (d, J=2.4 Hz, 1H, ArH), 6.90 (dd, J=9.0, 2.4 Hz, 1H, ArH), 6.81 (br. s, 1H, ArH), 6.56 (br. s, 1H, ArH), 3.86 (s, 3H, OMe), 3.37 (s, 2H, CH$_2$), 2.86 (m, 2H, CH$_2$), 2.66 (m, 2H, CH$_2$), 2.53 (s, 3H, COMe), 2.40 (s, 6H, 2×NMe), 2.22 (s, 3H, ArMe), 2.20 (s, 3H, ArMe), 1.67 (s, 6H, 2×CMe); $^{13}$C NMR (75.5 MHz, CDCl$_3$) δ 170.0, 169.0, 156.3, 149.3, 138.0, 136.3, 133.9, 132.7, 130.7, 123.1, 122.6, 113.0, 101.8, 58.8, 55.8, 45.1, 39.2, 31.6, 25.6, 21.8, 20.3.

Example 1-17: 2-Methoxyethyl 3-(2-(dimethylamino)ethyl)-1H-indole-1-carboxylate Formate (Compound 25)

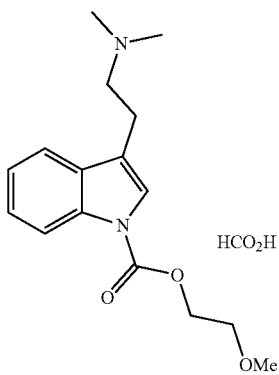 [SMILES: COCCOC(=O)n1cc(CCN(C)C)c2ccccc21 ; "HCO2H"]

To a solution of DMT (100 mg, 0.53 mmol) in THF (8 mL) at −78° C. under an atmosphere of N$_2$ was added NaHMDS, 1M in THF (1.06 mL, 1.06 mmol) and the mixture was stirred for 30 min at −78° C. 2-Methoxyethyl chloroformate (147 mg, 123 µL, 1.06 mmol) was added, the mixture was stirred at −78° C. for 20 min, then allowed to warm to rt and stirred for 2 h. H$_2$O (2 mL) was added and the mixture was concentrated under reduced pressure. The residue was purified by reversed-phase HPLC, eluting with 0 to 100% acetonitrile in 0.1% formic acid to give the product (45 mg). A further batch was prepared on the same scale to afford 40 mg of material.

The materials from batches 1 and 2 (85 mg) were combined to afford 2-methoxyethyl 3-(2-(dimethylamino)ethyl)-1H-indole-1-carboxylate formate (Compound 25, 81 mg, 23%) as an oil. LC-MS (+ve mode): m/z=291.15 [M+H]$^+$; $^1$H NMR (300 MHz CDCl$_3$) δ 8.49 (s, 1H, HCO), 8.18 (d, J=8.1 Hz, 1H, ArH), 7.57 (m, 1H, ArH), 7.49 (s, 1H, ArH), 7.35 (m, 1H, ArH), 7.30 (m, 1H, ArH), 4.56 (m, 2H, CH$_2$), 3.76 (m, 2H, CH$_2$), 3.42 (s, 3H, OMe), 3.09 (m, 4H, 2×CH$_2$), 2.68 (s, 6H, 2×NMe); $^{13}$C NMR (75.5 MHz, CDCl$_3$) δ 167.7, 129.8, 125.1, 123.1, 122.9, 118.8, 117.1, 115.5, 70.3, 65.9, 59.1, 57.4, 43.2, 21.2.

Example 1-18: 2-Methoxyethyl 3-(2-(dimethylamino)ethyl)-5-methoxy-1H-indole-1-carboxylate formate (Compound 22)

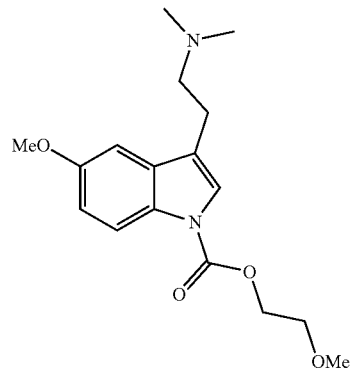 [SMILES: COCCOC(=O)n1cc(CCN(C)C)c2cc(OC)ccc21]

Compound 22 was prepared using the procedure similar to that in Example 1-17 for Compound 25. The materials from batches 1 and 2 (127 mg) were combined and the resultant material was purified by column chromatography on silica gel (MeOH/EtOAc (containing 0.1% triethylamine), 0:1 to 1:1) to afford 2-methoxyethyl 3-(2-(dimethylamino)ethyl)-5-methoxy-1H-indole-1-carboxylate (Compound 22, 51 mg, 15%) as a semi-solid. LC-MS (+ve mode): m/z=321.10 [M+H]$^+$; $^1$H NMR (300 MHz, CDCl$_3$) δ 8.04 (d, J=9.0 Hz, 1H, ArH), 7.42 (s, 1H, ArH), 7.00 (d, J=2.4 Hz, 1H, ArH), 6.94 (dd, J=9.0, 2.5 Hz, 1H, ArH), 4.54 (m, 2H, CH$_2$), 3.87 (s, 3H, ArOMe), 3.75 (m, 2H, CH$_2$), 3.44 (s, 3H, OMe), 2.87 (m, 2H, CH$_2$), 2.67 (m, 2H, CH$_2$), 2.38 (s, 6H, 2×NMe); $^{13}$C NMR (75.5 MHz, CDCl$_3$) δ 158.7, 156.1, 131.5, 123.0, 123.0, 119.3, 116.1, 113.0, 102.0, 70.4, 65.7, 59.0, 59.0, 55.8, 45.3, 23.3.

Example 1-19: 4-(3-(2-(dimethylamino)ethyl)-1H-indol-1-yl)-4-oxobutanoic acid formate salt (Compound 529)

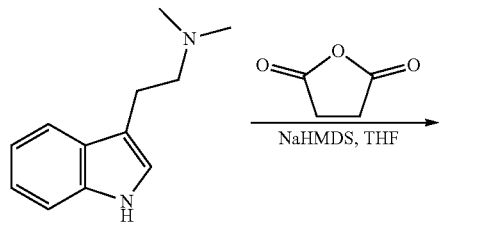

NaHMDS, 1M in THF (1.06 mL, 0.56 mmol) was added to a mixture of DMT (100 mg, 0.53 mmol) in THF (5 mL) at −78° C. and the mixture was stirred for 30 min. Succinic anhydride (106 mg, 1.06 mmol) was added and the resulting mixture was stirred at −78° C. for 30 min, then allowed to warm to rt and stirred for 16 h. H$_2$O (1 mL) was added and the mixture was concentrated under reduced pressure. The residue was purified using preparative HPLC using H$_2$O (0.1% formic acid) in 30% acetonitrile to afford Compound 529 (50 mg, 32%) as a solid. LC-MS (+ve mode): m/z=289.10 [M+H]$^+$; $^1$H NMR (300 MHz, CD$_3$OD) δ 8.42 (s, 1H, HCO), 8.37 (m, 1H, ArH), 7.62 (m, 1H, ArH), 7.30 (m, 2H, 2×ArH), 3.45 (m, 2H, CH$_2$), 3.15 (m, 2H, CH$_2$), 2.93 (s, 6H, 2×NMe), 2.71 (t, J=6.8 Hz, 2H, CH$_2$); $^{13}$C NMR (75.5 MHz, CD$_3$OD) δ 171.2, 154.0, 129.6, 125.0, 123.3, 123.3, 118.3, 116.3, 116.2, 56.6, 42.2, 30.9, 29.4, 20.1.

Example 1-20: 4-(3-(2-(dimethylamino)ethyl)-5-methoxy-1H-indol-1-yl)-4-oxobutanoic acid (Compound 530)

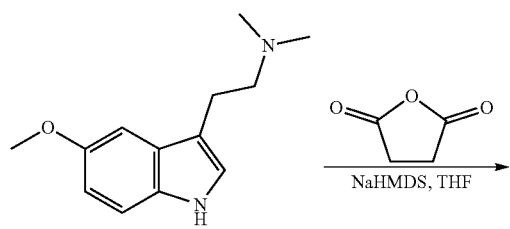

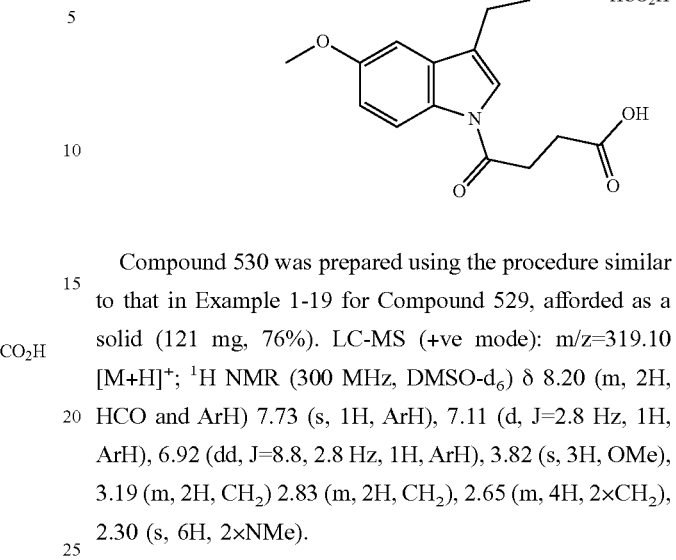

Compound 530 was prepared using the procedure similar to that in Example 1-19 for Compound 529, afforded as a solid (121 mg, 76%). LC-MS (+ve mode): m/z=319.10 [M+H]$^+$; $^1$H NMR (300 MHz, DMSO-d$_6$) δ 8.20 (m, 2H, HCO and ArH) 7.73 (s, 1H, ArH), 7.11 (d, J=2.8 Hz, 1H, ArH), 6.92 (dd, J=8.8, 2.8 Hz, 1H, ArH), 3.82 (s, 3H, OMe), 3.19 (m, 2H, CH$_2$) 2.83 (m, 2H, CH$_2$), 2.65 (m, 4H, 2×CH$_2$), 2.30 (s, 6H, 2×NMe).

Example 1-21: 5-(3-(2-(dimethylamino)ethyl)-1H-indol-1-yl)-5-oxopentanoic acid (Compound 531)

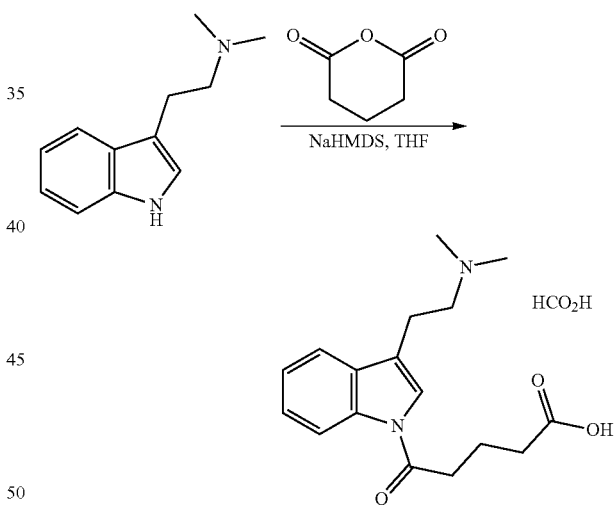

Compound 531 was prepared using the procedure similar to that in Example 1-19 for Compound 529, afforded as an oil (53 mg, 29%). LC-MS (+ve mode): m/z=303.10 [M+H]$^+$; $^1$H NMR (300 MHz, CD$_3$OD) δ 8.43 (dd, J=6.9, 1.4 Hz, 1H ArH), 8.39 (s, 1H, HCO), 7.77 (s, 1H, ArH), 7.66 (dd, J=6.9, 2.0, 1H, ArH), 7.35 (m, 2H, 2×ArH), 3.51 (m, 2H, CH$_2$), 3.22 (m, 2H, CH$_2$), 3.06 (m, 2H, CH$_2$), 2.97 (s, 6H, 2×NMe), 2.47 (m, 2H, CH$_2$), 2.10 (m, 2H, CH$_2$); $^{13}$C NMR (75.5 MHz, CD$_3$OD) δ 176.4, 171.6, 166.6, 136.0, 129.6, 125.1, 123.4, 123.3, 118.2, 116.3, 106.3, 56.6, 42.1, 34.4, 33.1, 20.1, 20.1.

Example 1-22: 5-(3-(2-(dimethylamino)ethyl)-5-methoxy-1H-indol-1-yl)-5-oxopentanoic acid (Compound 532)

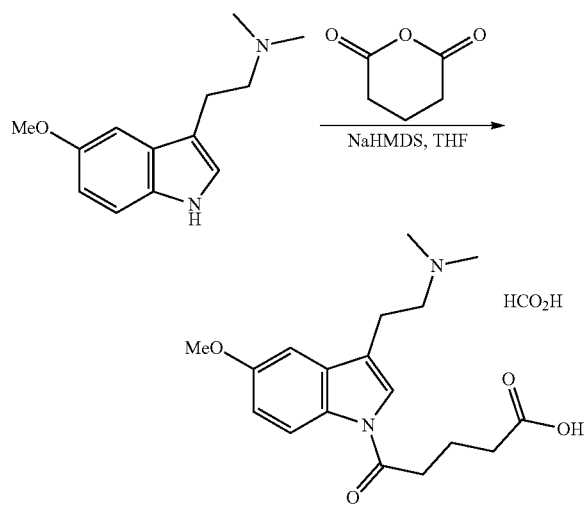

Compound 532 was prepared using the procedure similar to that in Example 1-19 for Compound 529, afforded as an oil (64 mg, 36%). LC-MS (+ve mode): m/z=333.10 [M+H]$^+$; $^1$H NMR (300 MHz, DMSO-d$_6$) δ 8.24 (s, 1H, HCO), 8.20 (br, 1H, ArH), 7.69 (s, 1H, ArH), 7.12 (d, J=2.4 Hz, 1H, ArH), 6.92 (dd, J=9.0, 2.4 Hz, 1H, ArH), 3.80 (s, 3H, OMe), 2.99 (t, J=7.2 Hz, 2H, CH$_2$), 2.83 (m, 2H, CH$_2$), 2.73 (m, 2H, CH$_2$), 2.36 (m, 7H, 2×NMe+CH$_2$), 1.90 (m, 2H, CH$_2$).

Example 1-23: (Pivaloyloxy)methyl 3-(2-(dimethylamino)ethyl)-5-methoxy-1H-indole-1-carboxylate (Compound 369)

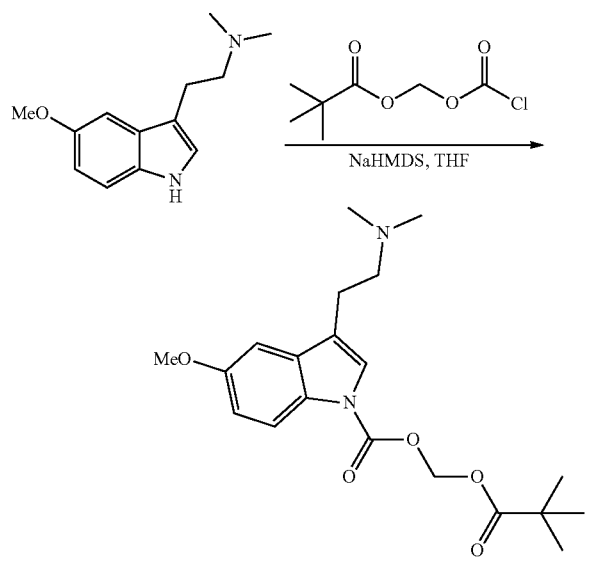

NaHMDS, 1M in THF (1.33 mL, 1.33 mmol) was added to a solution of 5-OMe-DMT (145 mg, 0.67 mmol) in THF (5 mL) at −78° C. and stirred for 30 min. Chlorocarbonyl-oxy-methyl, 2,2 dimethylpropanoate (129 mg, 0.67 mmol) was added and the resulting mixture was stirred at −78° C. for 30 min, then allowed to warm to rt and stirred for 16 h. H$_2$O (1 mL) was added and the mixture was concentrated under reduced pressure. The residue was purified by column chromatography on silica gel eluting (MeOH (0.1% Et$_3$N)/EtOAc (0.1% Et$_3$N), followed by preparative-HPLC using a gradient of H$_2$O in acetonitrile to afford Compound 369 (46 mg, 17%) as a solid. LC-MS (+ve mode): m/z=377.20 [M+H]$^+$; $^1$H NMR (300 MHz, CD$_3$OD) δ 7.87 (br. s, 1H, ArH), 7.33 (s, 1H, ArH), 6.98 (d, J=2.5 Hz, 1H, ArH), 6.84 (dd, J=8.8, 2.5 Hz, 1H, ArH), 5.92 (s, 2H, CH$_2$), 3.75 (s, 3H, OMe), 2.78 (m, 2H, CH$_2$), 2.78 (m, 2H, CH$_2$), 2.26 (s, 6H, 2×NMe), 1.12 (s, 9H, $^t$Bu); $^{13}$C NMR (75.5 MHz, CD$_3$OD) δ 177.0, 131.5, 122.5, 120.0, 115.5, 112.9, 101.7, 80.9, 58.3, 54.7, 43.9, 38.4, 29.4, 25.8, 22.3.

Example 1-24: (Pivaloyloxy)methyl 3-(2-(dimethylamino)ethyl)-1H-indole-1-carboxylate diformate (Compound 337)

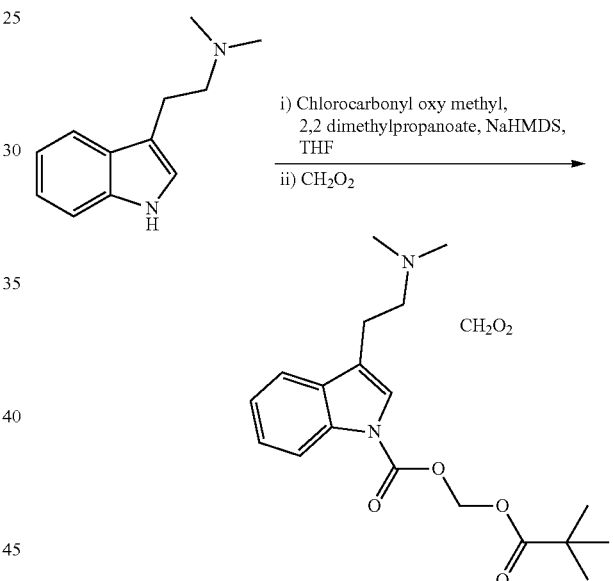

NaHMDS, 1M in THF (5.5 mL, 5.5 mmol) was added to a solution of DMT (0.52 g, 2.75 mmol) in anhydrous THF (40 mL) at −78° C. and stirred for 30 min. Chlorocarbonyl oxy methyl, 2,2 dimethylpropanoate (0.54 g, 2.75 mmol) was added and the mixture was stirred at −78° C. for 30 min, then allowed to warm to rt and stirred for 16 h. The mixture was concentrated to a semi-solid, which was purified using column chromatography on silica gel eluting with a gradient of MeOH (0.1% Et$_3$N) in EtOAc (0.1% Et$_3$N) followed by reversed-phase chromatography using a gradient of H$_2$O (formic acid 0.1%) in acetonitrile to afford Compound 337 (211 mg, 19%) as a solid. LC-MS (+ve mode): m/z=347.15 [M+H]$^+$; $^1$H NMR (300 MHz, CD$_3$OD) δ 8.44 (s, 1H, HCO$_2$H), 8.13 (d, J=7.8 Hz, 1H, ArH), 7.65 (m, 2H, 2×ArH), 7.36 (m, 2H, 2×ArH), 6.05 (s, 2H, CH$_2$), 3.43 (m, 2H, CH$_2$), 3.17 (m, 2H, CH$_2$), 2.92 (s, 6H, 2×NMe), 1.12 (s, 9H, $^t$Bu); $^{13}$C NMR (75 MHz, CD$_3$OD) δ 177.0, 167.7, 135.6, 129.8, 125.0, 123.3, 123.0, 118.7, 116.8, 115.0, 81.0, 56.5, 42.1, 38.4, 25.8, 20.0.

Example 1-25: Methyl 4-(3-(2-(dimethylamino)ethyl)-1H-indol-1-yl)-4-oxobutanoate (Compound 533)

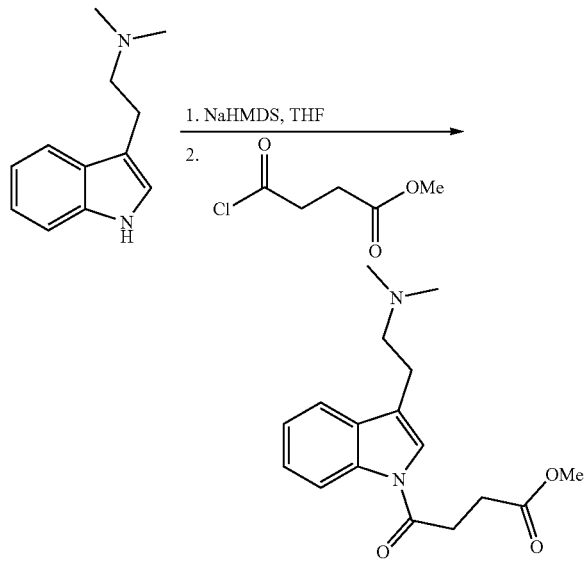

NaHMDS, 1M in THF (1.12 mL, 1.12 mmol) was added to a stirred solution of DMT (200 mg, 1.06 mmol) in THF (5 mL) at −78° C. After 30 min the resulting mixture was added dropwise to O-methyl succinyl chloride [CAS No: 1490-25-1] (163 mg, 1.08 mmol) and the mixture was stirred at rt for 16 h. EtOAc (30 mL) was added and the mixture was washed with saturated aqueous NaHCO$_3$ (50 mL) and brine (50 mL). The organic layer was dried (MgSO$_4$), filtered and the filtrate was concentrated under reduced pressure. The crude residue was purified by column chromatography on silica gel (eluting with a gradient of MeOH in CH$_2$Cl$_2$) to give methyl 4-(3-(2-(dimethylamino)ethyl)-1H-indol-1-yl)-4-oxobutanoate (100 mg, 34%) as a solid. LC-MS (+ve mode): m/z=303.10 [M+H]$^+$; $^1$H NMR (300 MHz, CDCl$_3$) δ 8.41 (d, J=7.8 Hz, 1H, ArH), 7.54 (d, J=7.8 Hz, 1H, ArH), 7.33 (m, 3H, 3×ArH), 3.73 (s, 3H, OMe), 3.25 (t, J=9.3 Hz, 2H, CH$_2$), 2.87 (m, 4H, 2×CH$_2$), 2.65 (m, 2H, CH$_2$), 2.35 (s, 6H, 2×NMe); $^3$C NMR (75.5 MHz, CDCl$_3$) δ 173.0, 169.5, 130.7, 129.2, 125.4, 125.4, 123.6, 121.3, 119.0, 116.8, 59.3, 52.2, 45.6, 30.8, 28.5, 23.6.

Example 1-26: Methyl 4-(3-(2-(dimethylamino)ethyl)-5-methoxy-1H-indol-1-yl)-4-oxobutanoate (Compound 534)

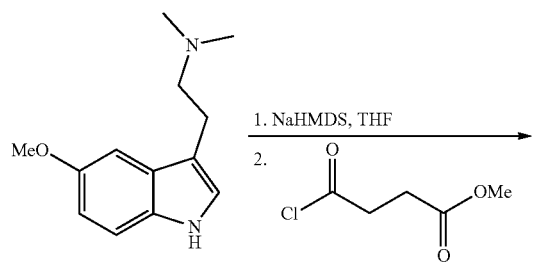

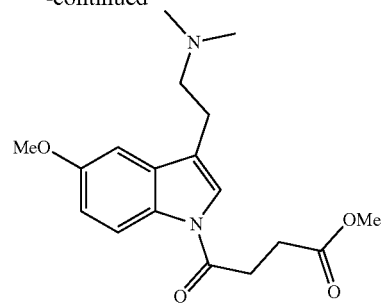

Compound 534 was prepared using the procedure similar to that in Example 1-25 for Compound 533, afforded as an oil (54 mg, 31%). LC-MS (+ve mode): m/z=333.15 [M+H]$^+$; $^1$H NMR (300 MHz, CDCl$_3$) δ 8.28 (d, J=8.7 Hz, 1H, ArH), 7.27 (s, 1H, ArH), 6.93 (m, 2H, 2×ArH), 3.84 (s, 3H, OMe), 3.71 (s, 3H, OMe), 3.19 (t, J=6.9 Hz, 2H, CH$_2$), 2.81 (m, 4H, 2×CH$_2$), 2.62 (m, 2H, CH$_2$), 2.32 (s, 6H, 2×NMe); $^3$C NMR (75.5 MHz, CDCl$_3$) δ 173.0, 169.1, 156.5, 131.7, 130.7, 121.9, 121.1, 117.5, 113.2, 102.1, 59.1, 55.8, 52.1, 45.5, 30.5, 28.5, 23.6.

Example 1-27: (S)-di-tert-butyl (6-(3-(2-(dimethylamino)ethyl)-1H-indol-1-yl)-6-oxohexane-1,5-diyl)dicarbamate (Compound 535)

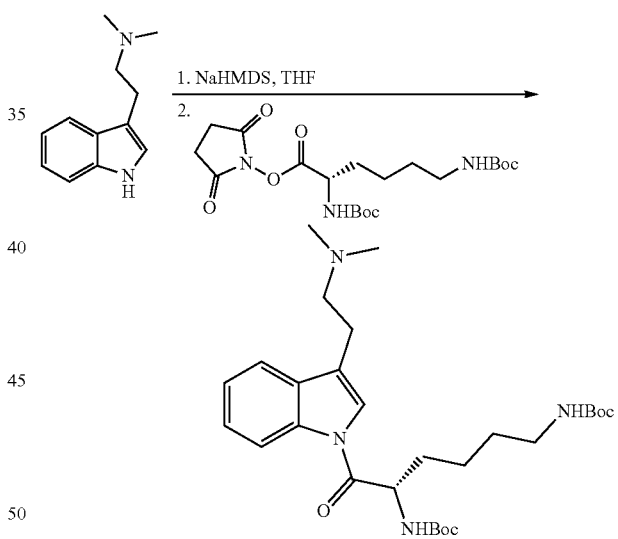

NaHMDS, 1M in THF (1.67 mL, 1.67 mmol) was added to a stirred solution of DMT (300 mg, 1.59 mmol) in THF (5 mL) at −78° C. After 30 min, a solution of Boc-lysine-(Boc)-O-succinimide [CAS No: 30189-36-7] (0.67 g, 1.51 mmol) in THF (5 mL) was added and the mixture was stirred at rt for 16 h. The mixture was concentrated under reduced pressure and the residue was purified by column chromatography on silica gel (eluting with a gradient of MeOH/EtOAc) to give (S)-di-tert-butyl (6-(3-(2-(dimethylamino)ethyl)-1H-indol-1-yl)-6-oxohexane-1,5-diyl)dicarbamate (186 mg, 23%) as a solid. LC-MS (+ve mode): m/z=517.35 [M+H]$^+$; $^1$H NMR (300 MHz, CDCl$_3$) δ 8.44 (d, J=8.1 Hz, 1H, ArH), 7.54 (dd, J=7.5, 1.8 Hz, 1H, ArH), 7.35 (m, 3H, 3×ArH), 5.46 (d, J=9.0 Hz, 1H, NH), 5.05 (m, 1H, CH), 4.62 (br. s, 1H, NH), 3.09 (m, 2H, CH$_2$), 2.90 (t, J=7.5 Hz, 2H, CH$_2$), 2.67 (t, J=7.2 Hz, 2H, CH$_2$), 2.36 (s, 6H, 2×NMe), 1.93 (m, 2H, CH$_2$), 1.75 (m, 2H, CH$_2$), 1.55 (m, 2H, CH$_2$), 1.46 (s, 9H, $^t$Bu), 1.42 (s, 9H, $^t$Bu); $^{13}$C NMR (75.5 MHz, CDCl$_3$) δ 170.8, 156.2, 155.7, 136.2, 131.0, 125.7, 124.1, 122.0, 121.2, 119.1, 117.0, 80.4, 77.4, 59.0, 52.8, 45.5, 40.3, 33.4, 28.6, 28.5, 23.5, 22.6.

Example 1-28: (S)-di-tert-butyl (6-(3-(2-(dimethylamino)ethyl)-5-methoxy-1H-indol-1-yl)-6-oxohexane-1,5-diyl)dicarbamate (Compound 536)

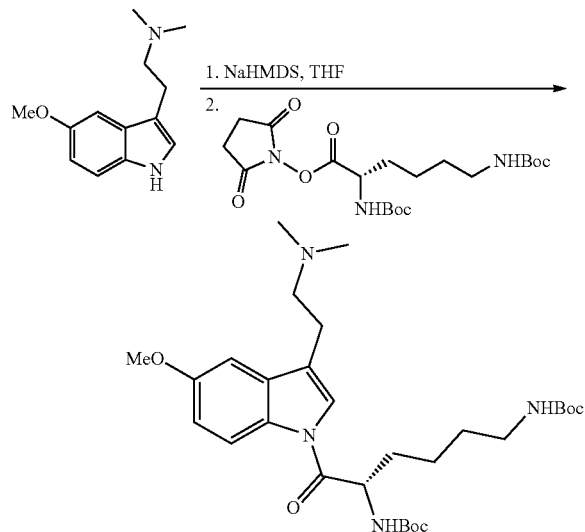

Compound 536 was prepared according to a procedure analogous to that provided in Example 1-27 for Compound 536, and was obtained as a solid (234 mg, 43%). LC-MS (+ve mode): m/z=547.35 [M+H]$^+$; $^1$H NMR (300 MHz, CDCl$_3$) δ 8.32 (d, J=8.7 Hz, 1H, ArH), 7.35 (s, 1H, ArH), 6.97 (m, 2H, 2×ArH), 5.43 (d, J=8.7 Hz, 1H, NH), 5.01 (m, 1H, CH), 4.62 (br. s, 1H, NH), 3.87 (s, 3H, OMe), 3.10 (br. s, 2H, CH$_2$), 2.87 (t, J=7.2 Hz, 2H, CH$_2$), 2.66 (t, J=7.2 Hz, 2H, CH$_2$), 2.37 (s, 6H, 2×NMe, 1.91 (m, 2H, CH$_2$), 1.74 (m, 2H, CH$_2$), 1.50 (m, 2H, CH$_2$), 1.45 (s, 9H, $^t$Bu), 1.42 (s, 9H, $^t$Bu).

Example 1-29: (S)-2,6-diamino-1-(3-(2-(dimethylamino)ethyl)-1H-indol-1-yl)hexan-1-one trihydrochloride (Compound 537)

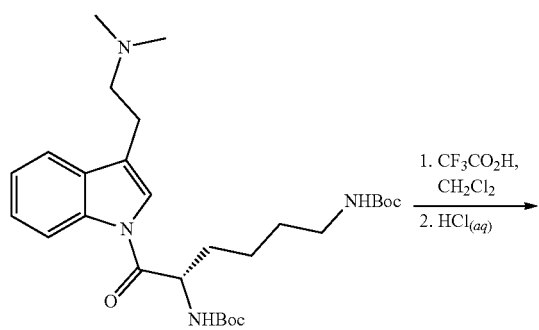

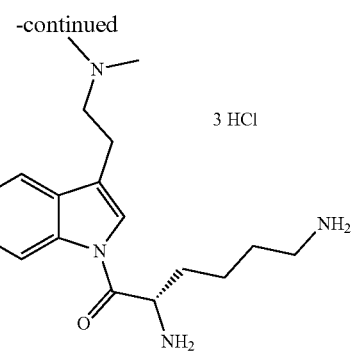

TFA (2.05 g, 1.38 mL, 18 mmol was added to a solution of (S)-di-tert-butyl (6-(3-(2-(dimethylamino)ethyl)-1H-indol-1-yl)-6-oxohexane-1,5-diyl)dicarbamate (Compound 535, 186 mg, 0.36 mmol) in DCM (5 mL) and the mixture was stirred at rt for 1 h. The mixture was concentrated under reduced pressure and the residue was azeotroped with CHCl$_3$ (4×10 mL) and MeOH (10 mL). The residue was dissolved in 1M HCl (2 mL, 2 mmol) and the resulting hydrochloride was purified by reversed-phase chromatography on silica eluting with a gradient of MeCN in 0.02% HCl$_{(aq.)}$ to afford (S)-2,6-diamino-1-(3-(2-(dimethylamino)ethyl)-1H-indol-1-yl)hexan-1-one trihydrochloride (Compound 537, 102 mg, 67%) a solid. ESI MS: m/z=317.20 consistent for protonated parent ion of free-base [M+H]$^+$; 1H NMR (300 MHz, CD$_3$OD) δ 8.42 (dd, J=6.3, 2.4 Hz, 1H, ArH), 7.88 (s, 1H, ArH), 7.70 (dd, J=6.3, 2.1 Hz, 1H, ArH), 7.38 (m, 2H, 2×ArH), 5.04 (m, 1H, CH), 3.56 (m, 2H, CH$_2$), 3.24 (m, 2H, CH$_2$), 2.99 (s, 6H, 2×NMe), 2.90 (t, J=7.5 Hz, 2H, CH$_2$), 2.10 (m, 2H, CH$_2$), 1.70 (m, 2H, CH$_2$), 1.53 (m, 2H, CH$_2$); $^{13}$C NMR (75.5 MHz, CD$_3$OD) δ 169.0, 137.4, 131.3, 127.2, 125.9, 123.9, 120.3, 120.2, 117.8, 57.7, 54.0, 43.6, 40.1, 32.1, 28.1, 22.6, 21.4.

Example 1-30: (S)-2,6-diamino-1-(3-(2-(dimethylamino)ethyl)-5-methoxy-1H-indol-1-yl)hexan-1-one trihydrochloride (Compound 538)

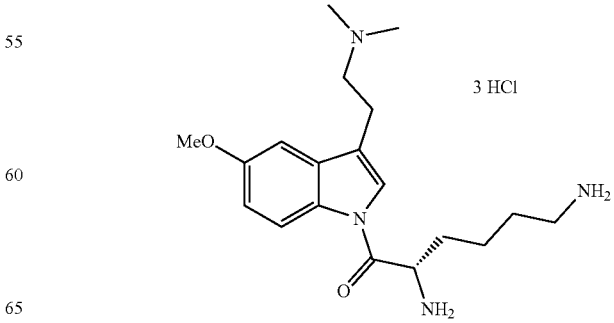

Compound 538 was prepared using the procedure similar to that in Example 1-29 for Compound 537, afforded as a solid (142 mg, 72%). ESI MS: m/z=347.25 consistent for protonated parent ion of free-base [M+H]$^+$; $^1$H NMR (300 MHz, CD$_3$OD) δ 8.32 (d, J=9.0 Hz, 1H, ArH), 7.85 (s, 1H, ArH), 7.20 (d, J=2.7 Hz, 1H, ArH), 7.00 (dd, J=9.3, 2.7 Hz, 1H, ArH), 5.01 (m, 1H, CH), 3.88 (s, 3H, OMe), 3.55 (m, 2H, CH$_2$), 3.22 (m, 2H, CH$_2$), 3.00 (s, 6H, 2×NMe), 2.91 (m, 2H, CH$_2$), 2.09 (m, 2H, CH$_2$), 1.70 (m, 2H, CH$_2$), 1.57 (m, 2H, CH$_2$); $^{13}$C NMR (75.5 MHz, CD$_3$OD) δ 168.4, 159.0, 132.5, 131.7, 124.4, 120.3, 118.6, 115.2, 103.3, 57.7, 56.2, 53.8, 43.6, 40.1, 32.2, 28.2, 22.6, 21.4.

Example 1-31: (S)-tert-butyl (1-(3-(2-(dimethyl-amino)ethyl)-1H-indol-1-yl)-1-oxopropan-2-yl)carbamate (Compound 539)

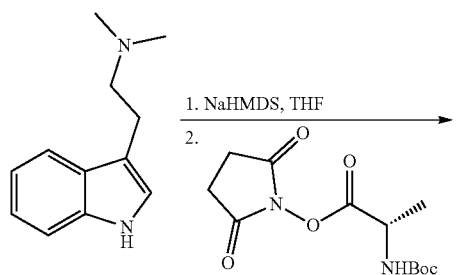

NaHMDS, 1M in THF (1.11 mL, 1.11 mmol) was added to a stirred solution of DMT (200 mg, 1.06 mmol) in anhydrous THF (5 mL) at −78° C. After 30 min, Boc-alanine-O-succinimide (288 mg, 1.01 mmol) was added and the mixture was warmed to rt and stirred for 16 h. The solvent was removed and the residual material was purified by column chromatography on silica gel, first eluting with EtOAc, followed by a gradient of MeOH in EtOAc (0.1% Et$_3$N) to afford Compound 539 (222 mg, 65%) as an oil. TLC: R$_f$=0.16 (EtOAc-MeOH, 1:1 v/v); LC-MS (+ve mode): m/z=360.20 [M+H]$^+$; $^1$H NMR (300 MHz, CDCl$_3$) δ 8.37 (d, J=8.4 Hz, 1H, ArH), 7.47 (m, 1H, ArH), 7.28 (m, 3H, 3×ArH), 5.42 (d, J=6.8 Hz, 1H, NH), 5.00 (m, 1H, CH), 2.80 (m, 2H, CH$_2$), 2.59 (m, 2H, CH$_2$), 2.28 (s, 6H, 2×NMe,) 1.38 (s, 12H, $^t$Bu, CH$_3$).

Example 1-32: (S)-2-amino-1-(3-(2-(dimethyl-amino)ethyl)-1H-indol-1-yl)propan-1-one dihydrochloride (Compound 540)

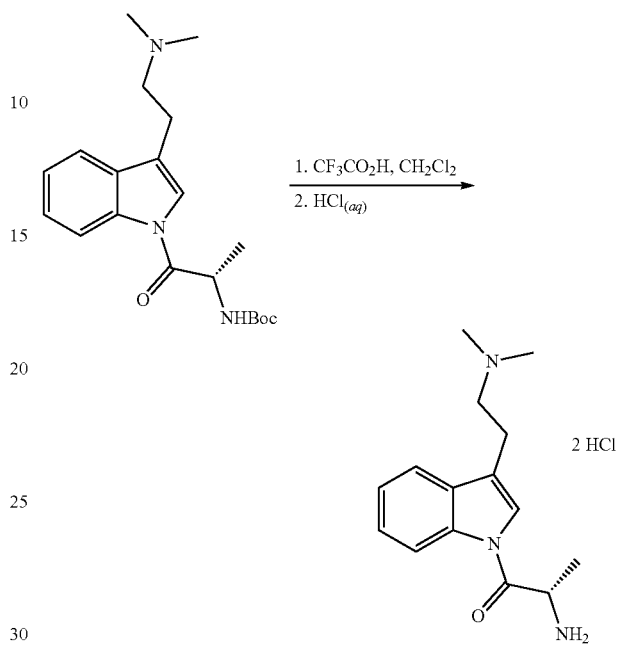

TFA (4.07 g, 2.72 mL, 35.6 mmol) was added to a solution of (S)-tert-butyl (1-(3-(2-(dimethylamino)ethyl)-1H-indol-1-yl)-1-oxopropan-2-yl)carbamate (Compound 539, 256 mg, 0.71 mmol) in DCM (5 mL) at rt and stirring was continued for 4 h. The mixture was concentrated and azeotroped with CHCl$_3$ (4×10 mL) and MeOH (10 mL). The residue was dissolved in 1M HCl (2 mL, 2 mmol) and purified by reversed-phase chromatography on silica eluting with a gradient of acetonitrile in 0.02% HCl$_{(aq.)}$ to afforded Compound 540 (236 mg, quant.) as a solid. LC-MS (+ve mode): m/z=260.15 [M+H]$^+$; $^1$H NMR (300 MHz, CD$_3$OD) δ 8.43 (m, 1H, ArH), 7.81 (s, 1H, ArH), 7.71 (m, 1H, ArH), 7.41 (m, 2H, ArH), 4.98 (q, J=7.1 Hz, 1H, CH), 3.55 (m, 2H, CH$_2$), 3.24 (m, 2H, CH$_2$), 3.00 (s, 6H, Hz, 2×NMe), 1.70 (d, J=7.1 Hz, 3H, CH$_3$); $^{13}$C NMR (75.5 MHz, CD$_3$OD) δ 168.3, 136.0, 129.8, 125.8, 124.5, 122.2, 118.8, 118.7, 113.6, 56.3, 49.0, 42.2, 20.0, 16.2, 7.9.

Example 1-33: (S)-tert-butyl (1-(3-(2-(dimethyl-amino)ethyl)-5-methoxy-1H-indol-1-yl)-1-oxopropan-2-yl)carbamate (Compound 541)

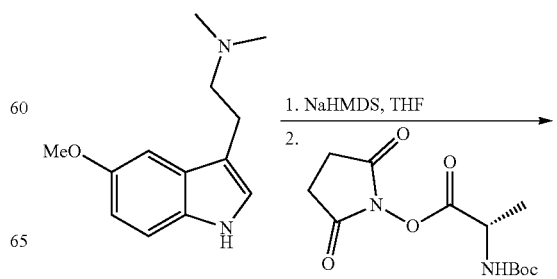

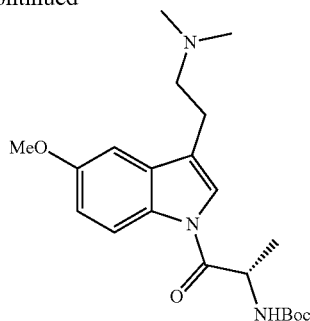

NaHMDS, 1M in THF (0.74 mL, 0.74 mmol) was added to a stirred mixture of 5-OMe-DMT (154 mg, 71.0 mmol) in anhydrous THF (5 mL) at −78° C. After 30 min, Boc-alanine-O-succinimide (193 mg, 0.67 mmol) was added and the mixture was warmed to rt and stirred for 16 h. The solvent was removed, and the residue was purified by column chromatography on silica gel, first eluting with EtOAc, followed by a gradient of MeOH in EtOAc (0.1% Et$_3$N) to afford Compound 541 (132 mg, 47%) as an oil. TLC: R$_f$=0.18 (EtOAc-MeOH, 1: 1 v/v); LC-MS (+ve mode): m/z=390.20 [M+H]$^+$; $^1$H NMR (300 MHz, CDCl$_3$) δ 8.25 (d, J=8.9 Hz, 1H, ArH), 7.27 (s, 1H, ArH), 6.90 (m, 2H, 2×ArH), 5.38 (d, J=8.8 Hz, 1H, NH), 5.00 (m, 1H, CH), 3.81 (s, 3H, OMe), 2.82 (m, 2H, CH$_2$), 2.62 (m, 2H, CH$_2$), 2.32 (s, 6H, 2×NMe) 1.39 (s, 12H, $^t$Bu, CH$_3$).

Example 1-34: (S)-2-amino-1-(3-(2-(dimethylamino)ethyl)-5-methoxy-1H-indol-1-yl)propan-1-one dihydrochloride (Compound 542)

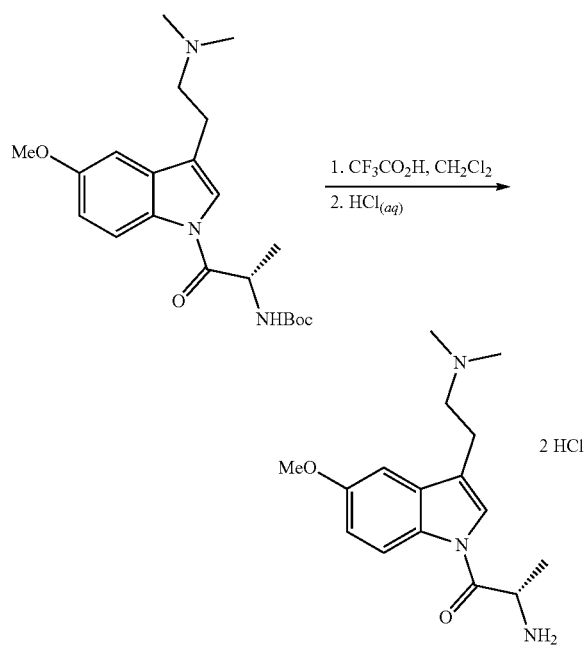

TFA (1.88 g, 1.26 mL, 16.5 mmol) was added to a solution of (S)-tert-butyl (1-(3-(2-(dimethylamino)ethyl)-5-methoxy-1H-indol-1-yl)-1-oxopropan-2-yl)carbamate (Compound 541, 132 mg, 0.33 mmol) in DCM (5 mL) at rt and stirring was continued for 4 h. The mixture was concentrated and azeotroped with CHCl$_3$ (4×10 mL) and MeOH (10 mL). The residue was dissolved in 1M HCl (2 mL, 2 mmol) and purified by reversed-phase chromatography on silica eluting with a gradient of acetonitrile in 0.02% HCl$_{(aq.)}$ to give the product (40 mg, 72%) as a solid. LC-MS (+ve mode): m/z=290.15 [M+H]$^+$; $^1$H NMR (300 MHz, CD$_3$OD) δ 8.22 (d, J=9.0 Hz, 1H, ArH), 7.76 (s, 1H, ArH), 7.13 (d, J=2.4 Hz, 1H, ArH), 6.92 (dd, J=9.0, 2.4 Hz, 1H, ArH), 4.92 (m, 1H, CH), 3.80 (s, 3H, OMe), 3.47 (m, 2H, CH$_2$), 3.13 (m, 2H, CH$_2$), 2.91 (d, J=3.0 Hz, 6H, 2×NMe), 1.61 (d, J=7.2 Hz, 3H, CH$_3$); $^3$C NMR (75.5 MHz, CD$_3$OD) δ 157.6, 131.0, 130.4, 123.0, 118.8, 117.1, 113.8, 102.8, 101.9, 56.3, 54.9, 48.9, 42.2, 42.2, 20.1, 16.4.

Example 1-35: (S)-tert-butyl (1-(3-(2-(dimethylamino)ethyl)-1H-indol-1-yl)-1-oxo-3-phenylpropan-2-yl)carbamate (Compound 543)

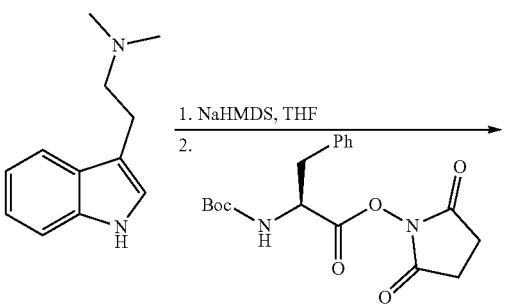

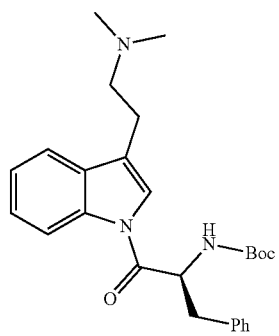

NaHMDS, 1M in THF (0.97 mL, 0.97 mmol) was added to a stirred mixture of DMT (173 mg, 0.92 mmol) in anhydrous THF (13 mL) at −78° C. After 30 min, the resulting mixture was added dropwise to Boc-Phenylalanine-OSu (300 mg, 0.83 mmol) and stirring was continued at rt for 16 h. The mixture was concentrated to dryness before being dissolved into a mixture of DCM (20 mL) and NaHCO$_3$ (20 mL). The phases were separated, and the organic phase washed with H$_2$O (2×20 mL), brine (20 mL), dried (MgSO$_4$), filtered and the filtrate was concentrated. The residue was purified by column chromatography on silica gel eluting with a gradient of MeOH/DCM to Compound 543 (111 mg, 31%) as a semi-solid. LC-MS (+ve mode): m/z=436.20 [M+H]$^+$.

Example 1-36: (S)-tert-butyl (1-(3-(2-(dimethyl-amino)ethyl)-1H-indol-1-yl)-3-methyl-1-oxobutan-2-yl)carbamate (Compound 544)

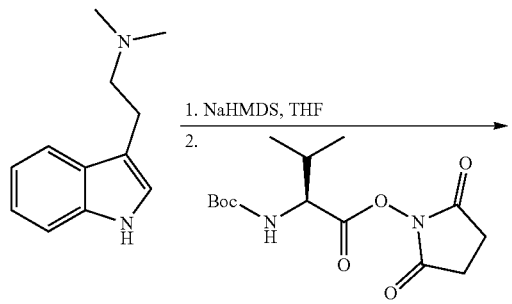

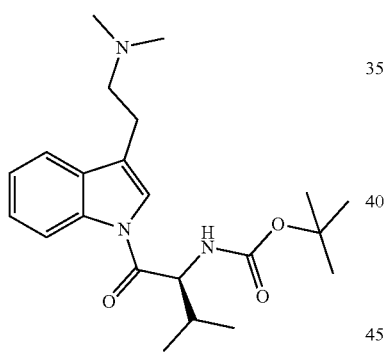

NaHMDS, IM in THF (0.97 mL, 0.97 mmol) was added to a stirred solution of DMT (173 mg, 0.92 mmol) in anhydrous THF (13 mL) at −78° C. After 30 min the mixture was added dropwise to Boc-Valine-OSu (260 mg, 0.83 mmol) and the mixture was warmed to rt and stirred for 16 h. The mixture was concentrated to dryness before being dissolved into a mixture of DCM (20 mL) and NaHCO$_3$ (20 mL). The phases were separated, and the organic phase washed with H$_2$O (2×20 mL), brine (20 mL), dried (MgSO$_4$), filtered and the filtrate was concentrated. The residue was purified by column chromatography on silica gel, eluting with a gradient of MeOH in DCM to give the product (245 mg, 76%) as a semi-solid. LC-MS (+ve mode): m/z=388.20 [M+H]$^+$; $^1$H NMR (300 MHz, CDCl$_3$) δ 8.39 (d, J=9.0 Hz, 1H, ArH), 7.53 (d, J=9.0 Hz, 1H, ArH), 7.44 (s, 1H, ArH), 7.30 (m, 2H, ArH), 5.27 (d, J=12.0 Hz, 1H, NH), 4.82 (m, 1H, CH), 3.33 (m, 4H, 2×CH$_2$), 2.87 (d, J=6.0 Hz, 6H, 2×NMe), 2.12 (m, 1H, CH), 1.38 (s, 9H, $^t$Bu), 0.98 (d, J=6.0 Hz, 3H, CH$_3$), 0.89 (d, J=6.0 Hz, 3H, CH$_3$).

Example 1-37: (S)-2-amino-1-(3-(2-(dimethyl-amino)ethyl)-1H-indol-1-yl)-3-methylbutan-1-one dihydrochloride (Compound 545)

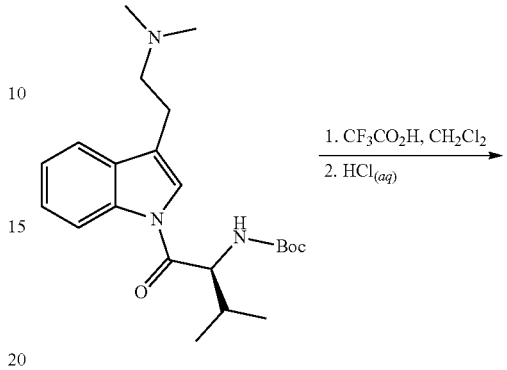

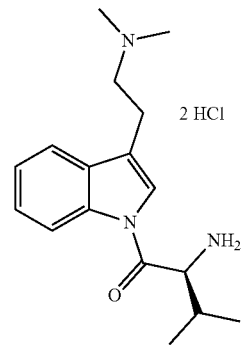

(S)-tert-butyl (1-(3-(2-(dimethylamino)ethyl)-1H-indol-1-yl)-3-methyl-1-oxobutan-2-yl)carbamate (Compound 544, 245 mg, 0.63 mmol) was dissolved into DCM (12.5 mL) at rt and TFA (2.42 mL, 31.6 mmol) was added. The mixture was stirred at rt for 3 h, then concentrated under reduced pressure, azeotroping with CHCl$_3$ (4×10 mL). The residue was purified by column chromatography on silica gel, eluting with a gradient of MeOH in CH$_2$Cl$_2$. This material was further purified by reversed-phase chromatography on silica eluting with a gradient of acetonitrile in 0.02% HCl$_{(aq.)}$ to afforded Compound 545 (85.3 mg, 38%) as a solid. LC-MS (+ve mode): m/z=288.15 [M+H]$^+$; $^1$H NMR (300 MHz, D$_2$O) δ 8.31 (d, J=6.0 Hz, 1H, ArH), 7.62 (m, 2H, 2×ArH), 7.41 (m, 2H, 2×ArH), 4.82 (d, J=6.0 Hz, 1H, CH), 3.46 (m, 2H, CH$_2$), 3.17 (m, 2H, CH$_2$), 2.89 (d, J=1.7 Hz, 6H, 2×NMe), 2.43 (m, 1H, CH), 1.07 (d, J=9.0 Hz, 3H, CH$_3$), 0.94 (d, J=9.0 Hz, 3H, CH$_3$); $^{13}$C NMR (75.5 MHz, CDCl$_3$) δ 168.2, 135.6, 129.8, 126.4, 125.1, 122.8, 119.2, 119.0, 116.4, 57.9, 56.3, 42.8, 42.7, 30.2, 20.0, 18.0, 16.0.

Example 1-38: (S)-tert-butyl (1-(3-(2-(dimethylamino)ethyl)-5-methoxy-1H-indol-1-yl)-3-methyl-1-oxobutan-2-yl)carbamate (Compound 546)

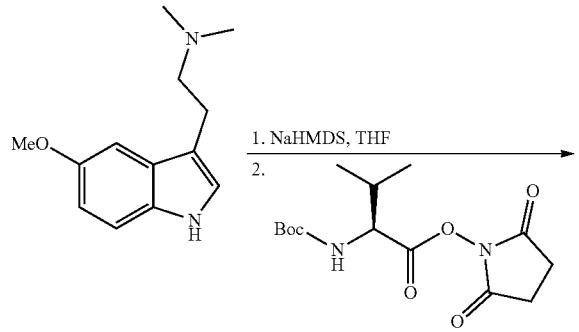

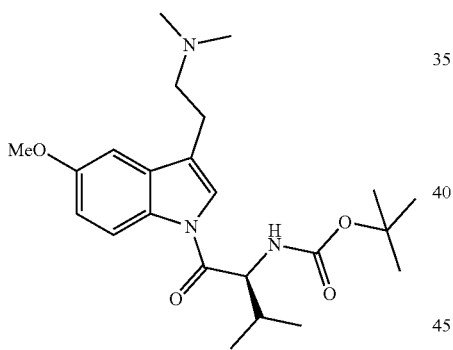

NaHMDS, 1M in THF (0.97 mL, 0.97 mmol) was added to a stirred solution of 5-OMe-DMT (210 mg, 0.92 mmol) in anhydrous THF (13 mL) at −78° C. After 30 min the mixture was added dropwise to Boc-valine-OSu (260 mg, 0.83 mmol) and the mixture was warmed to rt and stirred for 16 h. The mixture was concentrated to dryness, then dissolved into a mixture of DCM (20 mL) and NaHCO$_3$ (20 mL). The phases were separated, and the organic phase was washed with H$_2$O (2×20 mL), brine (20 mL), dried (MgSO$_4$), filtered and the filtrate was concentrated to give an oil. The residue was purified by column chromatography on silica gel, eluting with a gradient of MeOH in DCM to afford Compound 546 (216 mg, 56%) as a semi-solid. LC-MS (+ve mode): m/z=418.25 [M+H]$^+$; $^1$H NMR (300 MHz, CDCl$_3$) δ 8.27 (d, J=8.9 Hz, 1H, ArH), 7.30 (s, 1H, ArH), 6.95 (d, J=2.4 Hz, 1H, ArH), 6.89 (dd, J=8.9, 2.4 Hz, 1H, ArH), 5.30 (d, J=9.2 Hz, 1H, CH), 4.83 (m, 1H, CH), 3.81 (s, 3H, OMe), 2.82 (m, 2H, CH$_2$), 2.62 (m, 2H, CH$_2$), 2.33 (s, 6H, 2×NCH$_3$), 2.13 (m, 1H, CH), 1.38 (s, 9H, 3×CH$_3$), 0.97 (d, J=6.8 Hz, 3H, CH$_3$), 0.87 (d, J=6.8 Hz, 3H, CH$_3$).

Example 1-39: (S)-2-amino-1-(3-(2-(dimethylamino)ethyl)-5-methoxy-1H-indol-1-yl)-3-methylbutan-1-one dihydrochloride (Compound 547)

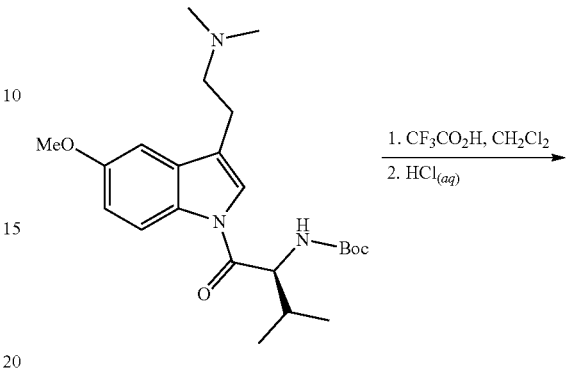

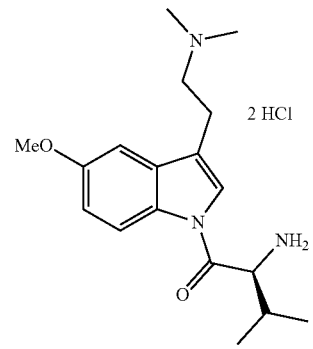

(S)-tert-butyl (1-(3-(2-(dimethylamino)ethyl)-5-methoxy-1H-indol-1-yl)-3-methyl-1-oxobutan-2-yl)carbamate (Compound 546, 216 mg, 0.52 mmol) was dissolved into DCM (11 mL) at rt and TFA (2.95 g, 1.98 mL, 25.9 mmol) was added. The mixture was stirred at rt for 1 h, then the solvent was removed under reduced pressure, azeotroping with CHCl$_3$ (4×10 mL). The crude residue was purified by reversed-phase chromatography on silica eluting with a gradient of acetonitrile in 0.02% HCl$_{(aq.)}$ to afford Compound 547 (168 mg, 83%) as an oil. LC-MS (+ve mode): m/z=318.15 [M+H]$^+$; $^1$H NMR (300 MHz, D$_2$O) δ 8.20 (d, J=9.0 Hz, 1H, ArH), 7.58 (s, 1H, ArH), 7.11 (d, J=2.4 Hz, 1H, ArH), 7.01 (dd, J=9.0, 2.4 Hz, 1H, ArH), 4.78 (d, J=5.1 Hz, 1H, CH), 3.82 (s, 3H, OMe), 3.45 (m, 2H, CH$_2$), 3.12 (m, 2H, CH$_2$), 2.89 (d, J=1.8 Hz, 6H, 2×NCH$_3$), 2.41 (m, 1H, CH), 1.05 (d, J=6.9 Hz, 3H, CH$_3$), 0.94 (d, J=6.9 Hz, 3H, CH$_3$); $^{13}$C NMR (75.5 MHz, CDCl$_3$) δ 167.7, 156.6, 131.1, 130.3, 123.6, 118.9, 117.4, 113.9, 102.8, 57.7, 56.2, 55.9, 42.7, 30.3, 20.0, 18.0, 16.0.

Example 1-40: (S)-2-amino-1-(3-(2-(dimethyl-amino)ethyl)-1H-indol-1-yl)-3-phenylpropan-1-one bis-hydrochloride (Compound 548)

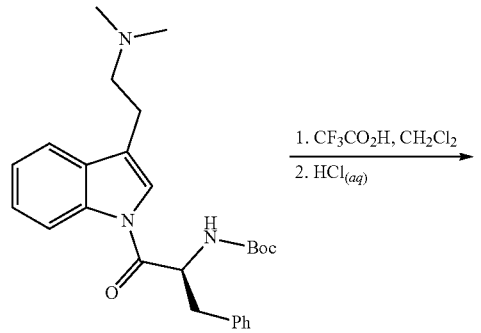

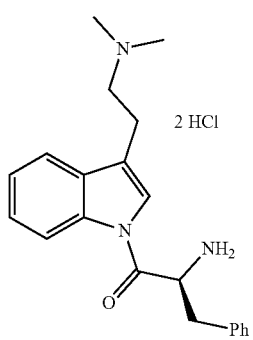

(S)-Tert-butyl (1-(3-(2-(dimethylamino)ethyl)-1H-indol-1-yl)-1-oxo-3-phenylpropan-2-yl)carbamate (Compound 543, 111 mg, 0.25 mmol) was dissolved into DCM (5 mL) and TFA (1.43 g, 0.96 mL, 12.5 mmol) was added. The reaction mixture was stirred at rt for 1 h, then the solvent was removed under reduced pressure, azeotroping the residue with $CHCl_3$ (4×10 mL). The residue was purified by reversed-phase chromatography on silica eluting with a gradient of acetonitrile in 0.02% hydrochloric acid to afford Compound 548 as a bis-hydrochloride salt (40.8 mg, 48%) as a solid. LC-MS (+ve mode): m/z=336.15 [M+H]$^+$; $^1$H NMR (300 MHz, $D_2O$) δ 8.29 (d, J=6.0 Hz, 1H, ArH), 7.55 (d, J=9.0 Hz, 1H, ArH), 7.40 (m, 2H, ArH), 7.10 (m, 6H, ArH), 5.12 (dd, J=9.0, 6.0 Hz, 1H, CH), 3.33 (dd, J=13.8, 5.7 Hz, 1H, 0.5×$CH_2$), 3.21 (m, 3H, 0.5×$CH_2$+$CH_2$), 2.91 (m, 8H, 2×$NCH_3$ and $CH_2$); $^{13}$C NMR (75.5 MHz, $D_2O$) δ 168.0, 135.2, 133.5, 129.7, 129.3, 129.1, 128.9, 128.0, 126.3, 125.1, 122.3, 119.1, 118.6, 116.4, 56.3, 53.9, 42.8, 42.6, 37.5, 19.7.

Example 1-41: (S)-tert-butyl (1-(3-(2-(dimethyl-amino)ethyl)-5-methoxy-1H-indol-1-yl)-1-oxo-3-phenylpropan-2-yl)carbamate (Compound 549)

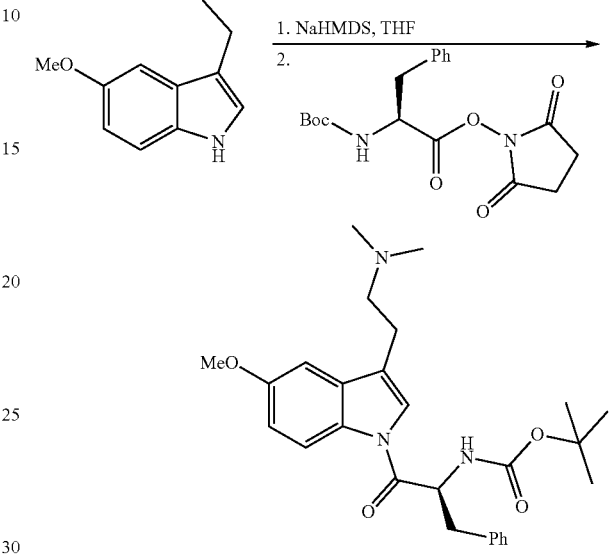

NaHMDS, 1M in THF (0.97 mL, 0.97 mmol) was added to a stirred solution of 5-OMe-DMT (210 mg, 0.96 mmol) in anhydrous THF (13 mL) at −78° C. After 30 min, the resulting mixture was added dropwise to Boc-phenylalanine-OSu (300 mg, 0.83 mmol) and stirring was continued at rt for 16 h. The reaction mixture was concentrated to dryness before being dissolved into a mixture of DCM (20 mL) and $NaHCO_3$ (20 mL). The phases were separated, and the organic phase washed with $H_2O$ (2×20 mL), brine (20 mL), dried ($MgSO_4$), filtered and the filtrate was concentrated to give a crude oil. The residue was purified by column chromatography on silica gel, eluting with a gradient of MeOH in DCM to afford Compound 549 (261 mg, 67%) as a semi-solid. LC-MS (+ve mode): m/z=466.25 [M+H]$^+$.

Example 1-42: (S)-2-amino-1-(3-(2-(dimethyl-amino)ethyl)-5-methoxy-1H-indol-1-yl)-3-phenyl-propan-1-one bis-hydrochloride (Compound 550)

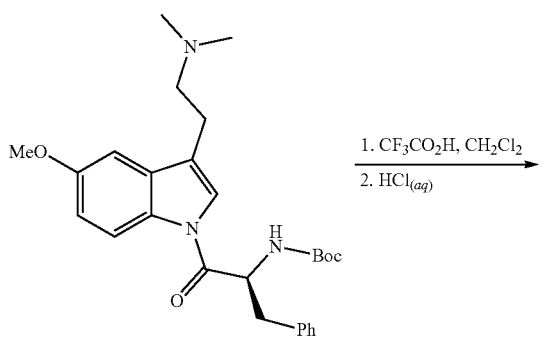

-continued

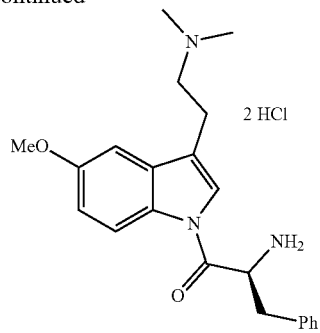

(S)-tert-butyl (1-(3-(2-(dimethylamino)ethyl)-5-methoxy-1H-indol-1-yl)-1-oxo-3-phenylpropan-2-yl)carbamate (Compound 549, 261 mg, 0.56 mmol) was dissolved into DCM (11 mL) and TFA (3.19 g, 2.14 mL, 28.0 mmol) was added. The reaction mixture was stirred at rt for 1 h, then the solvent was removed under reduced pressure, azeotroping with CHCl$_3$ (4×10 mL). The residue was purified by reversed-phase chromatography on silica eluting with a gradient of acetonitrile in 0.02% hydrochloric acid to afford Compound 550 as a bis-hydrochloride salt (244 mg, 83%) as a solid. LC-MS (+ve mode): m/z=366.20 [M+H]$^+$; $^1$H NMR (300 MHz, D$_2$O) δ 8.17 (d, J=9.9 Hz, 1H, ArH), 7.13 (m, 3H, 3×ArH), 7.01 (m, 5H, 5×ArH), 5.07 (dd, J=9.3, 5.7 Hz, 1H, CH), 3.81 (s, 3H, OMe), 3.38 (dd, J=13.5, 5.7 Hz, 1H, 0.5×CH$_2$), 3.18 (m, 3H, 0.5×CH$_2$+CH$_2$), 2.89 (m, 8H, 2×NCH$_3$ and CH$_2$); $^{13}$C NMR (75.5 MHz, D$_2$O) δ 167.5, 164.9, 156.6, 133.1, 131.1, 129.9, 129.3, 128.9, 128.0, 118.5, 117.4, 113.7, 102.7, 56.2, 55.8, 53.7, 42.8, 42.6, 37.6, 36.9, 31.3, 19.6.

Example 1-43: 2-(Dimethylamino)-1-(3-(2-(dimethylamino)ethyl)-1H-indol-1-yl)ethan-1-one hydrochloride (Compound 551)

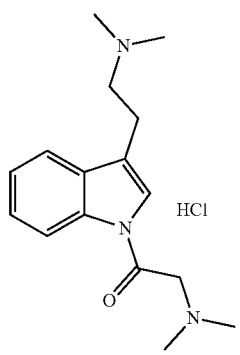 [SMILES: CN(C)CCc1cn(C(=O)CN(C)C)c2ccccc12 ; Cl]

To a solution of N,N-dimethyltryptamine (282 mg, 1.50 mmol) in anhydrous THF (20 mL) at −78° C. under an atmosphere of N$_2$ was added NaHMDS, 1M in THE (6.0 mL, 6.0 mmol) and the mixture was stirred at −78° C. for 30 min. 2-(Dimethylamino)acetyl chloride hydrochloride (475 mg, 3.00 mmol) was added and the mixture was stirred at −78° C. for 5 min, then warmed to rt and stirred for 4 h. H$_2$O (3 mL) was added and the mixture was concentrated, and the residue was purified by reversed-phase chromatography, eluting with 0 to 100% acetonitrile in 0.02% hydrochloric acid to give 2-(dimethylamino)-1-(3-(2-(dimethylamino)ethyl)-1H-indol-1-yl)ethan-1-one HCl (Compound 551, 79 mg, 17%) as a solid. LC-MS (+ve mode): m/z=274.15 [M+H]$^+$; $^1$H NMR (300 MHz, D$_2$O) δ 8.37 (br, 1H, ArH), 7.73 (br, 1H, ArH), 7.51 (m, 3H, 3×ArH), 4.89 (s, 2H, CH$_2$), 3.56 (m, 2H, CH$_2$), 3.26 (m, 2H, CH$_2$), 3.14 (s, 6H, 2×NMe), 2.98 (s, 6H, 2×NMe); $^{13}$C NMR (75.5 MHz, D$_2$O) δ 163.6, 134.9, 129.6, 126.3, 124.9, 121.9, 121.9, 119.3, 119.1, 59.0, 56.4, 44.2, 42.8, 20.0.

Example 1-44: 2-(Dimethylamino)-1-(3-(2-(dimethylamino)ethyl)-5-methoxy-1H-indol-1-yl)ethan-1-one formate (Compound 552)

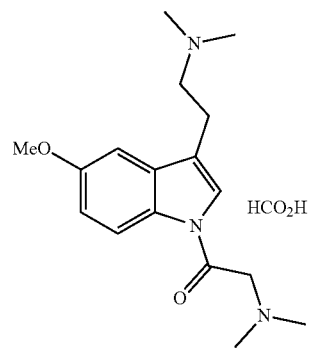 [SMILES: COc1ccc2c(c1)c(CCN(C)C)cn2C(=O)CN(C)C ; "HCO2H"]

To a solution of 5-methoxy-N,N-dimethyltryptamine (229 mg, 1.05 mmol) in anhydrous THF (12 mL) at −78° C. under an atmosphere of N$_2$ was added NaHMDS, 1M in THF (5.5 mL, 5.5 mmol) and the mixture was stirred at −78° C. for 30 min. 2-(Dimethylamino)acetyl chloride hydrochloride (0.67 g, 4.2 mmol) was added and the mixture was stirred at −78° C. for 10 min, then warmed to rt and stirred for 3 h. H$_2$O (2 mL) was added, the mixture was concentrated and the residue was purified by reversed-phase chromatography, eluting with 0 to 100% acetonitrile in 0.1% formic acid to give 2-(dimethylamino)-1-(3-(2-(dimethylamino)ethyl)-5-methoxy-1H-indol-1-yl)ethan-1-one formate (Compound 552, 108 mg, 29%) as a solid. LC-MS (+ve mode): m/z=304.15 [M+H]$^+$; $^1$H NMR (300 MHz, D$_2$O) δ 8.27 (br, 1H, ArH), 7.50 (s, 1H, ArH), 7.21 (d, J=2.5 Hz, 1H, ArH), 7.12 (dd, J=9.0, 2.5 Hz, 1H, ArH), 4.87 (s, 2H, CH$_2$), 3.93 (s, 3H, OMe), 3.55 (m, 2H, CH$_2$), 3.22 (m, 2H, CH$_2$), 3.14 (s, 6H, 2×NMe), 2.98 (s, 6H, 2×NMe); $^{13}$C NMR (75.5 MHz, D$_2$O) δ 163.1, 156.5, 130.2, 122.7, 119.0, 114.0, 110.7, 110.0, 102.8, 56.2, 55.9, 44.2, 43.5, 42.8, 20.0.

Example 1-45: (S)-2-amino-N-(2-(3-(2-(dimethylamino)ethyl)-1H-indol-1-yl)-2-oxoethyl)-N-methyl-3-phenylpropanamide (Compound 553)

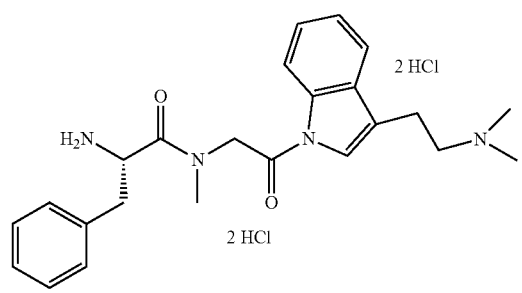 [SMILES: CN(C)CCc1cn(C(=O)CN(C)C(=O)[C@@H](N)Cc2ccccc2)c2ccccc12]

Step 1: (S)-2,5-dioxopyrrolidin-1-yl 2-(2-((tert-butoxycarbonyl)amino)-N-methyl-3-phenylpropanamido)acetate

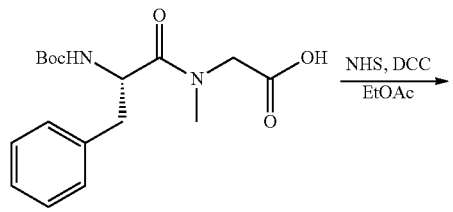

Boc-phenylalanine-N-methyl-glycine [CAS No: 108787-68-4] (500 mg, 1.49 mmol) and N-hydroxysuccinimide (188.5 mg, 1.63 mmol) were dissolved in EtOAc (50 mL) and cooled to 0° C. Dicyclohexylcarbodiimide (338 mg, 1.64 mmol) was added and the mixture was stirred at 0° C. for 2 h, then allowed to rt and stirred overnight. The mixture was filtered through Celite and the filtrate was concentrated to give the product (766 mg, quant) as a solid, which was used without further purification. LC-MS (+ve mode): m/z=434.15 [M+H]$^+$.

Step 2: (S)-tert-butyl (1-((2-(3-(2-(dimethylamino)ethyl)-1H-indol-1-yl)-2-oxoethyl)(methyl)amino)-1-oxo-3-phenylpropan-2-yl)carbamate

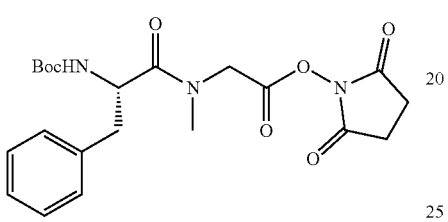

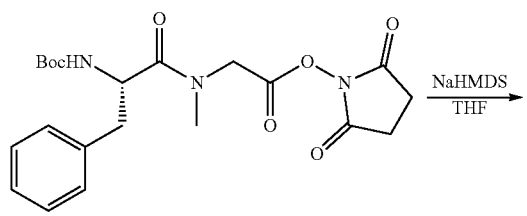

NaHMDS, 1M in THF (1.67 mL, 1.67 mmol) was added to a stirred solution of DMT (200 mg, 1.06 mmol) in anhydrous THF (5 mL) at −78° C. After 30 min, a solution of Boc-phenylalanine-N-methyl-glycine-OSu (367 mg, 0.85 mmol) in THF (5 mL) was added and the mixture was warmed to rt and stirred for 16 h. The solvent was removed and the residual material was purified by column chromatography on silica gel, eluting with a gradient of MeOH in DCM to the product (33 mg, 8%) as a solid. LC-MS (+ve mode): m/z=507.30 [M+H]$^+$; 1H NMR (300 MHz, CDCl$_3$) δ 8.32 (d, J=7.8 Hz, 1H, ArH), 7.51 (m, 1H, ArH), 7.32 (m, 6H, 6×ArH), 7.00 (m, 2H, 2×ArH), 5.56 (m, 1H, NH), 4.90 (m, 1H, CH), 4.61 (s, 2H, CH$_2$), 3.07 (m, 6H, 3×CH$_2$), 2.95 (s, 3H, NMe), 2.59 (s, 6H, 2×NMe), 1.34, (s, 9H, $^t$Bu).

Step 3: (S)-2-amino-N-(2-(3-(2-(dimethylamino)ethyl)-1H-indol-1-yl)-2-oxoethyl)-N-methyl-3-phenylpropanamide dihydrochloride

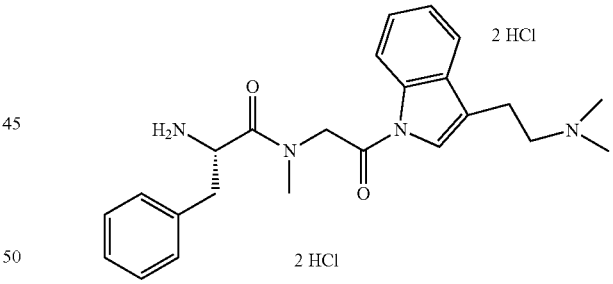

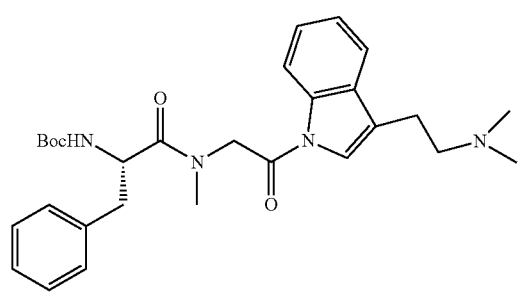

TFA (0.57 g, 0.38 mL, 5.03 mmol) was added to a mixture of (S)-tert-butyl (1-((2-(3-(2-(dimethylamino)ethyl)-1H-indol-1-yl)-2-oxoethyl)(methyl)amino)-1-oxo-3-phenylpropan-2-yl)carbamate (51 mg, 0.10 mmol) in DCM (1.4 mL) at rt and stirring was continued for 3 h. The mixture was concentrated and azeotroped with CHCl$_3$ (4×10 mL) and the residue was purified by reversed-phase chromatography on silica eluting with a gradient of acetonitrile in 0.02% HCl$_{(aq.)}$ to give the product as a bis-hydrochloride salt (40 mg, 83%) an oil. LC-MS (+ve mode): m/z=407.25 [M+H]$^+$; $^1$H NMR (300 MHz, CD$_3$OD) δ 8.42 (m, 1H, ArH), 7.80 (m, 1H, ArH), 7.73 (m, 1H, ArH), 7.41 (m, 7H, 7×ArH), 4.97 (obs, 2H, CH$_2$), 4.83 (m, 1H, CH), 3.57 (m, 2H, CH$_2$), 3.07 (m, 4H, 2×CH$_2$), 3.08 (s, 3H, NMe), 3.02 (s, 6H, 2×NMe).

Example 1-46: (S)-2-amino-N-(2-(3-(2-(dimethylamino)ethyl)-5-methoxy-1H-indol-1-yl)-2-oxoethyl)-N-methyl-3-phenylpropanamide (Compound 554)

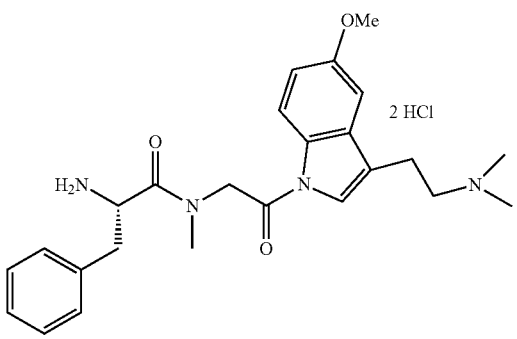 [SMILES: COc1ccc2c(c1)c(CCN(C)C)cn2C(=O)CN(C)C(=O)[C@@H](N)Cc1ccccc1]

Step 1: (S)-tert-butyl (1-((2-(3-(2-(dimethylamino)ethyl)-5-methoxy-1H-indol-1-yl)-2-oxoethyl)(methyl)amino)-1-oxo-3-phenylpropan-2-yl)carbamate

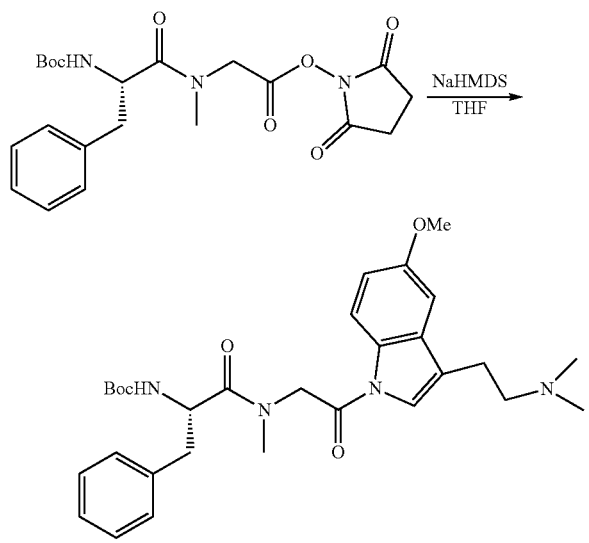

NaHMDS, 1M in THF (0.96 mL, 0.96 mmol) was added to a stirred solution of 5-OMe-DMT (200 mg, 0.91 mmol) in anhydrous THF (5 mL) at −78° C. After 30 min, a solution of Boc-phenylalanine-N-methyl-glycine-OSu (317 mg, 0.73 mmol) in THF (5 mL) was added and the mixture was warmed to rt and stirred for 16 h. The solvent was removed and the residual material was purified by column chromatography on silica gel, eluting with a gradient of MeOH in DCM to give the product (55 mg, 11%) as a solid. LC-MS (+ve mode): m/z=537.25 [M+H]$^+$; $^1$H NMR (300 MHz, CDCl$_3$) δ 8.20 (d, J=9.0 Hz, 1H, ArH), 7.35 (s, 1H, ArH), 7.17 (m, 5H, 5×ArH), 7.24 (d, J=2.7 Hz, 1H, ArH), 7.90 (dd, J=9.0, 2.7 Hz, 2H, 1H, NH), 4.88 (m, 1H, CH), 4.60 (s, 2H, CH$_2$), 3.83 (s, 3H, OMe), 3.07 (m, 6H, 3×CH$_2$), 2.94 (s, 3H, NMe), 2.66 (s, 6H, 2×NMe), 1.34, (s, 9H, $^t$Bu).

Step 2: (S)-2-amino-N-(2-(3-(2-(dimethylamino)ethyl)-5-methoxy-1H-indol-1-yl)-2-oxoethyl)-N-methyl-3-phenylpropanamide

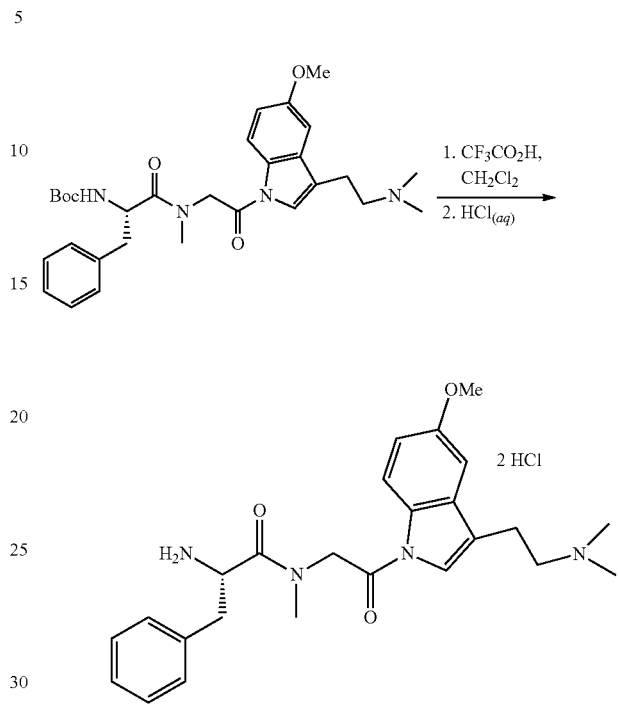

TFA (0.58 g, 0.39 mL, 5.13 mmol) was added to a solution of (S)-tert-butyl (1-((2-(3-(2-(dimethylamino)ethyl)-5-methoxy-1H-indol-1-yl)-2-oxoethyl)(methyl)amino)-1-oxo-3-phenylpropan-2-yl)carbamate (55 mg, 0.10 mmol) in DCM (1.5 mL) at rt and stirring was continued for 2 h. The mixture was concentrated and azeotroped with CHCl$_3$ (4×10 mL) and the residue was purified by reversed-phase chromatography on silica eluting with a gradient of acetonitrile in 0.02% HCl$_{(aq.)}$ to give the product (19 mg, 37%) an oil. LC-MS (+ve mode): m/z=437.30 [M+H]$^+$.

Example 1-47: 2,2-dimethyl-3-(pivaloyloxy)propyl 3-(2-(dimethylamino)ethyl)-5-methoxy-1H-indole-1-carboxylate formate (Compound 555)

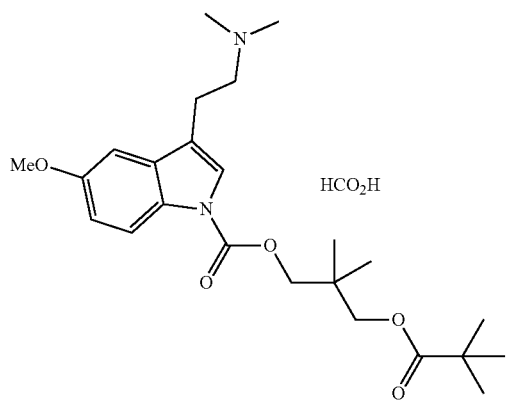 [SMILES: COc1ccc2c(c1)c(CCN(C)C)cn2C(=O)OCC(C)(C)COC(=O)C(C)(C)C ; "HCO2H"]

Step 1: 3-((chlorocarbonyl)oxy)-2,2-dimethylpropyl pivalate

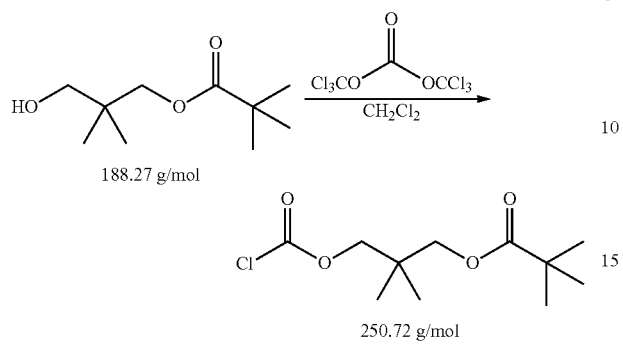

To a solution of 3-hydroxy-2,2-dimethylpropyl pivalate (346 mg, 1.84 mmol) in DCM (5 mL) was added DMAP (0.72 g, 5.81 mmol) and triphosgene (202 mg, 0.68 mmol) and the mixture was stirred at rt for 1 hour. This solution was used directly in the next step.

Step 2: 2,2-dimethyl-3-(pivaloyloxy)propyl 3-(2-(dimethylamino)ethyl)-5-methoxy-1H-indole-1-carboxylate formate

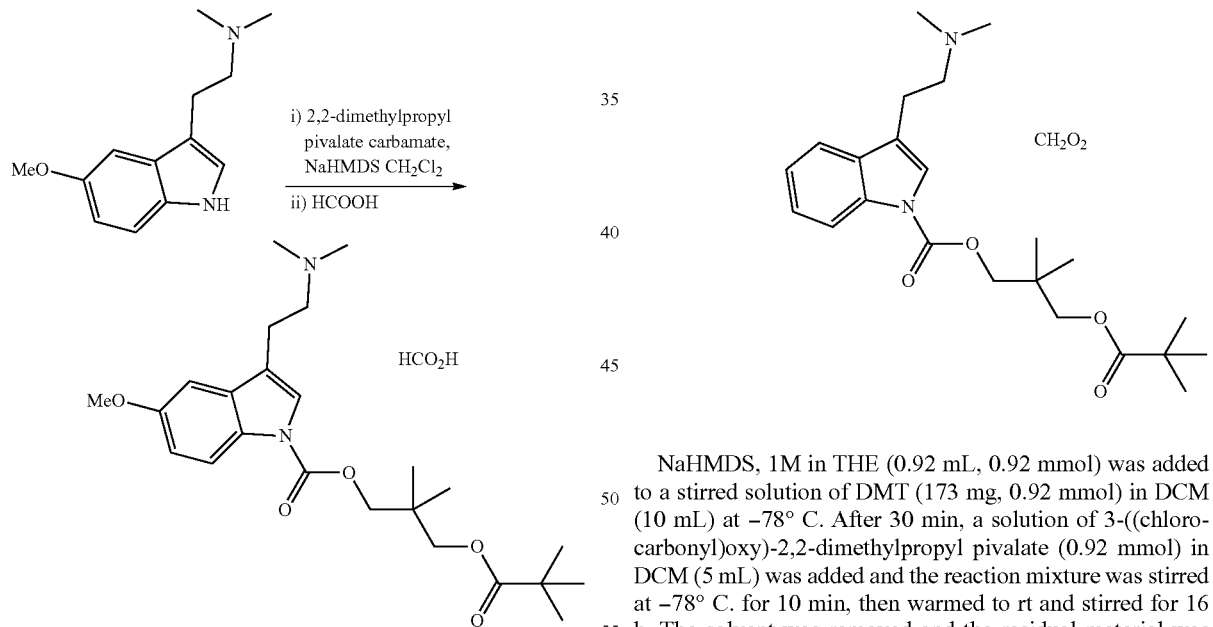

NaHMDS, 1M in THF (0.96 mL, 0.96 mmol) was added to a stirred solution of 5-OMe-DMT (200 mg, 0.91 mmol) in DCM (10 mL) at −78° C. After 30 min, a solution of 3-((chlorocarbonyl)oxy)-2,2-dimethylpropyl pivalate (0.92 mmol) in DCM (5 mL) was added and the mixture stirred at −78° C. for 10 min, then the mixture warmed to rt and stirred for 16 h. The mixture was concentrated and the residual material was purified by column chromatography on silica gel, eluting with a gradient of MeOH in DCM followed by reversed-phase chromatography, eluting with 0 to 100% acetonitrile in 0.1% formic acid to afford Compound 555 (52 mg, 13%) as an oil. LC-MS (+ve mode): m/z=433.25 [M+H]$^+$; $^1$H NMR (300 MHz, CD$_3$OD) δ 8.42 (s, 1H, HCO$_2$H), 8.02 (d, J=9.0 Hz, 1H, ArH), 7.60 (s, 1H, ArH), 7.13 (d, J=2.5 Hz, 1H, ArH), 6.97 (dd, J=9.0, 2.5 Hz, 1H ArH), 4.27 (s, 2H, CH$_2$), 4.00 (s, 2H,CH$_2$), 3.86 (s, 3H, OMe), 3.44 (m, 2H, CH$_2$), 3.15 (m, 2H, CH$_2$), 2.93 (s, 6H, 2×CH$_3$), 1.19 (s, 9H, $^t$Bu), 1.11 (s, 6H, 2×CH$_3$); $^{13}$C NMR (75.5 MHz, CDCl$_3$) δ 178.3, 167.4, 156.5, 150.4, 130.5, 123.7, 115.8, 115.5, 113.2, 101.5, 71.2, 68.6, 56.6, 54.8, 48.4, 48.2, 47.9, 47.6, 47.3, 47.0, 46.7, 42.2, 38.6, 35.0, 26.2, 20.7, 20.1.

Example 1-48: 2,2-Dimethyl-3-(pivaloyloxy)propyl 3-(2-(dimethylamino)ethyl)-1H-indole-1-carboxylate formate (Compound 556)

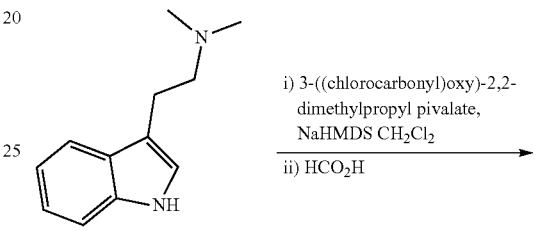

NaHMDS, 1M in THF (0.92 mL, 0.92 mmol) was added to a stirred solution of DMT (173 mg, 0.92 mmol) in DCM (10 mL) at −78° C. After 30 min, a solution of 3-((chlorocarbonyl)oxy)-2,2-dimethylpropyl pivalate (0.92 mmol) in DCM (5 mL) was added and the reaction mixture was stirred at −78° C. for 10 min, then warmed to rt and stirred for 16 h. The solvent was removed and the residual material was purified by column chromatography on silica gel, eluting with a gradient of MeOH in DCM, followed by reversed-phase chromatography, eluting with 0 to 100% acetonitrile in 0.1% formic acid to afford Compound 556 (97 mg, 23%) as an oil. LC-MS (+ve mode): m/z=403.25 [M+H]$^+$; $^1$H NMR (300 MHz, CD$_3$OD) δ 8.15 (d, J=7.9 Hz, 1H, ArH), 7.62 (m, 1H, ArH), 7.54 (s, 1H, ArH), 7.33 (m, 2H, 2×ArH), 4.31 (s, 2H, CH$_2$), 4.04 (s, 2H, CH$_2$), 3.00 (m, 2H, CH$_2$), 2.82 (m, 2H, CH$_2$), 2.46 (s, 6H, 2×NMe), 1.12 (s, 9H, $^t$Bu), 1.14 (s, 6H, 2×CH$_3$); $^{13}$C NMR (75 MHz, CD$_3$OD) δ 203.4, 201.2, 178.4, 124.4, 122.6, 122.2, 122.1, 118.9, 118.6, 114.7, 69.0, 68.9, 58.4, 43.7, 38.6, 34.7, 26.2, 20.6.

Example 1-49: 2-(1-di(dimethylamino)phosphoryl-indol-3-yl)-N,N-dimethyl-ethanamine (Compound 557)

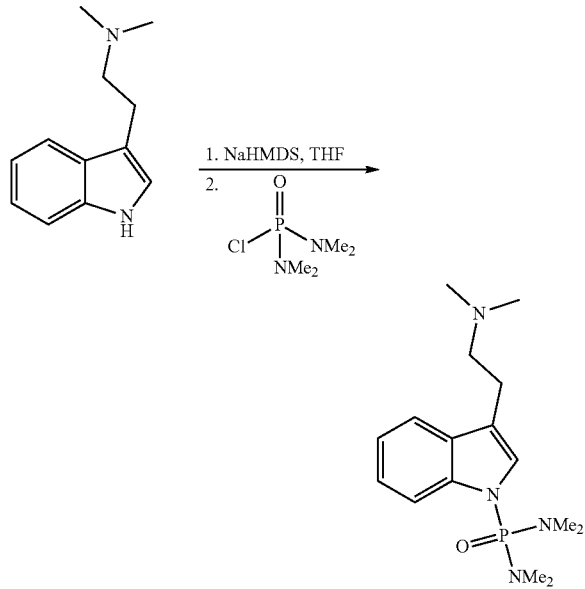

NaHMDS, 1M in THF (1.12 mL, 1.12 mmol) was added to a stirred solution of DMT (200 mg, 1.06 mmol) in anhydrous THF (5 mL) at −78° C. After 30 min, N,N,N,N-tetramethylphosphorodiaminic chloride (181 mg, 0.16 mL, 1.06 mmol) was added and the mixture was warmed to rt and stirred for 16 h. The solvent was removed under vacuum and the crude residue was purified by column chromatography on silica gel, eluting with a gradient of MeOH in DCM to afford Compound 557 (251 mg, 74%) as an oil. TLC: $R_f$=0.55 (DCM-MeOH, 8: 2 v/v); LC-MS (+ve mode): m/z=323.15 [M+H]$^+$; $^1$H NMR (300 MHz, CDCl$_3$) δ 7.82 (m, 1H, ArH), 7.53 (m, 1H, ArH), 7.18 (m, 3H, 3×ArH), 3.10 (m, 2H, CH$_2$), 2.95 (m, 2H, CH$_2$), 2.68 (d, 12.0 Hz, $^3J_{(H-P)}$=10.2 Hz, 2×PNMe), 2.63 (s, 6H, 2×NMe); $^{13}$C NMR (75.5 MHz, CDCl$_3$) δ 138.1 (d, $^3J_{(C-P)}$=4.3 Hz), 130.3 (d, $^2J_{(C-P)}$=8.2 Hz), 125.9 (d, $^2J_{(C-P)}$=5.7 Hz), 123.6, 121.5, 118.6, 115.8 (d, $^3J_{(C-P)}$=7.2 Hz), 114.6, 58.6, 44.2, 36.7 (d, $^2J_{(C-P)}$=4.2 Hz), 22.2; $^{31}$P NMR (121.5 MHz, CDCl$_3$) δ 14.56.

Example 1-50: 2-(1-di(dimethylamino)phosphoryl-5-methoxy-indol-3-yl)-N,N-dimethyl-ethanamine (Compound 558)

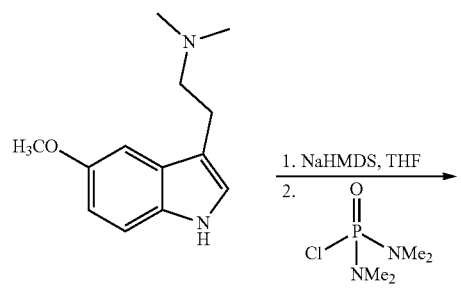

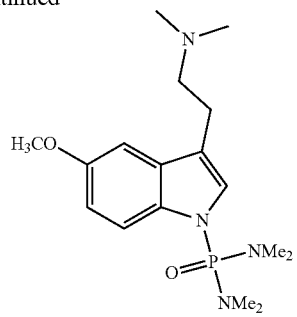

NaHMDS, 1M in THF (0.96 mL, 0.96 mmol) was added to a stirred mixture of 5-OMe-DMT (200 mg, 0.92 mmol) in anhydrous THF (5 mL) at −78° C. After 30 min, N,N,N,N-tetramethylphosphorodiaminic chloride (157 mg, 0.14 mL, 0.92 mnmol) was added and the mixture was warmed to rt and stirred for 16 h. The solvent was removed under vacuum and the residue was purified by column chromatography on silica gel eluting with a gradient of MeOH in DCM to afford Compound 558 (157 mg, 48%) as an oil. TLC: $R_f$=0.34 (DCM-MeOH, 8:2 v/v); LC-MS (+ve mode): m/z=353.15 [M+H]$^+$; $^1$H NMR (300 MHz, CDCl$_3$) δ 7.70 (d, J=9.0, 1H, ArH), 7.02 (m, 2H, 2×ArH), 6.85 (dd, J=9.0, 2.4 Hz, 1H, ArH), 3.83 (s, 3H, OMe), 2.96 (m, 2H, CH$_2$), 2.77 (m, 2H, CH$_2$), 2.67 (s, 6H, 2×PNMe), 2.63 (s, 6H, 2×PNMe), 2.45 (s, 6H, 2×NMe); $^{13}$C NMR (75.5 MHz, CDCl$_3$) δ 155.2, 132.9 (d, $^3J_{(C-P)}$=4.3 Hz), 131.3 (d, $^2J_{(C-P)}$=8.3 Hz), 126.3 (d, $^2J_{(C-P)}$=5.7 Hz), 116.7 (d, $^3J_{(C-P)}$=7.3 Hz), 115.3, 112.8, 101.1, 59.1, 55.9, 44.8, 36.7 (d, $^2J_{(C-P)}$=4.2 Hz), 23.0; $^{31}$P NMR (121.5 MHz, CDCl$_3$) δ 14.64.

Example 1-51: bis(3-(2-(Dimethylamino)ethyl)-1H-indol-1-yl)methanone di-formate (Compound 170)

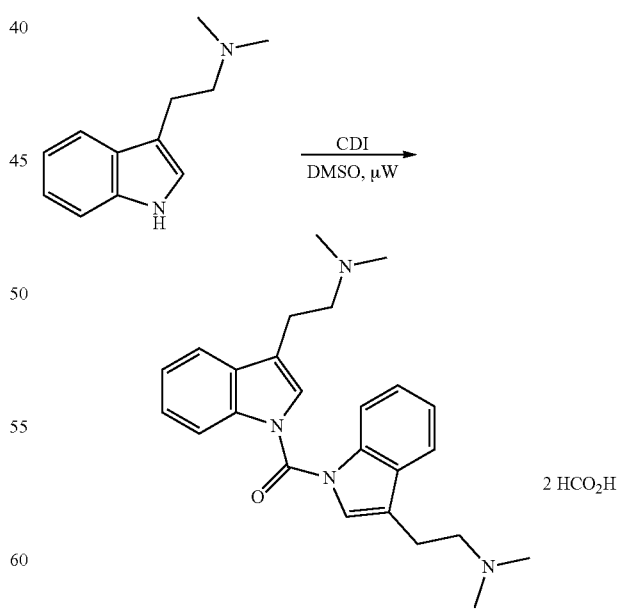

To a mixture of N,N-dimethyltryptamine (162 mg, 0.86 mmol) in DMSO (1.5 mL) was added carbonyldiimidazole (68 mg, 0.42 mmol) and the mixture was heated to 120° C. under microwave irradiation and stirred for 2 h. The mixture was quenched with saturated aqueous NaHCO₃ (10 mL) and extracted with EtOAc (3×25 mL). The combined organic layers were washed with H₂O (20 mL), saturated brine (20 mL), dried (MgSO₄) and concentrated under reduced pressure. This material was purified by reversed-phase chromatography, eluting with 0 to 100% acetonitrile in 0.1% formic acid to afford Compound 170 (48 mg, 35%) as an oil. LC-MS (+ve mode): m/z=403.25 [M+H]J; ¹H NMR (300 MHz, MeCN-d₃) δ 8.43 (s, 2H, 2×HCO), 7.99 (m, 2H, 2×ArH), 7.74 (m, 2H, 2×ArH), 7.53 (s, 2H, 2×ArH), 7.38 (m, 4H, 4×ArH), 3.06 (m, 4H, 2×CH₂), 2.96 (m, 4H, 2×CH₂), 2.50 (s, 12H, 4×NMe).

Example 1-52: bis(3-(2-(Dimethylamino)ethyl)-5-methoxy-1H-indol-1-yl)methanone di-formate (Compound 169)

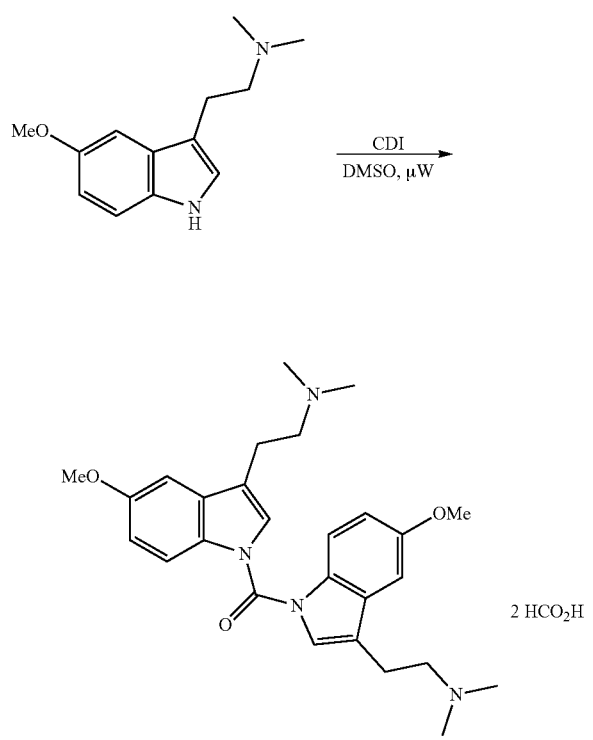

To a solution of 5-methoxy-N,N-dimethyltryptamine (175 mg, 0.80 mmol) in DMSO (1.5 mL) was added CDI (63 mg, 0.39 mmol) and the mixture was heated to 120° C. under microwave irradiation and stirred for 2 h. The mixture was quenched with saturated aqueous NaHCO₃ (20 mL) and extracted with EtOAc (60 mL). The combined organic layers were washed with H₂O (20 mL), saturated brine (20 mL), dried (MgSO₄), filtered and concentrated to give an oil (186 mg). This material was purified by reversed-phase chromatography, eluting with 0 to 100% acetonitrile in 0.1% formic acid to afford Compound 169 (75.9 mg, 35%) as a solid. LC-MS (+ve mode): m/z=463.25 [M+H]⁺; ¹H NMR (300 MHz, MeCN-d₃) δ 8.28 (s, 2H, 2×HCO), 7.89 (d, J=9.0 Hz, 2H, 2×ArH), 7.58 (s, 2H, 2×ArH), 7.24 (d, J=2.4 Hz, 2H, 2×ArH), 7.00 (dd, J=9.0, 2.4 Hz, 2H, 2×ArH), 3.91 (s, 6H, 2×OMe), 3.30 (m, 4H, 2×CH₂), 3.15 (m, 4H, 2×CH₂), 2.73 (s, 12H, 4×NMe).

Example 1-53: (3-(2-(Dimethylamino)ethyl)-1H-indol-1-yl)methanol (Compound 559)

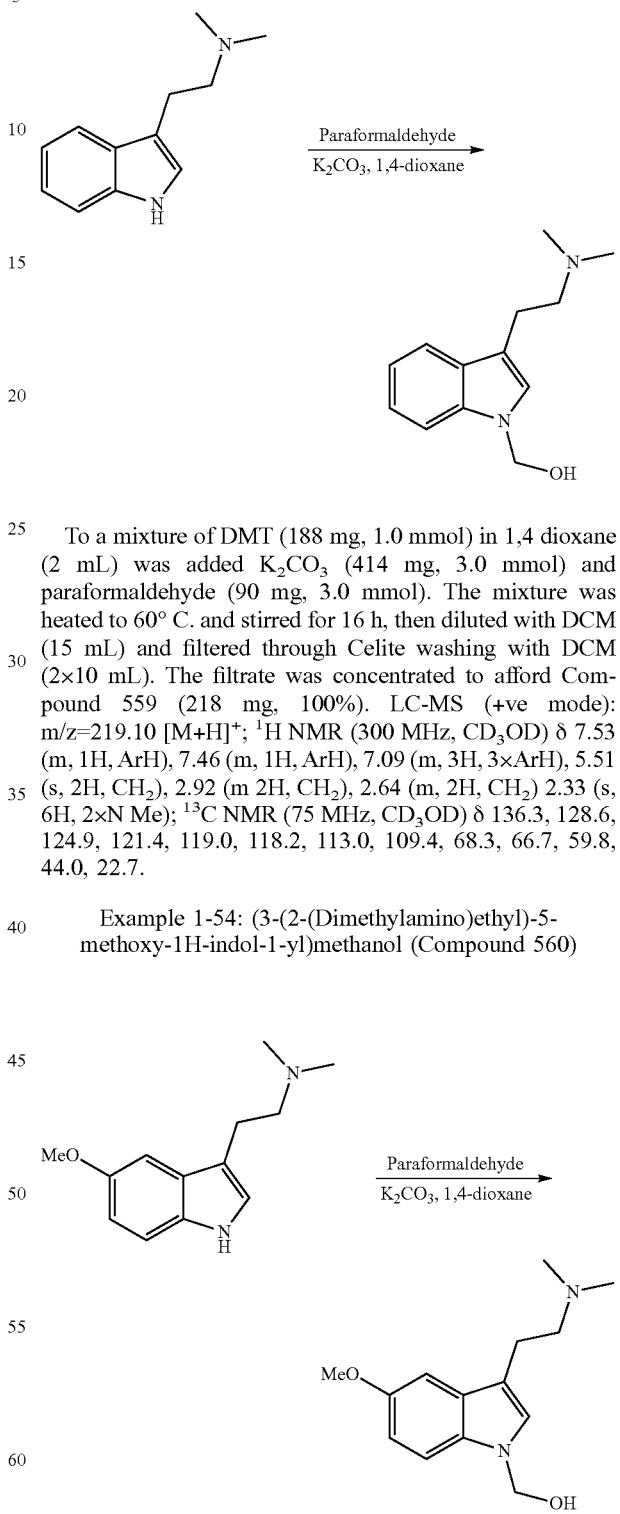

To a mixture of DMT (188 mg, 1.0 mmol) in 1,4 dioxane (2 mL) was added K₂CO₃ (414 mg, 3.0 mmol) and paraformaldehyde (90 mg, 3.0 mmol). The mixture was heated to 60° C. and stirred for 16 h, then diluted with DCM (15 mL) and filtered through Celite washing with DCM (2×10 mL). The filtrate was concentrated to afford Compound 559 (218 mg, 100%). LC-MS (+ve mode): m/z=219.10 [M+H]⁺; ¹H NMR (300 MHz, CD₃OD) δ 7.53 (m, 1H, ArH), 7.46 (m, 1H, ArH), 7.09 (m, 3H, 3×ArH), 5.51 (s, 2H, CH₂), 2.92 (m 2H, CH₂), 2.64 (m, 2H, CH₂) 2.33 (s, 6H, 2×N Me); ¹³C NMR (75 MHz, CD₃OD) δ 136.3, 128.6, 124.9, 121.4, 119.0, 118.2, 113.0, 109.4, 68.3, 66.7, 59.8, 44.0, 22.7.

Example 1-54: (3-(2-(Dimethylamino)ethyl)-5-methoxy-1H-indol-1-yl)methanol (Compound 560)

To a solution of 5-OMe-DMT (218 mg, 1.0 mmol) in 1,4 dioxane (2 mL) was added K₂CO₃ (414 mg, 3.0 mmol) and paraformaldehyde (90 mg, 3.0 mmol). The mixture was heated to 60° C. and stirred for 16 h, then diluted with DCM (15 mL) and filtered through Celite, washing with DCM (2×10 mL). The filtrate was concentrated to afford Compound 560 (190 mg, 76%) as an oil. LC-MS (+ve mode): m/z=249.15 [M+H]$^+$; $^1$H NMR (300 MHz, CD$_3$OD) δ 7.35 (d, J=8.9 Hz, 1H, Ar—H), 7.07 (s, 1H, ArH), 7.02 (d, J=2.4 Hz, 1H ArH), 6.83 (dd, ArH, J=8.9, 2.7 Hz, 1H), 5.47 (s, 2H, CH$_2$), 3.82 (s, 3H, OMe), 2.89 (m, 2H, CH$_2$), 2.64 (m, 2H, CH$_2$), 2.35 (s, 6H, 2×NMe); $^{13}$C NMR (75.5 MHz, CD$_3$OD) δ 154.2, 131.6, 125.6, 112.6, 111.3, 110.2, 100.3, 68.5, 59.6, 54.9, 44.0, 22.7.

Example 1-55: (3-(2-(dimethylamino)ethyl)-1H-indol-1-yl)methyl pivalate (Compound 187)

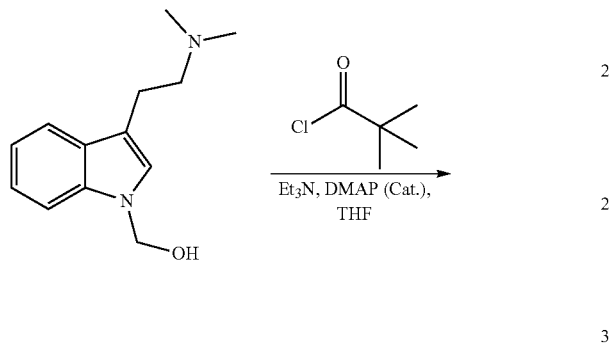

To (3-(2-(dimethylamino)ethyl)-1H-indol-1-yl)methanol (Compound 559, 109 mg, 0.5 mmol) in DCM (5 mL) at rt was added pivaloyl chloride (180 mg, 183 μL, 1.5 mmol), Et$_3$N (228 mg, 247 μL, 2.25 mmol) and DMAP (10 mg, 0.13 mmol). The mixture was stirred at rt for 16 h, then concentrated under vacuum and the crude residue was purified by column chromatography on silica gel, eluting with a gradient of MeOH in EtOAc to afford Compound 187 (91 mg, 60%) as an oil. LC-MS (+ve mode): m/z=303.10 [M+H]$^+$; $^1$H NMR (300 MHz, CD$_3$OD) δ 7.57 (m, 1H, ArH), 7.51 (m, 1H, ArH), 7.17 (m, 3H, 3×ArH), 6.15 (s, 2H, CH$_2$), 2.98 (m 2H, CH$_2$), 2.76 (m, 2H, CH$_2$), 2.43 (s, 6H, 2×NMe), 1.13 (s, 9H, $^t$Bu); $^{13}$C NMR (75 MHz, CD$_3$OD) δ 179.5, 138.1, 130.0, 127.3, 123.5, 121.3, 119.7, 115.0, 110.9, 69.9, 60.6, 45.1, 39.9, 28.6, 27.3, 23.6.

Example 1-56: (3-(2-(Dimethylamino)ethyl)-5-methoxy-1H-indol-1-yl)methyl pivalate (Compound 188)

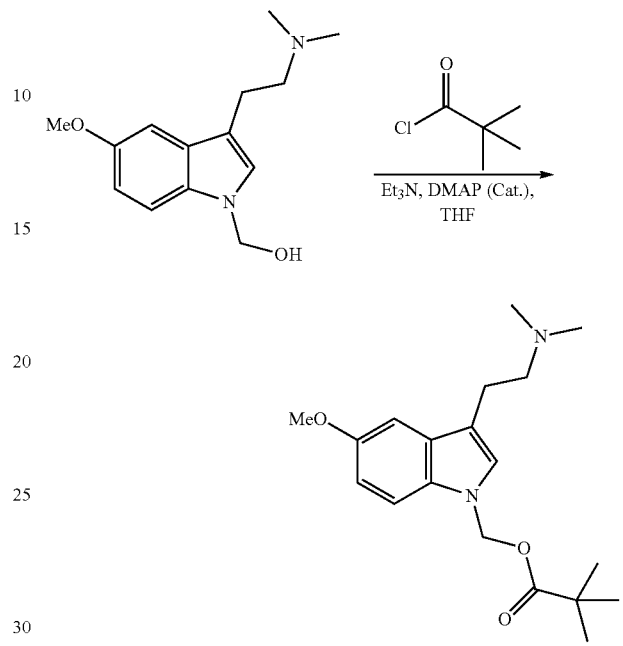

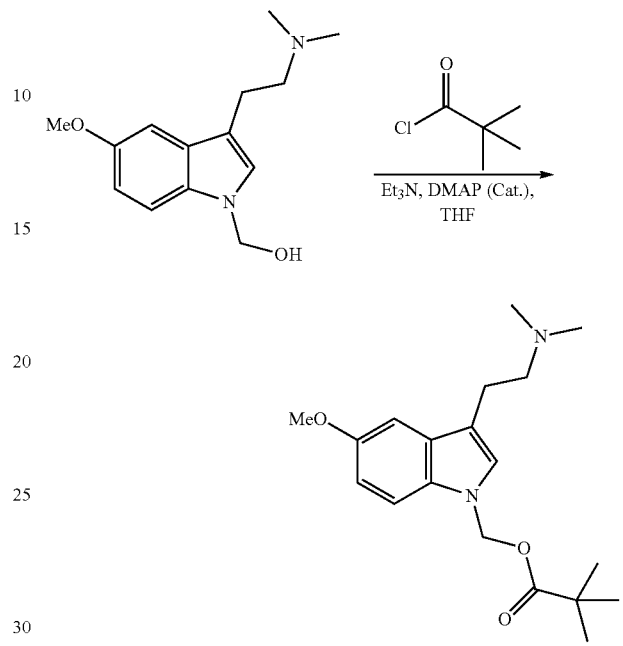

To (3-(2-(dimethylamino)ethyl)-5-methoxy-1H-indol-1-yl)methanol (Compound 560, 95 mg, 0.38 mmol.) in DCM (5 mL) at rt was added pivaloyl chloride (44.6 mg, 46 μL, 0.38 mmol), Et$_3$N (115 mg, 106 μL, 1.14 mmol) and DMAP (10 mg, 0.13 mmol). The mixture was stirred at rt for 16 h, then concentrated under vacuum and the residue was purified by column chromatography on silica gel, eluting with a gradient of MeOH in EtOAc to afford Compound 188 (30 mg, 23%) as an oil. LC-MS (+ve mode): m/z=333.15 [M+H]$^+$; $^1$H NMR (300 MHz, CD$_3$OD) δ 7.40 (d, J=8.8 Hz, 1H, ArH), 7.15 (s, 1H, ArH), 7.06 (d, J=2.4 Hz, 1H, ArH), 6.88 (dd, J=8.8, 2.4 Hz, 1H), 6.10 (s, 2H, CH$_2$), 3.85 (s, 3H, OMe), 2.92 (m 2H, CH$_2$), 2.71 (m, 2H, CH$_2$) 2.40 (s, 6H, 2×NMe) 1.12 (s, 9H, $^t$Bu); $^{13}$C NMR (75 MHz, CD$_3$OD) δ 154.8, 126.7, 126.5, 111.9, 111.7, 110.5, 110.3, 100.6, 100.4, 68.6, 59.0, 58.8, 54.9, 43.4, 27.0, 25.9, 22.0.

Example 1-57: (3-(2-(Dimethylamino)ethyl)-1H-indol-1-yl)methyl ethyl carbonate (Compound 561)

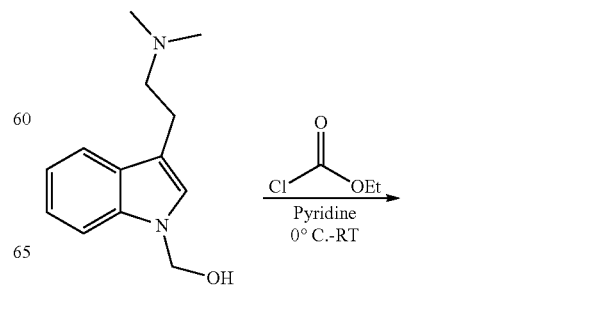

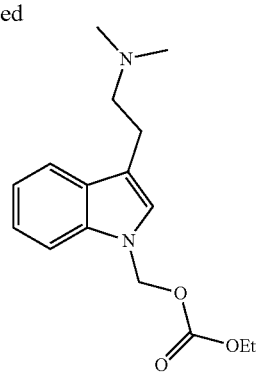

To (3-(2-(dimethylamino)ethyl)-5-methoxy-1H-indol-1-yl)methanol (Compound 559, 218 mg, 1.0 mmol) in anhydrous pyridine (5 mL) at 0° C. under an atmosphere of $N_2$ was added ethyl chloroformate (119 mg, 105 μL, 1.1 mmol) dropwise. The mixture was slowly warmed to rt and stirred for 1 h, then concentrated under vacuum and EtOAc (50 mL) and NaHCO$_3$ (25 mL) added. The phases were separated, and the organic phase was washed with H$_2$O (25 mL), brine (25 mL), dried (MgSO$_4$), filtered and the filtrate was concentrated to afford Compound 561 (169 mg) as an oil. LC-MS (+ve mode): m/z=291.15 [M+H]$^+$.

Example 1-58: (3-(2-(Dimethylamino)ethyl)-5-methoxy-1H-indol-1-yl)methyl ethyl carbonate (Compound 562)

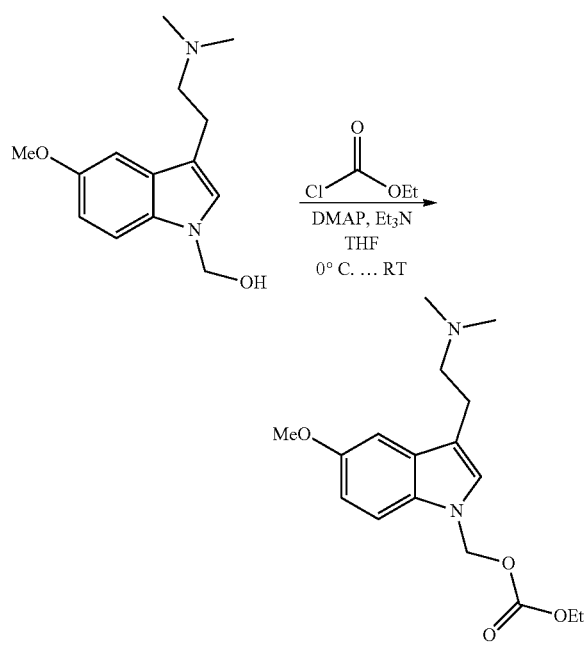

To (3-(2-(dimethylamino)ethyl)-1H-indol-1-yl)methanol (Compound 560, 125 mg, 0.5 mmol), DMAP (2 mg, 15 μmol) and trimethylamine (101 mg, 139 μmol) in anhydrous THF (5 mL) at 0° C. under an atmosphere of N$_2$ was added a solution of ethyl chloroformate (70 mg, 60 μL, 0.65 mmol) in anhydrous THF (0.4 mL) dropwise. The mixture was stirred at 0° C. for 1 h, then slowly warmed to rt and stirred for 18 h. Additional DMAP (24 mg, 180 μmol) and triethylamine (101 mg, 139 μmol) were added followed by a solution of ethyl chloroformate (109 mg, 96 μmol, 1.0 mmol) in anhydrous THF (1 mL). The reaction mixture was stirred at rt for an additional 24 h, then concentrated under reduced pressure to afford Compound 562 (189 mg) as an oil. LC-MS (+ve mode): m/z=343.10 [M+Na]$^+$.

Example 1-59: Di-tert-butyl ((3-(2-(dimethylamino)ethyl)-1H-indol-1-yl)methyl) phosphate (Compound 264)

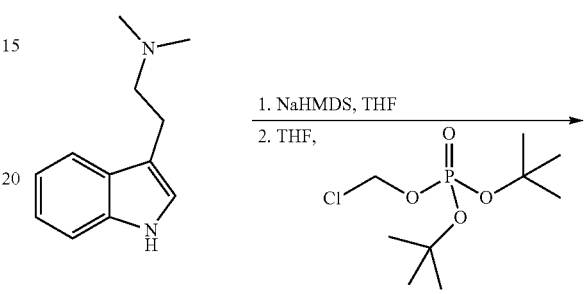

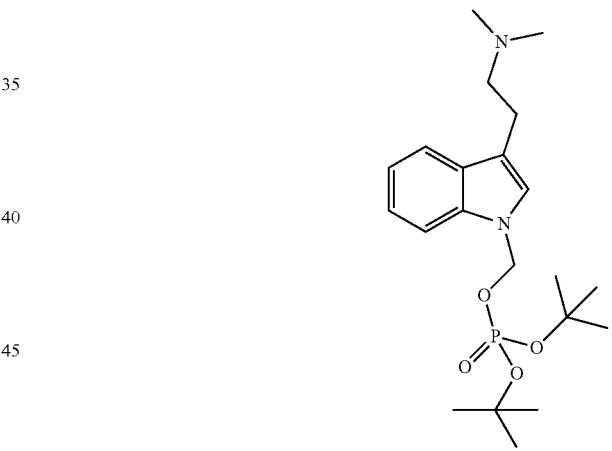

NaHMDS, 1M in THF (1.4 mL, 1.4 mmol) was added to a stirred solution of DMT (250 mg, 1.33 mmol) in anhydrous THF (18 mL) at −78° C. After 30 min, the mixture was added dropwise to di-tert-butyl chloromethyl phosphate (310 mg, 1.20 mmol), the mixture was warmed to rt and stirred for 16 h, then concentrated to dryness and dissolved into a mixture of DCM (20 mL) and NaHCO$_3$ (20 mL). The phases were separated, and the organic phase washed with H$_2$O (2×20 mL), brine (20 mL), dried (MgSO$_4$), filtered and the filtrate was concentrated under vacuum. The crude residue was purified by column chromatography on silica gel, eluting with MeOH in DCM, followed by reversed-phase chromatography, eluting with MeCN in H$_2$O and subsequently purification using a Biotage® KP-Amino D column, eluting with a mixture of PE in EtOAc to MeOH in EtOAc to afford Compound 264 (123 mg).cLC-MS (+ve mode): m/z=411.20 [M+H]$^+$.

Example 1-60: Di-tert-butyl ((3-(2-(dimethylamino)ethyl)-5-methoxy-1H-indol-1-yl)methyl) phosphate (Compound 256)

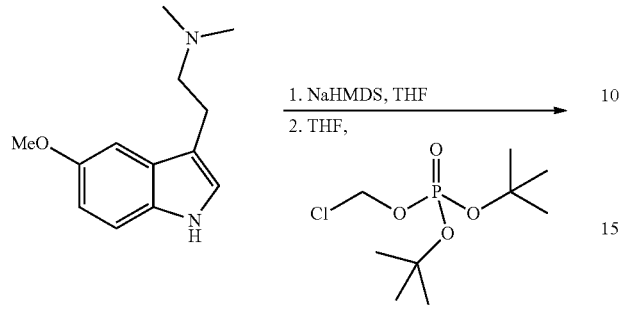

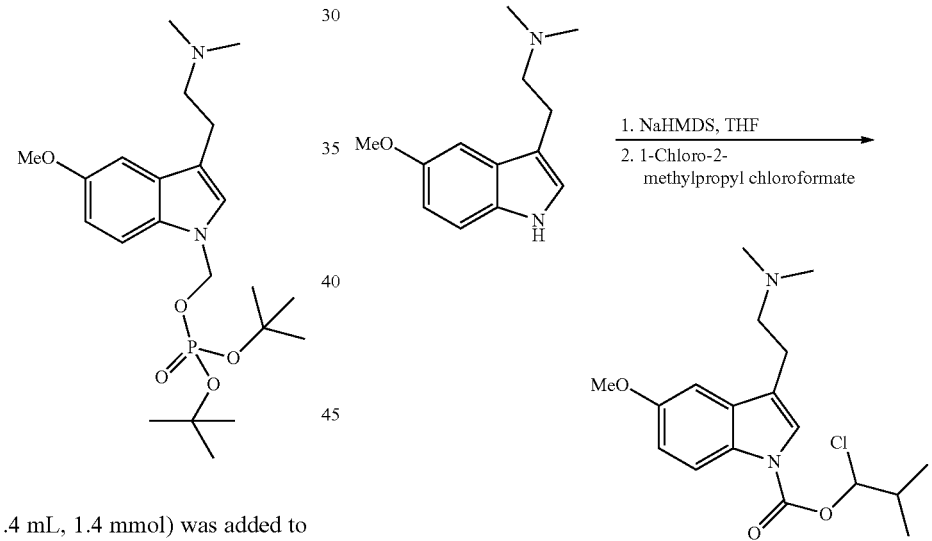

NaHMDS, 1M in THF (1.4 mL, 1.4 mmol) was added to a stirred solution of 5-OMe-DMT (150 mg, 0.69 mmol) in anhydrous THF (9 mL) at −78° C. After 30 min, the resulting mixture was added dropwise to di-tert-butyl chloromethyl phosphate (160 mg, 0.62 mmol), the mixture was warmed to rt and stirring was continued for 16 h at rt. The mixture was concentrated to dryness, then dissolved into a mixture of DCM (20 mL) and NaHCO$_3$ (20 mL). The phases were separated, and the organic phase washed with H$_2$O (2×20 mL), brine (20 mL), dried (MgSO$_4$), filtered and the filtrate was concentrated under vacuum. The residue was purified by column chromatography on silica gel, eluting with MeOH in DCM, followed by reversed-phase chromatography, eluting with MeCN in H$_2$O and subsequently purification using a Biotage® KP-Amino D column, eluting with a mixture of PE to EtOAc to MeOH in EtOAc to afford Compound 256 (74 mg). LC-MS (+ve mode): m/z=441.20 [M+H]$^+$.

Example 1-61: 1-(((S)-2-amino-3-methylbutanoyl)oxy)-2-methylpropyl 3-(2-(dimethylamino)ethyl)-5-methoxy-1H-indole-1-carboxylate di-trifluoroacetate (Compound 563)

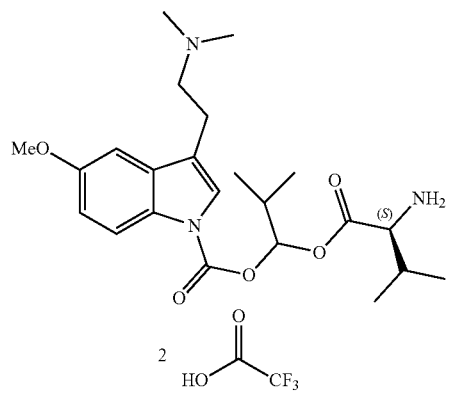

Step 1: 1-Chloro-2-methylpropyl 3-(2-(dimethylamino)ethyl)-5-methoxy-1H-indole-1-carboxylate NaHMDS, 1M in THF (3.25 mL, 3.25 mmol) was added to a stirred solution of 5-OMe-DMT (355 mg, 1.63 mmol) in anhydrous THF (16 mL) at −78° C. After 30 min, 1-chloro-2-methylpropyl chloroformate (556 mg, 474 µL, 3.25 mmol) was added dropwise and stirring was continued for 30 min at −78° C., then allowed to warm to rt and stirred for 2 h. The mixture was quenched with H$_2$O (10 mL) and concentrated to dryness and the residual material was dissolved in a mixture of DCM (15 mL) and H$_2$O (15 mL). The phases were separated, and the organic phase was washed with H$_2$O (2×15 mL), sat. brine (20 mL), dried (Na$_2$SO$_4$), filtered and the filtrate was concentrated to give a semi-solid. The material was purified by column chromatography on silica gel, eluting with a gradient of MeOH in EtOAc containing 0.1% Et$_3$N to give the product (154 mg, 27%) as an oil. LC-MS (+ve mode): m/z=343.10 & 345.10 [M+H]$^+$;

¹H NMR (300 MHz, CDCl₃) δ 8.00 (br, 1H, ArH), 7.29 (s, 1H, ArH), 6.95 (d, J=2.5 Hz, 1H, ArH), 6.89 (dd, J=8.9, 2.5 Hz, 1H, ArH), 6.47 (d, J=4.6 Hz, 1H, CH), 3.81 (s, 3H, OCH₃), 2.80 (m, 2H, CH₂), 2.61 (m, 2H, CH₂), 2.31 (s, 6H, 2×NCH₃), 1.11 (dd, J=6.8, 4.5 Hz, 6H, 2×CH₃).

Step 2: N-(tert-Butoxycarbonyl)-L-valinate Cesium Salt

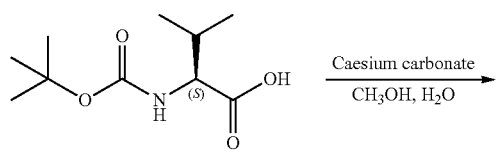

N-(tert-Butoxycarbonyl)-L-valine (1.24 g, 5.70 mmol) was dissolved in MeOH (24 mL) and H₂O (2.4 mL). A 20% w/w aqueous solution of Cs₂CO₃ was added dropwise until pH 7 was achieved. The solution was concentrated in vacuo to give a clear residue, which was lyophilised to give N-(tert-butoxycarbonyl)-L-valine cesium salt (1.99 g, quant) as a solid.

Step 3: 1-(((S)-2-((tert-butoxycarbonyl)amino)-3-methylbutanoyl)oxy)-2-methylpropyl 3-(2-(dimethylamino)ethyl)-5-methoxy-1H-indole-1-carboxylate

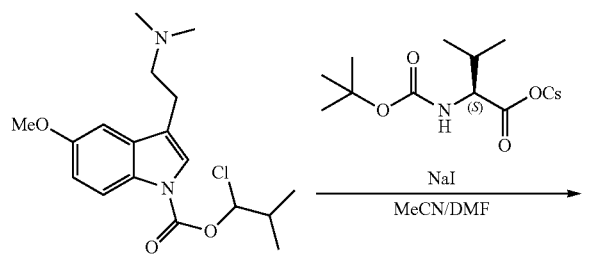

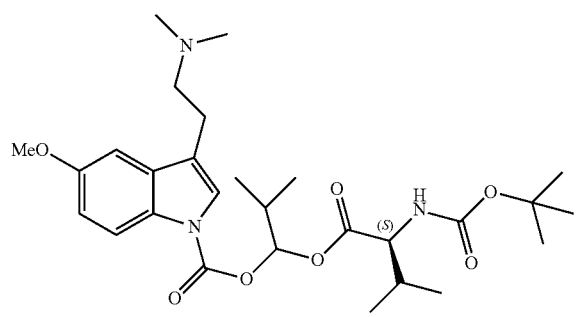

1-Chloro-2-methylpropyl 3-(2-(dimethylamino)ethyl)-5-methoxy-1H-indole-1-carboxylate (154 mg, 0.44 mmol) was dissolved in MeCN (8 mL), then N-(tert-butoxycarbonyl)-L-valinate cesium salt (236 mg, 0.68 mmol) and NaI (66 mg, 0.44 mmol) were added. The mixture was heated to 70° C. and stirred overnight. DMF (4 mL) was added and the mixture was stirred at 70° C. for a further 72 h. The mixture was concentrated under reduced pressure and the residue was purified twice by column chromatography on silica gel, eluting with a gradient of MeOH in EtOAc to give the product (77 mg) as a solid. LC-MS (+ve mode): m/z=534.30 [M+H]⁺

Step 4: 1-(((S)-2-amino-3-methylbutanoyl)oxy)-2-methylpropyl 3-(2-(dimethylamino)ethyl)-5-methoxy-1H-indole-1-carboxylate

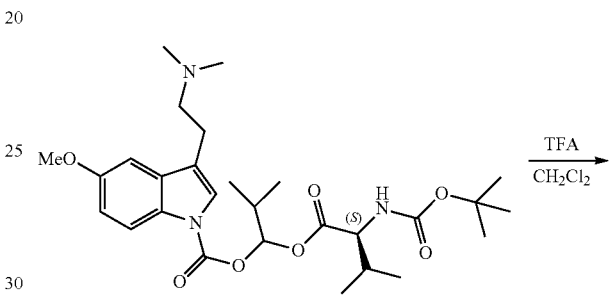

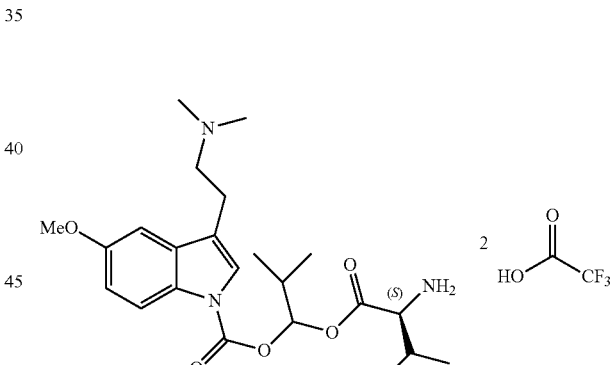

1-(((S)-2-((tert-butoxycarbonyl)amino)-3-methylbutanoyl)oxy)-2-methylpropyl 3-(2-(dimethylamino)ethyl)-5-methoxy-1H-indole-1-carboxylate (77 mg, 0.14 mmol) was dissolved in DCM (1.5 mL) at rt and TFA (0.82 g, 0.56 mL, 7.2 mmol) was added dropwise. The mixture was stirred at rt for 2 h, then concentrated under vacuum and the residue was purified by reversed-phase chromatography eluting with a gradient of acetonitrile in H₂O to afford Compound 563 (34.8 mg, 38%) as a semi-solid. LC-MS (+ve mode): m/z=434.20 [M+H]⁺; 1H NMR (300 MHz, CD₃OD) δ 7.93 (d, J=8.6 Hz, 1H, ArH), 7.54 (s, 1H, ArH), 7.10 (d, J=2.3 Hz, 1H, ArH), 6.93 (m, 2H, ArH and CH), 4.02 (d, J=4.1 Hz, 1H, CH), 3.80 (s, 3H, OCH₃), 3.41 (m, 2H, CH₂), 3.10 (m, 2H, CH₂), 2.91 (s, 6H, 2×NCH₃), 2.23 (m, 1H, CH), 1.08 (dd, J=6.8, 4.9 Hz, 6H, 2×CH₃), 0.98 (dd, J=7.0, 4.3 Hz, 6H, 2×CH₃).

Example 1-62: 1-(((S)-2-amino-3-methylbutanoyl)oxy)-2-methylpropyl 3-(2-(dimethylamino)ethyl)-1H-indole-1-carboxylate di-trifluoroacetate (Compound 564)

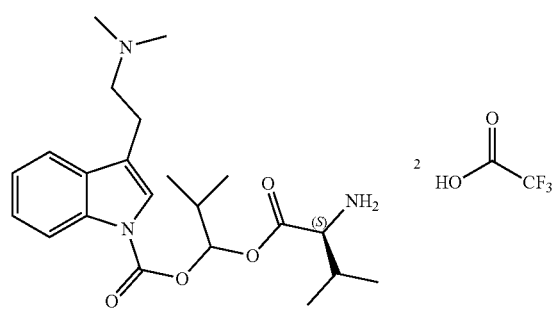
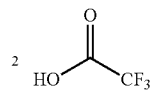

Step 1: 1-Chloro-2-methylpropyl 3-(2-(dimethylamino)ethyl)-1H-indole-1-carboxylate

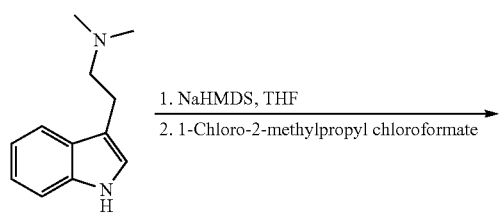

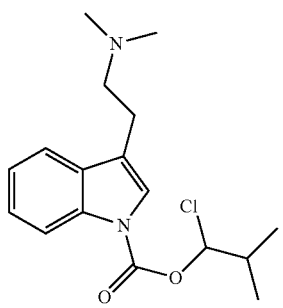

NaHMDS, 1M in THF (3.06 mL, 3.06 mmol) was added to a stirred solution of DMT (288 mg, 1.53 mmol) in anhydrous THF (15 mL) at −78° C. After 30 min, 1-chloro-2-methylpropyl chloroformate (523 mg, 446 µL, 3.06 mmol) was added dropwise and stirring was continued at −78° C. for 30 min, then allowed to warm to rt and stirred for 2.5 h. The mixture was quenched with $H_2O$ (10 mL), then concentrated to dryness and dissolved in a mixture of DCM (15 mL) and $H_2O$ (15 mL). The phases were separated and the organic phase was washed with $H_2O$ (2×15 mL), sat. brine (20 mL), dried ($Na_2SO_4$) and concentrated under vacuum. The residue was purified by column chromatography on silica gel, eluting with a gradient of MeOH in EtOAC to give the product (98 mg, 20%) as a semi-solid. LC-MS (+ve mode): m/z=323.10 [M+H]$^+$; $^1$H NMR (300 MHz, CDCl$_3$) δ 8.13 (br, 1H, ArH), 7.60 (d, J=7.6 Hz, 1H, ArH), 7.41 (s, 1H, ArH), 7.31 (m, 2H, 2×ArH), 6.48 (d, J=4.6 Hz, 1H, CH), 3.32 (m, 2H, CH$_2$), 3.22 (m, 2H, CH$_2$), 2.82 (s, 6H, 2×NCH$_3$), 2.31 (m, 1H, CH), 1.13 (dd, J=6.8, 5.1 Hz, 6H, 2×CH$_3$).

Step 2: 1-(((S)-2-((tert-butoxycarbonyl)amino)-3-methylbutanoyl)oxy)-2-methylpropyl 3-(2-(dimethylamino)ethyl)-1H-indole-1-carboxylate

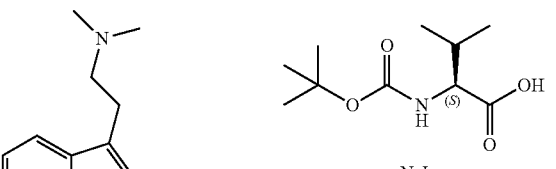

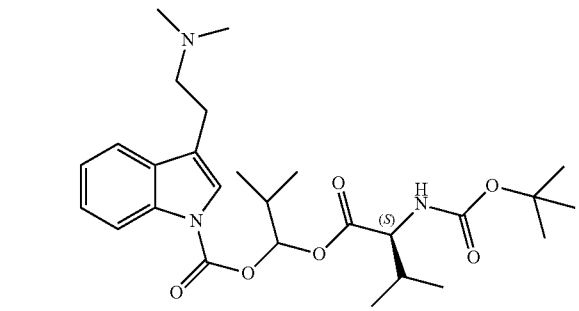

1-Chloro-2-methylpropyl 3-(2-(dimethylamino)ethyl)-1H-indole-1-carboxylate (98 mg, 0.30 mmol) was dissolved in DMF (6 mL), then N-(tert-butoxycarbonyl)-L-valine (132 mg, 0.61 mmol), N,N-diisopropylethylamine (196 mg, 265 µL, 1.52 mmol) and NaI (46 mg, 0.30 mmol) were added. The mixture was heated to 60° C. and stirred for 4 h, then heated to 70° C. and stirred for a further 96 h. The sample was concentrated under vacuum and the residue was purified by column chromatography on silica gel, eluting with a gradient of MeOH in EtOAc to give the product (78 mg) as a semi-solid. LC-MS (+ve mode): m/z=504.30 [M+H]$^+$.

Step 3: 1-(((S)-2-amino-3-methylbutanoyl)oxy)-2-methylpropyl 3-(2-(dimethylamino)ethyl)-1H-indole-1-carboxylate di-trifluoroacetate

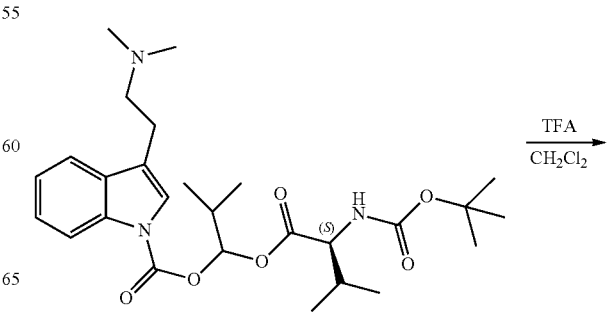

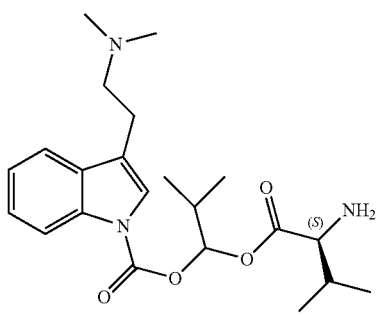

1-(((S)-2-((tert-butoxycarbonyl)amino)-3-methylbutanoyl)oxy)-2-methylpropyl 3-(2-(dimethylamino)ethyl)-1H-indole-1-carboxylate (78 mg, 0.16 mmol) was dissolved in DCM (1.6 mL) at rt and TFA (0.88 g, 0.6 mL, 7.7 mmol) was added dropwise. The mixture was stirred at rt for 1.5 h, then concentrated under vacuum and the residue was purified by reverse phase chromatography eluting with a gradient of acetonitrile in H$_2$O to afford Compound 564 (15.2 mg) as a semi-solid. LC-MS (+ve mode): m/z=404.25 [M+H]$^+$; $^1$H NMR (300 MHz, CD$_3$OD) δ 8.04 (m, 1H, ArH), 7.59 (m, 2H, ArH), 7.28 (m, 2H, ArH), 6.92 (d, J=4.8 Hz, 1H, CH), 4.01 (d, J=4.1 Hz, 1H, CH), 3.41 (m, 2H, CH$_2$), 3.11 (dd, J=9.8, 6.3 Hz, 2H, CH$_2$), 2.89 (s, 6H, 2×NCH$_3$), 2.24 (m, 2H, 2×CH), 1.38 (m, 6H, 2×CH$_3$), 0.96 (dd, J=7.0, 4.0 Hz, 6H, 2×CH$_3$).

Example 1-63: tert-Butyl (((3-(2-(dimethylamino)ethyl)-5-methoxy-1H-indole-1-carbonyl)oxy)methyl) succinate (Compound 565)

Cesium 4-(tert-butoxy)-4-oxobutanoate

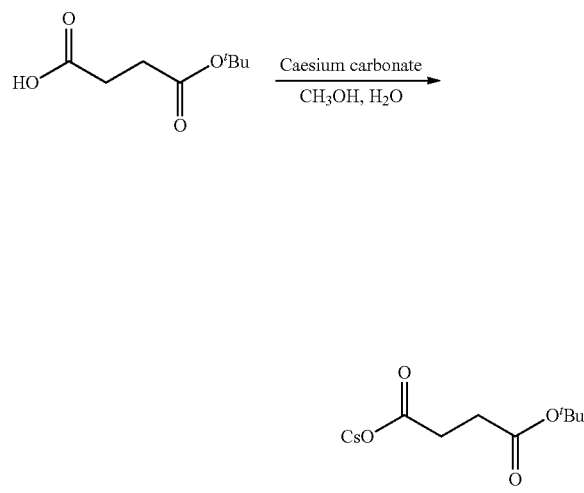

4-(tert-Butoxy)-4-oxobutanoic acid (0.50 g, 2.88 mmol) was dissolved in MeOH (12 mL) and H$_2$O (1.2 mL). A 20% w/w aqueous solution of Cs$_2$CO$_3$ was added dropwise until pH 7 was achieved. The mixture was concentrated in vacuo to give a clear residue, which was lyophilised overnight to give the product (0.88 g, quant) as a solid.

Chloromethyl 3-(2-(dimethylamino)ethyl)-5-methoxy-1H-indole-1-carboxylate

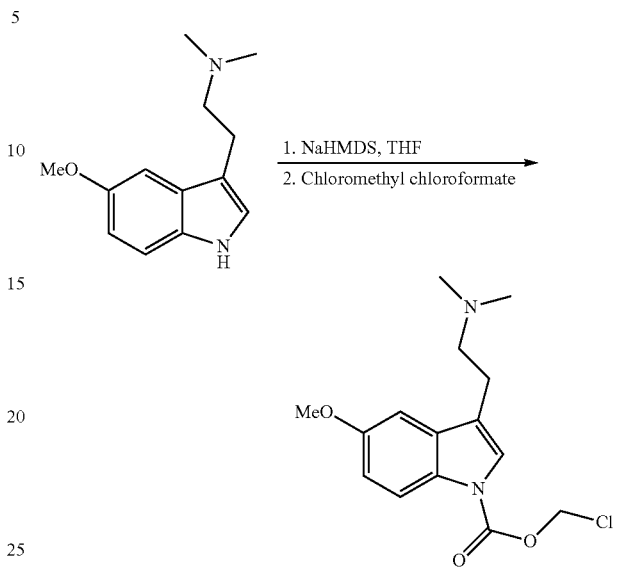

NaHMDS, 1M in THF (1.8 mL, 1.8 mmol) was added to a stirred solution of 5-OMe-DMT (200 mg, 0.92 mmol) in anhydrous THF (13 mL) at −78° C. After 30 min, chloromethyl chloroformate (236 mg, 163 µL, 1.83 mmol) was added dropwise, the mixture was allowed to warm to rt and stirring was continued for 20 h. The mixture was concentrated to dryness and the residue was purified by column chromatography on silica gel, eluting with a gradient of MeOH in EtOAc to give the product (261 mg, 91%) as a semi-solid, containing ~15% of 5-OMe-DMT. LC-MS (+ve mode): m/z=311.05 and 313.05 [M+H]$^+$.

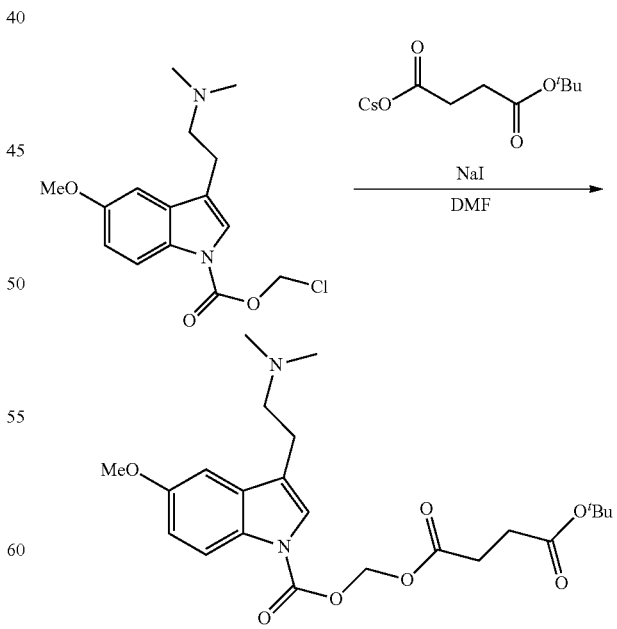

Chloromethyl 3-(2-(dimethylamino)ethyl)-5-methoxy-1H-indole-1-carboxylate (205 mg, 0.66 mmol) was dissolved in DMF (4 mL), then cesium 4-(tert-butoxy)-4- oxobutanoate (202 mg, 0.66 mmol) and NaI (99 mg, 0.66 mmol) were added. The mixture was heated to 60° C. and stirred overnight, then concentrated under vacuum. The residue was purified by column chromatography on silica gel, eluting with a gradient of PE and MeOH in EtOAc to afford Compound 565 (86 mg) as an oil. This was used without further purification. LC-MS (+ve mode): m/z=449.20 [M+H]$^+$.

Example 1-63: 4-(((3-(2-(Dimethylamino)ethyl)-5-methoxy-1H-indole-1-carbonyl)oxy)methoxy)-4-oxobutanoic acid (Compound 566)

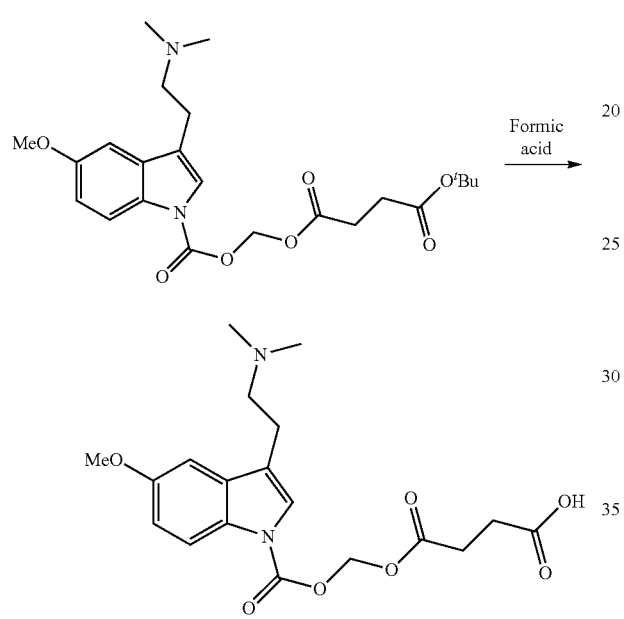

tert-Butyl (((3-(2-(dimethylamino)ethyl)-5-methoxy-1H-indole-1-carbonyl)oxy)methyl) succinate (Compound 564, 19 mg, 0.04 mmol) was stirred in formic acid (0.5 mL) for 2 h, then concentrated under vacuum to afford Compound 566 (17 mg) as a solid. LC-MS (+ve mode): m/z=393.15 [M+H]$^+$.

Example 1-64: 5-(((3-(2-(Dimethylamino)ethyl)-5-methoxy-1H-indole-1-carbonyl)oxy)methoxy)-5-oxopentanoic acid (Compound 567)

Cesium 5-(tert-butoxy)-5-oxopentanoate

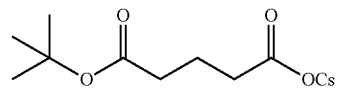

To a solution of pentanedioc acid mono-tert-butyl ester (300 mg, 1.59 mmol) in MeOH (4.40 mL) and H$_2$O (0.44 mL) was added a 20% w/w aqueous solution of Cs$_2$CO$_3$ until pH 7 was achieved. The mixture was concentrated, azeotroping with MeCN (2×10 mL) to give the product as a semi-solid.

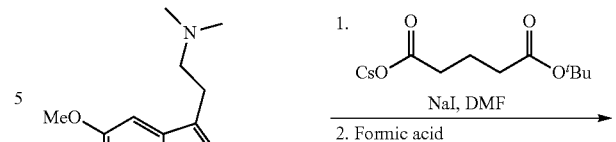

Chloromethyl 3-(2-(dimethylamino)ethyl)-5-methoxy-1H-indole-1-carboxylate formate (50 mg, 0.16 mmol) was dissolved in DMF (1 mL), then cesium 5-(tert-butoxy)-5-oxopentanoate (52 mg, 0.16 mmol) and NaI (24 mg, 0.16 mmol) were added. The mixture was heated to 60° C. and stirred overnight, then concentrated under vacuum to give a solid. The solid was stirred in formic acid (1 mL) for 2 h, then concentrated under vacuum to afford Compound 567 (150 mg) as a solid. LC-MS (+ve mode): m/z=407.15 [M+H]$^+$.

Example 1-65: 6-(((3-(2-(Dimethylamino)ethyl)-5-methoxy-1H-indole-1-carbonyl)oxy)methoxy)-6-oxohexanoic acid (Compound 568)

Cesium 6-(tert-butoxy)-6-oxohexanoate

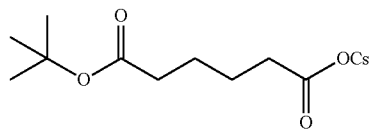

To a solution of 6-(tert-butoxy)-6-oxohexanoic acid (375 mg, 1.85 mmol) in MeOH (7.70 mL) and H$_2$O (0.77 mL) was added a 20% w/w aqueous solution of was added dropwise until pH 7 was achieved. The reaction mixture was concentrated, azeotroping with MeCN (2×10 mL) to give the product as a semi-solid.

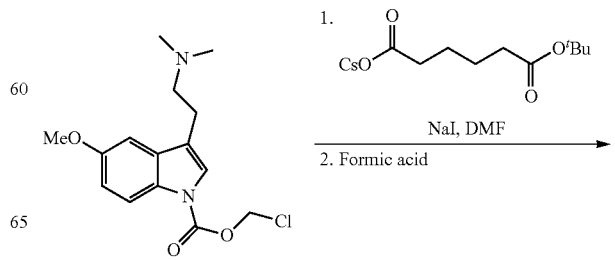

-continued

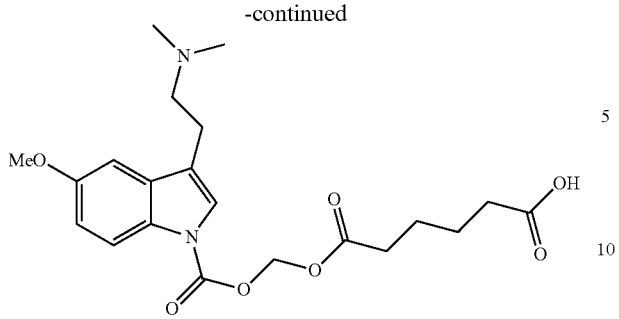

Chloromethyl 3-(2-(dimethylamino)ethyl)-5-methoxy-1H-indole-1-carboxylate formate salt (50 mg, 0.16 mmol) was dissolved in DMF (1 mL), then cesium 6-(tert-butoxy)-6-oxohexanoate (52 mg, 0.16 mmol) and NaI (24 mg, 0.16 mmol) were added. The mixture was heated to 60° C. and stirred overnight, then concentrated under vacuum to give a solid. The solid was stirred in formic acid (1 mL) for 2 h, then concentrated under vacuum to afford Compound 568 (74 mg) as a solid. LC-MS (+ve mode): m/z=421.15 [M+H]$^+$.

Example 1-66: Chloromethyl 3-(2-(dimethylamino) ethyl)-1H-indole-1-carboxylate (Compound 569)

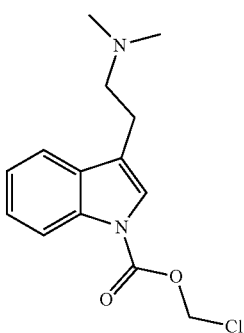 [SMILES: CN(C)CCc1cn(C(=O)OCCl)c2ccccc12]

To a solution of DMT (1.00 g, 5.3 mmol) in anhydrous tetrahydrofuran (60 mL) at −78° C. under an atmosphere of N$_2$ was added NaHMDS, 1M in THF (10.6 mL, 10.6 mmol) and the mixture was stirred for 30 min at −78° C. Chloromethyl chloroformate (1.37 g, 0.94 mL, 10.6 mmol) was added dropwise, the mixture was stirred at −78° C. for 15 min and then warmed to rt and stirred for 2 h. H$_2$O (5 mL) was added, the mixture was concentrated under vacuum and the residue was purified by column chromatography on silica gel, eluting with 0 to 50% MeOH in EtOAc to afford Compound 569 (996 mg) as an oil. LC-MS (+ve mode): m/z=281.10 [M+H]$^+$.

Example 1-67: tert-Butyl (((3-(2-(dimethylamino) ethyl)-1H-indole-1-carbonyl)oxy)methyl) glutarate (Compound 570)

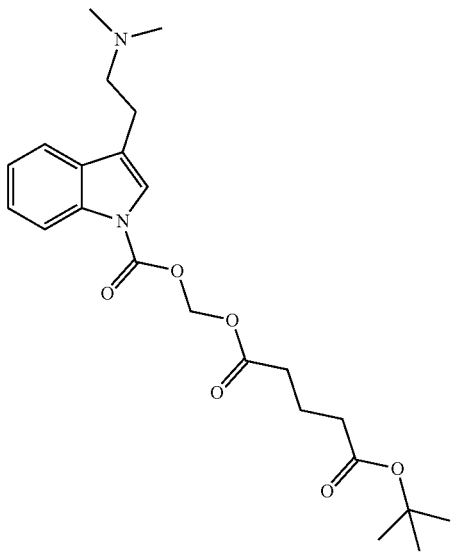 [SMILES: CN(C)CCc1cn(C(=O)OCOC(=O)CCCC(=O)OC(C)(C)C)c2ccccc12]

To a solution of chloromethyl 3-(2-(dimethylamino) ethyl)-1H-indole-1-carboxylate (80 mg, 0.29 mmol) in anhydrous DMF (0.5 mL) under an atmosphere of N$_2$ was added NaI (43 mg, 0.29 mmol) and a solution of cesium 5-(tert-butoxy)-5-oxopentanoate (91 mg, 0.29 mmol) in anhydrous DMF (1 mL). The mixture was stirred at rt overnight, then heated to 80° C. and stirred for 2.5 h. The mixture was cooled to rt and concentrated to afford Compound 570 as an oil. LC-MS (+ve mode): m/z=433.20 [M+H]$^+$.

Example 1-68: 5-(((3-(2-(dimethylamino)ethyl)-1H-indole-1-carbonyl)oxy)methoxy)-5-oxopentanoic acid (Compound 571)

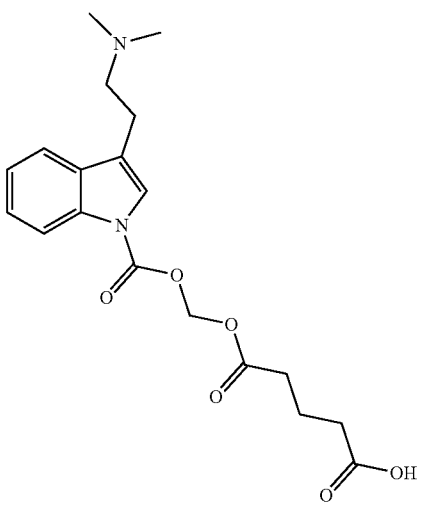 [SMILES: CN(C)CCc1cn(C(=O)OCOC(=O)CCCC(=O)O)c2ccccc12]

To tert-butyl (((3-(2-(dimethylamino)ethyl)-1H-indole-1-carbonyl)oxy)methyl) glutarate (Compound 570) was added formic acid (2 mL) and the mixture was stirred at rt for 1 h, then concentrated under vacuum to afford Compound 571. LC-MS (+ve mode): m/z=377.15 [M+H]$^+$.

Example 1-69: tert-Butyl (((3-(2-(dimethylamino) ethyl)-1H-indole-1-carbonyl)oxy)methyl) adipate (Compound 572)

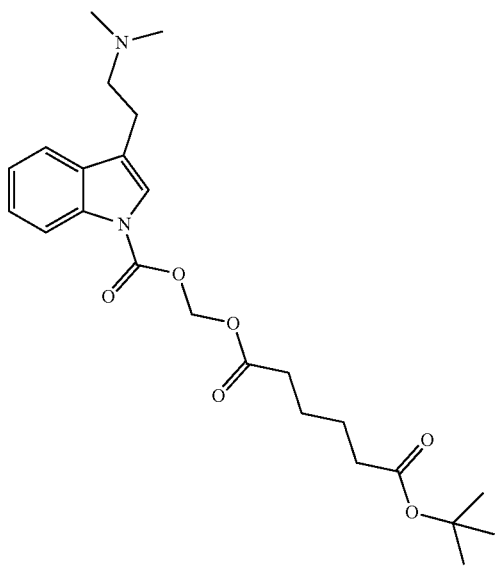 [SMILES: CN(C)CCc1cn(C(=O)OCOC(=O)CCCCC(=O)OC(C)(C)C)c2ccccc12]

To a solution of chloromethyl 3-(2-(dimethylamino) ethyl)-1H-indole-1-carboxylate (80 mg, 0.29 mmol) in anhydrous DMF (0.5 mL) under an atmosphere of $N_2$ was added NaI (43 mg, 0.29 mmol) and a solution of cesium 6-(tert-butoxy)-6-oxohexanoate (91 mg, 0.29 mmol) in anhydrous DMF (1 mL). The mixture was stirred overnight at rt, then heated to 80° C. and stirred for 2.5 h. The mixture was cooled to rt and concentrated under vacuum to afford Compound 572 as an oil. LC-MS (+ve mode): m/z=447.20 [M+H]$^+$.

Example 1-70: 6-(((3-(2-(Dimethylamino)ethyl)-1H-indole-1-carbonyl)oxy)methoxy)-6-oxohexanoic acid (Compound 573)

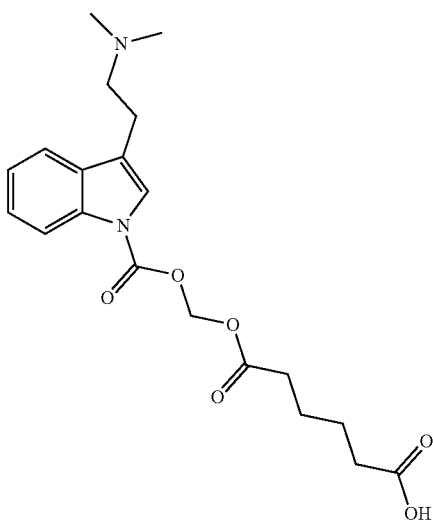 [SMILES: CN(C)CCc1cn(C(=O)OCOC(=O)CCCCC(=O)O)c2ccccc12]

To tert-butyl (((3-(2-(dimethylamino)ethyl)-1H-indole-1-carbonyl)oxy)methyl) adipate (Compound 572) was added formic acid (2 mL) and the reaction mixture was stirred at rt for 0.5 h. The mixture was concentrated under vacuum to afford Compound 573. LC-MS(+ve mode): m/z=391.20 [M+H]$^+$.

Example 1-71: Ethyl 3-(((3-(2-(dimethylamino) ethyl)-1H-indol-1-yl)sulfonyl)oxy)-2,2-dimethylpropanoate (Compound 457)

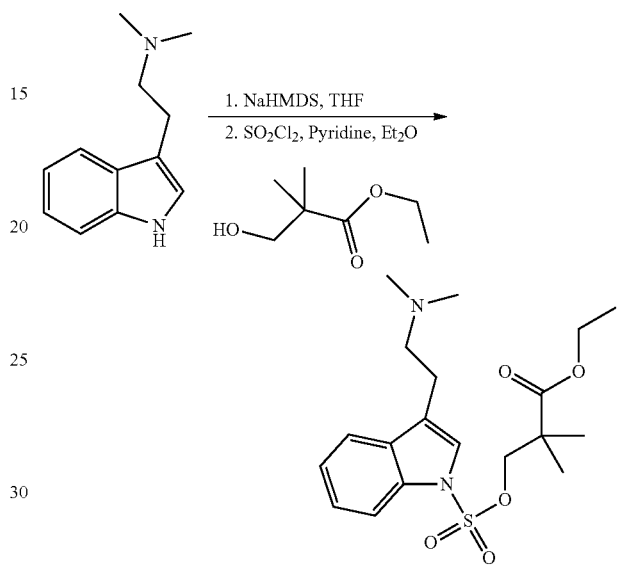

Sulfuryl chloride (143 mg, 86 µL, 1.06 mmol) in Et$_2$O (20 mL) was added dropwise to a solution of ethyl 3-hydroxy-2,2-dimethylpropanoate (254 mg, 1.74 mmol) and pyridine (84 mg, 86 µL, 1.06 mmol) in Et$_2$O (5 mL) at −78° C. and stirring was continued at −78° C. for 30 min, then filtered through Celite and the filtrate was concentrated under vacuum to give a colourless oil which was used directly in the next step.

NaHMDS, 1M in THF (1.12 mL, 1.12 mmol) was added to a solution of DMT (200 mg, 1.06 mmol) in anhydrous THF (5 mL) at −78° C. and stirring was continued at −78° C. 30 min, after which time a THF solution of ethyl 3-((chlorosulfonyl)oxy)-2,2-dimethylpropanoate (3 mL) was added and the mixture was warmed to rt and stirred for 72 h, then concentrated under vacuum to afford Compound 457 (512 mg) as a semi-solid. LC-MS (+ve mode): m/z=397.15 [M+H]$^+$.

Example 1-72: Ethyl 3-(((3-(2-(dimethylamino) ethyl)-5-methoxy-1H-indol-1-yl)sulfonyl)oxy)-2,2-dimethylpropanoate (Compound 433)

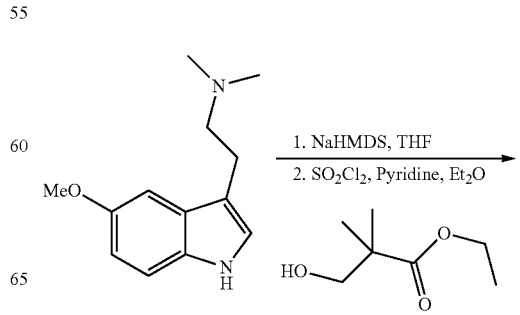

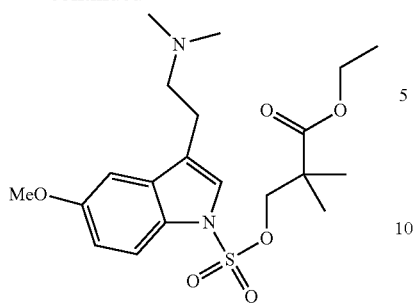

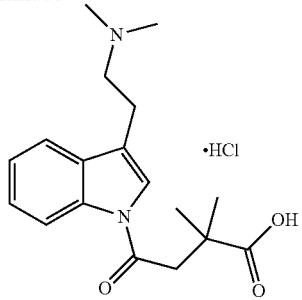

Sulfuryl chloride (143 mg, 86 μL, 1.06 mmol) in Et₂O (20 mL) was added dropwise to a solution of ethyl 3-hydroxy-2,2-dimethylpropanoate (254 mg, 1.74 mmol) and pyridine (84 mg, 86 μL, 1.06 mmol) in Et₂O (5 mL) at −78° C. and stirring was continued at −78° C. for 30 min, then filtered through Celite and the filtrate was concentrated under vacuum to give an oil, which was used directly in the next step.

NaHMDS, 1M in THF (1.12 mL, 1.12 mmol) was added to a solution of 5-OMe-DMT (231 mg, 1.06 mmol) in anhydrous THF (5 mL) at −78° C. and stirring was continued at −78° C. for 30 min, after which time a THF solution of ethyl 3-((chlorosulfonyl)oxy)-2,2-dimethylpropanoate (3 mL) was added. The mixture was warmed to rt and stirred for 72 h, then concentrated under vacuum to afford Compound 433 (574 mg) as a semi-solid. LC-MS (+ve mode): m/z=427.15 [M+H]⁺.

Example 1-73: 4-(3-(2-(dimethylamino)ethyl)-1H-indol-1-yl)-2,2-dimethyl-4-oxobutanoic Acid HCl Salt (Compound 576)

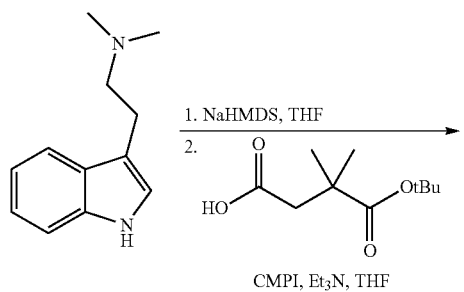

NaHMDS, 1M in THF (2.23 mL, 2.23 mmol) was added to a stirred solution of DMT (400 mg, 2.12 mmol) in anhydrous THF (10 mL) at −78° C. In a separate vessel, 4-(tert-butoxy)-3,3-dimethyl-4-oxobutanoic acid (0.53 g, 2.12 mmol) and 2-chloro-1-methylpyridinium iodide (0.60 g, 2.34 mmol) were dissolved in anhydrous THF (10 mL). Et₃N (472 mg, 0.66 mL, 4.66 mmol) was added and the mixture was stirred at rt. After 30 min, the DMT solution was added and the mixture was stirred at rt for 16 h, then concentrated under vacuum and the residue was purified by column chromatography on silica gel, eluting with a gradient of MeOH in DCM to afford an oil (1.2 g, quant.). TLC: R_f=0.63 (DCM-MeOH, 8:2 v/v); LC-MS (+ve mode): m/z=373.20 [M+H]⁺.

The above material was dissolved in DCM (15 mL) and TFA (12.1 g, 8.2 mL, 106 mmol) was added at rt. The mixture was stirred at rt for 2 h, then concentrated under vacuum and azeotroped with CHCl₃ (3×20 mL) to give a dark residue, which was taken up in 1M HCl(3 mL) and purified by reversed-phase chromatography on silica eluting with a gradient of acetonitrile in 0.02% hydrochloric acid to afford Compound 576 (170 mg, 23% over 2 steps) as a solid. TLC: R_f=0.33 (DCM-MeOH, 8:2 v/v); LC-MS (+ve mode): m/z=317.15 [M+H]⁺; ¹H NMR (300 MHz, CDCl₃) δ 8.39 (dd, J=8.7, 1.8 Hz, 1H, ArH), 7.77 (s, 1H, ArH), 7.67 (m, 1H, ArH), 7.33 (m, 2H, 2×ArH), 3.54 (m, 2H, CH₂), 3.32 (s, 2H, CH₂), 3.22 (m, 2H, CH₂), 3.00 (s, 6H, 2×CH₃), 1.41 (s, 6H, 2×CH₃); ¹³C NMR (75.5 MHz, CDCl₃) δ 181.1, 171.1, 137.4, 130.9, 126.5, 124.7, 124.7, 119.7, 117.7, 117.5, 58.0, 46.2, 43.6, 41.4, 26.2, 21.5.

Example 1-74: 4-(3-(2-(dimethylamino)ethyl)-5-methoxy-1H-indol-1-yl)-2,2-dimethyl-4-oxobutanoic Acid HCl Salt (Compound 577)

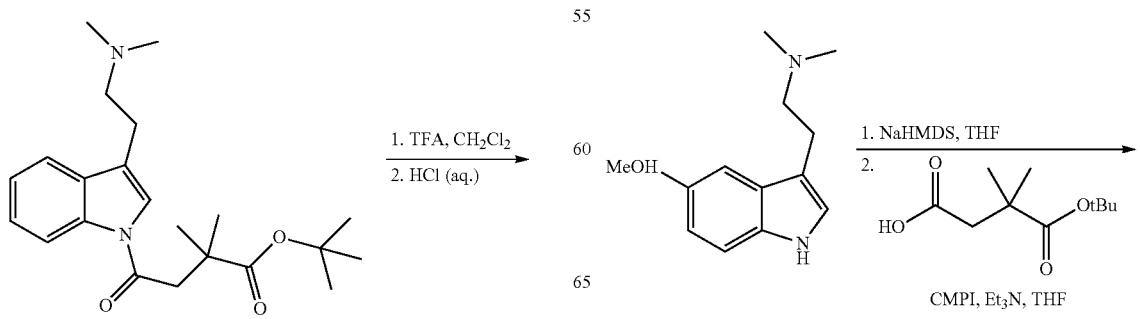

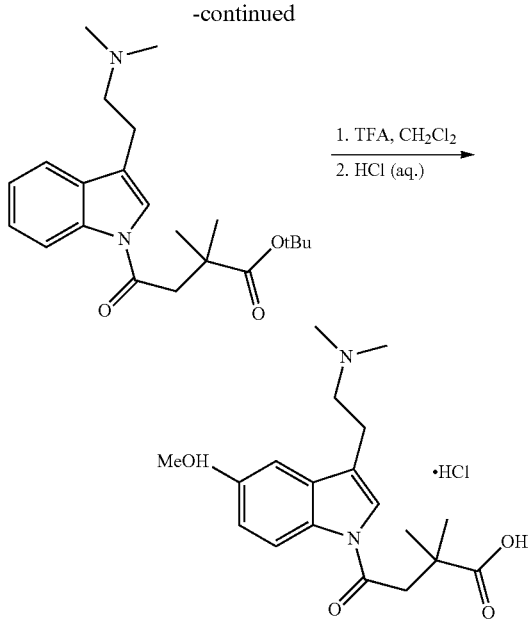

NaHMDS, 1M in THF (0.96 mL, 0.96 mmol) was added to a stirred solution of 5-OMe-DMT (200 mg, 0.92 mmol) in anhydrous THF (5 mL) at −78° C. In a separate vessel, 4-(tert-butoxy)-3,3-dimethyl-4-oxobutanoic acid (187 mg, 0.92 mmol) and 2-chloro-1-methylpyridinium iodide (220 mg, 1.01 mmol) were dissolved in anhydrous THF (5 mL). Et$_3$N (204 mg, 0.28 mL, 2.02 mmol) was added and the mixture was stirred at rt for 30 min, then the 5-OMe-DMT solution was added and the mixture was stirred at rt for 16 h. The solvent was removed under vacuum and the residue was purified by column chromatography on silica gel, eluting with a gradient of MeOH in DCM to afford an oil. TLC: R$_f$=0.68 (DCM-MeOH, 8:2 v/v); LC-MS (+ve mode): m/z=403.20 [M+H]$^+$.

The above material was dissolved in DCM (15 mL) and TFA (2.91 g, 1.96 mL, 25.5 mmol) was added at rt. The mixture was stirred at rt for 2 h, then concentrated under vacuum and azeotroped with CHCl$_3$ (3×20 mL) to give an oil, which was taken up in 0.5 M HCl (2 mL) and purified by reversed-phase chromatography on silica, eluting with a gradient of acetonitrile in 0.02% hydrochloric acid to afford Compound 577 (86 mg, 24% over 2 steps) as a solid. TLC: R$_f$=0.26 (DCM-MeOH, 8:2 v/v); LC-MS (+ve mode): m/z=347.15 [M+H]$^+$; $^1$H NMR (300 MHz, CD$_3$OD) δ 8.27 (d, J=9.0 Hz, 1H, ArH), 7.66 (s, 1H, ArH), 7.12 (d, J=2.4 Hz, 1H, ArH), 6.95 (dd, J=9.0, 2.7 Hz, 1H, ArH), 3.90 (s, 3H, OCH$_3$), 3.51 (m, 2H, CH$_2$), 3.30 (s, 2H, CH$_2$) 3.21 (m, 2H, CH$_2$), 3.02 (s, 6H, 2×CH$_3$), 1.44 (s, 6H, 2×CH$_3$); $^{13}$C NMR (75.5 MHz, CD$_3$OD) δ 180.7, 170.2, 157.5, 131.4, 131.4, 124.6, 118.1, 117.0, 114.3, 102.4, 57.5, 56.1, 45.7, 43.4, 41.0, 26.1, 21.2.

Example 2: Pharmacokinetics of Selected Compounds Following a Single Intravenous or Oral Administration in Rats A pharmacokinetic (PK) study was performed in three male Sprague-Dawley (SD) rats following intravenous (IV) or oral (PO) administration of dimethyltryptamine (DMT), 5-methoxydimethyltryptamine (5-OMe-DMT), Compound 19 or Compound 20 at 1 mg/kg (IV) or 10 mg/kg (PO).

In Vivo Methods.
Rat Strain.

Sprague-Dawley rats were supplied by Charles River (Margate UK) and were specific pathogen free. Male rats weighed between 175-225 g on receipt and were allowed to acclimatise for 5-7 days.

Animal Housing.

Rats were group housed in sterilised individual ventilated cages that exposed the animals at all times to HEPA filtered sterile air. Animals had free access to food and water (sterile) and sterile aspen chip bedding (changed at least once weekly). The room temperature was maintained at 22° C.+/−1° C., with a relative humidity of 60% and maximum background noise of 56 dB. Rats were exposed to 12-hour light/dark cycles.

Treatment.

Each test compound and control (DMT or 5-OMe-DMT) were diluted with 10% v/v DMSO, 40% v/v PEG-400, 50% v/v water. The test compound or the control (DMT or 5-OMe-DMT) were administered in a dose volume of 2 mL/kg for intravenous administration (IV) and 5 mL/kg for oral administration (PO).

Single IV/PO Dose Pharmacokinetics Study in Rats.

Each test compound was administered as a single IV bolus (via a lateral tail-vein) or a single oral gavage in cohorts of 3 rats per administration route. Following dose administrations, a 100 μL whole blood sample (EDTA) was collected via the tail-vein at time-points described in TABLE 8. The blood sample was centrifuged to separate plasma. Approximately 40 μL of the separated plasma was dispensed per time-point, per rat, in a 96 well plate and frozen until analysis. Bioanalysis was carried out on the separated plasma samples.

TABLE 8

Sample collection points for single IV and oral dose pharmacokinetics study.

| Group | Prodrug | Drug | Route | Dose (mg/kg) | Blood sample collection (post dose) | No. of rats |
|---|---|---|---|---|---|---|
| 1 | Cpd 20 | DMT | IV | 1 | 5 min, 15 min, 30 min, 1 h, 2 h, 4 h, 7 h, 24 h | 3 |
| 2 | Cpd 20 | DMT | PO | 10 | 15 min, 30 min, 45 min, 1 h, 2 h, 4 h, 7 h, 24 h | 3 |
| 3 | Cpd 19 | 5-OMe-DMT | IV | 1 | 5 min, 15 min, 30 min, 1 h, 2 h, 4 h, 7 h, 24 h | 3 |
| 4 | Cpd 19 | 5-OMe_DMT | PO | 10 | 15 min, 30 min, 45 min, 1 h, 2 h, 4 h, 7 h, 24 h | 3 |

Bioanalysis Methods.
DMT—Stock Preparation.
  2.4 mL of DMSO was pipetted into an amber vial containing 2.4 mg salt-free DMT. The contents were mixed by vortex to provide a ~1000 μg/mL standard solution in DMSO.
5-OMe-DMT—Stock Preparation.
  2.5 mL of DMSO was pipetted into amber vial containing 2.5 mg salt-free 5-OMe-DMT. The contents were mixed by vortex to provide a ~1000 μg/mL standard solution in DMSO).
Preparation of Calibration and Quality Control Standards.
  Separate calibration curve and QC standards were prepared from individual standard to minimise the chance of MRM crosstalk during analysis. The dilutions were performed as detailed in TABLE 9 and TABLE 10. Spiking volumes were 3 μL per 30 μL plasma.

TABLE 9

Preparation of 1 to 5000 ng/mL Cal and QC working solution.

| Working Solution ID | Solution Prepared From | Starting Solution Conc. (μg/mL) | Starting Solution Volume (μL) |
|---|---|---|---|
| Preparation of Calibrator Working Solutions | | | |
| DMSO | — | — | — |
| WS1 | DMSO | 1000 | 50 |
| WS2 | DMSO | 1000 | 25 |
| WS3 | DMSO | 1000 | 10 |
| WS4 | WS1 | 50 | 100 |
| WS5 | WS2 | 25 | 100 |
| WS6 | WS3 | 10 | 100 |
| WS7 | WS4 | 5 | 100 |
| WS8 | WS5 | 2.5 | 100 |
| WS9 | WS6 | 1 | 100 |
| WS10 | WS7 | 0.5 | 100 |
| WS11 | WS8 | 0.25 | 100 |
| WS12 | WS9 | 0.1 | 100 |
| Preparation of QC Working Solutions | | | |
| DMSO | — | — | — |
| QC-WS1 | DMSO | 1000 | 40 |
| QC-WS2 | QC-WS1 | 40 | 100 |
| QC-WS3 | QC-WS2 | 4 | 100 |
| QC-WS4 | QC-WS3 | 0.4 | 100 |

TABLE 10

Preparation of 1 to 5000 ng/mL Cal and QC working solution (cont.).

| Working Solution ID | 50/50 MeOH/H2O Volume (μL) | Working Solution Conc. (μg/mL) | Calibrant Conc. (ng/mL) | Calibrant ID (for sample list) |
|---|---|---|---|---|
| Preparation of Calibrator Working Solutions | | | | |
| DMSO | — | 1000 | — | — |
| WS1 | 950 | 50 | 5000 | Cal 12 5000 ng/mL |
| WS2 | 975 | 25 | 2500 | Cal 11 2500 ng/mL |
| WS3 | 990 | 10 | 1000 | Cal 10 1000 ng/mL |
| WS4 | 900 | 5 | 500 | Cal 9 500 ng/mL |
| WS5 | 900 | 2.5 | 250 | Cal 8 250 ng/mL |
| WS6 | 900 | 1 | 100 | Cal 7 100 ng/mL |
| WS7 | 900 | 0.5 | 50 | Cal 6 50 ng/mL |
| WS8 | 900 | 0.25 | 25 | Cal 5 25 ng/mL |
| WS9 | 900 | 0.1 | 10 | Cal 4 10 ng/mL |
| WS10 | 900 | 0.05 | 5 | Cal 3 5 ng/mL |
| WS11 | 900 | 0.025 | 2.5 | Cal 2 2.5 ng/mL |
| WS12 | 900 | 0.01 | 1 | Cal 1 1 ng/mL |
| Preparation of QC Working Solutions | | | | |
| DMSO | — | 1000 | — | — |
| QC-WS1 | 960 | 40 | 4000 | QC 4 4000 ng/mL |
| QC-WS2 | 900 | 4 | 400 | QC 3 400 ng/mL |
| QC-WS3 | 900 | 0.4 | 40 | QC 2 40 ng/mL |
| QC-WS4 | 900 | 0.04 | 4 | QC 1 4 ng/mL |

All samples were diluted to volume with 50:50 methanol/water (v/v) in individual 1.5 mL Eppendorf tubes and mixed by vortexing.
  The control matrix was rat plasma (male Sprague Dawley, EDTA). Calibration and quality control (QC) standards were prepared by spiking control matrix with working solutions containing DMT or 5OMe-DMT.
Dose Formulation Samples.
  Dose formulation samples were diluted in two steps with 50:50 (v/v) methanol/water to an appropriate concentration, then diluted 10:90 (v/v) with control matrix to match to the calibration standard in plasma.
Sample Extraction Procedure.
  Calibration and QC standards, incurred samples, blank matrix and dose formulation samples were extracted by protein precipitation, via the addition of a bespoke acetonitrile ($CH_3CN$)-based Internal Standard (IS) solution, containing compounds including Metoprolol and Rosuvastatin, both of which were monitored for during analysis. Following centrifugation, a 40 μL aliquot of supernatant was diluted by the addition of 80 μL water. The prepared sample extracts were analysed by LC-MS/MS.
Example Bioanalytical Method and Assay Procedure.
  1 According to the plate layout, aliquot to wells in 0.8 mL 96-well plate (Abgene). 30 μL for Calibration, QC standards, blanks and dose formulation check.
  2 Prepare Calibration and QC standards according to the assay information. Dilute dose formulation according to the assay information. Aliquot incurred samples according to the plate layout & assay information.
  3 Add 90 μL of $CH_3CN$ internal standard and vortex mix for 5 minutes at 850 rpm
  4 Centrifuge at nominally 4000 rpm for 10 minutes
  6 Transfer 40 μL of supernatant into a new 0.8 mL Abgene plate.
  6 Add 80 μL of water to all transferred supernatant.
  7 Vortex mix for 30 seconds at 1400 rpm
  8 Analyse immediately by LC-MS/MS or store at +4° C. until analysis.
  The analysis was performed using the following solvent system and gradient described in TABLE 11.

TABLE 11

| Instrument Name | Agilent ™ 1290 Infinity Binary HPLC Pump Column Oven Agilent ™ 1290 Infinity HPLC dual needle injection autosampler |
|---|---|
| Column | Kinetex ™ XB-C18, 2.6 μm, 50 × 2.1 mm |
| Column Temperature | 50° C. |
| Autosampler Temperature | 10° C. |
| Mobile Phase | Eluent A: 2.5 mmol/L ammonium formate (aq) + 0.1% formic acid (v/v) |
| | Eluent B: Methanol |

TABLE 11-continued

|  | Time (min) | Flow Rate (μl/min) | % Mobile Phase A | % Mobile Phase B |
|---|---|---|---|---|
| Gradient Profile | 0 | 800 | 98 | 2 |
|  | 0.1 | 800 | 98 | 2 |
|  | 1 | 800 | 5 | 95 |
|  | 1.5 | 800 | 5 | 95 |
|  | 1.55 | 800 | 98 | 2 |
|  | 1.8 | 800 | 98 | 2 |
| Flow | 0.8 mL/min | | | |
| Stop time | 1.8 minutes | | | |
| Injection Volume | 2 μL | | | |

Mass spectrometer parameters for detection of DMT and 5OMe-DMT in blood plasma are provided in TABLE 12.

TABLE 12

Instrument: ABSciex 6500 QTrap using an ESI source in positive ion mode.

| Compound | Precursor ion (m/z) | Product ion (m/z) | Dwell time (ms) | DP (V) | CE (V) | CXP (V) | Ionisation Mode |
|---|---|---|---|---|---|---|---|
| DMT | 189.1 | 58.1 | 10.0 | 25.0 | 16.3 | 6.8 | +ve |
| DMT | 189.1 | 144.3 | 10.0 | 25.0 | 24.3 | 15.3 | +ve |
| OMe-DMT | 219.1 | 58.0 | 10.0 | 21.4 | 16.9 | 13.2 | +ve |
| OMe-DMT | 219.1 | 159.2 | 10.0 | 21.4 | 36.4 | 18.6 | +ve |

Example 2-1: In Vivo Pharmacokinetic Analysis of DMT

The pharmacokinetic properties of DMT after IV (1 mg/kg) and oral administration (10 mg/kg) in a rat model were assessed. The PK parameters of DMT are summarized in Table 2-1. The mean concentration-time profiles of DMT following oral dosing of DMT to Male SD rats (1 mg/kg for IV dosing, and 10 mg/kg for oral dosing) are shown in FIG. 1.

TABLE 2-1

PK Parameters of DMTH

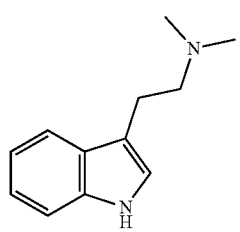

| PK Parameter | DMT IV 1 mg/kg Plasma Mean / Median | SD | DMT PO 10 mg/kg Plasma Mean / Median | SD | DMT IV 1 mg/kg Plasma (t= 0 to 1hr) Mean / Median | SD | DMT PO 10 mg/kg Plasma (t= 0 to 1hr) Mean / Median | SD |
|---|---|---|---|---|---|---|---|---|
| Dose (mg/kg) | 1.00 | — | 10.0 | — | 1.00 | — | 10.0 | — |
| C0/Cmax (ng/mL) | 2001 | — | 13.1 | 3.93 | 2001 | — | 8.87 | 7.63 |
| C0/Cmax (nM) | 10629 | — | 69.4 | 20.9 | 10629 | — | 47.1 | 40.5 |
| Clast (ng/mL) | 7.12 | — | 1.52 | 0.556 | 5.51 | — | 3.18 | 1.25 |
| tlast (h) | 1.50 | — | 24.0 | — | 1.00 | — | 1.02 | — |
| tmax (h) | — | — | 2.00 | — | — | — | 2.00 | — |
| t1/2 (h) | 0.146 | — | 21.1 | 6.22 | 0.140 | — | — | — |
| MRT (h) | 0.152 | — | — | — | 0.132 | — | — | — |
| Vdss (L/kg) | 0.774 | — | — | — | 0.645 | — | — | — |
| CL/CL_F (mL/min/kg) | 85.8 | — | 1639 | 503 | 87.1 | — | — | — |

TABLE 2-1-continued

PK Parameters of DMTH

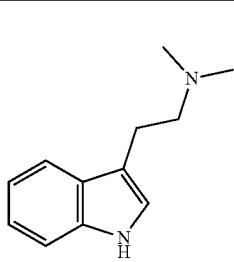

| PK Parameter | DMT IV 1 mg/kg Plasma Mean / Median | SD | DMT PO 10 mg/kg Plasma Mean / Median | SD | DMT IV 1 mg/kg Plasma (t= 0 to 1hr) Mean / Median | SD | DMT PO 10 mg/kg Plasma (t= 0 to 1hr) Mean / Median | SD |
|---|---|---|---|---|---|---|---|---|
| AUCinf (ng.hr/mL) | 216 | — | — | — | 214 | — | — | — |
| AUCinf (nM.hr) | 1145 | — | — | — | 1136 | — | — | — |
| AUC0-t (ng.hr/mL) | 214 | — | 59.1 | 3.65 | 213 | — | 4.51 | 2.86 |
| AUC0-t (nM.hr) | 1136 | — | 314 | 19.4 | 1129 | — | 23.9 | 15.2 |
| Fraction Absorbed | — | — | — | — | — | — | — | — |
| Bioavailability (%) Using AUCinf | — | — | — | — | — | — | — | — |
| Bioavailability (%) Using AUC0-t | — | — | — | — | — | — | 0.212 | 0.134 |
| Number of Points used for Lambda z | 3.00 | — | 3.33 | 0.577 | 3.50 | — | — | — |
| AUC % Extrapolation to infinity | 0.690 | — | 42.6 | 14.3 | 0.502 | — | — | — |
| AUC % Back Extrapolation to C0 | 66.4 | — | — | — | 67.2 | — | — | — |

Example 2-2: In Vivo Pharmacokinetic Analysis of 5-MeO-DMT

Figure 2:
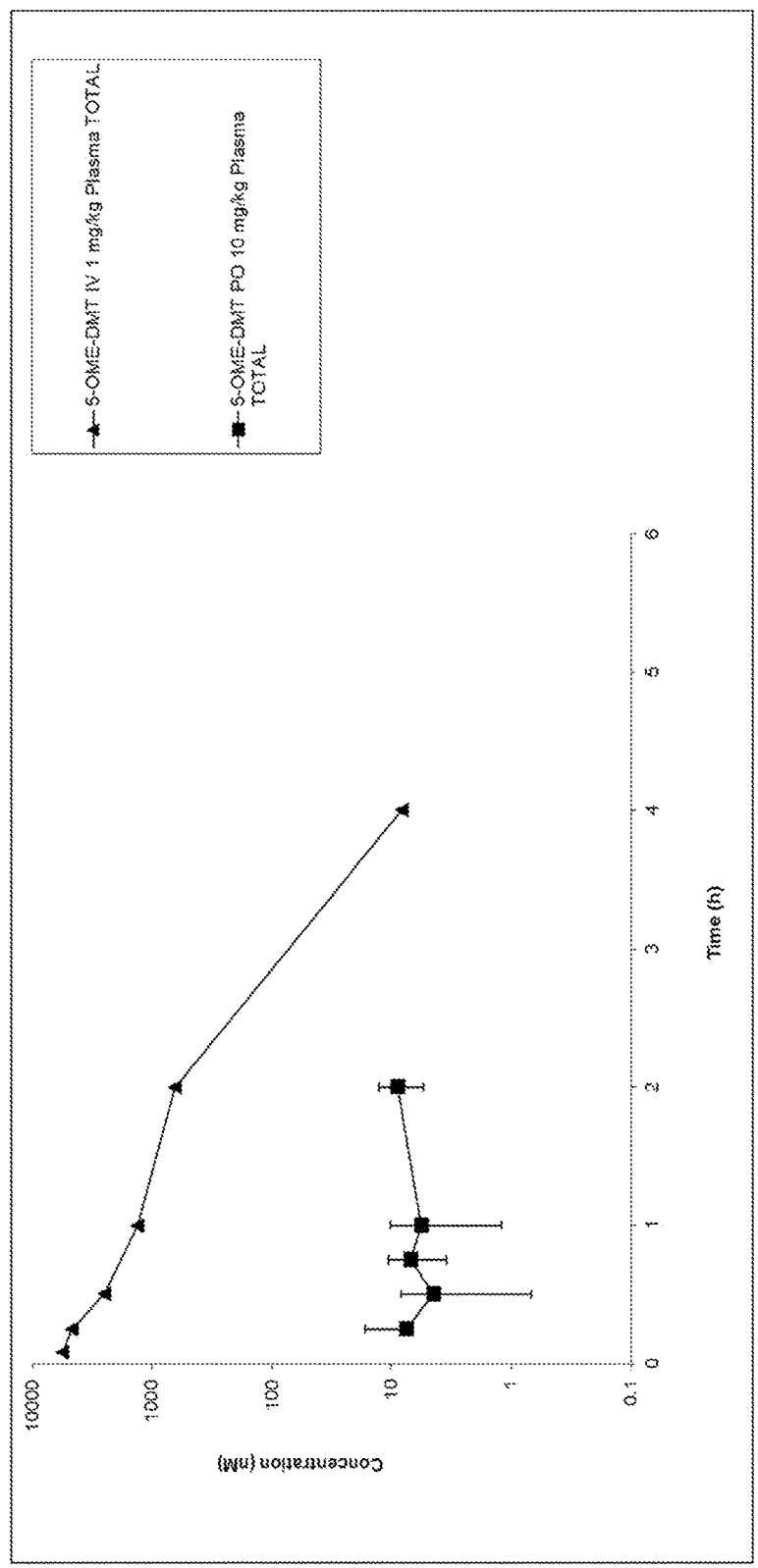
FIG. 2 shows the mean concentration-time profiles of DMT following oral dosing of 5-MeO-DMT to Male SD rats (1 mg/kg for IV dosing, and 10 mg/kg for oral dosing).

The pharmacokinetic properties of 5-MeO-DMT after IV (1 mg/kg) and oral administration (10 mg/kg) in a rat model were assessed. The PK parameters of 5-MeO-DMT are summarized in Table 2-2. The mean concentration-time profiles of DMT following oral dosing of 5-MeO-DMT to Male SD rats (1 mg/kg for IV dosing, and 10 mg/kg for oral dosing) are shown in FIG. 2.

TABLE 2-2

PK Parameters of 5-MeO-DMT

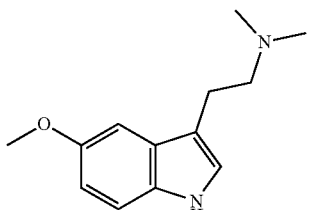

| PK Parameter | 5-MeO-DMT IV 1 mg/kg Plasma Mean / Median | SD | 5-MeO-DMT PO 10 mg/kg Plasma Mean / Median | SD |
|---|---|---|---|---|
| Dose (mg/kg) | 1.00 | — | 10.0 | — |
| C0/Cmax (ng/mL) | 1889 | — | 3.03 | 1.55 |

TABLE 2-2-continued

PK Parameters of 5-MeO-DMT

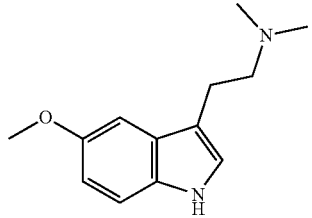

| PK Parameter | 5-MeO-DMT IV 1 mg/kg Plasma Mean / Median | SD | 5-MeO-DMT PO 10 mg/kg Plasma Mean / Median | SD |
|---|---|---|---|---|
| C0/Cmax (nM) | 8655 | — | 13.9 | 7.09 |
| Clast (ng/mL) | 1.68 | — | 1.95 | 0.784 |
| tlast (h) | 5.50 | — | 2.00 | — |
| tmax (h) | — | — | 2.00 | — |
| t1/2 (h) | 0.510 | — | — | — |
| MRT (h) | 0.624 | — | — | — |
| Vdss (L/kg) | 0.818 | — | — | — |
| CL/CL_F (mL/min/kg) | 24.6 | — | — | — |
| AUCinf (ng.hr/mL) | 1081 | — | — | — |
| AUCinf (nM.hr) | 4953 | — | — | — |
| AUC0-t (ng.hr/mL) | 1080 | — | — | — |

TABLE 2-2-continued

PK Parameters of 5-MeO-DMT

|  | 5-MeO-DMT IV 1 mg/kg Plasma | | 5-MeO-DMT PO 10 mg/kg Plasma | |
|---|---|---|---|---|
| PK Parameter | Mean / Median | SD | Mean / Median | SD |
| AUC0-t (nM.hr) | 4948 | — | — | — |
| Number of Points used for Lambda z | 6.00 | — | — | — |
| AUC % Extrapolation to infinity | 0.204 | — | — | — |
| AUC % Back Extrapolation to C0 | 26.8 | — | — | — |

Example 2-3: Pharmacokinetic Analysis of Compound 20

Figure 3:
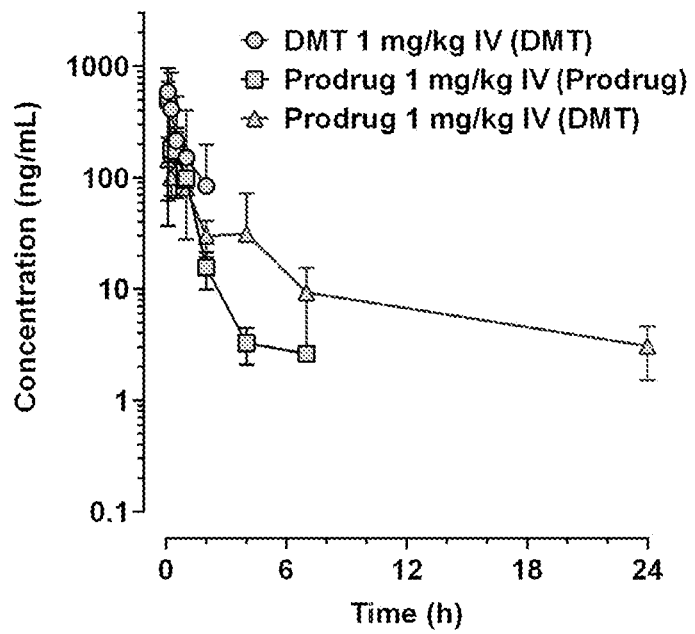
FIG. 3 depicts the time course of blood plasma concentrations of N,N-dimethyltryptamine (DMT) and corresponding prodrug Compound 20 in Sprague-Dawley rats that have been intravenously administered (IV) Compound 20 at 1 mg/kg (Panel A) or orally administered (PO) Compound 20 at 10 mg/kg (Panel B).
Figure 3:
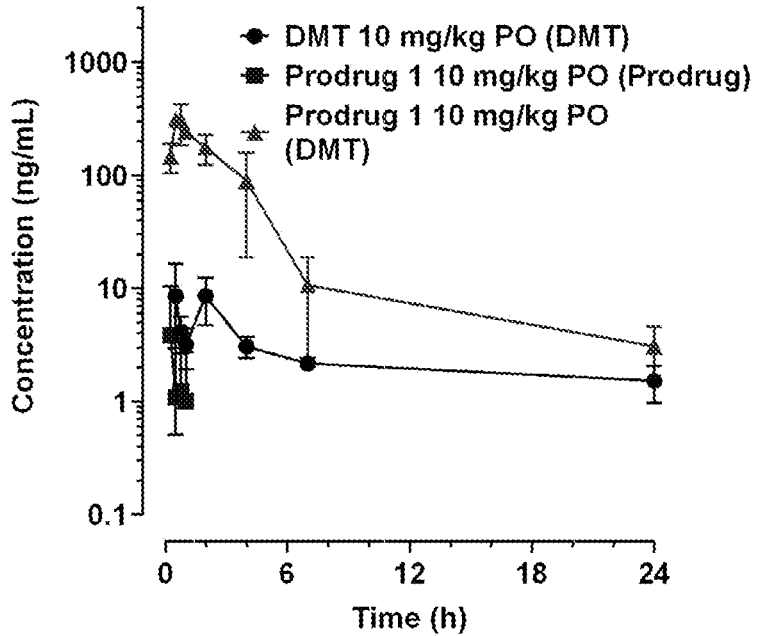

FIG. 3, Panel A is a chart that depicts (1) the time course of blood plasma concentrations of N,N-dimethyltryptamine (DMT) (trianglular points) and Compound 20 (square points) in Sprague-Dawley rats that were intravenously (IV) administered Compound 20 at 1 mg/kg, and (2) the time course of blood plasma concentrations of N,N-dimethyltryptamine (DMT) in Sprague-Dawley rats intravenously (IV) administered 1 mg/kg DMT as a control (circle points).

FIG. 3, Panel B is a chart that depicts (1) the time course of blood plasma concentrations of N,N-dimethyltryptamine (DMT) (trianglular points) and Compound 20 (square points) in Sprague-Dawley rats that were orally (PO) administered Compound 20 at 10 mg/kg, and (2) the time course of blood plasma concentrations of N,N-dimethyltryptamine (DMT) in Sprague-Dawley rats orally (PO) administered 10 mg/kg DMT as a control (circle points). TABLE 2-3 provides corresponding quantitative values for the data series represented by triangular points in FIG. 3, Panel B.

TABLE 2-3

| | Summary of DMT conc. determined following PO dosing of Compound 20 to male Sprague Dawley rat at 10 mg/kg | |
|---|---|---|
| Nominal Sampling Timepoint (h) | Mean Concentration (nM) | SD (nM) |
| 0.25 | 782 | 223 |
| 0.50 | 1637 | 197 |
| 0.75 | 1619 | 639 |
| 1.00 | 1308 | 196 |
| 2.00 | 936 | 282 |
| 4.00 | 473 | 374 |
| 7.00 | 56.8 | 43.9 |
| 24.00 | 16.28 | 8.26 |

The pharmacokinetic properties of Compound 20 after IV or oral administration in a rat model were assessed. Compound 20: Chemical name: ethyl 3-[2-(dimethylamino) ethyl]indole-1-carboxylate; Structural class: carbamate; Mechanistic class: presumed carboxyesterases.

Figure 4:
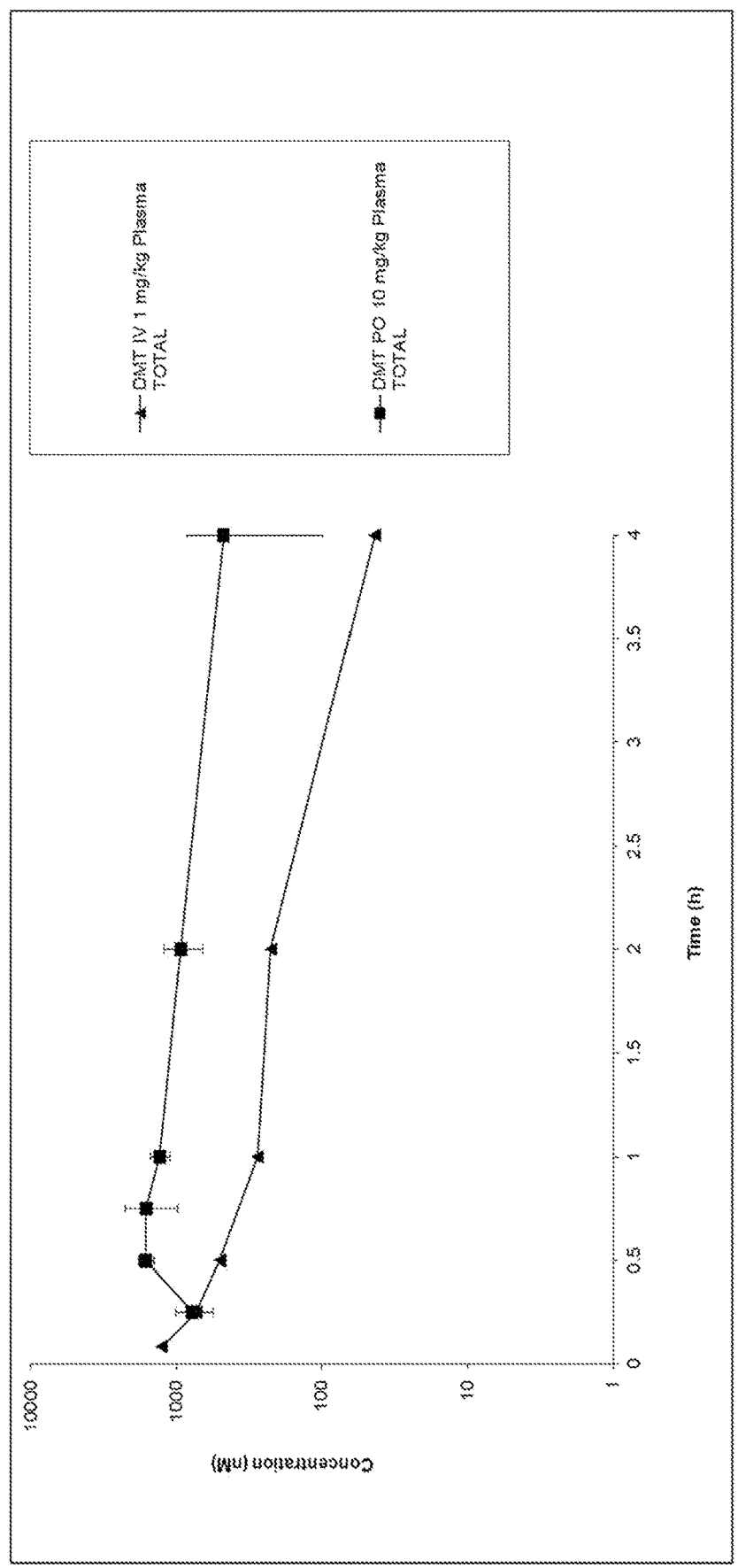
FIG. 4 shows the mean concentration-time profiles of DMT following IV or oral dosing of Compound 20 to Male SD rats (1 mg/kg for IV dosing, 10 mg/kg for oral dosing).
Figure 5:
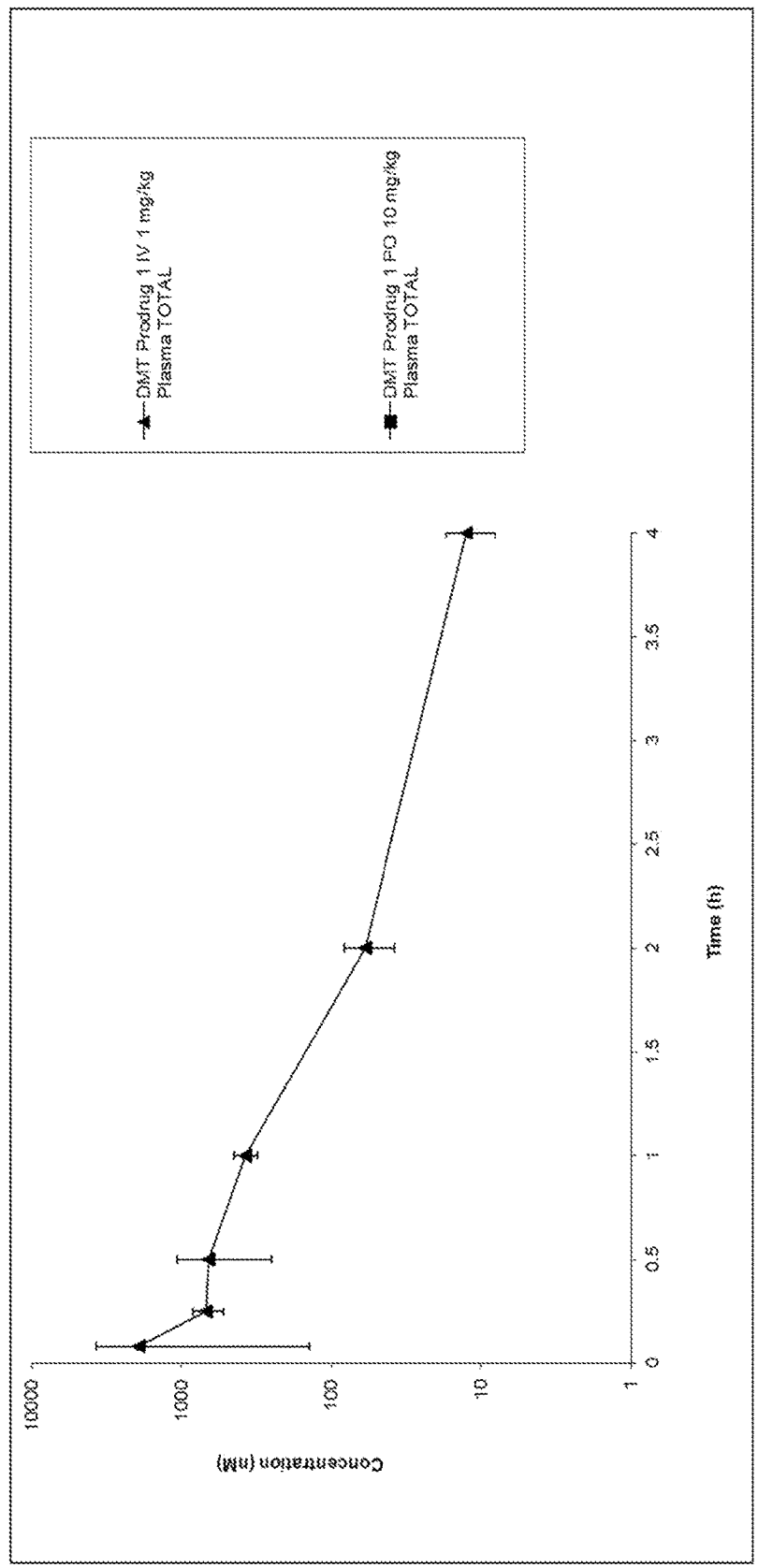
FIG. 5 shows the mean concentration-time profiles of Compound 20 following IV or oral dosing of Compound 20 to Male SD rats (1 mg/kg for IV dosing, 10 mg/kg for oral dosing).

The PK parameters of Compound 20 are summarized in Table 2-3A. The mean concentration-time profiles of DMT following IV or oral dosing of Compound 20 to Male SD rats (1 mg/kg for IV dosing, 10 mg/kg for oral dosing) are shown in FIG. 4. The mean concentration-time profiles of Compound 20 following IV or oral dosing of Compound 20 to Male SD rats (1 mg/kg for IV dosing, 10 mg/kg for oral dosing) are shown in FIG. 5.

TABLE 2-3A

| | PK parameters of Compound 20 after IV or Oral Administration of Compound 20 | | | |
|---|---|---|---|---|
| | Compound 20 IV 1 mg/kg Plasma | | Compound 20 PO 10 mg/kg Plasma | |
| PK Parameter | Mean/Median | SD | Mean/Median | SD |
| Dose (mg/kg) | 1.00 | — | 10.0 | — |
| C0/Cmax (ng/mL) | 936 | 1100 | 11.5 | — |
| C0/Cmax (nM) | 3594 | 4228 | 44.3 | — |
| Clast (ng/mL) | 3.26 | 1.20 | 3.01 | — |
| tlast (h) | 4.00 | | 1.00 | — |
| tmax (h) | — | | 0.250 | — |
| t½ (h) | 0.614 | 0.0440 | — | — |
| MRT (h) | 0.810 | 0.216 | — | — |
| Vdss (L/kg) | 3.53 | 2.05 | — | — |
| CL/CL_F (mL/min/kg) | 67.9 | 27.2 | — | — |
| AUCinf (ng · hr/mL) | 282 | 138 | — | — |
| AUCinf (nM · hr) | 1084 | 530 | — | — |
| AUC0-t (ng · hr/mL) | 279 | 137 | 4.78 | — |
| AUC0-t (nM · hr) | 1072 | 526 | 18.4 | — |
| AUC % Extrapolation to infinity | 1.073 | 0.2440 | — | — |
| AUC % Back Extrapolation to C0 | 17.5 | 11.8 | — | — |

Example 2-4: In Vivo Pharmacokinetic Analysis of Compound 19

Figure 6:
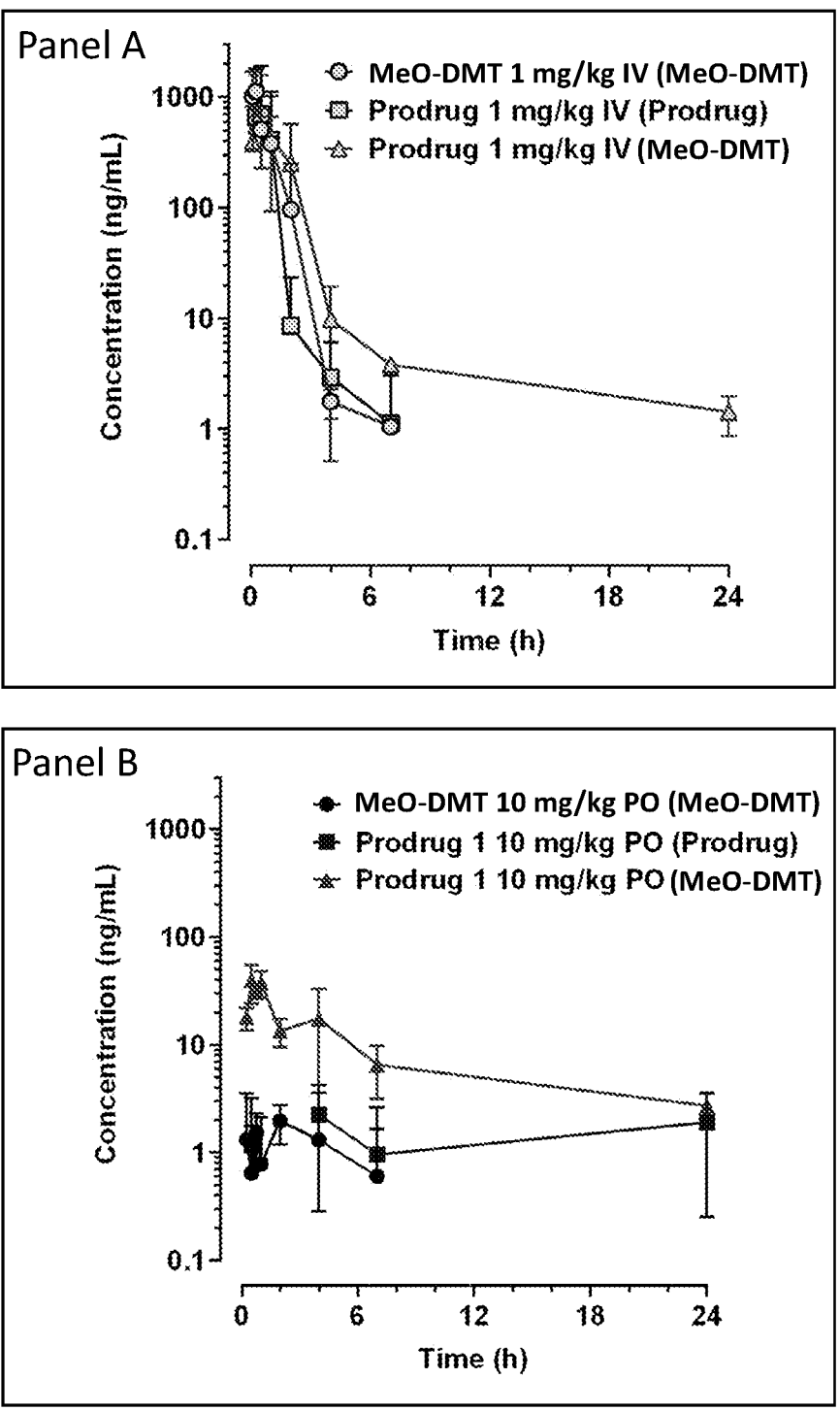
FIG. 6 depicts the time course of blood plasma concentrations of 5-methoxy-N,N-dimethyltryptamine (5-MeO-DMT) and corresponding prodrug Compound 19 in Sprague-Dawley rats that have been intravenously administered (IV) Compound 19 at 1 mg/kg (Panel A) or orally administered (PO) Compound 19 at 10 mg/kg (Panel B).

FIG. 6, Panel A is a chart that depicts (1) the time course of blood plasma concentrations of 5-methoxy-N,N-dimethyltryptamine (5-MeO-DMT) (trianglular points) and Compound 19 (square points) in Sprague-Dawley rats that were intravenously (IV) administered Compound 19 at 1 mg/kg, and (2) the time course of blood plasma concentrations of 5-methoxy-N,N-dimethyltryptamine (5-MeO-DMT) in Sprague-Dawley rats intravenously (IV) administered 1 mg/kg 5-MeO-DMT as a control (circle points).

FIG. 6, Panel B is a chart that depicts (1) the time course of blood plasma concentrations of 5-methoxy-N,N-dimethyltryptamine (5-MeO-DMT) (trianglular points) and Compound 19 (square points) in Sprague-Dawley rats that were orally (PO) administered Compound 19 at 10 mg/kg, and (2) the time course of blood plasma concentrations of 5-methoxy-N,N-dimethyltryptamine (5-MeO-DMT) in Sprague-Dawley rats orally (PO) administered 10 mg/kg 5-MeO-DMT as a control (circle points). TABLE 2-4 provides corresponding quantitative values for the data series represented by triangular points in FIG. 6, Panel B.

TABLE 2-4

| | Summary of 5-OMe-DMT conc. determined following PO dosing of Compound 19 to male Sprague Dawley rat at 10 mg/kg | |
|---|---|---|
| Nominal Sampling Timepoint (h) | Mean Concentration (nM) | SD (nM) |
| 0.25 | 81.9 | 19.7 |
| 0.50 | 181 | 69.5 |
| 0.75 | 146 | 23.9 |
| 1.00 | 173 | 48.4 |
| 2.00 | 61.5 | 18.2 |
| 4.00 | 80.1 | 70.3 |
| 7.00 | 29.9 | 15.4 |
| 24.0 | 12.5 | 4.12 |

The pharmacokinetic properties of Compound 19 after IV or oral administration in a rat model were assessed. Compound 19: Chemical name: ethyl 3-[2-(dimethylamino)ethyl]-5-methoxy-indole-1-carboxylate; Structural class: carbamate; Mechanistic class: presumed carboxyesterases.

Figure 7:
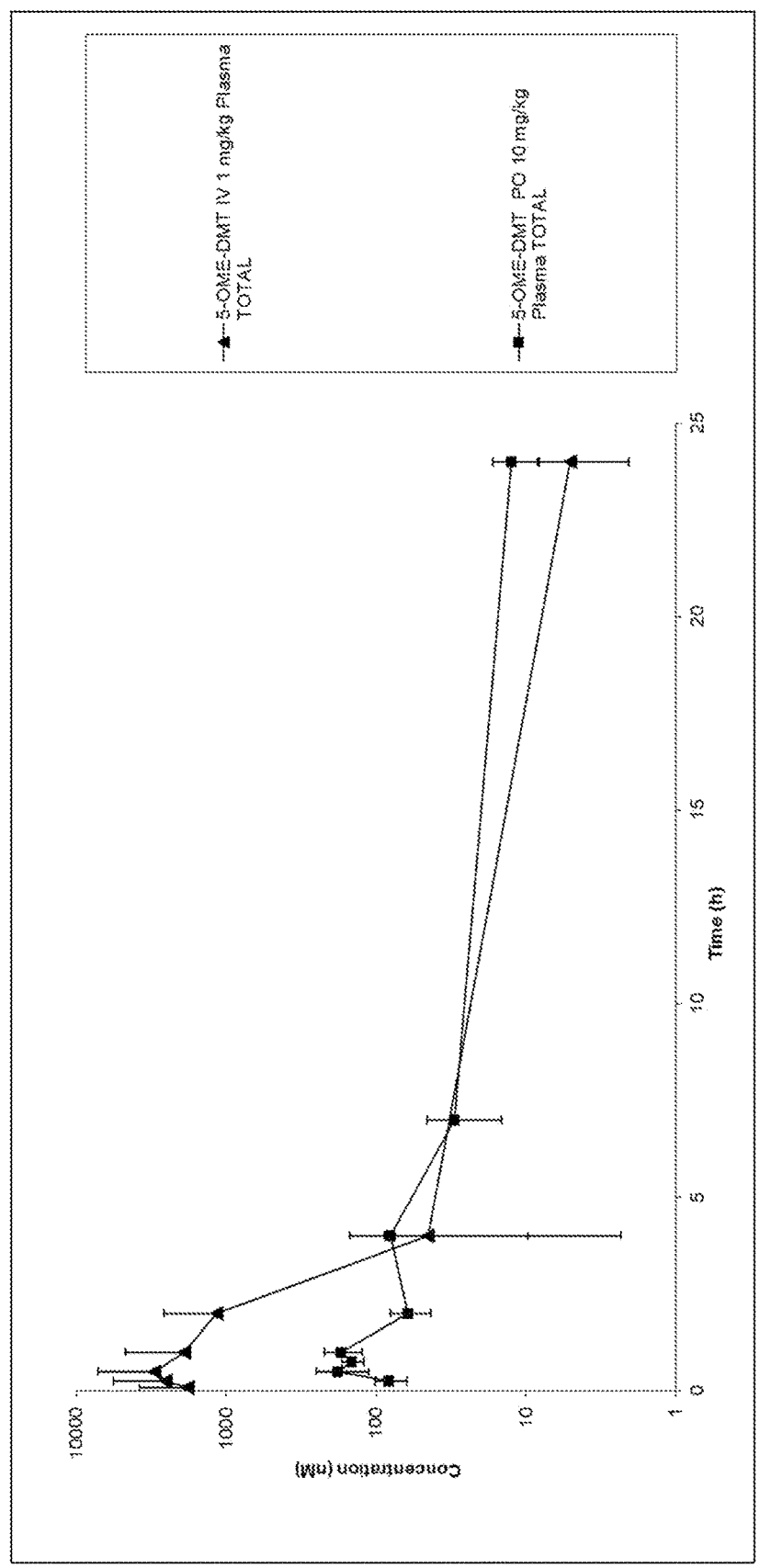

The PK parameters of Compound 19 are summarized in Table 24A. The mean concentration-time profiles of 5-methoxy-N,N-dimethyltryptamine (5-MeO-DMT) following IV or oral dosing of Compound 19 to Male SD rats (1 mg/kg for IV dosing, 10 mg/kg for oral dosing) are shown in FIG. 7.

TABLE 2-4A

| | PK Parameters of Compound 19 after IV or Oral Administration of Compound 19 | | | |
|---|---|---|---|---|
| | Compound 19 IV 1 mg/kg Plasma | | Compound 19 PO 1 mg/kg Plasma | |
| PK Parameter | Mean/Median | SD | Mean/Median | SD |
| Dose (mg/kg) | 1.00 | — | 10.0 | — |
| C0/Cmax (ng/mL) | 53726 | — | 2.37 | 2.05 |
| C0/Cmax (nM) | 185009 | — | 8.15 | 7.06 |
| Clast (ng/mL) | 2.95 | — | 1.90 | 1.64 |
| tlast (h) | 5.50 | — | 24.0 | — |
| tmax (h) | — | — | — | — |
| t½ (h) | — | — | — | — |
| AUC0-t (ng · hr/mL) | 4172 | — | 68.8 | — |
| AUC0-t (nM · hr) | 14367 | — | 237 | — |

TABLE 2-4A-continued

| | PK Parameters of Compound 19 after IV or Oral Administration of Compound 19 | | | |
|---|---|---|---|---|
| | Compound 19 IV 1 mg/kg Plasma | | Compound 19 PO 1 mg/kg Plasma | |
| PK Parameter | Mean/Median | SD | Mean/Median | SD |
| Number of Points used for Lambda z | 3.00 | — | — | — |
| AUC % Extrapolation to infinity | 0.104 | — | — | — |
| AUC % Back Extrapolation to C0 | 59.7 | — | — | — |

Example 2-5. Diisopropylphosphonate DMT Prodrug

Chemical name: 2-(1-diisopropoxyphosphorylindol-3-yl)-N,N-dimethyl-ethanamine

Structural class: phosphonate

Mechanistic class: presumed carboxyesterases+presumed phosphatases

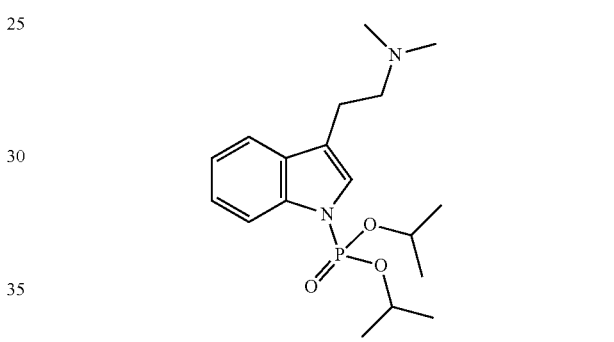

Figure 8:
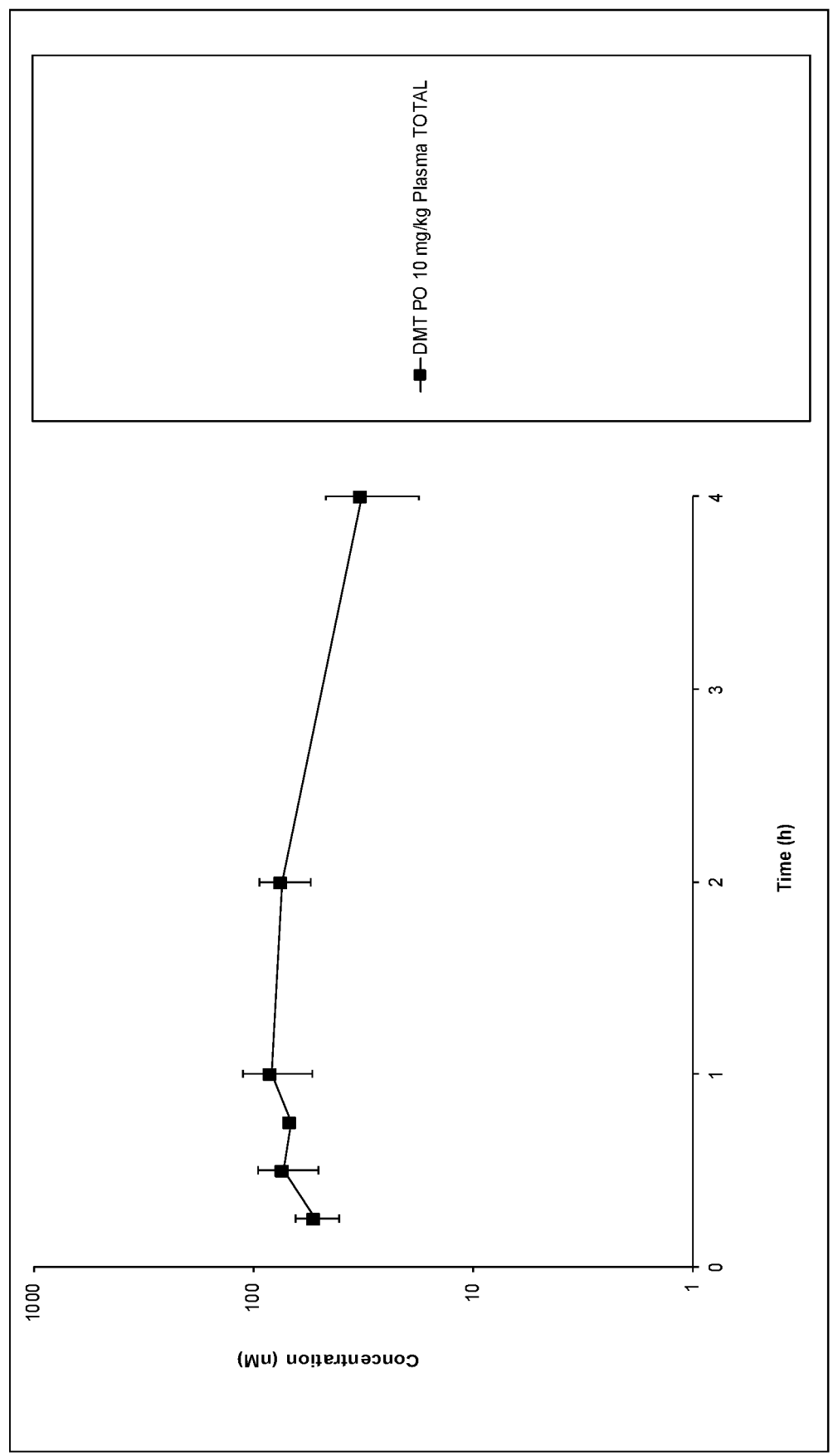
FIG. 8 shows the Mean Total Concentrations of DMT following PO administration of DMT Prodrug to male Sprague Dawley rat at 10 mg/kg.

FIG. 8 shows Mean Total Concentrations of DMT following PO administration of DMT Prodrug to male Sprague Dawley rat at 10 mg/kg.

Figure 9:
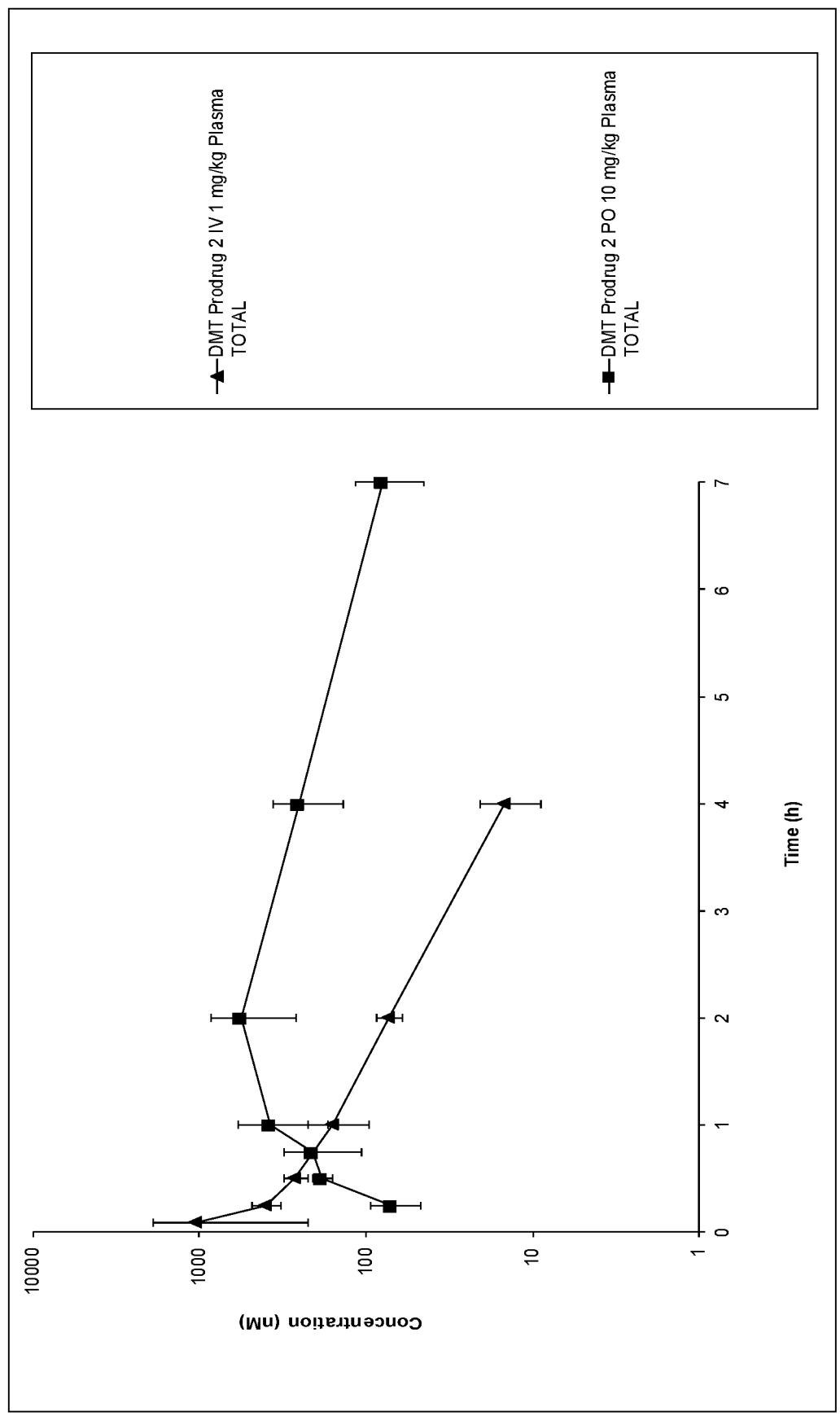
FIG. 9 shows the Mean Total Concentrations of DMT Prodrug following IV, PO administration to male Sprague Dawley rat at 1.10 mg/kg.

FIG. 9 shows Mean Total Concentrations of DMT Prodrug following IV, PO administration to male Sprague Dawley rat at 1.10 mg/kg.

TABLE 2-5

| | DMT Prodrug PK parameters | | | | | |
|---|---|---|---|---|---|---|
| | DMT Prodrug IV 1 mg/kg Plasma | | DMT Prodrug PO 10 mg/kg Plasma | | DMT Prodrug PO 10 mg/kg Plasma [Tlast = 4 h] | |
| PK Parameter | Mean/Median | SD | Mean/Median | SD | Mean/Median | SD |
| Dose (mg/kg) | 1.00 | — | 10.0 | — | 10.0 | — |
| C0/Cmax (ng/mL) | 2239 | 3209 | 195 | 103 | 195 | 103 |
| C0/Cmax (nM) | 6355 | 9107 | 554 | 293 | 554 | 293 |
| Clast (ng/mL) | 5.22 | 2.05 | 28.2 | 12.5 | 87.8 | 39.2 |
| tlast (h) | 4.00 | — | 7.00 | — | 4.00 | — |
| tmax (h) | — | — | 2.00 | — | 2.00 | — |
| t1/2 (h) | 0.865 | 0.156 | — | — | — | — |
| MRT (h) | 0.869 | 0.434 | — | — | — | — |
| Vdss (L/kg) | 4.21 | 3.05 | — | — | — | — |
| CL/CL_F (mL/min/kg) | 70.2 | 35.9 | — | — | — | — |
| AUCinf (ng · hr/mL) | 311 | 217 | — | — | — | — |

TABLE 2-5-continued

| | DMT Prodrug PK parameters | | | | | |
|---|---|---|---|---|---|---|
| | DMT Prodrug IV 1 mg/kg Plasma | | DMT Prodrug PO 10 mg/kg Plasma | | DMT Prodrug PO 10 mg/kg Plasma [Tlast = 4 h] | |
| PK Parameter | Mean/ Median | SD | Mean/ Median | SD | Mean/ Median | SD |
| AUCinf (nM · hr) | 881 | 617 | — | — | — | — |
| AUC0-t (ng · hr/mL) | 304 | 220 | 644 | 290 | 489 | 235 |
| AUC0-t (nM · hr) | 862 | 625 | 1828 | 822 | 1389 | 666 |
| Bioavailability (%) Using AUC0-t | — | — | — | — | 16.1 | 7.72 |
| Number of Points used for Lambda z | 4 | — | — | — | — | — |
| AUC % Extrapolation to infinity | 3.21 | 2.39 | — | — | — | — |
| AUC % Back Extrapolation to C0 | 36.7 | 25.8 | — | — | — | — |

Example 2-6. Diisopropylphosphonate 5-MeO-DMT Prodrug

Chemical name: 2-(1-diisopropoxyphosphoryl-5-methoxy-indol-3-yl)-N,N-dimethyl-ethanamine Structural class: phosphonate Mechanistic class: presumed carboxyesterases+presumed phosphatases

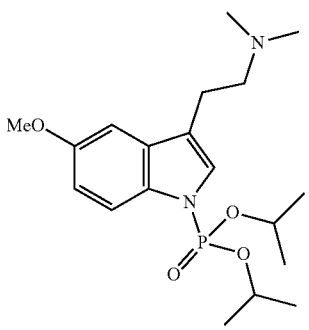 [SMILES: COc1ccc2c(c1)c(CCN(C)C)cn2P(=O)(OC(C)C)OC(C)C]

Figure 10:
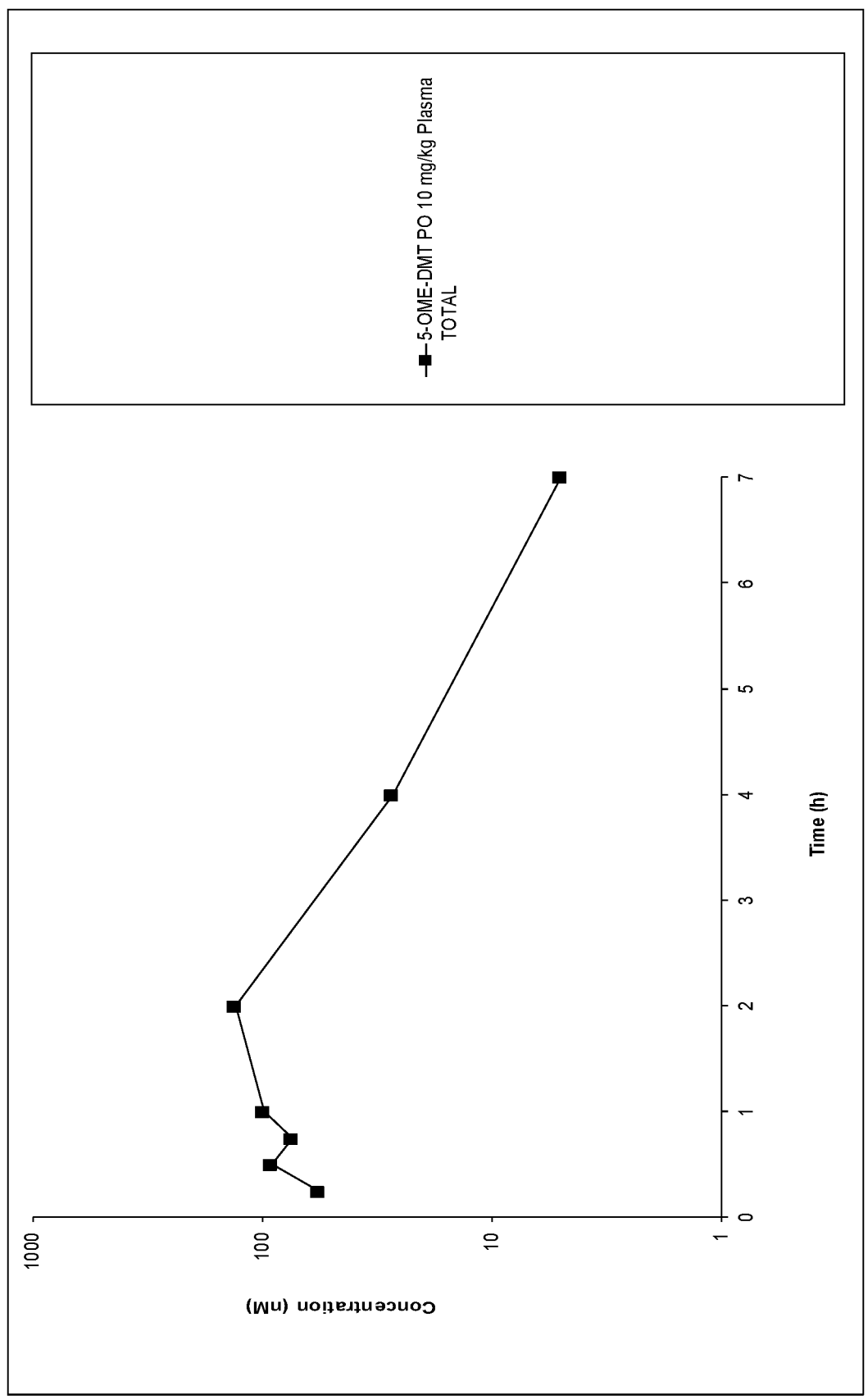
FIG. 10 shows the Mean Total concentrations of 5-MeO-DMT following PO administration of 5-MeO-DMT Prodrug to male Sprague Dawley rat at 10 mg/kg.

FIG. 10. Mean Total concentrations of 5-MeO-DMT following PO administration of 5-MeO-DMT Pro-drug to male Sprague Dawley rat at 10 mg/kg.

Figure 11:
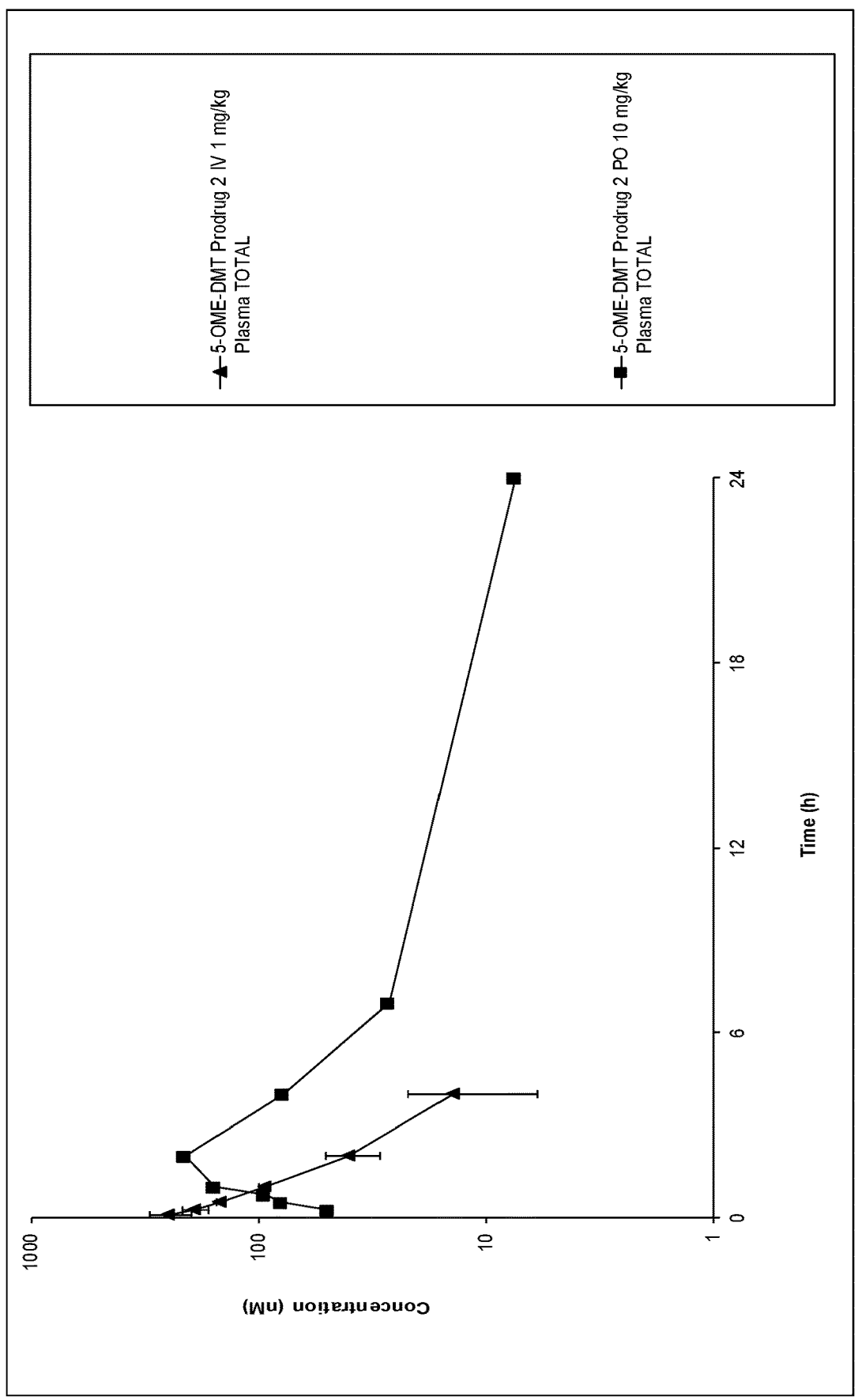
FIG. 11 shows the Mean Total concentrations of 5-MeO-DMT Prodrug following IV, PO administration to male Sprague Dawley rat at 1.10 mg/kg.

FIG. 11. Mean Total concentrations of 5-MeO-DMT Prodrug following IV, PO administration to male Sprague Dawley rat at 1.10 mg/kg.

TABLE 2-6

| | 5-MeO-DMT Prodrug PK Parameters | | |
|---|---|---|---|
| | 5-MeO-DMT Prodrug IV 1 mg/kg Plasma | | 5-MeO-DMT Prodrug PO 10 mg/kg Plasma |
| PK Parameter | Mean/Median | SD | Mean/Median |
| Dose (mg/kg) | 1.00 | — | 10.0 |
| C0/Cmax (ng/mL) | 112 | 37.2 | 80.4 |
| C0/Cmax (nM) | 294 | 97.2 | 210 |

TABLE 2-6-continued

| | 5-MeO-DMT Prodrug PK Parameters | | |
|---|---|---|---|
| | 5-MeO-DMT Prodrug IV 1 mg/kg Plasma | | 5-MeO-DMT Prodrug PO 10 mg/kg Plasma |
| PK Parameter | Mean/Median | SD | Mean/Median |
| Clast (ng/mL) | 5.32 | 3.04 | 2.84 |
| tlast (h) | 4.00 | — | 24.1 |
| tmax (h) | — | — | 2.00 |
| t½ (h) | 1.01 | 0.229 | 7.00 |
| MRT (h) | 1.39 | 0.358 | — |
| Vdss (L/kg) | 12.2 | 1.32 | — |
| CL/CL_F (mL/min/kg) | 150 | 22.8 | 450 |
| AUCinf (ng · hr/mL) | 113 | 18.1 | 381 |
| AUCinf (nM · hr) | 295 | 47.3 | 995 |
| AUC0-t (ng · hr/mL) | 104 | 11.6 | 352 |
| AUC0-t (nM · hr) | 273 | 30.3 | 921 |
| Bioavailability (%) Using AUCinf | — | — | 33.8 |
| Number of Points used for Lambda z | 5 | — | 3 |
| AUC % Extrapolation to infinity | 7.01 | 4.51 | 7.77 |
| AUC % Back Extrapolation to C0 | 7.68 | 2.16 | — |

Example 2-7. Isopropyl Carbamate DMT Prodrug

| Dosed Test Article: | DMT CP-2 |
|---|---|
| Dose Route: | Oral |
| Nominal Dose Concentration: | 10 mg/Kg |
| Analytes: Pro-Drug | DMT CP-2 |
| Metabolite | DMT |

Chemical name: isopropyl 3-[2-(dimethylamino)ethyl]indole-1-carboxylate

Structural class: carbamate

Mechanistic class: presumed carboxyesterases

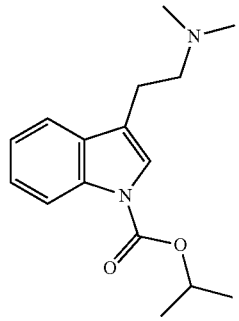 [SMILES: CC(C)OC(=O)n1cc(CCN(C)C)c2ccccc21]

Figure 12:
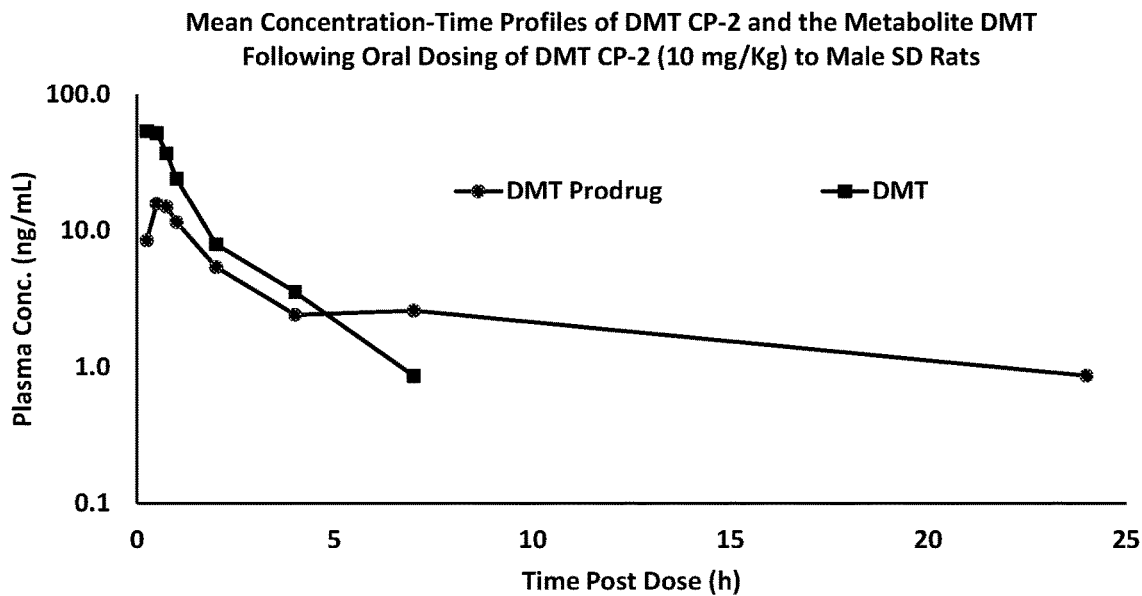
FIG. 12 shows the Mean Concentration-Time Profiles of DMT CP-2 and Metabolite DMT Following Oral Dosing of DMT CP-2 (10 mg/Kg) to Male SD Rats.

FIG. 12. Mean Concentration-Time Profiles of DMT CP-2 and Metabolite DMT Following Oral Dosing of DMT CP-2 (10 mg/Kg) to Male SD Rats

TABLE 2-7

| DMT Prodrug and DMT PK Parameters Mean Pharmacokinetic Parameters | | |
|---|---|---|
| PK Parameter | DMT CP-2 | DMT |
| Cmax (ng/mL) | 17.4 | 58.8 |
| Tmax (h) | 0.500 | 0.500 |
| MRT (h) | 2.96 | 1.32 |
| Tlast (h) | 4.00 | 4.00 |
| AUC0-last (h*ng/mL) | 39.4 | 65.5 |
| AUC0-24 (h*ng/mL) | 60.9 | — |
| AUC0-inf (h*ng/mL) | 45.5 | 69.0 |
| T½ (h) | 4.04 | 1.21 |

* Median calculated for Tmax and Tlast.

Example 2-8. tert-butyl Carbamate DMT Prodrug

| Dosed Test Article: | DMT CP-3 |
|---|---|
| Dose Route: | Oral |
| Nominal Dose Concentration: | 10 mg/Kg |
| Analytes: Pro-Drug | DMT CP-3 |
| Metabolite | DMT |

Chemical name: tert-butyl 3-[2-(dimethylamino)ethyl]indole-1-carboxylate

Structural class: carbamate

Mechanistic class: presumed carboxyesterases

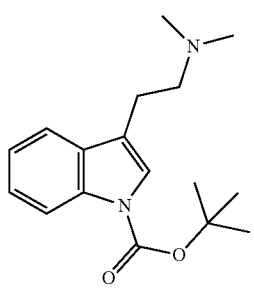 [SMILES: CN(C)CCc1cn(C(=O)OC(C)(C)C)c2ccccc12]

Figure 13:
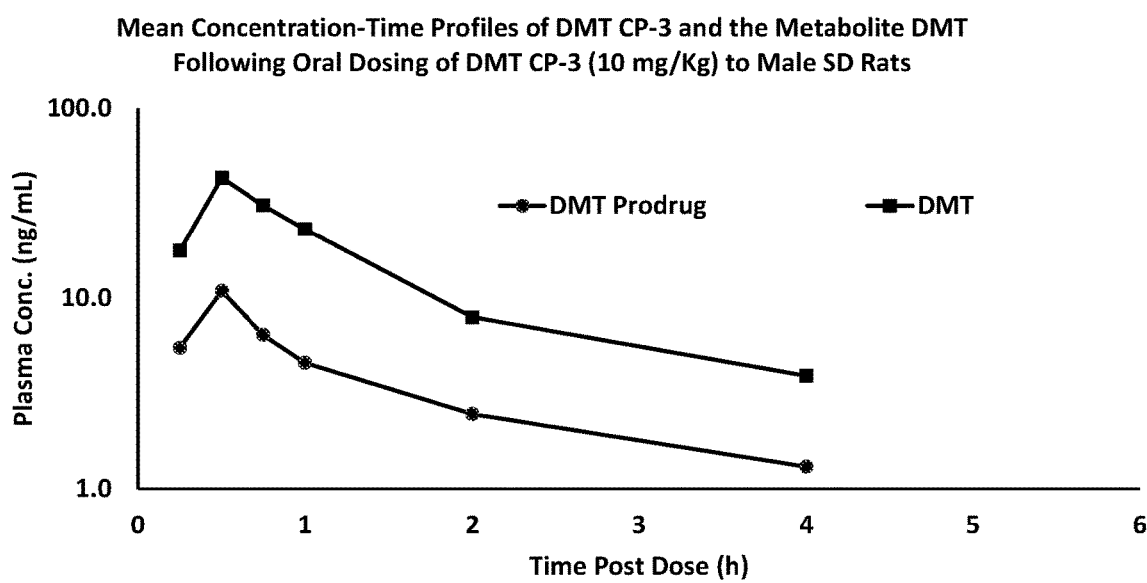
FIG. 13 shows the Mean Concentration-Time Profiles of DMT CP-3 and the Metabolite DMT Following Oral Dosing of DMT CP-3 (10 mg/Kg) to Male SD Rats.

FIG. 13. Mean Concentration-Time Profiles of DMT CP-3 and the Metabolite DMT Following Oral Dosing of DMT CP-3 (10 mg/Kg) to Male SD Rats

TABLE 2-8

| DMT Prodrug and DMT PK Parameters Mean Pharmacokinetic Parameters | | |
|---|---|---|
| PK Parameter | DMT Prodrug | DMT |
| Cmax (ng/mL) | 11.1 | 44.1 |
| Tmax (h) | 0.500 | 0.500 |
| MRT (h) | 1.39 | 1.28 |
| Tlast (h) | 4.00 | 4.00 |
| AUC0-last (h*ng/mL) | 13.8 | 55.0 |
| AUC0-24 (h*ng/mL) | — | — |
| AUC0-inf (h*ng/mL) | 17.5 | 64.1 |
| T½ (h) | 1.87 | 1.35 |

* Median calculated for Tmax and Tlast.

Example 2-9. Propyl Carbamate DMT Prodrug

| Dosed Test Article: | DMT CP-4 |
|---|---|
| Dose Route: | Oral |
| Nominal Dose Concentration: | 10 mg/Kg |
| Analytes: Pro-Drug | DMT CP-4 |
| Metabolite | DMT |

Chemical name: propyl 3-[2-(dimethylamino)ethyl]indole-1-carboxylate

Structural class: carbamate

Mechanistic class: presumed carboxyesterases

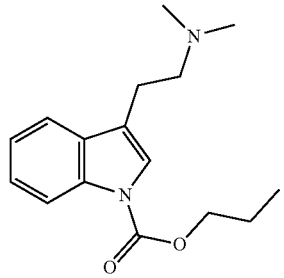 [SMILES: CCCOC(=O)n1cc(CCN(C)C)c2ccccc21]

Figure 14:
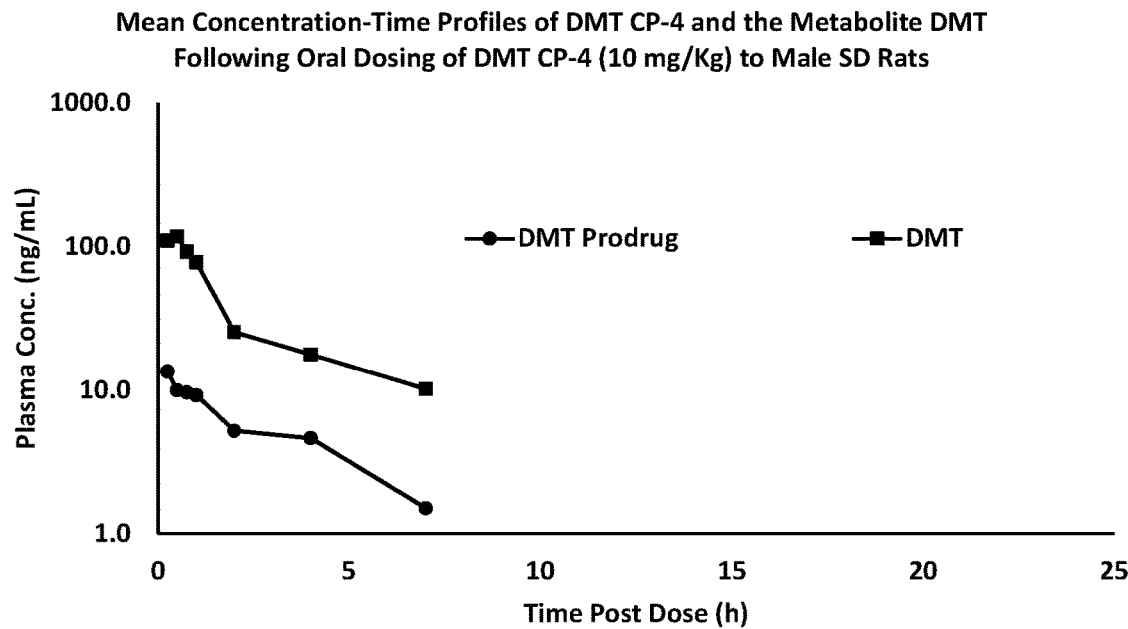
FIG. 14 shows the Mean Concentration-Time Profiles of DMT CP-4 and the Metabolite DMT Following Oral Dosing of DMT CP-4 (10 mg/Kg) to Male SD Rats.

FIG. 14. Mean Concentration-Time Profiles of DMT CP-4 and the Metabolite DMT Following Oral Dosing of DMT CP-4 (10 mg/Kg) to Male SD Rats

TABLE 2-9

| DMT Prodrug and DMT PK Parameters Mean Pharmacokinetic Parameters | | |
|---|---|---|
| PK Parameter | DMT Prodrug | DMT |
| Cmax (ng/mL) | 14.3 | 128 |
| Tmax (h) | 0.375 | 0.500 |
| MRT (h) | 1.46 | 1.95 |
| Tlast (h) | 4.50 | 7.00 |
| AUC0-last (h*ng/mL) | 28.2 | 227.0 |
| AUC0-24 (h*ng/mL) | — | — |
| AUC0-inf (h*ng/mL) | 30.9 | 306.0 |
| T½ (h) | 1.35 | 4.6 |

* Median calculated for Tmax and Tlast.

Example 2-10. Isobutyl Carbamate DMT Prodrug

| Dosed Test Article: | DMT CP-5 |
|---|---|
| Dose Route: | Oral |
| Nominal Dose Concentration: | 10 mg/Kg |
| Analytes: Pro-Drug | DMT CP-5 |
| Metabolite | DMT |

Chemical name: isobutyl 3-[2-(dimethylamino)ethyl]indole-1-carboxylate

Structural class: carbamate

Mechanistic class: presumed carboxyesterases

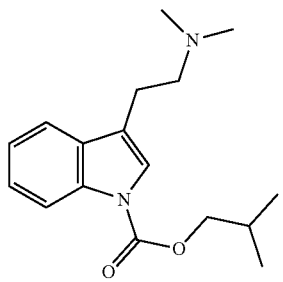 [SMILES: CC(C)COC(=O)n1cc(CCN(C)C)c2ccccc21]

Figure 15:
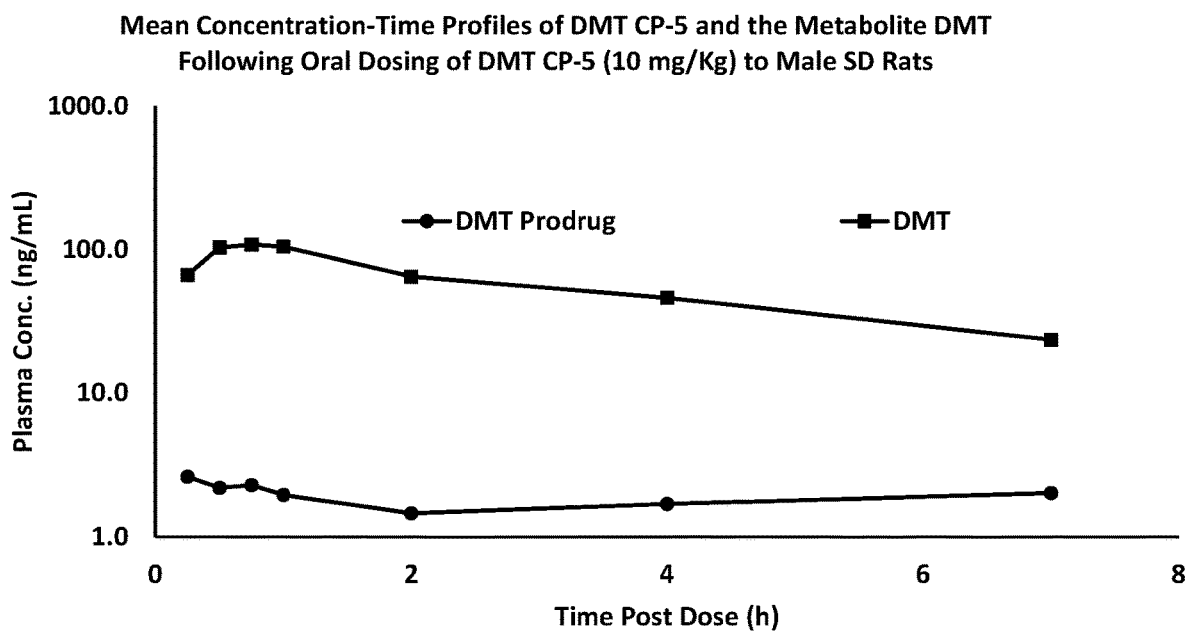
FIG. 15 shows the Mean Concentration-Time Profiles of DMT CP-5 and the Metabolite DMT Following Oral Dosing of DMT CP-5 (10 mg/Kg) to Male SD Rats.

FIG. 15. Mean Concentration-Time Profiles of DMT CP-5 and the Metabolite DMT Following Oral Dosing of DMT CP-5 (10 mg/Kg) to Male SD Rats

TABLE 2-10

| DMT Prodrug and DMT PK Parameters Mean Pharmacokinetic Parameters | | |
|---|---|---|
| PK Parameter | DMT Prodrug | DMT |
| Cmax (ng/mL) | 2.92 | 120 |
| Tmax (h) | 1.000 | 0.500 |
| MRT (h) | 2.09 | 2.63 |
| Tlast (h) | 4.00 | 7.00 |
| AUC0-last (h*ng/mL) | 8.63 | 386.0 |
| AUC0-24 (h*ng/mL) | — | — |
| AUC0-inf (h*ng/mL) | 71.5 | 443.0 |
| T½ (h) | 19.10 | 1.84 |

* Median calculated for Tmax and Tlast.

Example 2-11. Methyl amide DMT Prodrug

| Dosed Test Article: | DMT AP-1 |
|---|---|
| Dose Route: | Oral |
| Nominal Dose Concentration: | 10 mg/Kg |
| Analytes: Pro-Drug | DMT AP-1 |
| Metabolite | DMT |

Chemical name: 1-[3-[2-(dimethylamino)ethyl]indol-1-yl]ethenone

Structural class: amide

Mechanistic class: presumed amidases

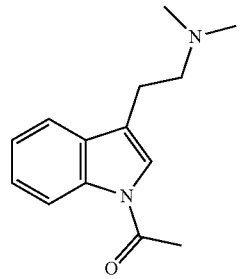 [SMILES: CC(=O)n1cc(CCN(C)C)c2ccccc21]

Figure 16:
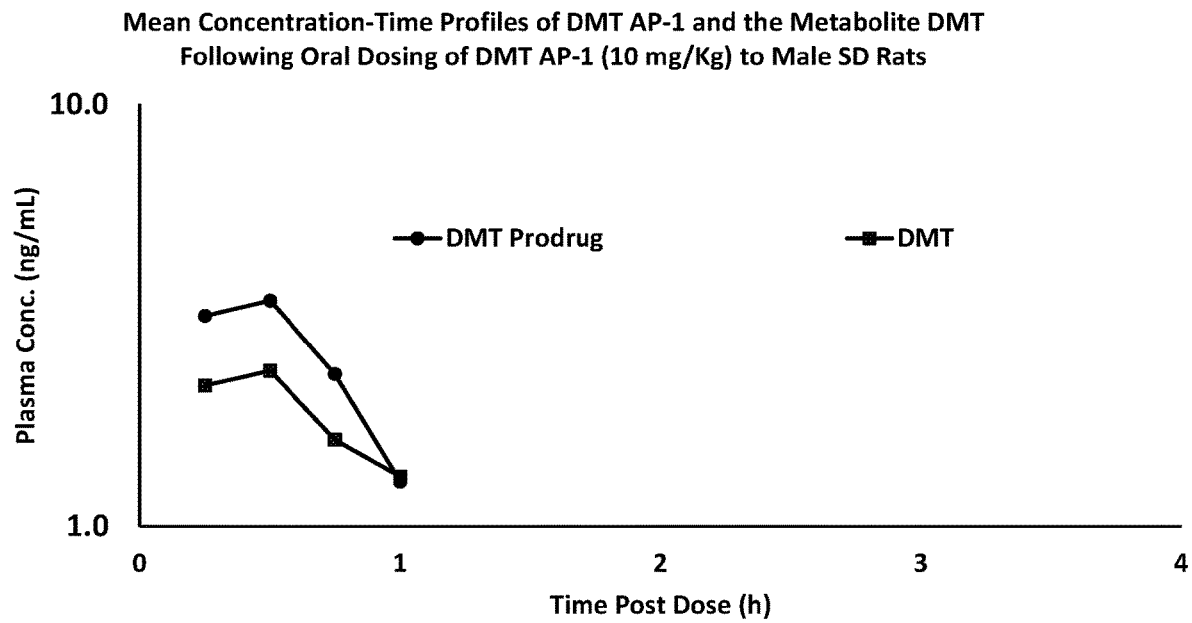
FIG. 16 shows the Mean Concentration-Time Profiles of DMT AP-1 and the Metabolite DMT Following Oral Dosing of DMT AP-1 (10 mg/Kg) to Male SD Rats.

FIG. 16. Mean Concentration-Time Profiles of DMT AP-1 and the Metabolite DMT Following Oral Dosing of DMT AP-1 (10 mg/Kg) to Male SD Rats

TABLE 2-11

| DMT Prodrug and DMT PK Parameters Mean Pharmacokinetic Parameters | | |
|---|---|---|
| PK Parameter | DMT Prodrug | DMT |
| Cmax (ng/mL) | 3.53 | 2.42 |
| Tmax (h) | 0.500 | 0.500 |
| MRT (h) | 0.58 | 0.695 |
| Tlast (h) | 1.00 | 1.00 |
| AUC0-last (h*ng/mL) | 2.16 | 1.9 |
| AUC0-24 (h*ng/mL) | — | — |
| AUC0-inf (h*ng/mL) | — | 3.7 |
| T½ (h) | — | 1.13 |

* Median calculated for Tmax and Tlast.

Example 2-12. Isopropyl Carbamate 5-MeO-DMT Prodrug

| Dosed Test Article: | 5-MeO-DMT CP-2 |
|---|---|
| Dose Route: | Oral |
| Nominal Dose Concentration: | 10 mg/Kg |
| Analytes: Pro-Drug | 5-MeO-DMT CP-2 |
| Metabolite | 5-MeO-DMT |

Chemical name: isopropyl 3-[2-(dimethylamino)ethyl]-5-methoxy-indole-1-carboxylate Structural class: carbamate Mechanistic class: presumed carboxyesterases

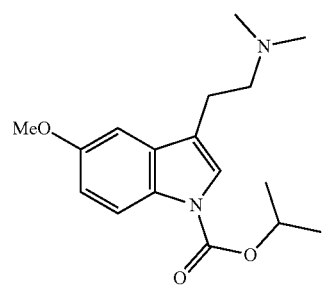 [SMILES: COc1ccc2c(c1)c(CCN(C)C)cn2C(=O)OC(C)C]

Figure 17:
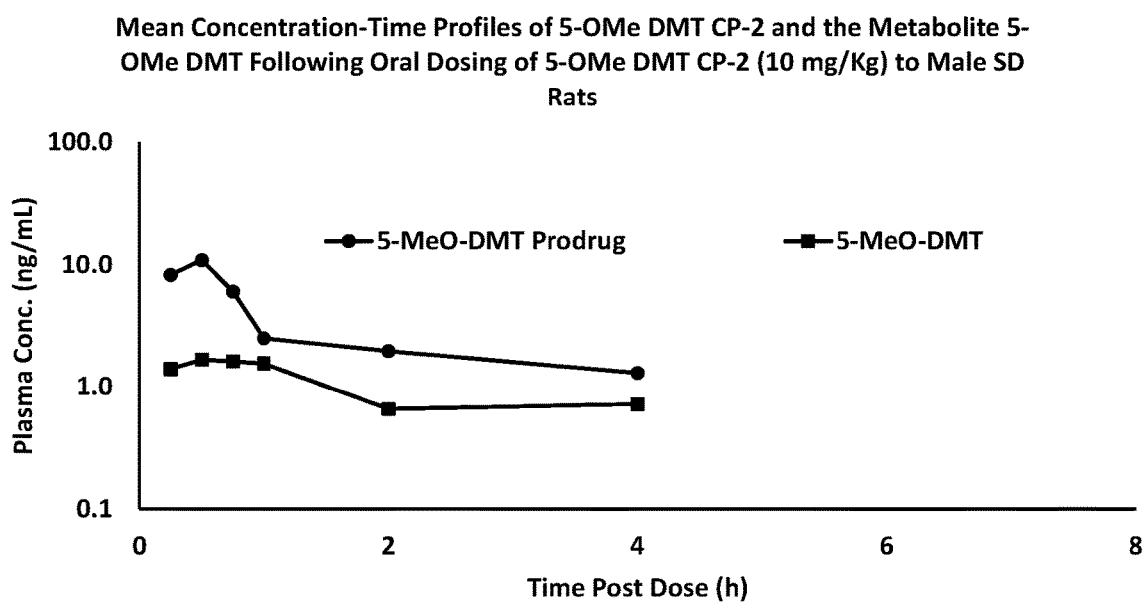
FIG. 17 shows the Mean Concentration-Time Profiles of 5-MeO-DMT CP-2 and the Metabolite 5-MeO-DMT Following Oral Dosing of 5-MeO-DMT CP-2 (10 mg/Kg) to Male SD Rats.

FIG. 17. Mean Concentration-Time Profiles of 5-MeO-DMT CP-2 and the Metabolite 5-MeO DMT Following Oral Dosing of 5-MeO-DMT CP-2 (10 mg/Kg) to Male SD Rats

TABLE 2-12

| PK Parameter | 5-MeO-DMT Prodrug | 5-MeO-DMT |
|---|---|---|
| 5-MeO-DMT Prodrug and 5-MeO-DMT PK Parameters Mean Pharmacokinetic Parameters | | |
| Cmax (ng/mL) | 5.7 | 1.81 |
| Tmax (h) | 0.750 | 0.500 |
| MRT (h) | 1.13 | 1.27 |
| Tlast (h) | 2.50 | 2.00 |
| AUC0-last (h*ng/mL) | 6.8 | 3.2 |
| AUC0-24 (h*ng/mL) | — | — |
| AUC0-inf (h*ng/mL) | 16.7 | 6.4 |
| T½ (h) | 1.80 | 2.35 |

* Median calculated for Tmax and Tlast.

Example 2-13. tert-Butyl Carbamate 5-MeO-DMT Prodrug

| Dosed Test Article: | 5-MeO-DMT CP-3 |
|---|---|
| Dose Route: | Oral |
| Nominal Dose Concentration: | 10 mg/Kg |
| Analytes: Pro-Drug | 5-MeO DMT CP-3 |
| Metabolite | 5-MeO-DMT |

Chemical name: tert-butyl 3-[2-(dimethylamino)ethyl]-5-methoxy-indole-1-carboxylate
Structural class: carbamate
Mechanistic class: presumed carboxyesterases

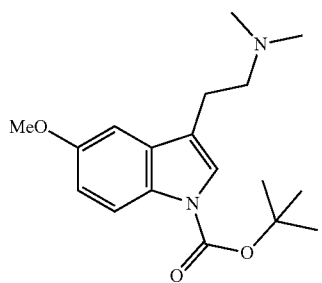 [SMILES: COc1ccc2c(c1)c(CCN(C)C)cn2C(=O)OC(C)(C)C]

Figure 18:
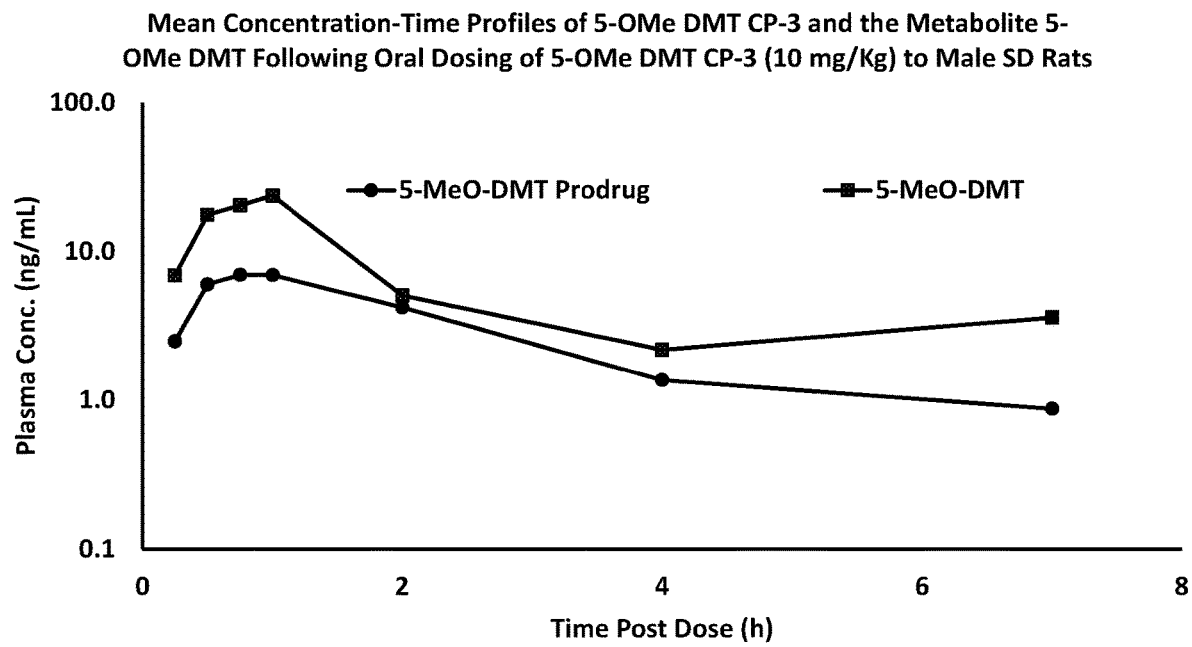
FIG. 18 shows the Mean Concentration-Time Profiles of 5-MeO-DMT CP-3 and the Metabolite 5-MeO-DMT Following Oral Dosing of 5-MeO-DMT CP-3 (10 mg/Kg) to Male SD Rats.

FIG. 18. Mean Concentration-Time Profiles of 5-MeO-DMT CP-3 and the Metabolite 5-MeO DMT Following Oral Dosing of 5-MeO-DMT CP-3 (10 mg/Kg) to Male SD Rats.

TABLE 2-13

| PK Parameter | 5-MeO-DMT Prodrug | 5-MeO-DMT |
|---|---|---|
| 5-MeO-DMT Prodrug and 5-MeO-DMT PK Parameters Mean Pharmacokinetic Parameters | | |
| Cmax (ng/mL) | 7.51 | 24.1 |
| Tmax (h) | 0.750 | 1.000 |
| MRT (h) | 1.84 | 1.91 |
| Tlast (h) | 4.00 | 4.00 |
| AUC0-last (h*ng/mL) | 17.3 | 38.3 |
| AUC0-24 (h*ng/mL) | — | — |
| AUC0-inf (h*ng/mL) | 25.0 | NC |
| T½ (h) | 1.58 | NC |

* Median calculated for Tmax and Tlast.

Example 2-14. Propyl Carbamate 5-MeO-DMT Prodrug

Chemical name: propyl 3-[2-(dimethylamino)ethyl]-5-methoxy-indole-1-carboxylate
Structural class: carbamate
Mechanistic class: presumed carboxyesterase

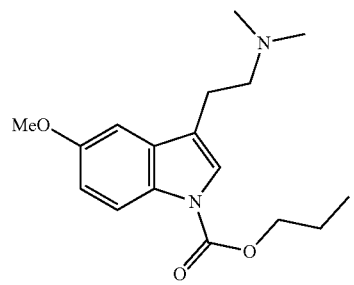 [SMILES: CCCOC(=O)n1cc(CCN(C)C)c2cc(OC)ccc21]

Figure 19:
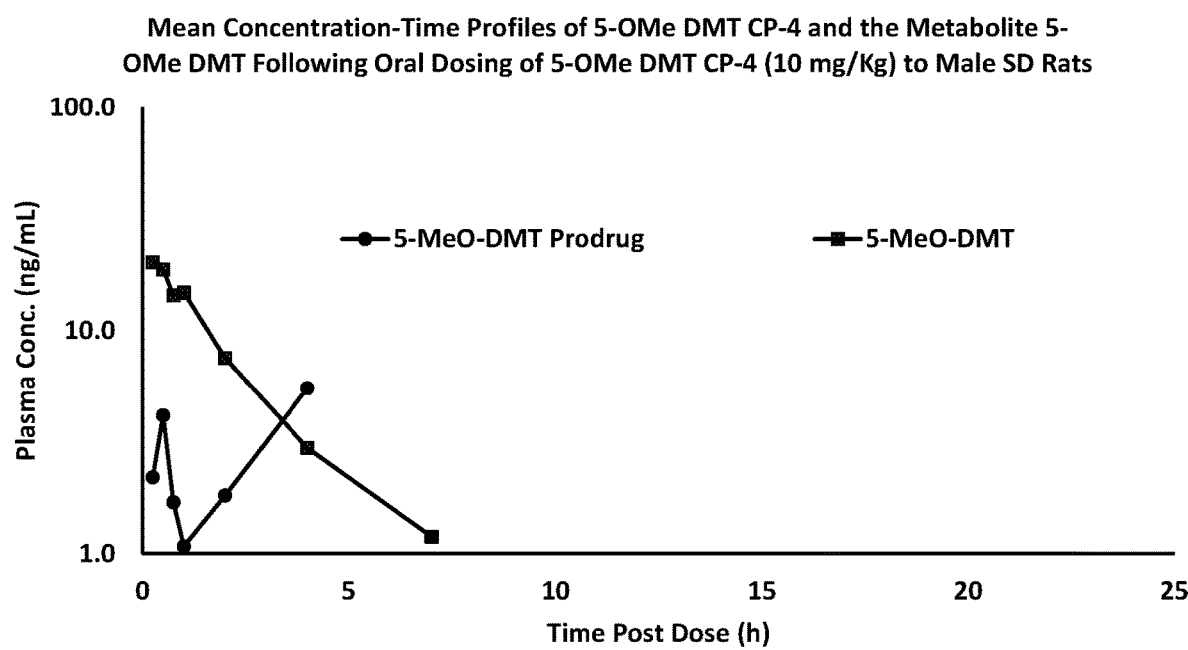
FIG. 19 shows the Mean Concentration-Time Profiles of 5-MeO-DMT CP-4 and the Metabolite 5-MeO-DMT Following Oral Dosing of 5-MeO-DMT CP-4 (10 mg/Kg) to Male SD Rats.

FIG. 19. Mean Concentration-Time Profiles of 5-MeO-DMT CP-4 and the Metabolite 5-MeO DMT Following Oral Dosing of 5-MeO-DMT CP-4 (10 mg/Kg) to Male SD Rats

TABLE 2-14

| PK Parameter | 5-MeO-DMT Prodrug | 5-MeO-DMT |
|---|---|---|
| 5-MeO-DMT Prodrug and 5-MeO-DMT PK Parameters Mean Pharmacokinetic Parameters | | |
| Cmax (ng/mL) | 4.85 | 24 |
| Tmax (h) | 2.250 | 0.500 |
| MRT (h) | 2.05 | 1.87 |
| Tlast (h) | 3.00 | 7.00 |
| AUC0-last (h*ng/mL) | 6.45 | 43.1 |
| AUC0-24 (h*ng/mL) | — | — |
| AUC0-inf (h*ng/mL) | NC | 47.2 |
| T½ (h) | NC | 2.01 |

* Median calculated for Tmax and Tlast.

Example 2-15. Isobutyl Carbamate 5-MeO-DMT Prodrug

Chemical name: Isobutyl 3-[2-(dimethylamino)ethyl]-6-methoxy-indole-1-carboxylate
Structural class: carbamate
Mechanistic class: presumed carboxyesterases

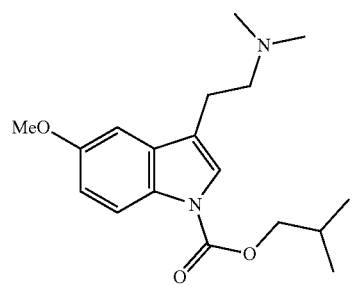 [SMILES: COc1ccc2c(c1)c(CCN(C)C)cn2C(=O)OCC(C)C]

Figure 20:
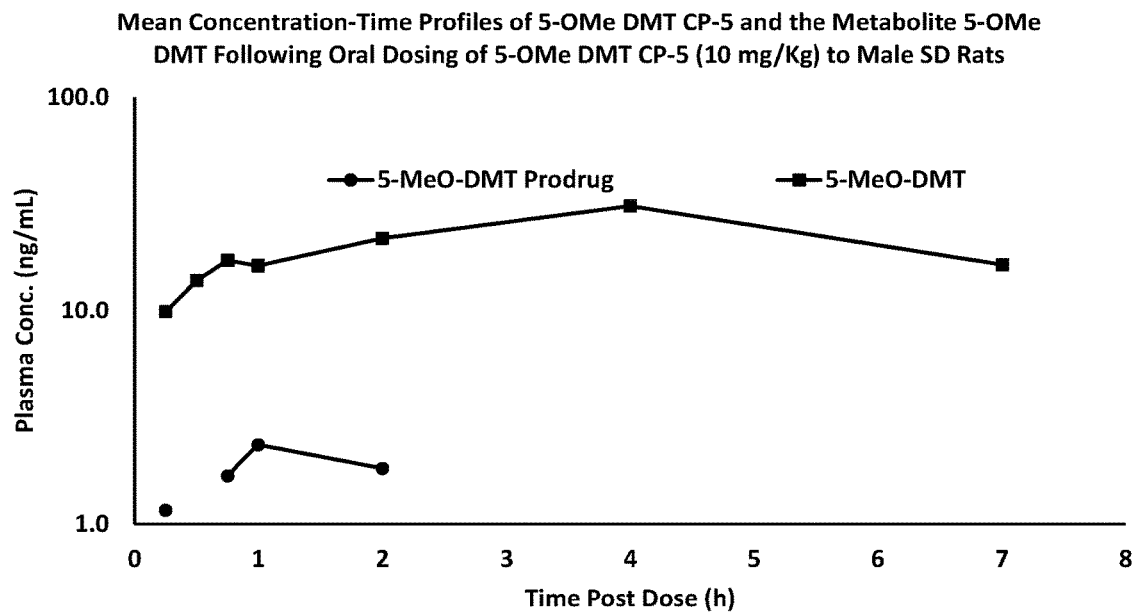
FIG. 20 shows the Mean Concentration-Time Profiles of 5-MeO-DMT CP-5 and the Metabolite 5-MeO-DMT Following Oral Dosing of 5-MeO-DMT CP-5 (10 mg/Kg) to Male SD Rats.

FIG. 20. Mean Concentration-Time Profiles of 5-MeO-DMT CP-5 and the Metabolite 5-MeO-DMT Following Oral Dosing of 5-MeO-DMT CP-5 (10 mg/Kg) to Male SD Rats

TABLE 2-15

5-MeO-DMT Prodrug and 5-MeO-DMT PK Parameters
Mean Pharmacokinetic Parameters

| PK Parameter | 5-MeO-DMT Prodrug | 5-MeO-DMT |
|---|---|---|
| Cmax (ng/mL) | 2.09 | 35.1 |
| Tmax (h) | 1.500 | 4.000 |
| MRT (h) | 1.07 | 3.81 |
| Tlast (h) | 1.50 | 7.00 |
| AUC0-last (h*ng/mL) | 2.11 | 155.0 |
| AUC0-24 (h*ng/mL) | — | — |
| AUC0-inf (h*ng/mL) | NC | NC |
| T½ (h) | NC | NC |

* Median calculated for Tmax and Tlast.

Example 2-16. Methyl amide 5-MeO-DMT Prodrug

Chemical name: 1-[3-[2-(dimethylamino)ethyl]-5-methoxy-indol-1-yl]ethanone
Structural class: amide
Mechanistic class: presumed amidases

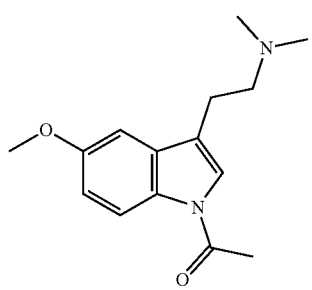

Figure 21:
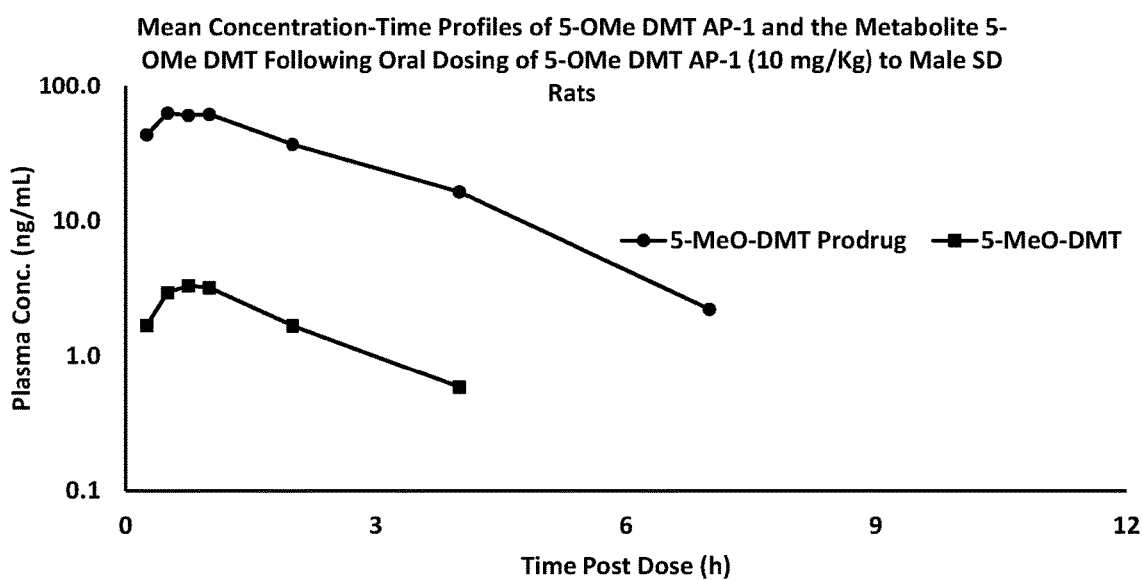
FIG. 21 shows Mean Concentration-Time Profiles of 5-MeO-DMT AP-1 and the Metabolite 5-MeO-DMT Following Oral Dosing of 5-MeO-DMT AP-1 (10 mg/Kg) to Male SD Rats.

FIG. 21. Mean Concentration-Time Profiles of 5-MeO-DMT AP-1 and the Metabolite 5-MeO-DMT Following Oral Dosing of 5-MeO-DMT AP-1 (10 mg/Kg) to Male SD Rats

TABLE 2-16

5-MeO-DMT Prodrug and 5-MeO-DMT PK Parameters
Mean Pharmacokinetic Parameters

| PK Parameter | 5-MeO-DMT Prodrug | 5-MeO-DMT |
|---|---|---|
| Cmax (ng/mL) | 69 | 3.5 |
| Tmax (h) | 0.500 | 0.750 |
| MRT (h) | 2.06 | 1.55 |
| Tlast (h) | 7.00 | 4.00 |
| AUC0-last (h*ng/mL) | 180 | 7.1 |
| AUC0-24 (h*ng/mL) | — | — |
| AUC0-inf (h*ng/mL) | 192.0 | 9.1 |
| T½ (h) | 1.24 | 1.31 |

* Median calculated for Tmax and Tlast.

Example 2-17. DMT Benzamide

| Dosed Test Article: | DMT Non-Lipid Prodrug 4 (DMT Benzamide) |
|---|---|
| Dose Route: | Oral |
| Nominal Dose Concentration: | 10 mg/Kg |
| Analytes: | Pro-Drug DMT Non-Lipid Prodrug 4 |
| | Metabolite DMT |

Chemical name: [3-[2-dimethylamino)ethyl]indol-1-yl]-phenyl-methanone
Structural class: amide
Mechanistic class: presumed amidases

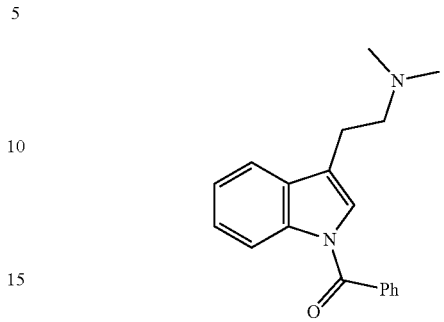

Figure 22:
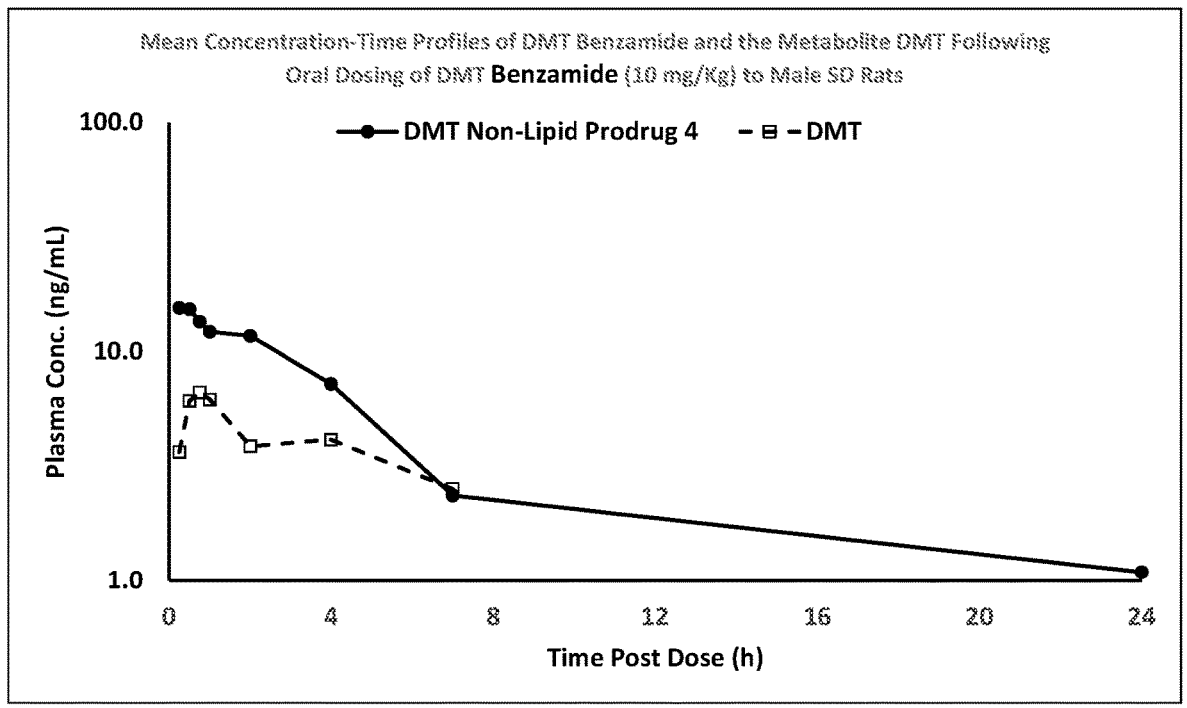
FIG. 22 shows the Mean Concentration-Time Profiles of DMT Benzamide and the Metabolite DMT Following Oral Dosing of DMT Benzamide (10 mg/Kg) to Male SD Rats.

FIG. 22. Mean Concentration-Time Profiles of DMT Benzamide and the Metabolite DMT Following Oral Dosing of DMT Benzamide (10 mg/Kg) to Male SD Rats

TABLE 2-17

DMT Prodrug and DMT PK Parameters
Mean PK Parameters

| PK Parameter | DMT Prodrug | DMT |
|---|---|---|
| Cmax (ng/mL) | 17.7 | 8.62 |
| Tmax (h) | 1.00 | 1.00 |
| MRT (h) | 3.41 | 3.02 |
| Tlast (h) | 7.00 | 7.00 |
| AUC0-last (h*ng/mL) | 66.5 | 27.9 |
| AUC0-24 (h*ng/mL) | — | — |
| AUC0-inf (h*ng/mL) | 104 | 47.3 |
| T½ (h) | 10.3 | 6.36 |

* Median calculated for Tmax and Tlast.

Example 2-18. 5-MeO-DMT Succinate

| Dosed Test Article: | 5-MeO-DMT Non-Lipid Prodrug 5 (5-MeO-DMT succinate) |
|---|---|
| Dose Route: | Oral |
| Nominal Dose Concentration: | 10 mg/Kg |
| Analytes: | 5-MeO-DMT Non-Lipid Prodrug 5 |
| | 5-MeO-DMT |

Chemical name: 4-(3-(2-(dimethylamino)ethyl)-5-methoxy-1H-indol-1-yl)-4-oxobutanoic acid
Structural class: amide
Mechanistic class: Presumed pH-dependent cyclization

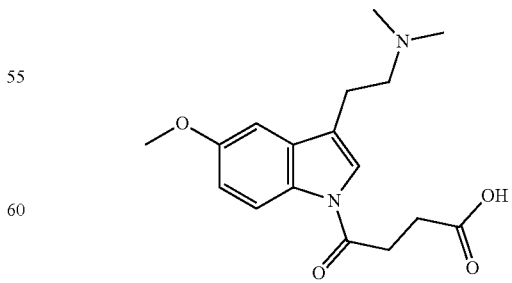

Figure 23:
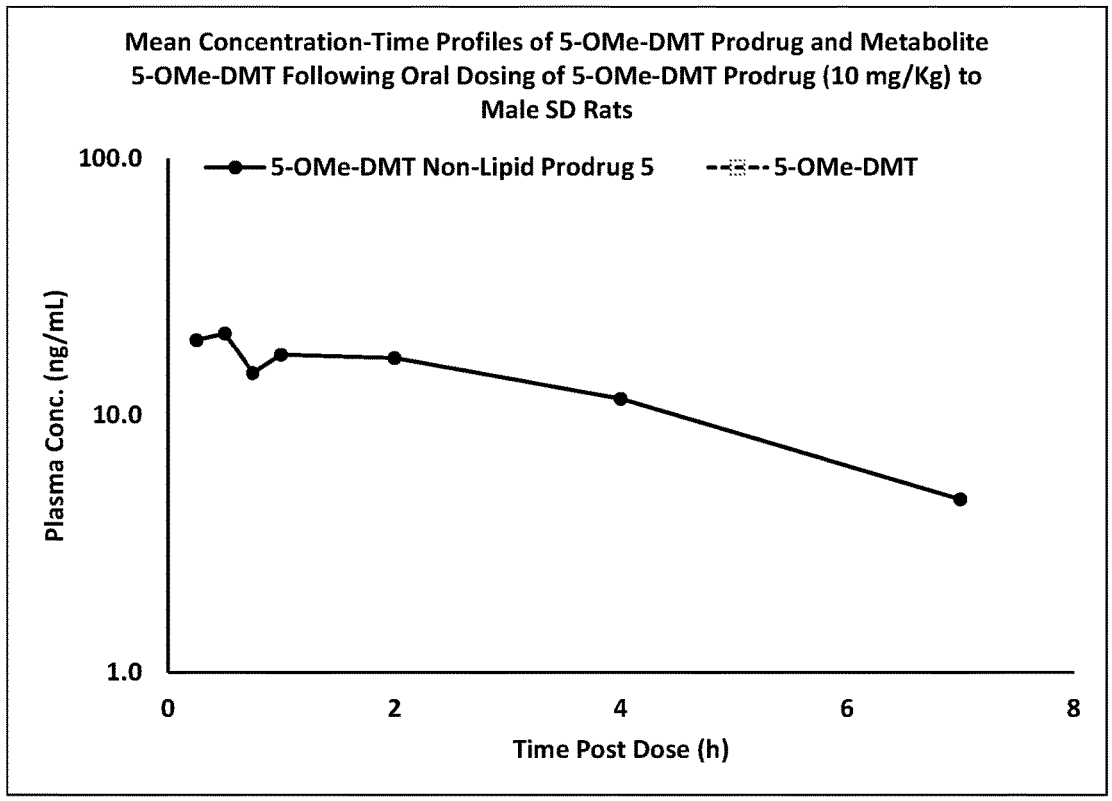
FIG. 23 shows the Mean Concentration-Time Profiles of 5-MeO-DMT Prodrug and Metabolite 5-MeO-DMT Following Oral Dosing of 5-MeO-DMT Prodrug (10 mg/Kg) to Male SD Rats.

FIG. 23. Mean Concentration-Time Profiles of 5-MeO-DMT Prodrug and Metabolite 5-MeO-DMT Following Oral Dosing of 5-MeO-DMT Prodrug (10 mg/Kg) to Male SD Rats

TABLE 2-18

5-MeO-DMT Prodrug and 5-MeO-DMT PK parameters
Mean PK Parameters

| PK Parameter | 5-MeO-DMT Non-Lipid Prodrug 5 | 5-MeO-DMT |
|---|---|---|
| Cmax (ng/mL) | 23.0 | NC |
| Tmax (h)* | 0.500 | NC |
| MRT (h) | 2.74 | NC |
| Tlast (h)* | 7.00 | NC |
| AUC0-last (h*ng/mL) | 85.7 | NC |
| AUC0-24 (h*ng/mL) | — | NC |
| AUC0-inf (h*ng/mL) | — | NC |
| T½ (h) | — | NC |

* Median calculated for Tmax and Tlast.

Example 2-19. 5-MeO-DMT Glutarate

| Dosed Test Article: | 5-MeO-DMT Non-Lipid Prodrug 6 (5-MeO-DMT glutarate) |
|---|---|
| Dose Route: | Oral |
| Nominal Dose Concentration: | 10 mg/Kg |
| Analytes: Pro-Drug | 5-MeO-DMT Non-Lipid Prodrug 6 |
| Metabolite | 5-MeO-DMT |

Chemical name: 5-(3-(2-(dimethylamino)ethyl)-5-methoxy-1H-indol-1-yl)-5-oxopentanoic acid Structural class: amide Mechanistic class: Presumed pH-dependent cyclization

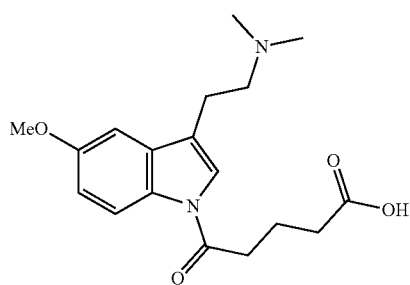 [SMILES: COc1ccc2c(c1)c(CCN(C)C)cn2C(=O)CCCC(=O)O]

Figure 24:
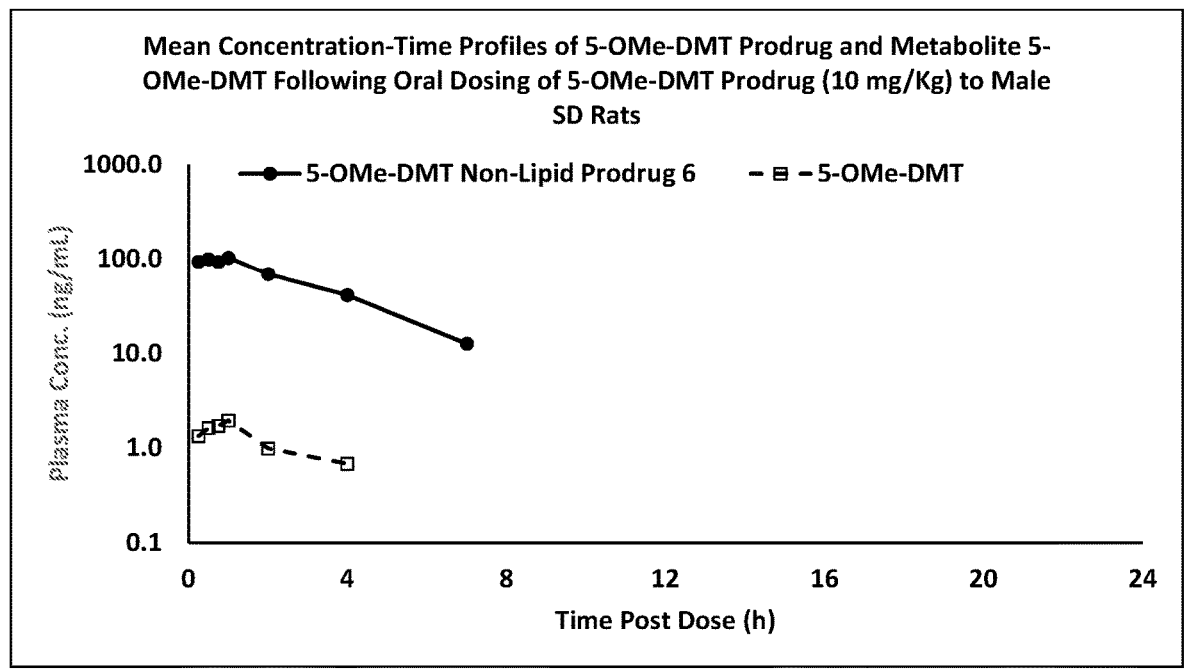
FIG. 24 shows the Mean Concentration-Time Profiles of 5-MeO-DMT Prodrug and Metabolite 5-MeO-DMT Following Oral Dosing of 5-MeO-DMT Prodrug (10 mg/Kg) to Male SD Rats.

FIG. 24. Mean Concentration-Time Profiles of 5-MeO-DMT Prodrug and Metabolite 5-MeO-DMT Following Oral Dosing of 5-MeO-DMT Prodrug (10 mg/Kg) to Male SD Rats

TABLE 2-19

5-MeO-DMT Prodrug and 5-MeO-DMT PK parameters
Mean PK Parameters

| PK Parameter | 5-MeO-DMT Non-Lipid Prodrug 6 | 5-MeO-DMT |
|---|---|---|
| Cmax (ng/mL) | 106 | 2.14 |
| Tmax (h)* | 1.00 | 0.750 |
| MRT (h) | 2.34 | 1.19 |
| Tlast (h)* | 7.00 | 2.00 |
| AUC0-last (h*ng/mL) | 362 | 3.39 |
| AUC0-24 (h*ng/mL) | — | — |
| AUC0-inf (h*ng/mL) | 399 | 7.96 |
| T½ (h) | 2.02 | 2.99 |

* Median calculated for Tmax and Tlast.

Example 2-20. 5-MeO-DMT Methylpivaloyl Carbamate

| Dosed Test Article: | 5-MeO-DMT methylpivaloyl carbamate |
|---|---|
| Dose Route: | Oral |
| Nominal Dose Concentration: | 10 mg/Kg |
| Analyte: | 5-MeO-DMT |

Chemical name: (Pivaloyloxy)methyl 3-(2-(dimethylamino)ethyl)-5-methoxy-1H-indole-1-carboxylate Structural class: carbamate Mechanistic class: presumed carboxyesterases+chemical breakdown

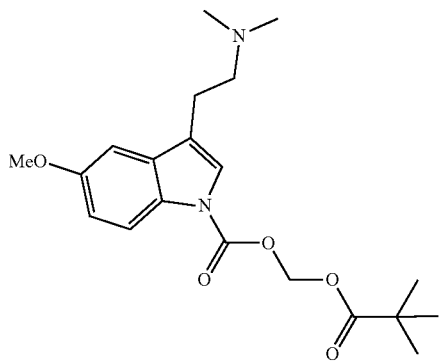 [SMILES: COc1ccc2c(c1)c(CCN(C)C)cn2C(=O)OCOC(=O)C(C)(C)C]

Figure 25:
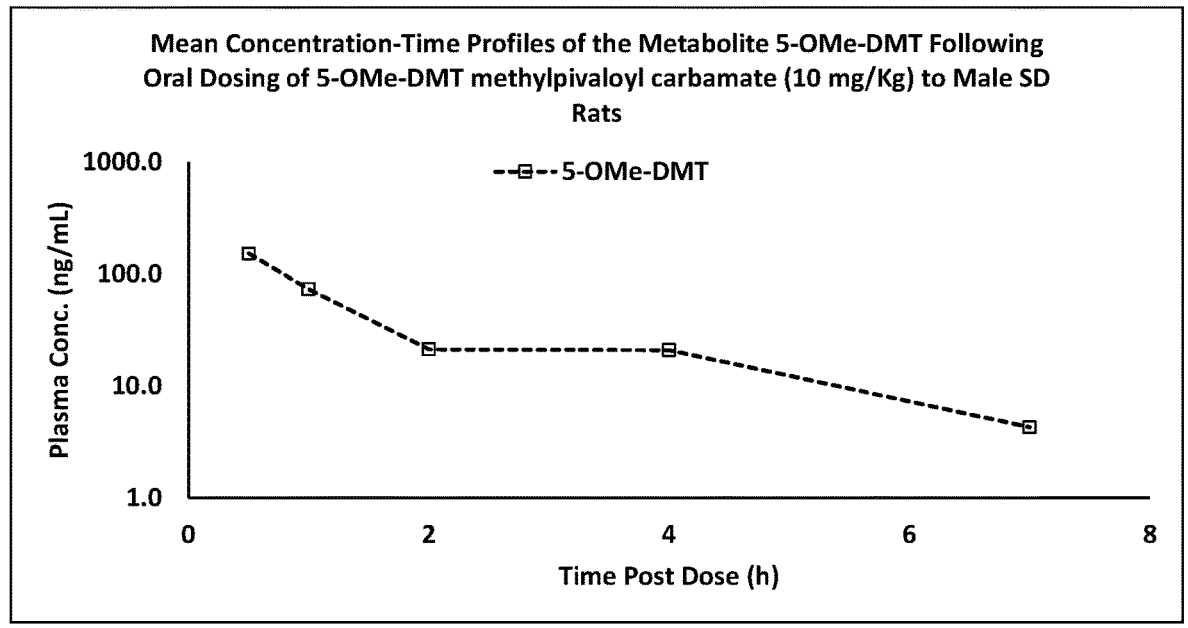
FIG. 25 shows the Mean Concentration-Time Profiles of the Metabolite 5-MeO-DMT Following Oral Dosing of 5-MeO-DMT methylpivaloyl carbamate (10 mg/Kg) to Male SD Rats.

FIG. 25. Mean Concentration-Time Profiles of the Metabolite 5-MeO-DMT Following Oral Dosing of 5-MeO-DMT methylpivaloyl carbamate (10 mg/Kg) to Male SD Rats

TABLE 2-20

5-MeO-DMT PK parameters
Mean* PK Parameters

| PK Parameter | 5-MeO-DMT |
|---|---|
| Cmax (ng/mL) | 152 |
| Tmax (h) | 0.50 |
| MRT (h) | 1.85 |
| Tlast (h) | 7.00 |
| AUC0-last (h*ng/mL) | 222 |
| AUC0-24 (h*ng/mL) | — |
| AUC0-inf (h*ng/mL) | 242.0 |
| T½ (h) | 2.34 |

*Median calculated for Tmax and Tlast.

Example 2-21. DMT Methoxyethyl Carbamate

| Dosed Test Article: | DMT methoxyethyl carbamate formate |
|---|---|
| Dose Route: | Oral |
| Nominal Dose Concentration: | 10 mg/Kg |
| Analyte: | DMT |

Chemical name: 2-methoxyethyl 3-(2-(dimethylamino)ethyl)-1H-indole-1-carboxylate formate Structural class: carbamate Mechanistic class: presumed carboxyesterases

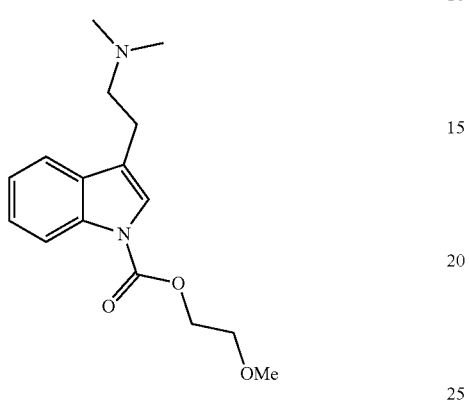

Figure 26:
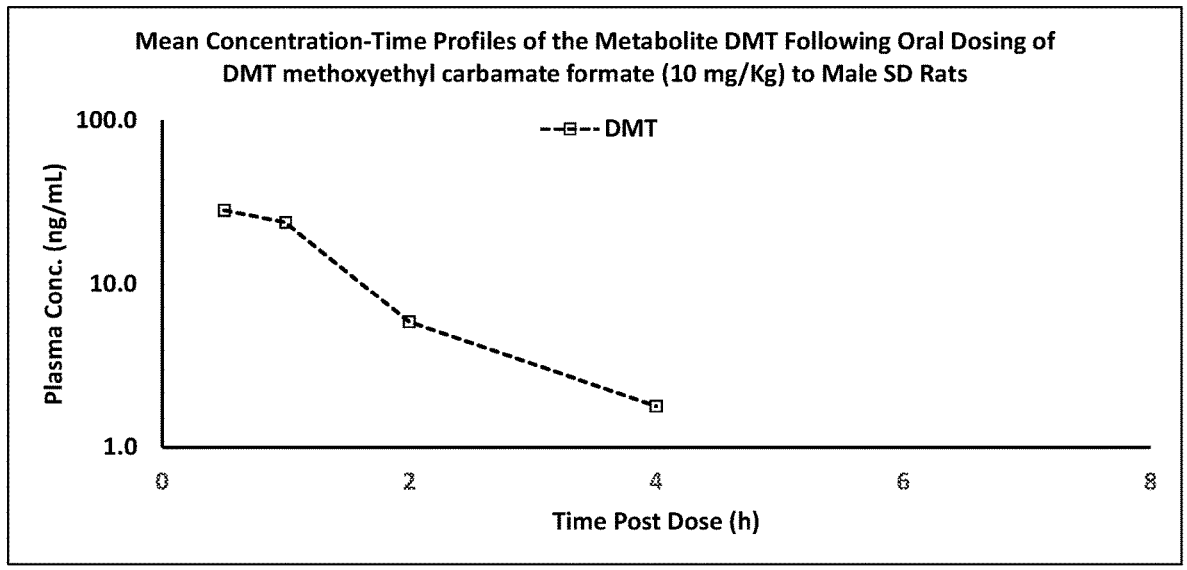
FIG. 26 shows the Mean Concentration-Time Profiles of the Metabolite DMT Following Oral Dosing of DMT methoxyethyl carbamate formate (10 mg/Kg) to Male SD Rats.

FIG. 26. Mean Concentration-Time Profiles of the Metabolite DMT Following Oral Dosing of DMT methoxyethyl carbamate formate (10 mg/Kg) to Male SD Rats

TABLE 2-21

| DMT PK parameters Mean* PK Parameters | |
|---|---|
| PK Parameter | DMT |
| Cmax (ng/mL) | 28.70 |
| Tmax (h) | 0.50 |
| MRT (h) | 1.16 |
| Tlast (h) | 4.00 |
| AUC0-last (h*ng/mL) | 42.4 |
| AUC0-24 (h*ng/mL) | — |
| AUC0-inf (h*ng/mL) | 42 |
| T½ (h) | 0.779 |

Example 2-22. 5-MeO-DMT Methoxyethyl Carbamate Formate

| | |
|---|---|
| Dosed Test Article: | 5-MeO-DMT methoxyethyl carbamate |
| Dose Route: | Oral |
| Nominal Dose Concentration: | 10 mg/Kg |
| Analyte: | 5-MeO-DMT |

Figure 27:
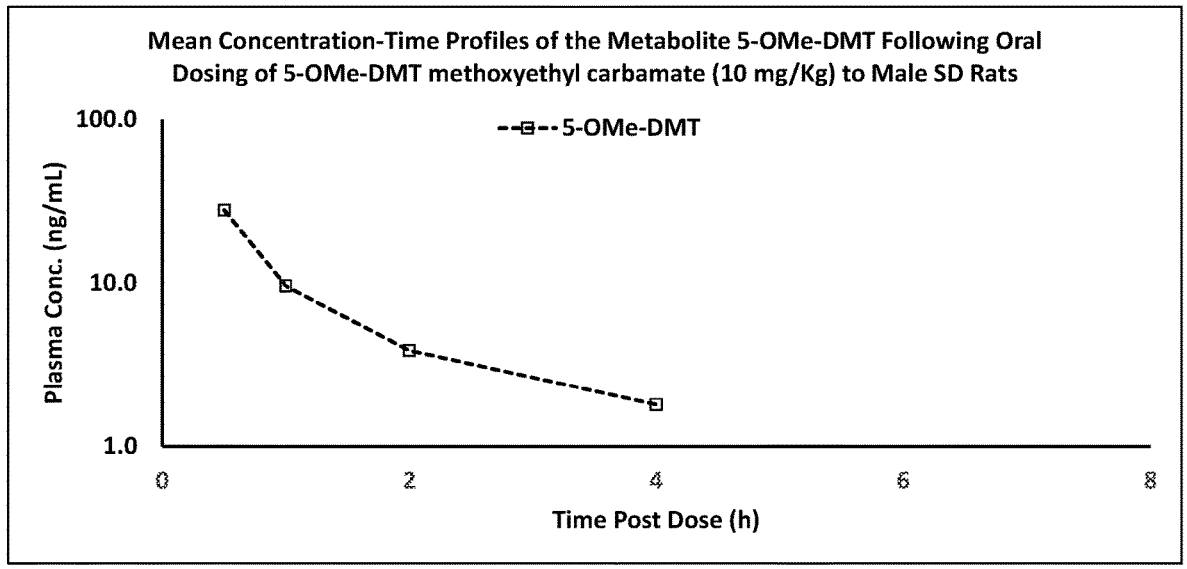
FIG. 27 shows the Mean Concentration-Time Profiles of the Metabolite 5-MeO-DMT Following Oral Dosing of 5-MeO-DMT methoxyethyl carbamate (10 mg/Kg) to Male SD Rats.

Chemical name: 2-methoxyethyl 3-(2-(dimethylamino)ethyl)-5-methoxy-1H-indole-1-carboxylate Structural class: carbamate Mechanistic class: presumed carboxyesterases FIG. 27. Mean Concentration-Time Profiles of the Metabolite 5-MeO-DMT Following Oral Dosing of 5-MeO-DMT methoxyethyl carbamate (10 mg/Kg) to Male SD Rats

TABLE 2-22

| 5-MeO-DMT PK parameters Mean* PK Parameters | |
|---|---|
| PK Parameter | 5-MeO-DMT |
| Cmax (ng/mL) | 27.9 |
| Tmax (h) | 0.5 |
| MRT (h) | 0.9 |
| Tlast (h) | 2.0 |
| AUC0-last (h*ng/mL) | 25 |
| AUC0-24 (h*ng/mL) | — |
| AUC0-inf (h*ng/mL) | 37.9 |
| T½ (h) | 1.36 |

*Median calculated for Tmax and Tlast.

Example 2-23. DMT Trimethyl Lock Amide

| | |
|---|---|
| Dosed Test Article: | DMT trimethyl lock amide |
| Dose Route: | Oral |
| Nominal Dose Concentration: | 10 mg/Kg |
| Analyte: | DMT |

Chemical name: 2-(4-(3-(2-(dimethylamino)ethyl)-1H-indol-1-yl)-2-methyl-4-oxobutan-2-yl)-3,5-dimethylphenyl acetate Structural class: amide Mechanistic class: presumed carboxyesterases+intramolecular cyclization

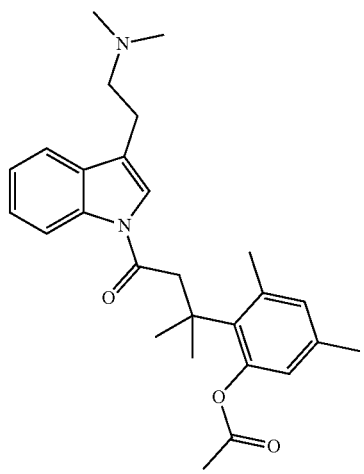 [SMILES: CC(=O)Oc1cc(C)cc(C)c1C(C)(C)CC(=O)n1cc(CCN(C)C)c2ccccc21]

Figure 28:
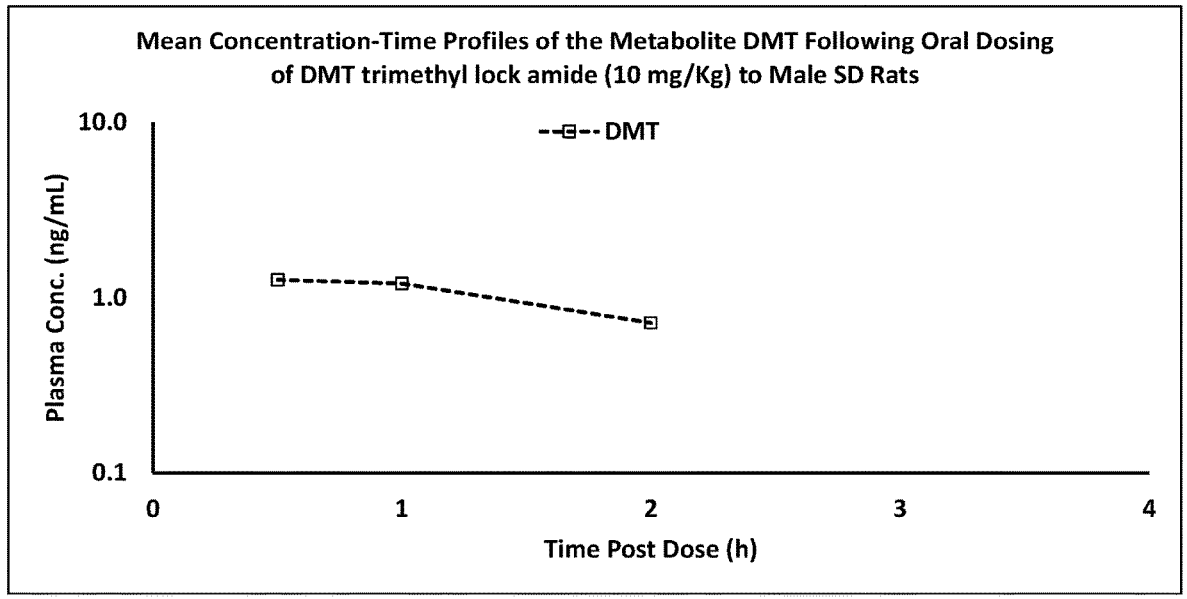
FIG. 28 shows the Mean Concentration-Time Profiles of the Metabolite DMT Following Oral Dosing of DMT trimethyl lock amide (10 mg/Kg) to Male SD Rats.

FIG. 28. Mean Concentration-Time Profiles of the Metabolite DMT Following Oral Dosing of DMT trimethyl lock amide (10 mg/Kg) to Male SD Rats

TABLE 2-23

| DMT PK parameters Mean* PK Parameters | |
|---|---|
| PK Parameter | DMT |
| Cmax (ng/mL) | 1.33 |
| Tmax (h) | 0.50 |
| MRT (h) | 0.80 |
| Tlast (h) | 1.00 |
| AUC0-last (h*ng/mL) | 1.22 |
| AUC0-24 (h*ng/mL) | — |
| AUC0-inf (h*ng/mL) | NC |
| T½ (h) | NC |

*Median calculated for Tmax and Tlast.

Example 2-24. 5-MeO-DMT Trimethyl Lock Amide

| | |
|---|---|
| Dosed Test Article: | 5-MeO-DMT trimethyl lock amide |
| Dose Route: | Oral |
| Nominal Dose Concentration: | 10 mg/Kg |
| Analyte: | 5-MeO-DMT |

Chemical name: 2-(4-(3-(2-(dimethylamino)ethyl)-5-methoxy-1H-indol-1-yl)-2-methyl-4-oxobutan-2-yl)-3,5-dimethylphenyl Structural class: amide Mechanistic class: presumed carboxyesterases+intramolecular cyclization

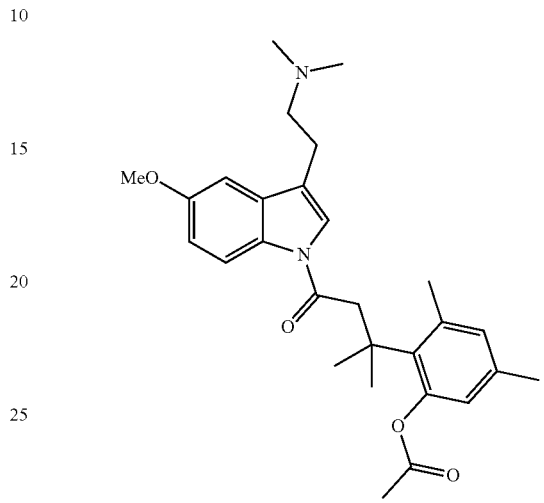

Figure 29:
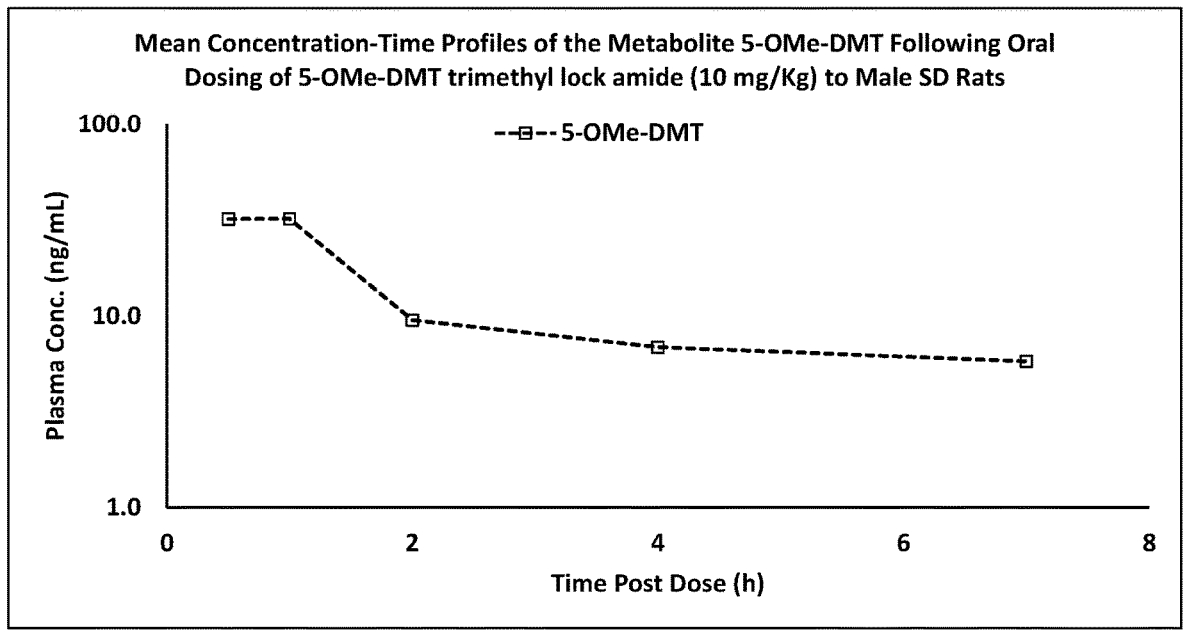
FIG. 29 shows the Mean Concentration-Time Profiles of the Metabolite 5-MeO-DMT Following Oral Dosing of 5-MeO-DMT trimethyl lock amide (10 mg/Kg) to Male SD Rats.

FIG. 29. Mean Concentration-Time Profiles of the Metabolite 5-MeO-DMT Following Oral Dosing of 5-MeO-DMT trimethyl lock amide (10 mg/Kg) to Male SD Rats

TABLE 2-24

| 5-MeO-DMT PK parameters Mean* PK Parameters | |
|---|---|
| PK Parameter | 5-MeO-DMT |
| Cmax (ng/mL) | 37.70 |
| Tmax (h) | 1.00 |
| MRT (h) | 2.49 |
| Tlast (h) | 7.00 |
| AUC0-last (h*ng/mL) | 80.5 |
| AUC0-24 (h*ng/mL) | — |
| AUC0-inf (h*ng/mL) | 100 |
| T½ (h) | 2.91 |

*Median calculated for Tmax and Tlast.

Example 2-25. DMT 4-Piperidinopiperidine Urea Formate

| | |
|---|---|
| Dosed Test Article: | DMT 4-Piperidinopiperidine urea formate |
| Dose Route: | Oral |
| Nominal Dose Concentration: | 10 mg/Kg |
| Analyte: | DMT |

Chemical name: [1,4'-Bipiperidin]-1'-yl(3-(2-(dimethylamino)ethyl)-1H-indol-1-yl)methanone
Structural class: urea
Mechanistic class: presumed amidases

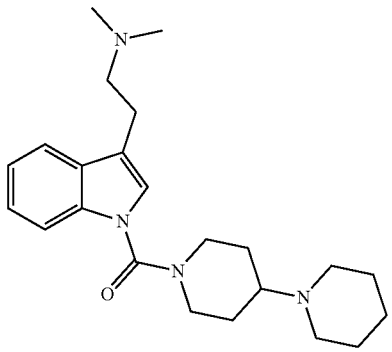 [SMILES: CN(C)CCc1cn(C(=O)N2CCC(N3CCCCC3)CC2)c2ccccc12]

TABLE 27

Mean Concentration-Time Profiles of the Metabolite DMT 4-Piperidinopiperidine urea formate (10 mg/Kg) to Male SD Rats
Mean Plasma Concentration (ng/mL)

| Time (h) | DMT |
|---|---|
| 0.50 | BLQ |
| 1.00 | BLQ |
| 2.00 | BLQ |
| 4.00 | BLQ |
| 7.00 | BLQ |
| 24.0 | BLQ |

BLQ: Below Lower Limit of Quantification (0.5 ng/mL)

Example 2-26. 5-MeO-DMT 4-Piperidinopiperidine Urea Formate

| Dosed Test Article: | 5-MeO-DMT 4-Piperidinopiperidine urea formate |
|---|---|
| Dose Route: | Oral |
| Nominal Dose Concentration: | 10 mg/Kg |
| Analyte: | 5-MeO-DMT |

Chemical name: [1,4'-bipiperidin]-1'-yl(3-(2-(dimethylamino)ethyl)-5-methoxy-1H-indol-1-yl)methanone
Structural class: urea
Mechanistic class: presumed amidases

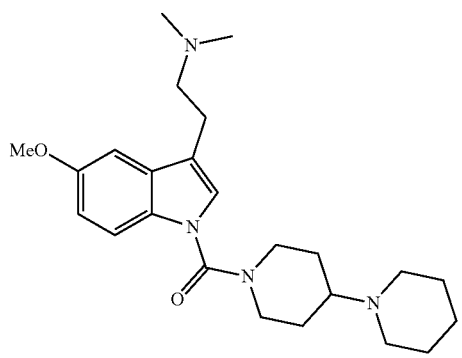 [SMILES: COc1ccc2c(c1)c(CCN(C)C)cn2C(=O)N1CCC(N2CCCCC2)CC1]

Figure 30:
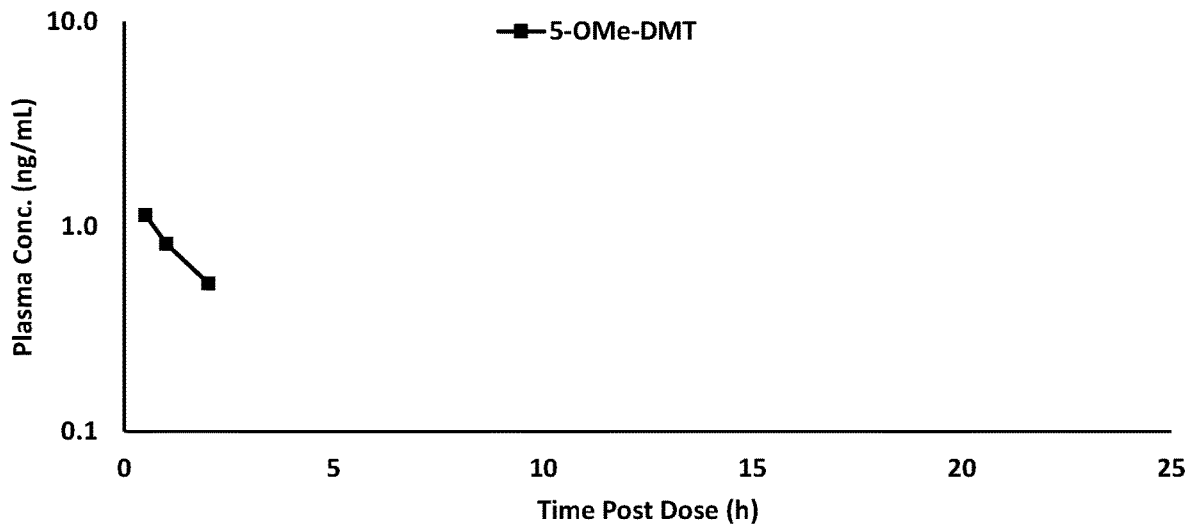
FIG. 30 shows the Mean Concentration-Time Profiles of Metabolite 5-MeO-DMT Following Oral Dosing of 5-MeO-DMT 4-Piperidinopiperidine urea formate (10 mg/Kg) to Male SD Rats.

FIG. 30. Mean Concentration-Time Profiles of Metabolite 5-MeO-DMT Following Oral Dosing of 5-MeO-DMT 4-Piperidinopiperidine urea formate (10 mg/Kg) to Male SD Rats

TABLE 2-26

5-MeO-DMT PK parameters
Mean* Pharmacokinetic Parameters

| PK Parameter | 5-MeO-DMT |
|---|---|
| Cmax (ng/mL) | 1.14 |
| Tmax (h) | 0.50 |
| MRT (h) | 0.728 |
| Tlast (h) | 1.00 |
| AUC0-last (h*ng/mL) | 1.08 |
| AUC0-24 (h*ng/mL) | — |
| AUC0-inf (h*ng/mL) | NC |
| T½ (h) | NC |

*Median calculated for Tmax and Tlast.
NC: Not Calculated

Example 2-27. 5-MeO-DMT N,N-Dimethyl Urea Formate

| Dosed Test Article: | 5-MeO-DMT N,N-dimethyl urea formate |
|---|---|
| Dose Route: | Oral |
| Nominal Dose Concentration: | 10 mg/Kg |
| Analyte: | 5-MeO-DMT |

Chemical name: 3-(2-(dimethylamino)ethyl)-5-methoxy-N,N-dimethyl-1H-indole-1-carboxamide
Structural class: urea
Mechanistic class: presumed amidases

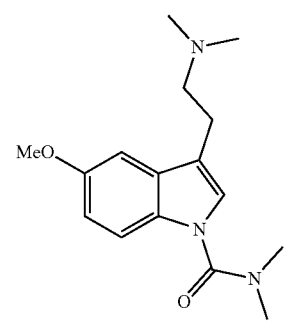 [SMILES: COc1ccc2c(c1)c(CCN(C)C)cn2C(=O)N(C)C]

Figure 31:
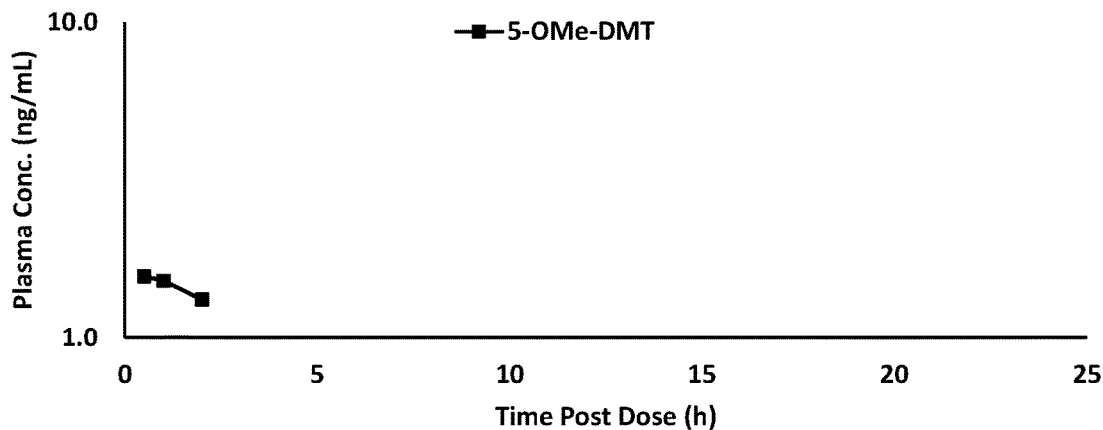
FIG. 31 shows the Mean Concentration-Time Profiles of Metabolite 5-MeO-DMT Following Oral Dosing of the 5-MeO-DMT N,N-dimethyl urea formate prodrug of 5-MeO-DMT (10 mg/Kg) to Male SD Rats.

FIG. 31. Mean Concentration-Time Profiles of Metabolite 5-MeO-DMT Following Oral Dosing of the 5-MeO-DMT N,N-dimethyl urea formate prodrug of 5-MeO-DMT (10 mg/Kg) to Male SD Rats

TABLE 2-27

5-MeO-DMT PK parameters
Mean* Pharmacokinetic Parameters

| PK Parameter | 5-MeO-DMT |
|---|---|
| Cmax (ng/mL) | 1.74 |
| Tmax (h) | 1.00 |
| MRT (h) | 1.12 |
| Tlast (h) | 2.00 |
| AUC0-last (h*ng/mL) | 2.58 |

TABLE 2-27-continued

| 5-MeO-DMT PK parameters Mean* Pharmacokinetic Parameters | |
|---|---|
| PK Parameter | 5-MeO-DMT |
| AUC0-24 (h*ng/mL) | — |
| AUC0-inf (h*ng/mL) | NC |
| T½ (h) | NC |

*Median calculated for Tmax and Tlast.
NC: Not Calculated

Example 2-28. DMT Lysine Tri-Hydrochloride

| Dosed Test Article: | DMT Lysine tri-hydrochloride |
|---|---|
| Dose Route: | Oral |
| Nominal Dose Concentration: | 10 mg/Kg |
| Analyte: | DMT |

Chemical name: (S)-di-tert-butyl (6-(3-(2-(dimethylamino)ethyl)-1H-indol-1-yl)-6-oxohexane-1,5-diyl)dicarbamate Structural class: amide Mechanistic class: presumed amidases

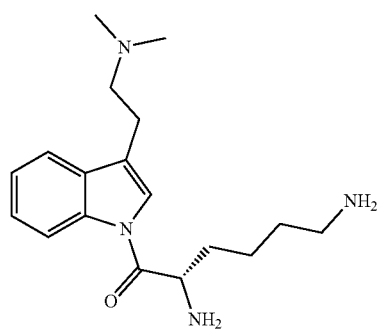 [SMILES: CN(C)CCc1cn(C(=O)[C@@H](N)CCCCN)c2ccccc12]

Figure 32:
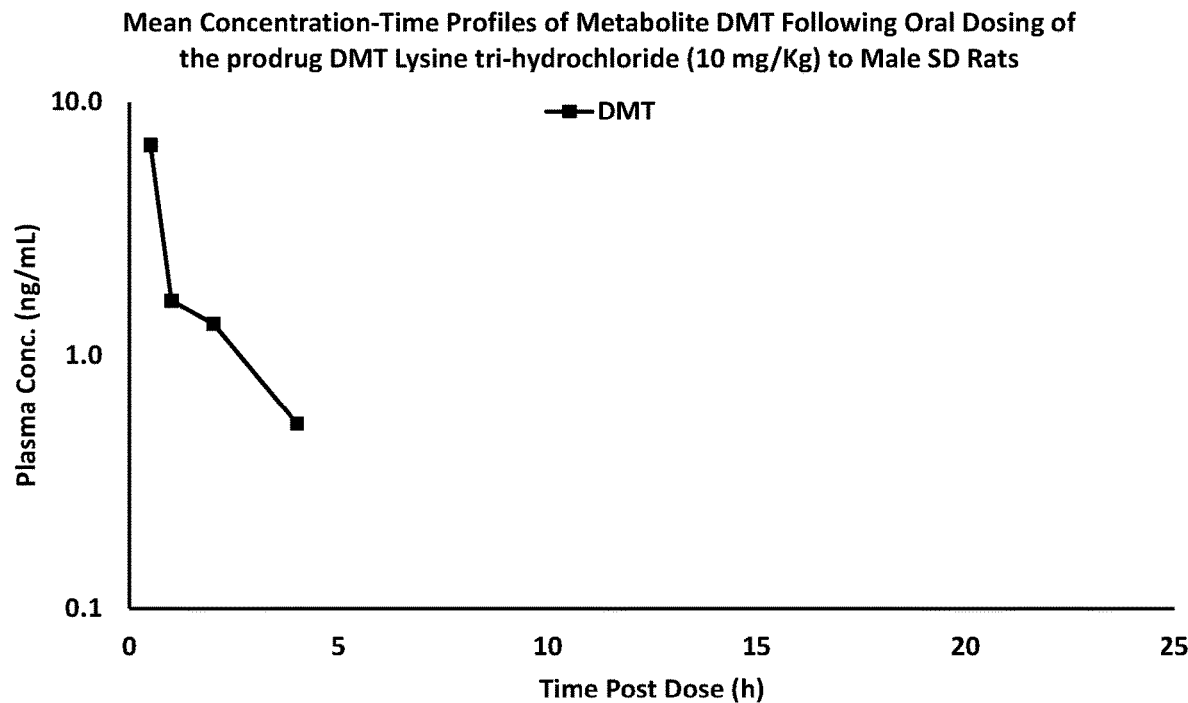
FIG. 32 shows the Mean Concentration-Time Profiles of Metabolite DMT Following Oral Dosing of the prodrug DMT Lysine tri-hydrochloride (10 mg/Kg) to Male SD Rats.

FIG. 32. Mean Concentration-Time Profiles of Metabolite DMT Following Oral Dosing of the prodrug DMT Lysine tri-hydrochloride (10 mg/Kg) to Male SD Rats

TABLE 2-28

| DMT PK parameters Mean* Pharmacokinetic Parameters | |
|---|---|
| PK Parameter | DMT |
| Cmax (ng/mL) | 6.76 |
| Tmax (h) | 0.50 |
| MRT (h) | 1.17 |
| Tlast (h) | 4.00 |
| AUC0-last (h*ng/mL) | 6.56 |
| AUC0-24 (h*ng/mL) | — |
| AUC0-inf (h*ng/mL) | 9.62 |
| T½ (h) | 1.71 |

*Median calculated for Tmax and Tlast.

Example 2-29. 5-MeO-DMT Lysine Tri-Hydrochloride

| Dosed Test Article: | 5-MeO-DMT Lysine tri-hydrochloride |
|---|---|
| Dose Route: | Oral |
| Nominal Dose Concentration: | 10 mg/Kg |
| Analyte: | 5-MeO-DMT |

Chemical name: (S)-2,6-diamino-1-(3-(2-(dimethylamino)ethyl)-5-methoxy-1H-indol-1-yl)hexan-1-one Structural class: amide Mechanistic class: presumed amidases

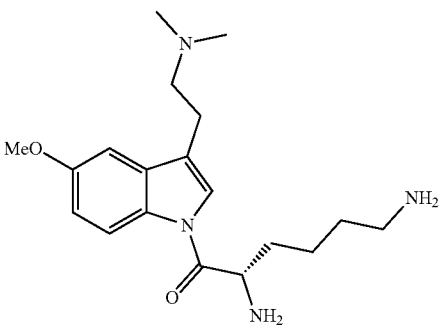 [SMILES: COc1ccc2c(c1)c(CCN(C)C)cn2C(=O)[C@@H](N)CCCCN]

Figure 33:
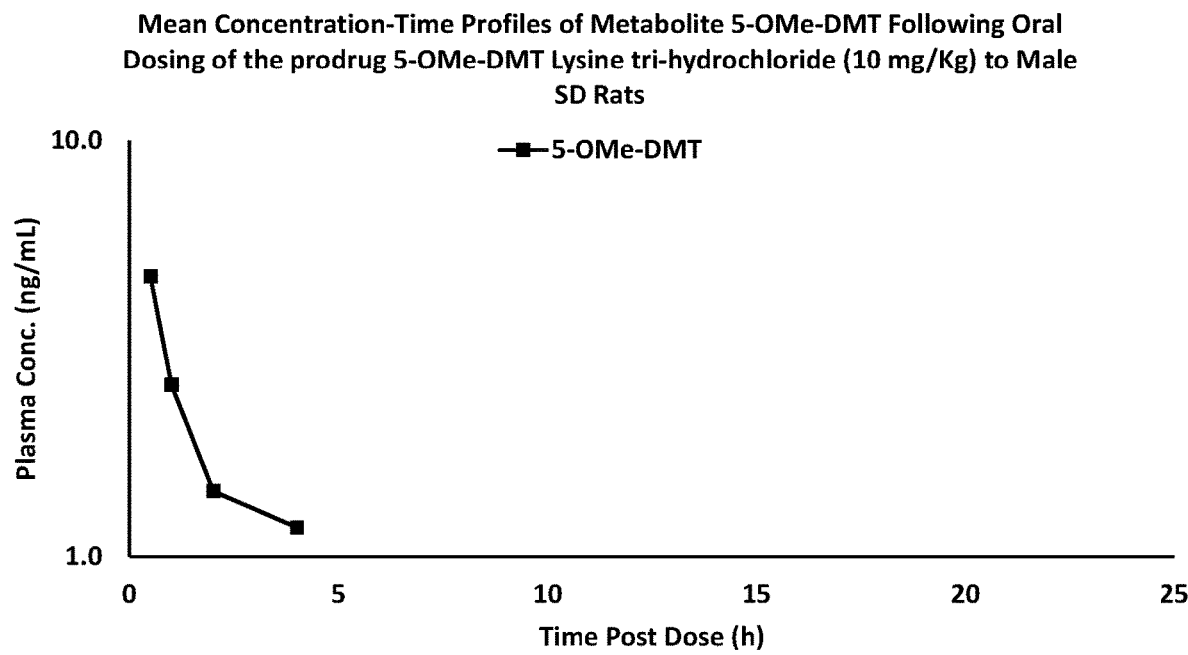
FIG. 33 shows the Mean Concentration-Time Profiles of Metabolite 5-MeO-DMT Following Oral Dosing of the prodrug 5-MeO-DMT Lysine tri-hydrochloride (10 mg/Kg) to Male SD Rats.

FIG. 33. Mean Concentration-Time Profiles of Metabolite 5-MeO-DMT Following Oral Dosing of the prodrug 5-MeO-DMT Lysine tri-hydrochloride (10 mg/Kg) to Male SD Rats

TABLE 2-29

| 5-MeO-DMT PK parameters Mean* Pharmacokinetic Parameters | |
|---|---|
| PK Parameter | 5-MeO-DMT |
| Cmax (ng/mL) | 4.72 |
| Tmax (h) | 0.50 |
| MRT (h) | 1.57 |
| Tlast (h) | 4.00 |
| AUC0-last (h*ng/mL) | 7.63 |
| AUC0-24 (h*ng/mL) | — |
| AUC0-inf (h*ng/mL) | 13.4 |
| T½ (h) | 3.16 |

*Median calculated for Tmax and Tlast.

Example 2-30. Di-DMT Urea (Symmetrical Urea) Di-Formate Salt

| Dosed Test Article: | Di-DMT urea (symmetrical urea) di-formate salt |
|---|---|
| Dose Route: | Oral |
| Nominal Dose Concentration: | 10 mg/Kg |
| Analyte: | DMT |

Chemical name: bis(3-(2-dimethylamno)ethyl-1H-indol-1-ylmethanone

Structural class: symmetrical dimer (urea)

Mechanistic class: presumed amidases

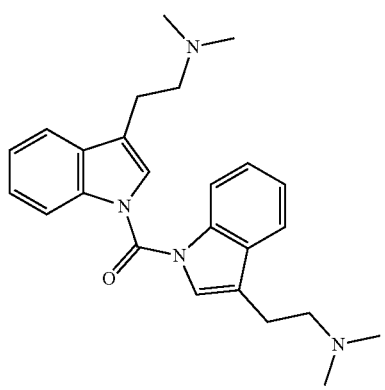 [SMILES: CN(C)CCc1cn(C(=O)n2cc(CCN(C)C)c3ccccc32)c2ccccc12]

Figure 34:
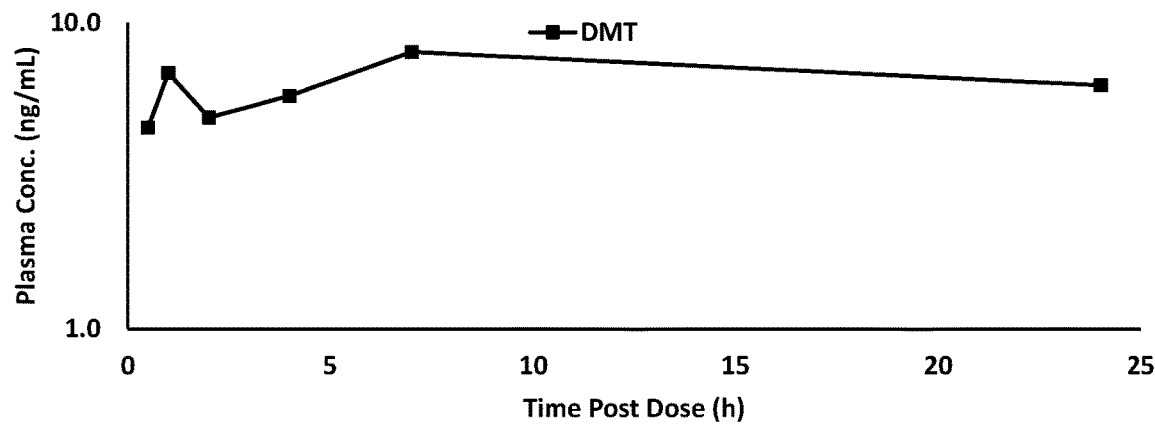
FIG. 34 shows the Mean Concentration-Time Profiles of Metabolite DMT Following Oral Dosing of the prodrug Di-DMT urea (symmetrical urea) di-formate salt (10 mg/Kg) to Male SD Rats.

FIG. 34. Mean Concentration-Time Profiles of Metabolite DMT Following Oral Dosing of the prodrug Di-DMT urea (symmetrical urea) di-formate salt (10 mg/Kg) to Male SD Rats

TABLE 2-30

| DMT PK parameters Mean* Pharmacokinetic Parameters | |
|---|---|
| PK Parameter | DMT |
| Cmax (ng/mL) | 8.04 |
| Tmax (h) | 7.00 |
| MRT (h) | 11.8 |
| Tlast (h) | 24.0 |
| AUC0-last (h*ng/mL) | 163 |
| AUC0-24 (h*ng/mL) | 163 |
| AUC0-inf (h*ng/mL) | NC |
| T½ (h) | NC |

*Median calculated for Tmax and Tlast.

Example 2-31. Di-5-MeO-DMT Urea (Symmetrical Urea) Di-Formate Salt

| Dosed Test Article: | Di-5-MeO-DMT urea (symmetrical urea) di-formate salt |
|---|---|
| Dose Route: | Oral |
| Nominal Dose Concentration: | 10 mg/Kg |
| Analyte: | 5-MeO-DMT |

Chemical name: bis(3-(2-(dimethylamino)ethyl)-5-methoxy-1H-indol-1-yl)methanone

Structural class: symmetrical dimer (urea)

Mechanistic class: presumed amidases

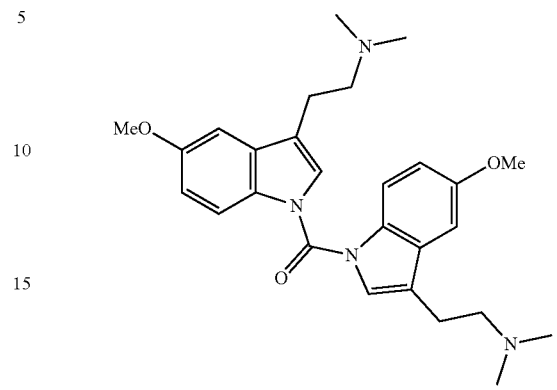

Figure 35:
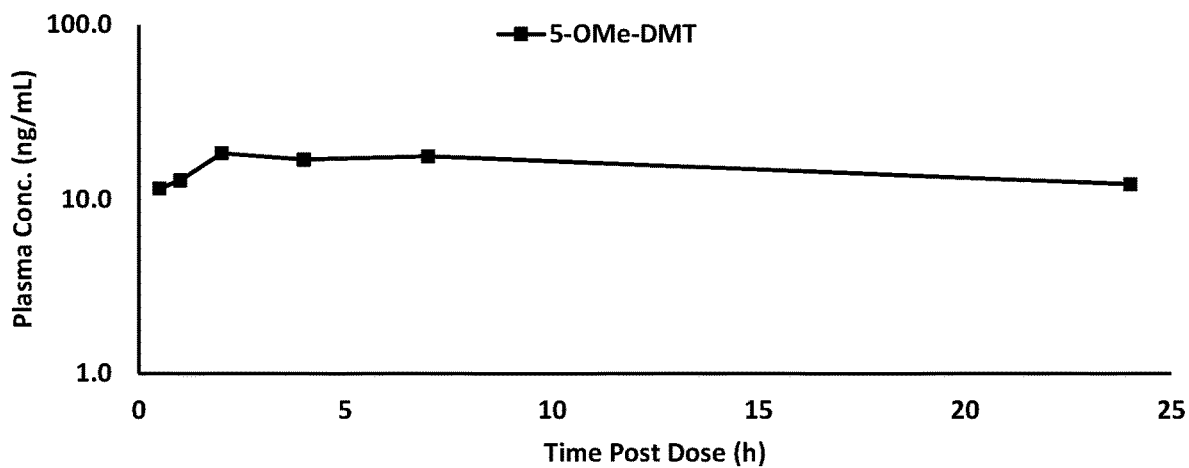
FIG. 35 shows the Mean Concentration-Time Profiles of Metabolite 5-MeO-DMT Following Oral Dosing of the prodrug Di-5-MeO-DMT urea (symmetrical urea) di-formate salt (10 mg/Kg) to Male SD Rats.

FIG. 35. Mean Concentration-Time Profiles of Metabolite 5-MeO-DMT Following Oral Dosing of the prodrug Di-5-MeO-DMT urea (symmetrical urea) di-formate salt (10 mg/Kg) to Male SD Rats

TABLE 2-31

| 5-MeO-DMT PK parameters Mean* Pharmacokinetic Parameters | |
|---|---|
| PK Parameter | 5-MeO-DMT |
| Cmax (ng/mL) | 19.1 |
| Tmax (h) | 2.00 |
| MRT (h) | 10.9 |
| Tlast (h) | 24.0 |
| AUC0-last (h*ng/mL) | 366 |
| AUC0-24 (h*ng/mL) | 366 |
| AUC0-inf (h*ng/mL) | 995 |
| T½ (h) | 33.3 |

*Median calculated for Tmax and Tlast.

Example 32. DMT Valine Di-Hydrochloride

| Dosed Test Article: | DMT Valine di-hydrochloride |
|---|---|
| Dose Route: | Oral |
| Nominal Dose Concentration: | 10 mg/Kg |
| Analyte: | DMT |

Chemical name: (S)-2-amino-1-(3-(2-(dimethylamino)ethyl)-1H-indol-1-yl)-3-methylbutan-1-one Structural class: amide Mechanistic class: presumed amidases

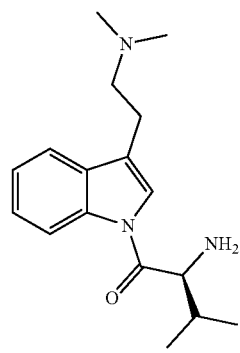 [SMILES: CC(C)[C@H](N)C(=O)n1cc(CCN(C)C)c2ccccc21]

Figure 36:
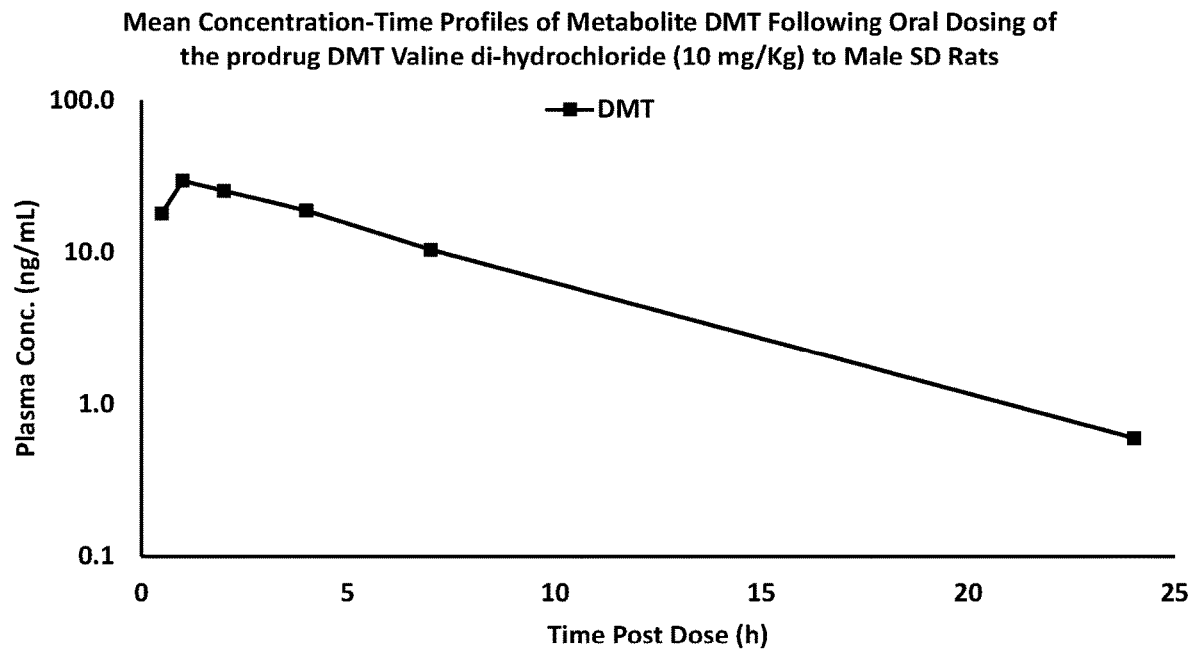
FIG. 36 shows the Mean Concentration-Time Profiles of Metabolite DMT Following Oral Dosing of the prodrug DMT Valine di-hydrochloride (10 mg/Kg) to Male SD Rats.

FIG. 36. Mean Concentration-Time Profiles of Metabolite DMT Following Oral Dosing of the prodrug DMT Valine di-hydrochloride (10 mg/Kg) to Male SD Rats

TABLE 2-32

| DMT PK parameters Mean* Pharmacokinetic Parameters | |
|---|---|
| PK Parameter | DMT |
| Cmax (ng/mL) | 31.1 |
| Tmax (h) | 1.00 |
| MRT (h) | 3.73 |
| Tlast (h) | 7.00 |
| AUC0-last (h*ng/mL) | 174 |
| AUC0-24 (h*ng/mL) | 268 |
| AUC0-inf (h*ng/mL) | 205 |
| T½ (h) | 3.69 |

*Median calculated for Tmax and Tlast.

Example 2-33. 5-MeO-DMT Valine Di-Hydrochloride

| Dosed Test Article: | 5-MeO-DMT Valine di-hydrochloride |
|---|---|
| Dose Route: | Oral |
| Nominal Dose Concentration: | 10 mg/Kg |
| Analyte: | 5-MeO-DMT |

Chemical name: (S)-2-amino-1-(3-(2-(dimethylamino)ethyl)-5-methoxy-1H-indol-1-yl)-3-methylbutan-1-one Structural class: amide Mechanistic class: presumed amidases

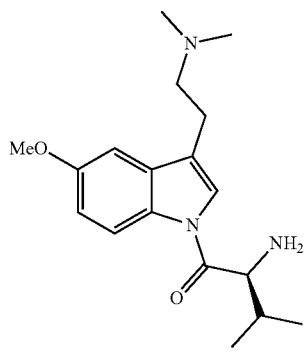 [SMILES: COc1ccc2c(c1)c(CCN(C)C)cn2C(=O)[C@@H](N)C(C)C]

Figure 37:
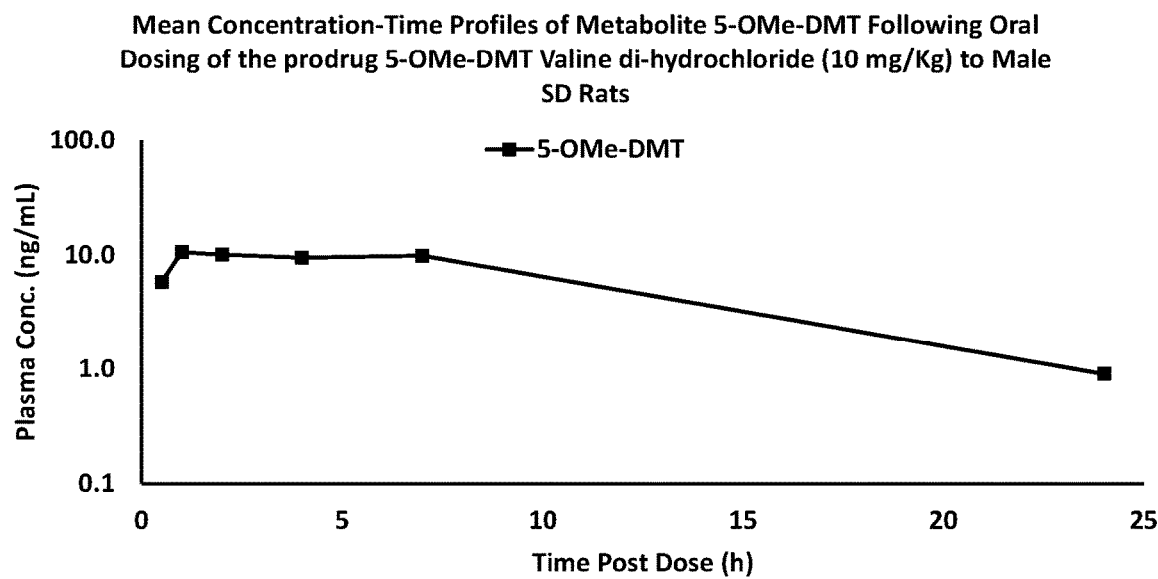
FIG. 37 shows the Mean Concentration-Time Profiles of Metabolite 5-MeO-DMT Following Oral Dosing of the prodrug 5-MeO-DMT Valine di-hydrochloride (10 mg/Kg) to Male SD Rats.

FIG. 37. Mean Concentration-Time Profiles of Metabolite 5-MeO-DMT Following Oral Dosing of the prodrug 5-MeO-DMT Valine di-hydrochloride (10 mg/Kg) to Male SD Rats

TABLE 2-33

| 5-MeO-DMT PK parameters Mean* Pharmacokinetic Parameters | |
|---|---|
| PK Parameter | 5-MeO-DMT |
| Cmax (ng/mL) | 11.1 |
| Tmax (h) | 2.00 |
| MRT (h) | 6.47 |
| Tlast (h) | 24.0 |

TABLE 2-33-continued

| 5-MeO-DMT PK parameters Mean* Pharmacokinetic Parameters | |
|---|---|
| PK Parameter | 5-MeO-DMT |
| AUC0-last (h*ng/mL) | 155 |
| AUC0-24 (h*ng/mL) | 155 |
| AUC0-inf (h*ng/mL) | 150 |
| T½ (h) | 5.54 |

*Median calculated for Tmax and Tlast.

Example 2-34. 5-MeO-DMT N,N-dimethylglycine formate

| Dosed Test Article: | 5-MeO-DMT N,N-dimethylglycine formate |
|---|---|
| Dose Route: | Oral |
| Nominal Dose Concentration: | 10 mg/Kg |
| Analyte: | 5-MeO-DMT |

Chemical name: 2-(dimethylamino)-1-(3-(2-(dimethylamino)ethyl)-5-methoxy-1H-indol-1-yl)ethan-1-one Structural class: amide Mechanistic class: presumed amidases

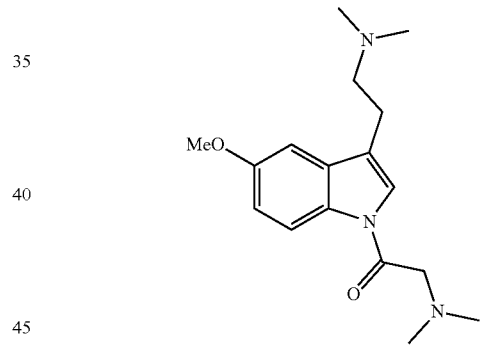

Figure 38:
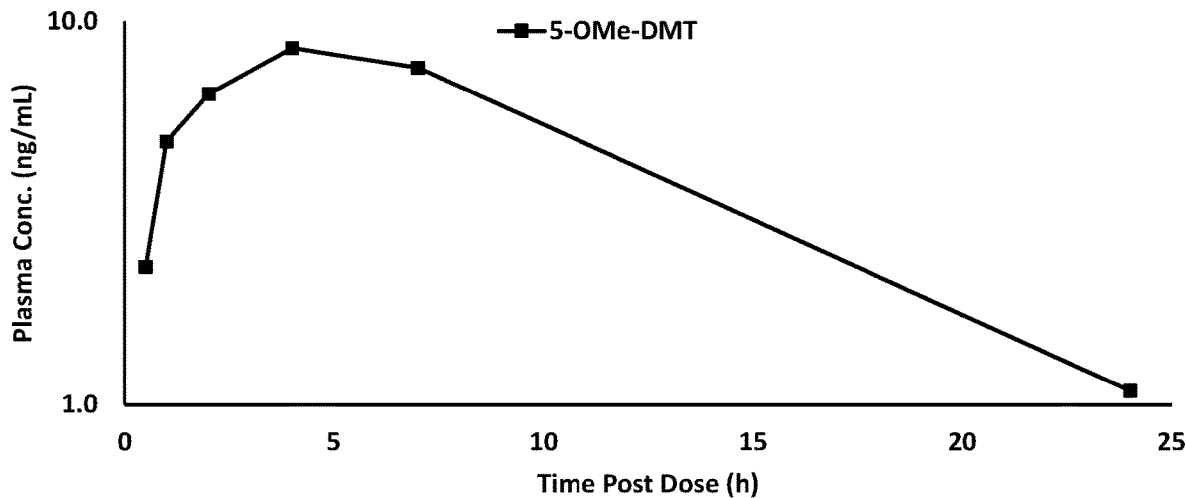
FIG. 38 shows the Mean Concentration-Time Profiles of Metabolite 5-MeO-DMT Following Oral Dosing of the prodrug 5-MeO-DMT N,N-dimethylglycine formate (10 mg/Kg) to Male SD Rats.

FIG. 38. Mean Concentration-Time Profiles of Metabolite 5-MeO-DMT Following Oral Dosing of the prodrug 5-MeO-DMT N,N-dimethylglycine formate (10 mg/Kg) to Male SD Rats

TABLE 2-34

| 5-MeO-DMT PK parameters Mean* Pharmacokinetic Parameters | |
|---|---|
| PK Parameter | 5-MeO-DMT |
| Cmax (ng/mL) | 8.58 |
| Tmax (h) | 4.00 |
| MRT (h) | 7.13 |
| Tlast (h) | 24.0 |
| AUC0-last (h*ng/mL) | 121 |
| AUC0-24 (h*ng/mL) | 121 |
| AUC0-inf (h*ng/mL) | 134 |
| T½ (h) | 6.46 |

*Median calculated for Tmax and Tlast.

Example 2-35. Phe-N-Me-Gly DMT di-hydrochloride (DMT Dipeptide)

| Dosed Test Article: | Phe-N—Me-Gly DMT di-hydrochloride (DMT dipeptide) |
|---|---|
| Dose Route: | Oral |
| Nominal Dose Concentration: | 10 mg/Kg |
| Analyte: | DMT |

Chemical name: (S)-2-amino-N-(2-(3-(2-(dimethylamino)ethyl)-1H-indol-1-yl)-2-oxoethyl)-N-methyl-3-phenylpropanamide Structural class: amide Mechanistic class: pH-dependent cyclization

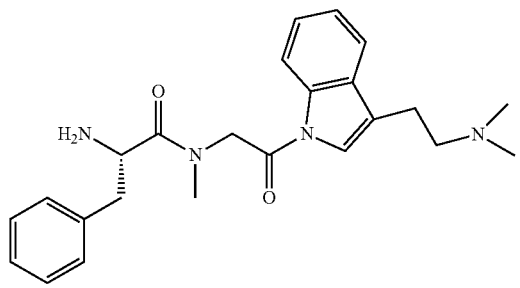 [SMILES: CN(C)CCc1cn(C(=O)CN(C)C(=O)[C@@H](N)Cc2ccccc2)c2ccccc12]

Figure 39:
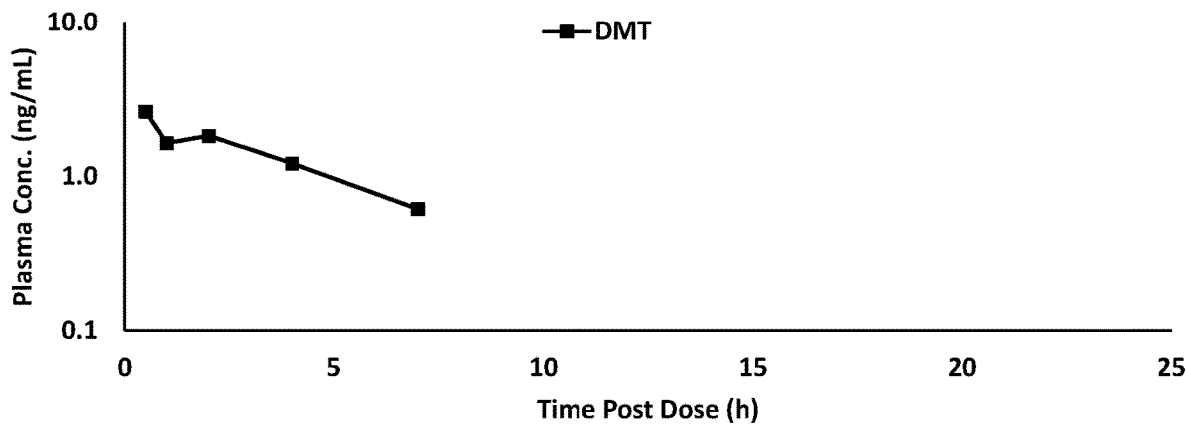
FIG. 39 shows the Mean Concentration-Time Profiles of Metabolite DMT Following Oral Dosing of the prodrug Phe-N-Me-Gly DMT di-hydrochloride (DMT dipeptide) (10 mg/Kg) to Male SD Rats.

FIG. 39. Mean Concentration-Time Profiles of Metabolite DMT Following Oral Dosing of the prodrug Phe-N-Me-Gly DMT di-hydrochloride (DMT dipeptide) (10 mg/Kg) to Male SD Rats Table 2-35. DMT PK parameters

TABLE 2-35

| DMT PK parameters Mean* Pharmacokinetic Parameters | |
|---|---|
| PK Parameter | DMT |
| Cmax (ng/mL) | 2.43 |
| Tmax (h) | 0.50 |
| MRT (h) | 2.30 |
| Tlast (h) | 4.00 |
| AUC0-last (h*ng/mL) | 7.17 |
| AUC0-24 (h*ng/mL) | — |
| AUC0-inf (h*ng/mL) | 12.0 |
| T½ (h) | 3.31 |

*Median calculated for Tmax and Tlast.

Example 2-36. DMT Alanine di-hydrochloride IDC-1001 TI

| Dosed Test Article: | DMT Alanine di-hydrochloride |
|---|---|
| Dose Route: | Oral |
| Nominal Dose Concentration: | 10 mg/Kg |
| Analyte: | DMT |

Chemical name: (S)-2-amino-1-(3-(2-(dimethylamino)ethyl)-1H-indol-1-yl)propan-1-one Structural class: amide Mechanistic class: presumed amidases

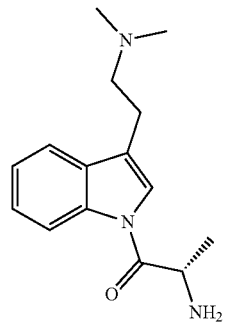 [SMILES: C[C@H](N)C(=O)n1cc(CCN(C)C)c2ccccc21]

Figure 40:
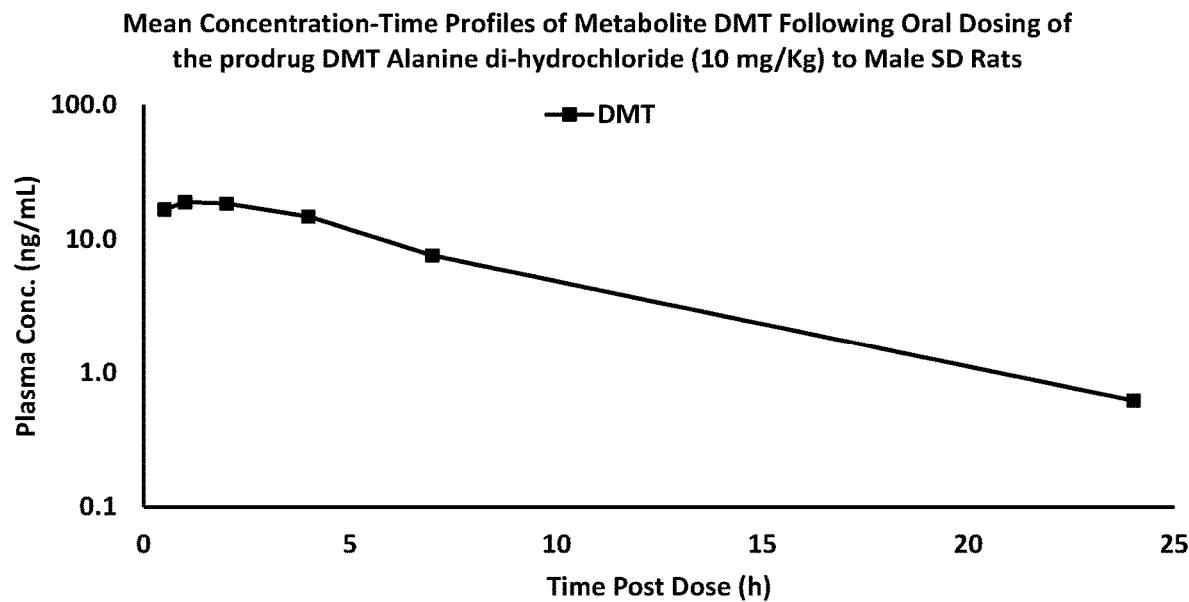
FIG. 40 shows the Mean Concentration-Time Profiles of Metabolite DMT Following Oral Dosing of the prodrug DMT Alanine di-hydrochloride (10 mg/Kg) to Male SD Rats.

FIG. 40. Mean Concentration-Time Profiles of Metabolite DMT Following Oral Dosing of the prodrug DMT Alanine di-hydrochloride (10 mg/Kg) to Male SD Rats

TABLE 2-36

| DMT PK parameters Mean* Pharmacokinetic Parameters | |
|---|---|
| PK Parameter | DMT |
| Cmax (ng/mL) | 20.2 |
| Tmax (h) | 0.50 |
| MRT (h) | 3.73 |
| Tlast (h) | 7.00 |
| AUC0-last (h*ng/mL) | 126 |
| AUC0-24 (h*ng/mL) | 195 |
| AUC0-inf (h*ng/mL) | 153 |
| T½ (h) | 4.08 |

* Median calculated for Tmax and Tlast.

Example 2-37. 5-MeO-DMT Alanine di-hydrochloride

| Dosed Test Article: | 5-MeO-DMT Alanine di-hydrochloride |
|---|---|
| Dose Route: | Oral |
| Nominal Dose Concentration: | 10 mg/Kg |
| Analyte: | 5-MeO-DMT |

Chemical name: (S)-2-amino-1-(3-(2-(dimethylamino)ethyl)-5-methoxy-1H-indol-1-yl)propan-1-one
Structural class: amide
Mechanistic class: presumed amidases

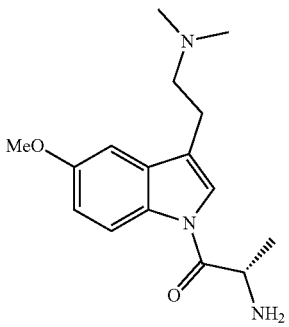 [SMILES: COc1ccc2c(c1)c(CCN(C)C)cn2C(=O)[C@H](C)N]

Figure 41:
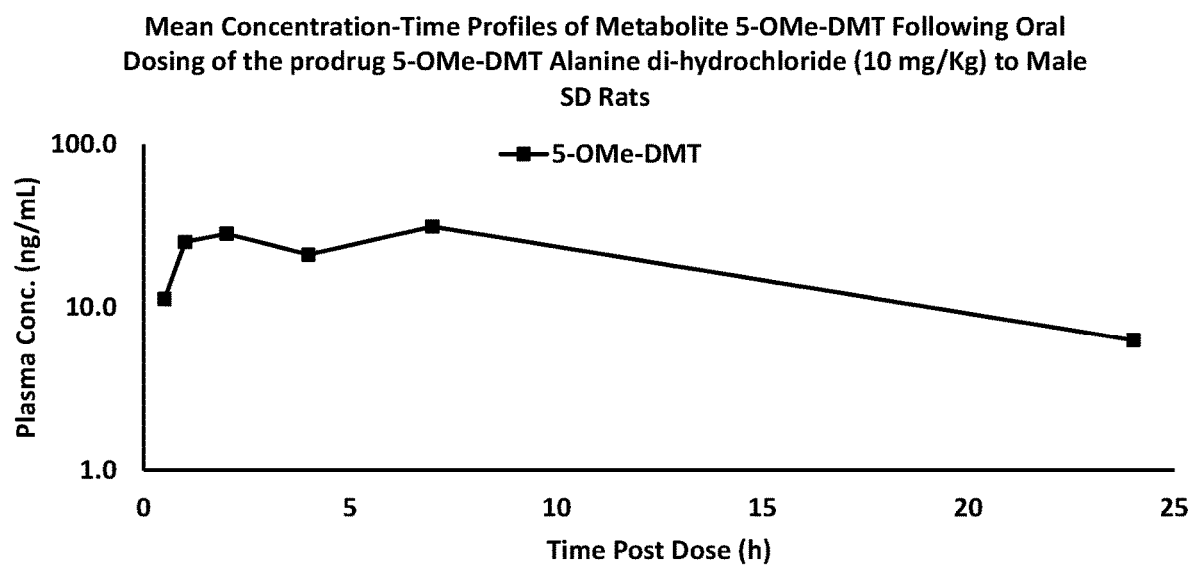
FIG. 41 shows the Mean Concentration-Time Profiles of Metabolite 5-MeO-DMT Following Oral Dosing of the prodrug 5-MeO-DMT Alanine di-hydrochloride (10 mg/Kg) to Male SD Rats.

FIG. 41. Mean Concentration-Time Profiles of Metabolite 5-MeO-DMT Following Oral Dosing of the prodrug 5-MeO-DMT Alanine di-hydrochloride (10 mg/Kg) to Male SD Rats

TABLE 2-37

| 5-MeO-DMT PK parameters Mean* Pharmacokinetic Parameters | |
|---|---|
| PK Parameter | 5-MeO-DMT |
| Cmax (ng/mL) | 34.7 |
| Tmax (h) | 2.00 |
| MRT (h) | 7.78 |
| Tlast (h) | 24.0 |
| AUC0-last (h*ng/mL) | 488 |
| AUC0-24 (h*ng/mL) | 488 |
| AUC0-inf (h*ng/mL) | 630 |
| T½ (h) | 10.0 |

*Median calculated for Tmax and Tlast.

Example 2-38. DMT tetramethylphosphorodiamide

| Dosed Test Article: | DMT tetramethylphosphorodiamide |
|---|---|
| Dose Route: | Oral |
| Nominal Dose Concentration: | 10 mg/Kg |
| Analyte: | DMT |

Chemical name: 2-(1-di(dimethylamino)phosphoryl-indol-3-yl)-N,N-dimethyl-ethanamine
Structural class: phosphorodiamidate prodrug
Mechanistic class: presumed phosphatase

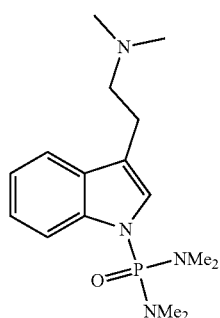

Figure 42:
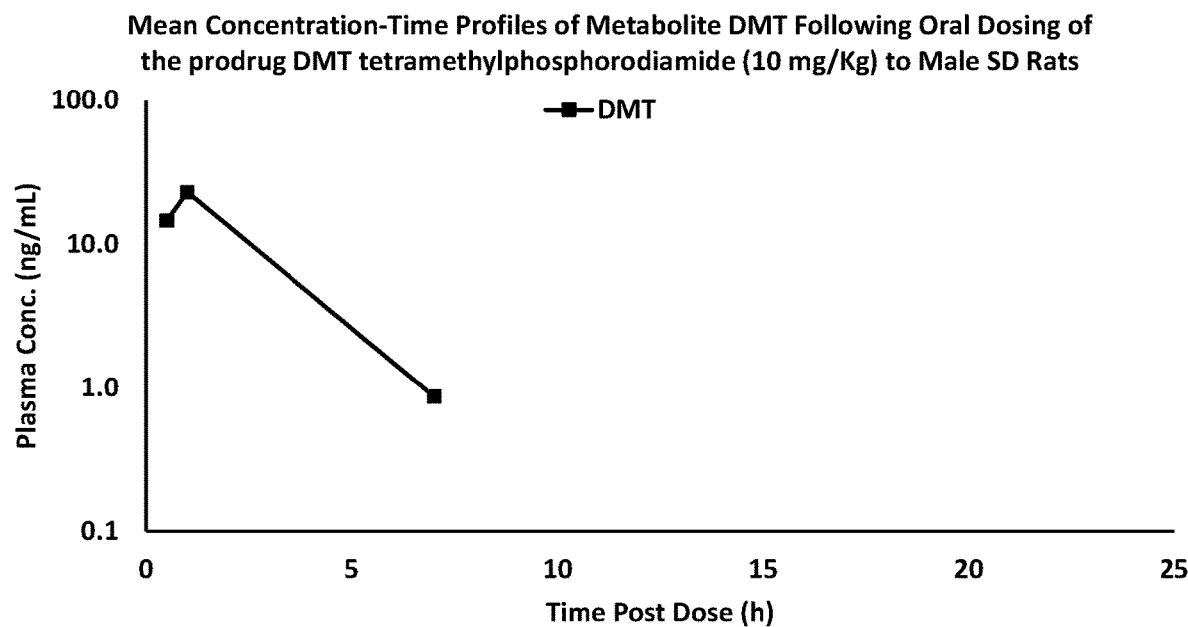
FIG. 42 shows the Mean Concentration-Time Profiles of Metabolite DMT Following Oral Dosing of the prodrug DMT tetramethylphosphorodiamide (10 mg/Kg) to Male SD Rats.

FIG. 42. Mean Concentration-Time Profiles of Metabolite DMT Following Oral Dosing of the prodrug DMT tetramethylphosphorodiamide (10 mg/Kg) to Male SD Rats

TABLE 2-38

| DMT PK Parameters Mean* Pharmacokinetic Parameters | |
|---|---|
| PK Parameter | DMT |
| Cmax (ng/mL) | 23.0 |
| Tmax (h) | 1.00 |
| MRT (h) | 1.14 |
| Tlast (h) | 7.00 |
| AUC0-last (h*ng/mL) | 84.7 |
| AUC0-24 (h*ng/mL) | NC |
| AUC0-inf (h*ng/mL) | NC |
| T½ (h) | NC |

*Median calculated for Tmax and Tlast.
NC: Not Calculated

Example 2-39. 5-MeO-DMT tetramethylphosphorodiamide

| Dosed Test Article: | 5-MeO-DMT tetramethylphosphorodiamide |
|---|---|
| Dose Route: | Oral |
| Nominal Dose Concentration: | 10 mg/Kg |
| Analyte: | 5-MeO-DMT |

Chemical name: 2-(1-di(dimethylamino)phosphoryl-5-methoxy-indol-3-yl)-N,N-dimethyl-ethanamine
Structural class: phosphorodiamidate prodrug
Mechanistic class: presumed phosphatase

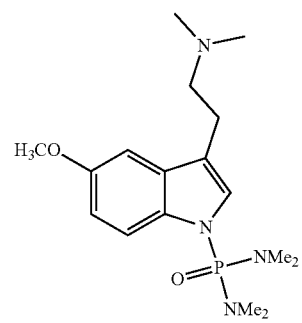 [SMILES: COc1ccc2c(c1)c(CCN(C)C)cn2P(=O)(N(C)C)N(C)C]

Figure 43:
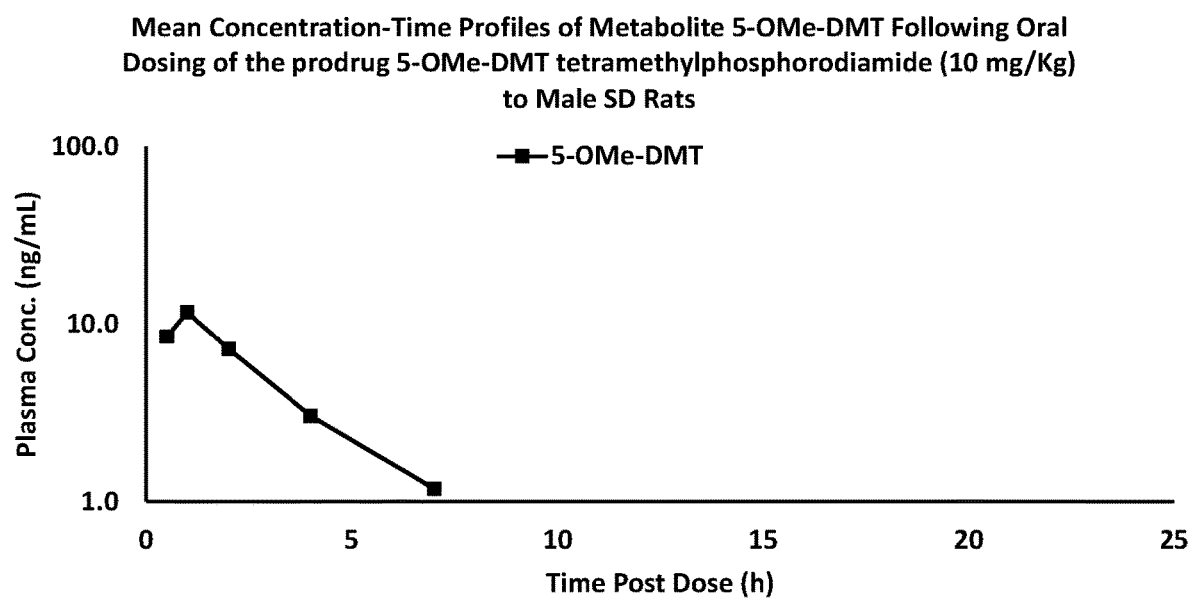
FIG. 43 shows Mean Concentration-Time Profiles of Metabolite 5-MeO-DMT Following Oral Dosing of the prodrug 5-MeO-DMT tetramethylphosphorodiamide (10 mg/Kg) to Male SD Rats.

FIG. 43. Mean Concentration-Time Profiles of Metabolite 5-MeO-DMT Following Oral Dosing of the prodrug 5-MeO-DMT tetramethylphosphorodiamide (10 mg/Kg) to Male SD Rats

TABLE 2-39

| 5-MeO-DMT PK Parameters Mean* Pharmacokinetic Parameters | |
|---|---|
| PK Parameter | 5-MeO-DMT |
| Cmax (ng/mL) | 11.7 |
| Tmax (h) | 1.00 |
| MRT (h) | 2.28 |
| Tlast (h) | 7.00 |
| AUC0-last (h*ng/mL) | 33.3 |
| AUC0-24 (h*ng/mL) | NC |

TABLE 2-39-continued

5-MeO-DMT PK Parameters
Mean* Pharmacokinetic Parameters

| PK Parameter | 5-MeO-DMT |
|---|---|
| AUC0-inf (h*ng/mL) | 36.6 |
| T½ (h) | 1.96 |

*Median calculated for Tmax and Tlast.
NC: Not Calculated

Example 2-40. DMT Phenylalanine di-hydrochloride

| Dosed Test Article: | DMT Phenylalanine di-hydrochloride |
|---|---|
| Dose Route: | Oral |
| Nominal Dose Concentration: | 10 mg/Kg |
| Analyte: | DMT |

Chemical name: (S)-2-amino-1-(3-(2-(dimethylamino)ethyl)-1H-indol-1-yl)-3-phenylpropan-1-one bis-hydrochloride Structural class: amino acid prodrug Mechanistic class: presumed amidase

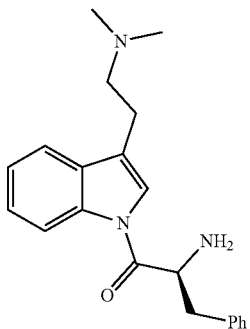 [SMILES: CN(C)CCc1cn(C(=O)[C@@H](N)Cc2ccccc2)c2ccccc12]

Figure 44:
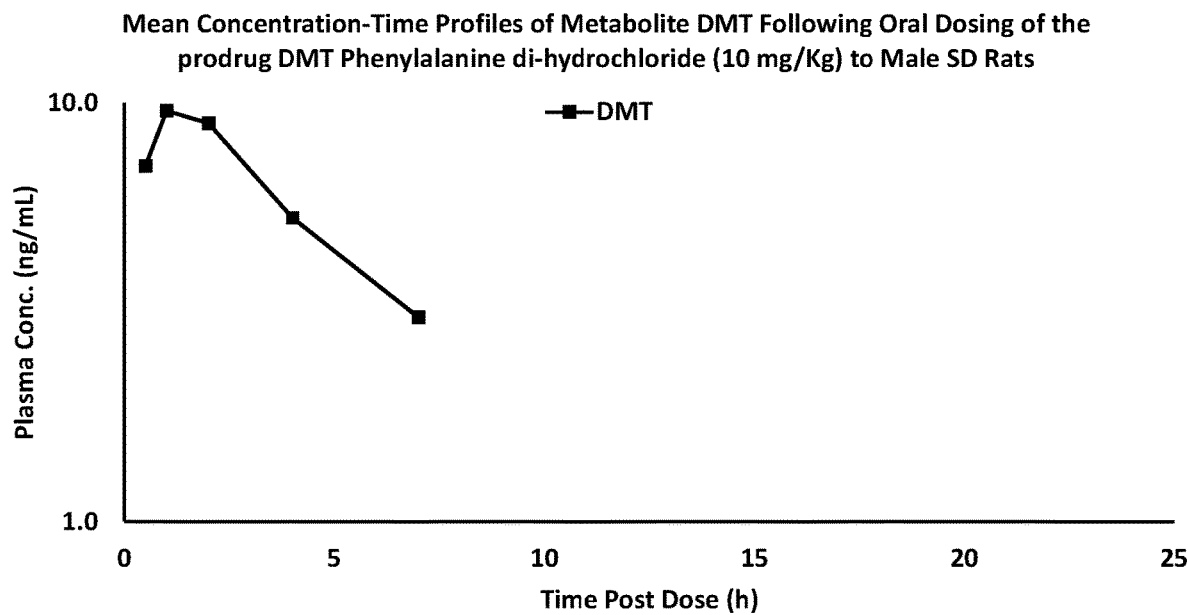
FIG. 44 shows the Mean Concentration-Time Profiles of Metabolite DMT Following Oral Dosing of the prodrug DMT Phenylalanine di-hydrochloride (10 mg/Kg) to Male SD Rats.

FIG. 44. Mean Concentration-Time Profiles of Metabolite DMT Following Oral Dosing of the prodrug DMT Phenylalanine di-hydrochloride (10 mg/Kg) to Male SD Rats

TABLE 2-40

DMT PK Parameters
Mean* Pharmacokinetic Parameters

| PK Parameter | DMT |
|---|---|
| Cmax (ng/mL) | 10.2 |
| Tmax (h) | 1.00 |
| MRT (h) | 2.93 |
| Tlast (h) | 7.00 |
| AUC0-last (h*ng/mL) | 42.0 |
| AUC0-24 (h*ng/mL) | NC |
| AUC0-inf (h*ng/mL) | 76.7 |
| T½ (h) | 6.38 |

*Median calculated for Tmax and Tlast.
NC: Not Calculated

Example 2-41. 5-MeO-DMT Phenylalanine di-hydrochloride

| Dosed Test Article: | 5-MeO-DMT Phenylalanine di-hydrochloride |
|---|---|
| Dose Route: | Oral |
| Nominal Dose Concentration: | 10 mg/Kg |
| Analyte: | 5-MeO-DMT |

Chemical name: (S)-2-amino-1-(3-(2-(dimethylamino)ethyl)-5-methoxy-1H-indol-1-yl)-3-phenylpropan-1-one bis-hydrochloride Structural class: amino acid prodrug Mechanistic class: presumed amidase

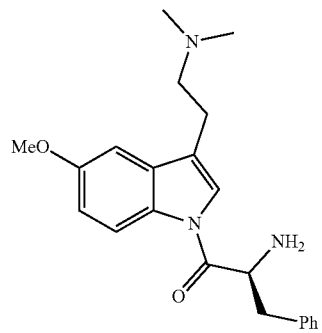 [SMILES: COc1ccc2c(c1)c(CCN(C)C)cn2C(=O)[C@@H](N)Cc1ccccc1]

Figure 45:
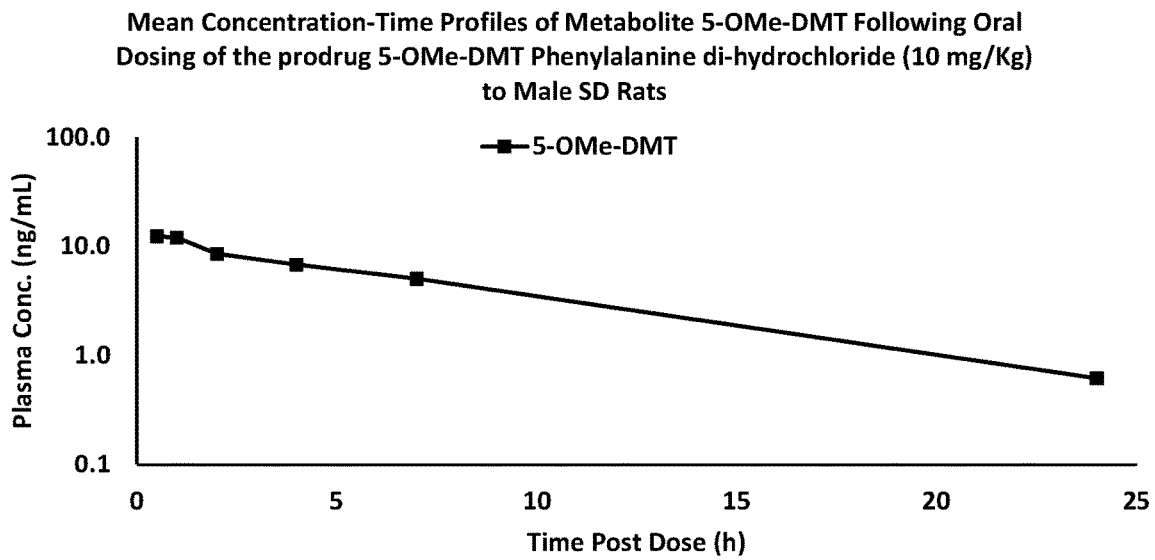
FIG. 45 shows the Mean Concentration-Time Profiles of Metabolite 5-MeO-DMT Following Oral Dosing of the prodrug 5-MeO-DMT Phenylalanine di-hydrochloride (10 mg/Kg) to Male SD Rats.

FIG. 45. Mean Concentration-Time Profiles of Metabolite 5-MeO-DMT Following Oral Dosing of the prodrug 5-MeO-DMT Phenylalanine di-hydrochloride (10 mg/Kg) to Male SD Rats

TABLE 41

5-MeO-DMT PK Parameters
Mean* Pharmacokinetic Parameters

| PK Parameter | 5-MeO-DMT |
|---|---|
| Cmax (ng/mL) | 13.3 |
| Tmax (h) | 0.50 |
| MRT (h) | 4.85 |
| Tlast (h) | 24.0 |
| AUC0-last (h*ng/mL) | 86.2 |
| AUC0-24 (h*ng/mL) | 104 |
| AUC0-inf (h*ng/mL) | 99.8 |
| T½ (h) | 5.37 |

*Median calculated for Tmax and Tlast.

Example 2-42. 5-MeO-DMT 2,2-Dimethylpropyl Pivalate Carbamate Formate

| Dosed Test Article: | 5-MeO-DMT 2,2-dimethylpropyl pivalate carbamate formate |
|---|---|
| Dose Route: | Oral |
| Nominal Dose Concentration: | 10 mg/Kg |
| Analyte: | 5-MeO-DMT |

Chemical name: 2,2-dimethyl-3-(pivaloyloxy)propyl 3-(2-(dimethylamino)ethyl)-5-methoxy-1H-indole-1-carboxylate formate Structural class: carbamate prodrug Mechanistic class: presumed carboxyesterases+intramolecular cyclization

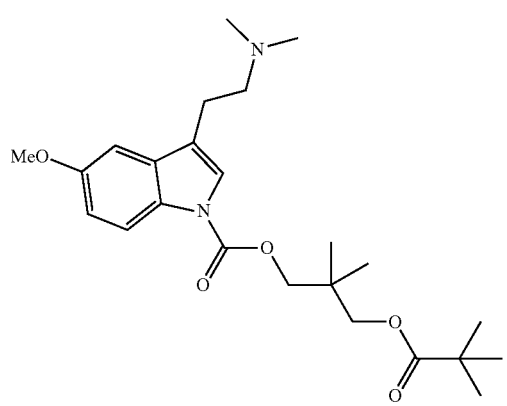 [SMILES: COc1ccc2c(c1)c(CCN(C)C)cn2C(=O)OCC(C)(C)COC(=O)C(C)(C)C]

Figure 46:
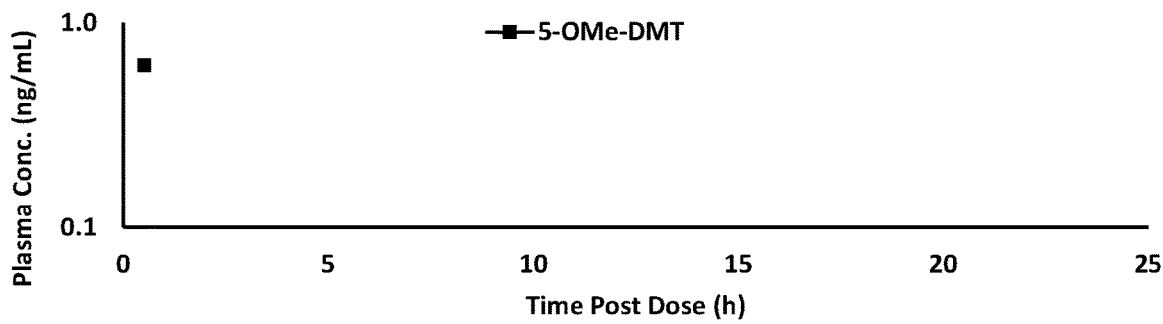
FIG. 46 shows the Mean Concentration-Time Profiles of Metabolite 5-MeO-DMT Following Oral Dosing of the prodrug 5-MeO-DMT 2,2-dimethylpropyl pivalate carbamate formate (10 mg/Kg) to Male SD Rats.

FIG. 46. Mean Concentration-Time Profiles of Metabolite 5-MeO-DMT Following Oral Dosing of the prodrug 5-MeO-DMT 2,2-dimethylpropyl pivalate carbamate formate (10 mg/Kg) to Male SD Rats

TABLE 2-42

| 5-MeO-DMT PK Parameters | |
|---|---|
| Mean* Pharmacokinetic Parameters | |
| PK Parameter | 5-MeO-DMT |
| Cmax (ng/mL) | 0.623 |
| Tmax (h) | 0.50 |
| MRT (h) | 0.50 |
| Tlast (h) | 0.50 |
| AUC0-last (h*ng/mL) | 0.156 |
| AUC0-24 (h*ng/mL) | NC |
| AUC0-inf (h*ng/mL) | NC |
| T½ (h) | NC |

*Median calculated for Tmax and Tlast.
NC: Not Calculated

Example 2-43. DMT N,N-Dimethylglycine Hydrochloride

| Dosed Test Article: | DMT N,N-dimethylglycine hydrochloride |
|---|---|
| Dose Route: | Oral |
| Nominal Dose Concentration: | 10 mg/Kg |
| Analyte: | DMT |

Chemical name: 2-(dimethylamino)-1-(3-(2-(dimethylamino)ethyl)-1H-indol-1-yl)ethan-1-one hydrochloride Structural class: amino acid prodrug Mechanistic class: presumed amidase

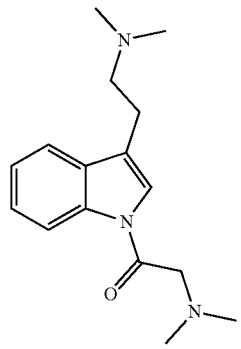 [SMILES: CN(C)CCc1cn(C(=O)CN(C)C)c2ccccc12]

Figure 47:
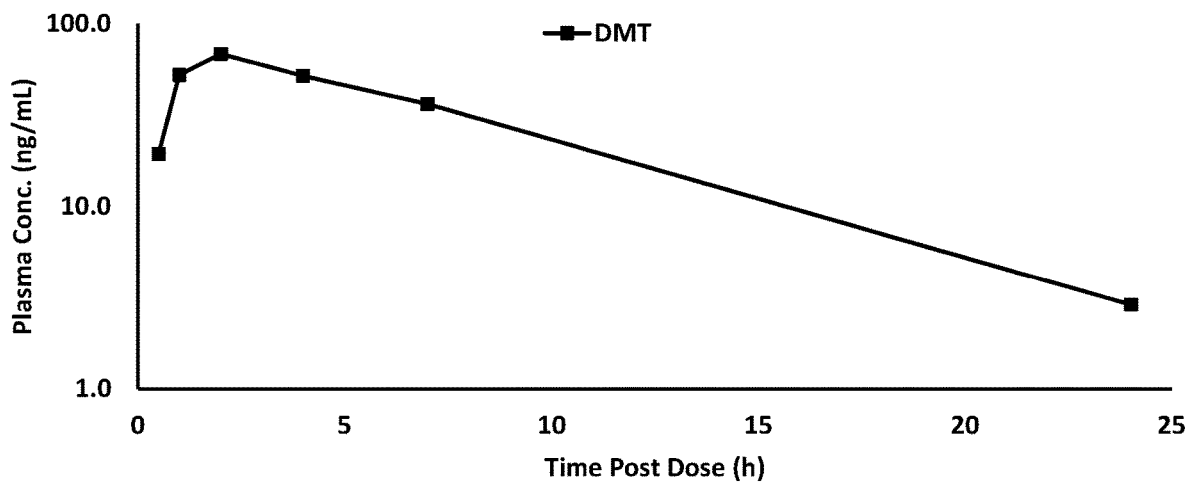
FIG. 47 shows the Mean Concentration-Time Profiles of Metabolite DMT Following Oral Dosing of the prodrug DMT N,N-dimethylglycine hydrochloride (10 mg/Kg) to Male SD Rats.

FIG. 47. Mean Concentration-Time Profiles of Metabolite DMT Following Oral Dosing of the prodrug DMT N,N-dimethylglycine hydrochloride (10 mg/Kg) to Male SD Rats

TABLE 2-43

| DMT PK Parameters | |
|---|---|
| Mean* Pharmacokinetic Parameters | |
| PK Parameter | DMT |
| Cmax (ng/mL) | 68.4 |
| Tmax (h) | 2.00 |
| MRT (h) | 5.84 |
| Tlast (h) | 24.0 |
| AUC0-last (h*ng/mL) | 670 |
| AUC0-24 (h*ng/mL) | 670 |
| AUC0-inf (h*ng/mL) | 690 |
| T½ (h) | 4.78 |

*Median calculated for Tmax and Tlast.

Example 2-44. DMT N,N-Dimethyl Urea Formate

| Dosed Test Article: | DMT N,N-dimethyl urea formate |
|---|---|
| Dose Route: | Oral |
| Nominal Dose Concentration: | 10 mg/Kg |
| Analyte: | DMT |

Chemical name: 3-[2-(dimethylamino)ethyl]-N,N-dimethyl-indole-1-carboxamide

Structural class: urea prodrug

Mechanistic class: presumed amidase

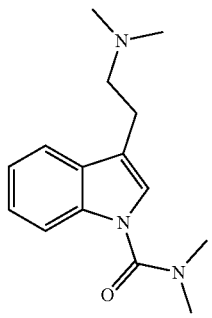

TABLE 2-44

Mean Concentration-Time Profiles of Metabolite DMT
Following Oral Dosing of the prodrug DMT N,N-dimethyl
urea formate (10 mg/Kg) to Male SD Rats
Mean Plasma Concentrations (ng/mL)

| Time (h) | DMT |
|---|---|
| 0.50 | BLQ |
| 1.00 | BLQ |
| 2.00 | BLQ |
| 4.00 | BLQ |
| 7.00 | BLQ |
| 24.0 | BLQ |

BLQ: Below Lower Limit of Quantification (0.5 ng/mL)

Example 2-45. DMT methyl pivalate

| | |
|---|---|
| Dosed Test Article: | DMT methyl pivalate |
| Dose Route: | Oral |
| Nominal Dose Concentration: | 10 mg/Kg |
| Analyte: | DMT |

Chemical name: (3-(2-(dimethylamino)ethyl)-1H-indol-1-yl)methyl pivalate

Structural class: acyloxymethyl prodrug

Mechanistic class: presumed carboxyesterase+chemical breakdown

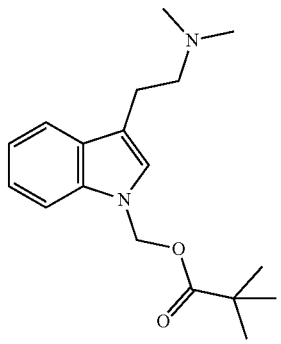 [SMILES: CN(C)CCc1cn(COC(=O)C(C)(C)C)c2ccccc12]

Figure 48:
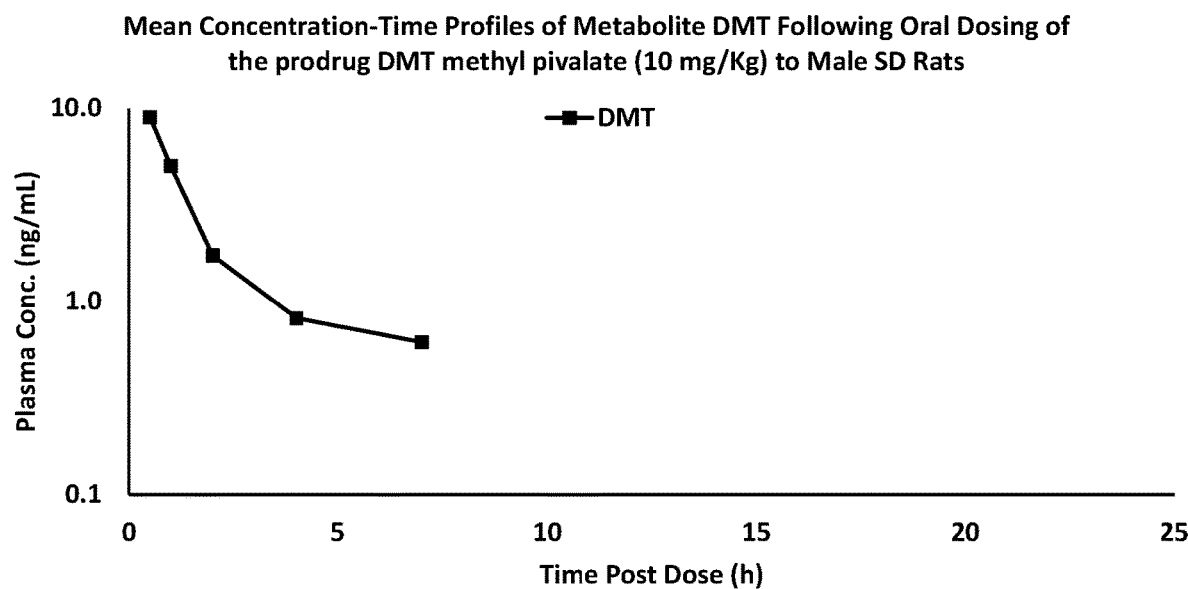
FIG. 48 shows the Mean Concentration-Time Profiles of Metabolite DMT Following Oral Dosing of the prodrug DMT methyl pivalate (10 mg/Kg) to Male SD Rats.

FIG. 48. Mean Concentration-Time Profiles of Metabolite DMT Following Oral Dosing of the prodrug DMT methyl pivalate (10 mg/Kg) to Male SD Rats

TABLE 2-45

DMT PK Parameters
Mean* Pharmacokinetic Parameters

| PK Parameter | DMT |
|---|---|
| Cmax (ng/mL) | 9.02 |
| Tmax (h) | 0.50 |
| MRT (h) | 1.17 |
| Tlast (h) | 4.00 |
| AUC0-last (h*ng/mL) | 10.2 |
| AUC0-24 (h*ng/mL) | NC |
| AUC0-inf (h*ng/mL) | 17.0 |
| T½ (h) | 2.04 |

*Median calculated for Tmax and Tlast.
NC: Not Calculated

Example 2-46. 5-MeO-DMT methyl pivalate

| | |
|---|---|
| Dosed Test Article: | 5-MeO-DMT methyl pivalate |
| Dose Route: | Oral |
| Nominal Dose Concentration: | 10 mg/Kg |
| Analyte: | 5-MeO-DMT |

Chemical name: (3-(2-(Dimethylamino)ethyl)-5-methoxy-1H-indol-1-yl)methyl pivalate Structural class: acyloxymethyl prodrug Mechanistic class: presumed carboxyesterase+chemical breakdown

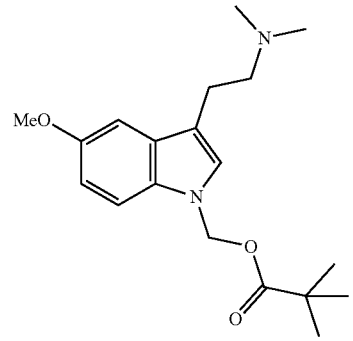 [SMILES: COc1ccc2c(c1)c(CCN(C)C)cn2COC(=O)C(C)(C)C]

Figure 49:
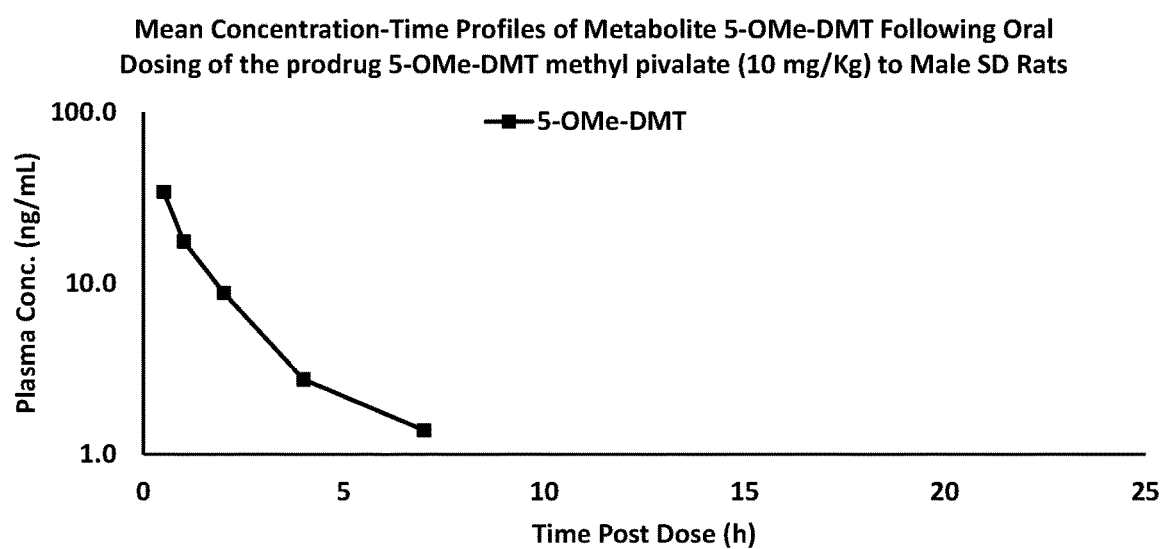
FIG. 49 shows the Mean Concentration-Time Profiles of Metabolite 5-MeO-DMT Following Oral Dosing of the prodrug 5-MeO-DMT methyl pivalate (10 mg/Kg) to Male SD Rats.

FIG. 49. Mean Concentration-Time Profiles of Metabolite 5-MeO-DMT Following Oral Dosing of the prodrug 5-MeO-DMT methyl pivalate (10 mg/Kg) to Male SD Rats

TABLE 2-46

5-MeO-DMT PK Parameters
Mean* Pharmacokinetic Parameters

| PK Parameter | 5-MeO-DMT |
|---|---|
| Cmax (ng/mL) | 34.4 |
| Tmax (h) | 0.50 |
| MRT (h) | 1.41 |
| Tlast (h) | 4.00 |
| AUC0-last (h*ng/mL) | 48.8 |
| AUC0-24 (h*ng/mL) | — |
| AUC0-inf (h*ng/mL) | 53.3 |
| T½ (h) | 1.34 |

*Median calculated for Tmax and Tlast.
NC: Not Calculated

Example 2-47. DMT-3,3-dimethylsuccinate hydrochloride

| | |
|---|---|
| Dosed Test Article: | DMT-3,3-dimethylsuccinate hydrochloride |
| Dose Route: | Oral |
| Nominal Dose Concentration: | 10 mg/Kg |
| Analyte: | DMT |

Chemical name: 4-(3-(2-(dimethylamino)ethyl)-1H-indol-1-yl)-2,2-dimethyl-4-oxobutanoic acid HCl salt Structural class: amide prodrug Mechanistic class: presumed pH-dependent cyclization

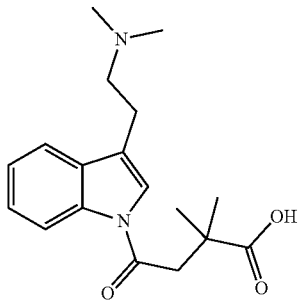 [SMILES: CN(C)CCc1cn(C(=O)CC(C)(C)C(=O)O)c2ccccc12]

TABLE 2-47

Mean Concentration-Time Profiles of Metabolite DMT Following Oral Dosing of the prodrug DMT-3,3-dimethylsuccinate hydrochloride (10 mg/Kg) to Male SD Rats
Mean Plasma Concentrations (ng/mL)

| Time (h) | DMT |
|---|---|
| 0.50 | BLQ |
| 1.00 | BLQ |
| 2.00 | BLQ |
| 4.00 | BLQ |
| 7.00 | BLQ |
| 24.0 | BLQ |

BLQ: Below Lower Limit of Quantification (0.5 ng/mL)

Example 2-48. 5-MeO-DMT-3,3-dimethylsuccinate hydrochloride

| Dosed Test Article: | 5-MeO-DMT-3,3-dimethylsuccinate hydrochloride |
|---|---|
| Dose Route: | Oral |
| Nominal Dose Concentration: | 10 mg/Kg |
| Analyte: | 5-MeO-DMT |

Chemical name: 4-(3-(2-(dimethylamino)ethyl)-5-methoxy-1H-indol-1-yl)-2,2-dimethyl-4-oxobutanoic acid HCl salt Structural class: amide prodrug Mechanistic class: presumed pH-dependent cyclization

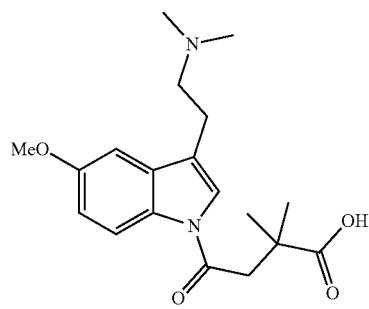 [SMILES: COc1ccc2c(c1)c(CCN(C)C)cn2C(=O)CC(C)(C)C(=O)O]

Figure 50:
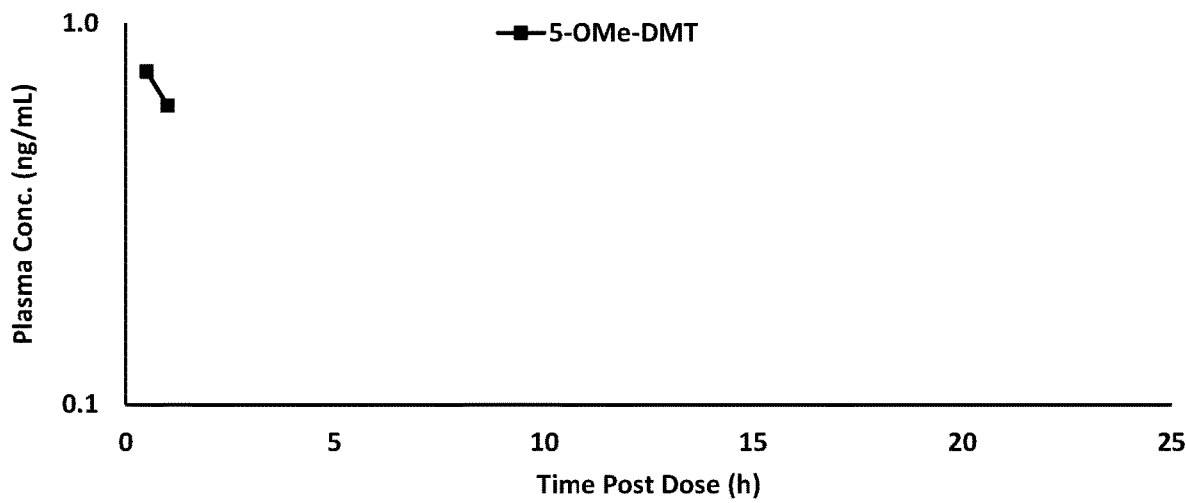
FIG. 50 shows the Mean Concentration-Time Profiles of Metabolite 5-MeO-DMT Following Oral Dosing of the prodrug 5-MeO-DMT-3,3-dimethylsuccinate hydrochloride (10 mg/Kg) to Male SD Rats.

FIG. 50. Mean Concentration-Time Profiles of Metabolite 5-MeO-DMT Following Oral Dosing of the prodrug 5-MeO-DMT-3,3-dimethylsuccinate hydrochloride (10 mg/Kg) to Male SD Rats

TABLE 2-48

5-MeO-DMT PK Parameters
Mean* Pharmacokinetic Parameters

| PK Parameter | 5-MeO-DMT |
|---|---|
| Cmax (ng/mL) | 0.692 |
| Tmax (h) | 1.00 |
| MRT (h) | 0.765 |
| Tlast (h) | 1.00 |
| AUC0-last (h*ng/mL) | 0.449 |
| AUC0-24 (h*ng/mL) | NC |
| AUC0-inf (h*ng/mL) | NC |
| T½ (h) | NC |

*Median calculated for Tmax and Tlast.
NC: Not Calculated

Example 2-49. DMT 2,2-Dimethylpropyl Pivalate Carbamate Formate

| Dosed Test Article: | DMT 2,2-dimethylpropyl pivalate carbamate formate |
|---|---|
| Dose Route: | Oral |
| Nominal Dose Concentration: | 10 mg/Kg |
| Analyte: | DMT |

Chemical name: 2,2-Dimethyl-3-(pivaloyloxy)propyl 3-(2-(dimethylamino)ethyl)-1H-indole-1-carboxylate formate Structural class: carbamate prodrug Mechanistic class: presumed carboxesterase+intramolecular cyclization

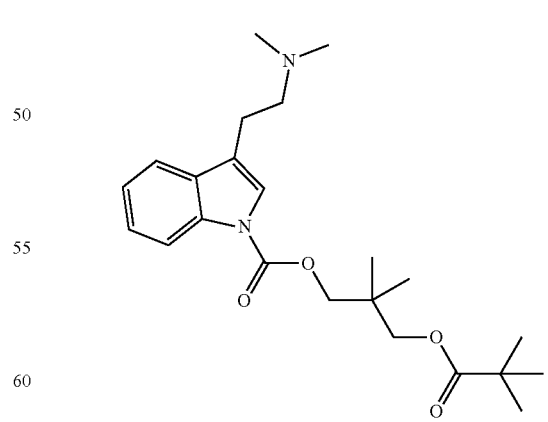

Figure 51:
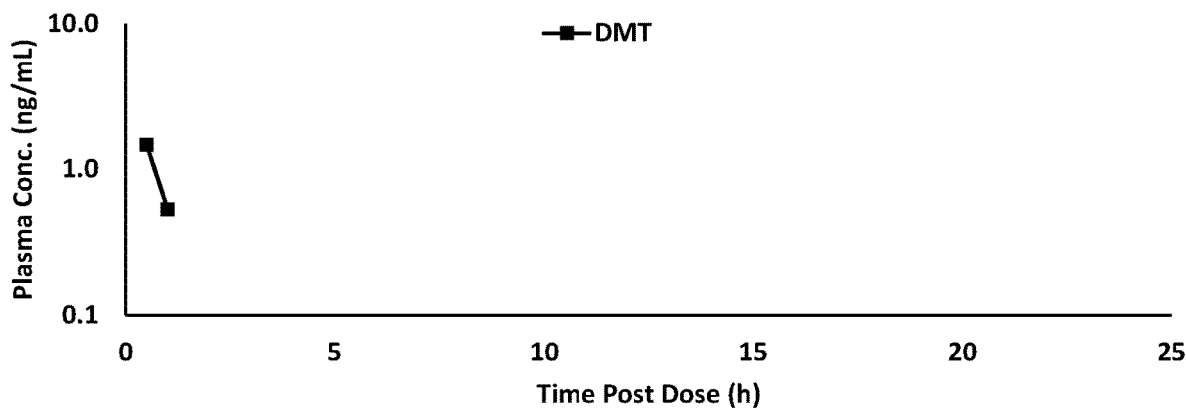
FIG. 51 shows the Mean Concentration-Time Profiles of Metabolite DMT Following Oral Dosing of the prodrug DMT 2,2-dimethylpropyl pivalate carbamate formate (10 mg/Kg) to Male SD Rats.

FIG. 51. Mean Concentration-Time Profiles of Metabolite DMT Following Oral Dosing of the prodrug DMT 2,2-dimethylpropyl pivalate carbamate formate (10 mg/Kg) to Male SD Rats

TABLE 2-49

DMT PK Parameters
**Mean* Pharmacokinetic Parameters**

| PK Parameter | DMT |
|---|---|
| Cmax (ng/mL) | 1.47 |
| Tmax (h) | 0.50 |
| MRT (h) | 0.528 |
| Tlast (h) | 0.50 |
| AUC0-last (h*ng/mL) | 0.522 |
| AUC0-24 (h*ng/mL) | NC |
| AUC0-inf (h*ng/mL) | NC |
| T½ (h) | NC |

*Median calculated for Tmax and Tlast.
NC: Not Calculated

Example 2-50. DMT Methyl Alcohol

| | |
|---|---|
| Dosed Test Article: | DMT methyl alcohol |
| Dose Route: | Oral |
| Nominal Dose Concentration: | 10 mg/Kg |
| Analyte: | DMT |

Chemical name: (3-(2-(dimethylamino)ethyl)-1H-indol-1-yl)methanol

Structural class: methyleneoxy prodrug

Mechanistic class: presumed chemical breakdown

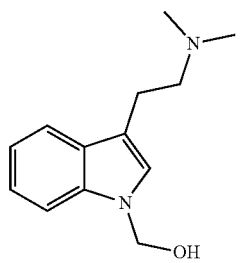 [SMILES: CN(C)CCc1cn(CO)c2ccccc12]

Figure 52:
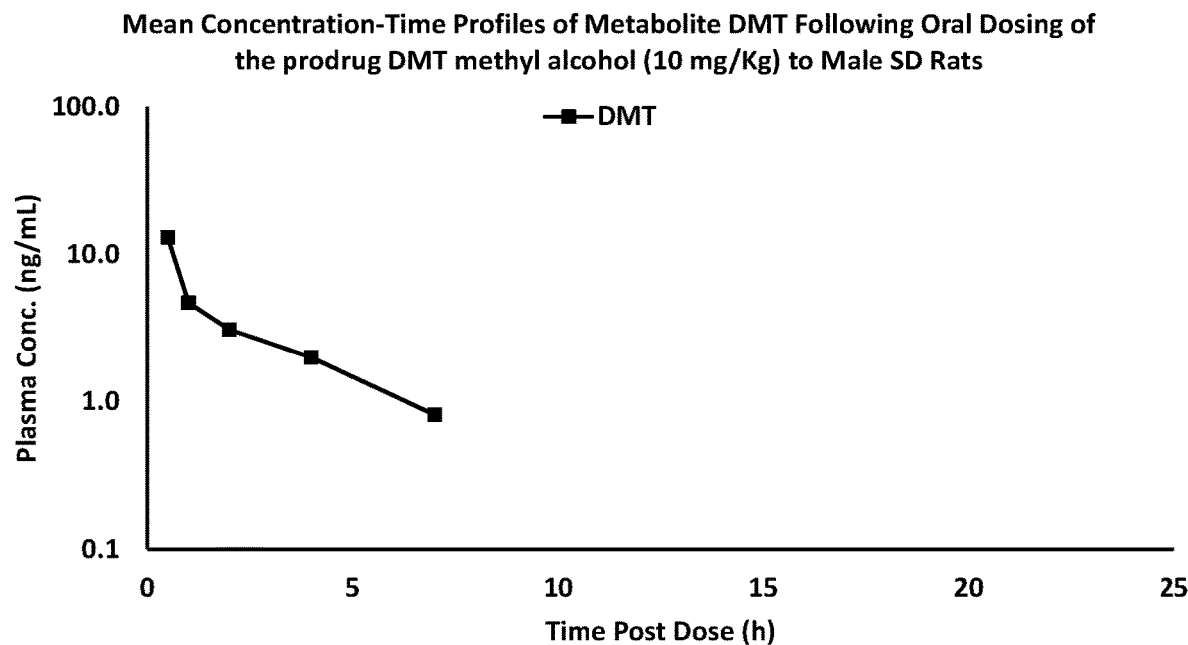
FIG. 52 shows the Mean Concentration-Time Profiles of Metabolite DMT Following Oral Dosing of the prodrug DMT methyl alcohol (10 mg/Kg) to Male SD Rats.

FIG. 52. Mean Concentration-Time Profiles of Metabolite DMT Following Oral Dosing of the prodrug DMT methyl alcohol (10 mg/Kg) to Male SD Rats

TABLE 2-50

DMT PK Parameters
**Mean* Pharmacokinetic Parameters**

| PK Parameter | DMT |
|---|---|
| Cmax (ng/mL) | 13.1 |
| Tmax (h) | 0.50 |
| MRT (h) | 1.21 |
| Tlast (h) | 2.00 |
| AUC0-last (h*ng/mL) | 14.8 |
| AUC0-24 (h*ng/mL) | NC |
| AUC0-inf (h*ng/mL) | 28.4 |
| T½ (h) | 2.52 |

*Median calculated for Tmax and Tlast.
NC: Not Calculated

Example 2-51. 5-MeO-DMT Methyl Alcohol

| | |
|---|---|
| Dosed Test Article: | 5-MeO-DMT methyl alcohol |
| Dose Route: | Oral |
| Nominal Dose Concentration: | 10 mg/Kg |
| Analyte: | 5-MeO-DMT |

Chemical name: (3-(2-(Dimethylamino)ethyl)-5-methoxy-1H-indol-1-yl)methanol

Structural class: methyleneoxy prodrug

Mechanistic class: presumed chemical breakdown

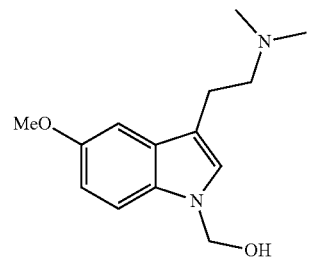

Figure 53:
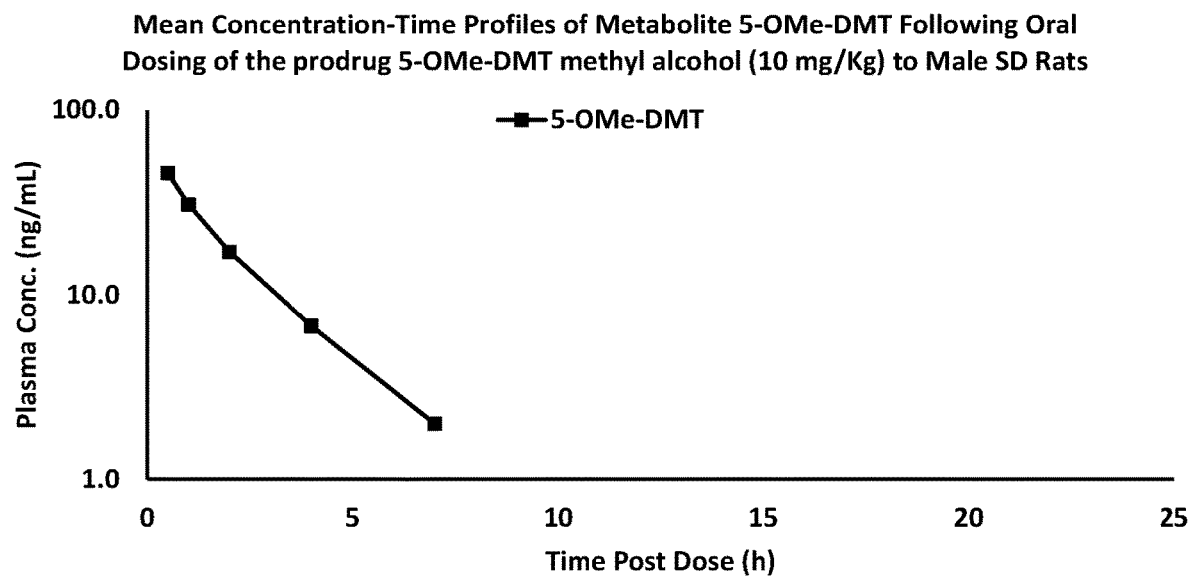
FIG. 53 shows the Mean Concentration-Time Profiles of Metabolite 5-MeO-DMT Following Oral Dosing of the prodrug 5-MeO-DMT methyl alcohol (10 mg/Kg) to Male SD Rats.

FIG. 53. Mean Concentration-Time Profiles of Metabolite 5-MeO-DMT Following Oral Dosing of the prodrug 5-MeO-DMT methyl alcohol (10 mg/Kg) to Male SD Rats

TABLE 2-51

5-MeO-DMT PK Parameters
**Mean* Pharmacokinetic Parameters**

| PK Parameter | 5-MeO-DMT |
|---|---|
| Cmax (ng/mL) | 46.0 |
| Tmax (h) | 0.50 |
| MRT (h) | 1.89 |
| Tlast (h) | 7.00 |
| AUC0-last (h*ng/mL) | 85.8 |
| AUC0-24 (h*ng/mL) | NC |
| AUC0-inf (h*ng/mL) | 96.0 |
| T½ (h) | 1.70 |

*Median calculated for Tmax and Tlast.
NC: Not Calculated

Example 2-52. 5-MeO-DMT Carboxy-Isopropyl Valinate Di-Trifluoroacetate

| | |
|---|---|
| Dosed Test Article: | 5-MeO-DMT carboxy-isopropyl valinate di-trifluoroacetate |
| Dose Route: | Oral |
| Nominal Dose Concentration: | 10 mg/Kg |
| Analyte: | 5-MeO-DMT |

Chemical name: 1-S)-2-amino-3-methylbutanoyl)oxy)-2-methylpropyl 3-(2-(dimethylamino)ethyl)-5-methoxy-1H-indole-1-carboxylate di-trifluoroacetate Structural class: acyloxymethyl carbamate prodrug Mechanistic class: presumed carboxyesterase+chemical breakdown

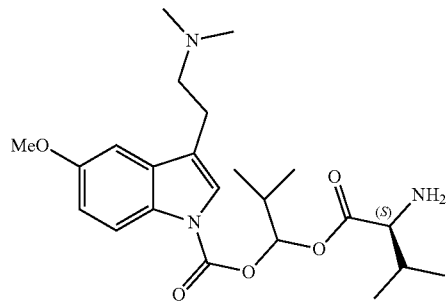

Figure 54:
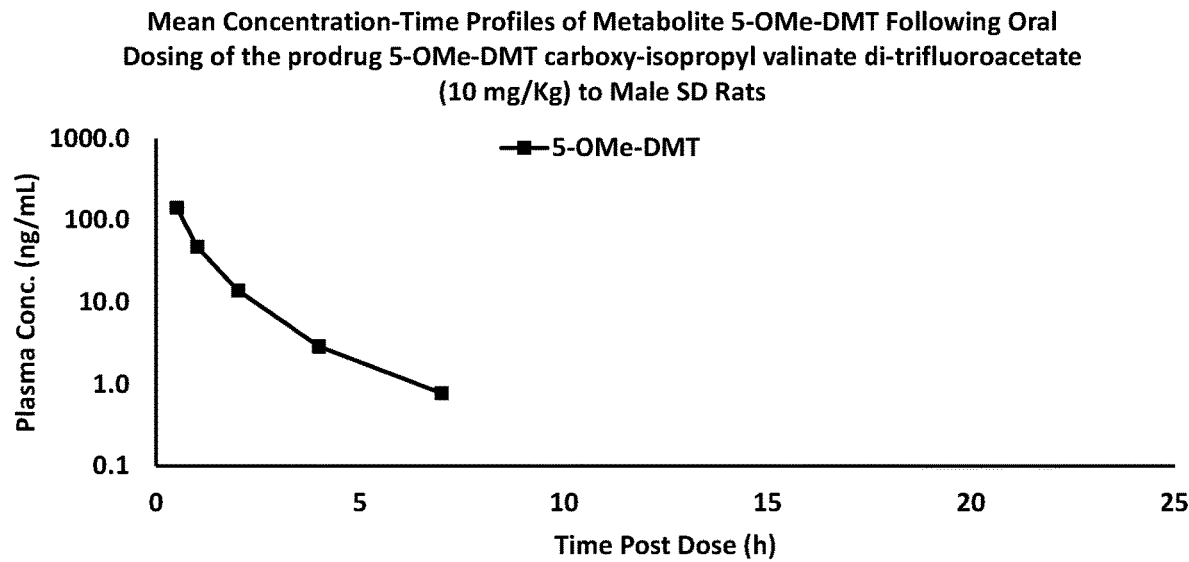
FIG. 54 shows the Mean Concentration-Time Profiles of Metabolite 5-MeO-DMT Following Oral Dosing of the prodrug 5-MeO-DMT carboxy-isopropyl valinate di-trifluoroacetate (10 mg/Kg) to Male SD Rats.

FIG. 54. Mean Concentration-Time Profiles of Metabolite 5-MeO-DMT Following Oral Dosing of the prodrug 5-MeO-DMT carboxy-isopropyl valinate di-trifluoroacetate (10 mg/Kg) to Male SD Rats

TABLE 2-52

| 5-MeO-DMT PK Parameters | |
|---|---|
| Mean* Pharmacokinetic Parameters | |
| PK Parameter | 5-MeO-DMT |
| Cmax (ng/mL) | 143 |
| Tmax (h) | 0.50 |
| MRT (h) | 1.00 |
| Tlast (h) | 4.00 |
| AUC0-last (h*ng/mL) | 133 |
| AUC0-24 (h*ng/mL) | NC |
| AUC0-inf (h*ng/mL) | 135 |
| T½ (h) | 0.904 |

*Median calculated for Tmax and Tlast.
NC: Not Calculated

Example 2-53. DMT Methyl Succinate

| Dosed Test Article: | DMT methyl succinate |
|---|---|
| Dose Route: | Oral |
| Nominal Dose Concentration: | 10 mg/Kg |
| Analyte: | DMT |

Chemical name: methyl 4-(3-(2-(dimethylamino)ethyl)-1H-indol-1-yl)-4-oxobutanoate Structural class: amide prodrug Mechanistic class: presumed carboxyesterase+pH-dependent cyclization

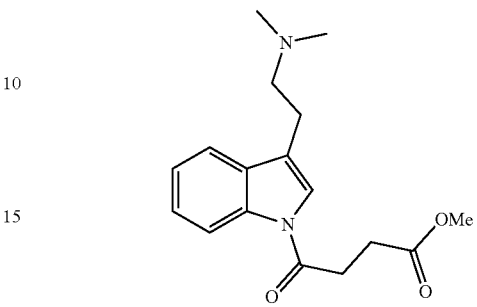

Figure 55:
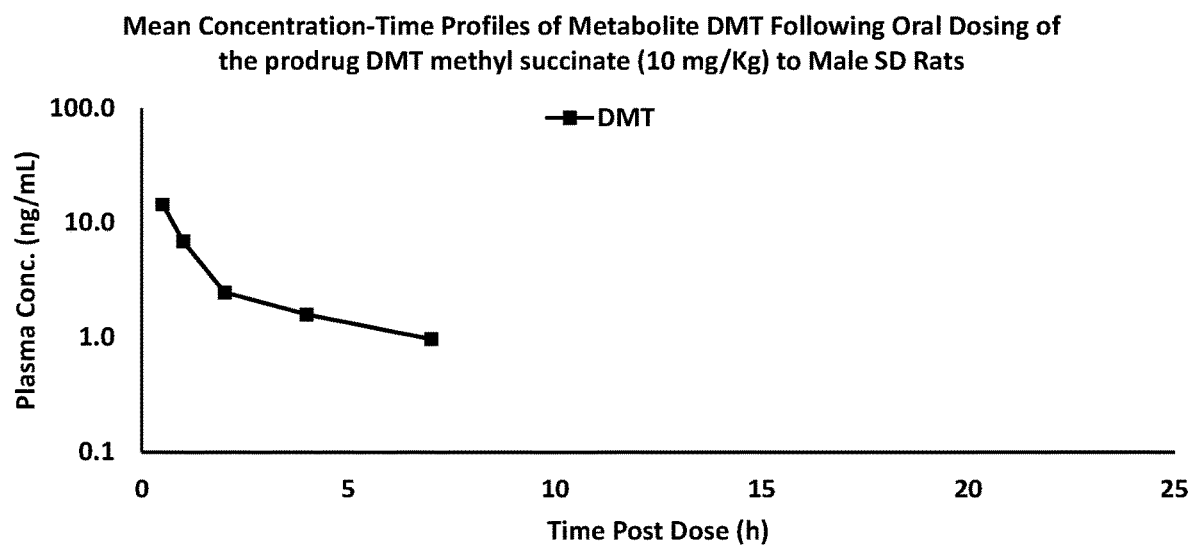
FIG. 55 shows the Mean Concentration-Time Profiles of Metabolite DMT Following Oral Dosing of the prodrug DMT methyl succinate (10 mg/Kg) to Male SD Rats.

FIG. 55. Mean Concentration-Time Profiles of Metabolite DMT Following Oral Dosing of the prodrug DMT methyl succinate (10 mg/Kg) to Male SD Rats

TABLE 2-53

| DMT PK Parameters | |
|---|---|
| Mean* Pharmacokinetic Parameters | |
| PK Parameter | DMT |
| Cmax (ng/mL) | 14.6 |
| Tmax (h) | 0.50 |
| MRT (h) | 1.75 |
| Tlast (h) | 7.00 |
| AUC0-last (h*ng/mL) | 20.7 |
| AUC0-24 (h*ng/mL) | NC |
| AUC0-inf (h*ng/mL) | 24.5 |
| T½ (h) | 2.60 |

*Median calculated for Tmax and Tlast.

Example 2-54. 5-MeO-DMT Methyl Succinate

| Dosed Test Article: | 5-MeO-DMT methyl succinate |
|---|---|
| Dose Route: | Oral |
| Nominal Dose Concentration: | 10 mg/Kg |
| Analyte: | 5-MeO-DMT |

Chemical name: methyl 4-(3-(2-(dimethylamino)ethyl)-5-methoxy-1H-indol-1-yl)-4-oxobutanoate Structural class: amide prodrug Mechanistic class: presumed carboxyesterase+pH-dependent cyclization

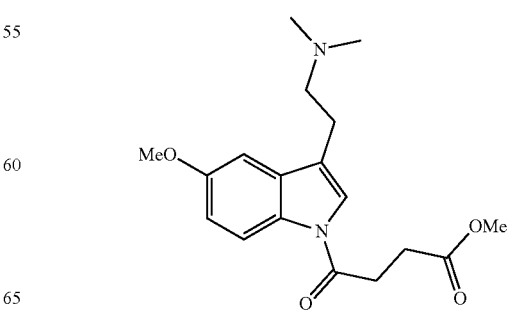

Figure 56:
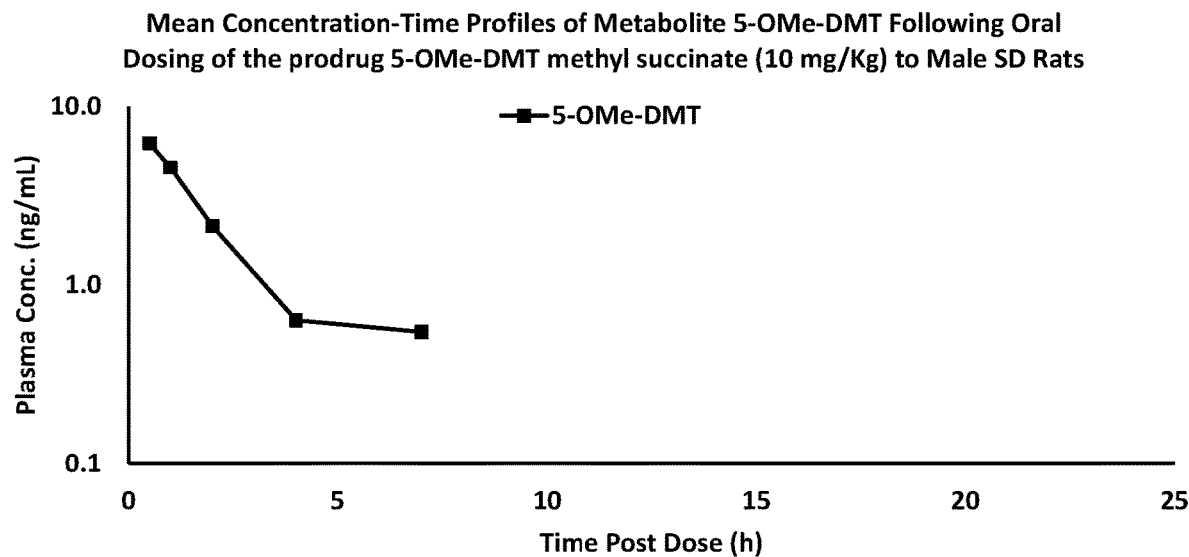
FIG. 56 shows the Mean Concentration-Time Profiles of Metabolite 5-MeO-DMT Following Oral Dosing of the prodrug 5-MeO-DMT methyl succinate (10 mg/Kg) to Male SD Rats.

FIG. 56. Mean Concentration-Time Profiles of Metabolite 5-MeO-DMT Following Oral Dosing of the prodrug 5-MeO-DMT methyl succinate (10 mg/Kg) to Male SD Rats

TABLE 2-54

5-MeO-DMT PK Parameters
Mean* Pharmacokinetic Parameters

| PK Parameter | 5-MeO-DMT |
|---|---|
| Cmax (ng/mL) | 6.23 |
| Tmax (h) | 0.50 |
| MRT (h) | 1.37 |
| Tlast (h) | 4.00 |
| AUC0-last (h*ng/mL) | 10.4 |
| AUC0-24 (h*ng/mL) | NC |
| AUC0-inf (h*ng/mL) | 15.1 |
| T½ (h) | 1.53 |

*Median calculated for Tmax and Tlast.

Example 2-55. DMT Methylpivaloyl Carbamate Formate

| Dosed Test Article: | DMT methylpivaloyl carbamate formate |
|---|---|
| Dose Route: | Oral |
| Nominal Dose Concentration: | 10 mg/Kg |
| Analyte: | DMT |

Chemical name: (pivaloyloxy)methyl 3-(2-(dimethylamino)ethyl)-1H-indole-1-carboxylate diformate Structural class: carbamate prodrug Mechanistic class: presumed carboxyesterase+chemical breakdown

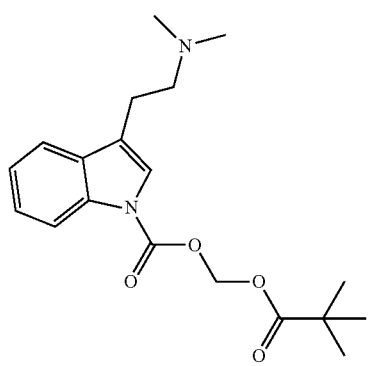 [SMILES: CN(C)CCc1cn(C(=O)OCOC(=O)C(C)(C)C)c2ccccc12]

Figure 57:
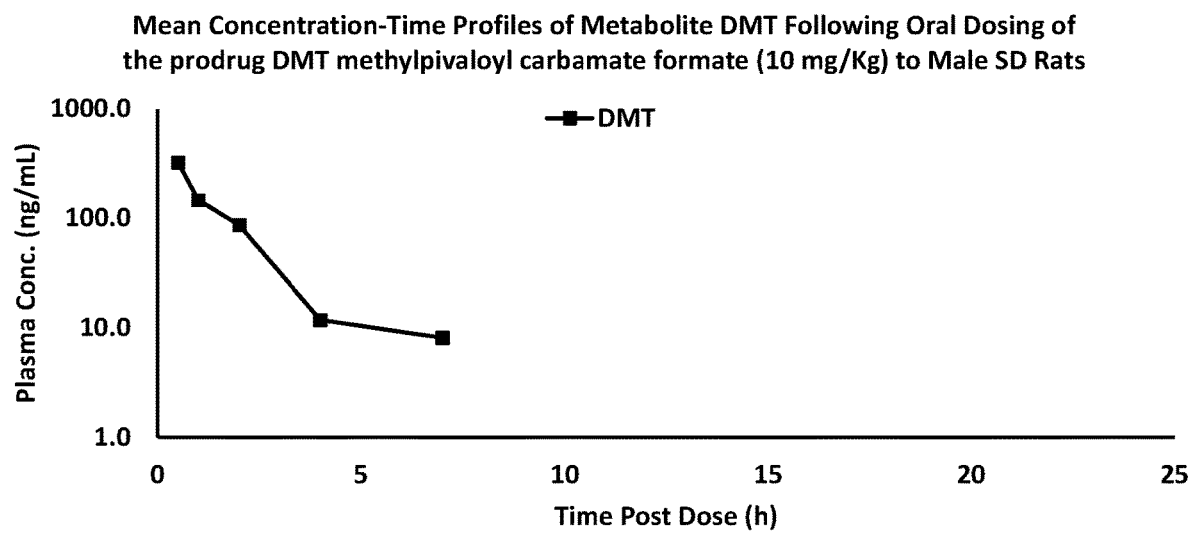
FIG. 57 shows the Mean Concentration-Time Profiles of Metabolite DMT Following Oral Dosing of the prodrug DMT methylpivaloyl carbamate formate (10 mg/Kg) to Male SD Rats.

FIG. 57. Mean Concentration-Time Profiles of Metabolite DMT Following Oral Dosing of the prodrug DMT methylpivaloyl carbamate formate (10 mg/Kg) to Male SD Rats

TABLE 2-55

DMT PK Parameters
Mean* Pharmacokinetic Parameters

| PK Parameter | DMT |
|---|---|
| Cmax (ng/mL) | 324 |
| Tmax (h) | 0.50 |
| MRT (h) | 1.48 |
| Tlast (h) | 7.00 |
| AUC0-last (h*ng/mL) | 441 |

TABLE 2-55-continued

DMT PK Parameters
Mean* Pharmacokinetic Parameters

| PK Parameter | DMT |
|---|---|
| AUC0-24 (h*ng/mL) | NC |
| AUC0-inf (h*ng/mL) | 462 |
| T½ (h) | 1.64 |

*Median calculated for Tmax and Tlast.

Example 2-56. Glutarate Prodrug of DMT

| Dosed Test Article: | Glutarate prodrug of DMT |
|---|---|
| Dose Route: | Oral |
| Nominal Dose Concentration: | 10 mg/Kg |
| Analyte: | DMT |

Chemical name: 5-(3-(2-(dimethylamino)ethyl)-1H-indol-1-yl)-5-oxopentanoic acid

Structural class: amide prodrug

Mechanistic class: presumed pH-dependent cyclization

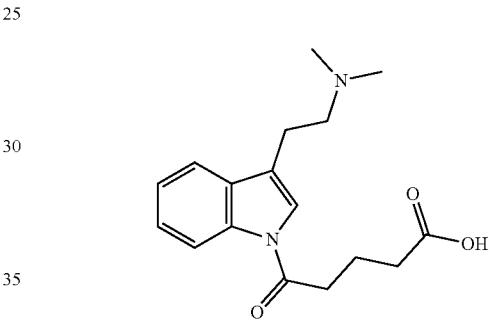

Figure 58:
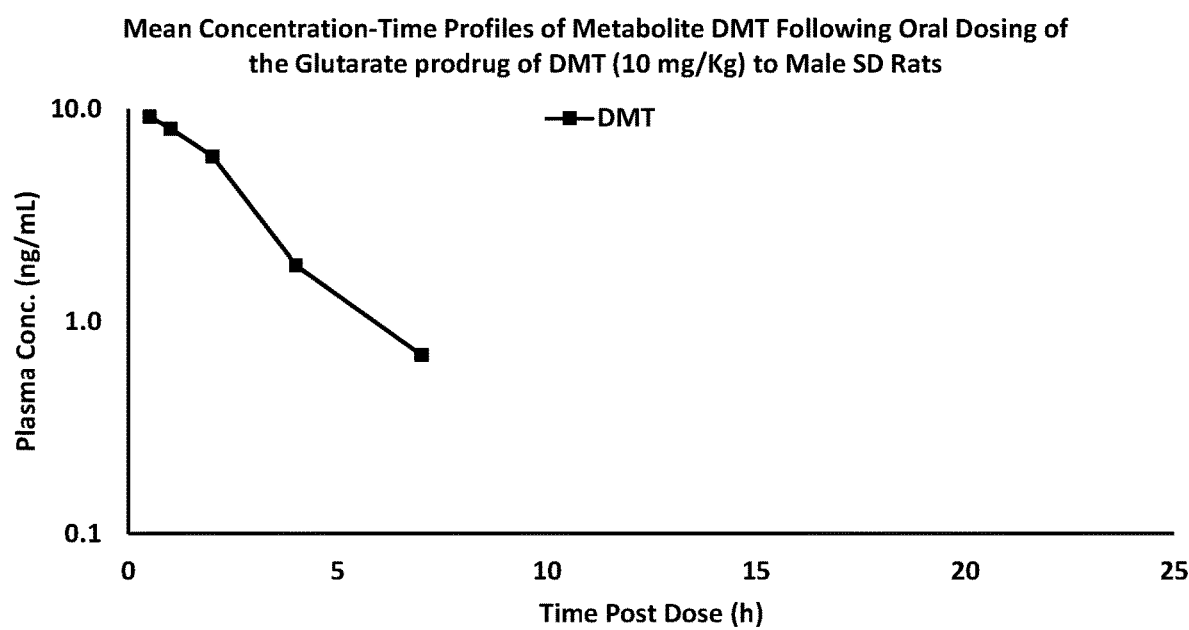
FIG. 58 shows the Mean Concentration-Time Profiles of Metabolite DMT Following Oral Dosing of the Glutarate prodrug of DMT (10 mg/Kg) to Male SD Rats.

FIG. 58. Mean Concentration-Time Profiles of Metabolite DMT Following Oral Dosing of the Glutarate prodrug of DMT (10 mg/Kg) to Male SD Rats

TABLE 2-56

DMT PK Parameters
Mean* Pharmacokinetic Parameters

| PK Parameter | DMT |
|---|---|
| Cmax (ng/mL) | 9.19 |
| Tmax (h) | 0.50 |
| MRT (h) | 1.92 |
| Tlast (h) | 7.00 |
| AUC0-last (h*ng/mL) | 24.2 |
| AUC0-24 (h*ng/mL) | NC |
| AUC0-inf (h*ng/mL) | 26.2 |
| T½ (h) | 1.57 |

*Median calculated for Tmax and Tlast.

A comparison of the results from Example 2-3 through Example 2-37 reveals that various derivative forms of DMT or 5-OMe-DMT described herein have vastly different pharmacokinetic properties. Oral administration of the compounds tested in Examples 2-3 through Example 2-37 resulted in total measured bodily plasma exposure to DMT or 5-OMe-DMT spanning a range of several orders of magnitude when comparing different DMT or 5-OMe-DMT derivative compounds. These results were unexpected and not predictable based solely on structural knowledge of the compounds.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

The invention claimed is:

1. A compound of Formula (I), or a pharmaceutically acceptable salt thereof:

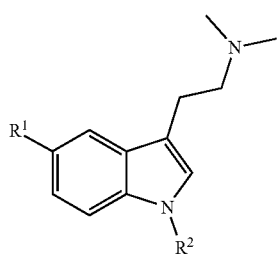
(I)

wherein:

R$^1$ is methoxy or hydrogen;

R$^2$ is —C(O)R$^4$, —C(O)OCH(R$^5$)OC(O)OR$^6$,

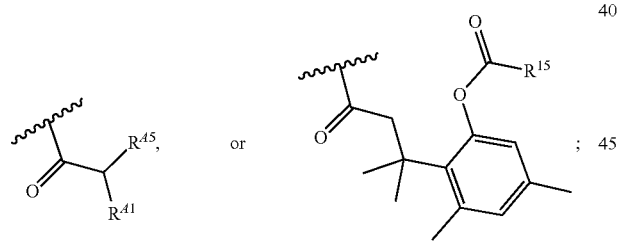

R$^4$ is alkyl, which is substituted with —N(R$^{18}$)R$^{19}$;

R$^5$ is hydrogen, alkyl, or cycloalkyl;

R$^6$ is alkyl, cycloalkyl, or —CH(R$^{41}$)NH$_2$;

R$^{41}$ is alkyl or an amino acid side chain;

R$^{45}$ is —N(R$^{18}$)R$^{19}$ or —N(R$^{13}$)C(O)R$^{14}$;

R$^{13}$ is hydrogen; R$^{14}$ is alkyl;

R$^{15}$ is alkyl, heteroalkyl, cycloalkyl, aryl, or heteroaryl, each of which is unsubstituted or substituted with one or more R$^B$; and each of R$^{18}$ and R$^{19}$ is independently hydrogen or alkyl.

2. The compound of claim 1, wherein the compound of Formula (I) has the structure of Formula (Ik), or a pharmaceutically acceptable salt thereof:

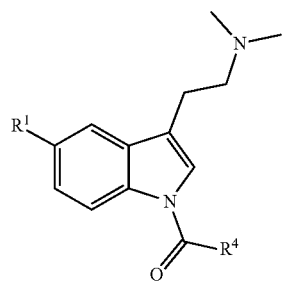
(Ik)

wherein:

R$^4$ is alkyl, which is substituted with —N(R$^{18}$)R$^{19}$; wherein alkyl is methyl, ethyl, n-propyl, isopropyl, n-butyl, tert-butyl, 3-methyl-1-butyl, n-pentyl, n-hexyl, n-heptyl, n-octyl, or n-nonyl; and each of R$^{18}$ and R$^{19}$ is hydrogen; or each of R$^{18}$ and R$^{19}$ is alkyl.

3. The compound of claim 1, having the structure of Formula (Ik3), or a pharmaceutically acceptable salt thereof:

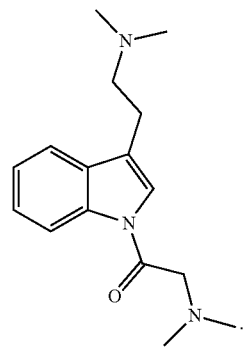 [SMILES: CN(C)CCc1cn(C(=O)CN(C)C)c2ccccc12]

4. The compound of claim 1, wherein the compound of Formula (I) has the structure of Formula (Ik3), or a pharmaceutically acceptable salt thereof:

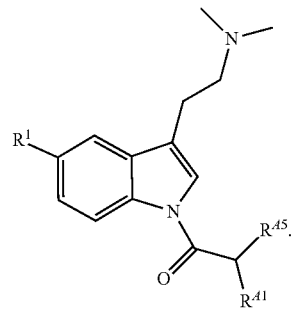
(Ik3)

5. The compound of claim 4, or a pharmaceutically acceptable salt thereof, wherein:

R$^{45}$ is —N(R$^{18}$)R$^{19}$; and

R$^{41}$ is methyl, ethyl, n-propyl, isopropyl, tert-butyl, CH(Me)Et, CH$_2$CH(Me)$_2$, or CH$_2$CH$_2$SMe.

6. The compound of claim 4, or a pharmaceutically acceptable salt thereof, wherein:

each of $R^{18}$ and $R^{19}$ is hydrogen; or each of $R^{18}$ and $R^{19}$ is alkyl; or $R^{18}$ is hydrogen, and $R^{19}$ is methyl, ethyl, isopropyl, tert-butyl, or phenyl.

7. The compound of claim 4, or a pharmaceutically acceptable salt thereof, wherein:

$R^{45}$ is —N($R^{13}$)C(O)$R^{14}$;

$R^{14}$ is methyl, ethyl, n-propyl, isopropyl, n-butyl, tert-butyl, n-pentyl, or 3-methyl-1-butyl; and $R^{41}$ is methyl, ethyl, n-propyl, isopropyl, tert-butyl, CH(Me)Et, CH$_2$CH(Me)$_2$, or CH$_2$CH$_2$SMe.

8. The compound of claim 4, or a pharmaceutically acceptable salt thereof, wherein the compound has one of the following structures:

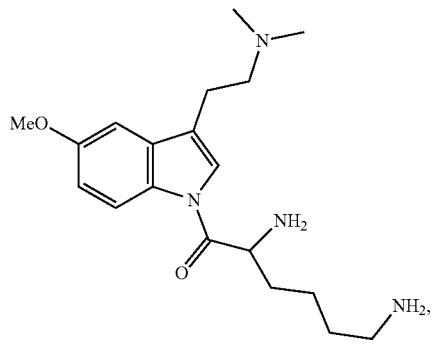

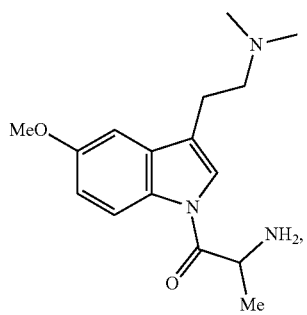

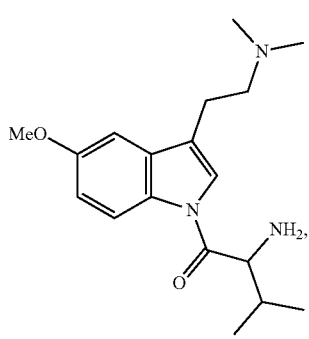

-continued

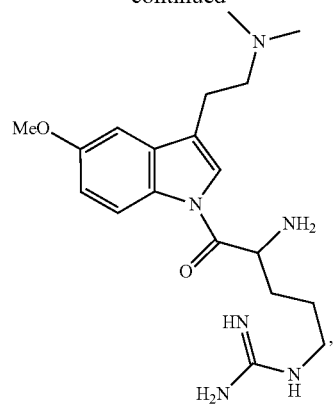

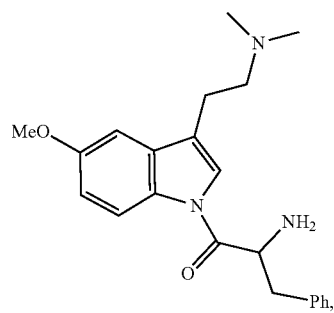

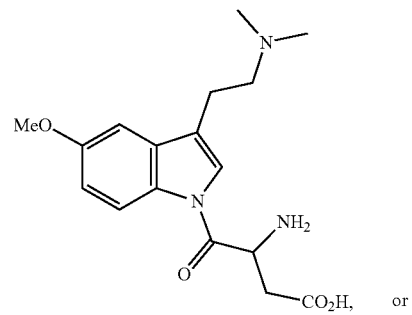 or

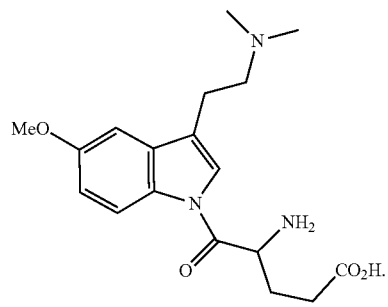

9. The compound of claim 4, or a pharmaceutically acceptable salt thereof, wherein the compound has one of the following structures:

10. The compound of claim 4, or a pharmaceutically acceptable salt thereof, wherein the compound has one of the following structures:

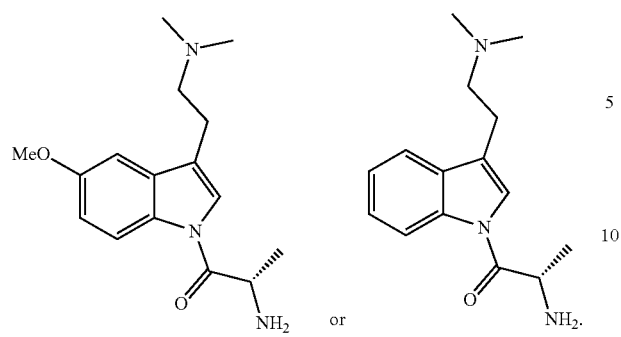

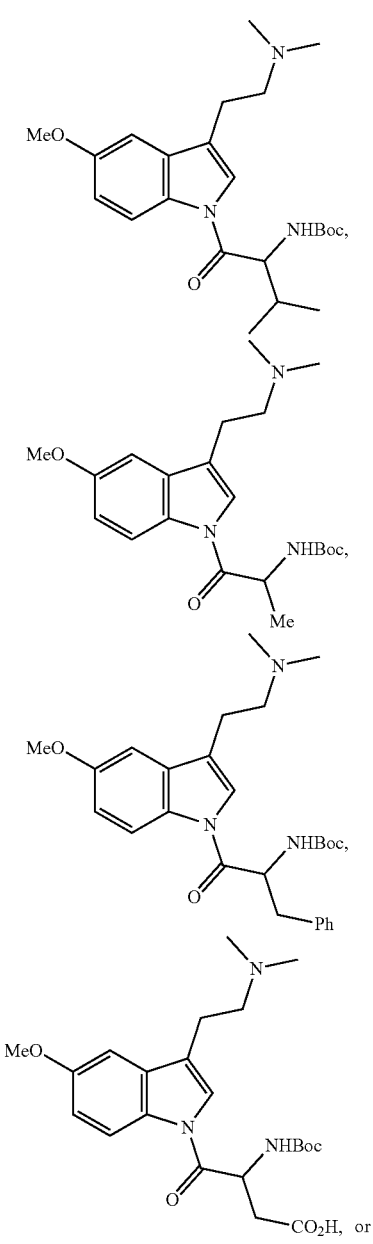

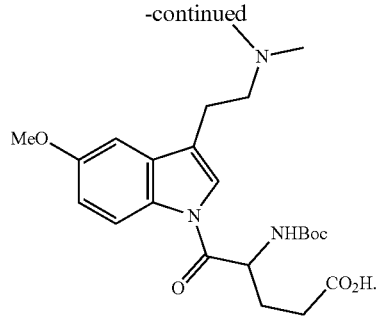

11. A compound of Formula (Iq), or a pharmaceutically acceptable salt thereof:

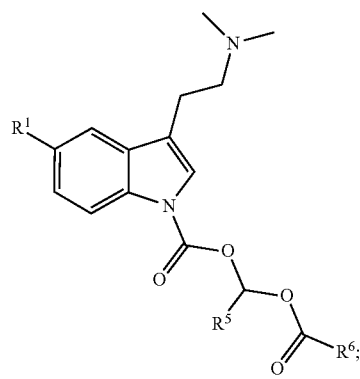

(Iq)

wherein $R^1$ is methoxy or hydrogen;

$R^5$ is hydrogen, alkyl, or cycloalkyl;

$R^6$ is alkyl, cycloalkyl, or —CH($R^{A1}$)NH$_2$; and $R^{A1}$ alkyl or an amino acid side chain.

12. The compound of claim 11, or a pharmaceutically acceptable salt thereof, wherein:

$R^5$ is hydrogen, alkyl, or cycloalkyl: and $R^6$ is alkyl or cycloalkyl.

13. The compound of claim 12, or a pharmaceutically acceptable salt thereof, wherein:

$R^5$ is methyl, isopropyl, tert-butyl, or —CH(Et)$_2$.

14. The compound of claim 13, or a pharmaceutically acceptable salt thereof, wherein:

$R^6$ is methyl, ethyl, isopropyl, n-propyl, tert-butyl, 3-methyl-1-butyl, n-pentyl, n-hexyl, cyclopropyl, cyclobutyl, cyclopentyl, cyclohexyl, or cycloheptyl.

15. The compound of claim 14, or a pharmaceutically acceptable salt thereof, wherein:

$R^6$ is methyl, ethyl, isopropyl, tert-butyl, or cyclopropyl.

16. The compound of claim 11, or a pharmaceutically acceptable salt thereof, wherein:

$R^1$ is hydrogen, $R^5$ is hydrogen, and $R^6$ is tert-butyl; or $R^1$ is methoxy, $R^5$ is hydrogen, and $R^6$ is tert-butyl.

17. The compound of claim 11, or a pharmaceutically acceptable salt thereof, wherein:

$R^6$ is —CH($R^{A1}$)NH$_2$; and $R^{A1}$ is methyl, ethyl, n-propyl, isopropyl, tert-butyl, CH(Me)Et, CH$_2$CH(Me)$_2$, or CH$_2$CH$_2$SMe.

18. The compound of claim 11, or a pharmaceutically acceptable salt thereof, wherein the compound has one of the following structures:

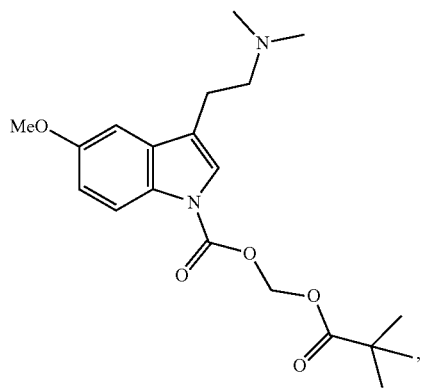 [SMILES: COc1ccc2c(c1)c(CCN(C)C)cn2C(=O)OC(C)OC(=O)C(C)(C)C]

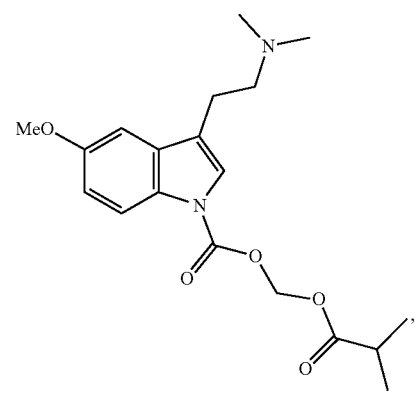

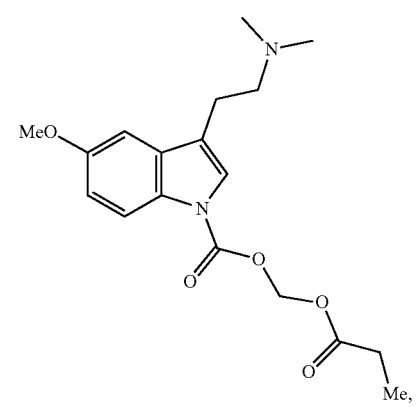

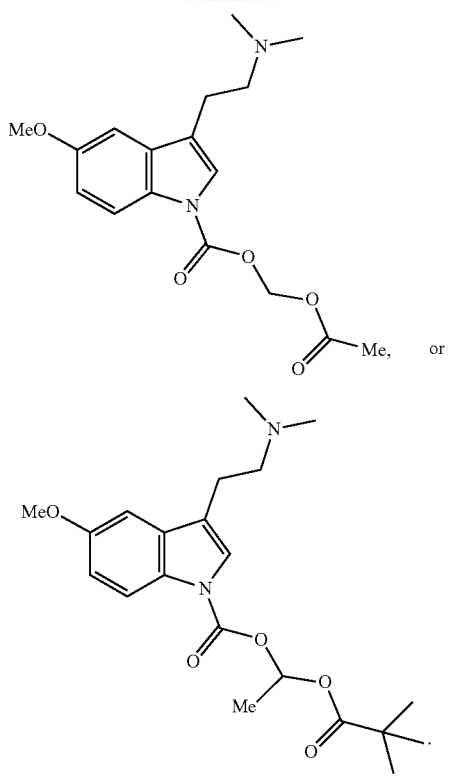

or

19. The compound of claim 11, or a pharmaceutically acceptable salt thereof, wherein the compound has one of the following structures:

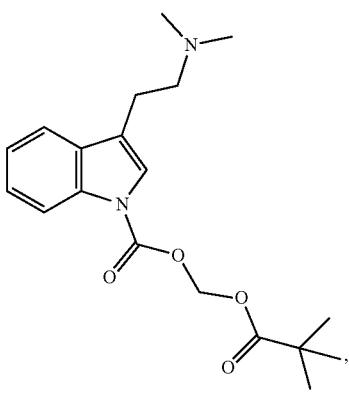

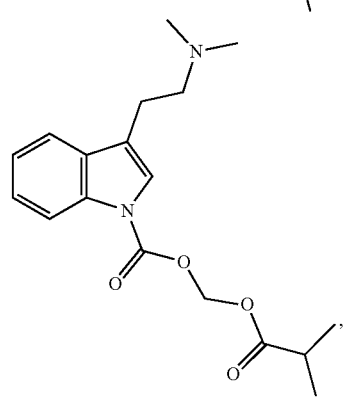

715
-continued

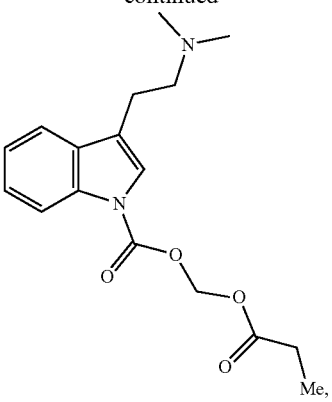

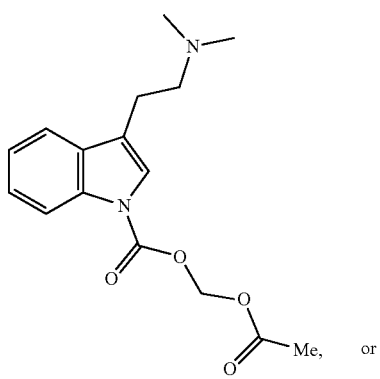

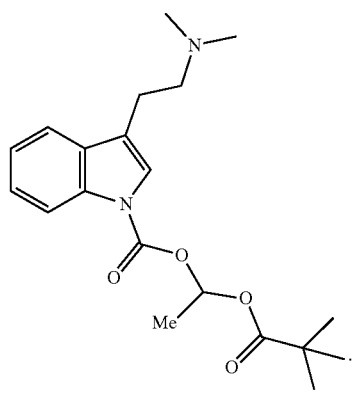 [SMILES: CC(OC(=O)n1cc(CCN(C)C)c2ccccc21)OC(=O)C(C)(C)C]

20. The compound of claim 11, or a pharmaceutically acceptable salt thereof, wherein the compound has one of the following structures:

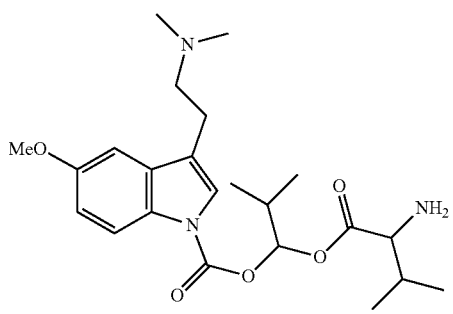

716
-continued

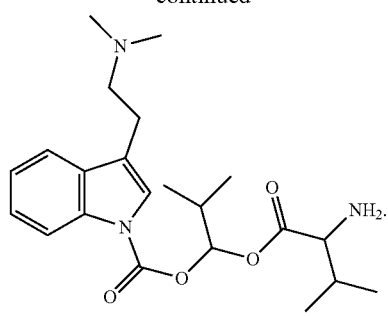

21. The compound of claim 11, or a pharmaceutically acceptable salt thereof, wherein the compound has the following structure:

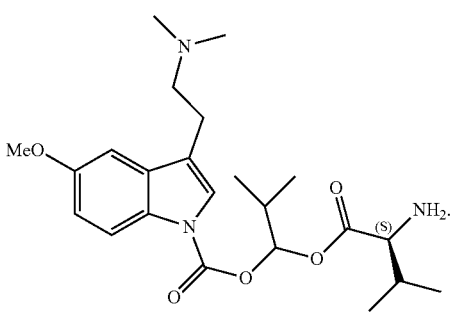

22. The compound of claim 1, wherein the compound of Formula (I) has the structure of Formula (Is), or a pharmaceutically acceptable salt thereof:

Formula (Is)

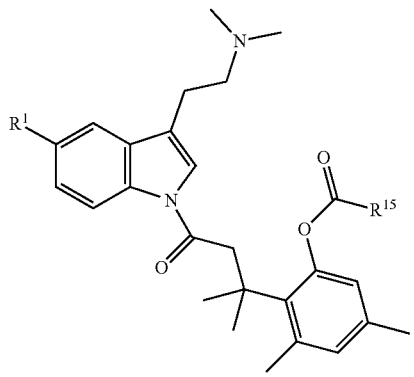

wherein:

R$^{15}$ is alkyl or cycloalkyl.

23. The compound of claim 22, or a pharmaceutically acceptable salt thereof, wherein:

R$^{15}$ is methyl, ethyl, n-propyl, isopropyl, n-butyl, or tert-butyl.

24. The compound of claim 22, or a pharmaceutically acceptable salt thereof, wherein:

$R^1$ is hydrogen, and $R^{15}$ is methyl: or $R^1$ is methoxy, and $R^{15}$ is methyl.

25. The compound of claim 22, or a pharmaceutically acceptable salt thereof, wherein the compound has one of the following structures:

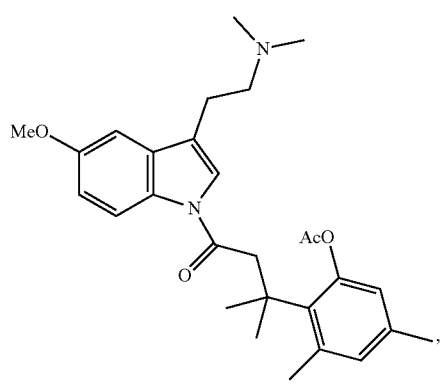

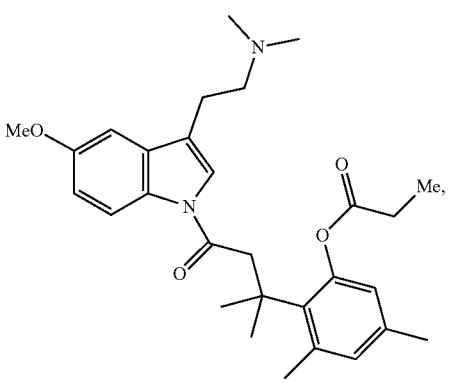

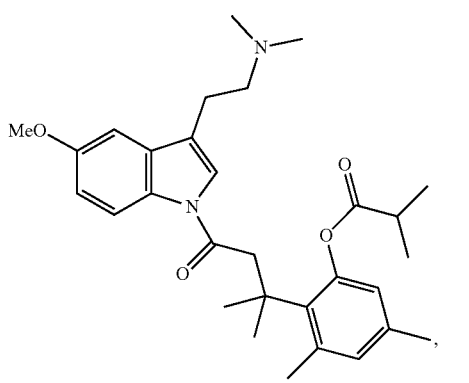, or

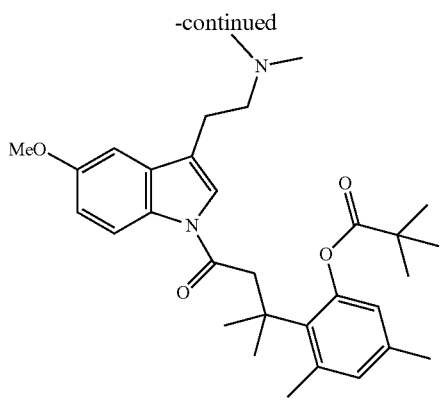

26. The compound of claim 22, or a pharmaceutically acceptable salt thereof, wherein the compound has one of the following structures:

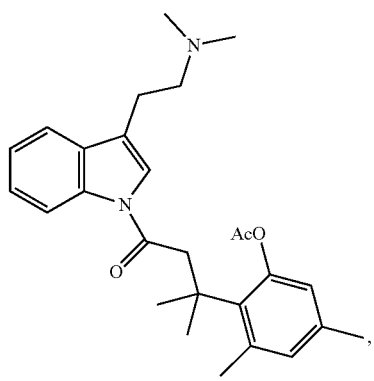

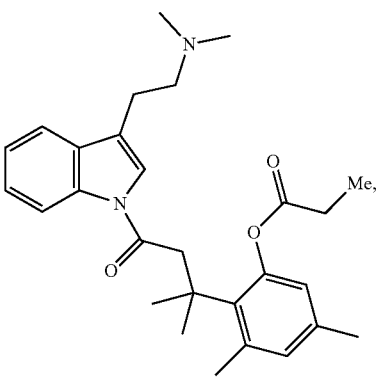

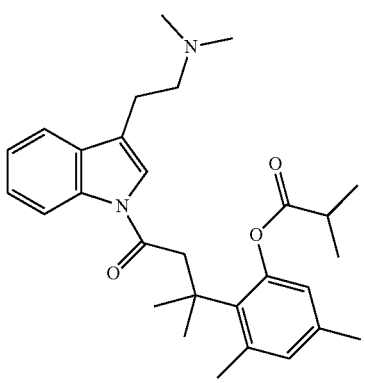, or

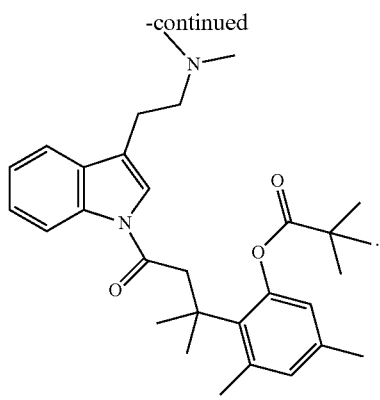

27. A pharmaceutically composition comprising a compound according to claim 1, or a pharmaceutically acceptable salt thereof, and a pharmaceutically acceptable excipient.

28. A method of treating major depression in a human comprising administering an effective amount of a compound of claim 1, or a pharmaceutically acceptable salt thereof, to the human in need thereof, wherein the administration of the effective amount of the compound of claim 1 provides blood plasma concentrations of N,N-dimethyltryptamine (DMT) or 5-methoxy-N,N-dimethyltryptamine (5-MeO-DMT) in the human that are effective for the treatment of major depression.

* * * * *